(12) United States Patent
Bao et al.

(10) Patent No.: US 10,329,289 B2
(45) Date of Patent: Jun. 25, 2019

(54) 6,7-DIHYDRO-5H-PYRROLO[3,4-B]PYRIDIN-5-ONE ALLOSTERIC MODULATORS OF THE M4 MUSCARINIC ACETYLCHOLINE RECEPTOR

(71) Applicants: Jianming Bao, Shanghai (CN); Xiaolei Gao, Bridgewater, NJ (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Debra L. Ondeyka, Fanwood, NJ (US); Andrew W. Stamford, Chatham, NJ (US); Fengqi Zhang, Edison, NJ (US)

(72) Inventors: Jianming Bao, Shanghai (CN); Xiaolei Gao, Bridgewater, NJ (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Debra L. Ondeyka, Fanwood, NJ (US); Andrew W. Stamford, Chatham, NJ (US); Fengqi Zhang, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/386,009

(22) Filed: Dec. 21, 2016

(65) Prior Publication Data

US 2017/0183342 A1 Jun. 29, 2017

Related U.S. Application Data

(60) Provisional application No. 62/419,630, filed on Nov. 9, 2016.

(30) Foreign Application Priority Data

Dec. 23, 2015 (WO) ................ PCT/CN2015/098382

(51) Int. Cl.
| | | |
|---|---|---|
| C07D 471/04 | (2006.01) | |
| C07F 9/22 | (2006.01) | |
| C07D 519/00 | (2006.01) | |
| C07D 491/048 | (2006.01) | |
| C07D 471/08 | (2006.01) | |
| C07D 491/052 | (2006.01) | |
| A61K 31/437 | (2006.01) | |
| A61P 25/00 | (2006.01) | |

(52) U.S. Cl.
CPC ......... *C07D 471/04* (2013.01); *C07D 471/08* (2013.01); *C07D 491/048* (2013.01); *C07D 491/052* (2013.01); *C07D 519/00* (2013.01); *C07F 9/222* (2013.01)

(58) Field of Classification Search
CPC ................ C07D 471/04; C07D 519/00; C07D 491/048; C07D 491/052; C07D 471/08; C07F 9/222
See application file for complete search history.

(56) References Cited

U.S. PATENT DOCUMENTS

| | | |
|---|---|---|
| 5,574,044 A | 11/1996 | Thompson et al. |
| 5,691,323 A | 11/1997 | Thompson et al. |
| 6,699,880 B1 | 3/2004 | Yamakawa et al. |
| 6,900,224 B2 | 5/2005 | Ledoussal et al. |
| 7,074,801 B1 | 7/2006 | Yoshida et al. |
| 7,858,635 B2 | 12/2010 | Makings et al. |
| 7,964,602 B2 | 6/2011 | MacDonald et al. |
| 8,071,776 B2 | 12/2011 | Rubio Esteban et al. |
| 8,168,639 B2 | 5/2012 | Kogan |
| 8,349,850 B2 | 1/2013 | Tworowski et al. |
| 8,614,319 B2 | 12/2013 | Tworowski et al. |
| 9,034,872 B2 | 5/2015 | Tworowski et al. |
| 9,056,875 B2 | 6/2015 | Lindsley et al. |
| 9,056,876 B2 | 6/2015 | Conn et al. |
| 9,493,481 B2 | 11/2016 | Lindsley et al. |
| 9,593,106 B2 | 3/2017 | Livermore et al. |
| 9,637,498 B2 | 5/2017 | Lindsley et al. |
| 9,670,183 B2 | 6/2017 | Brown et al. |
| 9,758,506 B2 | 9/2017 | Brown et al. |
| 9,868,746 B2 | 1/2018 | Lindsley et al. |
| 2007/0004763 A1 | 1/2007 | Baindur et al. |
| 2008/0306107 A1 | 12/2008 | Griffin et al. |
| 2016/0200733 A1 | 7/2016 | Lindsley et al. |
| 2017/0096437 A1 | 4/2017 | Congreve et al. |
| 2017/0369505 A1 | 12/2017 | Lindsley et al. |

FOREIGN PATENT DOCUMENTS

| | | |
|---|---|---|
| JP | 2013237634 | 11/2013 |
| JP | 2014047192 | 3/2014 |

(Continued)

OTHER PUBLICATIONS

Vardigan, J. D., "Improved cognition without adverse effects: novel M1 muscarinic potentiator compares favorably to donepezil and xanomeline in rhesus monkey." Psychopharmacology 232.11 (2015): 1859-1866.*

(Continued)

*Primary Examiner* — John M Mauro
(74) *Attorney, Agent, or Firm* — J. Eric Thies; John C. Todaro

(57) ABSTRACT

The present invention is directed to 6,7-dihydro-5H-pyrrolo [3,4-b]pyridine-5-one compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

20 Claims, No Drawings

(56) References Cited

FOREIGN PATENT DOCUMENTS

| | | |
|---|---|---|
| JP | 2014062063 | 4/2014 |
| WO | WO1999032481 | 7/1999 |
| WO | WO2005100351 | 10/2005 |
| WO | WO2006125180 | 11/2006 |
| WO | WO2006135649 | 12/2006 |
| WO | WO2011087776 | 7/2011 |
| WO | WO2012020813 | 2/2012 |
| WO | WO2012154731 | 11/2012 |
| WO | WO2013056015 | 4/2013 |
| WO | WO2013122107 | 8/2013 |
| WO | WO2014035829 | 3/2014 |
| WO | WO2014101373 | 7/2014 |
| WO | WO2016147011 | 9/2016 |
| WO | WO2017021728 | 2/2017 |
| WO | WO2017077292 | 5/2017 |
| WO | WO2017107087 | 6/2017 |
| WO | WO2017112556 | 6/2017 |
| WO | WO2017112719 | 6/2017 |

OTHER PUBLICATIONS

Bewley, Blake R., et al., Discovery of a novel, CNS penetrant M4PAM chemotype based on a 6-fluoro-4-(piperiden-1-yl)quinoline-3-carbonitrile core, Bioorganic and Med Chem Letters, 2017, 4274-4279, 27.

Byun, Nellie B, et al., Antipsychotic Drug-like Effects of the Selective M4 Muscarinic Acetylcholine Receptor Positive Allosteric Modulator VU02552100, Neuropsychopharmacology, 2014, 1578-1593, 39.

Eglen, Richard M., Muscarinic receptor ligands and their therapeutic potential, Current Opinion in Chemical Biology, 1999, 426-432, 3.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric moduclators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VUO476406, a non-human primate in vivo tool compound for translational pharmacology, Bioorganic and Med Chem Letters, 2017, 2296-2301, 27.

Salovich, James M., et al., Discovery of N-(4-methoxy-7-methylbenzo[d]thiazol-2-yl) . . . , Bioorganic and Med Chem Letters, 2012, 5084-5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

PCT Search Report and Written Opinion for PCT/US2016/067905 dated Feb. 22, 2017; 12 pages.

PCT Search Report and Written Opinion for PCT/CN2015/098382 dated Jul. 6, 2016; 14 pages.

\* cited by examiner

6,7-DIHYDRO-5H-PYRROLO[3,4-B]PYRIDIN-5-ONE ALLOSTERIC MODULATORS OF THE M4 MUSCARINIC ACETYLCHOLINE RECEPTOR

CROSS REFERENCE TO RELATED APPLICATIONS

This application claims priority under 35 U.S.C. § 119(b) from International Application No. PCT/CN15/098382, filed Dec. 23, 2015, and claims priority under 35 U.S.C. § 119(e) from U.S. Ser. No. 62/419,630, filed Nov. 9, 2016.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to 6,7-dihydro-5H-pyrrolo[3,4-b]pyridine-5-one compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

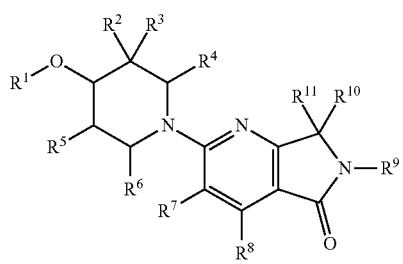

wherein:
R$^1$ is selected from the group consisting of:
 (1) hydrogen;
 (2) —C$_{1-6}$alkyl, which is unsubstituted or substituted with substituents selected from the group consisting of: hydroxy, fluoro, —CN, —O—C$_{1-6}$alkyl, C$_{3-6}$cycloalkyl, bicycle[1.1.1]pentane, tetrahydrofuranyl, phenyl, pyridyl, oxazolyl, —$NH_2$, —$NH(-C_{1-6}alkyl)$, —$N(-C_{1-6}alkyl)_2$, and —$N(C=O)-C_{1-6}alkyl$, wherein the $C_{1-6}$alkyl or $C_{3-6}$cycloalkyl is unsubstituted or substituted with substituents selected from the group consisting of: fluoro, cyano, $CF_3$, $C_{1-6}$alkyl or —O—$C_{1-6}$alkyl; (3) a phenyl, heteroaryl or heterocyclyl ring, wherein the phenyl, heteroaryl or heterocyclyl ring is substituted with one or more $R^{1a}$, $R^{1b}$ and $R^{1c}$, wherein $R^{1a}$, $R^{1b}$ and $R^{1c}$ are independently selected from the group consisting of:
(a) hydrogen,
(b) hydroxy,
(c) halogen,
(d) $C_{1-6}$alkyl, which is unsubstituted or substituted with substituents selected from the group consisting of: hydroxy, cyclopropyl, cyclobutyl, cyclopentyl, azetidinyl, fluoro, —$OCH_3$, —$OCH_2CH_2OCH_3$, —(C=O)—$C_{1-6}$alkyl, —$NH_2$, —$NH(C_{1-6}alkyl)$, —$N(C_{1-6}alkyl)_2$, and —$N(C_{3-6}cycloalkyl)$,
(e) —O—$C_{1-6}$alkyl, which is unsubstituted or substituted with substituents selected from the group consisting of: hydroxy, cyclopropyl, cyclobutyl, cyclopentyl, azetidinyl, fluoro, —$OCH_3$, —$NH_2$, —$NH(C_{1-6}alkyl)$, —$N(C_{1-6}alkyl)_2$, —$N(C_{3-6}cycloalkyl)$, and —$NH(C=O)(C_{1-6}alkyl)$,
(f) $C_{3-6}$cycloalkyl, which is unsubstituted or substituted with substituents selected from the group consisting of: $C_{1-6}$alkyl, hydroxy, cyclopropyl, cyclobutyl, cyclopentyl, azetidinyl, fluoro, —$OCH_3$, —$NH_2$, —$NH(C_{1-6}alkyl)$, —$N(C_{1-6}alkyl)_2$, and —$N(C_{3-6}cycloalkyl)$,
(g) —$NH_2$,
(h) —$NH(C_{1-6}alkyl)$,
(i) —$NH(C_{2-6}alkyl)$-OH,
(j) —$N(C_{1-6}alkyl)_2$,
(k) —$N(C_{3-6}cycloalkyl)$,
(l) —$SO_2$—$C_{1-6}$alkyl,
(m) —(C=O)H,
(n) —(C=O)—$C_{1-6}$alkyl,
(o) —(C=O)O—$C_{1-6}$alkyl, and
(p) —CN;
$R^2$ and $R^3$ are independently selected from the group consisting of:
(1) hydrogen,
(2) fluoro,
(3) hydroxy, and
(4) —$CH_3$;
$R^4$ is hydrogen or methyl, and $R^6$ is hydrogen or methyl, or $R^4$ and $R^6$ are joined together with a —$(CH_2)_2$— to form a bridged ring with the piperidine ring to which they are attached;
$R^5$ is hydrogen, or where $R^2$ is hydrogen, $R^3$ and $R^5$ may be joined together with a —$(CH_2)$— to form a bridged ring with the piperidine ring to which they are attached;
$R^7$ and $R^8$ are independently selected from the group consisting of:
(1) hydrogen,
(2) $C_{1-6}$alkyl, which is unsubstituted or substituted with substituents selected from the group consisting of: hydroxy, fluoro, and —$OCH_3$,
(3) —CH=$CH_2$,
(4) cyclopropyl,
(5) -fluoro,
(6) -chloro,
(7) -bromo,
(8) —CN,
(9) —(C=O)H, and
(10) —(C=O)O—$C_{1-6}$alkyl;

$R^9$ is selected from the group consisting of:
(1) hydrogen,
(2) —$C_{1-6}$alkyl, which is unsubstituted or substituted with substituents selected from the group consisting of: hydroxy, methoxy, fluoro, —C(=O)O—$C_{1-6}$alkyl, —$NH_2$, —$NH(C_{1-6}alkyl)$, —$N(C_{1-6}alkyl)_2$, —C(=O)$NH_2$, —C(=O)OH, oxetanyl, or pyridyl;
(3) —$C_{3-6}$cycloalkyl,
(4) —C(=O)O—$C_{1-6}$alkyl, and
(5) —P(O)(OH)$_2$;
each of $R^{10}$ and $R^{11}$ is independently selected from the group consisting of:
(1) hydrogen,
(2) —OH,
(3) —$CH_3$,
(4) —$CH_2OH$,
(5) —$CH_2CH_2OH$, and
(6) —$C(CH_3)_2OH$,
or $R^{10}$ and $R^{11}$ taken together form a cyclopropyl group, a =$CH_2$ group or a keto group;
or a pharmaceutically acceptable salt thereof.

An embodiment of the present invention includes compounds of the formula Ia:

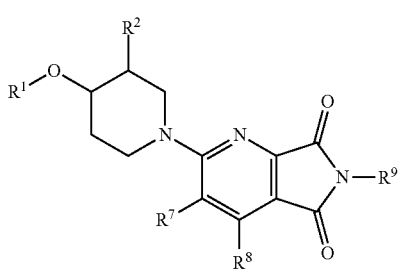

Ia wherein $R^1$, $R^2$, $R^7$, $R^8$ and $R^9$ are defined herein; or a pharmaceutically acceptable salt thereof.

An embodiment of the present invention includes compounds of the formula Ib:

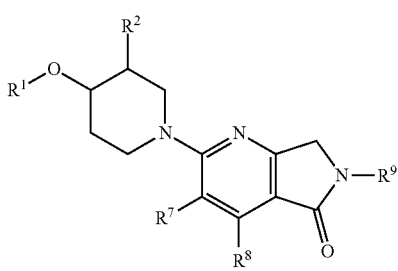

Ib wherein $R^1$, $R^2$, $R^7$, $R^8$ and $R^9$ are defined herein; or a pharmaceutically acceptable salt thereof.

An embodiment of the present invention includes compounds of the formula Ic:

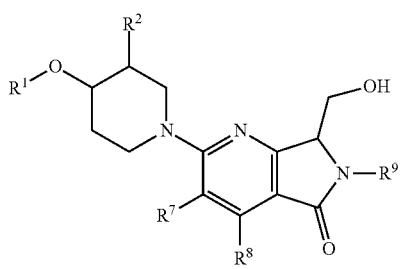

Ic wherein $R^1$, $R^2$, $R^7$, $R^8$ and $R^9$ are defined herein; or a pharmaceutically acceptable salt thereof.

An embodiment of the present invention includes compounds of the formula IIa:

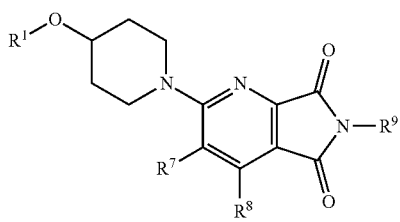

IIa wherein $R^1$, $R^7$, $R^8$ and $R^9$ are defined herein; or a pharmaceutically acceptable salt thereof.

An embodiment of the present invention includes compounds of the formula IIb:

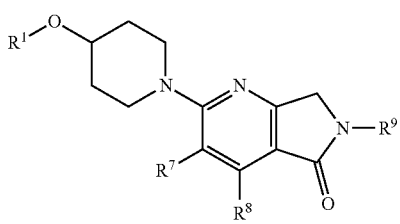

IIb wherein $R^1$, $R^7$, $R^8$ and $R^9$ are defined herein; or a pharmaceutically acceptable salt thereof.

An embodiment of the present invention includes compounds of the formula IIc:

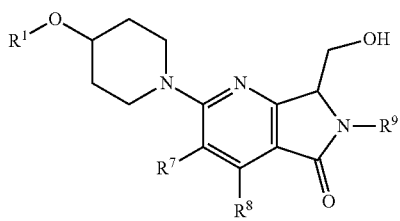

IIc wherein $R^1$, $R^7$, $R^8$ and $R^9$ are defined herein; or a pharmaceutically acceptable salt thereof.

An embodiment of the present invention includes compounds of the formula IIIa:

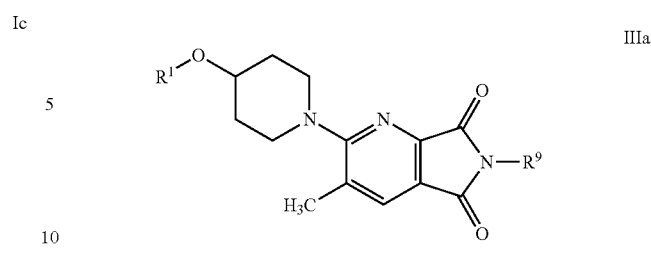

IIIa wherein $R^1$ and $R^9$ are defined herein; or a pharmaceutically acceptable salt thereof.

An embodiment of the present invention includes compounds of the formula IIIb:

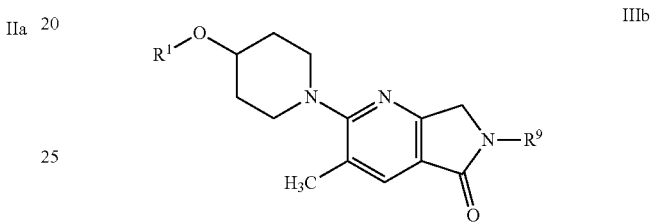

IIIb wherein $R^1$ and $R^9$ are defined herein; or a pharmaceutically acceptable salt thereof.

An embodiment of the present invention includes compounds of the formula IIIc:

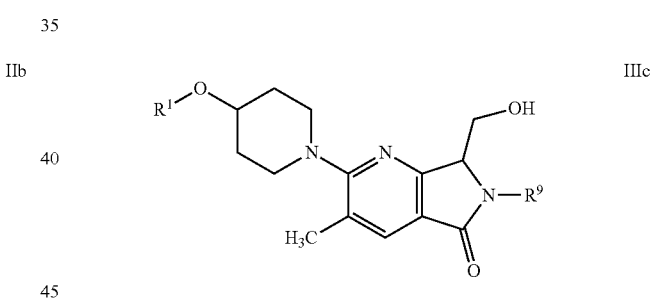

IIIc wherein $R^1$ and $R^9$ are defined herein; or a pharmaceutically acceptable salt thereof.

An embodiment of the present invention includes compounds of the formula IVa:

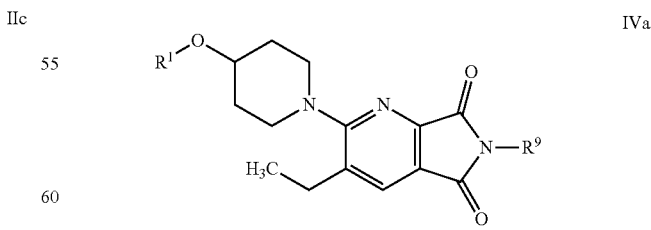

IVa wherein $R^1$ and $R^9$ are defined herein; or a pharmaceutically acceptable salt thereof.

An embodiment of the present invention includes compounds of the formula IVb:

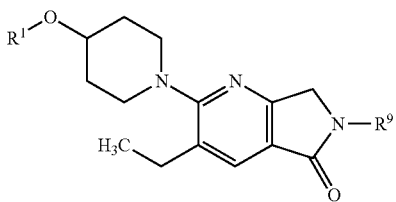

wherein $R^1$ and $R^9$ are defined herein; or a pharmaceutically acceptable salt thereof.

An embodiment of the present invention includes compounds of the formula IVc:

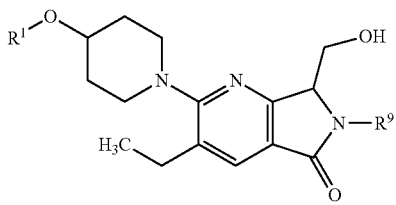

wherein $R^1$ and $R^9$ are defined herein; or a pharmaceutically acceptable salt thereof.

An embodiment of the present invention includes compounds wherein $R^1$ is selected from the group consisting of: benzodioxolyl, benzoimidazolyl, benzoxazolyl, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more of $R^{1a}$, $R^{1b}$ and $R^{1c}$.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-6}$alkyl, which is unsubstituted or substituted with substituents selected from the group consisting of: hydroxy, fluoro, and —$OCH_3$,
(e) —O—$C_{1-6}$alkyl, which is unsubstituted or substituted with substituents selected from the group consisting of: hydroxy, fluoro, and —$OCH_3$,
(f) $C_{3-6}$cycloalkyl, which is unsubstituted or substituted with a substituent selected from the group consisting of: $C_{1-6}$alkyl and hydroxy; and
(g) —CN.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-3}$alkyl, which is unsubstituted or substituted with a substituent selected from the group consisting of: hydroxy, 1-3 fluoro, and —$OCH_3$,
(e) —O—$C_{1-3}$alkyl, which is unsubstituted or substituted with a substituent selected from the group consisting of: 1-3 fluoro, and —$OCH_3$, and
(g) —CN.

An embodiment of the present invention includes compounds wherein $R^1$ is selected from the group consisting of:
(a) hydrogen,
(b) $C_{1-6}$alkyl, which is unsubstituted or substituted with cyclopropyl which is unsubstituted or substituted with substituents selected from the group consisting of: fluoro and $C_{1-6}$alkyl,
(c) dihydrofuropyridinyl,
(d) indazole, which is unsubstituted or substituted with $C_{1-3}$alkyl,
(e) tetrahydroisobenzofuranyl, which is unsubstituted or substituted with $C_{1-3}$alkyl,
(f) phenyl, which is unsubstituted or substituted with $C_{1-3}$alkyl or —CN, and
(g) pyridyl, which is unsubstituted or substituted with $C_{1-3}$alkyl or —O—$C_{1-3}$alkyl.

An embodiment of the present invention includes compounds wherein $R^1$ is selected from the group consisting of:
(a) $C_{1-6}$alkyl, which is unsubstituted or substituted with cyclopropyl, methyl-cyclopropyl, dimethyl-cyclopropyl, methyl-fluoro-cyclopropyl, methyl-difluoro-cyclopropyl, or dimethyl-difluoro-cyclopropyl,
(b) indazole, which is unsubstituted or substituted with $C_{1-3}$alkyl,
(c) tetrahydroisobenzofuranyl, which is unsubstituted or substituted with $C_{1-3}$alkyl,
(d) phenyl, which is unsubstituted or substituted with $C_{1-3}$alkyl or —CN, and
(e) pyridyl, which is unsubstituted or substituted with $C_{1-3}$alkyl or —O—$C_{1-3}$alkyl.

An embodiment of the present invention includes compounds wherein $R^1$ is phenyl, which is unsubstituted or substituted with —CN. An embodiment of the present invention includes compounds wherein $R^1$ is pyridyl, which is unsubstituted or substituted with —$OCH_3$. An embodiment of the present invention includes compounds wherein $R^1$ is dihydrofuropyridinyl. An embodiment of the present invention includes compounds wherein $R^1$ is indazole, which is unsubstituted or substituted with methyl. An embodiment of the present invention includes compounds wherein $R^1$ is tetrahydroisobenzofuranyl. An embodiment of the present invention includes compounds wherein $R^1$ is dihydroisobenzofuranyl. An embodiment of the present invention includes compounds wherein $R^1$ is $CH_2$-(methyl)cyclopropyl. An embodiment of the present invention includes compounds wherein $R^1$ is $CH_2$-(dimethyl)-cyclopropyl. An embodiment of the present invention includes compounds wherein $R^1$ is $CH_2$-(methyl-fluoro)cyclopropyl. An embodiment of the present invention includes compounds wherein $R^1$ is $CH_2$-(methyl-difluoro)cyclopropyl. An embodiment of the present invention includes compounds wherein $R^1$ is $CH_2$-(dimethyl-difluoro)cyclopropyl.

An embodiment of the present invention includes compounds wherein $R^2$ and $R^3$ are each hydrogen. An embodiment of the present invention includes compounds wherein $R^2$ is fluoro and $R^3$ is hydrogen. An embodiment of the present invention includes compounds wherein $R^2$ is —$CH_3$ and $R^3$ is hydrogen. An embodiment of the present invention includes compounds wherein $R^2$ is fluoro and $R^3$ is fluoro.

An embodiment of the present invention includes compounds wherein $R^4$ is hydrogen and $R^6$ is hydrogen. An embodiment of the present invention includes compounds wherein $R^4$ and $R^6$ are joined together with a —$(CH_2)_2$— to form a bridged ring with the piperidine ring to which they are attached.

An embodiment of the present invention includes compounds wherein $R^5$ is hydrogen. An embodiment of the present invention includes compounds wherein $R^2$ is hydrogen, and $R^3$ and $R^5$ are joined together with a —$(CH_2)$— to form a bridged ring with the piperidine ring to which they are attached. An embodiment of the present invention includes compounds wherein $R^2$, $R^3$, $R^4$, $R^5$ and $R^6$ are each hydrogen.

An embodiment of the present invention includes compounds wherein $R^7$ is selected from the group consisting of:
(1) hydrogen,
(2) methyl,
(3) ethyl,
(4) —$CH_2OH$,
(5) —$CH_2F$,
(6) —$CHF_2$,
(7) —$CF_3$,
(8) —$CH=CH_2$,
(9) cyclopropyl,
(10) -fluoro,
(11) -chloro,
(12) -bromo,
(13) —CN,
(14) —(C=O)H, and
(15) —(C=O)O—$C_{1-6}$alkyl.

An embodiment of the present invention includes compounds wherein $R^7$ is —$CH_3$. An embodiment of the present invention includes compounds wherein $R^7$ is —$CF_3$.

An embodiment of the present invention includes compounds wherein $R^8$ is selected from the group consisting of:
(1) hydrogen,
(2) methyl,
(3) ethyl,
(4) —$CH_2OH$,
(5) —$CH_2F$,
(6) —$CHF_2$,
(7) —$CF_3$, and
(8) —(C=O)O—$C_{1-6}$alkyl.

An embodiment of the present invention includes compounds wherein $R^8$ is hydrogen. An embodiment of the present invention includes compounds wherein $R^8$ is —$CH_3$.

An embodiment of the present invention includes compounds wherein $R^9$ is selected from the group consisting of:
(1) hydrogen, and
(2) —$C_{1-6}$alkyl, which is unsubstituted or substituted with hydroxy, methoxy, 1-3 fluoro.

An embodiment of the present invention includes compounds wherein $R^9$ is hydrogen. An embodiment of the present invention includes compounds wherein $R^9$ is methyl. An embodiment of the present invention includes compounds wherein $R^9$ is —$CH_2CH_2OH$.

An embodiment of the present invention includes compounds wherein $R^{10}$ is hydrogen and $R^{11}$ is hydrogen. An embodiment of the present invention includes compounds wherein $R^{10}$ is —$CH_3$ and $R^{11}$ is hydrogen. An embodiment of the present invention includes compounds wherein $R^{10}$ is —$CH_3$ and $R^{11}$ is —$CH_3$. An embodiment of the present invention includes compounds wherein $R^{10}$ is —$CH_2OH$ and $R^{11}$ is hydrogen. An embodiment of the present invention includes compounds wherein $R^{10}$ and $R^{11}$ taken together form a cyclopropyl group. An embodiment of the present invention includes compounds wherein $R^{10}$ and $R^{11}$ taken together form a =$CH_2$ group. An embodiment of the present invention includes compounds wherein $R^{10}$ and $R^{11}$ taken together form a keto group.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least one of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Likewise, —N($C_{3-6}$cycloalkyl) refers to the presence of a nitrogen-containing saturated such a pyrrolidine or piperidine. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The term "heteroaryl" as used herein represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocyclyl below, "heteroaryl" is also understood to include the N-oxide derivative of any nitrogen-containing heteroaryl. In cases where the heteroaryl substituent is bicyclic and one ring is non-aromatic, in one embodiment, the attachment is via a carbon atom of the aromatic ring. Examples of heteroaryl include but are not limited to benzodioxolyl, benzofuranyl, benzofurazanyl, benzoimidazolyl, benzimidazolonyl, benzopyrazolyl, benzothiazolyl, benzotriazolyl, benzothiophenyl, benzoxazepinyl, benzooxazinonyl, benzooxazolonyl, benzoxazolyl, carbazolyl, carbolinyl, chromanyl, cinnolinyl, cyclopentapyridinyl, dihydrobenzo[1,4]dioxinyl, dihydrobenzofuranyl, dihydrobenzo[1,4]oxazinyl, dihydrofuropyridinyl, dihydroindolyl, dihydroisobenzofuranyl, dihydroisoquinolinonyl, dihydropyranopyridinyl, dihydroimidazopyridinyl, dihydropyrido[1,4]oxazinyl, dihydroquinolinone, furanyl, imidazolyl, indolinyl, indolyl, indanyl, indolazinyl, indazolyl, isobenzofuranyl, isobenzofuranonyl, isochromanonyl, isochromanyl, isoindolinyl, isoindolyl, isoxazolinyl, isoxazolyl, isoquinolyl, isothiazolyl, isoxazolyl, naphthpyridinyl, oxadiazolyl, oxazolyl, oxazolinyl, oxetanyl, oxoisoindolinyl, pyrazinyl, pyrazolopyridinyl, pyrazolyl, pyridazinyl, pyridopyridinyl, pyridazinyl, pyridyl, pyrimidinyl, pyrimidyl, pyrrolopyridinyl, pyrrolyl, quinazolinyl, quinolyl, quinoxalinyl, tetrahydrobenzooxepinyl, tetrahydroisoquinolinyl, tetrahydropyranyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. In one embodiment, the heterocyclyls contain about 5 to about 6 ring atoms. The heterocyclyl may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydropyran, tetrahydrothiophenyl, lactam, lactone, and the like. "Heterocyclyl" also includes heterocyclyl rings as described above wherein =O replaces two available hydrogens on the same ring carbon atom.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes that can be incorporated into the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature.

The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated.

The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 15000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, *cannabis*, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), (±)-2,3-dihydro-5,6-dimethoxy-2-[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3β inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SP1860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; aq: aqueous; BINAP: 2,2'-bis(diphenylphosphino)-1,1'-binaphthyl; Bn: benzyl; Ac: acetyl; Boc: tert-butyloxy carbonyl; BSA: bovine serum albumin; CAN: acetonitrile; Cbz: carboxylbenzyl; CbzCl: benzylchloroformate; CDI: carbonyl diimidazole; DAST: diethylaminosulfur trifluoride; DCM: dichloromethane; DCE: dichloroethane; DEA: diethylamine; DEAD: diethyl-azodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMS: dimethylsulfide; DMSO: dimethylsulfoxide; dppf: 1,1'-bis(diphenyl-phosphino)ferrocene; CH2Cl2: dichloromethane; EDC: N-(3-Dimethylaminopropyl)-N'-ethylcarbodiimide; Et3N: triethylamine; EtOAc: ethyl acetate; EtOH: ethanol; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; LHMDS: lithium bis(trimethylsilyl)amide; mCPBA: meta-chloroperbenzoic acid; MeOH: methanol; MgSO4: magnesium sulfate; Ms: methanesulfonyl; MTBE: methyl tert-butyl ether; MS: Mass spectra; NaHCO3: sodium bicarbonate; NaOH: sodium hydroxide; NBS: N-bromosuccinimide; NCS: N-chlorosuccinimide; NMM: N-methylmorpholine; NMR: nuclear magnetic resonance; PtO2: platinum oxide; PyClu: 1-(chloro-1-pyrrolidinylmethylene)-pyrrolidinium hexafluorophosphate; rt: room temperature; SEM: 2-(Trimethylsilyl)ethoxy]methyl; SFC: supercritical fluid chromatography; SOCl2: thionyl chloride; T3P: 2,4,6-tripropyl-1,3,5,2,4,6-trioxatriphosphorinane-2,4,6-trioxide; TBAF: tetra-n-butylammonium fluoride; TBS: tert-Butyldimethylsilyl; TEA: triethylamine; TES: Triethylsilyl; TFA: trifluoroacetic acid; Tf: triflate; TFAA: trifluoroacetic anhydride; THF: tetrahydrofuran; TIPS: tri-isopropylsilyl; TLC: thin layer chromatography; Ts: toluenesulfonyl; X-Phos: 2-(dicyclohexyl-phosphino)-2',4',6'-triisopropyl-biphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

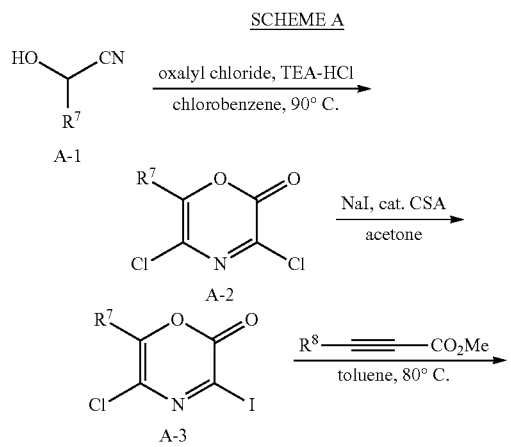

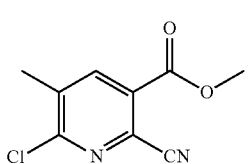

Intermediate A is prepared according to Scheme A via condensation of commercially available hydroxynitrile A-1 with oxalyl chloride to yield adduct A-2. A Finkelstein reaction of chloride A-2 with sodium iodide, catalyzed by camphorsulfonic acid (CSA), results in iodide product A-3. A hetero-Diels-Alder reaction of diene A-3 with a commercially available ynone gives pyridine A-4. A subsequent copper-meditated cyanation provides intermediate A.

Intermediate A1

Methyl 6-chloro-2-cyano-5-methylnicotinate
(Scheme A)

Step 1: 3,5-Dichloro-6-methyl-2H-1,4-oxazin-2-one

Into a 10-L 4-necked round-bottom flask was charged oxalic dichloride (3.32 kg, 26.2 mol) and chlorobenzene (3.5 L) under an inert atmosphere of nitrogen. A solution of 2-hydroxypropanenitrile (464.8 g, 6.54 mol) in chlorobenzene (500 mL) was added dropwise to the flask at 0° C. The system was heated to 90° C. and triethylamine hydrochloride (66.2 g, 481 mmol) was added in portions at 90° C. The resulting solution was stirred for 3 h before concentrating the mixture under reduced pressure. The resulting solution was diluted with ether (5 L) and the solids were filtered out. The filtrate concentrated and was then applied purified by silica gel column chromatography (0:1-1:4 ethyl acetate:petroleum ether) to yield the title compound.

Step 2:
5-Chloro-3-iodo-6-methyl-2H-1,4-oxazin-2-one

Into a 10-L 4-necked round-bottom flask was added 3,5-dichloro-6-methyl-2H-1,4-oxazin-2-one (470.8 g, 2.62 mol), acetone (10 L), NaI (1568 g, 10.5 mol) and camphorsulfonic acid (40 g, 172.2 mmol) under an atmosphere of nitrogen. The resulting solution was stirred for 3 h at 25° C. The mixture was concentrated and then diluted with water (20 L) and dichloromethane (3×5 L). The organic layers were combined and washed with brine (5 L). The mixture was dried over anhydrous sodium sulfate, filtered and was concentrated under reduced pressure to yield the title compound.

Step 3: Methyl 6-chloro-2-iodo-5-methylnicotinate

Into a 5-L 3-necked round-bottom flask was placed 5-chloro-3-iodo-6-methyl-2H-1,4-oxazin-2-one (638 g, 2.35 mol), toluene (2.3 L), and methyl prop-2-ynoate (592.8 g, 7.05 mol) under an atmosphere of nitrogen. The resulting solution was stirred for 2 days at 80° C. The reaction was cooled and the volatiles were removed under reduced pressure. The residue was purified by silica gel column chromatography (0:1-1:50 ethyl acetate:petroleum ether) to provide the major regioisomeric product as the title compound.

Step 4: Methyl 6-chloro-2-cyano-5-methylnicotinate

Into a 20-mL microwave tube was added methyl 6-chloro-2-iodo-5-methylpyridine-3-carboxylate (2 g, 6.42 mmol), DMF (15 mL), and CuCN (850 mg, 9.60 mmol). The resulting solution was stirred for 5 min at 100° C. by microwave irradiation. The mixture was diluted with water (20 mL) and a saturated, aqueous solution of $NH_4Cl$ (100 mL). Dichloromethane (2×20 mL) was used to extract the crude material and the organic layers were combined and dried over anhydrous sodium sulfate. The residue was purified by silica gel chromatography (0:1-1:8 ethyl acetate:petroleum ether) to provide the title compound. MS: 211 (M+1). $^1H$ NMR (500 MHz, $CDCl_3$): δ 7.87 (s, 1H), 3.95 (s, 4H), 2.37 (s, 3H).

The following intermediates in table A were prepared according to scheme A using the procedure outlined in the synthesis of intermediate A1 using commercially available hydroxynitriles in step 1 and using commercially available ynones for step 3.

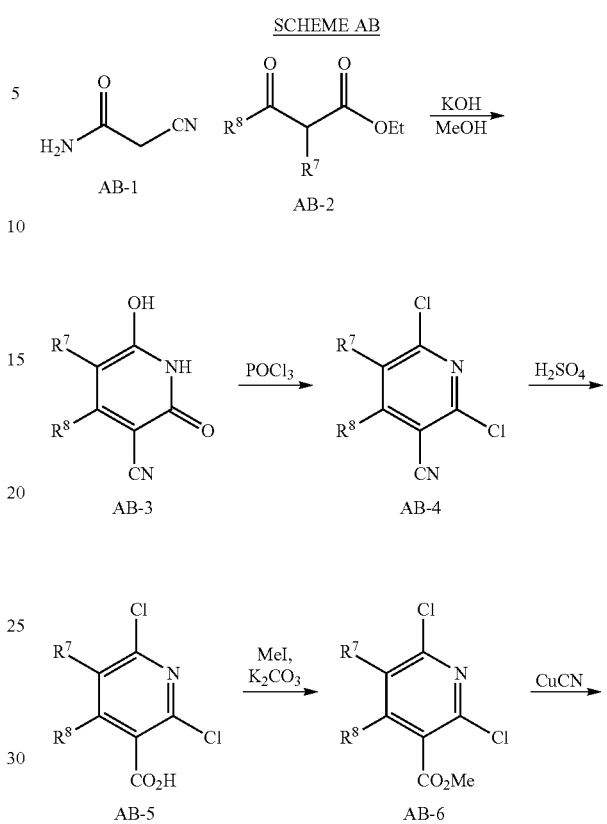

SCHEME AB

TABLE A

| Intermediate | Structure | Name | MS (M + 1) |
|---|---|---|---|
| A2 | 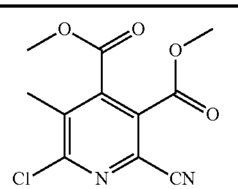 | dimethyl 6-chloro-2-cyano-5-methylpyridine-3,4-dicarboxylate | 269 |
| A3 | 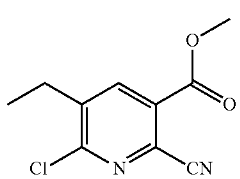 | methyl 6-chloro-2-cyano-5-ethylnicotinate | 225 |
| A4 | 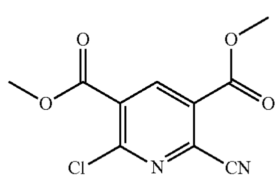 | dimethyl 2-chloro-6-cyanopyridine-3,5-dicarboxylate | 356 |
| A5 | 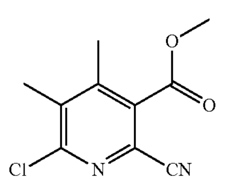 | methyl 6-chloro-2-cyano-4,5-dimethylnicotinate | 225 |

-continued

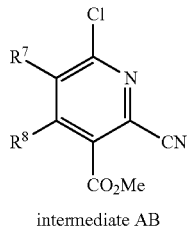

intermediate AB

An alternative method to the described procedure outlined in the synthesis of intermediate A is shown in Scheme AB. Intermediate AB is synthesized beginning from a condensation of 2-cyanoacetamide and β-keto ester AB-2 to form pyridone AB-3. Reaction with phosphoryl chloride provides pyridine AB-4, which is then transformed in 2-steps to ester AB-6 via intermediate acid AB-5. Cyanation via reaction with copper(I) cyanide provides intermediate AB.

Intermediate AB

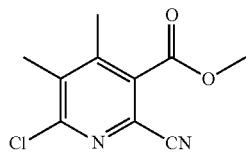

Methyl 6-chloro-2-cyano-4,5-dimethylnicotinate (Scheme AB)

Step 1: 6-Hydroxy-4,5-dimethyl-2-oxo-1,2-dihydropyridine-3-carbonitrile

To a solution of 2-cyanoacetamide (100 g, 1.2 mol) was dissolved in MeOH (1.5 L), was added ethyl 2-methyl-3-oxobutanoate (171 g, 1.2 mol) and potassium hydroxide (100 g, 1.8 mol). The resulting solution was stirred for 4 h at 65° C. before being cooled to 10° C. The solids were collected by filtration and were dissolved in 2 L of hot water (70° C.). The mixture was filtered and the filtrate was adjusted to pH-1 with aqueous hydrogen chloride (6 N). The solids were collected by filtration to yield the title compound.

Step 2: 2,6-Dichloro-4,5-dimethylpyridine-3-carbonitrile

To phosphoryl trichloride (126 mL) was added 2,6-dihydroxy-4,5-dimethylpyridine-3-carbonitrile (70 g, 426.41 mmol) in several batches. The system was sealed and the resulting solution was stirred for 6 h at 180° C. The reaction was cooled to RT and the mixture was poured into ice water (500 mL). The solids were collected by filtration to afford the title compound.

Step 3: 2,6-Dichloro-4,5-dimethylpyridine-3-carboxylic acid 2,6-Dichloro-4,5-dimethylpyridine-3-carbonitrile (100 g, 497.4 mmol) was dissolved in sulfuric acid (250 mL). Nitric acid (75 mL) was added dropwise at 110-150° C. over the course of 1 h and the resulting solution was stirred 110° C. for 1 h. The reaction was then poured into ice water (1 L) and the solids were collected by filtration. The material was then dissolved in EtOAc (200 mL), dried over anhydrous sodium sulfate and concentrated under reduced pressure to afford the title compound.

Step 4: Methyl 2,6-dichloro-4,5-dimethylpyridine-3-carboxylate

To a solution of 2,6-dichloro-4,5-dimethylpyridine-3-carboxylic acid (100 g, 454.4 mmol) in DMF (1.5 L) was added potassium carbonate (95 g, 682.4 mmol), iodomethane (129 g, 908.8 mmol). The resulting mixture was stirred for 1 h at RT before the reaction was quenched by the addition of ice water (1.5 L). The crude reaction was extracted with EtOAc (1 L×3), dried over anhydrous sodium sulfate and concentrated under reduced pressure. The residue was purified by silica gel chromatography (1/10 EtOAc/petroleum ether) to afford the title compound.

Step 5: Methyl 6-chloro-2-cyano-4,5-dimethylpyridine-3-carboxylate

A solution of methyl 2,6-dichloro-4,5-dimethylpyridine-3-carboxylate (1 g, 4.27 mmol) in NMP (5 mL) and copper (I) cyanide (570 mg, 6.36 mmol) was stirred for 2 h at 180° C. under an nitrogen atmosphere. After cooling to RT, the reaction mixture was poured into ice water and was extracted with EtOAc. The solids were filtered out and the filtrate was further extracted with EtOAc (3×) and the combined organic phases were dried over anhydrous sodium sulfate and concentrated. The crude material was purified by reverse phase HPLC (30-60% MeCN/water with 1% NH$_4$HCO$_3$ modifier) and then again by SFC (EnantioPak-A1 column, 20%/80% MeOH/CO$_2$) to afford the title compound. $^1$H NMR (400 MHz, CD$_3$OD): δ 4.01 (s, 3H), 2.51 (s, 3H), 2.48 (s, 3H).

SCHEME B

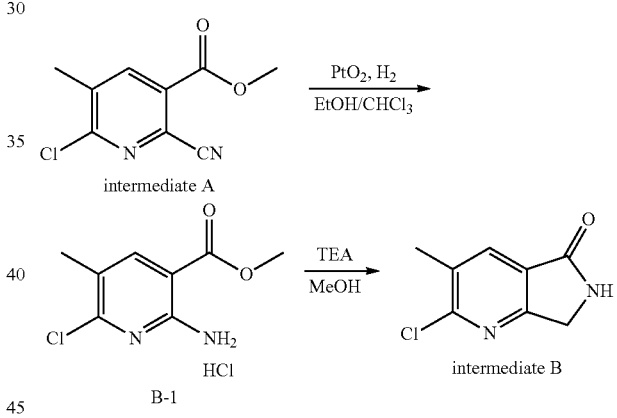

Intermediate B is prepared according to Scheme B in a two-step process from intermediate A via a platinum-mediated nitrile reduction and subsequent base-mediated cyclization of amine B-1.

Intermediate B1

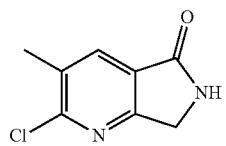

2-Chloro-3-methyl-6,7-dihydro-5H-pyrrolo[3,4-b]pyridin-5-one (Scheme B)

Step 1: Methyl 2-(aminomethyl)-6-chloro-5-methylnicotinate hydrochloride

Into a 5-L 2-necked round-bottom flask was placed methyl 6-chloro-2-cyano-5-methylpyridine-3-carboxylate (intermediate A1, 82 g, 389.3 mmol), 3:1 ethanol:chloroform (2.5 L) and PtO$_2$ (15 g). The resulting solution was stirred for 36 h at RT under an atmosphere of hydrogen. The solids were removed by filtration and the filtrate was concentrated under reduced pressure to yield the title compound.

Step 2: 2-Chloro-3-methyl-6,7-dihydro-5H-pyrrolo[3,4-b]pyridin-5-one

Into a 10-L 4-necked round-bottom flask purged and maintained with an inert atmosphere of nitrogen, was placed methyl 2-(aminomethyl)-6-chloro-5-methylpyridine-3-carboxylate hydrochloride (110 g, 438.06 mmol), methanol (6 L), TEA (221.6 g, 2.19 mol). The resulting solution was stirred for 12 h at RT. The solids were removed by filtration and the filtrate was concentrated under reduced pressure to yield the crude product. Addition of hot DCM eventually resulted in the formation of a precipitate which was isolated by filtration to yield the title compound. MS: 183 (M+1). $^1$H NMR (500 MHz, CDCl$_3$): δ 2.45 (s, 3H), 4.39 (s, 2H), 8.11 (s, 1H), 8.82 (s, 1H).

The following intermediates in table B were prepared according to scheme B using the procedure outlined in the synthesis of intermediate B1.

TABLE B

| Intermediate | Structure | Name | MS (M + 1) |
|---|---|---|---|
| B2 | ![structure] | 2-chloro-3-ethyl-6,7-dihydro-5H-pyrrolo[3,4-b]pyridin-5-one | 197 |

SCHEME C

![Scheme C structures showing C-1 → C-2 → C-3 → intermediate C1 and C2]

Intermediate C is prepared from protected piperidone C-1 which was converted to the enol silane C-2 under the action of TBSOTf in the presence of base. Electrophilic fluorination by SelectfluorR on C-2 provided the corresponding alpha-fluorinated product C-3. Reduction by sodium borohydride and subsequent chiral SFC separation provided intermediate C1 and intermediate C2 as single enantiomers.

Intermediate C1 and C2

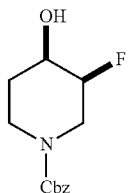

intermediate C1

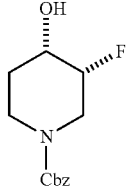

intermediate C2

Benzyl (3S,4R)-3-fluoro-4-hydroxypiperidine-1-carboxylate and benzyl (3R,4S)-3-fluoro-4-hydroxypiperidine-1-carboxylate (Scheme C)

Step 1: Benzyl 4-((tert-butyldimethylsilyl)oxy)-3,6-dihydropyridine-1(2H)-carboxylate To a solution of benzyl 4-oxopiperidine-1-carboxylate (260 g, 1.11 mmol) in DMF (700 mL) and was added DIPEA (216 g, 1.67 mol) and TBSOTf (83 g, 1.45 mol) at RT under an atmosphere of nitrogen. The reaction mixture was stirred for 16 h. After diluting with water (1.5 L) and extracting with EtOAc (1.5 L×3), the organic layers were combined and washed with brine (2 L×3) and concentrated. The residue was purified by silica gel column chromatography (50:1-20:1 petroleum ether:ethyl acetate) to obtain the title compound.

Step 2: Benzyl 3-fluoro-4-oxopiperidine-1-carboxylate

To a solution of benzyl 4-((tert-butyldimethylsilyl)oxy)-3,6-dihydropyridine-1(2H)-carboxylate (200 g, 0.58 mol) in MeCN (1.6 L) was added Selectfluor® (224 g, 0.63 mol) at 25° C. The reaction mixture was stirred for 10 h. The volatiles were removed under reduced pressure and the residue was diluted with EtOAc (2 L) and then washed with brine (1.5 L×3). The organic was concentrated in vacuo to give the title compound which was carried forward without further purification.

Step 3: Benzyl (3S,4R)-3-fluoro-4-hydroxypiperidine-1-carboxylate and benzyl (3R,4S)-3-fluoro-4-hydroxypiperidine-1-carboxylate To a solution of benzyl 3-fluoro-4-oxopiperidine-1-carboxylate (300 g, 1.19 mol) in MeOH (2.5 L) was added NaBH$_4$ (50 g, 1.31 mol) at 0° C. After stirring for 4 h at RT, the volatiles were removed under reduced pressure and the residue was diluted with EtOAc (2 L) and washed with water (2 L) and then brine (2 L×2). The organic was concentrated in vacuo and was purified on silica gel by column chromatography (10:1-2:1 petroleum ether:ethyl acetate) to obtain the racemic product. The material was then purified by chiral SFC (AD column, 30%/70% EtOH with 0.1% ammonium hydroxide modifier/CO$_2$) to afford intermediate C1 (faster eluting 3S,4R isomer): MS: 254 (M+1). $^1$H NMR (400 MHz, CDCl$_3$): δ 7.41-7.29 (m, 1H), 5.15 (s, 1H), 4.74-4.52 (m, 1H), 4.11-3.76 (m, 3H), 3.62-3.17 (m, 2H), 2.07 (br s, 1H), 1.93-1.70 (m, 2H). Intermediate C2 (slower eluting 3R,4S isomer): MS: 254 (M+1). $^1$H NMR (400 MHz, CDCl$_3$): δ 7.40-7.30 (m, 5H), 5.15 (s, 2H), 4.75-4.51 (m, 1H), 4.09-3.69 (m, 3H), 3.62-3.18 (m, 2H), 2.08 (br s, 1H), 1.93-1.71 (m, 2H).

SCHEME D

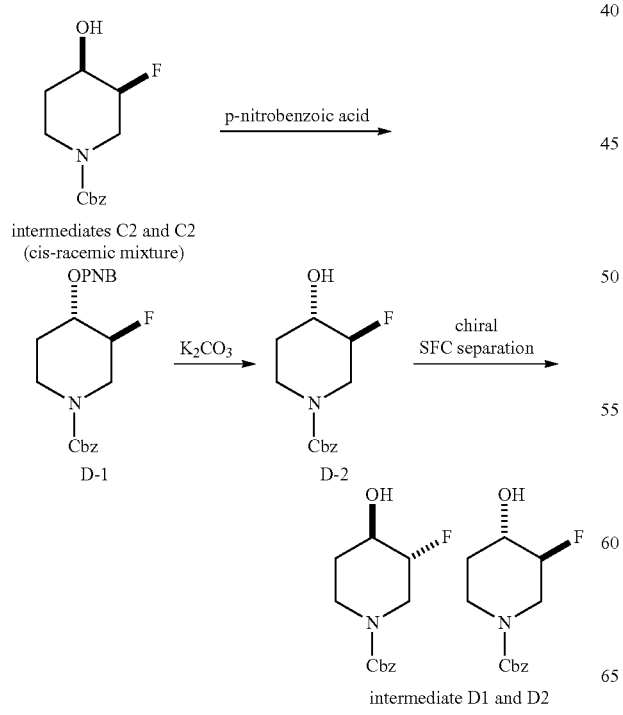

Intermediate D is prepared from a racemic mixture of intermediate C1 and intermediate C2 which is carried through a Mitsunobu reaction with p-nitrobenzoic acid to provide trans-racemic adduct D-1. Subsequent saponification reveals alcohol D-2. Chiral separation to resolve the enantiomers is carried out to provide intermediate D1 and intermediate D2 as single enantiomers.

Intermediate D1 and D2

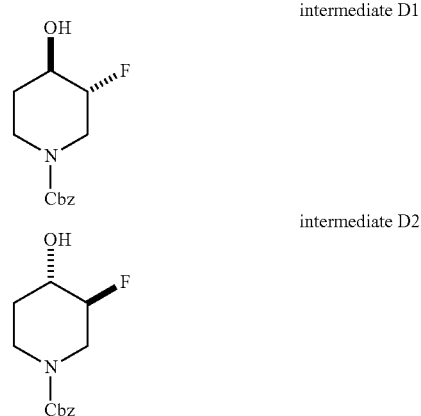

Benzyl (3R,4R)-3-fluoro-4-hydroxypiperidine-1-carboxylate and benzyl (3S,4S)-3-fluoro-4-hydroxypiperidine-1-carboxylate (Scheme D)

Step 1: Benzyl trans-3-fluoro-4-((4-nitrobenzol)oxy)piperidine-1-carboxylate To a stirred solution of benzyl cis-3-fluoro-4-hydroxypiperidine-1-carboxylate (60 g, 0.24 mol, intermediate C1 and C2) in THF (400 mL) was added p-nitrobenzoic acid (60 g, 0.36 mol) and Ph$_3$P (92 g, 0.35 mol) at RT. After cooling the mixture to ~0-5° C., DIAD (78 g, 0.39 mol) was added dropwise. The reaction was stirred 15 h at RT and was quenched with an aqueous, saturated NH$_4$Cl solution (600 mL) and was then extracted with EtOAc (500 mL×3). The combined organic layers were washed with brine (1 L), dried over anhydrous sodium sulfate and concentrated under reduced pressure. The residue was purified on silica gel by column chromatography (10:1 petroleum ether:ethyl acetate) to yield the title compound.

Step 2: Benzyl trans-3-fluoro-4-hydroxypiperidine-1-carboxylate

To a solution of benzyl cis-3-fluoro-4-((4-nitrobenzoyl)oxy)piperidine-1-carboxylate (90 g, 0.22 mol) in MeOH (900 mL) was added potassium carbonate (90 g, 0.65 mol). The resulting mixture was stirred at RT for 15 h and then the volatiles were removed under reduced pressure. The residue was partitioned between EtOAc (200 mL) and saturated NH$_4$Cl(aq) (200 mL). The aqueous layer was extracted with EtOAc (200 mL×2) and the combined organic layers were washed with brine (500 mL), dried over anhydrous sodium sulfate, filtered and concentrated. The residue was purified by silica gel column chromatography (1:1 petroleum ether: ethyl acetate) to afford the title compound.

Step 3: Benzyl (3R,4R)-3-fluoro-4-hydroxypiperidine-1-carboxylate and benzyl (3S,4S)-3-fluoro-4-hydroxypiperidine-1-carboxylate Benzyl trans-3-fluoro-4-hydroxypiperidine-1-carboxylate was resolved into single enantiomers via chiral SFC (AD column, 5-40% EtOH with 0.05% diethylamine modifier/$CO_2$) to afford intermediate D1 (faster eluting 3R,4R isomer): MS: 254 (M+1). $^1$H NMR (400 MHz, $CDCl_3$): δ 7.31-7.56 (m, 5H), 5.19 (s, 2H), 4.17-4.37 (m, 2H), 3.84-3.95 (m, 2H), 3.06-3.28 (m, 2H), 2.28 (s, 1H), 2.01 (s, 1H), 1.57 (s, 1H). Intermediate D2 (slower eluting 3S,4S isomer): MS: 254 (M+1). $^1$H NMR (400 MHz, $CDCl_3$): δ 7.31-7.56 (m, 5H), 5.19 (s, 2H), 4.17-4.37 (m, 2H), 3.84-3.95 (m, 2H), 3.06-3.28 (m, 2H), 2.28 (s, 1H), 2.01 (s, 1H), 1.57 (s, 1H).

SCHEME E

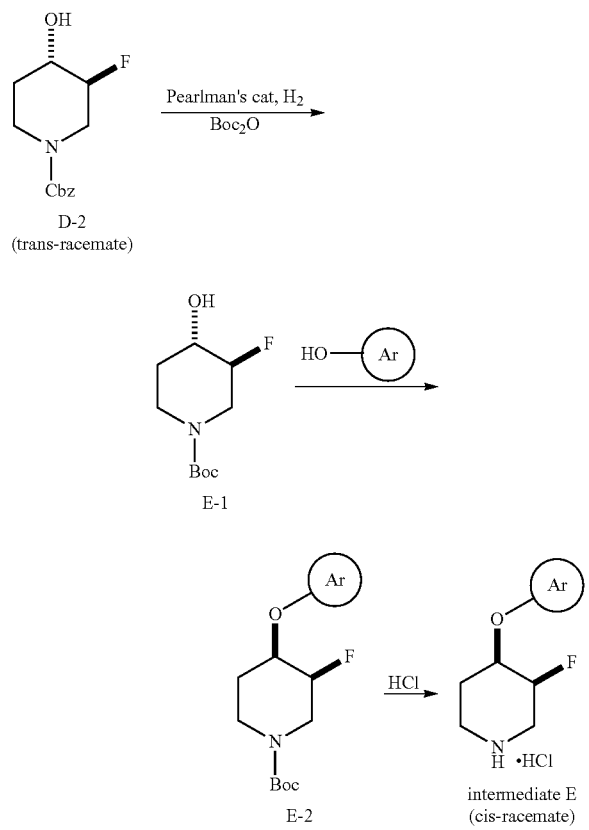

Intermediate E is prepared from a trans-racemate D-2. The piperidine N-protecting group was switched under reductive conditions in the presence of $Boc_2O$ to provide alcohol E-1. Mitsunobu reaction with a commercially available or known phenol (wherein Ar is an aromatic or heteroaromatic ring of $R^1$) provides the cis-racemic alcohol E-2. Deprotection of the piperidine was completed under acidic conditions to yield intermediate E. Chiral separation to resolve the enantiomers may be carried out on either the pentultimate compound E-2 or intermediate E to yield single enantiomer products.

Intermediate E1

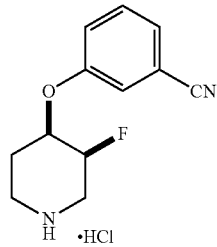 [SMILES: N#Cc1cccc(O[C@@H]2CCNC[C@@H]2F)c1 ; Cl]

3-(cis-3-Fluoropiperidin-4-yl)oxy)benzonitrile hydrochloride (Scheme E)

Step 1: tert-Butyl trans-3-fluoro-4-hydroxypiperidine-1-carboxylate

A mixture of benzyl cis-3-fluoro-4-hydroxypiperidine-1-carboxylate (40 g, 0.16 mol), $Boc_2O$ (45 g, 0.206 mol) and methanol (600 mL) was stirred in the presence of Pd(OH)$_2$/C under hydrogen (35 psi) at RT. Upon completion, the mixture was filtered and the filtrate was concentrated in vacuo. The resultant residue was purified by silica gel column chromatography (6:1 petroleum ether:ethyl acetate) to afford the title compound.

Step 2: tert-Butyl cis-4-(3-cyanophenoxy)-3-fluoropiperidine-1-carboxylate

To a flask with tert-butyl cis-3-fluoro-4-hydroxypiperidine-1-carboxylate (25 g, 98.8 mmol) in THF (500 mL) was added $PPh_3$ (77.5 g, 295.8 mmol) and 3-hydroxybenzonitrile (15 g, 120 mmol) at RT. DIAD (50 mL, 257.8 mmol) was added dropwise to the solution at 30-40° C. and the mixture was refluxed until the reaction was complete. The reaction was poured into 1 M aqueous NaOH and extracted with ethyl acetate (2×) and the organic layer was dried over anhydrous sodium sulfate and concentrated. The title compound was carried forward without further purification.

Step 3: 3-(cis-3-Fluoropiperidin-4-yl)oxy)benzonitrile hydrochloride

To a flask with crude tert-butyl cis-4-(3-cyanophenoxy)-3-fluoropiperidine-1-carboxylate in MeOH (100 mL) was added HCl (2 M in ether). The mixture was stirred at 30° C. for 2 h and the title compound was isolated by filtration. $^1$H NMR (400 MHz, $D_2O$): δ 7.25-7.65 (m, 5H), 5.35-5.25 (m, 1H), 4.7-4.8 (m, 1H), 3.8-3.7 (m, 1H), 3.5-3.1 (m, 3H), 2.25-2.1 (m, 2H).

Intermediate E2 and E3

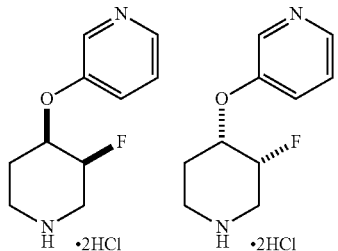 [SMILES: F[C@H]1CNCC[C@H]1Oc1cccnc1 ; F[C@@H]1CNCC[C@@H]1Oc1cccnc1 ; "·2HCl" ; "·2HCl"]

3-(((3R,4S)-3-Fluoropiperidin-4-yl)oxy)pyridine dihydrochloride and 3-(((3S,4R)-3-fluoropiperidin-4-yl)oxy)pyridine dihydrochloride (Scheme E)

Step 1: tert-Butyl-(3R,4S)-3-fluoro-4-(pyridin-3-yloxy)piperidine-1-carboxylate and tert-Butyl-(3S,4R)-3-fluoro-4-(pyridin-3-yloxy)piperidine-1-carboxylate Into a 10-L 4-necked round-bottom flask purged and maintained with an inert atmosphere of nitrogen was placed a solution of tert-butyl trans-3-fluoro-4-hydroxypiperidine-1-carboxylate (180 g, 821 mmol), pyridin-3-ol (117 g, 1.23 mol), and PPh$_3$ (323 g, 1.23 mol) in THF (4 L). This was followed by the dropwise addition of DIAD (249 g, 1.23 mol, 1.50 equiv) at 0° C. After stirring for 15 h at 40° C., the resulting mixture was concentrated under reduced pressure. The residue was purified by silica gel column chromatography (0:1-1:1 ethyl acetate:petroleum ether) to yield the product. The mixture of the two stereoisomers was purified by chiral SFC (AD-H column, 1:1 MeOH with 0.2% diethylamine modifier:CO$_2$) to afford the title compounds.

Step 1: 3-(((3R,4S)-3-Fluoropiperidin-4-yl)oxy)pyridine dihydrochloride and 3-(((3S,4R)-3-fluoropiperidin-4-yl)oxy)pyridine dihydrochloride Into two separate flasks was placed tert-butyl-(3R,4S)-3-fluoro-4-(pyridin-3-yloxy)piperidine-1-carboxylate and tert-butyl-(3S,4R)-3-fluoro-4-(pyridin-3-yloxy)piperidine-1-carboxylate (45 g, 151.85 mmol). To each flask was then added HCl in dioxane (4 M, 500 mL) and the reactions were stirred at RT. The products were collected by filtration to yield to afford intermediate E2 (faster eluting isomer): MS: 197 (M−2HCl+1). $^1$H NMR (400 MHz, D$_2$O): δ 2.23-2.31 (2H, s), 3.10-3.30 (1H, m), 3.40-3.60 (2H, m), 3.70-3.80 (1H, m), 4.90-5.10 (1H, m), 5.20-5.40 (1H, d), 7.90-8.00 (1H, m), 8.20-8.30 (1H, m), 8.45-8.55 (1H, d), 8.60-8.70 (1H, d). Intermediate E3 (slower eluting isomer): MS: 197 (M−2HCl+1). $^1$H NMR (300 MHz, D$_2$O): δ 2.20-2.31 (2H, m), 3.10-3.30 (1H, m), 3.40-3.60 (2H, m), 3.70-3.80 (1H, m), 4.90-5.10 (1H, m), 5.20-5.40 (1H, d), 7.90-8.00 (1H, m), 8.20-8.30 (1H, m), 8.45-8.55 (1H, d), 8.60-8.70 (1H, d).

SCHEME F

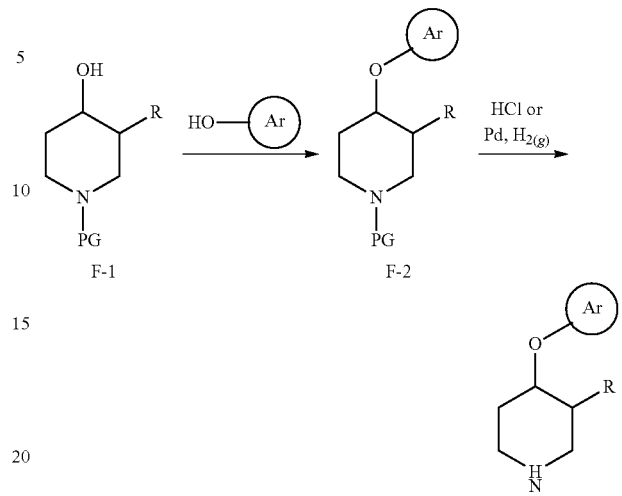

intermediate F

Intermediate F is prepared according to scheme F via Mitsunobu reaction of commercially available N-protected piperidine F-1 with known or prepared phenols (wherein Ar is an aromatic or heteroaromatic ring of R$^1$) to yield adduct F-2. Subsequent deprotection of ether F-2 provides intermediate F.

Intermediate F1

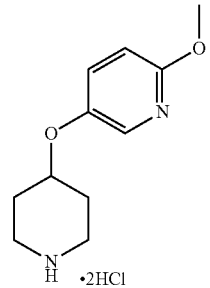

2-Methoxy-5-(piperidin-4-yloxy)pyridine dihydrochloride (Scheme F)

Step 1: tert-Butyl 4-((6-methoxypyridin-3-yl)oxy)piperidine-1-carboxylate

Into a 5-L 4-necked round-bottom flask purged and maintained with an inert atmosphere of nitrogen was placed a solution of 6-methoxypyridin-3-ol (200 g, 1.60 mol) in THF (1.5 L). tert-Butyl 4-hydroxypiperidine-1-carboxylate (386 g, 1.92 mol) and triphenylphosphine (545 g, 2.08 mol) were added followed by the dropwise addition of DIAD (420 g, 2.08 mol) at RT. After stirring for 1 h at 40° C., the resulting solution was diluted with water (2 L) and was partitioned with EtOAc (4 L). The organic layers were combined, washed with brine (2 L), dried over anhydrous sodium sulfate, filtered and concentrated. The residue was purified by silica gel column chromatography (1/10 ethyl acetate/petroleum ether) to yield the title compound.

Step 2: 2-Methoxy-5-(piperidin-4-yloxy)pyridine dihydrochloride

A solution of tert-butyl 4-((6-methoxypyridin-3-yl)oxy)piperidine-1-carboxylate (270 g, 875.6 mmol) in methanol (2 L) was bubbled slowly with HCl(g). The resulting solution was stirred for 2 h at RT. The volatiles were removed and the crude material was diluted with hot EtOAc:MeOH (8:1) and was then cooled to obtain a precipitate that was collected by filtration to yield the title compound. MS: 236 (M−2HCl+H). $^1$H NMR (300 MHz, D$_2$O): δ 7.79-7.98 (m, 2H), 7.24-7.23 (m, 1H), 4.0 (s, 3H), 3.36-3.40 (m, 2H), 3.15-3.26 (m, 2H), 1.97-2.14 (m, 4H).

Intermediate F2

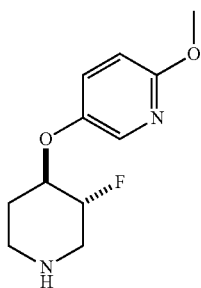 [SMILES: COc1ccc(O[C@@H]2CCNC[C@H]2F)cn1]

5-(((3R,4R)-3-Fluoropiperidin-4-yl)oxy)-2-methoxypyridine (Scheme F)

Step 1: Benzyl (3R,4R)-3-fluoro-4-((6-methoxypyridin-3-yl)oxy)piperidine-1-carboxylate To a flask with triphenylphosphine (1.204 g, 4.59 mmol) in toluene (4.5 mL) was added di-tert-butyl azodicarboxylate (0.916 g, 3.98 mmol) at 0° C. The reaction was warmed to RT and was stirred for 20 min before the addition of (3R,4S)-benzyl 3-fluoro-4-hydroxypiperidine-1-carboxylate (0.775 g, 3.06 mmol, intermediate C2) and 6-methoxypyridin-3-ol (0.383 g, 3.06 mmol) in a solution of toluene (4.5 mL). The reaction mixture was sonicated then heated to 80° C. for 16 h. The volatiles were removed under reduced pressure and the residue was dissolved in EtOAc. The organic layer was washed with aqueous 1 M NaOH (2×), water (2×) and brine before being dried over anhydrous sodium sulfate and concentrated under reduced pressure. The residue was purified by silica gel column chromatography (0-30% EtOAc in hexanes) to yield the title compound.

Step 2: 5-(((3R,4R)-3-Fluoropiperidin-4-yl)oxy)-2-methoxypyridine

A solution of benzyl (3R,4R)-3-fluoro-4-((6-methoxypyridin-3-yl)oxy)piperidine-1-carboxylate (1.04 g, 2.89 mmol) in methanol (20 mL) was prepared under an atmosphere of nitrogen. Pearlman's catalyst (20 wt %, 0.203 g, 0.289 mmol) was added and the system was degassed and placed under a balloon of hydrogen. After 2 h at RT, the mixture was filtered over Celite® and the filtrate was concentrated under reduced pressure to yield the title compound. MS: 227 (M+1).

The following intermediates in table F were prepared according to scheme F using the procedure outlined in the synthesis of intermediate F1 or F2 using commercially available, known or prepared phenols in step 1 and employing various azodicarboxylates with TBAD being the preferred reagent. In cases where additional chemical manipulation are to be carried out on the intermediate, the second step may be omitted.

TABLE F

| Intermediate | Structure | Name | MS (M + 1) |
|---|---|---|---|
| F3 | 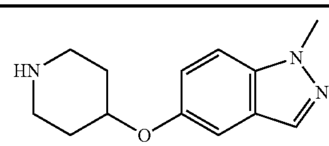 | 1-methyl-5-(piperidin-4-yloxy)-1H-indazole | 232 |
| F4 | 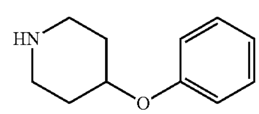 [SMILES: c1ccc(OC2CCNCC2)cc1] | 4-phenoxypiperidine | 178 |
| F5 | 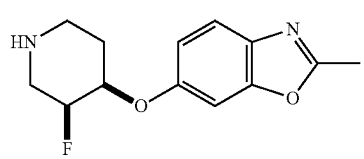 [SMILES: Cc1nc2ccc(O[C@@H]3CCNC[C@@H]3F)cc2o1] | 6-(((3S,4R)-3-fluoropiperidin-4-yl)oxy)-2-methylbenzo[d]oxazole | 251 |
| F6 | 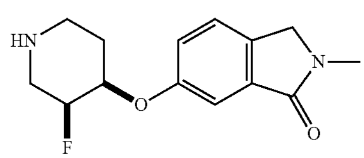 [SMILES: CN1Cc2ccc(O[C@@H]3CCNC[C@@H]3F)cc2C1=O] | 6-(((3S,4R)-3-fluoropiperidin-4-yl)oxy)-2-methylisoindolin-1-one | 265 |

TABLE F-continued

| Intermediate | Structure | Name | MS (M + 1) |
|---|---|---|---|
| F7 | 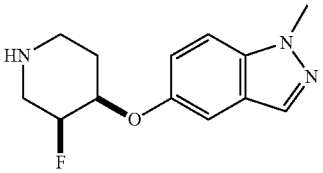 [SMILES: Cn1ncc2cc(O[C@@H]3CCNC[C@@H]3F)ccc21] | 5-(((3S,4R)-3-fluoropiperidin-4-yl)oxy)-1-methyl-1H-indazole | 250 |
| F8 | 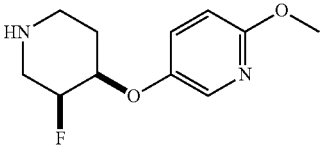 [SMILES: COc1ccc(O[C@@H]2CCNC[C@@H]2F)cn1] | 5-(((3R,4S)-3-fluoropiperidin-4-yl)oxy)-2-methoxypyridine | 227 |
| F9 | 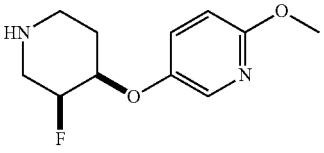 [SMILES: COc1ccc(O[C@@H]2CCNC[C@@H]2F)cn1] | 5-((cis-3-fluoropiperidin-4-yl)oxy)-2-methoxypyridine | 227 |
| F10 | 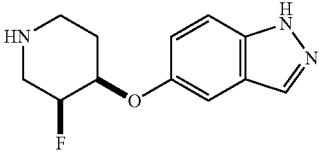 [SMILES: F[C@H]1CNCC[C@H]1Oc1ccc2[nH]ncc2c1] | 5-(((3S,4R)-3-fluoropiperidin-4-yl)oxy)-1H-indazole | 236 |
| F11 | 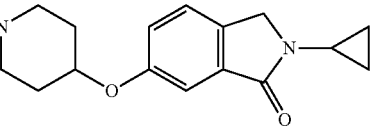 | 2-cyclopropyl-6-(piperidin-4-yloxy)isoindolin-1-one | 273 |
| F12 | 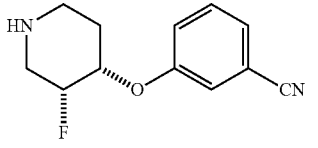 [SMILES: N#Cc1cccc(O[C@H]2CCNC[C@H]2F)c1] | 3-(((3R,4S)-3-fluoropiperidin-4-yl)oxy)benzonitrile | 221 |
| F13 | 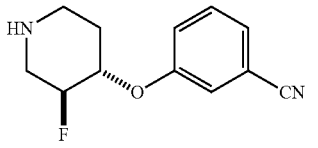 [SMILES: N#Cc1cccc(O[C@H]2CCNC[C@@H]2F)c1] | 3-(((3S,4S)-3-fluoropiperidin-4-yl)oxy)benzonitrile | 221 |
| F14 | 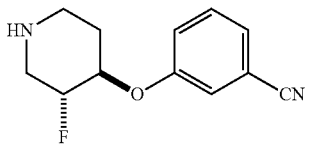 [SMILES: N#Cc1cccc(O[C@@H]2CCNC[C@H]2F)c1] | 3-(((3R,4R)-3-fluoropiperidin-4-yl)oxy)benzonitrile | 221 |
| F15 | 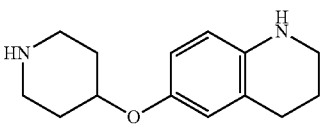 [SMILES: c1cc2c(cc1OC1CCNCC1)CCCN2] | 6-(piperidin-4-yloxy)-1,2,3,4-tetrahydroquinoline | 233 |

TABLE F-continued

| Intermediate | Structure | Name | MS (M + 1) |
|---|---|---|---|
| F16 | 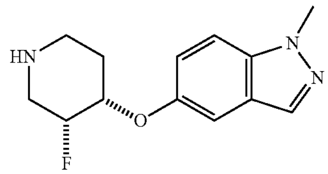 [SMILES: Cn1ncc2cc(O[C@H]3CCNC[C@H]3F)ccc21] | 5-(((3R,4S)-3-fluoropiperidin-4-yl)oxy)-1-methyl-1H-indazole | 250 |
| F17 | 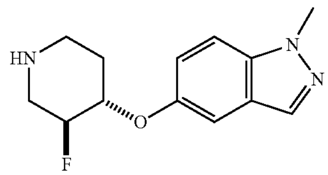 [SMILES: Cn1ncc2cc(O[C@H]3CCNC[C@@H]3F)ccc21] | 5-(((3S,4S)-3-fluoropiperidin-4-yl)oxy)-1-methyl-1H-indazole | 250 |
| F18 | 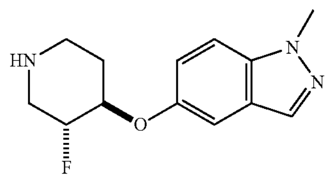 [SMILES: Cn1ncc2cc(O[C@@H]3CCNC[C@H]3F)ccc21] | 5-(((3R,4R)-3-fluoropiperidin-4-yl)oxy)-1-methyl-1H-indazole | 250 |
| F19 | 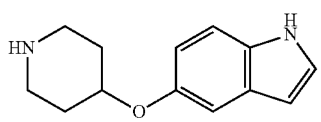 [SMILES: c1cc2cc(OC3CCNCC3)ccc2[nH]1] | 5-(piperidin-4-yloxy)-1H-indole | 217 |
| F20 | 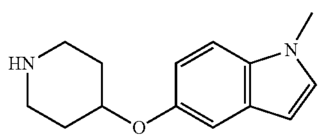 [SMILES: Cn1ccc2cc(OC3CCNCC3)ccc21] | 1-methyl-5-(piperidin-4-yloxy)-1H-indole | 231 |
| F21 | 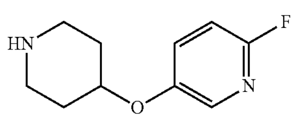 [SMILES: Fc1ccc(OC2CCNCC2)cn1] | 2-fluoro-5-(piperidin-4-yloxy)pyridine | 197 |
| F22 | 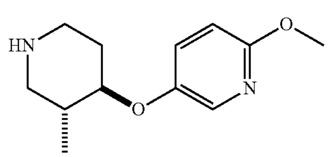 [SMILES: COc1ccc(O[C@@H]2CCNC[C@H]2C)cn1] | 2-methoxy-5-((trans-3-methylpiperidin-4-yl)oxy)pyridine | 223 |
| F23 | 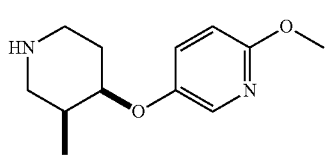 [SMILES: COc1ccc(O[C@@H]2CCNC[C@@H]2C)cn1] | 2-methoxy-5-((cis-3-methylpiperidin-4-yl)oxy)pyridine | 223 |
| F24 | 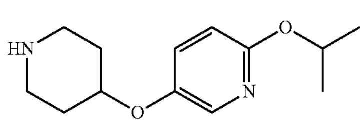 [SMILES: CC(C)Oc1ccc(OC2CCNCC2)cn1] | 2-isopropoxy-5-(piperidin-4-yloxy)pyridine | 237 |
| F25 | 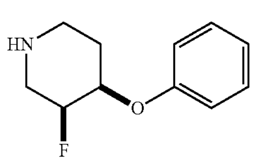 [SMILES: F[C@H]1CNCC[C@H]1Oc1ccccc1] | (3S,4R)-3-fluoro-4-phenoxypiperidine | 196 |

TABLE F-continued

| Intermediate | Name | MS (M + 1) |
|---|---|---|
| F26 | 2-cyclobutoxy-5-(piperidin-4-yloxy)pyridine | 249 |
| F27 | 4-((2,3-dihydrobenzo[b][1,4]dioxin-6-yl)oxy)piperidine | 236 |
| F28 | (3S,4R)-4-((1,3-dihydro-2-benzofuran-5-yl)oxy)-3-fluoropiperidine | 238 |
| F29 | (3S,4R)-4-((1,3-dihydro-2-benzofuran-4-yl)oxy)-3-fluoropiperidine | 238 |
| F30 | (3R,4R)-4-((1,3-dihydro-2-benzofuran-5-yl)oxy)-3-fluoropiperidine | 238 |
| F31 | 6-((6-methoxypyridin-3-yl)oxy)-3-azabicyclo[3.1.1]heptane | 221 |
| F32 | 5-(piperidin-4-yloxy)nicotinonitrile | 204 |
| F33 | 3-methoxy-5-(piperidin-4-yloxy)pyridine | 208 |
| F34 | 3-(piperidin-4-yloxy)-7,8-dihydro-5H-pyrano[4,3-b]pyridine | 235 |
| F35 | tert-butyl 4-(3-cyanophenoxy)piperidine-1-carboxylate | 206* |

TABLE F-continued

| Intermediate | Name | MS (M + 1) |
|---|---|---|
| F36 | 3-(piperidin-4-yloxy)-6,7-dihydro-5H-cyclopenta[b]pyridine | 219 |
| F37 | 6-(piperidin-4-yloxy)-3,4-dihydro-2H-pyrano[2,3-b]pyridine | 235 |
| F38 | (3S,4R)-3-fluoro-4-(4-fluorophenoxy)piperidine | 214 |
| F39 | 4-(((3S,4R)-3-fluoropiperidin-4-yl)oxy)-5,7-dihydrofuro[3,4-b]pyridine | 239 |
| F40 | 4-(((3R,4R)-3-fluoropiperidin-4-yl)oxy)-5,7-dihydrofuro[3,4-b]pyridine | 239 |
| F41 | 3-methyl-5-(piperidin-4-yloxy)pyridine | 193 |
| F42 | (3S,4R)-3-fluoro-4-(isochroman-6-yloxy)piperidine | 252 |
| F43 | (3S,4R)-3-fluoro-4-(isochroman-7-yloxy)piperidine | 252 |

*MS Data is for (M + 1 − Boc)

SCHEME G

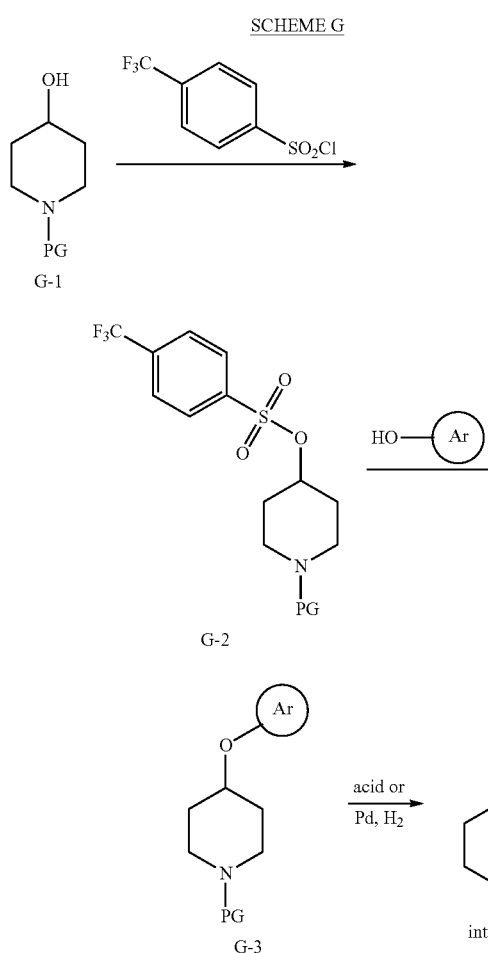

Intermediate G is prepared from a commercial alcohol G-1 (wherein PG is an amine protecting group), which after reaction with 4-(trifluoromethyl)benzenesulfonyl chloride forms adduct G-2. Displacement of sulfone G-2 by a known or prepared phenol or alcohol (wherein Ar is an aromatic or heteroaromatic ring of $R^1$) is carried out under the action of $K_3PO_4$ or $Cs_2CO_3$ to provide ether G-3. Deprotection under acidic or reductive conditions provides intermediate G.

Intermediate G1

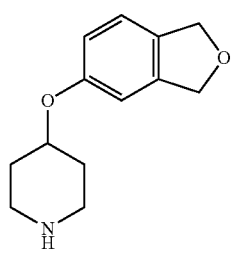 [SMILES: c1cc2c(cc1OC1CCNCC1)COC2]

4-((1,3-Dihydro-2-benzofuran-5-yl)oxy)piperidine
(Scheme G)

Step 1: Benzyl 4-(((4-(trifluoromethyl)phenyl)sulfon)oxy)piperidine-1-carboxylate A solution of benzyl 4-hydroxypiperidine-1-carboxylate (200 g, 808 mmol) and DCM (2 L) was cooled below 10° C. 4-(Trifluoromethyl)benzenesulfonyl chloride (296 g, 1.21 mol) was added followed by triethylamine (169 mL, 1.21 mol) and 4-dimethylaminopyridine (9.87 g, 81 mmol). The reaction was aged at 5° C. and slowly warmed to RT. The reaction was aged 14 h and was transferred to separatory funnel containing an aqueous 10% citric acid solution. The organic was dried over anhydrous $Na_2SO_4$ before concentrating to dryness. The residue was purified by silica gel column (0-50% EtOAc in hexanes) to give the title compound.

Step 2: Benzyl 4-((1,3-dihydro-2-benzofuran-5-yl)oxy)piperidine-1-carboxylate

To a flask was added benzyl 4-(((4(trifluoromethyl)phenyl)sulfonyl)oxy)piperidine-1-carboxylate (73.3 g, 165 mmol) and 1,3-dihydro-2-benzofuran-5-ol (15 g, 110 mmol), a fine powder of potassium tribasic phosphate (35.1 g, 165 mmol) and MeCN (150 mL). After being stirred at 60° C. for an appropriate period, the mixture was cooled and poured into water and then extracted with EtOAc. The organic layer was dried over anhydrous $Na_2SO_4$ before concentrating to dryness. The residue was purified by silica gel column (0-50% EtOAc in hexanes) to give the title compound.

Step 3: 4-((1,3-Dihydro-2-benzofuran-5-yl)oxy)piperidine

To a solution of benzyl 4-((1,3-dihydro-2-benzofuran-5-yl)oxy)piperidine-1-carboxylate (9.7 g, 27.4 mmol) in methanol (194 mL) was added Pd/C (10 wt %, 0.877 g, 2.74 mmol) under an atmosphere of $N_2(g)$. The system was purged and was placed under a balloon of $H_2(g)$ with stirring at RT. Upon completion, the reaction was filtered and the filtrate was concentrated to provide the title compound, which was carried forward without further purification. MS: 220 (M+1). The following intermediates in table G were prepared according to scheme G using the procedure outlined in the synthesis of intermediate G1. Alternative conditions are: (1) using tert-butyl 4-hydroxypiperidine-1-carboxylate in step 1, (2) using the combination of cesium carbonate as a base and DMF as the solvent in step 2, and (3) using TFA or HCl for N-Boc deprotection. In some cases, step 3 may be omitted to furnish the N-protected piperidine intermediate.

TABLE G

| Intermediate | Structure | Name | MS (M + 1) |
|---|---|---|---|
| G2 | 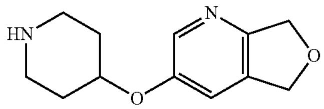 [SMILES: c1nc2c(cc1OC1CCNCC1)COC2] | 3-(piperidin-4-yloxy)-5,7-dihydrofuro[3,4-b]pyridine | 221 |
| G3 | 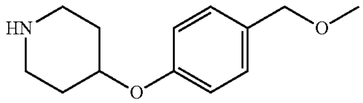 [SMILES: COCc1ccc(OC2CCNCC2)cc1] | 4-(4-(methoxymethyl)phenoxy)piperidine | 222 |
| G4 | 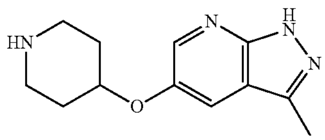 [SMILES: Cc1n[nH]c2ncc(OC3CCNCC3)cc12] | 3-methyl-5-(piperidin-4-yloxy)-1H-pyrazolo[3,4-b]pyridine | NMR data[1] |
| G5 | 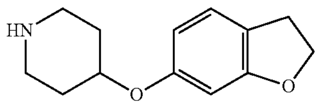 [SMILES: c1cc2c(cc1OC1CCNCC1)OCC2] | 4-((2,3-dihydrobenzofuran-6-yl)oxy)piperidine | 220 |
| G6 | 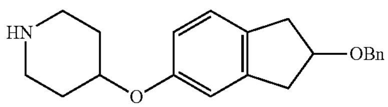 [SMILES: c1ccc(COC2Cc3ccc(OC4CCNCC4)cc3C2)cc1] | 4-((2-(benzyloxy)-2,3-dihydro-1H-inden-5-yl)oxy)piperidine | 324 |
| G7[2] | 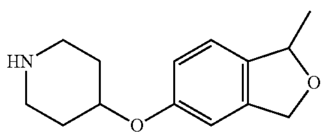 | 4-((1-methyl-1,3-dihydro-2-benzofuran-5-yl)oxy)piperidine | 234 |
| G8 | 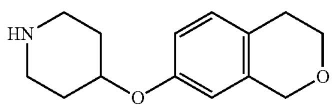 [SMILES: c1cc2c(cc1OC1CCNCC1)COCC2] | 4-(isochroman-7-yloxy)piperidine | 234 |
| G9[3] | 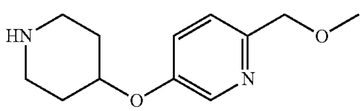 [SMILES: COCc1ccc(OC2CCNCC2)cn1] | 2-(methoxymethyl)-5-(piperidin-4-yloxy)pyridine | 223 |
| G10 | 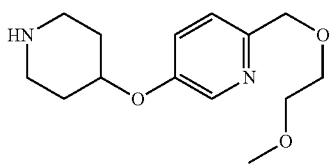 [SMILES: COCCOCc1ccc(OC2CCNCC2)cn1] | 2-((2-methoxyethoxy)methyl)-5-(piperidin-4-yloxy)pyridine | 267 |
| G11[4] | 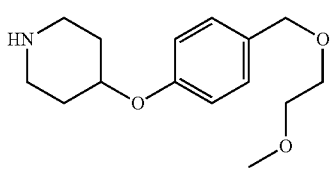 | 4-(4-((2-methoxyethoxy)methyl)phenoxy)piperidine | 266 |
| G12 | 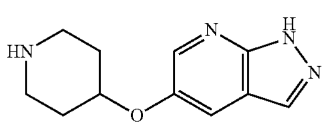 [SMILES: c1nc2[nH]ncc2cc1OC1CCNCC1] | 5-(piperidin-4-yloxy)-1H-pyrazolo[3,4-b]pyridine | 219 |
| G13[5] | 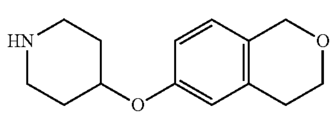 [SMILES: c1cc2c(cc1OC1CCNCC1)CCOC2] | 4-(isochroman-6-yloxy)piperidine | 234 |

TABLE G-continued

| Intermediate | Name | MS (M + 1) |
|---|---|---|
| G14[6] | 4-((2,2-difluorobenzo[d][1,3]dioxol-5-yl)oxy)piperidine | 258 |
| G15 | 1,2-dimethyl-5-(piperidin-4-yloxy)-1H-benzo[d]imidazole | 246 |
| G16 | 1,2-dimethyl-6-(piperidin-4-yloxy)-1H-benzo[d]imidazole | 246 |
| G17 | methyl 2-(5-(piperidin-4-yloxy)-1H-indazol-1-yl)acetate | 290 |
| G18 | 4-(3-(methylsulfonyl)phenoxy)piperidine | 256 |
| G19 | 2-((piperidin-4-yloxy)methyl)pyridine | 193 |
| G20 | 4-((1-methyl-1H-pyrazol-4-yl)oxy)piperidine | 182 |
| G21 | 6-(piperidin-4-yloxy)-2,3-dihydrofuro[3,2-b]pyridine | 221 |
| G22[7] | 5-(piperidin-4-yloxy)-1,3-dihydrobenzo[c]thiophene 2,2-dioxide | 268 |
| G23 | 6-(piperidin-4-yloxy)-[1,2,4]triazolo[1,5-a]pyridine | 219 |
| G24 | 6-(piperidin-4-yloxy)imidazo[1,2-a]pyridine | 218 |

TABLE G-continued

| Intermediate | Name | MS (M + 1) |
|---|---|---|
| G25 | 5-(piperidin-4-yloxy)-1,3-dihydrobenzo[c]thiophene 2-oxide | 252 |
| G26 | 2-methyl-5-(piperidin-4-yloxy)-2H-indazole | 232 |
| G27[8] | tert-butyl 4-((1-(2-methoxyethyl)-1H-pyrazol-3-yl)oxy)piperidine-1-carboxylate | 326 |
| G28 | 7-((tert-butyldimethylsilyl)oxy)-3-(piperidin-4-yloxy)-6,7-dihydro-5H-cyclopenta[b]pyridine | 349 |
| G29 | 4-(2,2,2-trifluoroethoxy)piperidine | 184 |
| G30 | 4-((piperidin-4-yloxy)methyl)pyridine | 193 |
| G31 | 3-((piperidin-4-yloxy)methyl)pyridine | 193 |
| G32 | 4-((1-ethyl-1H-pyrazol-4-yl)oxy)piperidine | 196 |
| G33[9] | 4-((1-phenyl-1H-pyrazol-4-yl)oxy)piperidine | 244 |

[1]$^1$H NMR (400 MHz, methanol-$d_4$): δ 8.32 (1 H, s), 8.04 (1 H, s), 4.49-4.53 (1 H, m), 3.00-3.10 (2 H, m), 2.85-2.92 (2 H, m), 2.35 (3 H, s), 1.85-2.00 (2 H, m), 1.65-1.75 (2 H, m).
[2]Phenol may be prepared according to literature procedures, see e.g.: Wu, H.-J.; et al. *J. Org. Chem.* 1998, 63, 5064-5070.
[3]Phenol may be prepared according to literature procedures, see e.g.: Klapars, A..; et al. *J. Org. Chem.* 2008, 73, 4986-4993.
[4]Phenol may be prepared according to literature procedures, see e.g.: Saa, J. M..; et al. *J. Org. Chem.* 1988, 53, 4263-4273.
[5]Phenol may be prepared according to literature procedures, see e.g.: Schieler, L.; Sprenger, R. D. *J. Am. Chem. Soc.* 1951, 73, 4045-4046.
[6]Phenol may be prepared according to literature procedures, see e.g.: Yoshihiro, et al. PCT Patent Publ'n WO2011/059021.
[7]Phenol may be prepared according to literature procedures, see e.g.: Kanematsu, K.; Kinoyama, I. *J. Chem. Soc., Chem. Commun.* 1992, 10, 735-736.
[8]Phenol may be prepared according to literature procedures, see e.g.: Kanouni, et al. PCT Patent Publ'n WO2014/151106.
[9]Phenol may be prepared according to literature procedures, see e.g.: Lamberth, C. *Org. Prep. Proc. Int.* 2002, 34, 98-102.

SCHEME H

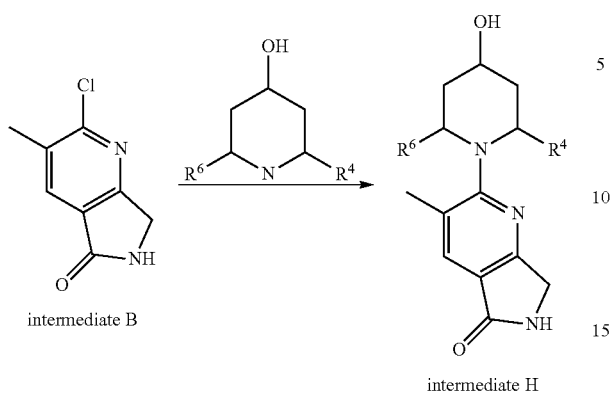

intermediate B → intermediate H

Intermediate H is prepared from an $S_NAr$ reaction of intermediate B with commercial or prepared piperidin-4-ols.

Intermediate H1

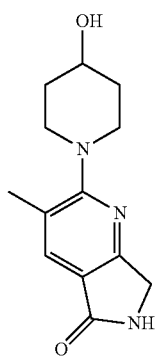 [SMILES: Cc1cc2c(nc1N1CCC(O)CC1)CNC2=O]

2-(4-Hydroxypiperidin-1-yl)-3-methyl-6,7-dihydro-5H-pyrrolo[3,4-b]pyridin-5-one (Scheme H)

A solution of 2-chloro-3-methyl-6,7-dihydro-5H-pyrrolo[3,4-b]pyridin-5-one (4 g, 21.9 mmol, intermediate B1) in neat piperidin-4-ol (10.0 g, 99 mmol) was stirred at 140° C. for 2 h. The reaction mixture was cooled and water (20 mL) was added. The mixture was stirred at RT for 30 min and the precipitate was filtered to yield the title compound. MS: 248 (M+1).

The following intermediates in table H were prepared according to scheme H using the procedure outlined in the synthesis of intermediate H1 using commercially available or prepared piperidines with alternative conditions of using NMP as solvent and sodium bicarbonate as the base.

TABLE H

| Intermediate | Structure | Name | MS (M + 1) |
|---|---|---|---|
| H2* | (structure) | 2-(3-hydroxy-8-azabicyclo[3.2.1]octan-8-yl)-3-methyl-6,7-dihydro-5H-pyrrolo[3,4-b]pyridin-5-one | 274 |
| H3** | (structure) | 2-(3-hydroxy-8-azabicyclo[3.2.1]octan-8-yl)-3-methyl-6,7-dihydro-5H-pyrrolo[3,4-b]pyridin-5-one | 274 |
| H4 | (structure) | 3-ethyl-2-(4-hydroxypiperidin-1-yl)-6,7-dihydro-5H-pyrrolo[3,4-b]pyridin-5-one | 262 |

*Intermediate H2 was synthesized using exo-8-azabicyclo[3.2.1]octan-3-ol
**Intermediate H3 was synthesized using endo-8-azabicyclo[3.2.1]octan-3-ol

SCHEME I

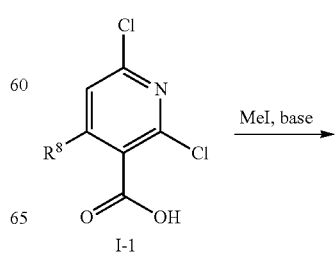

I-1 → (MeI, base)

-continued

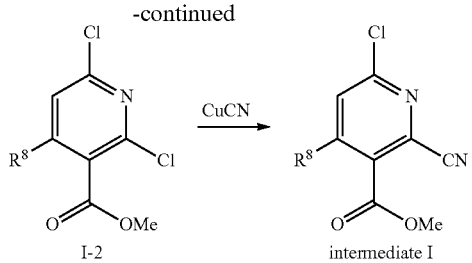

Intermediate I is prepared from commercially available nicotinic acid I-1 and is transformed to the corresponding ester I-2 via a base-mediated alkylation. Selective cyanation of dichloride I-2 provides intermediate I.

Intermediate I1

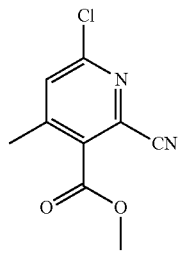

Methyl 6-chloro-2-cyano-4-methylnicotinate (Scheme I)

Step 1: Methyl 2,6-dichloro-4-methylnicotinate

To a solution of 2,6-dichloro-4-methylnicotinic acid (10 g, 48.5 mmol) in DMF (162 mL) was added potassium carbonate (10.06 g, 72.8 mmol) and MeI (12 mL, 192 mmol) at 0° C. The reaction mixture was stirred at RT for 3 h and was subsequently poured into water. This mixture was extracted with EtOAc and the organic layer was washed with water and brine, dried over anhydrous sodium sulfate and concentrated in vacuo. The crude material was used without further purification.

Step 2: Methyl 6-chloro-2-cyano-4-methylnicotinate

A solution of methyl 2,6-dichloro-4-methylnicotinate (3 g, 13.6 mmol) and copper(I) cyanide (1.83 g, 20.5 mmol) in NMP (13.6 mL) was degassed and placed under nitrogen. The system was heated to 180° C. for 2 h under microwave irradiation. The mixture was diluted with 10% aqueous ammonium hydroxide (22 mL) and was filtered over Celite® (EtOAc wash). The organic layer was washed with water, dried over anhydrous sodium sulfate and concentrated to dryness. The residue was purified by column chromatography on silica gel (0-20% EtOAc in hexanes) to yield the title compound. MS: 211 (M+1).

The following intermediates in table I were prepared according to scheme I using the procedure outlined in the synthesis of intermediate I1 using commercially available nicotinic acids.

TABLE I

| Intermediate | Structure | Name | MS (M + 1) |
|---|---|---|---|
| I2 | 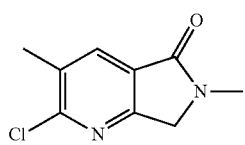 | methyl 6-chloro-2-cyanonicotinate | 197 |

SCHEME J

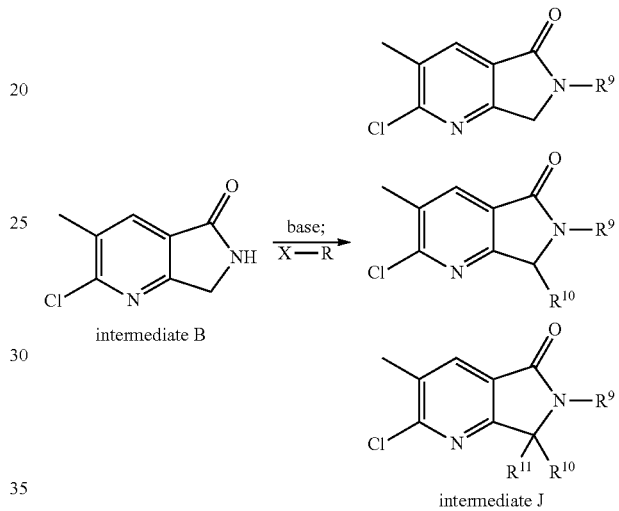

Intermediate J is prepared according to Scheme J from intermediate B after treatment with base followed by an alkyl halide. Depending on the reagents and conditions utilized the mono-, bis- and tris-adducts may be obtained.

Intermediate J1

2-Chloro-3,6-dimethyl-6,7-dihydro-5H-pyrrolo[3,4-b]pyridin-5-one (Scheme J)

To 2-chloro-3-methyl-6,7-dihydro-5H-pyrrolo[3,4-b]pyridin-5-one (5 g, 27.4 mmol, intermediate B1) in DMSO (137 mL) was added LHMDS (1 M in THF, 27.4 mL, 27.4 mmol). The reaction was sonicated and stirred at RT for 10 min. Iodomethane (1.71 mL, 27.4 mmol) was added dropwise at RT. Upon reaction completion the reaction was diluted with water (600 mL), aqueous 1 M HCl (10 mL) and DCM (200 mL). The mixture was stirred and filtered before the organic layer was separated, dried over anhydrous sodium sulfate and concentrated. The residue was taken up in hot ether and upon cooling, the resultant solids were collected by filtration (1:1 ether:heptanes wash) to yield the title compound. MS: 197 (M+1).

Intermediate J2

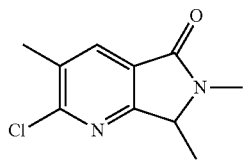

2-Chloro-3,6,7-trimethyl-6,7-dihydro-5H-pyrrolo[3,4-b]pyridin-5-one (Scheme J)

A solution of 2-chloro-3-methyl-6,7-dihydro-5H-pyrrolo[3,4-b]pyridin-5-one (5 g, 27.4 mmol, intermediate B1), in DMF (200 mL), was flushed with N₂(g) before NaH (1.205 g, 30.1 mmol, 60%) was added at room temperature. The reaction mixture was stirred at RT for 1 h, before iodomethane (7.77 g, 54.8 mmol) was added. After stirring at for 2 h, it was heated to 65° C. for 3 h and was worked up with EtOAc and water. The organic layer was collected and the major product was isolated after purification on a silica gel column (40% EtOAc in hexanes) to yield the title compound. MS: 211 (M+1).

Intermediate J3

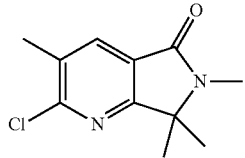

2-Chloro-3,6,7,7-tetramethyl-6,7-dihydro-5H-pyrrolo[3,4-b]pyridin-5-one (Scheme J)

From the same reaction as described in the procedure for intermediate J2 (vide supra) was obtained the title compound as the minor product. MS: 225 (M+1).

SCHEME K

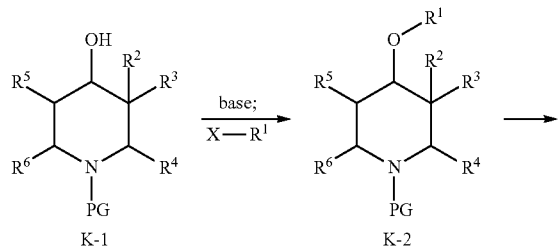

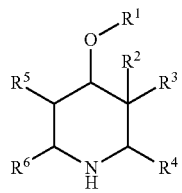

intermediate K

Intermediate K is prepared according to Scheme K from N-protected piperidine alcohol K-1 in a two-step procedure involving base-mediated alkylation to form adduct K-2 and subsequent deprotection to reveal the piperidine amine.

Intermediate K

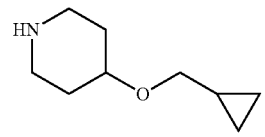 [SMILES: C1CC(OCC2CC2)CCN1]

4-(Cyclopropylmethoxy)piperidine (Scheme K)

Step 1: tert-Butyl 4-(cyclopropylmethoxy)piperidine-1-carboxylate

To a solution of tert-butyl 4-hydroxypiperidine-1-carboxylate (400 mg, 1.987 mmol) in DMF (4 mL) was added sodium hydride (95 mg, 2.39 mmol, 60%) at 0° C. The reaction was stirred for 1 h before (bromomethyl)cyclopropane (322 mg, 2.39 mmol) and sodium iodide (14.90 mg, 0.099 mmol) were added. The reaction was stirred for 20 h at RT and then the mixture was treated with water (25 mL) and extracted with DCM (25 mL×3). The combined organic layers were dried over anhydrous sodium sulfate, filtered and concentrated. The residue was purified by flash silica gel chromatography (0-25% THF in petroleum ether) to give the title compound.

Step 2: 4-(Cyclopropylmethoxy)piperidine

A solution of tert-butyl 4-(cyclopropylmethoxy)piperidine-1-carboxylate (290 mg, 1.136 mmol) in 4 M HCl in EtOAc (3 mL) was stirred at RT for 1 h. Volatiles were removed from the reaction under reduced pressure. The residue was dissolved in MeOH (2 mL) and basified by saturated aqueous NaHCO₃ to pH 8. The mixture was concentrated and the residue was treated with EtOAc (5 mL), filtered and concentrated to afford the title compound. ¹H NMR (400 MHz, CDCl₃): δ 3.50-3.53 (1H, m), 3.28 (2H, d, J=6.8 Hz), 3.17-3.21 (2H, m), 2.87-2.90 (2H, m), 1.99-2.04 (2H, m), 1.67-1.71 (2H, m), 1.06-1.03 (1H, m), 0.52-0.57 (2H, m), 0.17-0.21 (2H, m).

The following intermediates in table K were prepared according to scheme K using the procedure outlined in the synthesis of intermediate K1 using commercially available or prepared alkyl halides, mesylates or tosylates. In cases where additional chemical manipulation are to be carried out on the intermediate, the second step may be omitted.

TABLE K

| Intermediate | Name | MS (M + 1) |
|---|---|---|
| K2 | benzyl 4-((2-methylallyl)oxy)piperidine-1-carboxylate | 290 |
| K3 | 4-(cyclobutylmethoxy)piperidine | 170 |
| K4 | 4-(2-(azetidin-1-yl)ethoxy)piperidine | 278 |
| K5 | N-(2-(piperidin-4-yloxy)ethyl)acetamide | 280 |
| K6 | 4-(cyclopentylmethoxy)piperidine | NMR data[1] |
| K7 | 1-((piperidin-4-yloxy)methyl)cyclopropane-1-carbonitrile | NMR data[2] |
| K8 | tert-butyl 4-((3-methylbut-2-en-1-yl)oxy)piperidine-1-carboxylate | 184* |
| K9 | 2-((piperidin-4-yloxy)methyl)oxazole | 183 |
| K10 | benzyl 4-(2-methylenebutoxy)piperidine-1-carboxylate | 304 |
| K11 | 4-(bicyclo[1.1.1]pentan-1-ylmethoxy)piperidine | 182 |

TABLE K-continued

| Intermediate | Structure | Name | MS (M + 1) |
|---|---|---|---|
| K12 | 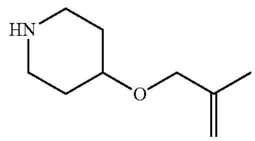 | 4-((2-methylallyl)oxy)piperidine | NMR data³ |
| K13 | 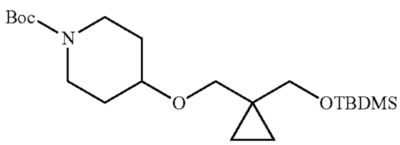 [SMILES: CC(C)(C)OC(=O)N1CCC(OCC2(CO[Si](C)(C)C(C)(C)C)CC2)CC1] | tert-butyl 4-((1-(((tert-butyldimethylsilyl)oxy)methyl)cyclopropyl)methoxy)piperidine-1-carboxylate | 400 |
| K14 | 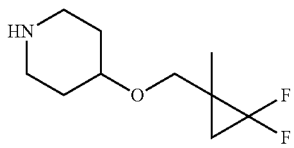 | 4-((2,2-difluoro-1-methylcyclopropyl)methoxy)piperidine | 206 |
| K15 | 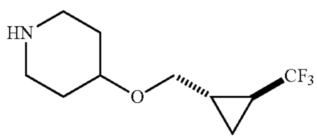 | 4-(((trans)-2-(trifluoromethyl)cyclopropyl)methoxy)piperidine | 222 |
| K16 | 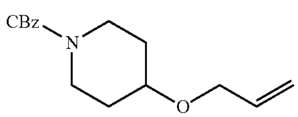 | benzyl 4-(allyloxy)piperidine-1-carboxylate | 276 |
| K17 | 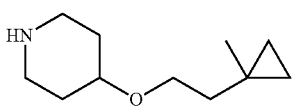 | 4-(2-(1-methylcyclopropyl)ethoxy)piperidine | 184 |
| K18 | 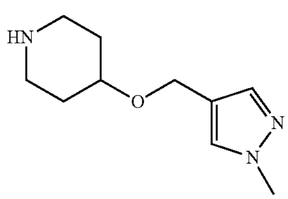 | 4-((1-methyl-1H-pyrazol-4-yl)methoxy)piperidine | 196 |
| K19 | 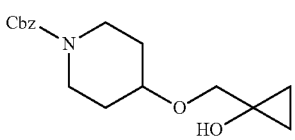 [SMILES: O=C(OCc1ccccc1)N1CCC(OCC2(O)CC2)CC1] | tert-butyl 4-((1-hydroxycyclopropyl)methoxy)piperidine-1-carboxylate | 306 |
| K20 | 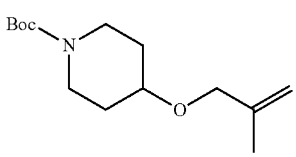 [SMILES: C=C(C)COC1CCN(C(=O)OC(C)(C)C)CC1] | tert-butyl 4-((2-methylallyl)oxy)piperidine-1-carboxylate | 156* |
| K21 | 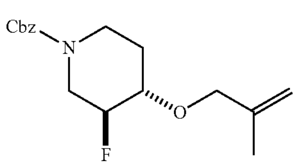 [SMILES: C=C(C)CO[C@H]1CCN(C(=O)OCc2ccccc2)C[C@@H]1F] | benzyl-(3S,4S)-3-fluoro-4-((2-methylallyl)oxy)piperidine-1-carboxylate | 308 |

TABLE K-continued

| Intermediate | Structure | Name | MS (M + 1) |
|---|---|---|---|
| K22 | Cbz-N-piperidine with 3-F and 4-O-CH2-C(CH3)=CH2 | benzyl (3S,4R)-3-fluoro-4-((2-methylallyl)oxy)piperidine-1-carboxylate | 308 |

*MS data is equal to (M + 1 − Boc)
[1]$^1$H NMR (400 MHz, methanol-$d_4$): δ 3.59-3.68 (m, 1 H), 3.35 (d, J = 6.80 Hz, 2 H), 3.20-3.25 (m, 2 H), 3.03-3.14 (m, 2 H), 2.09-2.16 (m, 1 H), 1.91-2.03 (m, 2 H), 1.81-1.88 (m, 2 H), 1.67-1.75 (m, 2 H), 1.45-1.65 (m, 4 H), 1.16-1.36 (m, 2 H).
[2]$^1$H NMR (400 MHz, CDCl$_3$): δ 3.71-3.73 (1 H, m), 3.48 (2 H, s), 3.17-3.21 (2 H, m), 3.84-3.87 (2 H, m), 1.98-2.02 (2 H, m), 1.69-1.73 (2 H, m), 1.26-1.30 (2 H, m), 0.98-1.00 (2 H, m).
[3]$^1$H NMR (500 MHz, CDCl$_3$): δ 7.78 (s, 1 H), 6.11 (br s, 1 H), 5.01 (s, 1 H), 4.90 (s, 1 H), 4.34 (s, 2 H), 3.97 (s, 2 H), 3.55 (m, 3 H), 3.03 (t, 2 H), 2.34 (s, 3 H), 2.02 (s, 2 H), 1.78 (m, 5 H).

SCHEME L

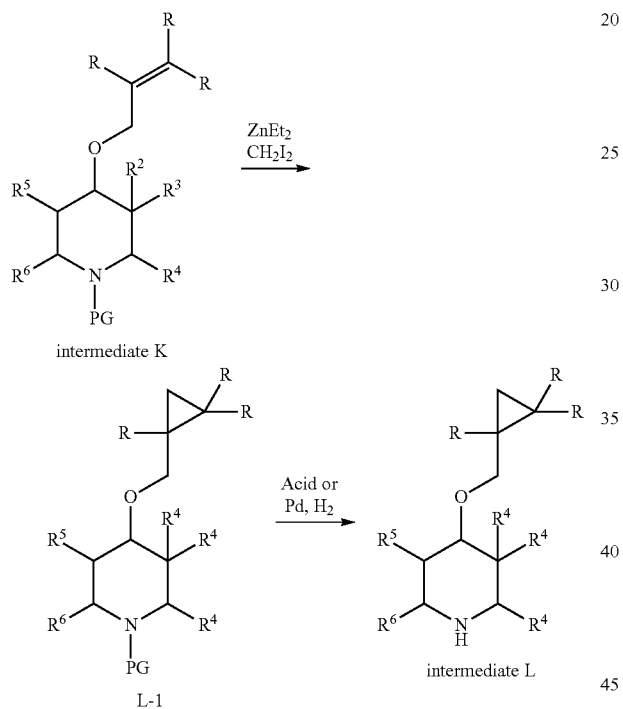

Intermediate L (wherein R is independently selected from fluoro and $C_{1-6}$alkyl) is prepared according to Scheme L from N-protected piperidine alcohol intermediate K in a two-step procedure involving Simmons-Smith reaction to form adduct L-1 and subsequent deprotection to reveal the piperidine amine.

Intermediate L1

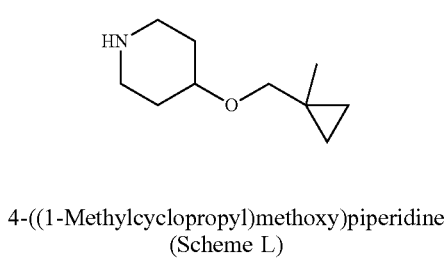

4-((1-Methylcyclopropyl)methoxy)piperidine
(Scheme L)

Step 1: Benzyl 4-((1-methylcyclopropyl)methoxy)piperidine-1-carboxylate

To a solution of benzyl 4-((2-methylallyl)oxy)piperidine-1-carboxylate (9 g, 31.1 mmol) in DCM (100 mL) were added diiodomethane (41.7 g, 156 mmol) and diethylzinc (93 ml, 93 mmol) at −5° C. for 3 h. The reaction mixture was diluted with water (100 mL) and extracted with EtOAc (100 mL×3). The combined organic layers were washed with brine (80 mL), dried over anhydrous sodium sulfate, filtered and the filtrate was concentrated in vacuo. The residue was purified by chromatography column (15% EtOAc in petroleum ether) to give the title compound.

Step 2: 4-((1-Methylcyclopropyl)methoxy)piperidine

To a solution of benzyl 4-((1-methylcyclopropyl)methoxy)piperidine-1-carboxylate (1 g, 3.30 mmol) in MeOH (10 mL) was added Pd/C (10 wt %, 3.51 g, 3.30 mmol). The reaction was stirred under an atmosphere of H$_2$ (15 psi) at RT for 1 h. The mixture was filtered and the filtrate was concentrated in vacuo to yield the title compound. MS: 170 (M+1).

Intermediate L1A

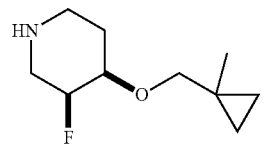

(3S,4R)-3-Fluoro-4-((1-methylcyclopropyl)methoxy)piperidine (Scheme L)

Step 1: (3S,4R)-Benzyl 4-((1-methylcyclopropyl)methoxy)piperidine-1-carboxylate (3S,4R)-Benzyl 3-fluoro-4-((2-methylallyl)oxy)piperidine-1-carboxylate (2.08 g, 6.77 mmol) was dissolved in DCM (40 mL) and the solution was cooled to 0° C. under a nitrogen atmosphere. Diiodomethane (2.73 mL, 33.8 mmol) was added followed by the dropwise addition of diethylzinc (1 M in hexanes, 20.3 mL, 20.3 mmol). The reaction was allowed to stir for 16 h and was allowed to gradually warm to RT. The reaction was carefully quenched with aqueous NaHCO$_3$ (saturated) and once gas evolution ceased the mixture was diluted with DCM. The milky suspension was filtered and then the filtrate was partitioned with water followed by brine. The organic was dried over anhydrous sodium sulfate, filtered and concentrated before purification by silica gel chromatography (10-40% EtOAc/hexanes) to afford the title compound. MS: 322 (M+1).

Step 2: (3S,4R)-3-Fluoro-4-((1-methylcyclopropyl)methoxy)piperidine (3S,4R)-Benzyl 3-fluoro-4-((1-methylcyclopropyl)methoxy)piperidine-1-carboxylate (1.86 g, 5.79 mmol) was dissolved in MeOH (25 mL). The system was evacuated and placed under a nitrogen atmosphere, then palladium hydroxide on carbon (20%, 0.406 g, 0.579 mmol) was added. The system was placed under a hydrogen atmosphere and was stirred for 3 h before the mixture was filtered (MeOH wash) and concentrated to afford the title compound that was used without further purification. MS: 188 (M+1).

The following intermediates in table L were prepared according to scheme L using the procedure outlined in the synthesis of intermediate L1. In cases where the piperidine is Boc-protected, use an acid such was HCl or TFA for step 2. Additionally step 2 may be omitted when subsequent chemical manipulations are required.

TABLE L

| Intermediate | Structure | Name | MS (M + 1) |
|---|---|---|---|
| L2 | Boc-piperidine-O-CH2-(2,2-dimethylcyclopropyl) | tert-butyl 4-((2,2-dimethylcyclopropyl)methoxy)piperidine-1-carboxylate | 184* |
| L3 | HN-piperidine-O-CH2-(1-ethylcyclopropyl) | 4-((1-ethylcyclopropyl)methoxy)piperidine | 184 |
| L4 | HN-piperidine(F)-O-CH2-(2,2-dimethylcyclopropyl) | (3S,4R)-4-((2,2-dimethylcyclopropyl)methoxy)-3-fluoropiperidine | 188 |
| L5 | HN-piperidine(F)-O-CH2-(2,2-dimethylcyclopropyl) | (3R,4R)-4-((2,2-dimethylcyclopropyl)methoxy)-3-fluoropiperidine | 188 |

*MS Data is for (M + 1 – Boc)

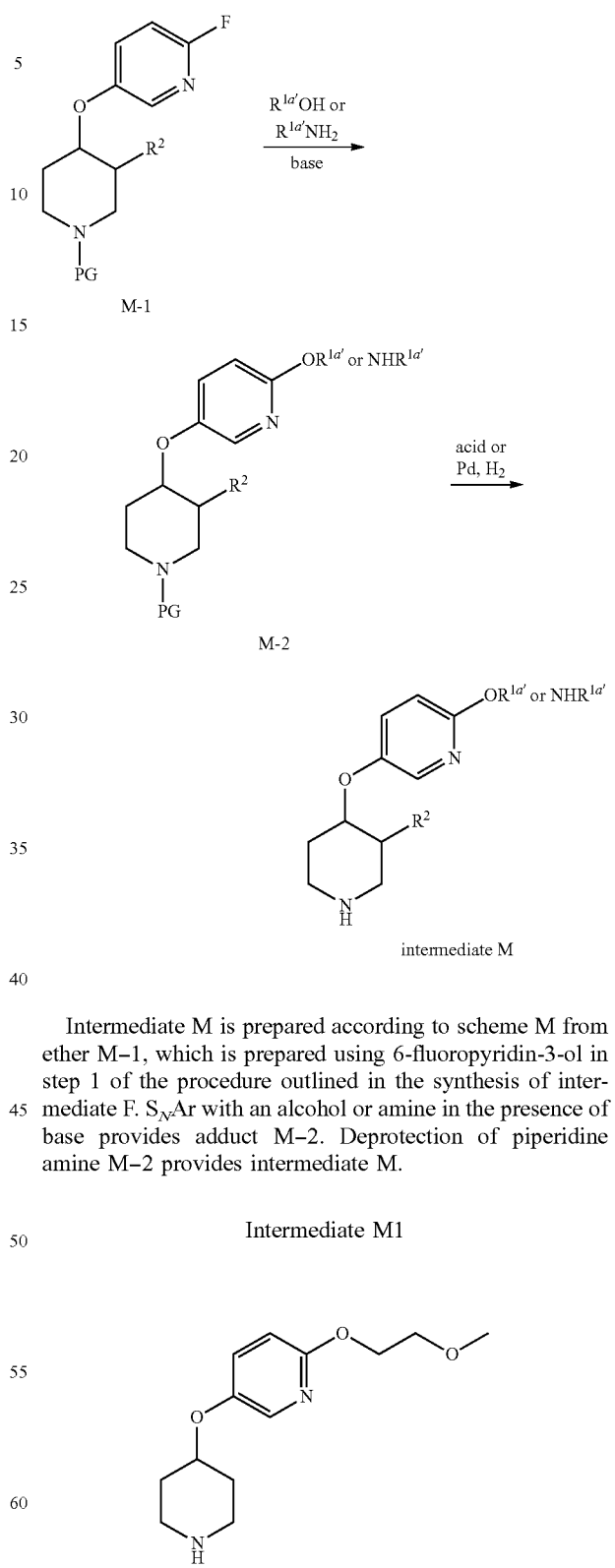

SCHEME M

M-1

M-2 intermediate M

Intermediate M is prepared according to scheme M from ether M–1, which is prepared using 6-fluoropyridin-3-ol in step 1 of the procedure outlined in the synthesis of intermediate F. S$_N$Ar with an alcohol or amine in the presence of base provides adduct M–2. Deprotection of piperidine amine M–2 provides intermediate M.

Intermediate M1

2-(2-Methoxyethoxy)-5-(piperidin-4-yloxy)pyridine (Scheme M)

Step 1: tert-Butyl 4-((6-(2-(dimethylamino)ethoxy)pyridin-3-yl)oxy)piperidine-1-carboxylate To a solution of 2-(dimethylamino)ethanol (75 mg, 0.844 mmol) in DMF (2 mL) was added sodium hydride (33.7 mg, 0.844 mmol, 60%) at 0° C. The mixture was stirred for 20 min under an atmosphere of nitrogen. Tert-Butyl 4-((6-fluoropyridin-3-yl)oxy)piperidine-1-carboxylate (50 mg, 0.169 mmol) was added to the mixture and the reaction was gradually warmed to 50° C. and stirred for 18 h. The reaction was quenched with 50% aqueous NH₄Cl (40 mL) and the mixture was extracted with EtOAc (20 mL×3). The combined organic layers were dried over anhydrous sodium sulfate, filtered and concentrated. The residue was purified by prep-TLC (10:1 DCM:MeOH) to yield the title compound.

Step 2: 2-(2-Methoxyethoxy)-5-(piperidin-4-yloxy)pyridine

A solution of tert-butyl 4-((6-(2-(dimethylamino)ethoxy)pyridin-3-yl)oxy)piperidine-1-carboxylate (50 mg, 0.142 mmol) in HCl (4 M in MeOH, 2 mL) was stirred at 20° C. for 1 h. The reaction was concentrated to give the title compound as the bis-HCl salt. MS: 253 (M−2HCl+H).

The following intermediates in table M were prepared according to scheme M using the procedure outlined in the synthesis of intermediate M1 using commercially available alcohols in step 1. In cases where additional chemical manipulations are required, step 2 may be omitted.

TABLE M

| Intermediate | Structure | Name | MS (M + 1) |
|---|---|---|---|
| M2 | 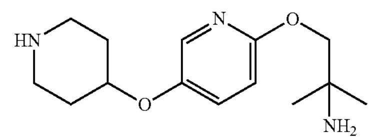 [SMILES: CC(C)(N)COc1ccc(OC2CCNCC2)cn1] | 2-methyl-1-((5-(piperidin-4-yloxy)pyridin-2-yl)oxy)propan-2-amine | 266 |
| M3 | 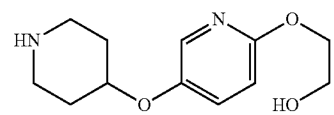 [SMILES: OCCOc1ccc(OC2CCNCC2)cn1] | 2-((5-(piperidin-4-yloxy)pyridin-2-yl)oxy)ethan-1-ol | 239 |
| M4 | 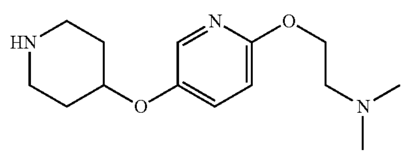 [SMILES: CN(C)CCOc1ccc(OC2CCNCC2)cn1] | N,N-dimethyl-2-((5-(piperidin-4-yloxy)pyridin-2-yl)oxy)ethan-1-amine | 266 |
| M5 | 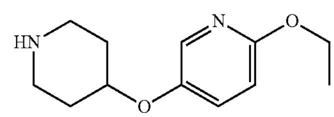 [SMILES: CCOc1ccc(OC2CCNCC2)cn1] | 2-ethoxy-5-(piperidin-4-yloxy)pyridine | 223 |
| M6 | 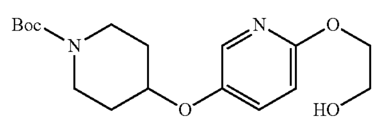 [SMILES: CC(C)(C)OC(=O)N1CCC(Oc2ccc(OCCO)nc2)CC1] | tert-butyl 4-((6-(2-hydroxyethoxy)pyridin-3-yl)oxy)piperidine-1-carboxylate | 339 |
| M7 | 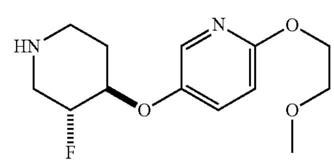 [SMILES: COCCOc1ccc(O[C@@H]2CCNC[C@H]2F)cn1] | 5-(((3R,4R)-3-fluoropiperidin-4-yl)oxy)-2-(2-methoxyethoxy)pyridine | 271 |
| M8 | 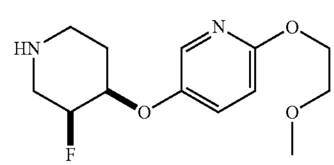 [SMILES: COCCOc1ccc(O[C@@H]2CCNC[C@@H]2F)cn1] | 5-(((3S,4R)-3-fluoropiperidin-4-yl)oxy)-2-(2-methoxyethoxy)pyridine | 271 |

SCHEME N

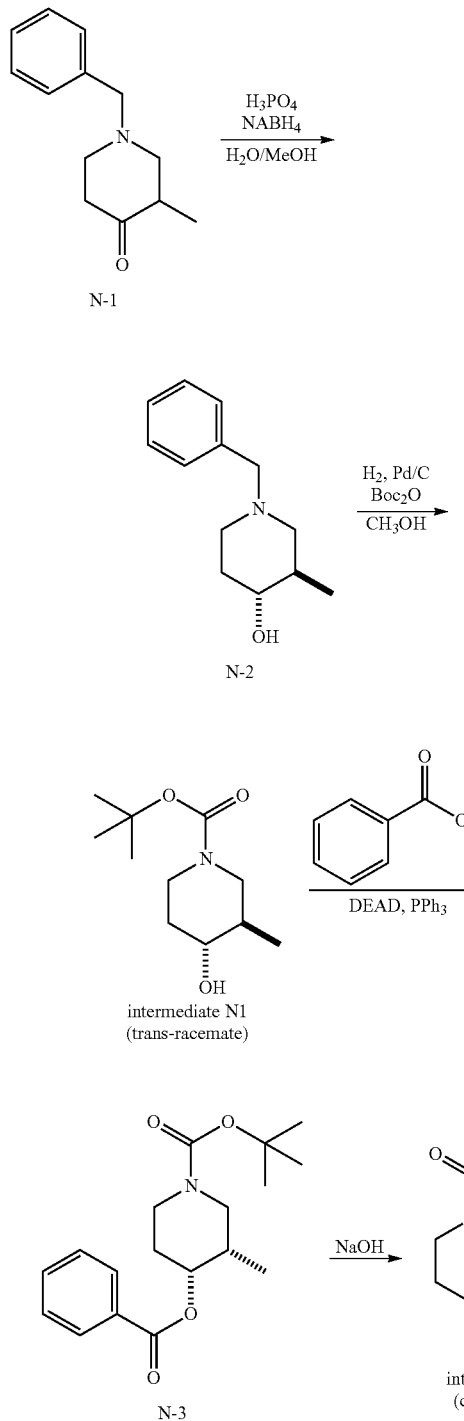

intermediate N1
(trans-racemate)

N-3 intermediate N2
(cis-racemate)

Intermediate N is prepared according to scheme N from piperidone N-1, which is reduced to the alcohol N-2. Reductive conditions in the presence of Boc-anhydride provides intermediate N1 as a trans-racemic mixture. Inversion of the alcohol is accomplished in a two-step procedure of a Mitsunobu reaction with benzoic acid to provide adduct N-3 and saponification to give intermediate N2 as a cis-racemic mixture.

Intermediate N1

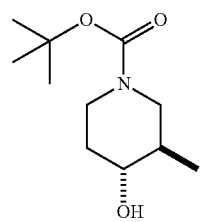

tert-Butyl trans-4-hydroxy-3-methylpiperidine-1-carboxylate
(Scheme N)

Step 1: trans-1-Benzyl-3-methylpiperidin-4-ol

Into a 5 L 4-necked round-bottom flask was placed water (1.04 L), methanol (450 mL), and 1-benzyl-3-methylpiperidin-4-one (150 g, 739 mmol). This was followed by the addition of $H_3PO_4$ (85.1 g, 738 mmol, 85%) dropwise with stirring at −10° C. $NaBH_4$ (56.0 g, 1.47 mol) was added in portions at −10° C. over 5 h. The resulting solution was stirred for 16 h at RT. The pH of the solution was adjusted to ~9 with 5 M aqueous sodium hydroxide. The resulting solution was extracted with ethyl acetate (200 mL×3). The organic layers were combined and treated with 2 M HCl to pH-5. The aqueous layer was adjusted to pH-9 with 5 M aqueous sodium hydroxide. The resulting solution was extracted with ethyl acetate (200 mL×3). The organic layers were combined, washed with brine (300 mL×2), dried over anhydrous sodium sulfate and concentrated in vacuo.

Step 2: tert-Butyl trans-4-hydroxy-3-methylpiperidine-1-carboxylate

Into a 2 L 4-necked round-bottom flask was added methanol (850 mL), Pd/C carbon (10%, 25 g), trans-1-benzyl-3-methylpiperidin-4-ol (56 g, 273 mmol) and di-tert-butyl dicarbonate (65.5 g, 300 mmol) under an atmosphere of nitrogen. The resulting mixture was stirred for 20 h under an atmosphere of $H_2$ at RT. The solids were removed by filtration and the filtrate was concentrated under vacuum. The residue was dissolved in DCM (500 mL) and was washed with water (300 mL) and brine (300 mL). The organic phase was dried over anhydrous $Na_2SO_4$ and concentrated under vacuum to yield the title compound. $^1$H NMR (400 MHz, $CDCl_3$): δ 0.93-1.01 (3H, m), 1.30-1.53 (11H, m), 1.89-1.92 (1H, d, J=12.8 Hz), 2.43-2.49 (1H, m), 2.80-2.86 (1H, m), 3.27-3.32 (1H, m), 3.94-4.05 (2H, m).

Intermediate N2

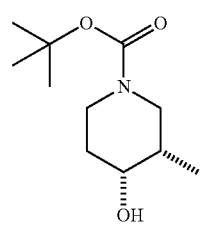

tert-Butyl cis-4-hydroxy-3-methylpiperidine-1-carboxylate
(Scheme N)

Step 1: tert-Butyl cis-4-(benzoyloxy)-3-methylpiperidine-1-carboxylate

To a 5 L 4-necked round-bottom flask was placed tetrahydrofuran (853 mL), benzoic acid (101.5 g, 832 mmol), triphenylmethane (217.8 g, 831 mmol) and trans-tert-butyl 4-hydroxy-3-methylpiperidine-1-carboxylate (135.3 g, 629 mmol, intermediate N1). Diethyl azodicarboxylate (144.8 g, 832.2 mmol) in tetrahydrofuran (500 mL) was added dropwise to the reaction at 0° C. The resulting solution was stirred 15 h at RT. The resulting mixture was concentrated under vacuum and the residue was applied directly onto a silica gel column (0:1-1:20 ethyl acetate:petroleum ether) to yield the title compound.

Step 2: tert-Butyl cis-4-hydroxy-3-methylpiperidine-1-carboxylate

To a 5-L 3-necked round-bottom flask was placed methanol (3.5 L), sodium hydroxide (109 g, 2.72 mol), and tert-butyl cis-4-(benzoyloxy)-3-methylpiperidine-1-carboxylate (173.5 g, 544 mmol) in methanol. The resulting solution was stirred for 2 h at RT before removing volatiles under reduced pressure. The residue was partitioned with EtOAc (1 L) and water (500 mL). The organic layer was washed with water (500 mL) and brine (500 mL), dried over anhydrous sodium sulfate and concentrated in vacuo. The residue was applied onto a silica gel column and eluted with (1:10-1:5 ethyl acetate:petroleum ether) to provide the title compound. $^1$H NMR (400 MHz, CDCl$_3$): δ 0.93-1.00 (3H, m), 1.46 (9H, m), 1.62-1.69 (2H, m), 1.74-1.80 (1H, m), 3.03-3.09 (1H, m), 3.30-3.36 (1H, m), 3.50-3.58 (2H, m), 3.87-3.88 (1H, m).

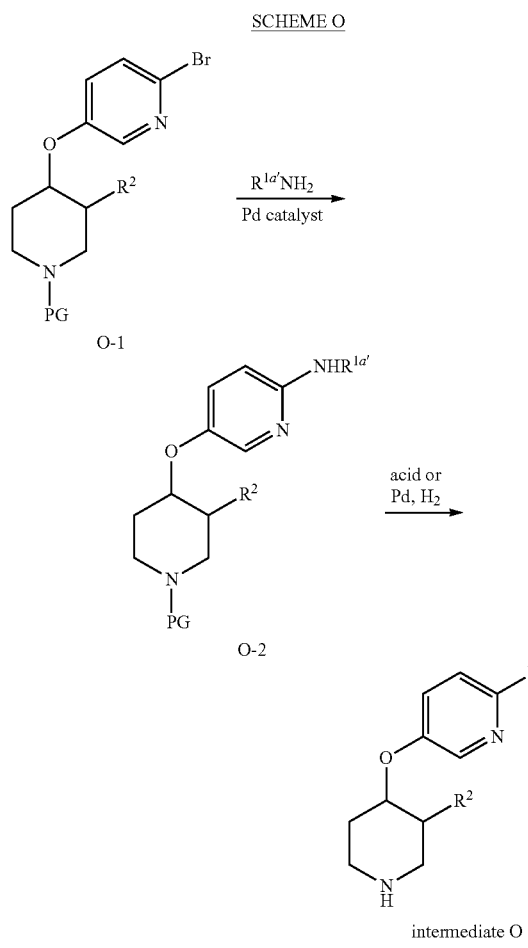

intermediate O

Intermediate O is prepared according to scheme O from ether O-1, which is prepared using 6-bromopyridin-3-ol in step 1 of the procedure outlined in the synthesis of intermediate F. Palladium-mediated C—N arylation with a commercially available amine provides adduct O-2. Deprotection of piperidine amine O-2 provides intermediate O.

Intermediate O

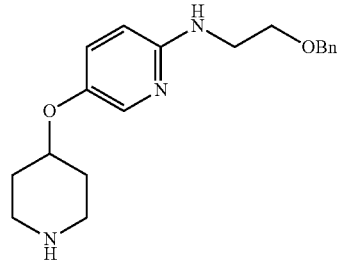 [SMILES: c1ccc(COCCNc2ccc(OC3CCNCC3)cn2)cc1]

N-(2-(benzyloxy)ethyl)-5-(piperidin-4-yloxy)pyridin-2-amine (Scheme O)

Step 1: tert-Butyl 4-((6-bromopyridin-3-yl)oxy)piperidine-1-carboxylate

To a solution of 6-bromopyridin-3-ol (2 g, 11.5 mmol), tert-butyl 4-hydroxypiperidine-1-carboxylate (2.78 g, 13.79 mmol) and (E)-di-tert-butyl diazene-1,2-dicarboxylate (3.97 g, 17.24 mmol) in toluene (80 mL) was added triphenylphosphine (4.52 g, 17.24 mmol). The reaction mixture was stirred at 80° C. for 15 h before volatiles were removed under reduced pressure. The crude material was purified by silica gel chromatography (0-10% EtOAc in petroleum ether) to yield the title compound.

Step 2: tert-Butyl 4-((6-((2-(benzyloxy)ethyl)amino)pyridin-3-yl)oxy)piperidine-1-carboxylate To a solution of tert-butyl 4-((6-bromopyridin-3-yl)oxy)piperidine-1-carboxylate (200 mg, 0.280 mmol), 2-(benzyloxy)ethanamine (50.8 mg, 0.336 mmol), sodium 2-methylpropan-2-olate (81 mg, 0.840 mmol), and 2-(dicyclohexylphosphino)-2',4',6'-triisopropylbiphenyl (13.34 mg, 0.028 mmol) in THF (5 mL) was added tris(dibenzylideneacetone)dipalladium(0) (25.6 mg, 0.028 mmol). The reaction mixture was stirred at 70° C. for 15 h before cooling to RT and partitioning with water (10 mL) and EtOAc (10 mL×3). The combined organic layers were washed with water (20 mL×3), dried with anhydrous sodium sulfate, filtered and concentrated under reduced pressure. The residue was purified by prep-TLC (1/1 EtOAc/petroleum ether) to provide the title compound.

Step 3: N-(2-(benzyloxy)ethyl)-5-(piperidin-4-yloxy)pyridin-2-amine

To a solution of tert-butyl 4-((6-((2-(benzyloxy)ethyl)amino)pyridin-3-yl)oxy)piperidine-1-carboxylate (100 mg, 0.234 mmol) in DCM (5 mL) was added TFA (0.5 mL). The reaction mixture was stirred at 10° C. for 1 h and the solvent was evaporated under reduced pressure to give the title compound that was used without further purification. MS: 328 (M+1).

SCHEME P

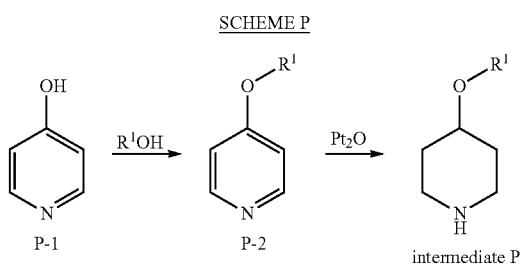

Intermediate P is prepared from 4-pyridinol P-1 which is transformed to ether P-2 via an Mitsunobu reaction with a commerically available alcohol. Hydrogenation of piperidine P-2 with a platinum catalyst provides intermediate P.

Intermediate P1

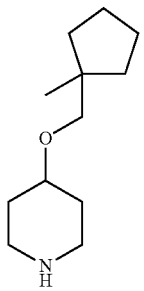

4-((1-Methylcyclopentyl)methoxy)piperidine
(Scheme P)

Step 1: 4-((1-Methylcyclopentyl)methoxy)pyridine

To a solution of (1-methylcyclopentyl)methanol (100 mg, 0.87 mmol), pyridin-4-ol (100 mg, 1.05 mmol) and triphenylphosphine (345 mg, 1.31 mmol) in toluene (5 mL) was added TBAD (302 mg, 1.31 mmol). The reaction mixture was stirred at 80° C. for 15 h. The reaction mixture cooled and then directly purified by prep-TLC (1/1 EtOAc/petroleum ether) to yield the title compound.

Step 2: 4-((1-Methylcyclopentyl)methoxy)piperidine

To a solution of 4-((1-methylcyclopentyl)methoxy)pyridine (30 mg, 0.157 mmol) in AcOH (5 mL) was added platinum(IV) oxide (3.56 mg, 0.016 mmol). The reaction mixture was stirred at 15° C. for 15 h under an atmosphere of $H_2$ (50 psi). The reaction mixture was filtered and the filtrate was evaporated under reduced pressure to give the title compound, which was used without further purification. MS: 198 (M+1).

The following intermediates in table P were prepared according to scheme P using the procedure outlined in the synthesis of intermediate P1 using commercially available alcohols in step 1.

TABLE P

| Intermediate | Structure | Name | MS (M + 1) |
|---|---|---|---|
| P2 | 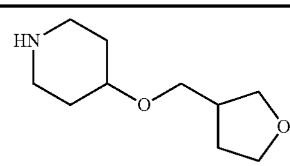 | methyl 2-cyano-5-methyl-6-(4-((tetrahydrofuran-3-yl)methoxy)piperidin-1-yl)nicotinate | 186 |
| P3 | 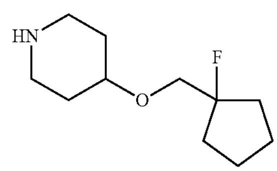 [SMILES: FC1(COC2CCNCC2)CCCC1] | 4-((1-fluorocyclopentyl)methoxy)piperidine | 202 |
| P4 | 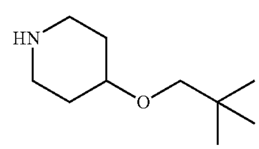 | 4-(neopentyloxy)piperidine | 172 |
| P5 | 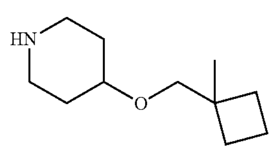 | 4-((1-methylcyclobutyl)methoxy)piperidine | 184 |
| P6 | 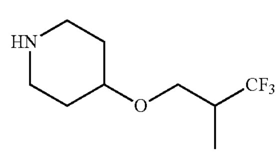 | 4-(3,3,3-trifluoro-2-methylpropoxy)piperidine | 212 |

TABLE P-continued

| Intermediate | Structure | Name | MS (M + 1) |
|---|---|---|---|
| P7 | 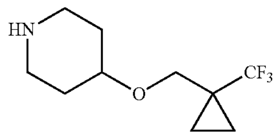 [SMILES: FC(F)(F)C1(COC2CCNCC2)CC1] | 4-((1-(trifluoromethyl)cyclopropyl)methoxy)piperidine | NMR data* |

*¹H NMR (400 MHz, methanol-d₄): δ 3.57-3.69 (1 H, m), 3.31 (2 H, s), 2.87-2.98 (2 H, m), 2.22-2.35 (2 H, m), 1.81-1.90 (2 H, m), 1.53-1.64 (2 H, m), 1.31-1.36 (2 H, m), 0.77-0.90 (2 H, m).

SCHEME Q

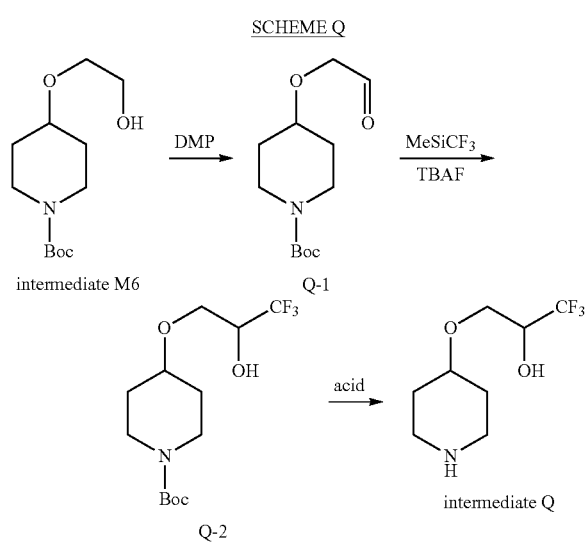

Intermediate Q is prepared from a product from intermediate M6 which is oxidized to the corresponding aldehyde Q-1 after reaction with Dess-Martin periodinane. Nucleophilic trifluoromethylation is carried out with the Ruppert-Prakash reagent in conjunction with TBAF to provide the adduct Q-2. Subsequent deprotection of piperidine Q-2 with an acid provides intermediate Q.

Intermediate Q

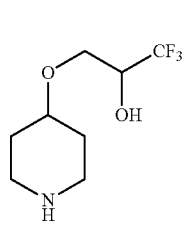 [SMILES: OC(COC1CCNCC1)C(F)(F)F]

1,1,1-Trifluoro-3-(piperidin-4-yloxy)propan-2-ol (Scheme Q)

Step 1: tert-Butyl 4-((6-(2-oxoethoxy)pyridin-3-yl)oxy)piperidine-1-carboxylate To a solution of the tert-butyl 4-((6-(2-hydroxyethoxy)pyridin-3-yl)oxy)piperidine-1-carboxylate (400 mg, 1.18 mmol, intermediate M6) in DCM (2.3 mL) 0° C. was added Dess-Martin periodinane (752 mg, 1.77 mmol). The resulting mixture was stirred at RT for 1 h. The mixture was partitioned with DCM and 1:1 mixture of saturated NaHCO₃ (aq) and 1.5 M Na₂S₂O₃(aq). The organic layer was washed with water, then brine and dried over anhydrous MgSO₄, filtered, and concentrated under reduced pressure to yield the title compound.

Step 2: tert-Butyl 4-((6-(3,3,3-trifluoro-2-hydroxypropoxy)pyridin-3-yl)oxy)piperidine-1-carboxylate A solution of tert-butyl 4-((6-(2-oxoethoxy)pyridin-3-yl)oxy)piperidine-1-carboxylate (300 mg, 0.892 mmol) and CsF (135 mg, 0.892 mmol) in THF (10 mL) was stirred at RT for 1 h. Trimethyl(trifluoromethyl)silane (127 mg, 0.892 mmol) was added and the reaction was stirred for 16 h. The mixture was treated with TBAF (1.78 mL, 1.78 mmol) and was stirred for 30 min and the volatiles were removed to yield the title compound as a crude material that was carried forward without further purification.

Step 3: 1,1,1-Trifluoro-3-(piperidin-4-yloxy)propan-2-ol

To a solution of tert-butyl 4-((6-(3,3,3-trifluoro-2-hydroxypropoxy)pyridin-3-yl)oxy)piperidine-1-carboxylate (200 mg, 0.492 mmol) in DCM (10 mL) was added TFA (2 mL, 26.0 mmol). The mixture was stirred at 20° C. for 1 h. The reaction was concentrated and was purified by HPLC (ACN/water with 0.1% TFA modifier) to give the title compound. MS: 198 (M+1).

SCHEME R

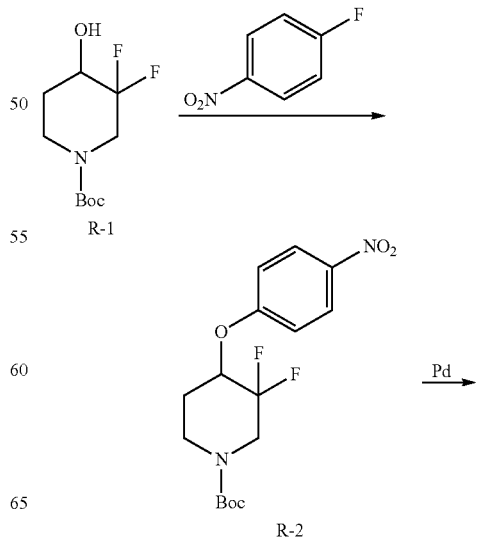

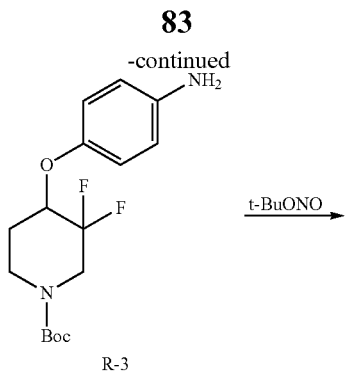

R-3

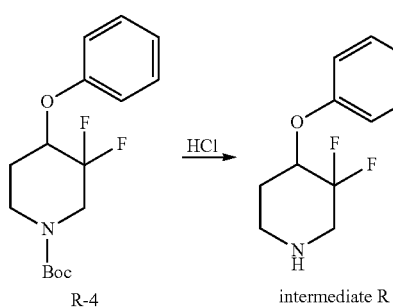

R-4  intermediate R

Intermediate R is prepared via S$_N$Ar reaction of commercially available piperidine R-1 and 1-fluoro-4-nitrobenzene. A two step procedure for the reduction of the aryl nitro R-2 is achieved by a palladium-catalyzed hydrogenation to form aniline R-3 and subsequent diazotization to produce phenyl ether R-4. Acid-mediated deprotection of N-Boc piperidine R-4 provides intermediate R.

Intermediate R

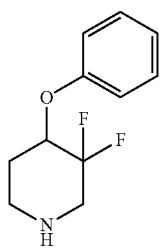

3,3-Difluoro-4-phenoxypiperidine (Scheme R)

Step 1: tert-Butyl 3,3-difluoro-4-(4-nitrophenoxy)piperidine-1-carboxylate

To a solution of tert-butyl 3,3-difluoro-4-hydroxypiperidine-1-carboxylate (800 mg, 3.37 mmol) in THF (8 mL) was added potassium 2-methylpropan-2-olate (757 mg, 6.74 mmol). A solution of 1-fluoro-4-nitrobenzene (523 mg, 3.71 mmol) in DMF (1 mL) was added to the mixture, the reaction was stirred at 50° C. for 5 h under an atmosphere of N$_2$(g). Upon completion the reaction was concentrated and the residue was purified by silica gel chromatography (10/1 petroleum ether/EtOAc) to give the title compound.

Step 2: tert-Butyl 4-(4-aminophenoxy)-3,3-difluoropiperidine-1-carboxylate

To a solution of tert-butyl 3,3-difluoro-4-(4-nitrophenoxy)piperidine-1-carboxylate (840 mg, 2.344 mmol) in EtOAc (15 mL) was added Pd/C (10%, 100 mg, 0.094 mmol). The reaction was stirred at RT under an atmosphere of H$_2$(g) for 4 h. The mixture was filtered and washed with MeOH (20 mL×4) and the filtrate was concentrated to yield the title compound, which was carried forward without further purification.

Step 3: tert-Butyl 3,3-difluoro-4-phenoxypiperidine-1-carboxylate

To a solution of tert-butyl 4-(4-aminophenoxy)-3,3-difluoropiperidine-1-carboxylate (700 mg, 2.132 mmol) in DMF (10 mL) was added tert-butyl nitrite (440 mg, 4.26 mmol). The resulting mixture was stirred at 50° C. under a N$_2$ atmosphere for 1 h. The reaction mixture was quenched with water (30 mL) and extracted with EtOAc (20 mL×3). The combined organic layers were washed with brine (40 mL), dried over anhydrous sodium sulfate, filtered, and concentrated in vacuo. The residue was purified by silica gel chromatography (50:1-2:1 petroleum ether:EtOAc) to give the title compound.

Step 4: tert-Butyl 3,3-difluoro-4-phenoxypiperidine-1-carboxylate

To a solution of tert-butyl 3,3-difluoro-4-phenoxypiperidine-1-carboxylate (330 mg, 1.05 mmol) in EtOAc (5 mL) was added HCl (4 N in dioxane, 2.0 mL, 24.4 mmol). The reaction was stirred at 27° C. for 1 h before quenching with aqueous NaOH (10 mL, 2 M) and partitioning with EtOAc (10 mL×3). The combined organic layers were washed with brine (10 mL), dried over sodium sulfate, filtered, and concentrated in vacuo to give the title compound. MS: 214 (M+1).

SCHEME S

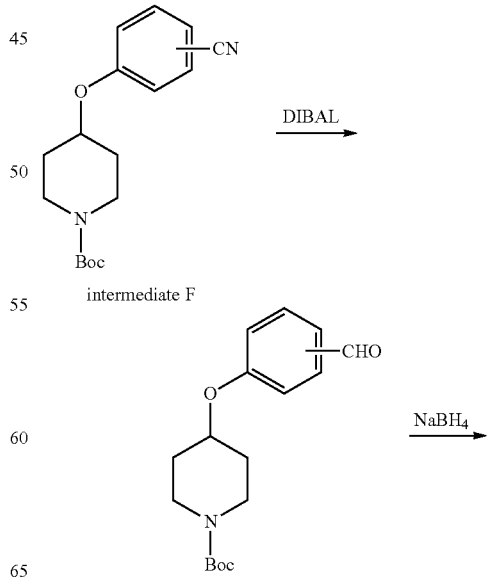

intermediate F

S-2

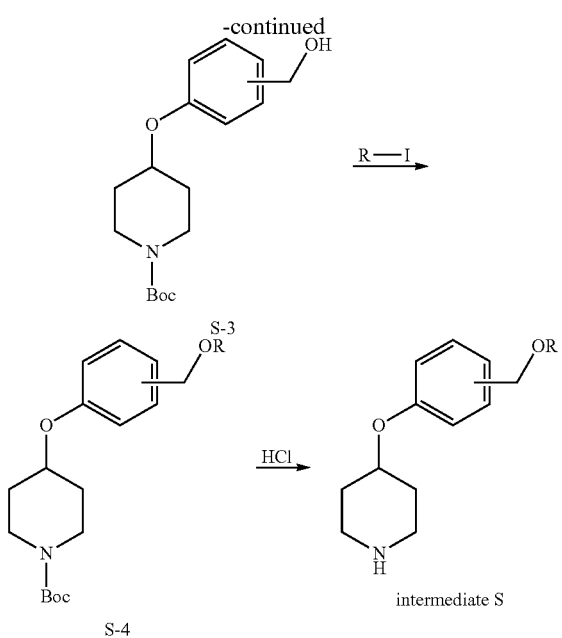

Intermediate S is prepared according to scheme S beginning with intermediate F, which has a nitrile substituent. First, a reduction with DIBAL furnishes aldehyde S-2 and then the corresponding alcohol S-3 is obtained after reaction with sodium borohydride. Alkylation of the alcohol S-3 with a commercially available alkyl iodide provides ether S-4. Acid-mediated deprotection of N-Boc piperidine S-4 provides intermediate S.

Intermediate S1

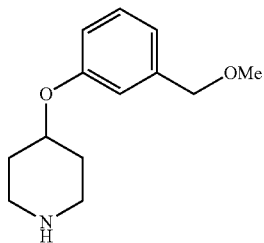 [SMILES: COCc1cccc(OC2CCNCC2)c1]

4-(3-(Methoxymethyl)phenoxy)piperidine (Scheme S)

Step 1: tert-Butyl 4-(3-formylphenoxy)piperidine-1-carboxylate

Diisobutylaluminum hydride (6.61 mL, 6.61 mmol) was added to a stirred, cooled −78° C. mixture of tert-butyl 4-(3-cyanophenoxy)piperidine-1-carboxylate (1 g, 3.31 mmol, intermediate F35) in DCM (20 mL). The mixture was stirred at −78° C. for 1 h and was then quenched with aqueous, saturated Rochelle's salt and partitioned with DCM. The organic layer was washed with brine, dried over anhydrous sodium sulfate and concentrated to give the title compound.

Step 2: tert-Butyl 4-(3-(hydroxymethyl)phenoxy)piperidine-1-carboxylate $NaBH_4$ (40.9 mg, 1.08 mmol) was added to a stirred, cooled 0° C. mixture of tert-butyl 4-(3-formylphenoxy)piperidine-1-carboxylate (220 mg, 0.720 mmol) in methanol (5 mL). The mixture was stirred at 0° C. for 1 h and was concentrated under reduced pressure upon completion. The residue was purified by silica gel column chromatography on silica gel (1/1 EtOAc/hexane) to give the title compound.

Step 3: tert-Butyl 4-(3-(methoxymethyl)phenoxy)piperidine-1-carboxylate

NaH (32.3 mg, 0.807 mmol, 60%) was added to a stirred, cooled 0° C. mixture of tert-butyl 4-(3-(hydroxymethyl)phenoxy)piperidine-1-carboxylate (124 mg, 0.403 mmol) in DMF (5 mL). The mixture was stirred at 0° C. for 15 min before MeI (0.05 mL, 0.807 mmol) was added. The reaction was allowed to gradually warm to RT and was stirred for 2 h. Water and EtOAc were added to the reaction and the organic layer was separated, washed with brine, dried over anhydrous sodium sulfate and concentrated to give the title compound, which was used without further purification.

Step 4: 4-(3-(methoxymethyl)phenoxy)piperidine

HCl (4 N in dioxane, 5 mL, 20.0 mmol) was added to a stirred mixture of tert-butyl 4-(3-(methoxymethyl)phenoxy)piperidine-1-carboxylate (130 mg, 0.403 mmol) in dioxane (5 mL). The mixture was stirred at RT for 12 h and upon reaction completion the volatiles were removed under reduced pressure. The residue was purified by silica gel column chromatography (15/1 DCM/2 N $NH_3$ in MeOH) to yield the title compound. MS: 222 (M+1).

The following intermediates in table S were prepared according to scheme S using the procedure outlined in the synthesis of intermediate S1 using commercially available alkyliodides in step 3.

TABLE S

| Intermediate | Structure | Name | MS (M + 1) |
|---|---|---|---|
| S2 | 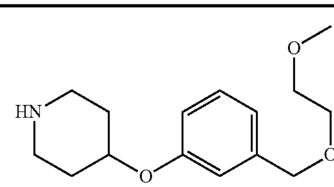 | 4-(3-((2-methoxyethoxy)methyl)phenoxy)piperidine | 266 |

87

SCHEME T

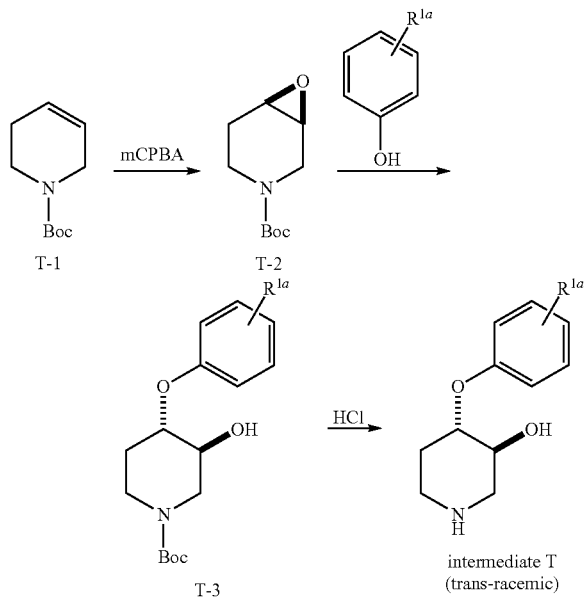

Intermediate T is prepared according to scheme T beginning with olefin T-1, which is reacted with mCPBA to form epoxide T-2. A base-mediated ring-opening reaction with commercial phenol provides adduct T-3, which provides intermediate T after an acid-mediated deprotection.

Intermediate T

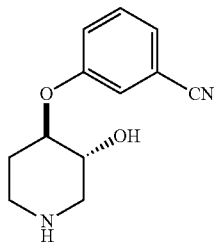 [SMILES: N#Cc1cccc(O[C@@H]2CCNC[C@H]2O)c1]

3-((trans-3-Hydroxypiperidin-4-yl)oxy)benzonitrile
(Scheme T)

Step 1: cis-tert-Butyl 7-oxa-3-azabicyclo[4.1.0]heptane-3-carboxylate

To a 1 L flask, with a large stir bar, is added tert-butyl 5,6-dihydropyridine-1(2H)-carboxylate (24.15 g, 132 mmol) and DCM (440 mL). The vessel is cooled in an ice/water bath and 3-chloroperoxybenzoic acid (45.5 g, 264 mmol) is added in one portion. After stirring for 30 min at 0° C., the cooling bath was removed and the mixture was allowed to stir for 24 h. To the suspension was added aqueous sodium metabisulfite (10%, 200 mL), water (100 mL) and DCM (200 mL) and was then stirred vigorously for 10 min. The organic layer is separated, washed with aqueous 1 N NaOH (3×200 mL), brine (200 mL), dried over anhydrous Na$_2$SO$_4$, filtered and concentrated in vacuo to yield the title compound.

88

Step 2: trans-tert-Butyl 4-(3-cyanophenoxy)-3-hydroxypiperidine-1-carboxylate

To a 1 L flask with stir bar was added aqueous sodium hydroxide (1 M, 9.54 g, 238 mmol), 3-hydroxybenzonitrile (28.4 g, 238 mmol) and water (139 mL). To that solution was added acetonitrile (380 mL) and then a solution of cis-tert-butyl 7-oxa-3-azabicyclo[4.1.0]heptane-3-carboxylate (25 g, 125 mmol) in acetonitrile (37 mL). Heat the reaction to reflux for 15 h. The reaction is cooled to RT and is poured in a separatory funnel containing water (400 mL) and DCM (800 mL). Separate the organic layer and wash with 2 N NaOH(aq) (200 mL), brine (200 mL) and dry over anhydrous Na$_2$SO$_4$, filter and concentrate in vacuo. The crude material was subjected to silica gel chromatography (0-50% EtOAc/hexanes) to yield the title compound.

Step 3: 3-((trans-3-Hydroxypiperidin-4-yl)oxy)benzonitrile hydrochloride

To a 500 mL flask with stir bar was added trans-tert-butyl 4-(3-cyanophenoxy)-3-hydroxypiperidine-1-carboxylate (13.07 g, 41.1 mmol) in dioxane (20 mL). To this solution is then added HCl (200 mL, 4 N in dioxane). The reaction is stirred at RT for 2 h at which point volatiles removed under reduced pressure to yield the title compound. MS: 219 (M+1).

SCHEME U

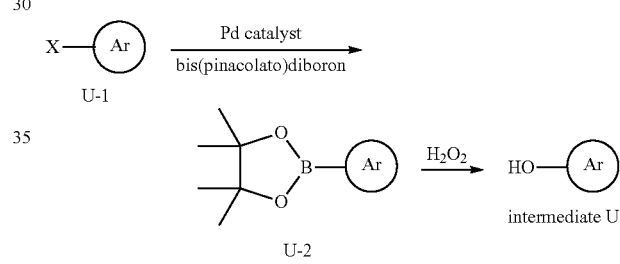

Intermediate U is prepared according to scheme U beginning with commercially available aryl halide U-1. A Miyaura borylation reaction provides boronic ester U-2 which is subsequently transformed by an oxidative hydroxylation to provide intermediate U.

Intermediate U1

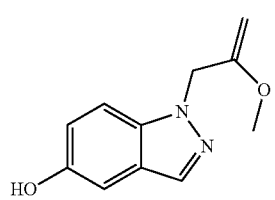

Methyl 2-(5-hydroxy-1H-indazol-1-yl)acetate
(Scheme U)

Step 1: Methyl 2-(1-methyl-5-(4,4,5,5-tetramethyl-1,3,2-dioxaborolan-2-yl)-1H-indazol-3-yl)acetate To a solution of methyl 2-(5-bromo-1-methyl-1H-indazol-3-yl)acetate (200 mg, 0.706 mmol) in dioxane (5 mL)

was added [1,1'-bis(diphenylphosphino)ferrocene]dichloro palladium(II) (51.7 mg, 0.071 mmol), 4,4,4',4',5,5,5',5'-octamethyl-2,2'-bi(1,3,2-dioxaborolane) (359 mg, 1.413 mmol) and potassium acetate (139 mg, 1.413 mmol). The reaction mixture was degassed and purged with nitrogen. The reaction was stirred 2 h at 80° C. and the mixture was filtered and concentrated to give the title compound.

Step 2: Methyl 2-(5-hydroxy-1H-indazol-1-yl)acetate

To a solution of methyl methyl 2-(1-methyl-5-(4,4,5,5-tetramethyl-1,3,2-dioxaborolan-2-yl)-1H-indazol-3-yl)acetate (200 mg, 0.606 mmol) in MeOH (4 mL) was added $H_2O_2$ (35%, 0.265 mL, 3.03 mmol). The mixture was stirred at 25° C. for 16 h. The reaction was quenched with aqueous, saturated $Na_2SO_3$ (10 mL) and then partitioned with water (10 mL) and EtOAc (20 mL×3). The combined organic phases were washed brine (5 mL), dried over anhydrous $Na_2SO_4$, filtered and concentrated. The residue was purified by reverse phase HPLC (ACN/water with 0.1% TFA modifier) to afford the title compound. MS: 221 (M+1).

The following intermediates in table U were prepared according to scheme U using the procedure outlined in the synthesis of intermediate U1 using known or prepared halides. In cases where the boronic ester or acid is commercially available, the first step is omitted.

TABLE U

| Intermediate | Structure | Name | MS (M + 1) |
|---|---|---|---|
| U2 | 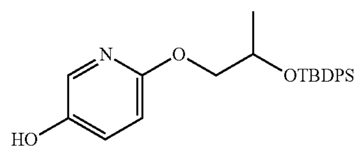 | 6-(2-((tert-butyldiphenylsilyl)oxy) propoxy)pyridin-3-ol | 408 |
| U3 | 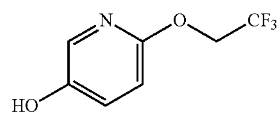 [SMILES: Oc1ccc(OCC(F)(F)F)nc1] | 6-(2,2,2-trifluoroethoxy)pyridin-3-ol | 194 |
| U4 | 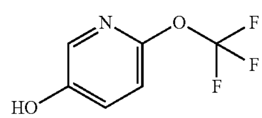 [SMILES: Oc1ccc(OC(F)(F)F)nc1] | 6-(trifluoromethoxy) pyridin-3-ol | 166 |
| U5 | 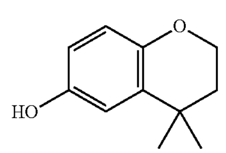 | 4,4-dimethylchroman-6-ol | 178 |
| U6 | 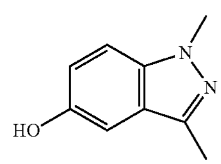 | 1,3-dimethyl-1H-indazol-5-ol | 168 |
| U7 | 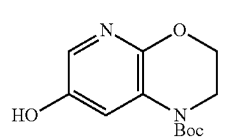 [SMILES: CC(C)(C)OC(=O)N1CCOc2ncc(O)cc21] | tert-butyl 7-hydroxy-2,3-dihydro-1H-pyrido[2,3-b][1,4]oxazine-1-carboxylate | 253 |
| U8 | 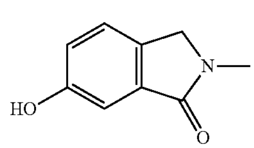 | 6-hydroxy-2-methylisoindolin-1-one | 164 |
| U9 | 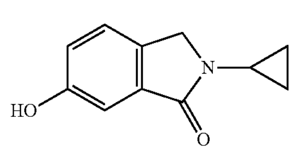 [SMILES: O=C1c2cc(O)ccc2CN1C1CC1] | 2-cyclopropyl-6-hydroxyisoindolin-1-one | 190 |

TABLE U-continued

| Intermediate | Name | MS (M + 1) |
|---|---|---|
| U10 | 6-isopropoxypyridin-3-ol | 154 |
| U11 | 6-cyclobutoxypyridin-3-ol | 166 |
| U12 | isochroman-7-ol | NMR data[1] |
| U13 | 6-((1-((tert-butyldiphenylsilyl)oxy)propan-2-yl)oxy)pyridin-3-ol | 408 |
| U14 | 3-methyl-1-((2-(trimethylsilyl)ethoxy)methyl)-1H-indazol-5-ol | 280 |
| U15 | 2-methyl-1-((2-(trimethylsilyl)ethoxy)methyl)-1H-benzo[d]imidazol-5-ol | 279 |
| U16[2] | 6-hydroxy-3-methyloxazolo[4,5-b]pyridin-2(3H)-one | 167 |
| U17 | 2-(benzyloxy)-2,3-dihydro-1H-inden-5-ol | NMR data[3] |
| U18 | 6-((2-methoxyethoxy)methyl)pyridin-3-ol | 184 |
| U19[4] | 1-((2-(trimethylsilyl)ethoxy)methyl)-1H-pyrazolo[3,4-b]pyridin-5-ol | 266 |
| U20[5] | tert-butyl 7-hydroxy-2,3-dihydro-4H-benzo[b][1,4]oxazine-4-carboxylate | 196[6] |

TABLE U-continued

| Intermediate | Structure | Name | MS (M + 1) |
|---|---|---|---|
| U21 | 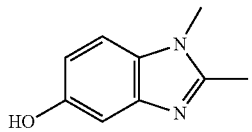 | 1,2-dimethyl-1H-benzo[d]imidazol-5-ol | 163 |
| U22 | 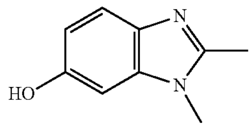 | 1,2-dimethyl-1H-benzo[d]imidazol-6-ol | 163 |
| U23[7] | 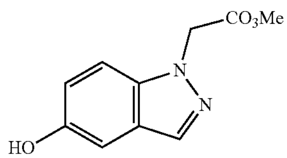 | methyl 2-(5-hydroxy-1H-indazol-1-yl)acetate | 207 |
| U24 | 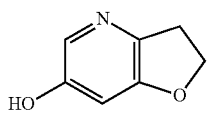 | 2,3-dihydrofuro[3,2-b]pyridin-6-ol | 138 |
| U25 | 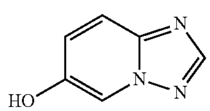 | [1,2,4]triazolo[1,5-a]pyridin-6-ol | 136 |
| U26 | 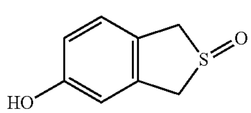 | 5-hydroxy-1,3-dihydrobenzo[c]thiophene 2-oxide | 169 |
| U27[8] | 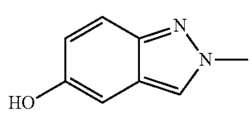 | 2-methyl-2H-indazol-5-ol | 149 |
| U28 | 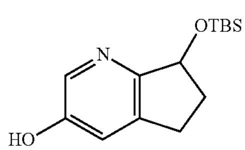 [SMILES: CC(C)(C)[Si](C)(C)OC1CCc2cc(O)cnc21] | 7-((tert-butyldimethylsilyl)oxy)-6,7-dihydro-5H-cyclopenta[b]pyridin-3-ol | 266 |

[1]$^1$H NMR (400 MHz, CDCl$_3$): δ 6.92 (1 H, d, J = 8.0 Hz), 6.59 (1 H, dd, J = 8.0, 2.0 Hz), 6.39 (1 H, s), 5.05 (1 H, br s), 4.65 (2 H, s), 3.89 (2 H, t, J = 6.0 Hz), 2.71 (2 H, t, J = 6.0 Hz).
[2]Starting bromide may be prepared according to literature procedures, see e.g.: Hoveyda, et al., PCT Patent Publ'n WO2011/151434.
[3]$^1$H NMR (400 MHz, CDCl$_3$): δ 7.27-7.42 (5 H, m), 7.03 (1 H, d, J = 8.0 Hz), 6.64 (1 H, s), 6.60 (1 H, d, J = 8.0 Hz), 4.60 (2 H, s), 4.40-4.48 (1 H, m), 3.06-3.17 (2 H, m), 2.92-3.03 (2 H, m).
[4]Starting bromide may be prepared according to literature procedures, see e.g.: Ahrendt, et al., PCT Patent Publ'n WO2009/111279.
[5]Starting bromide may be prepared according to literature procedures, see e.g.: Mori, et al. PCT Patent Publ'n WO2013/151033.
[6]MS Data is for (M + 1 − tBu)
[7]Starting bromide may be prepared according to literature procedures, see e.g.: Abeywardane, et al., PCT Patent Publ'n WO 2014/014874.
[8]Starting bromide may be prepared according to literature procedures, see e.g.: Wang, et al., PCT Patent Publ'n WO2015/065937.

SCHEME V

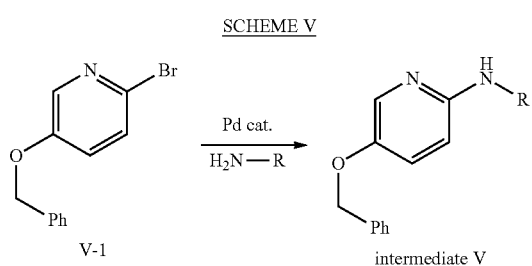

Intermediate V is prepared according to scheme V beginning with known bromide V-1 (Partridge, B. M.; Hartwig, J. F. *Org. Lett.* 2013, 15, 140-143). A palladium-catalyzed coupling reaction with an amine provides intermediate V.

Intermediate V

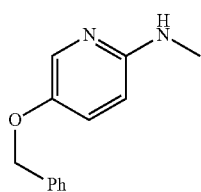 [SMILES: CNc1ccc(OCc2ccccc2)cn1]

5-(Benzyloxy)-N-methylpyridin-2-amine (Scheme V)

To a solution of 5-(benzyloxy)-2-bromopyridine (200 mg, 0.757 mmol), methanamine (70.6 mg, 2.272 mmol) and sodium 2-methylpropan-2-olate (437 mg, 4.54 mmol) in THF (5 mL) was added $Pd_2dba_3$ (69.3 mg, 0.076 mmol) and dicyclohexyl(2',4',6'-triisopropyl-[1,1'-biphenyl]-2-yl)phosphine (36.1 mg, 0.076 mmol). The reaction mixture was stirred at 60° C. for 15 h. The mixture was cooled and diluted with water (10 mL). After the mixture was extracted with EtOAc (10 mL×3), the combined organic fractions were washed with water (20 mL×3), dried (anhydrous $Na_2SO_4$), filtered and concentrated under reduced pressure. The residue was purified by prep-TLC (1/1 petroleum ether/EtOAc) to give the title compound. MS: 215 (M+1).

SCHEME W

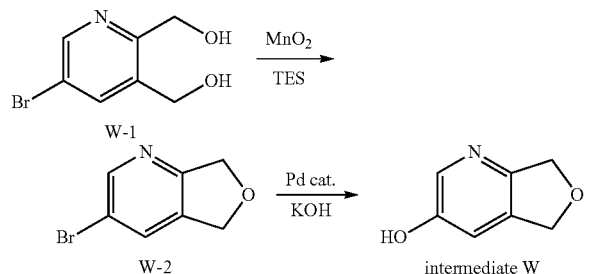

Intermediate W is prepared according to scheme W beginning with commercial diol W-1. A one-pot oxidation, cyclization, and reduction sequence results in the formation of bromide W-2. A palladium-catalyzed hydroxylation provides intermediate W.

Intermediate W

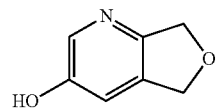

5,7-Dihydrofuro[3,4-b]pyridin-3-ol (Scheme W)

Step 1: 3-Bromo-5,7-dihydrofuro[3,4-b]pyridine

TFA (35.3 mL, 459 mmol) was added to a stirred mixture of (5-bromopyridine-2,3-diyl)dimethanol (10 g, 45.9 mmol) in DCM (100 mL) to form a homogeneous solution. Manganese dioxide (18.76 g, 183 mmol) was added to the reaction and the mixture was stirred for 10 min at RT before the addition of triethylsilane (14.65 mL, 92 mmol). After stirring for 4 h at RT, the reaction was filtered and concentrated. The residue was purified by column chromatography on silica gel (10/1 EtOAc/hexane) to yield the title compound.

Step 2: 5,7-Dihydrofuro[3,4-b]pyridin-3-ol

KOH (841 mg, 15.0 mmol) in water (10 mL) was added to a stirred mixture of 3-bromo-5,7-dihydrofuro[3,4-b]pyridine (500 mg, 2.50 mmol), tris(dibenzylideneacetone)dipalladium-chloroform adduct (388 mg, 0.375 mmol) and BrettPhos (403 mg, 0.750 mmol) in dioxane (10 mL). The reaction was stirred at 150° C. under microwave irradiation for 30 min. After cooling to RT, the reaction was partitioned and the lower layer was separated and concentrated. The residue was purified by column chromatography on silica gel (20/1 DCM/MeOH) to yield the title compound. $^1$H NMR (500 MHz, $CDCl_3$): δ 7.81 (1H, s), 6.94-6.99 (2H, m), 6.88 (1H, d, J=8.3 Hz), 6.24 (1H, s), 4.69 (2H, s), 4.57 (1H, m), 4.37 (2H, s), 3.58 (2H, m), 3.20 (2H, m), 2.37 (3H, s), 2.14 (2H, m), 1.98 (2H, m).

SCHEME X

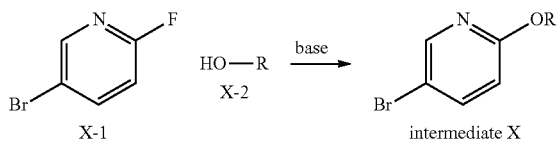

Intermediate X is prepared according to scheme X from an $S_NAr$ reaction of a commercial alcohol with 5-bromo-2-fluoropyridine.

Intermediate X1

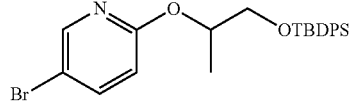

5-Bromo-2-((1-((tert-butyldiphenylsilyl)oxy)propan-2-yl)oxy)pyridine (Scheme X)

To a solution of 1-((tert-butyldiphenylsilyl)oxy)propan-2-ol (9.83 g, 31.3 mmol) in THF (50 mL) was added LHMDS (1 M in THF, 31.3 mL, 31.3 mmol) dropwise at 0° C. under a nitrogen atmosphere. After stirring for 20 min, 5-bromo-2-fluoropyridine (5 g, 28.4 mmol) in THF (5 mL) was added to the reaction. The reaction was allowed to warm to RT and was heated to 70° C. and stirred for 24 h. The reaction was quenched with saturated, aqueous NH$_4$Cl (10 mL) and partitioned with water (50 mL) and EtOAc (50 mL×3). The combined organic layers were dried over anhydrous Na$_2$SO$_4$, filtered and concentrated. The residue was purified by silica gel chromatography (0-25% EtOAc in petroleum ether) to give the title compound. MS: 470, 472 (M+1).

The following intermediates in table X were prepared according to scheme X using the procedure outlined in the synthesis of intermediate X1 using known alcohols.

Step 2: Bicyclo[1.1.1]pentan-1-ylmethyl methanesulfonate

To a solution of bicyclo[1.1.1]pentan-1-ylmethanol (219 mg, 0.00 mmol) and Et$_3$N (0.933 mL, 6.69 mmol) in THF (2 mL) was added Ms-Cl (0.348 mL, 4.46 mmol) at 0° C. The reaction was allowed to warm to RT and was stirred for 15 h. The mixture was treated with water (2 mL) and extracted with EtOAc (10 mL×3). The combined organic layers were dried over anhydrous Na$_2$SO$_4$, filtered and concentrated. The residue was purified by prep-TLC (5/1 petroleum ether/EtOAc) to yield the title compound. $^1$H NMR (400 MHz, CDCl$_3$): δ 4.13 (2H, s), 3.00 (3H, s), 2.56 (1H, s), 1.83 (6H, s).

TABLE X

| Intermediate | Structure | Name | MS (M + 1) |
|---|---|---|---|
| X2 | 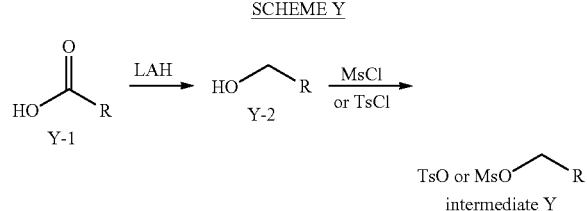 | 5-bromo-2-(2-((tert-butyldiphenylsilyl)oxy)propoxy)pyridine | 470, 472 |

SCHEME Y

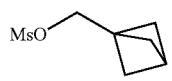

Intermediate Y is prepared according to scheme Y from the reduction of a commercial acid Y-1. Alcohol Y-2 is transformed into intermediate Y after exposure to mesyl or tosyl chloride in the presence of base.

Intermediate Y1

Bicyclo[1.1.1]pentan-1-ylmethyl methanesulfonate (Scheme Y)

Step 1: Bicyclo[1.1.1]pentan-1-ylmethanol

To a solution of bicyclo[1.1.1]pentane-1-carboxylic acid (250 mg, 2.230 mmol) in THF (1 mL) was added LiAlH$_4$ (127 mg, 3.34 mmol) at 0° C. The reaction was allowed to warm to RT and was stirred for 1 h before quenching with water (0.25 mL) and anhydrous Na$_2$SO$_4$ (1 g). After stirring for 20 min, the mixture was filtered and washed with THF. The crude solution was used directly in the next step without further purification.

The following intermediates in table Y were prepared according to scheme Y using the procedure outlined in the synthesis of intermediate Y. In cases where the alcohol is commercially available, the first step is omitted.

TABLE Y

| Intermediate | Structure | Name | MS (M + 1) |
|---|---|---|---|
| Y2 | 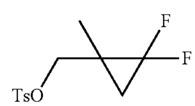 [SMILES: Cc1ccc(S(=O)(=O)OCC2(C)CC2(F)F)cc1] | (2,2-difluoro-1-methylcyclopropyl)methyl 4-methylbenzenesulfonate | 277 |
| Y3 | 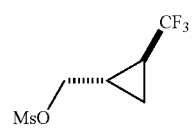 [SMILES: CS(=O)(=O)OC[C@H]1C[C@@H]1C(F)(F)F] | ((trans)-2-(trifluoromethyl)cyclopropyl)methyl methanesulfonate | 295 |
| Y4 | 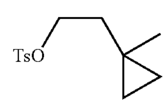 [SMILES: Cc1ccc(S(=O)(=O)OCCC2(C)CC2)cc1] | 2-(1-methylcyclopropyl)ethyl 4-methylbenzenesulfonate | 255 |

SCHEME Z

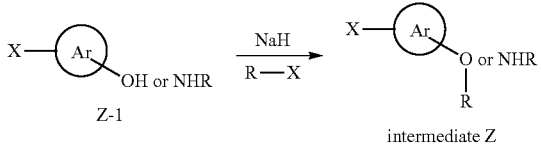

Intermediate Z is prepared according to scheme Z from a base-mediated alkylation of a commercial heterocycle Z-1 (wherein Ar is an aromatic or heteroaromatic ring of R$^1$).

Intermediate Z1

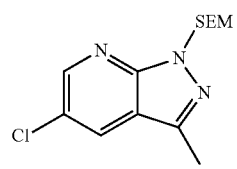 [SMILES: Cc1nn(COCC[Si](C)(C)C)c2ncc(Cl)cc12]

5-Chloro-3-methyl-1-((2-(trimethylsilyl)ethoxy)methyl)-1H-pyrazolo[3,4-b]pyridine (Scheme Z)

To a solution of compound 5-chloro-3-methyl-1H-pyrazolo[3,4-b]pyridine (200 mg, 1.193 mmol) in THF (3 mL) was added NaH (60%, 52.5 mg, 1.31 mmol) at 0° C. After 30 min, SEM-Cl (0.254 mL, 1.432 mmol) was added to the mixture at 0° C. and the reaction was allowed to warm and stir at RT for 16 h. The mixture was diluted with saturated NH$_4$Cl(aq) and extracted with EtOAc (3×10 mL). The combined organic layers were washed with brine and dried over anhydrous Na$_2$SO$_4$ before being concentrated to dryness. The residue was purified by silica gel chromatography (0-10% EtOAc in petroleum ether) give the title compound. MS: 298 (M+1).

The following intermediates in table Z were prepared according to scheme Z using the procedure outlined in the synthesis of intermediate Z1 using a commercial or known reagents.

TABLE Z

| Intermediate | Structure | Name | MS (M + 1) |
|---|---|---|---|
| Z2 | 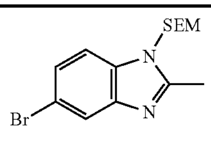 | 5-bromo-2-methyl-1-((2-(trimethylsilyl)ethoxy)methyl)-1H-benzo[d]imidazole | 341, 343 |
| Z3 | 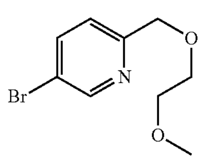 | 5-bromo-2-((2-methoxyethoxy)methyl)pyridine | 246, 248 |
| Z4 | 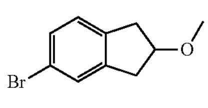 | 5-bromo-2-methoxy-2,3-dihydro-1H-indene | NMR data[1] |
| Z5[2] | 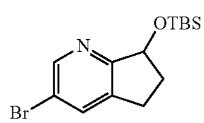 | 3-bromo-7-((tert-butyldimethylsilyl)oxy)-6,7-dihydro-5H-cyclopenta[b]pyridine | 329 |
| Z6 | 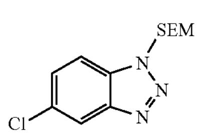 [SMILES: C[Si](C)(C)CCOCn1nnc2cc(Cl)ccc21] | 5-chloro-1-((2-(trimethylsilyl)ethoxy)methyl)-1H-benzo[d][1,2,3]triazole | 284 |

[1]$^1$H NMR (400 MHz, CDCl$_3$): δ 7.33 (1 H, s), 7.26 (1 H, s), 7.06 (1 H, d, J = 7.6 Hz), 4.19-4.23 (1 H, m), 3.34 (3 H, s), 3.03-3.15 (2 H, m), 2.91-2.98 (2 H, m).
[2]Starting bromide may be prepared according to literature procedures, see e.g.: Bara, et al., PCT Patent Publ'n WO2015/084692.

Scheme AA

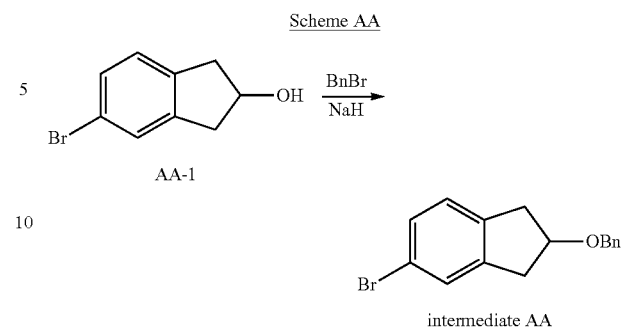

Intermediate AA is prepared according to scheme AA from a base-mediated alkylation of a commercial indane AA-1.

Intermediate AA

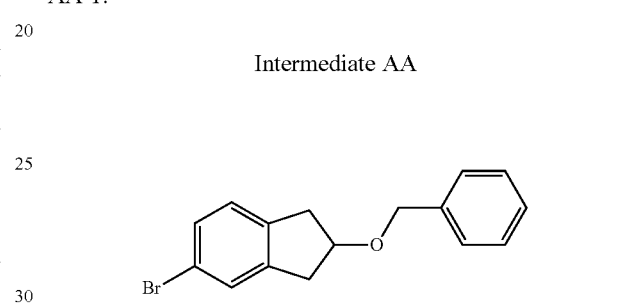

2-(Benzyloxy)-5-bromo-2,3-dihydro-1H-indene (Scheme AA)

To a solution of NaH (60%, 160 mg, 3.99 mmol) in dry THF (5 mL) at 0° C. was added a solution of 5-bromo-2,3-dihydro-1H-inden-2-ol (500 mg, 2.347 mmol) in dry THF (5 mL). The resulting solution was stirred for 30 min at 0° C. Benzyl bromide (0.335 mL, 2.82 mmol) was added and the solution was stirred at 25° C. for 15 h. The mixture was quenched by saturated, aqueous ammonium chloride (10 mL), which was extracted with EtOAc (40 mL×3). The combined organic layers were washed by brine (15 mL×3) and concentrated to give the crude product, which was purified by silica gel chromatography (1:0-10:1 petroleum ether:EtOAc) to afford the title compound. $^1$H NMR (400 MHz, CDCl$_3$): δ 7.25-7.37 (7H, m), 7.07 (1H, d, J=8.0 Hz), 4.57 (2H, s), 4.38-4.47 (1H, m), 2.95-3.23 (4H, m).

SCHEME BB

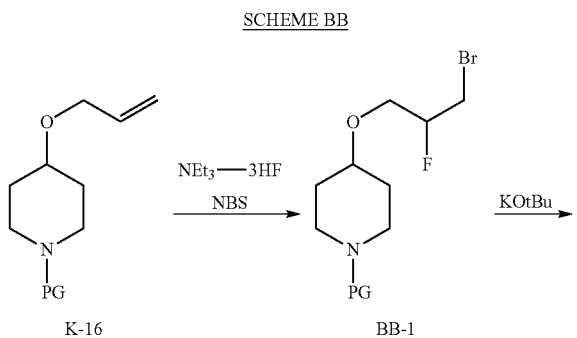

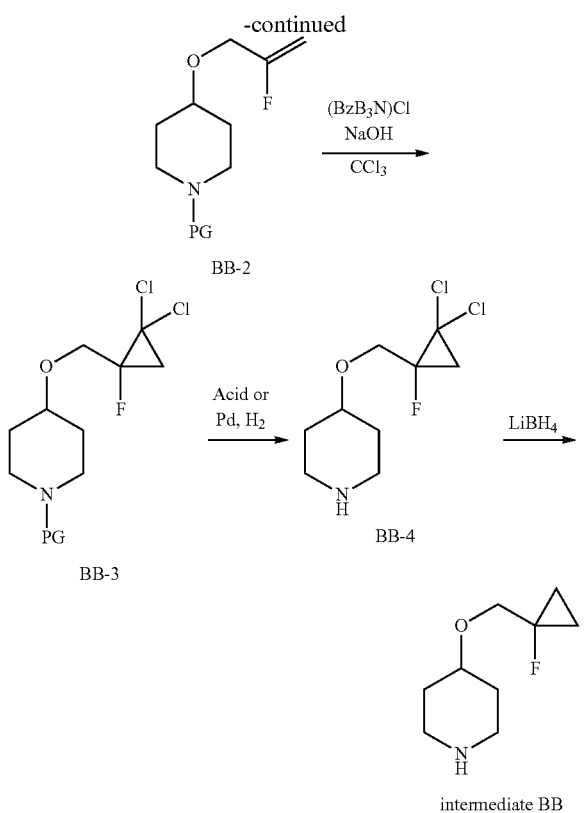

Intermediate BB is prepared according to scheme BB from prepared intermediate K16 which was reacted with triethylamine trihydrofluoride to yield trans-fluorobromination product BB-1. Elimination with a strong base provides allyl fluoride BB-2, which subjected to chlorocyclopanation reaction conditions to give BB-3. Deprotection of the piperidine provides BB-4 and a subsequent reduction provides intermediate BB.

Intermediate BB

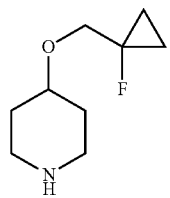 [SMILES: FC1(COC2CCNCC2)CC1]

4-((1-Fluorocyclopropyl)methoxy)piperidine
(Scheme BB)

Step 1: Benzyl 4-(3-bromo-2-fluoropropoxy)piperidine-1-carboxylate

To a solution of benzyl 4-(allyloxy)piperidine-1-carboxylate (4.2 g, 15.3 mmol) in DCM (100 mL) was added NBS (4.07 g, 22.9 mmol). At 0° C., triethylamine trihydrofluoride (9.84 g, 61 mmol) was added dropwise to the mixture before warming to RT and stirring for 16 h. The reaction mixture was quenched with water (100 mL) and extracted with DCM (3×100 mL). The combined organic layers were washed with brine, dried over anhydrous sodium sulfate and concentrated. The resultant residue was purified by silica gel chromatography (0-20% EtOAc in petroleum ether) to give the title compound.

Step 2: Benzyl 4-((2-fluoroallyl)oxy)piperidine-1-carboxylate

To a solution of benzyl 4-(3-bromo-2-fluoropropoxy)piperidine-1-carboxylate (18 g, 48.1 mmol) in THF (100 mL) was added potassium 2-methylpropan-2-olate (5.40 g, 48.1 mmol) at 0° C. The mixture was stirred at 20° C. for 16 h before quenching with water (100 mL). The mixture was extracted with EtOAc (3×100 mL) and the combined organic layers were washed with brine, dried over anhydrous sodium sulfate and concentrated. The resultant residue was purified by silica gel chromatography (0-20% EtOAc in petroleum ether) to give the title compound.

Step 3: Benzyl 4-((2,2-dichloro-1-fluorocyclopropyl)methoxy)piperidine-1-carboxylate To a solution of benzyl 4-((2-fluoroallyl)oxy)piperidine-1-carboxylate (1.5 g, 5.11 mmol) in CCl₃ (15 mL) was added N-benzyl-N,N-dibutylbutan-1-aminium chloride (0.160 g, 0.511 mmol). An aqueous sodium hydroxide (50%, 1.64 g, 20.45 mmol) was added dropwise to the mixture at 0° C. and the mixture was stirred at 15° C. for 16 h. The reaction was quenched by water (20 mL) and partitioned with DCM (3×10 mL). The combined organic layers were washed with brine, dried over anhydrous sodium sulfate, filtered and concentrated. The resultant residue was purified by silica gel chromatography (0-50% EtOAc in petroleum ether) to give the title compound.

Step 4: 4-((2,2-Dichloro-1-fluorocyclopropyl)methoxy)piperidine

A solution of benzyl 4-((2,2-dichloro-1-fluorocyclopropyl)methoxy)piperidine-1-carboxylate (600 mg, 1.595 mmol) in THF (30 mL) with Pd/C (16.97 mg, 0.159 mmol) was stirred at 40° C. for 2 h under an atmosphere of hydrogen. The reaction mixture was filtered and concentrated to give the crude title compound, which was carried forward without purification.

Step 5: 4-((1-Fluorocyclopropyl)methoxy)piperidine

To a solution of compound 4-((2,2-dichloro-1-fluorocyclopropyl)methoxy)piperidine (300 mg, 1.239 mmol) in THF (2 mL) was added LiAlH₄ (188 mg, 4.96 mmol) at 0° C. After stirring for 4 hr at 15° C., additional LiAlH₄ (188 mg, 4.96 mmol) was added. The reaction was stirred for 16 h before quenching with water (0.3 mL) and filtering off insolubles. The filtrate was concentrated to provide the title compound. MS: 174 (M+1).

SCHEME CC

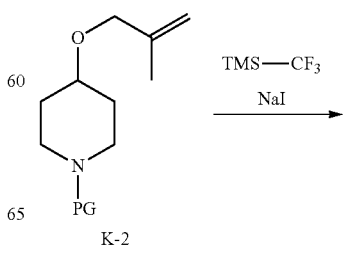

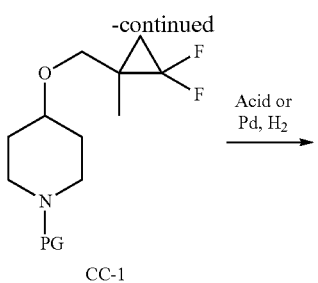

CC-1

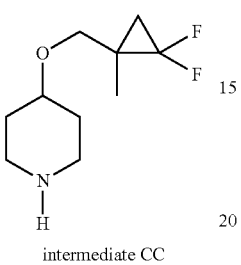

intermediate CC

Intermediate CC is prepared according to scheme CC from prepared intermediate K2 which was reacted with the Ruppert-Prakash reagent in the presence of sodium iodide to yield cyclopropyl adduct CC-1. Deprotection of the piperidine provides intermediate CC.

Intermediate CC

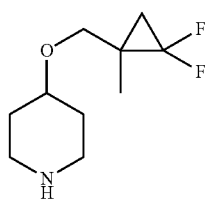

4-((2,2-Difluoro-1-methylcyclopropyl)methoxy) piperidine (Scheme CC)

Step 1: Benzyl 4-((2,2-difluoro-1-methylcyclopropyl)methoxy)piperidine-1-carboxylate Sodium iodide (200 mg, 1.33 mmol) was added to a solution of benzyl 4-((2-methylallyl)oxy)piperidine-1-carboxylate (1.163 g, 4.02 mmol) in THF (9 mL) under a nitrogen atmosphere in a pressure vessel. (Trifluoromethyl)trimethylsilane (2.0 mL, 14.1 mmol) was added, the reaction was sealed and was stirred at 65° C. for 15 h. Volatiles were removed under reduced pressure and the residue was purified by silica gel chromatography (5-35% EtOAc in hexanes) to provide the title compound.

Step 2: 4-((2,2-Difluoro-1-methylcyclopropyl)methoxy)piperidine

Benzyl 4-((2,2-difluoro-1-methylcyclopropyl)methoxy)piperidine-1-carboxylate (1.174 g, 3.46 mmol) was dissolved in MeOH (11.5 mL). The flask was evacuated and charged with nitrogen, then Pd/C (20%, 0.243 g, 0.346 mmol) was added to the solution and placed under an atmosphere of hydrogen. After stirring for 2 h, the mixture was filtered through celite and concentrated to provide the title compound. MS: 206 (M+1).

SCHEME DD

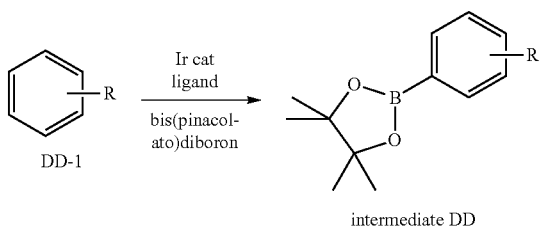

Intermediate DD is prepared according to scheme DD from known aryl compound DD-1 which was borylated via C—H activation using an iridium catalyst.

Intermediate DD

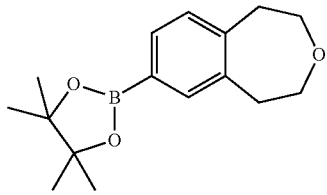 [SMILES: CC1(C)OB(c2ccc3c(c2)CCOCC3)OC1(C)C]

4,4,5,5-tetramethyl-2-(1,2,4,5-tetrahydrobenzo[d]oxepin-7-yl)-1,3,2-dioxaborolane (Scheme DD)

To a solution of 1,2,4,5-tetrahydrobenzo[d]oxepine (100 mg, 0.675 mmol) (for synthesis of this compound, see e.g.: Pehlivan, M. *Eur. J. Org. Chem.* 2012, 25, 4689-4693) and Bis(pinacolato)diboron (274 mg, 1.080 mmol) in dioxane (3 mL) was added (1,5-cyclooctadiene)(methoxy)iridium (I) dimer (44.7 mg, 0.067 mmol) and 4,4'-di-tert-butyl-2,2'-bipyridine (36.2 mg, 0.135 mmol) (18.11 mg, 0.067 mmol). The mixture was stirred at 100° C. for 16 h under an inert atmosphere. The volatiles were removed under reduced pressure and the residue was purified by silica gel chromatography (8-10% THF in petroleum ether) to give the title compound. MS: 275 (M+1).

The following intermediates in table DD were prepared according to scheme DD using the procedure outlined in the synthesis of intermediate DD1 using a commercial or known reagents.

TABLE DD

| Intermediate | Structure | Name | MS (M + 1) |
|---|---|---|---|
| DD2[1] | 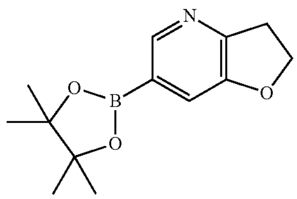 [SMILES: CC1(C)OB(c2cnc3c(c2)OCC3)OC1(C)C] | 6-(4,4,5,5-tetramethyl-1,3,2-dioxaborolan-2-yl)-2,3-dihydrofuro[3,2-b]pyridine | 248 |

[1]Heteroarene may be prepared according to literature procedures, see e.g.: Hayakawa, I.; et al. *Chem. Pharm. Bull.* 1984, 32, 4914-4922.

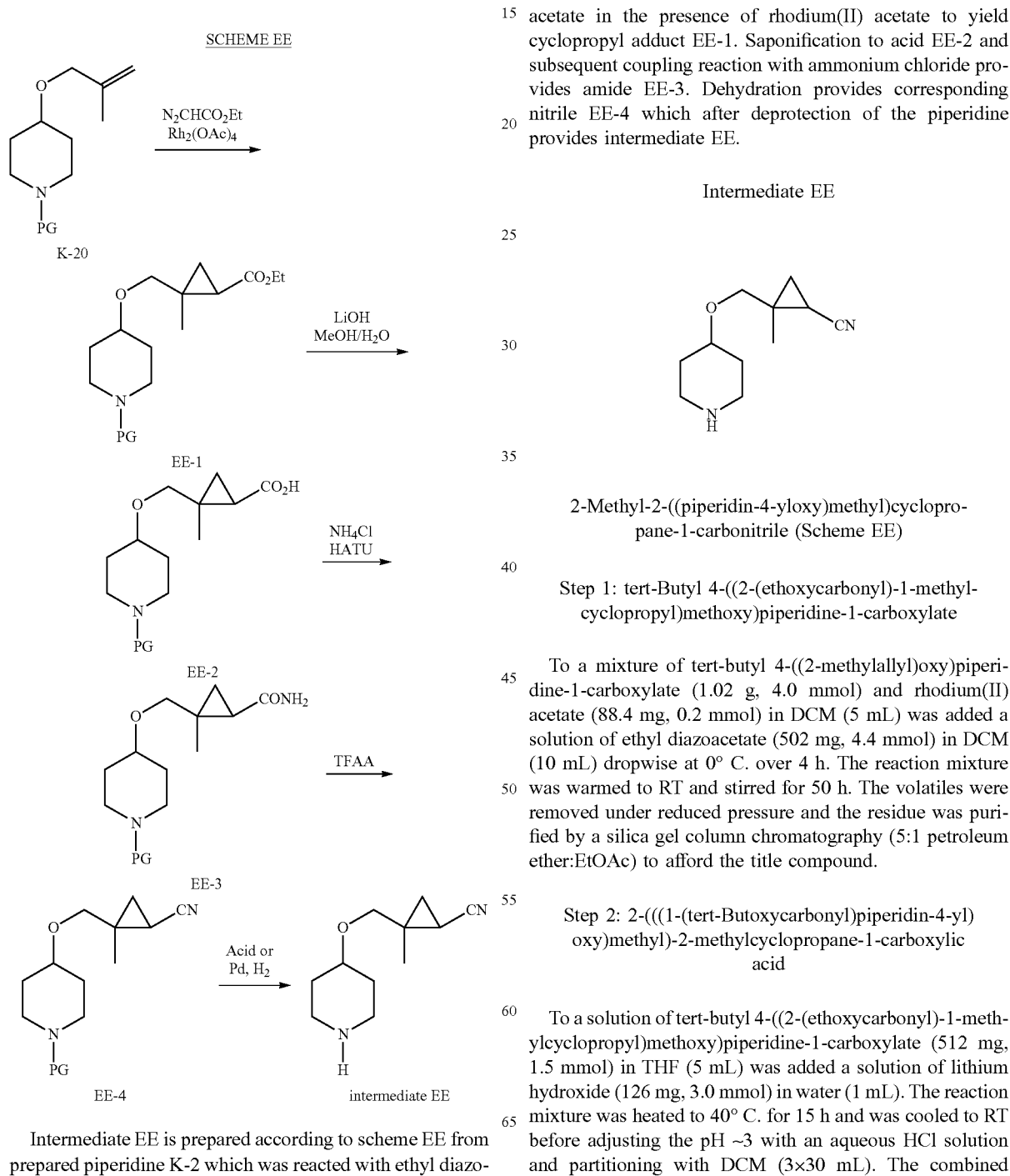

Intermediate EE is prepared according to scheme EE from prepared piperidine K-2 which was reacted with ethyl diazoacetate in the presence of rhodium(II) acetate to yield cyclopropyl adduct EE-1. Saponification to acid EE-2 and subsequent coupling reaction with ammonium chloride provides amide EE-3. Dehydration provides corresponding nitrile EE-4 which after deprotection of the piperidine provides intermediate EE.

Intermediate EE

2-Methyl-2-((piperidin-4-yloxy)methyl)cyclopropane-1-carbonitrile (Scheme EE)

Step 1: tert-Butyl 4-((2-(ethoxycarbonyl)-1-methylcyclopropyl)methoxy)piperidine-1-carboxylate To a mixture of tert-butyl 4-((2-methylallyl)oxy)piperidine-1-carboxylate (1.02 g, 4.0 mmol) and rhodium(II) acetate (88.4 mg, 0.2 mmol) in DCM (5 mL) was added a solution of ethyl diazoacetate (502 mg, 4.4 mmol) in DCM (10 mL) dropwise at 0° C. over 4 h. The reaction mixture was warmed to RT and stirred for 50 h. The volatiles were removed under reduced pressure and the residue was purified by a silica gel column chromatography (5:1 petroleum ether:EtOAc) to afford the title compound.

Step 2: 2-(((1-(tert-Butoxycarbonyl)piperidin-4-yl)oxy)methyl)-2-methylcyclopropane-1-carboxylic acid To a solution of tert-butyl 4-((2-(ethoxycarbonyl)-1-methylcyclopropyl)methoxy)piperidine-1-carboxylate (512 mg, 1.5 mmol) in THF (5 mL) was added a solution of lithium hydroxide (126 mg, 3.0 mmol) in water (1 mL). The reaction mixture was heated to 40° C. for 15 h and was cooled to RT before adjusting the pH ~3 with an aqueous HCl solution and partitioning with DCM (3×30 mL). The combined organic layers were dried over anhydrous sodium sulfate, filtered and concentrated to dryness to yield the title compound.

Step 3: tert-Butyl 4-((2-carbamoyl-1-methylcyclopropyl)methoxy)piperidine-1-carboxylate To a solution of tert-butyl 4-((2-(ethoxycarbonyl)-1-methylcyclopropyl)methoxy)piperidine-1-carboxylate (313 mg, 1.05 mmol) in DCM (10 mL) and triethylamine (320 mg, 3.15 mmol) was added HATU (598 mg, 1.58 mmol). The reaction mixture was stirred for 10 min before ammonium chloride (84 mg, 1.58 mmol) was added at RT. After stirring for 15 h, the reaction was diluted with water (10 mL) and extracted with DCM (3×30 mL). The combined organic layers were dried over anhydrous sodium sulfate, filtered and concentrated to dryness. The resultant residue was purified by a silica gel column chromatography (10:1 DCM:MeOH) to afford the title compound.

Step 4: tert-Butyl 4-((2-cyano-1-methylcyclopropyl)methoxy)piperidine-1-carboxylate To a solution of tert-butyl 4-((2-carbamoyl-1-methylcyclopropyl)methoxy)piperidine-1-carboxylate (320 mg, 1.02 mmol) in THF (5 mL) was added pyridine (324 mg, 4.1 mmol) at 0° C. The reaction mixture was stirred for 10 min before TFAA (514 mg, 2.4 mmol) was added. The system was gradually warmed to RT and was stirred 15 h, before removing volatiles under reduced pressure. The resultant residue was purified by a silica gel column chromatography (2:1 petroleum ether:EtOAc) to afford the title compound.

Step 5: 2-Methyl-2-((piperidin-4-yloxy)methyl)cyclopropane-1-carbonitrile

To a solution of tert-butyl 4-((2-cyano-1-methylcyclopropyl)methoxy)piperidine-1-carboxylate in DCM (10 mL) was added TFA (1 mL, 13.4 mmol) at 0° C. The reaction was stirred for 15 h before the volatiles were removed under reduced pressure to provide the title compound. MS: 195 (M+1).

SCHEME FF

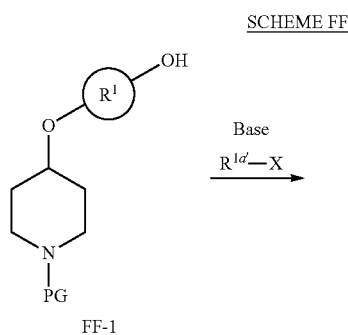

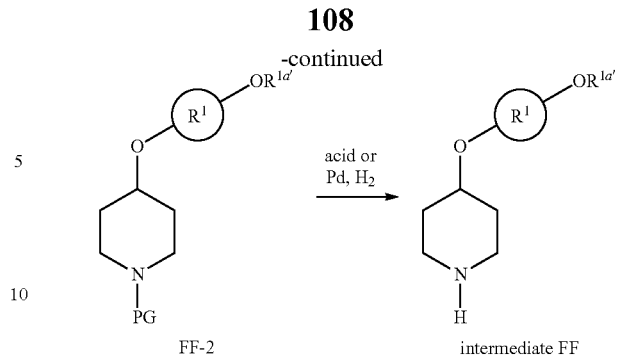

Intermediate FF is prepared according to scheme FF from prepared or known piperidine FF-1 which was reacted with an alkyl halide in the presence of base to provide alkyl adduct FF-2. Deprotection of the piperidine provides intermediate FF.

Intermediate FF

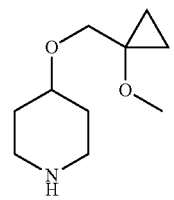

1-((Piperidin-4-yloxy)methyl)cyclopropan-1-ol
(Scheme FF)

Step 1: Benzyl 4-((1-methoxycyclopropyl)methoxy)piperidine-1-carboxylate

To a solution of benzyl 4-((1-hydroxycyclopropyl)methoxy)piperidine-1-carboxylate (100 mg, 0.327 mmol) in THF (3 mL) was added NaH (60%, 26.2 mg, 0.655 mmol) at 0° C. After 30 min, MeI (0.29 mL, 4.65 mmol) was added at 0° C. and the reaction was stirred for 12 h at RT. The mixture was quenched by saturated aqueous ammonium chloride (5 mL), extracted with EtOAc (3×15 mL). The combined organic layers were washed by brine (10 mL) and concentrated to afford the title compound.

Step 2: 1-((Piperidin-4-yloxy)methyl)cyclopropan-1-ol

To a solution of benzyl 4-((1-methoxycyclopropyl)methoxy)piperidine-1-carboxylate (100 mg, 0.313 mmol) in MeOH (5 mL) was added Pd/C (10%, 16.7 mg, 0.157 mmol). The reaction was placed under a hydrogen atmosphere (40 psi) for 3 h at 20° C. for 3 h. The mixture was filtered and the residue was concentrated to give title compound. $^1$H NMR (400 MHz, CDCl3): δ 7.79 (1H, s), 6.12 (1H, br s), 4.35 (2H, s), 3.63 (2H, s), 3.54-3.59 (3H, m), 3.39 (3H, s), 3.03 (2H, t, J=10.0 Hz), 2.34 (3H, s), 2.03-2.07 (2H, m), 1.74-1.83 (2H, m), 0.83-0.88 (2H, m), 0.58-0.63 (2H, m).

SCHEME GG

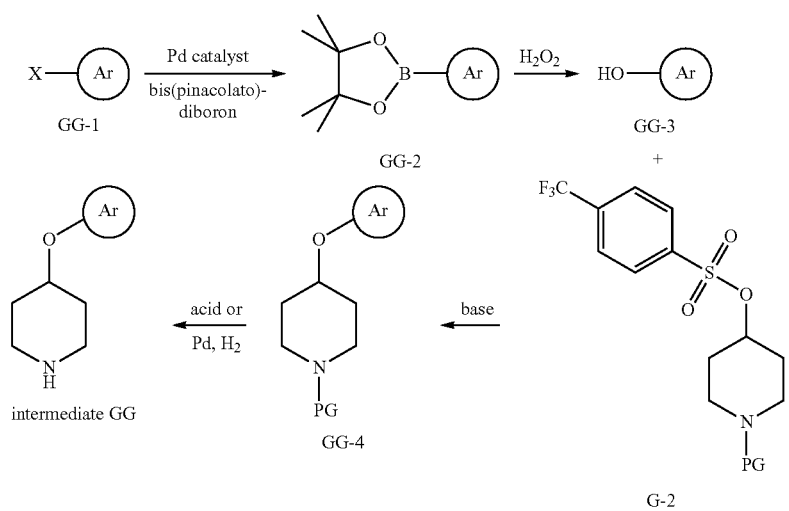

Intermediate GG is prepared from a known or commercial halide GG-1 which is transformed to the corresponding boronic ester GG-1 via a Miyaura borylation reaction. Oxidation provides the phenol GG-3 which participates in a displacement reaction with sulfone GG-2 to provide adduct GG-4. Deprotection under acidic or reductive conditions provides intermediate GG.

Intermediate GG1

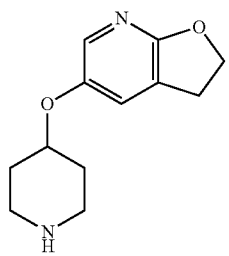 [SMILES: c1nc2c(cc1OC1CCNCC1)CCO2]

5-(Piperidin-4-yloxy)-2,3-dihydrofuro[2,3-b]pyridine (Scheme GG)

Step 1: 5-(4,4,5,5-Tetramethyl-1,3,2-dioxaborolan-2-yl)-2,3-dihydrofuro[2,3-b]pyridine To a solution of 5-bromo-2,3-dihydrofuro[2,3-b]pyridine (80 mg, 0.400 mmol) (for synthesis of this compound, see e.g.: Martin, R., et. al. Eur. J. Org. Chem. 2012, 47-52), bis(pinacolato)diboron (122 mg, 0.480 mmol) and potassium acetate (98 mg, 1.00 mmol) in dioxane (2 mL) was added PdCl$_2$(dppf) (29.3 mg, 0.040 mmol). After addition, the mixture was placed under a nitrogen atmosphere and was heated to 80° C. for 16 h. The mixture was concentrated, diluted with EtOAc (20 mL) and washed by water (20 mL). The organic phase was dried over anhydrous sodium sulfate, filtered and concentrated to afford the title compound.

Step 2: 2,3-Dihydrofuro[2,3-b]pyridin-5-ol

To a solution of 5-(4,4,5,5-tetramethyl-1,3,2-dioxaborolan-2-yl)-2,3-dihydrofuro[2,3-b]pyridine (120 mg, 0.243 mmol) in MeOH (3 mL) was added hydrogen peroxide (30%, 1 mL, 9.79 mmol). After stirring for 1 h at RT, the mixture was quenched with saturated aqueous sodium thiosulfate (10 mL) and diluted with EtOAc (15 mL). The organic phase was dried over anhydrous sodium sulfate, filtered and concentrated to afford the title compound.

Step 3: tert-Butyl 4-((2,3-dihydrofuro[2,3-b]pyridin-5-yl)oxy)piperidine-1-carboxylate To a solution of 2,3-dihydrofuro[2,3-b]pyridin-5-ol (80 mg, 0.58 mmol), tert-butyl 4-(((4-(trifluoromethyl)phenyl)sulfonyl)oxy)piperidine-1-carboxylate (358 mg, 0.88 mmol) in DMF (5 mL) was added cesium carbonate (570 mg, 1.75 mmol). After stirring at 75° C. for 16 h, the mixture was diluted with water (15 mL) and extracted by EtOAc (3×10 mL). The combined organic phases were washed by water (3×10 mL), dried over anhydrous sodium sulfate, filtered and concentrated. The residue was purified by silica gel chromatography (0-35% EtOAc in petroleum ether) to give the title compound.

Step 4: 5-(Piperidin-4-yloxy)-2,3-dihydrofuro[2,3-b]pyridine

To a solution of tert-butyl 4-((2,3-dihydrofuro[2,3-b]pyridin-5-yl)oxy)piperidine-1-carboxylate (65 mg, 0.203 mmol) in DCM (2 mL) was added TFA (0.2 mL, 2.60 mmol). After addition, the mixture was stirred at 20° C. for 15 min. The mixture was concentrated to afford the title compound. MS: 221 (M+1).

The following intermediates in table GG were prepared according to scheme GG using the procedure outlined in the synthesis of intermediate GG1 using a commercial or known reagents.

TABLE GG

| Intermediate | Structure | Name | MS (M + 1) |
|---|---|---|---|
| GG2 | 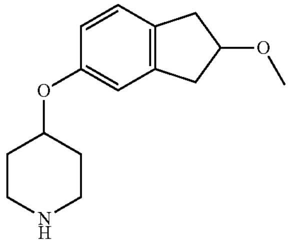 [SMILES: COC1Cc2ccc(OC3CCNCC3)cc2C1] | 4-((2-methoxy-2,3-dihydro-1H-inden-5-yl)oxy)piperidine | 248 |
| GG3 | 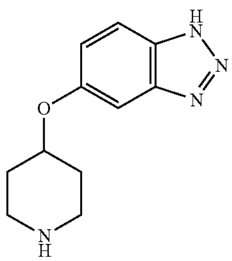 [SMILES: c1cc2[nH]nnc2cc1OC1CCNCC1] | 5-(piperidin-4-yloxy)-1H-benzo[d][1,2,3]triazole | 219 |

SCHEME HH

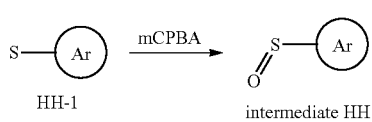

Intermediate HH is prepared under oxidative conditions to provide intermediate GG from a known or available thioether HH-1.

Intermediate HH

5-Bromo-1,3-dihydrobenzo[c]thiophene 2-oxide (Scheme HH)

To a solution of compound 5-bromo-1,3-dihydrobenzo[c]thiophene (731 mg, 3.40 mmol) in DCM (10 mL) was added m-CPBA (1005 mg, 4.08 mmol) at 0° C. After stirring for 1 h at RT, the mixture was quenched with aqueous, saturated $Na_2SO_3$ (20 mL) and partitioned with DCM (10 mL×3). The combined organic layers were washed with brine, dried over anhydrous sodium sulfate and concentrated. The residue was purified by silica gel chromatography (0-100% THF in petroleum ether) to yield the title compound. MS: 231, 233 (M+1).

SCHEME II

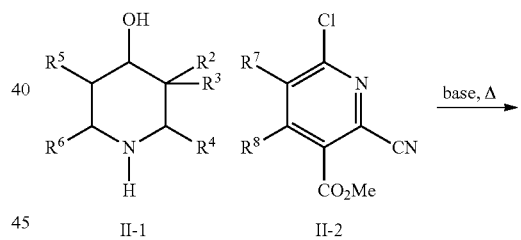

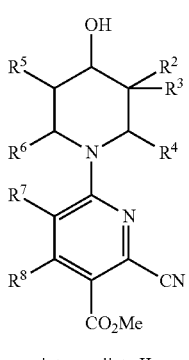

intermediate II

Intermediate II is prepared by an $S_NAr$ reaction of commercially available piperidinol II-1 with prepared 2-chloropyridine II-2 to provide intermediate II.

Intermediate II1

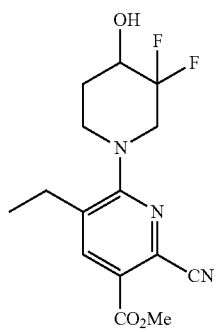 [SMILES: CCc1cc(C(=O)OC)c(C#N)nc1N1CCC(O)C(F)(F)C1]

Methyl 2-cyano-6-(3,3-difluoro-4-hydroxypiperidin-1-yl)-5-ethylnicotinate (Scheme II)

To a solution of 3,3-difluoropiperidin-4-ol (HCl salt, 73.8 mg, 0.383 mmol) in dry DMF (2 mL) was added methyl 6-chloro-2-cyano-5-ethylnicotinate (43 mg, 0.191 mmol) and DIPEA (74.2 mg, 0.574 mmol). The mixture was stirred at 80° C. for 15 h under an inert atmosphere. The reaction was cooled to RT and was treated with water (10 mL) and extracted with EtOAc (10 mL×3). The combined organic layers were dried over anhydrous sodium sulfate, filtered and concentrated to dryness. The residue was purified by silica gel chromatography (0-50% EtOAc in petroleum ether) to give the title compound. MS: 326 (M+1).

The following intermediates in table II were prepared according to scheme II using the procedure outlined in the synthesis of intermediate II1.

TABLE II

| Intermediate | Structure | Name | MS (M + 1) |
|---|---|---|---|
| II2 | 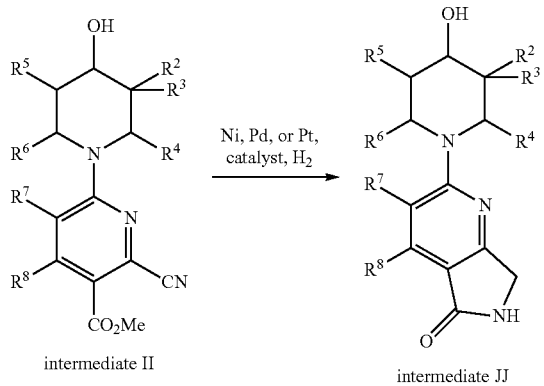 | methyl 2-cyano-6-(4-hydroxypiperidin-1-yl)-4,5-dimethylnicotinate | 290 |

SCHEME JJ

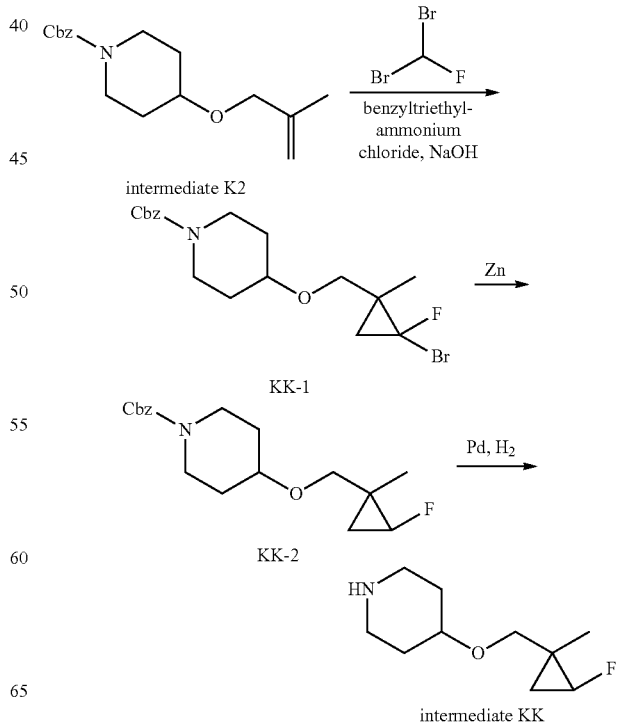

Intermediate JJ is prepared by exposure of intermediate II to hydrogenation conditions to elicit lactam formation.

Intermediate JJ

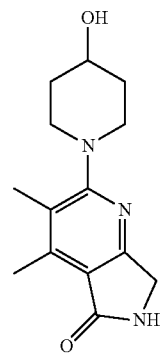 [SMILES: Cc1c(N2CCC(O)CC2)nc2c(c1C)C(=O)NC2]

2-(4-Hydroxypiperidin-1-yl)-3,4-dimethyl-6,7-dihydro-5H-pyrrolo[3,4-b]pyridin-5-one (Scheme JJ)

To methyl 2-cyano-6-(4-hydroxypiperidin-1-yl)-4,5-dimethylnicotinate (intermediate II2, 275 mg, 0.950 mmol) in EtOH (9505 μL) and AcOH (272 μL, 4.75 mmol) was added Pd/C (10 wt %, 101 mg, 0.095 mmol). The system was evacuated and flushed with nitrogen 3 times before placing under an atmosphere of hydrogen. After stirring for 15 h, the reaction was filtered and the volatiles were removed under reduced pressure. The residue was diluted in TEA (0.5 mL) and MeOH (5 mL) and stirred at RT for 8 h. The mixture was filtered over celite and filtrate was concentrated to provide the title compound. MS: 262 (M+1).

SCHEME KK

Intermediate KK is prepared by exposure of intermediate K2 to dibromofluoromethane to obtain cyclopropane KK-1. Hydrogenation conditions to elicit lactam formation.

Intermediate KK

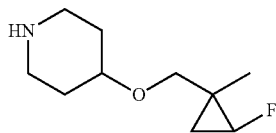

2-(4-Hydroxypiperidin-1-yl)-3,4-dimethyl-6,7-dihydro-5H-pyrrolo[3,4-b]pyridin-5-one (Scheme KK)

Step 1: Benzyl 4-((2-bromo-2-fluoro-1-methylcyclopropyl)methoxy)piperidine-1-carboxylate To a solution of benzyl 4-((2-methylallyl)oxy)piperidine-1-carboxylate (intermediate K2, 500 mg, 1.73 mmol) in DCM (5 mL) and water (0.5 mL) was added NaOH (346 mg, 8.64 mmol) and N-benzyl-N,N-diethylethanaminium chloride (5.90 mg, 0.026 mmol) and dibromofluoromethane (497 mg, 2.59 mmol). After stirring at 50° C. for 20 h, the reaction was treated with water (5 mL) and extracted with DCM (25 mL×3). The combined organic layers were dried over anhydrous sodium sulfate, filtered and concentrated. The resultant residue was purified by silica gel chromatography (0-40% EtOAc/petroleum ether) to give the title compound.

Step 2: Benzyl 4-((2-fluoro-1-methylcyclopropyl)methoxy)piperidine-1-carboxylate To a solution of benzyl 4-((2-bromo-2-fluoro-1-methylcyclopropyl)methoxy)piperidine-1-carboxylate (150 mg, 0.375 mmol) in EtOH (5 mL) was added zinc (49.0 mg, 0.749 mmol) and ammonium chloride (60.1 mg, 1.124 mmol). The reaction was stirred at 70° C. for 8 h. The mixture was filtered, concentrated and diluted with water (10 mL) and extracted with EtOAc (15 mL×3). The organic layers were concentrated to dryness to afford the title compound.

Step 3: 4-((2-Fluoro-1-methylcyclopropyl)methoxy)piperidine

To a solution of benzyl 4-((2-fluoro-1-methylcyclopropyl)methoxy)piperidine-1-carboxylate (300 mg, 0.933 mmol) in EtOH (10 mL) was added Pd/C (10 wt %, 99 mg, 0.933 mmol) under a nitrogen atmosphere. The reaction was stirred at RT for 2 h under a hydrogen atmosphere before the mixture was filtered and concentrated to provide the title compound. MS: 188 (M+1).

SCHEME LL

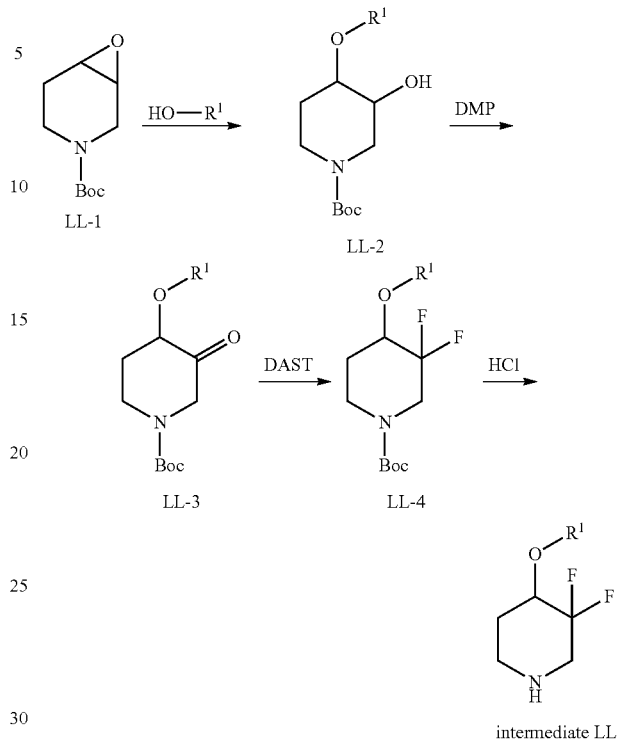

Intermediate LL is prepared via an nucleophilic electrophilic epoxide opening reaction between commercially available piperidine LL-1 and phenol to afford adduct LL-2. Oxidation of alcohol LL-2 provides ketone LL-3, which is subsequently reacted with DAST to give the corresponding difluoro product LL-4. Acid-mediated deprotection of N-Boc piperidine provides intermediate LL.

Intermediate LL

3,3-Difluoro-4-((1-methyl-1H-pyrazol-4-yl)oxy)piperidine (Scheme LL)

Step 1: tert-Butyl 3-hydroxy-4-((1-methyl-1H-pyrazol-4-yl)oxy)piperidine-1-carboxylate A mixture of tert-butyl 7-oxa-3-azabicyclo[4.1.0]heptane-3-carboxylate (1.2 g, 6.02 mmol), 1-methyl-1H-pyrazol-4-ol (0.768 g, 7.83 mmol) and cesium carbonate (2.94 g, 9.03 mmol) in DMF (15 mL) was stirred at 80° C. for 16 h. The mixture was cooled to RT dissolved in EtOAc (100 mL), washed with water (100 mL), dried over anhydrous sodium sulfate, filtered and concentrated. The crude material was purified by silica gel chromatography (1/1 petroleum ether/THF) to give the title compound.

Step 2: tert-Butyl 4-((1-methyl-1H-pyrazol-4-yl)oxy)-3-oxopiperidine-1-carboxylate A solution of tert-butyl 3-hydroxy-4-((1-methyl-1H-pyrazol-4-yl)oxy)piperidine-1-carboxylate (1.2 g, 4.04 mmol) and DMP (5.14 g, 12.1 mmol) in DCM (20 mL) was stirred at 25° C. for 16 h. The mixture was filtered and the filtrate was concentrated before purification by silica gel chromatography (1/1 petroleum ether/THF) to give the title compound.

Step 3: tert-Butyl 3,3-difluoro-4-((1-methyl-1H-pyrazol-4-yl)oxy)piperidine-1-carboxylate To a solution of tert-butyl 4-((1-methyl-1H-pyrazol-4-yl)oxy)-3-oxopiperidine-1-carboxylate (800 mg, 2.71 mmol) in DCM (10 mL) was added DAST (1.79 mL, 13.5 mmol). The reaction was stirred at RT for 16 h before it was carefully poured into aqueous $NaHCO_3$ (saturated, 30 mL). After extracting with DCM (50 mL), the organic layer was washed with water (30 mL), dried over anhydrous sodium sulfate, filtered and concentrated. Purification by silica gel chromatography (70:30 petroleum ether: THF) afforded the title compound.

Step 4: 3,3-Difluoro-4-((1-methyl-1H-pyrazol-4-yl)oxy)piperidine

To a solution of tert-butyl 3,3-difluoro-4-((1-methyl-1H-pyrazol-4-yl)oxy)piperidine-1-carboxylate (100 mg, 0.315 mmol) in dioxane (0.5 mL) was added hydrogen chloride (4 M in dioxane, 1 mL, 4.00 mmol). The reaction was stirred at RT for 1 hr and the volatiles were then removed under reduced pressure to afford the title compound. MS: 218 (M+1).

Compounds of formula (I) are synthesized from an $S_NAr$ reaction of prepared 2-chloro pyridines 1-1, and commercially available or prepared piperidines 1-2.

SCHEME 2

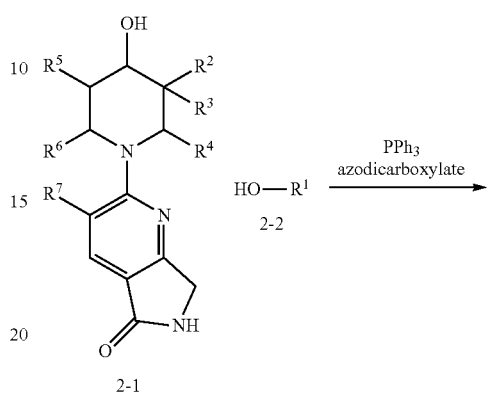

Compounds of formula (I) are synthesized from a Mitsunobu reaction using triphenyl phosphine and an azodicarboxylate with a known or prepared phenol 2-2 and prepared alcohol 2-1.

SCHEME 1

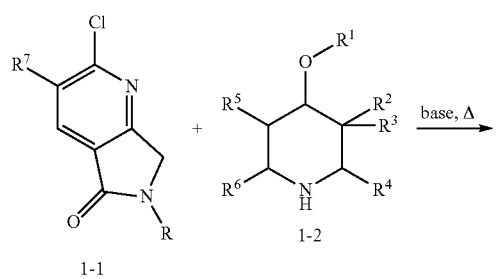

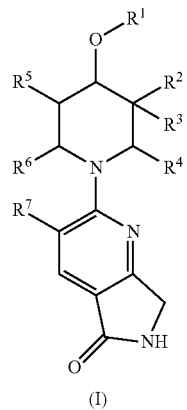

SCHEME 3

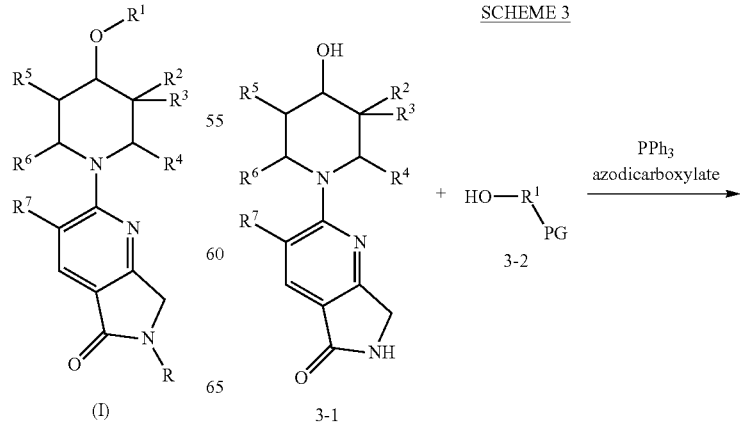

-continued

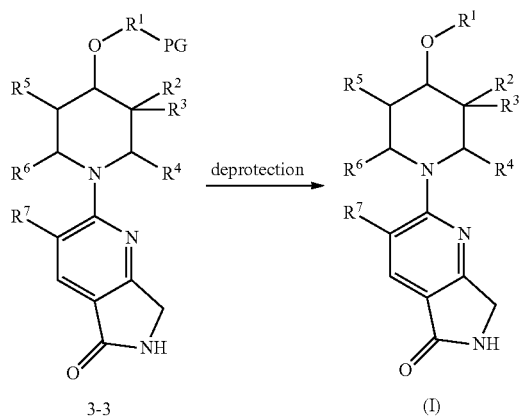

3-3

(I)

Compounds of formula (I) are synthesized from a Mitsunobu reaction using triphenyl phosphine and an azodicarboxylate with a known or prepared phenol 3-2 associated with a protecting group and prepared alcohol 3-1. Subsequent deprotection of adduct 3-3 is accomplished with exposure to acid or TBAF to provide compound (I).

SCHEME 4

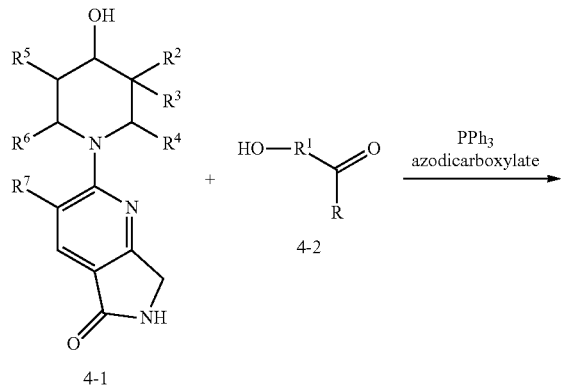

4-1

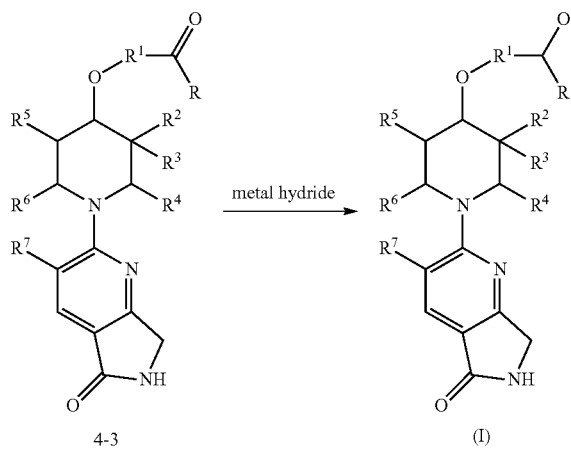

4-3

(I)

Compounds of formula (I) are synthesized from a Mitsunobu reaction using triphenyl phosphine and an azodicarboxylate with a known or prepared phenol 4-2 associated with a pendant carbonyl group and prepared alcohol 4-1. Subsequent reduction of carbonyl 4-3 with a metal hydride provides compound (I).

SCHEME 5

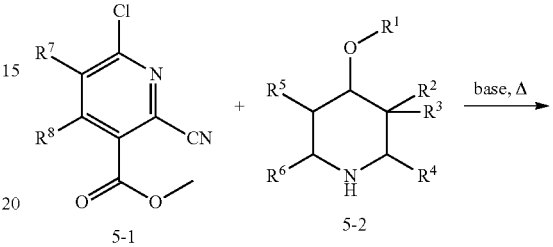

5-1        5-2

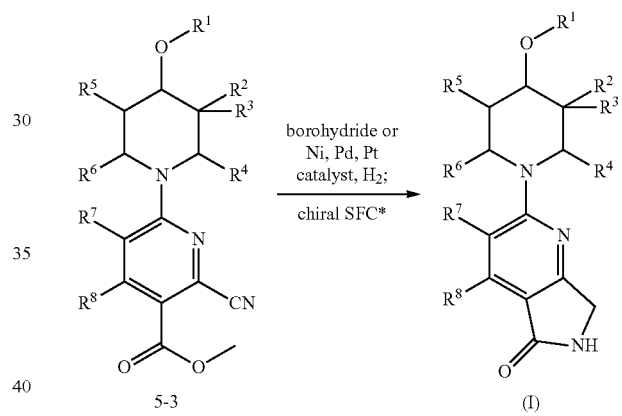

5-3        (I)

Compounds of formula (I) are synthesized from an S_NAr of prepared pyridine 5-1 and a known or prepared piperidine 5-2. Reduction of nitrile 5-3 can be carried out with a platinum, or palladium, or nickel-based catalyst or else a metal borohydride reagent such that the resultant amine cyclizes to form a lactam often in the presence of base. In cases where stereocenter(s) are present, additional chiral resolution of isomers may be carried out.

SCHEME 6

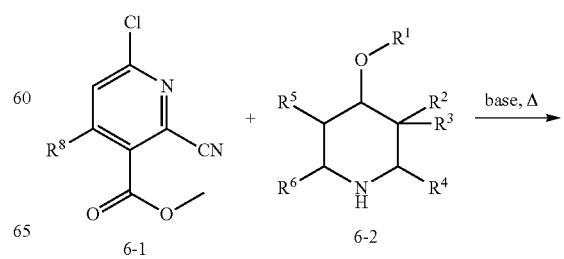

6-1        6-2

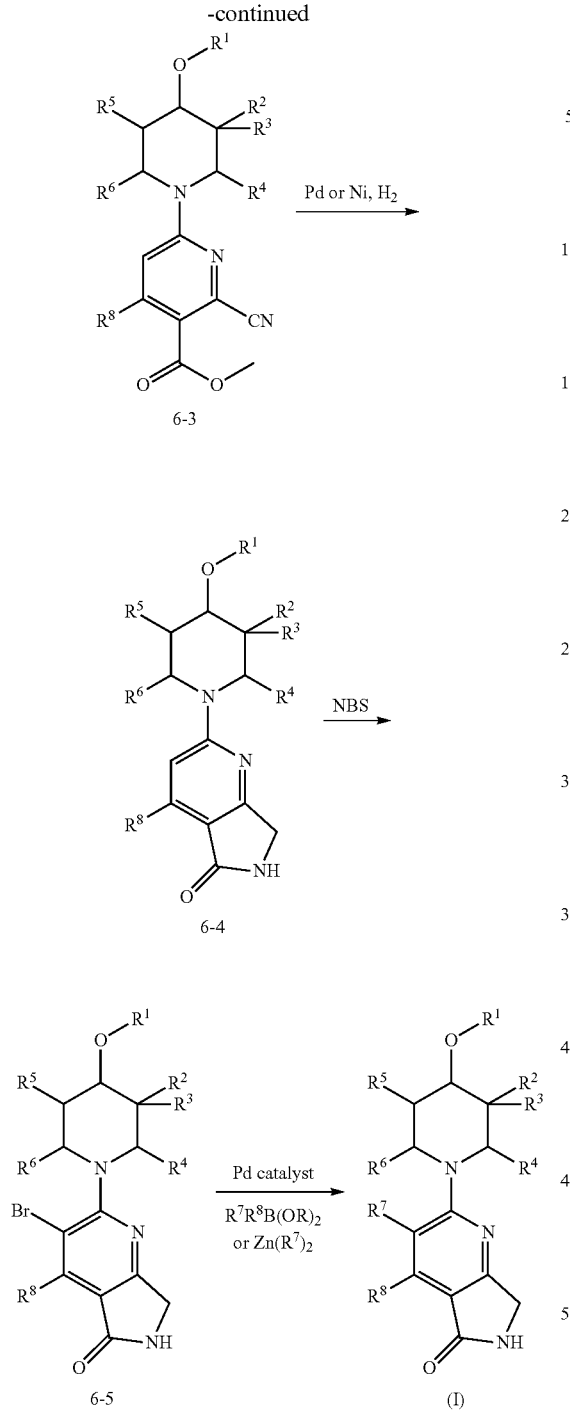

6-3

6-4

6-5 (I)

Compounds of formula (I) are synthesized from prepared nitrile 6-1 via a $S_NAr$ reaction with a known or prepared piperidine 6-2 to provide adduct 6-3. Reduction of intermediate 6-3 can be carried out with a palladium or nickel catalyst, wherein the amine will cyclize to form the lactam often in the presence of base to yield compound 6-4. Electrophilic bromination with NBS cleanly provides bromide 6-5 which is elaborated via a palladium-mediated Suzuki or Negishi reaction to form compound (I).

SCHEME 7

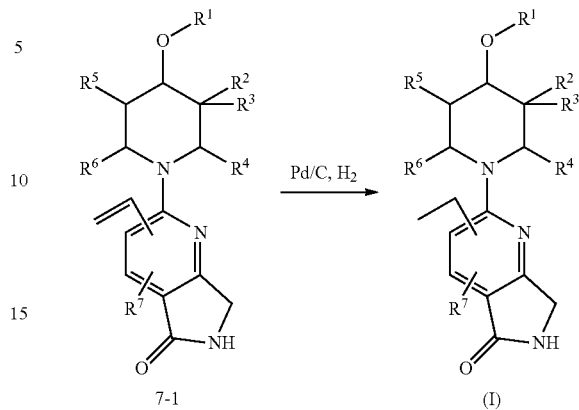

7-1 (I)

Compounds of formula (I) are synthesized via the reduction of olefin 7-1 by palladium-mediated hydrogenation.

SCHEME 8

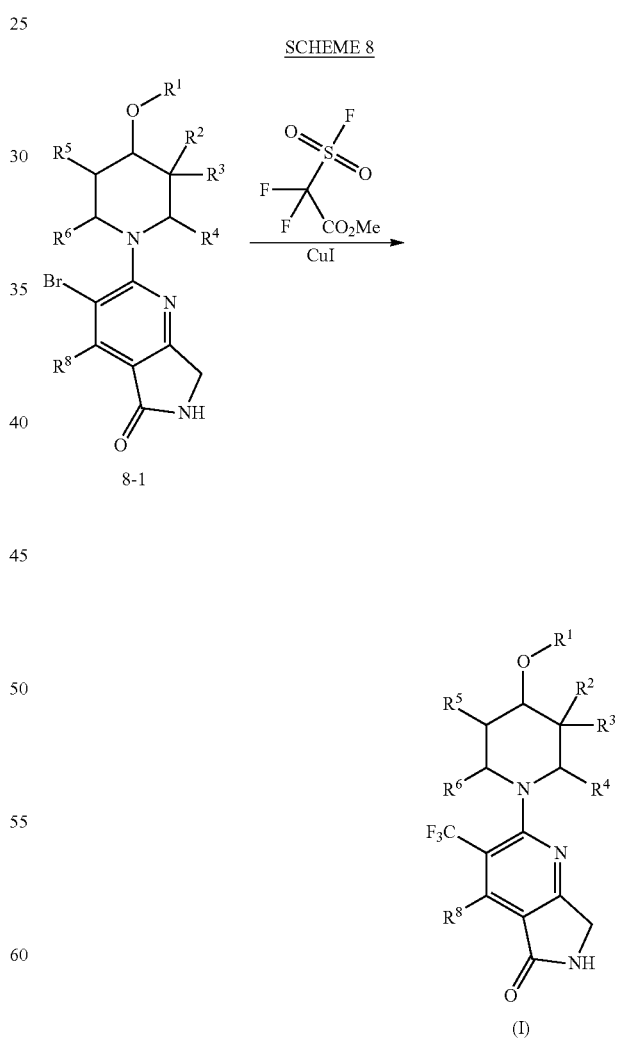

8-1

(I)

Compounds of formula (I) are synthesized from bromide 8-1 via copper-mediated trifluoromethylation.

SCHEME 9

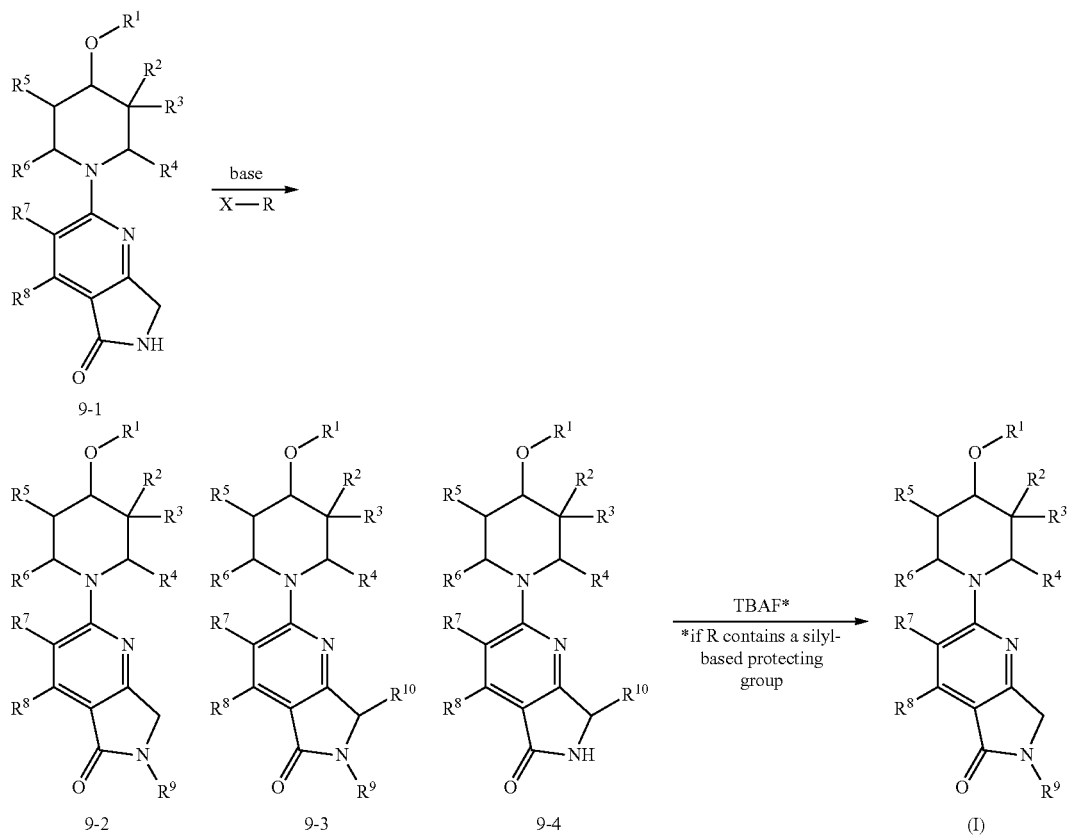

Compounds of formula (I) are synthesized via the alkylation of the lactam 9-1 with an alkyl halide or mesylate in the presence of a base such as LHMDS or NaH. Under reaction conditions using an equivalent of base, the major observed product is adduct 9-2 and in some cases the formation of the overalkylation product 9-3. Under reaction conditions using an excess of base, the major observed product is adduct 9-4. In cases where the added moiety contains a silyl protecting group, TBAF is used to unmask the alcohol to provide compound (I).

SCHEME 10

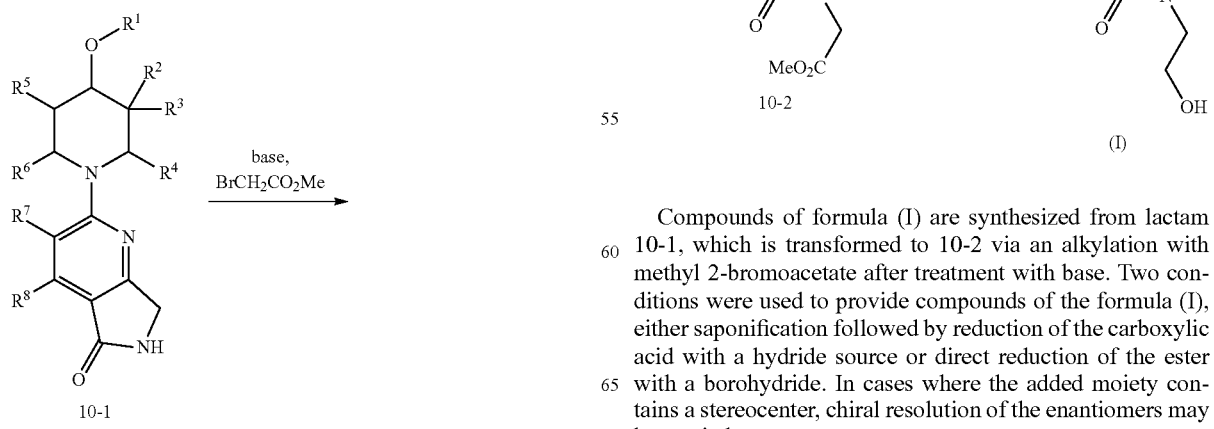

Compounds of formula (I) are synthesized from lactam 10-1, which is transformed to 10-2 via an alkylation with methyl 2-bromoacetate after treatment with base. Two conditions were used to provide compounds of the formula (I), either saponification followed by reduction of the carboxylic acid with a hydride source or direct reduction of the ester with a borohydride. In cases where the added moiety contains a stereocenter, chiral resolution of the enantiomers may be carried out.

SCHEME 11

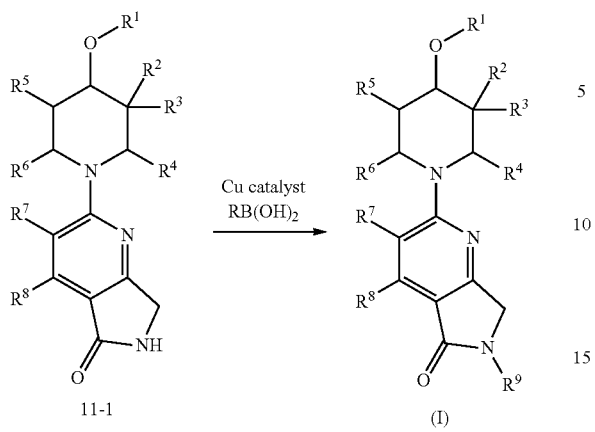

Compounds of formula (I) are synthesized from lactam 11-1 through a Chan-Lam coupling reaction.

SCHEME 12

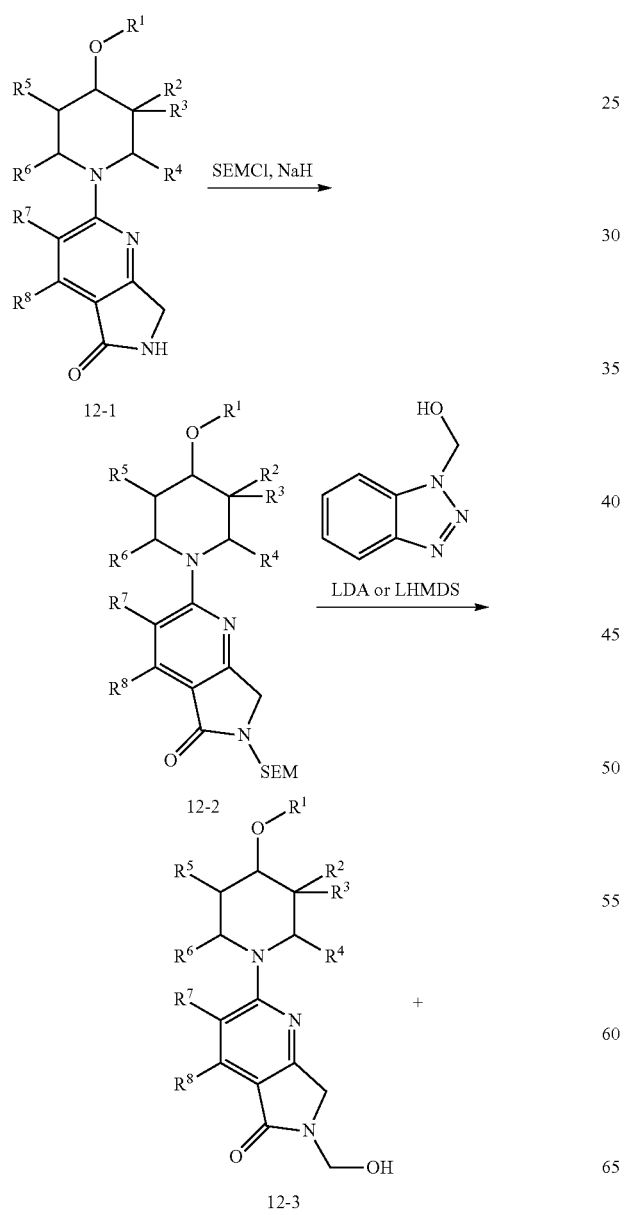

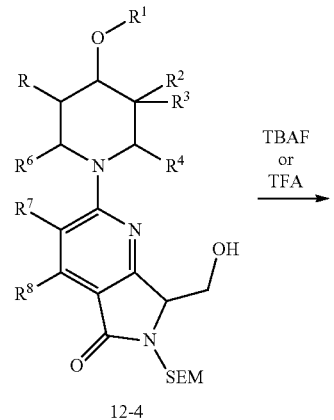

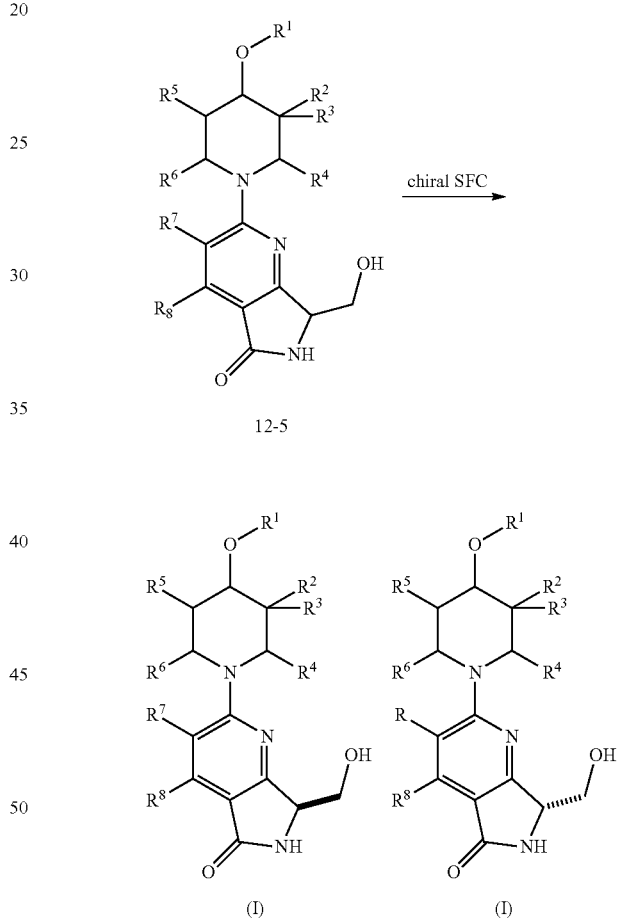

Compounds of formula (I) are synthesized from lactam 12-1 through an initial SEM-protection reaction to provide intermediate 12-2. 1-Hydroxymethylbenzotriazole is used for the in situ generation of anhydrous formaldehyde in the presence of the base to provide adduct 12-4. In some cases, the SEM group was found to form hydroxymethyl 12-3 as a by-product under the reaction condition. Deprotection of lactam 12-4 is accomplished using TBAF or TFA to provide 12-5. Chiral resolution is carried out by SFC to provide compounds of the formula (I).

SCHEME 13

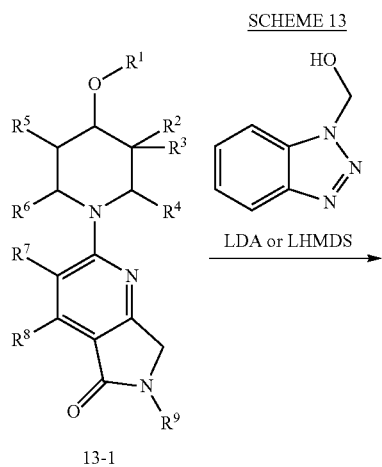

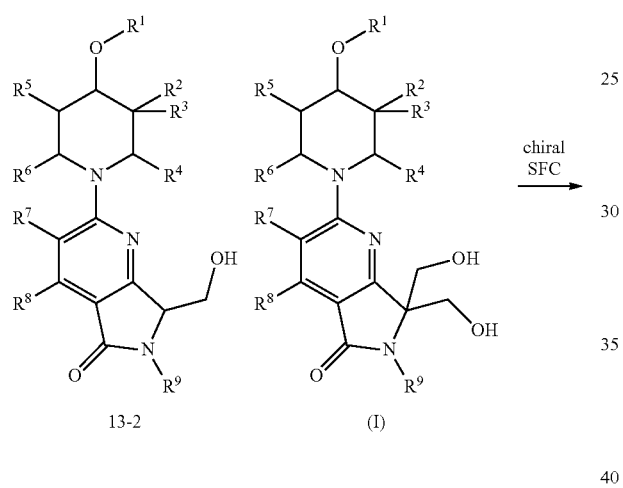

SCHEME 14

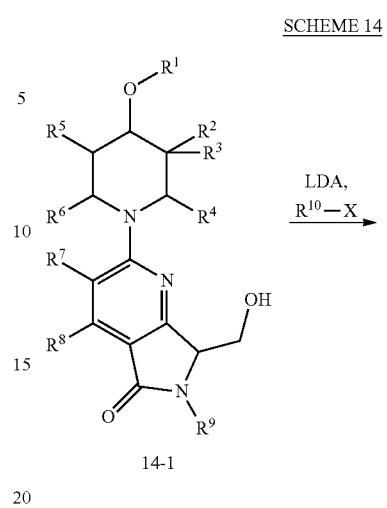

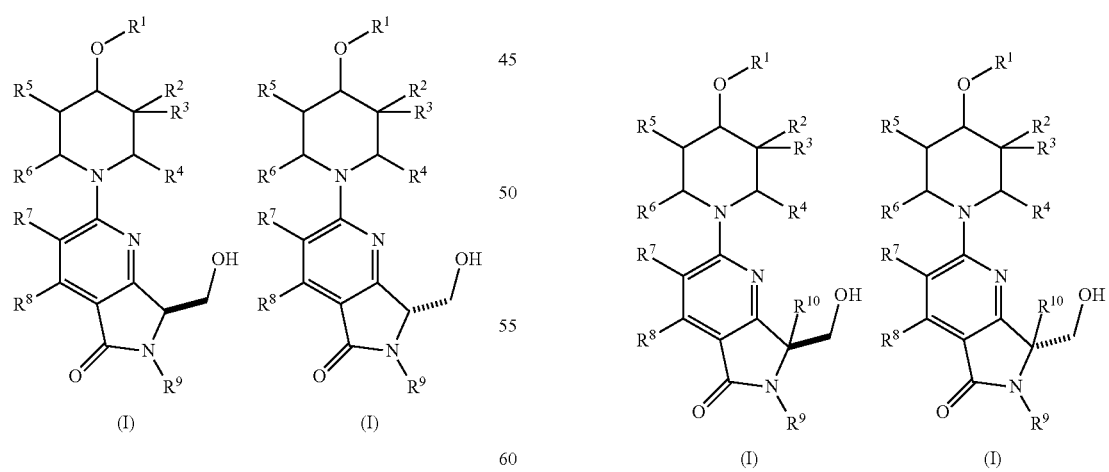

Compounds of formula (I) are synthesized from lactam 13-1 by an in situ generation of anhydrous formaldehyde in the presence of the base to provide adduct 13-2. Chiral resolution is carried out by SFC to provide compounds of the formula (I).

Compounds of formula (I) are synthesized from lactam 14-1 by a base-mediated alkylation with a commercial alkyl halide. Chiral resolution is carried out on adduct 14-2 by SFC to provide compounds of the formula (I).

SCHEME 15

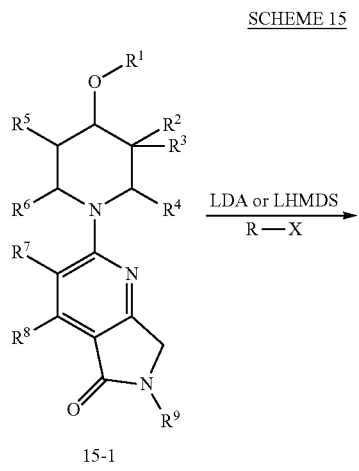

15-1

SCHEME 16

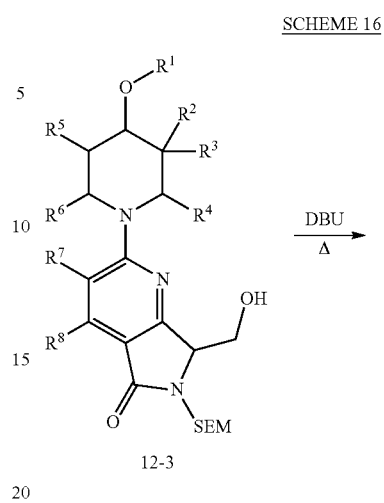

12-3

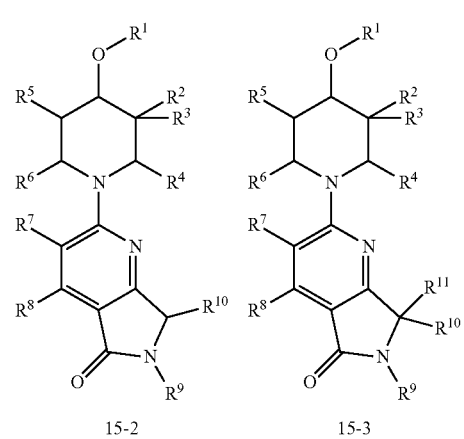

15-2          15-3

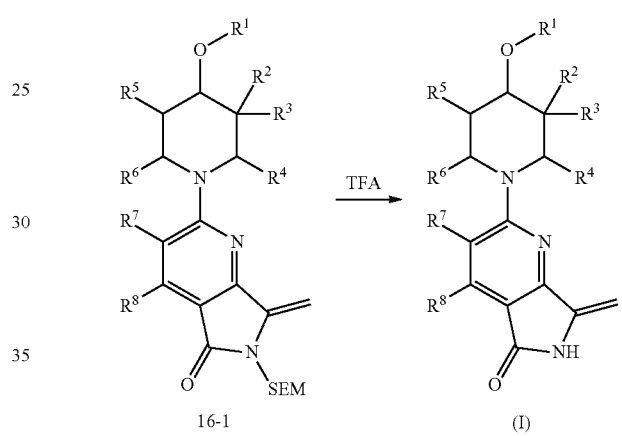

16-1          (I)

Compounds of formula (I) are synthesized from alcohol 12-3 through an base-mediated elimination reaction. Deprotection of lactam 16-1 is accomplished using TFA to provide compounds of formula (I).

SCHEME 17

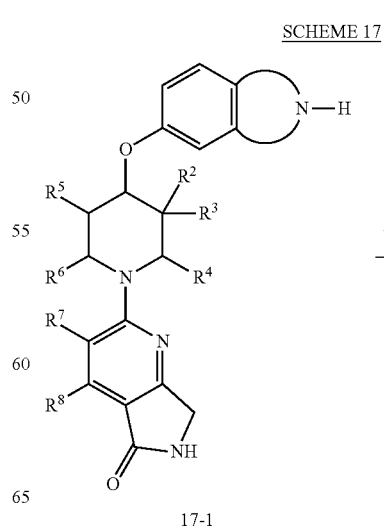

17-1

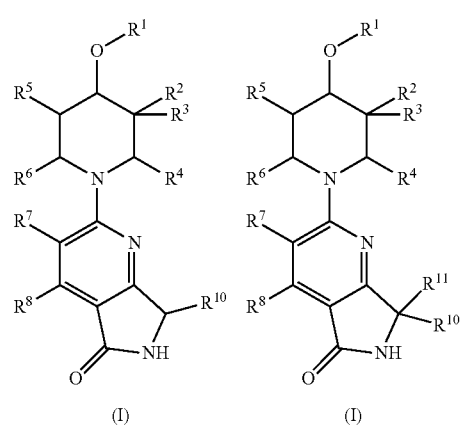

(I)          (I)

Compounds of formula (I) are synthesized from lactam 15-1 through an base-mediated alkylation with a commercial alkyl halide that can give rise to a mono- and bis-adduct, 15-2 and 15-3, respectively. TBAF is used to deprotect the lactam in cases where the 15-2 or 15-3 includes a silyl protecting group.

-continued
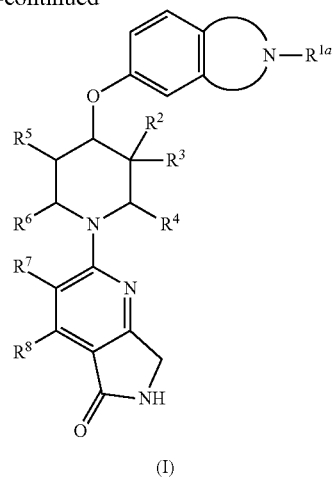
(I)
Compounds of formula (I) are synthesized from amine 17-1 through a reductive amination reaction with a commercially available aldehyde.
SCHEME 18
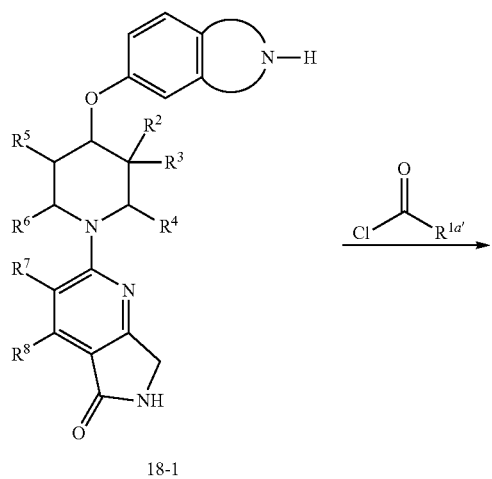
18-1
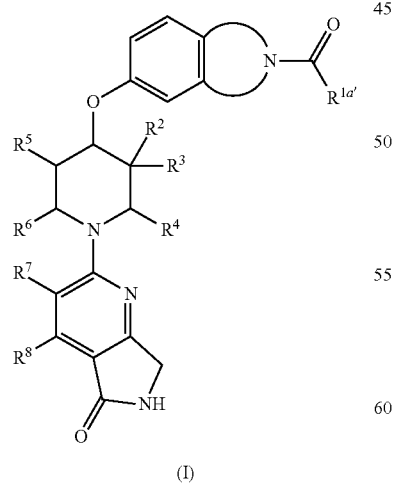
(I)
Compounds of formula (I) are synthesized from amine 18-1 through an acylation with a commercially available acyl chloride.
SCHEME 19
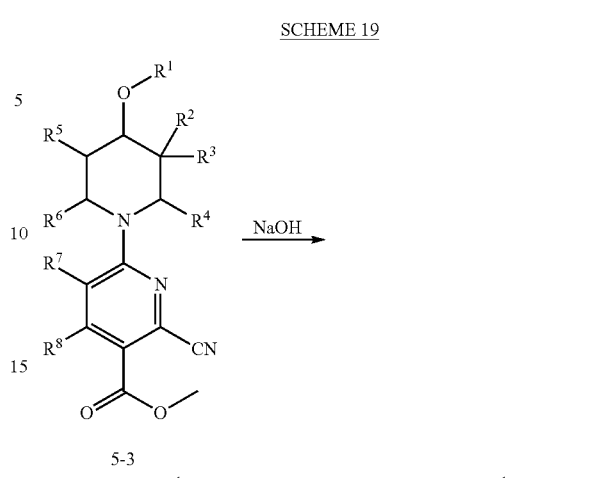
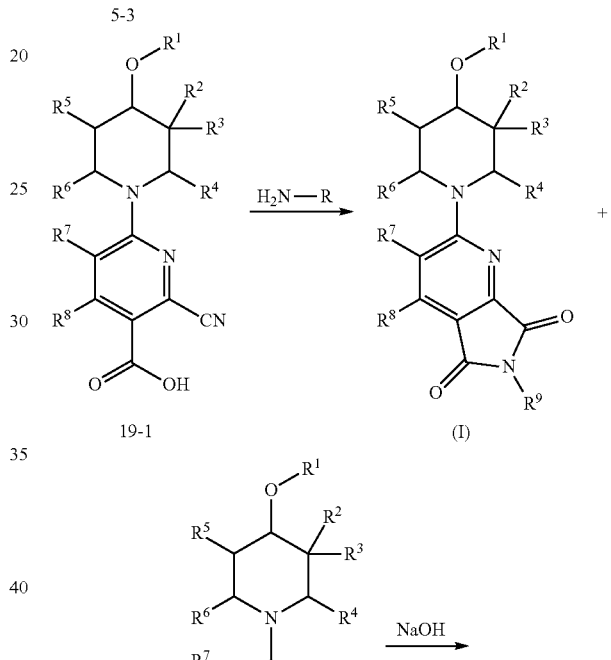
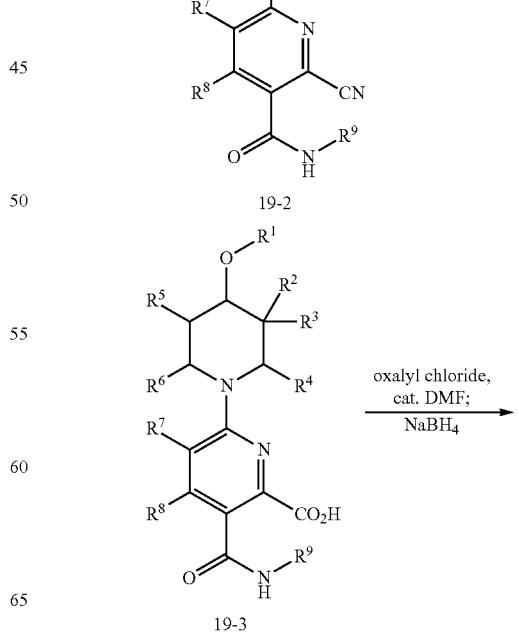

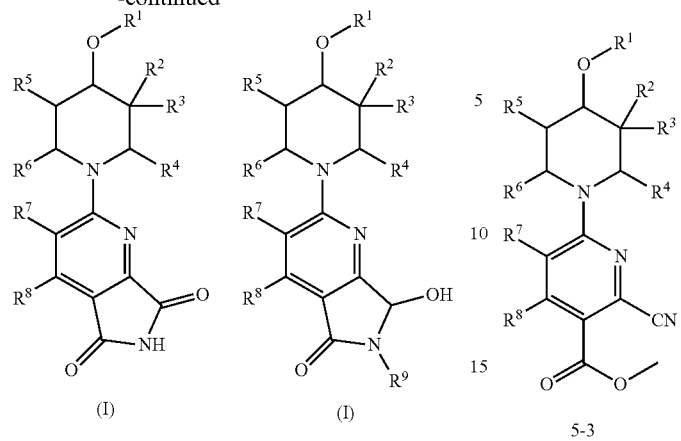

(I)    (I)

Compounds of formula (I) are synthesized from intermediate 5-3 (from scheme 5) which is saponified to carboxylate 19-1. Under coupling conditions with a commercially available amine, adduct 19-2 and compounds of the formula (I) are obtained. Saponification of nitrile 19-2 gives rise to carboxylic acid 19-3, which was carried forward into an acyl chloride formation with a reductive work-up to yield compounds of the formula (I).

SCHEME 20

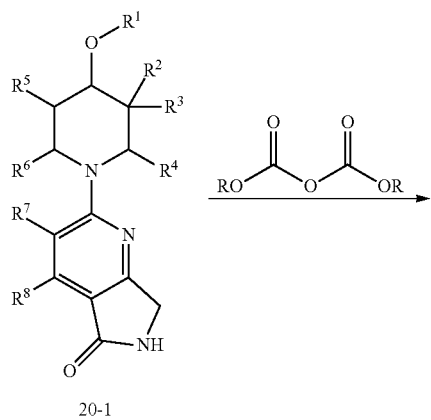

20-1

(I)

Compounds of formula (I) are synthesized from lactam 20-1 through reaction with a commercially available anhydride.

SCHEME 21

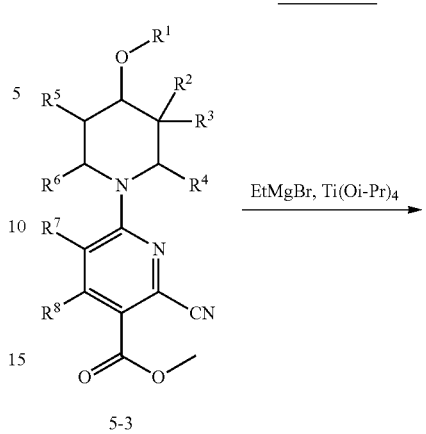

5-3

(I)

Compounds of formula (I) are synthesized from intermediate 5-3 (from scheme 5) through a Kulinkovich reaction.

SCHEME 22

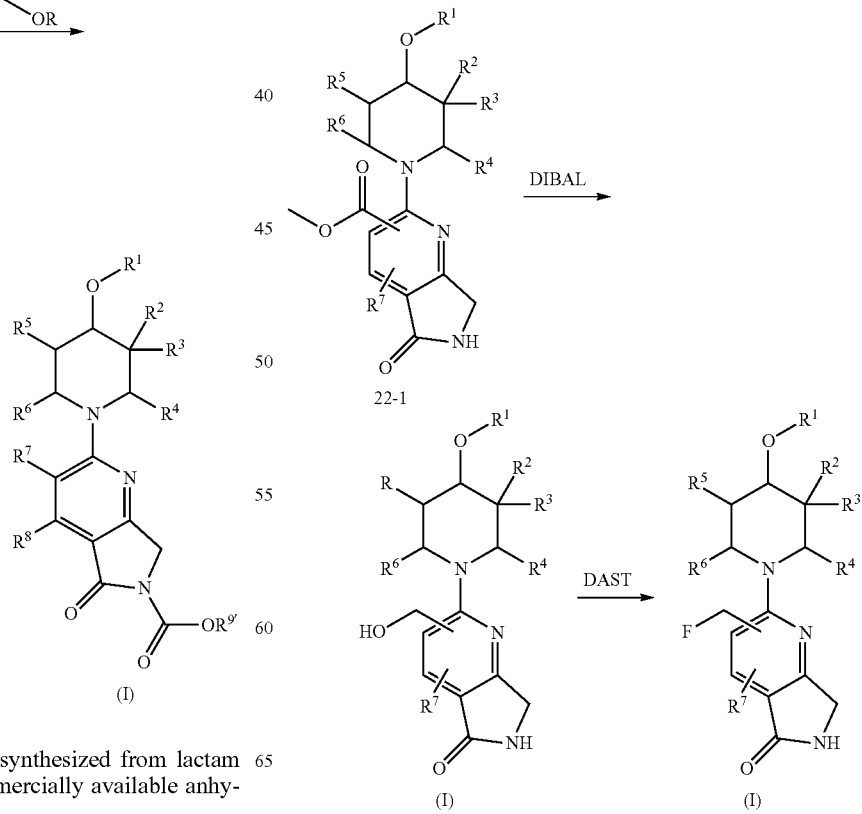

22-1

(I)    (I)

Compounds of formula (I) are synthesized from ester 22-1 which is reduced to the alcohol. Compounds of formula (I) are also prepared from a further reaction of the alcohol with DAST.

SCHEME 23

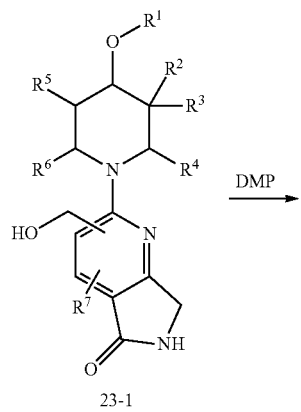

23-1

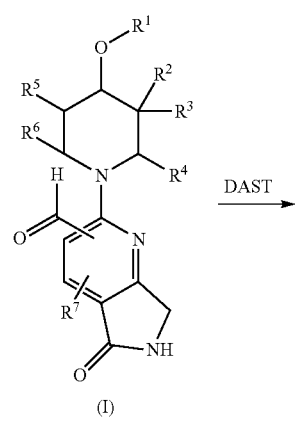

(I)         (I)

Compounds of formula (I) are synthesized from alcohol 23-1 through oxidation to the aldehyde using Dess-Martin reagent. Compounds of formula (I) are also prepared from a further reaction of the aldehyde with DAST.

SCHEME 24

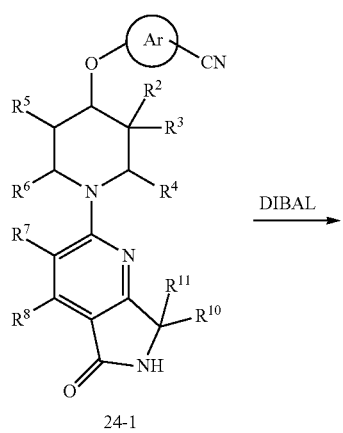

24-1

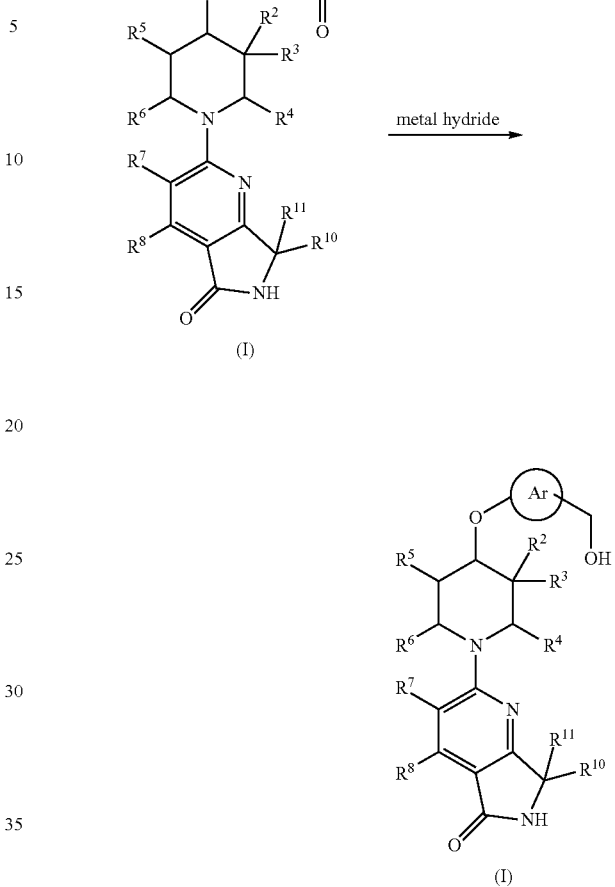

(I)

(I)

Compounds of formula (I) are synthesized from a reduction of nitrile 24-1 using DIBAL. Compounds of formula (I) are also prepared from a further reduction of the aldehyde using other metal hydrides to form the corresponding alcohol.

SCHEME 25

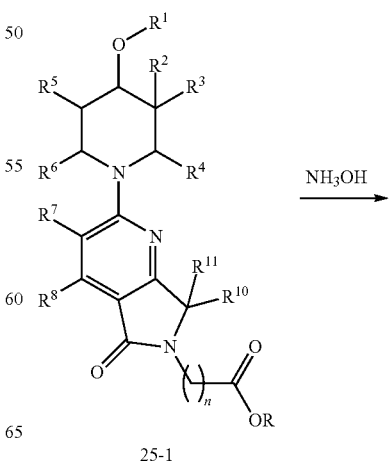

25-1

-continued

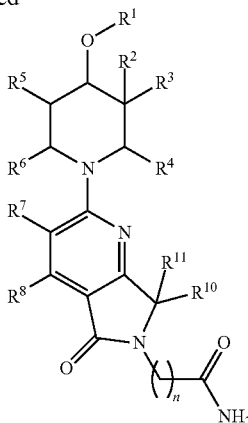

Compounds of formula (I) are synthesized from the reaction of ester 25-1 with ammonium hydroxide for form the corresponding carboxamide.

SCHEME 26

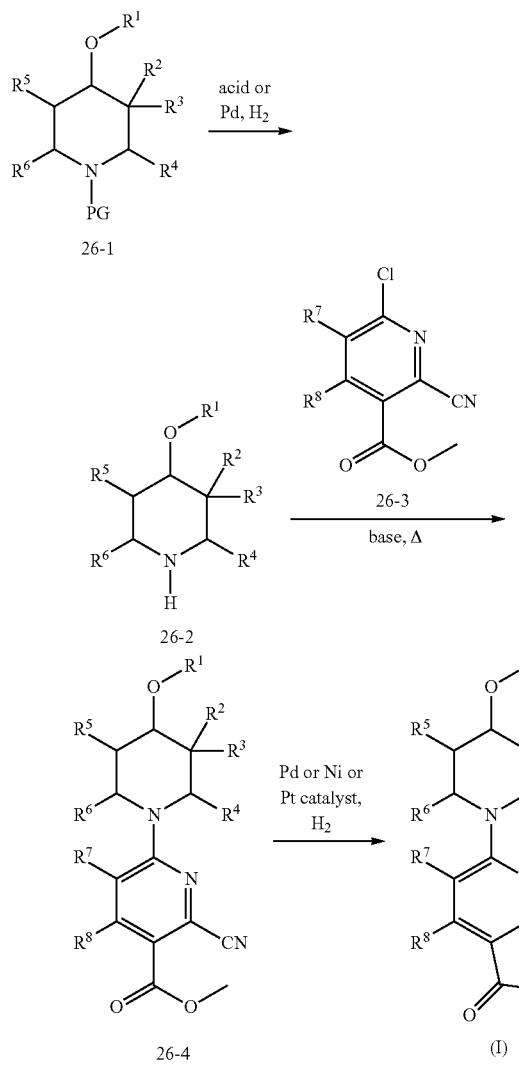

Compounds of formula (I) are synthesized from prepared N-protected piperidine 26-1 via either an acid-mediated deprotection or reductive conditions using Pd catalyst in the presence of hydrogen to form amine 26-2. A subsequent S$_N$Ar with prepared aryl chloride 26-3 forms adduct 26-4. Reduction of nitrile 26-4 can be carried out with a platinum, or palladium, or nickel-based catalyst such that the resultant amine cyclizes to form a lactam often in the presence of base.

SCHEME 27

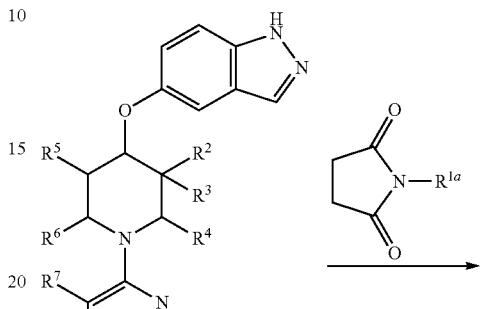

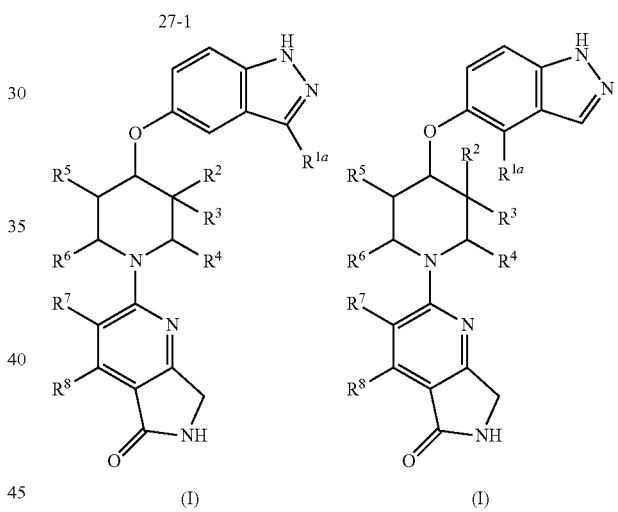

Compounds of formula (I) are synthesized from indazole 27-1 after reaction with a N-halosuccinimide.

SCHEME 28

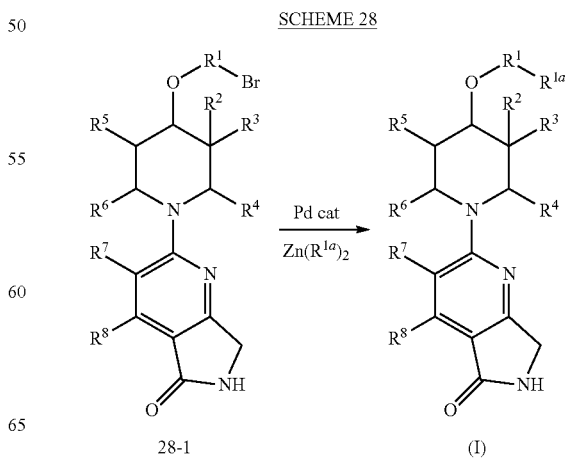

Compounds of formula (I) are synthesized from bromide 28-1 after a palladium-catalyzed Negishi reaction.

SCHEME 29

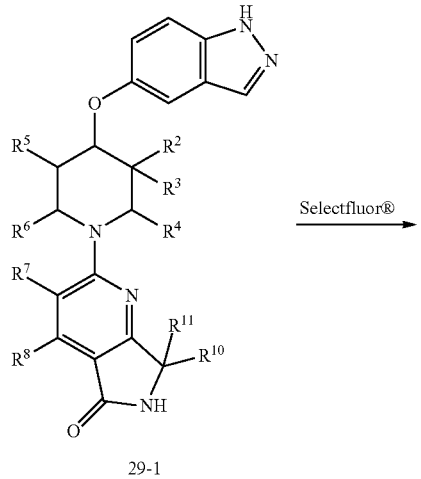

29-1

Selectfluor®

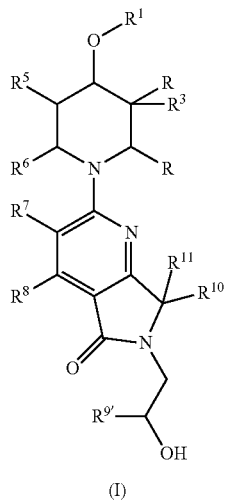

(I)

Compounds of formula (I) are synthesized from indazole 29-1 after reaction with Selectfluor®.

SCHEME 30

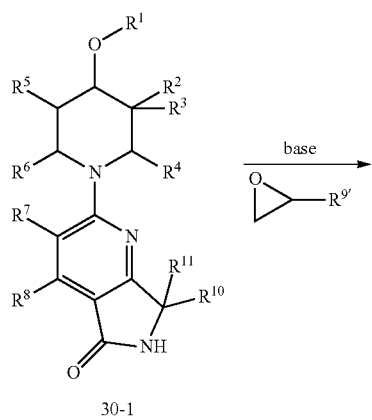

30-1 base

Compounds of formula (I) are synthesized from a base-mediated N-alkylation of lactam 30-1 through an epoxide ring-opening reaction with commercially available epoxides.

SCHEME 31

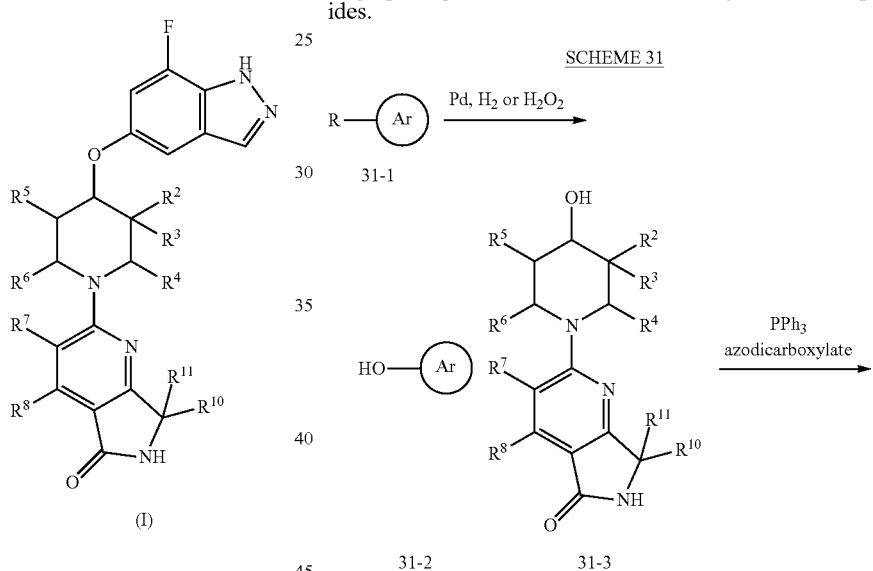

31-1   31-2   31-3

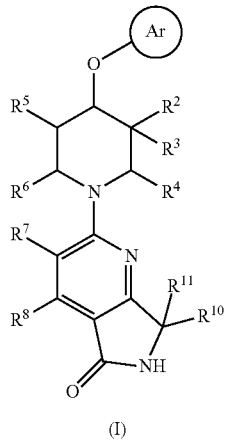

(I)

Compounds of formula (I) are synthesized from a known or prepared phenol precursor 31-1 that after treatment under reductive or oxidative reaction conditions reveals phenol 31-2. A Mitsunobu reaction using triphenyl phosphine and an azodicarboxylate with prepared alcohol 31-3 provides compounds having the formula (I).

SCHEME 32

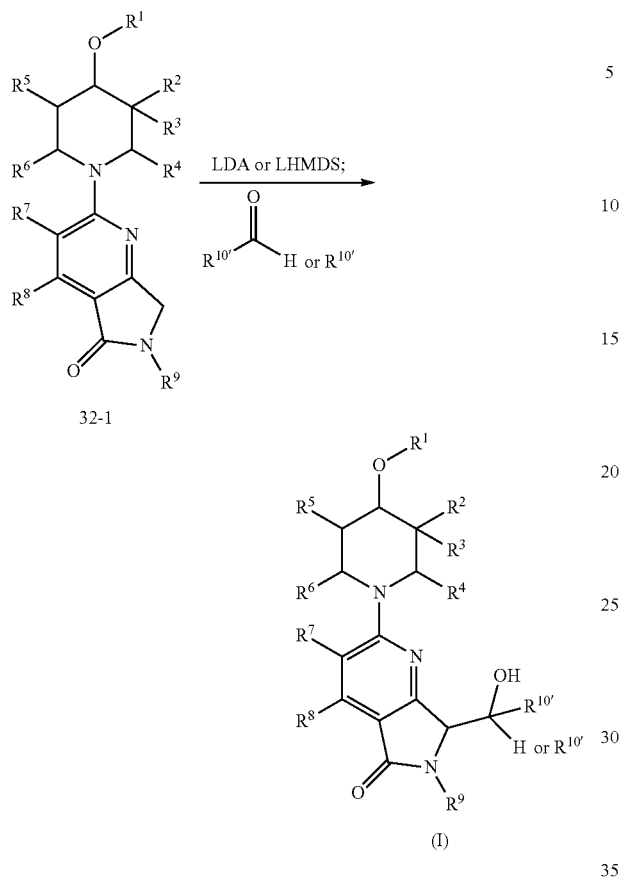

Compounds of formula (I) are synthesized from lactam 32-1 through an aldol reaction with a commercial aldehyde or ketone.

SCHEME 33

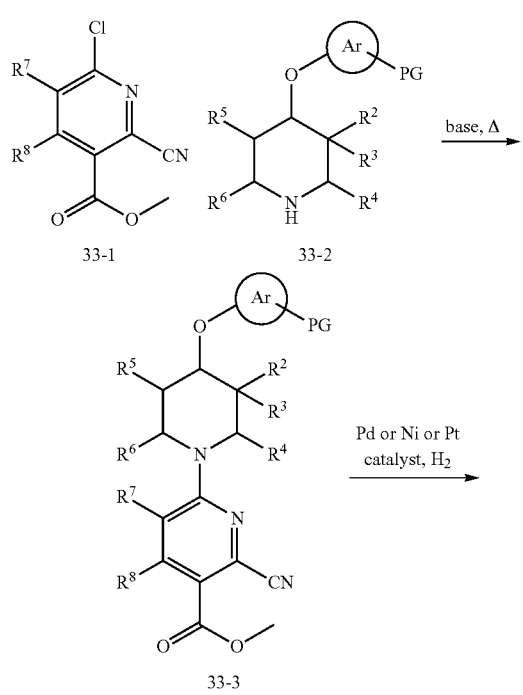

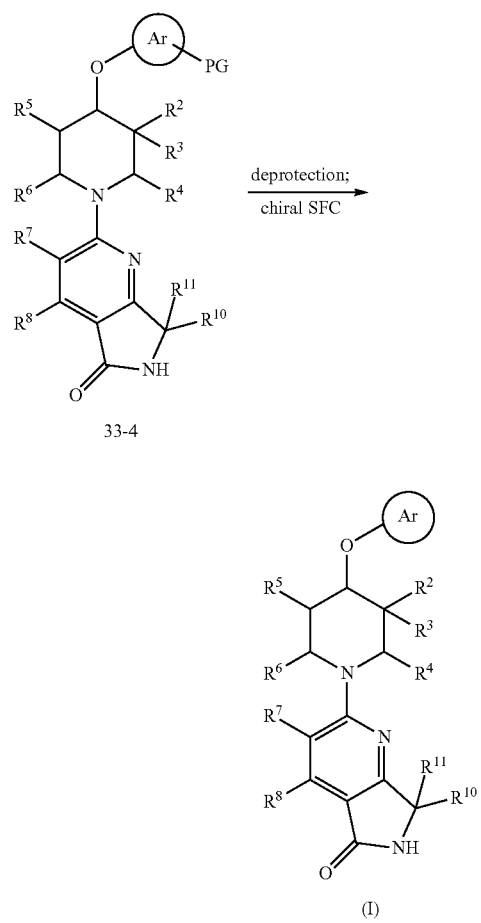

Compounds of formula (I) are synthesized from an S$_N$Ar reaction of prepared pyridine 33-1 and a known or prepared piperidine 33-2. Reduction of nitrile 33-3 can be carried out with a platinum, or palladium, or nickel-based catalyst such that the resultant amine cyclizes to form a lactam often in the presence of base. A final deprotection step, and in some examples a chiral resolution was carried out to provide compounds having the formula (I).

SCHEME 34

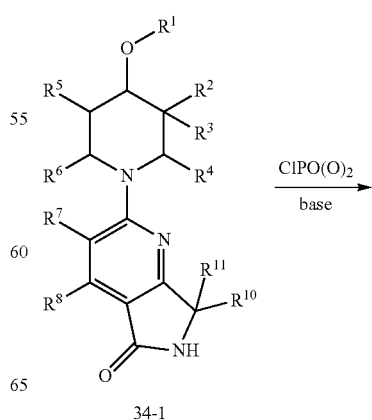

-continued
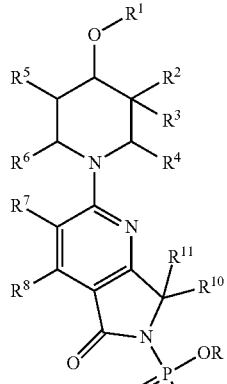
34-2
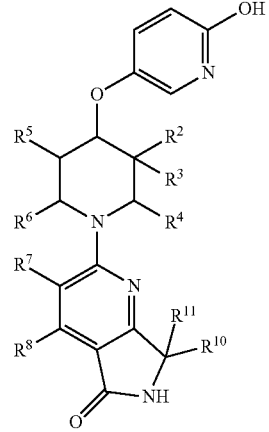
(I)
Compounds of formula (I) are synthesized from ether 35-1 by O-demethylation mediated by trimethylsilyliodide.
Compounds of formula (I) are synthesized from a base-mediated reaction of lactam 34-1 with chlorophosphate to yield adduct 34-2 followed by phosphodiester hydrolysis.
SCHEME 35
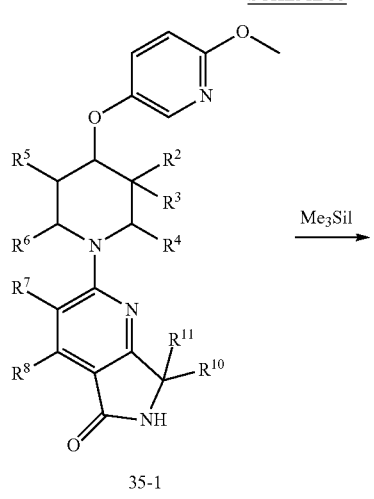
35-1
SCHEME 36
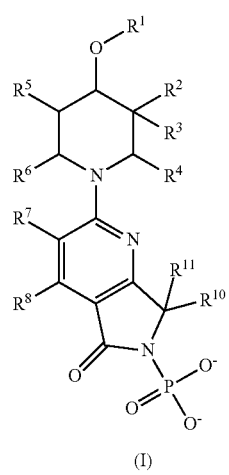
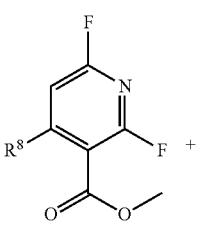 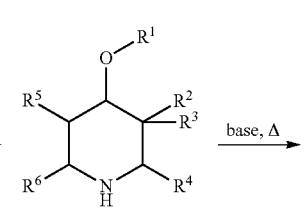
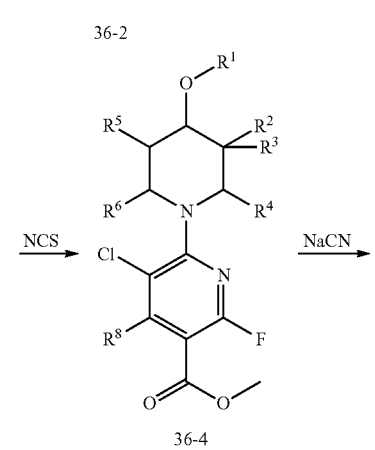

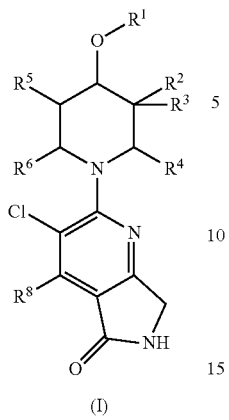

(I)

Compounds of formula (I) are synthesized beginning from an S<sub>N</sub>Ar reaction of commercial 2-fluoropyridine 36-1 with prepared piperidine 36-2. Adduct 36-3 is reacted with NCS to provide the chlorinated product 36-4. A second S<sub>N</sub>Ar reaction with sodium cyanide provides nitrile adduct 36-5. Methylation is carried out in the presence of base to provide Me-ester 36-6. Reduction of intermediate 36-6 can be carried out with a palladium or nickel catalyst, wherein the intermediary amine will cyclize to form the lactam often in the presence of base to afford compound (I).

SCHEME 37

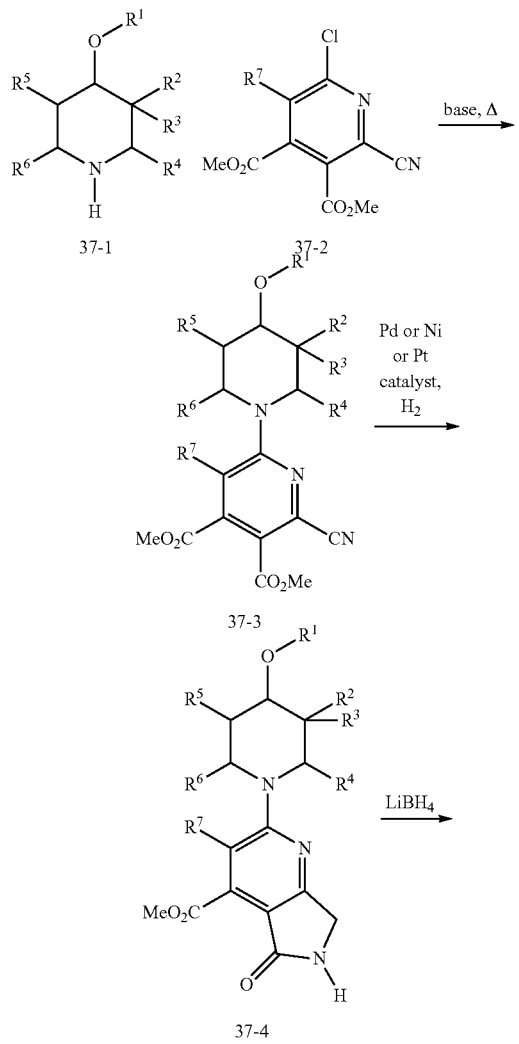

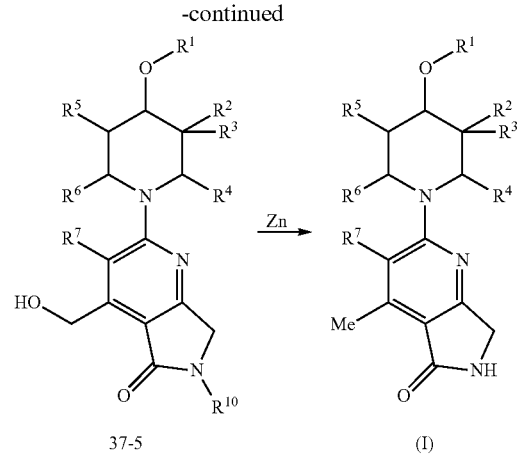

Compounds of the formula (I) are synthesized from prepared piperidine 37-1 and aryl chloride 37-2 to form adduct 37-3 in a S<sub>N</sub>Ar reaction. Reduction of nitrile 37-3 can be carried out with a platinum, palladium or nickel-based catalyst and hydrogen, such that the resultant amide cycles to form lactam 37-4, often in the presence of base. A 2-step procedure is used to reduce ester 37-4 to compounds of the formula (I) via a borohydride reduction followed by a second reduction using zinc-dust. In cases where a stereocenter is present in $R^1$, chiral resolution may be carried out as a final step.

SCHEME 38

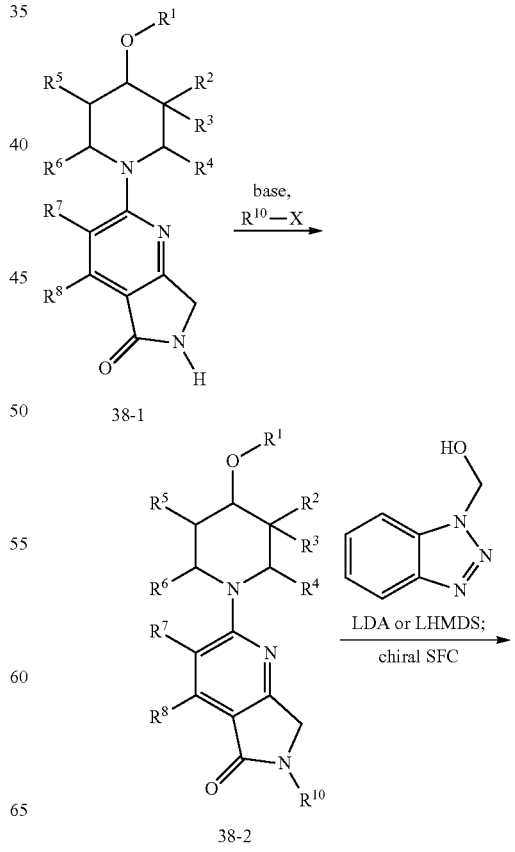

147

-continued

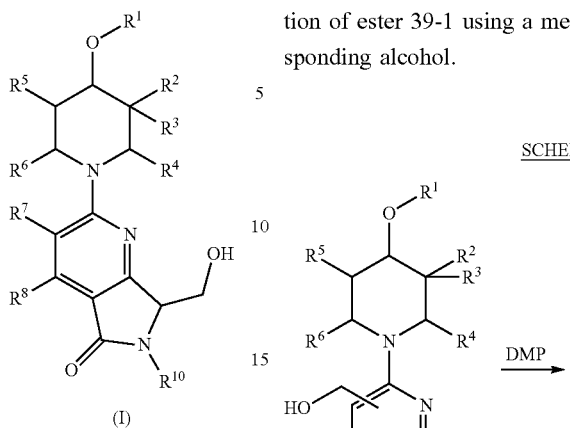

(I)

Compounds of formula (I) are synthesized from a base-mediated alkylation of lactam 38-1 with an alkyl halide to yield adduct 38-2. Hydroxylation by the in situ generation of anhydrous formaldehyde in the presence of base and subsequent chiral resolution provide compounds of the formula (I).

SCHEME 39

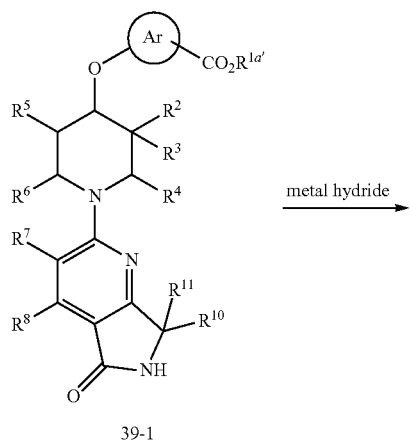

39-1

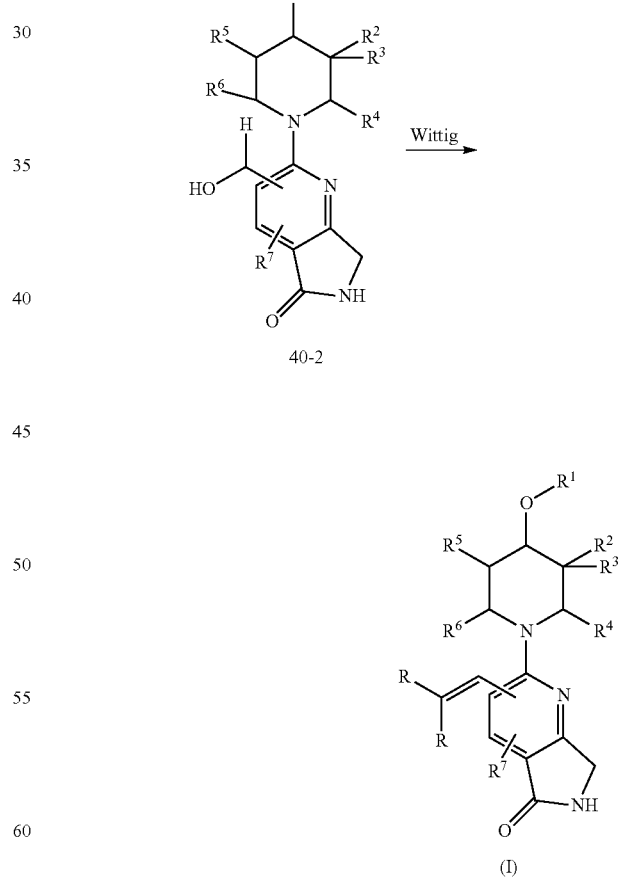

(I)

148

Compounds of formula (I) are synthesized from a reduction of ester 39-1 using a metal hydride to form the corresponding alcohol.

SCHEME 40

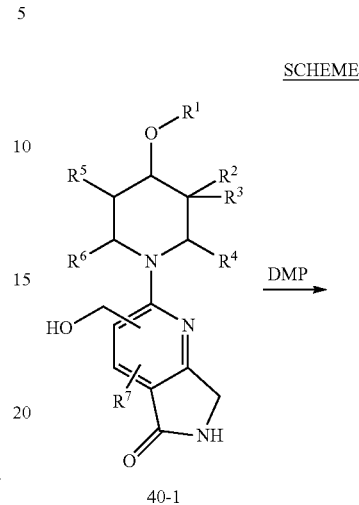

40-1

40-2

(I)

Compounds of formula (I) are synthesized from alcohol 40-1 through oxidation to the aldehyde 40-2 using Dess-Martin reagent and a subsequent Wittig reaction.

SCHEME 41

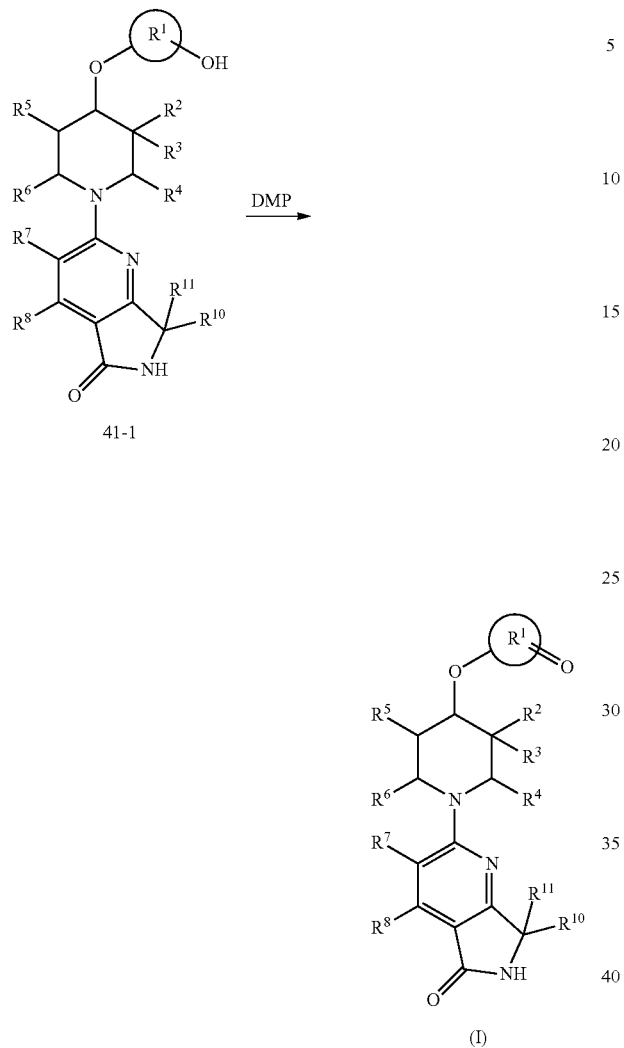

Compounds of formula (I) are synthesized from alcohol 41-1 after a Dess-Martin periodinane mediated oxidation reaction.

SCHEME 42

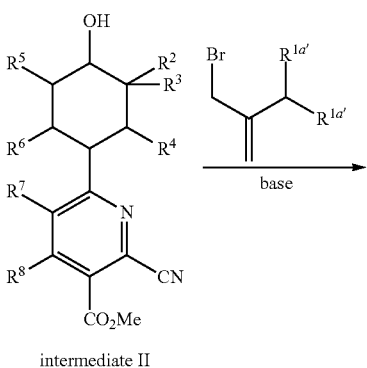

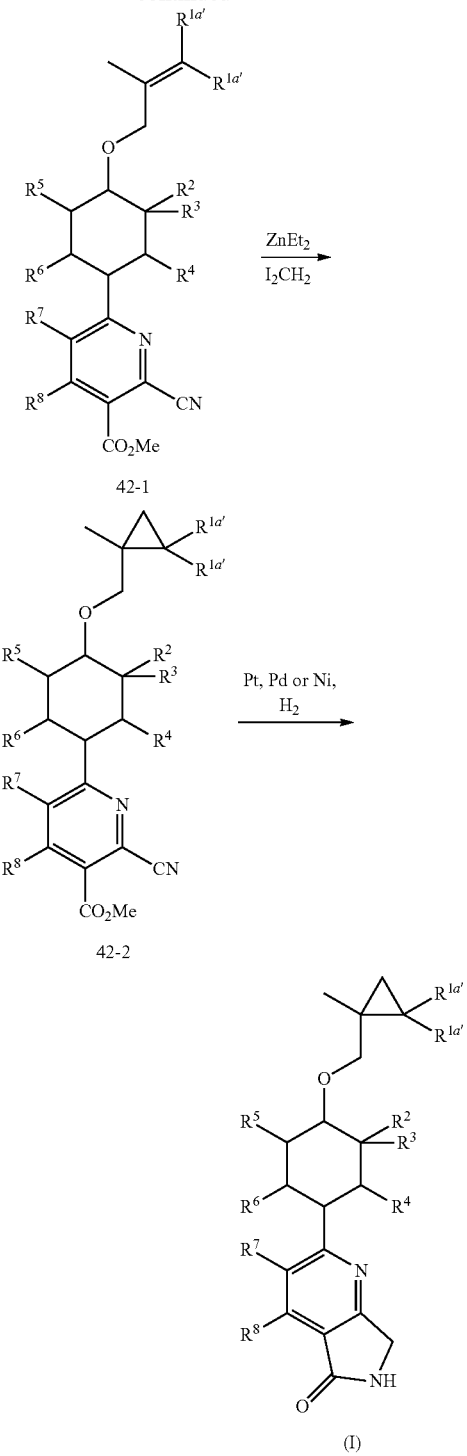

Compounds of the formula (I) are synthesized from a prepared alcohol intermediate II and alkylation to form adduct 42-1. Simmons-Smith reaction conditions provides cyclopropyl adduct 42-2. Reduction of nitrile 42-2 can be carried out with a platinum, palladium or nickel-based catalyst such that the resultant amide cycles to form compounds of the formula (I). In cases, where there is a stereocenter, an additional chiral resolution step may be carried out.

SCHEME 43

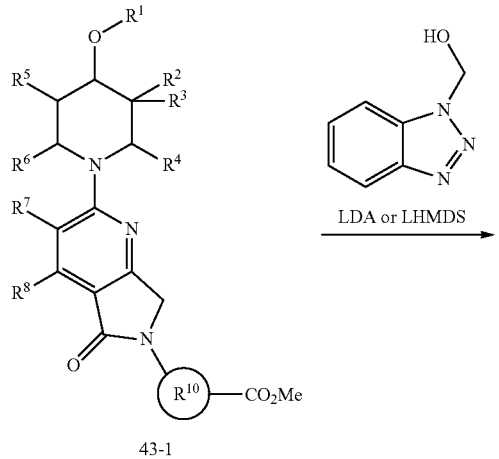

43-1

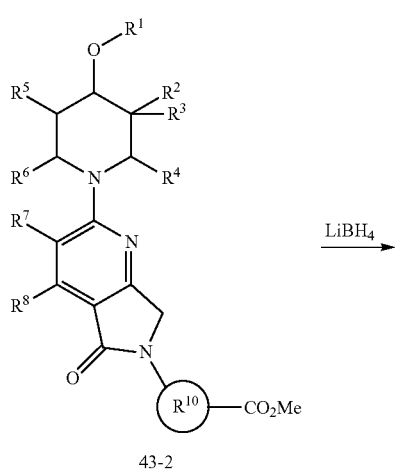

43-2

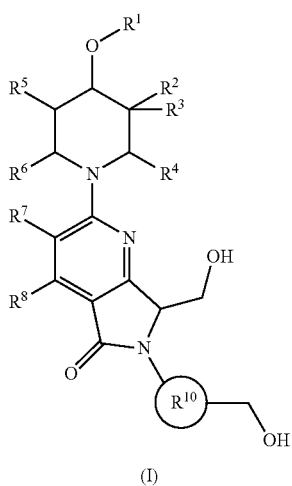

(I)

Compounds of formula (I) are synthesized via a hydroxylation reaction of lactam 43-1 by the in situ generation of anhydrous formaldehyde in the presence of base and subsequent reduction of ester 43-2 to provide compounds of the formula (I).

Example 1

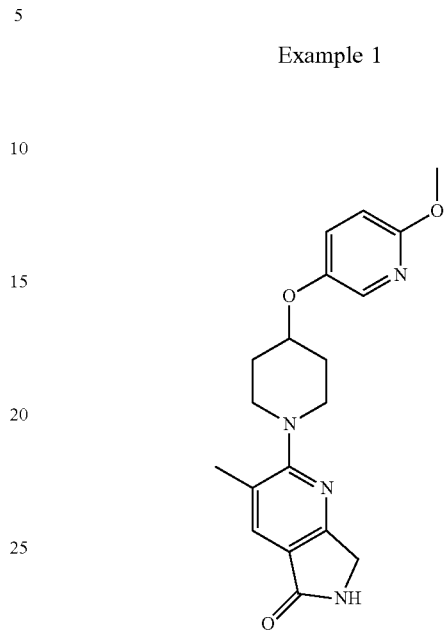

2-(4-((6-Methoxypyridin-3-yl)oxy)piperidin-1-yl)-3-methyl-6,7-dihydro-5H-pyrrolo[3,4-b]pyridin-5-one (Scheme 1)

To a 500 mL flask containing 2-chloro-3-methyl-6,7-dihydro-5H-pyrrolo[3,4-b]pyridin-5-one (18 g, 99 mmol, intermediate B1), 2-methoxy-5-(piperidin-4-yloxy)pyridine dihydrochloride (29.1 g, 104 mmol, intermediate F1) and sodium bicarbonate (33.1 g, 394 mmol) was added N-methyl-2-pyrrolidinone (246 mL). The system was fitted with a condenser and the system was heated to 160° C. and was stirred for 15 h. The mixture was cooled to RT and filtered and the filtrate was partitioned with water (1.5 L) and 1:5 EtOAc:DCM (500 mL). The organic layer was washed with 1:1 brine:water (500 mL), dried over anhydrous sodium sulfate, filtered over a small pad of celite/silicagel/activated carbon, and concentrated. The residue was dissolved in hot iPrOH with DCM (~10%) and the mixture was sonicated and heated to 60° C. for 30 min. After slowly cooling the mixture to RT, the solids were collected and washed with 1:1:1 ether:iPrOH:heptane and was lyophilized to yield the title compound. MS: 355 (M+1). $^1$H NMR (500 MHz, CDCl$_3$): δ 7.88 (1H, d, J=2.88 Hz), 7.81 (1H, s), 7.27 (1H, t, J=5.56 Hz), 6.72 (1H, d, J=8.91 Hz), 6.40 (1H, s), 4.38-4.39 (1H, m), 4.37 (1H, s), 3.91 (3H, s), 3.57 (3H, br s), 3.14-3.18 (2H, m), 2.37 (3H, s), 2.13 (2H, br s), 1.94-1.98 (2H, m).

Example 2A and 2B

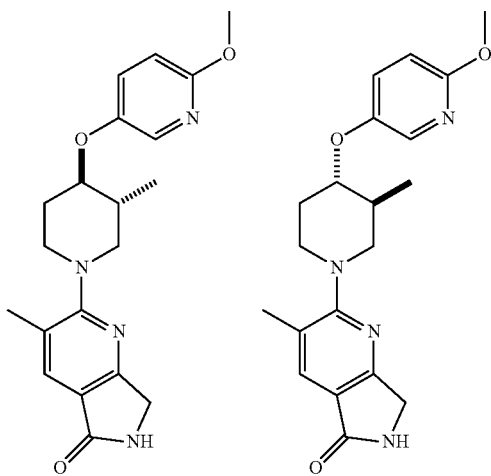

2-((3R,4R)-4-((6-methoxypyridin-3-yl)oxy)-3-methylpiperidin-1-yl)-3-methyl-6,7-dihydro-5H-pyrrolo[3,4-b]pyridin-5-one and 2-((3S,4S)-4-((6-methoxypyridin-3-yl)oxy)-3-methylpiperidin-1-yl)-3-methyl-6,7-dihydro-5H-pyrrolo[3,4-b]pyridin-5-one
(Scheme 1)

A suspension of 2-methoxy-5-((trans-3-methylpiperidin-4-yl)oxy)pyridine (245 mg, 1.10 mmol), 2-chloro-3-methyl-6,7-dihydro-5H-pyrrolo[3,4-b]pyridin-5-one (201 mg, 1.10 mmol, intermediate B1) and Hunig's base (384 μL, 2.20 mmol) in N-methyl-2-pyrrolidinone (3 mL) was prepared. The system was sealed and was heated to 175° C. for 19 h. After cooling, the reaction was diluted with EtOAc, washed with water (3×) and brine, dried over anhydrous sodium sulfate, filtered and concentrated. The residue was purified by mass triggered reverse phase HPLC (ACN/water with 0.1% NH$_3$OH modifier) to afford the racemate. The mixture of the two stereoisomers was resolved by chiral SFC (OJ-H column, 15% MeOH/CO$_2$) to afford isomer 2A (faster eluting): MS: 369 (M+1). 1H NMR (500 MHz, CDCl$_3$): δ 7.90 (1H, d, J=3.0 Hz), 7.83 (1H, s), 7.28-7.30 (1H, m), 6.73 (1H, d, J=8.9 Hz), 6.21 (1H, s), 4.38 (2H, s), 3.93 (3H, s), 3.85-3.87 (1H, m), 3.66 (2H, dd, J=12.7, 4.1 Hz), 2.97-3.02 (1H, m), 2.78 (1H, dd, J=13.1, 9.9 Hz), 2.39 (3H, s), 2.14-2.23 (2H, m), 1.79-1.86 (1H, m), 1.17 (3H, d, J=6.6 Hz). Isomer 2B (slower eluting): MS: 369 (M+1). $^1$H NMR (500 MHz, CDCl$_3$): δ 7.90 (1H, d, J=3.0 Hz), 7.83 (1H, s), 7.28-7.30 (1H, m), 6.73 (1H, d, J=8.9 Hz), 6.21 (1H, s), 4.38 (2H, s), 3.93 (3H, s), 3.85-3.87 (1H, m), 3.66 (2H, dd, J=12.7, 4.1 Hz), 2.97-3.02 (1H, m), 2.78 (1H, dd, J=13.1, 9.9 Hz), 2.39 (3H, s), 2.14-2.23 (2H, m), 1.79-1.86 (1H, m), 1.17 (3H, d, J=6.6 Hz).

The following examples in table 1 were prepared according to scheme 1 using the procedure outlined in the synthesis of Example 1 or Example 2A and 2B using known or prepared piperidines and 2-chloropyridines. Alternative conditions can be used in this reaction, such that the base is DIPEA, sodium bicarbonate, or tributylamine as appropriate for each substrate.

TABLE 1

| Example | Structure | Name | MS (M + 1) |
| --- | --- | --- | --- |
| 3 | 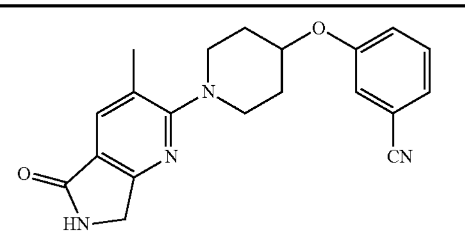 | 3-((1-(3-methyl-5-oxo-6,7-dihydro-5H-pyrrolo[3,4-b]pyridin-2-yl)piperidin-4-yl)oxy)benzonitrile | 349 |
| 3A | 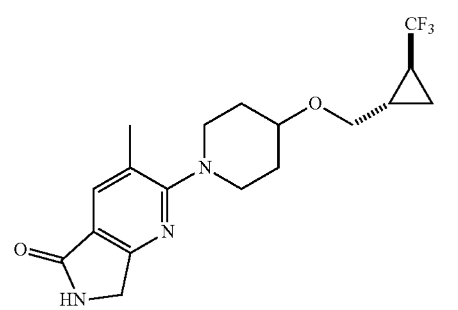 | 3-methyl-2-(4-(((trans)-2-(trifluoromethyl)cyclopropyl)methoxy)piperidin-1-yl)-6,7-dihydro-5H-pyrrolo[3,4-b]pyridin-5-one | 370 |
| 4 | 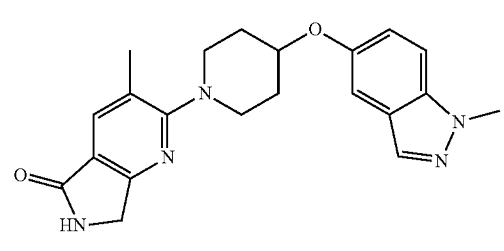 [SMILES: Cc1cc2c(nc1N1CCC(Oc3ccc4c(cnn4C)c3)CC1)CNC2=O] | 3-methyl-2-(4-((1-methyl-1H-indazol-5-yl)oxy)piperidin-1-yl)-6,7-dihydro-5H-pyrrolo[3,4-b]pyridin-5-one | 378 |

TABLE 1-continued

| Example | Structure | Name | MS (M + 1) |
|---|---|---|---|
| 4A | 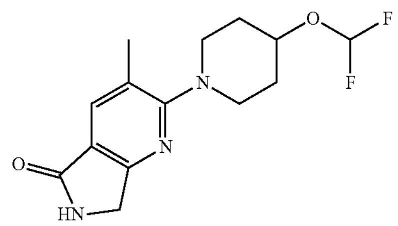 [SMILES: Cc1cc2c(nc1N1CCC(OC(F)F)CC1)CNC2=O] | 2-(4-(difluoromethoxy)piperidin-1-yl)-3-methyl-6,7-dihydro-5H-pyrrolo[3,4-b]pyridin-5-one | 298 |
| 5 | 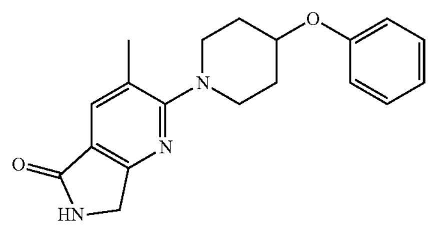 [SMILES: Cc1cc2c(nc1N1CCC(Oc3ccccc3)CC1)CNC2=O] | 3-methyl-2-(4-phenoxypiperidin-1-yl)-6,7-dihydro-5H-pyrrolo[3,4-b]pyridin-5-one | 324 |
| 5A | 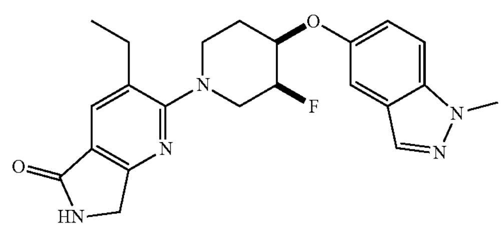 [SMILES: CCc1cc2c(nc1N1CC[C@@H](Oc3ccc4c(cnn4C)c3)[C@@H](F)C1)CNC2=O] | 3-ethyl-2-((3S,4R)-3-fluoro-4-((1-methyl-1H-indazol-5-yl)oxy)piperidin-1-yl)-6,7-dihydro-5H-pyrrolo[3,4-b]pyridin-5-one | 410 |
| 6 | 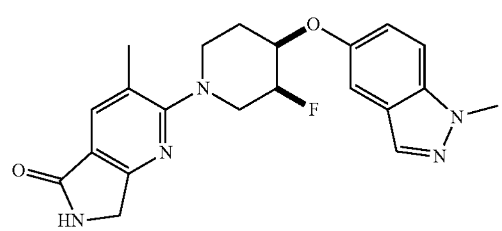 [SMILES: Cc1cc2c(nc1N1CC[C@@H](Oc3ccc4c(cnn4C)c3)[C@@H](F)C1)CNC2=O] | 2-((3S,4R)-3-fluoro-4-((1-methyl-1H-indazol-5-yl)oxy)piperidin-1-yl)-3-methyl-6,7-dihydro-5H-pyrrolo[3,4-b]pyridin-5-one | 424 |
| 6A | 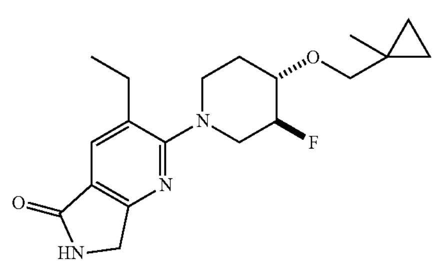 [SMILES: CCc1cc2c(nc1N1CC[C@H](OCC3(C)CC3)[C@@H](F)C1)CNC2=O] | 3-ethyl-2-((3S,4S)-3-fluoro-4-((1-methylcyclopropyl)methoxy)piperidin-1-yl)-6,7-dihydro-5H-pyrrolo[3,4-b]pyridin-5-one | 348 |
| 7 | 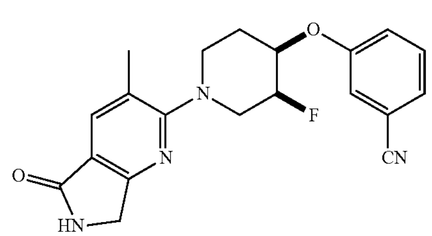 [SMILES: Cc1cc2c(nc1N1CC[C@@H](Oc3cccc(C#N)c3)[C@@H](F)C1)CNC2=O] | 3-((cis-3-fluoro-1-(3-methyl-5-oxo-6,7-dihydro-5H-pyrrolo[3,4-b]pyridin-2-yl)piperidin-4-yl)oxy)benzonitrile | 367 |

TABLE 1-continued

| Example | Name | MS (M + 1) |
|---|---|---|
| 8 | 2-((3S,4R)-4-((1H-indazol-5-yl)oxy)-3-fluoropiperidin-1-yl)-3-methyl-6,7-dihydro-5H-pyrrolo[3,4-b]pyridin-5-one | 382 |
| 8A<br>8B | (R)-2-(4-((2,2-difluoro-1-methylcyclopropyl)methoxy)piperidin-1-yl)-3-methyl-6,7-dihydro-5H-pyrrolo[3,4-b]pyridin-5-one<br>and<br>(S)-2-(4-((2,2-difluoro-1-methylcyclopropyl)methoxy)piperidin-1-yl)-3-methyl-6,7-dihydro-5H-pyrrolo[3,4-b]pyridin-5-one | 352<br>352 |
| 9 | 2-(4-(cyclopropylmethoxy)piperidin-1-yl)-3-methyl-6,7-dihydro-5H-pyrrolo[3,4-b]pyridin-5-one | 302 |
| 10 | 2-(4-((2-cyclopropyl-3-oxoisoindolin-5-yl)oxy)piperidin-1-yl)-3-methyl-6,7-dihydro-5H-pyrrolo[3,4-b]pyridin-5-one | 419 |
| 11 | 3-((1-(3,6-dimethyl-5-oxo-6,7-dihydro-5H-pyrrolo[3,4-b]pyridin-2-yl)piperidin-4-yl)oxy)benzonitrile | 363 |

TABLE 1-continued

| Example | Structure | Name | MS (M + 1) |
|---|---|---|---|
| 12 | 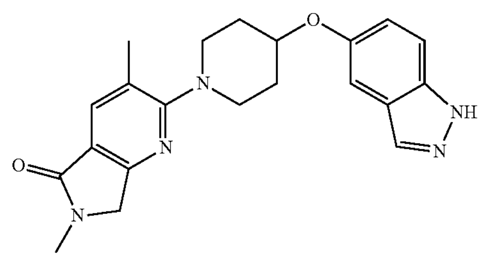 [SMILES: Cc1cc2c(nc1N1CCC(Oc3ccc4[nH]ncc4c3)CC1)CN(C)C2=O] | 2-(4-((1H-indazol-5-yl)oxy)piperidin-1-yl)-3,6-dimethyl-6,7-dihydro-5H-pyrrolo[3,4-b]pyridin-5-one | 378 |
| 13 | 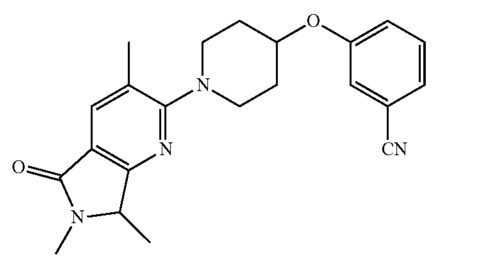 [SMILES: Cc1cc2c(nc1N1CCC(Oc3cccc(C#N)c3)CC1)C(C)N(C)C2=O] | 3-((1-(3,6,7-trimethyl-5-oxo-6,7-dihydro-5H-pyrrolo[3,4-b]pyridin-2-yl)piperidin-4-yl)oxy)benzonitrile | 377 |
| 14 | 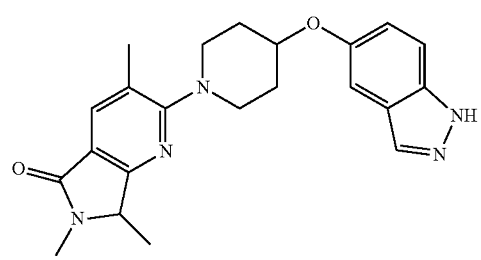 [SMILES: Cc1cc2c(nc1N1CCC(Oc3ccc4[nH]ncc4c3)CC1)C(C)N(C)C2=O] | 2-(4-((1H-indazol-5-yl)oxy)piperidin-1-yl)-3,6,7-trimethyl-6,7-dihydro-5H-pyrrolo[3,4-b]pyridin-5-one | 392 |
| 15 | 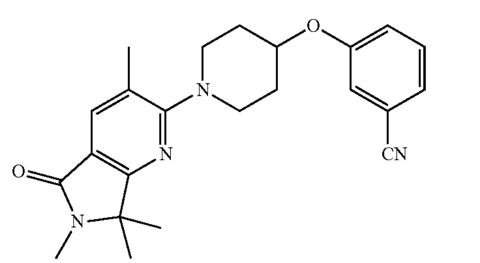 [SMILES: Cc1cc2c(nc1N1CCC(Oc3cccc(C#N)c3)CC1)C(C)(C)N(C)C2=O] | 3-((1-(3,6,7,7-tetramethyl-5-oxo-6,7-dihydro-5H-pyrrolo[3,4-b]pyridin-2-yl)piperidin-4-yl)oxy)benzonitrile | 391 |
| 16 | 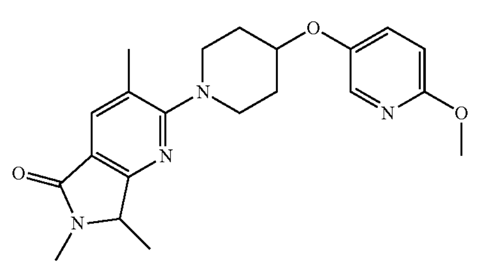 [SMILES: COc1ccc(OC2CCN(c3nc4c(cc3C)C(=O)N(C)C4C)CC2)cn1] | 2-(4-((6-methoxypyridin-3-yl)oxy)piperidin-1-yl)-3,6,7-trimethyl-6,7-dihydro-5H-pyrrolo[3,4-b]pyridin-5-one | 383 |
| 17 | 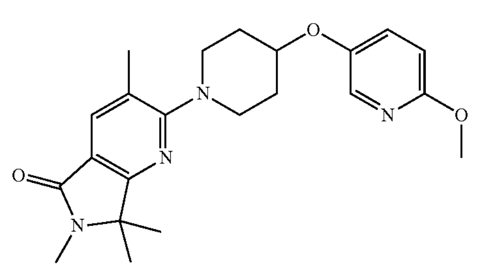 [SMILES: COc1ccc(OC2CCN(c3nc4c(cc3C)C(=O)N(C)C4(C)C)CC2)cn1] | 2-(4-((6-methoxypyridin-3-yl)oxy)piperidin-1-yl)-3,6,7,7-tetramethyl-6,7-dihydro-5H-pyrrolo[3,4-b]pyridin-5-one | 397 |

TABLE 1-continued

| Example | Structure | Name | MS (M + 1) |
|---|---|---|---|
| 18 | 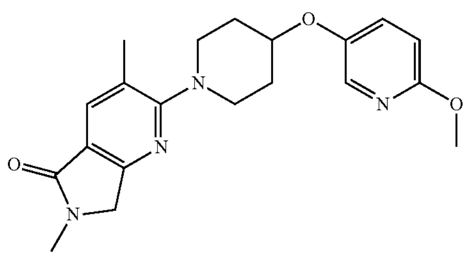 [SMILES: COc1ccc(OC2CCN(c3nc4c(cc3C)C(=O)N(C)C4)CC2)cn1] | 2-(4-((6-methoxypyridin-3-yl)oxy)piperidin-1-yl)-3,6-dimethyl-6,7-dihydro-5H-pyrrolo[3,4-b]pyridin-5-one | 369 |
| 19 | 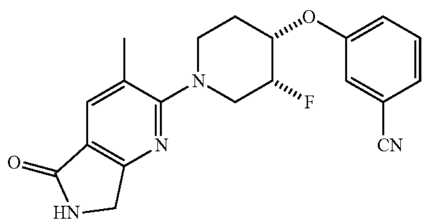 [SMILES: Cc1cc2c(nc1N1CC[C@H](Oc3cccc(C#N)c3)[C@H](F)C1)CNC2=O] | 3-(((3R,4S)-3-fluoro-1-(3-methyl-5-oxo-6,7-dihydro-5H-pyrrolo[3,4-b]pyridin-2-yl)piperidin-4-yl)oxy)benzonitrile | 367 |
| 20 | 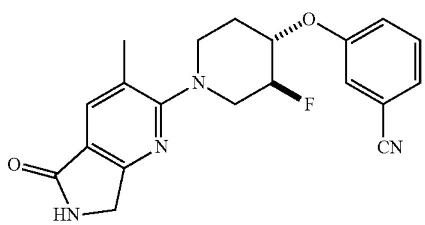 [SMILES: Cc1cc2c(nc1N1CC[C@H](Oc3cccc(C#N)c3)[C@@H](F)C1)CNC2=O] | 3-(((3S,4S)-3-fluoro-1-(3-methyl-5-oxo-6,7-dihydro-5H-pyrrolo[3,4-b]pyridin-2-yl)piperidin-4-yl)oxy)benzonitrile | 367 |
| 21 | 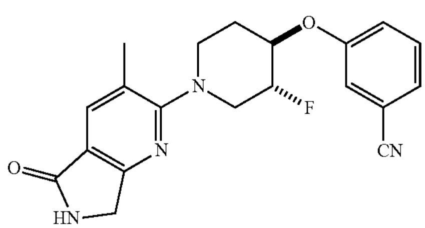 [SMILES: Cc1cc2c(nc1N1CC[C@@H](Oc3cccc(C#N)c3)[C@H](F)C1)CNC2=O] | 3-(((3R,4R)-3-fluoro-1-(3-methyl-5-oxo-6,7-dihydro-5H-pyrrolo[3,4-b]pyridin-2-yl)piperidin-4-yl)oxy)benzonitrile | 367 |
| 22 | 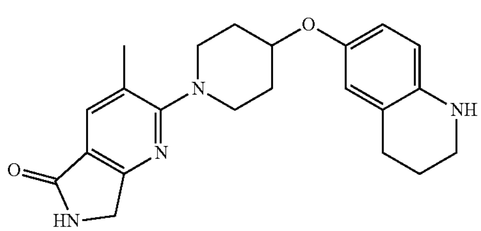 [SMILES: Cc1cc2c(nc1N1CCC(Oc3ccc4c(c3)CCCN4)CC1)CNC2=O] | 3-methyl-2-(4-((1,2,3,4-tetrahydroquinolin-6-yl)oxy)piperidin-1-yl)-6,7-dihydro-5H-pyrrolo[3,4-b]pyridin-5-one | 379 |
| 23 | 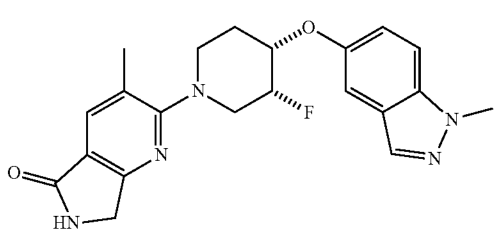 [SMILES: Cc1cc2c(nc1N1CC[C@H](Oc3ccc4c(cnn4C)c3)[C@H](F)C1)CNC2=O] | 2-((3R,4S)-3-fluoro-4-((1-methyl-1H-indazol-5-yl)oxy)piperidin-1-yl)-3-methyl-6,7-dihydro-5H-pyrrolo[3,4-b]pyridin-5-one | 396 |

TABLE 1-continued

| Example | Structure | Name | MS (M + 1) |
|---|---|---|---|
| 24 | 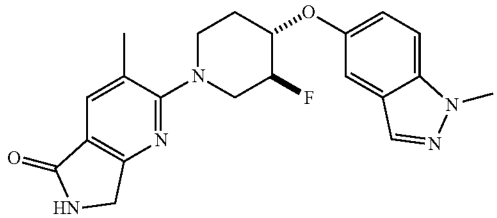 [SMILES: Cc1cc2c(nc1N1CC[C@H](Oc3ccc4c(cnn4C)c3)[C@@H](F)C1)CNC2=O] | 2-((3S,4S)-3-fluoro-4-((1-methyl-1H-indazol-5-yl)oxy)piperidin-1-yl)-3-methyl-6,7-dihydro-5H-pyrrolo[3,4-b]pyridin-5-one | 396 |
| 25 | 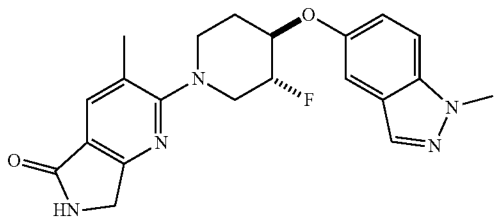 [SMILES: Cc1cc2c(nc1N1CC[C@@H](Oc3ccc4c(cnn4C)c3)[C@H](F)C1)CNC2=O] | 2-((3R,4R)-3-fluoro-4-((1-methyl-1H-indazol-5-yl)oxy)piperidin-1-yl)-3-methyl-6,7-dihydro-5H-pyrrolo[3,4-b]pyridin-5-one | 396 |
| 26 | 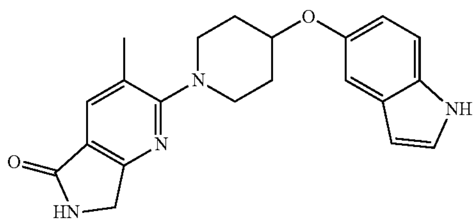 [SMILES: Cc1cc2c(nc1N1CCC(Oc3ccc4[nH]ccc4c3)CC1)CNC2=O] | 2-(4-((1H-indol-5-yl)oxy)piperidin-1-yl)-3-methyl-6,7-dihydro-5H-pyrrolo[3,4-b]pyridin-5-one | 363 |
| 27 | 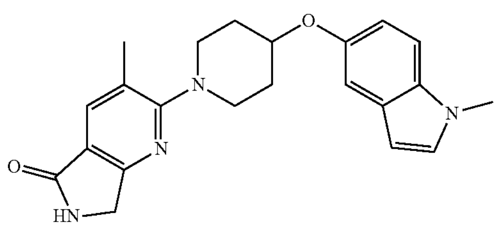 | 3-methyl-2-(4-((1-methyl-1H-indol-5-yl)oxy)piperidin-1-yl)-6,7-dihydro-5H-pyrrolo[3,4-b]pyridin-5-one | 377 |
| 28A 28B | | (R)-3-((1-(3,6,7-trimethyl-5-oxo-6,7-dihydro-5H-pyrrolo[3,4-b]pyridin-2-yl)piperidin-4-yl)oxy)benzonitrile and (S)-3-((1-(3,6,7-trimethyl-5-oxo-6,7-dihydro-5H-pyrrolo[3,4-b]pyridin-2-yl)piperidin-4-yl)oxy)benzonitrile | 377 377 |

TABLE 1-continued

| Example | Name | MS (M + 1) |
|---|---|---|
| 29A<br>29B | 2-((3S,4R)-4-((6-methoxypyridin-3-yl)oxy)-3-methylpiperidin-1-yl)-3-methyl-6,7-dihydro-5H-pyrrolo[3,4-b]pyridin-5-one and 2-((3R,4S)-4-((6-methoxypyridin-3-yl)oxy)-3-methylpiperidin-1-yl)-3-methyl-6,7-dihydro-5H-pyrrolo[3,4-b]pyridin-5-one | 369<br>369 |
| 30 | 2-((3R,4R)-3-fluoro-4-((6-methoxypyridin-3-yl)oxy)piperidin-1-yl)-3-methyl-6,7-dihydro-5H-pyrrolo[3,4-b]pyridin-5-one | 373 |
| 31 | 2-((3S,4R)-3-fluoro-4-((1-methyl-1H-indazol-5-yl)oxy)piperidin-1-yl)-3,6-dimethyl-6,7-dihydro-5H-pyrrolo[3,4-b]pyridin-5-one | 410 |
| 32 | 3,6-dimethyl-2-(4-((1-methyl-1H-indazol-5-yl)oxy)piperidin-1-yl)-6,7-dihydro-5H-pyrrolo[3,4-b]pyridin-5-one | 392 |
| 33 | 2-((3S,4R)-3-fluoro-4-((6-methoxypyridin-3-yl)oxy)piperidin-1-yl)-3,6-dimethyl-6,7-dihydro-5H-pyrrolo[3,4-b]pyridin-5-one | 387 |

TABLE 1-continued

| Example | Structure | Name | MS (M + 1) |
|---|---|---|---|
| 34 | 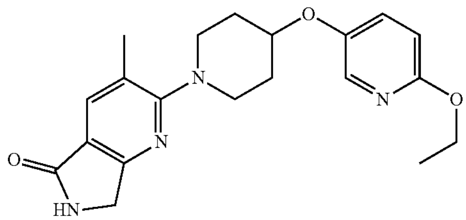 [SMILES: CCOc1ccc(OC2CCN(c3nc4c(cc3C)C(=O)NC4)CC2)cn1] | 2-(4-((6-ethoxypyridin-3-yl)oxy)piperidin-1-yl)-3-methyl-6,7-dihydro-5H-pyrrolo[3,4-b]pyridin-5-one | 369 |
| 35 | 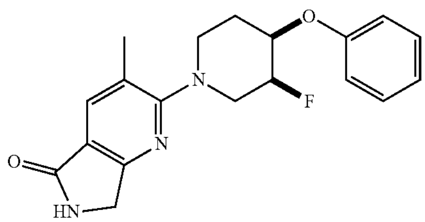 [SMILES: Cc1cc2c(nc1N1CC[C@@H](Oc3ccccc3)[C@@H](F)C1)CNC2=O] | 2-((3S,4R)-3-fluoro-4-phenoxypiperidin-1-yl)-3-methyl-6,7-dihydro-5H-pyrrolo[3,4-b]pyridin-5-one | 342 |
| 36 | 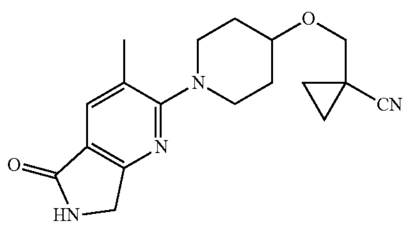 [SMILES: Cc1cc2c(nc1N1CCC(OCC3(C#N)CC3)CC1)CNC2=O] | 1-(((1-(3-methyl-5-oxo-6,7-dihydro-5H-pyrrolo[3,4-b]pyridin-2-yl)piperidin-4-yl)oxy)methyl)cyclopropane-1-carbonitrile | 327 |
| 37 | 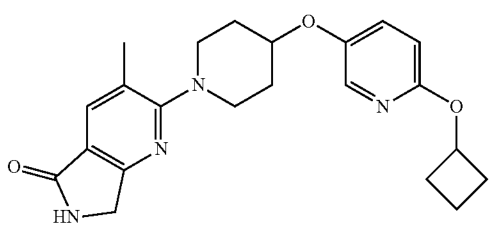 [SMILES: Cc1cc2c(nc1N1CCC(Oc3ccc(OC4CCC4)nc3)CC1)CNC2=O] | 2-(4-((6-cyclobutoxypyridin-3-yl)oxy)piperidin-1-yl)-3-methyl-6,7-dihydro-5H-pyrrolo[3,4-b]pyridin-5-one | 395 |
| 38 | 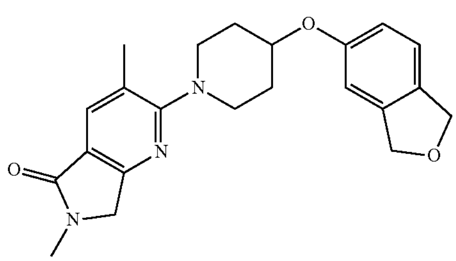 [SMILES: Cc1cc2c(nc1N1CCC(Oc3ccc4c(c3)COC4)CC1)CN(C)C2=O] | 2-(4-((1,3-dihydro-2-benzofuran-5-yl)oxy)piperidin-1-yl)-3,6-dimethyl-6,7-dihydro-5H-pyrrolo[3,4-b]pyridin-5-one | 380 |
| 39 | 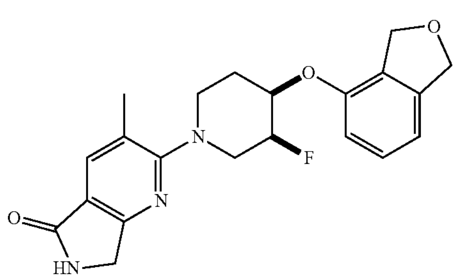 [SMILES: Cc1cc2c(nc1N1CC[C@@H](Oc3cccc4c3COC4)[C@@H](F)C1)CNC2=O] | 2-((3S,4R)-4-((1,3-dihydro-2-benzofuran-4-yl)oxy)-3-fluoropiperidin-1-yl)-3-methyl-6,7-dihydro-5H-pyrrolo[3,4-b]pyridin-5-one | 384 |

TABLE 1-continued

| Example | Structure | Name | MS (M + 1) |
|---|---|---|---|
| 40 | 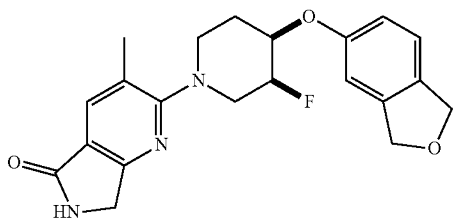 | 2-((3S,4R)-4-((1,3-dihydro-2-benzofuran-5-yl)oxy)-3-fluoropiperidin-1-yl)-3-methyl-6,7-dihydro-5H-pyrrolo[3,4-b]pyridin-5-one | 384 |
| 41 | 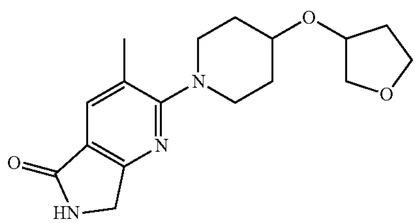 [SMILES: Cc1cc2c(nc1N1CCC(OC3CCOC3)CC1)CNC2=O] | 3-methyl-2-(4-((tetrahydrofuran-3-yl)oxy)piperidin-1-yl)-6,7-dihydro-5H-pyrrolo[3,4-b]pyridin-5-one | 318 |
| 42 | 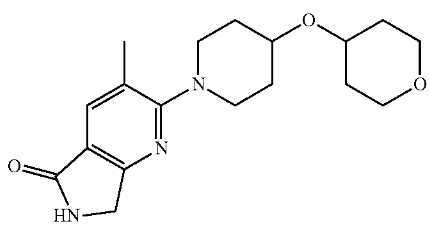 [SMILES: Cc1cc2c(nc1N1CCC(OC3CCOCC3)CC1)CNC2=O] | 3-methyl-2-(4-((tetrahydro-2H-pyran-4-yl)oxy)piperidin-1-yl)-6,7-dihydro-5H-pyrrolo[3,4-b]pyridin-5-one | 332 |
| 43A 43B | | 3-(((3R,4R)-3-hydroxy-1-(3-methyl-5-oxo-6,7-dihydro-5H-pyrrolo[3,4-b]pyridin-2-yl)piperidin-4-yl)oxy)benzonitrile and 3-(((3S,4S)-3-hydroxy-1-(3-methyl-5-oxo-6,7-dihydro-5H-pyrrolo[3,4-b]pyridin-2-yl)piperidin-4-yl)oxy)benzonitrile | 365 365 |
| 44 | 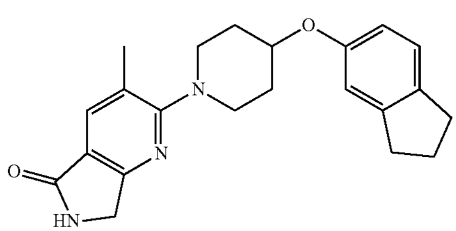 [SMILES: Cc1cc2c(nc1N1CCC(Oc3ccc4c(c3)CCC4)CC1)CNC2=O] | 2-(4-((2,3-dihydro-1H-inden-5-yl)oxy)piperidin-1-yl)-3-methyl-6,7-dihydro-5H-pyrrolo[3,4-b]pyridin-5-one | 364 |
| 45 | 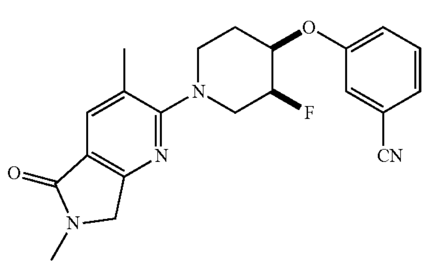 [SMILES: Cc1cc2c(nc1N1CC[C@@H](Oc3cccc(C#N)c3)[C@@H](F)C1)CN(C)C2=O] | 3-(((3S,4R)-1-(3,6-dimethyl-5-oxo-6,7-dihydro-5H-pyrrolo[3,4-b]pyridin-2-yl)-3-fluoropiperidin-4-yl)oxy)benzonitrile | 381 |

TABLE 1-continued

| Example | Structure | Name | MS (M + 1) |
|---|---|---|---|
| 46 | 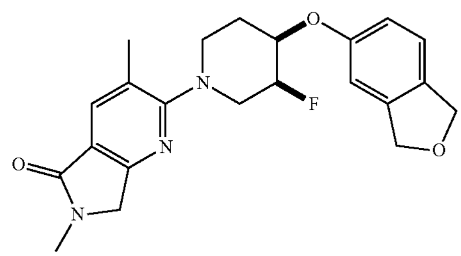 [SMILES: Cc1cc2c(nc1N1CC[C@@H](Oc3ccc4c(c3)COC4)[C@@H](F)C1)CN(C)C2=O] | 2-((3S,4R)-4-((1,3-dihydro-2-benzofuran-5-yl)oxy)-3-fluoropiperidin-1-yl)-3,6-dimethyl-6,7-dihydro-5H-pyrrolo[3,4-b]pyridin-5-one | 398 |
| 47 | 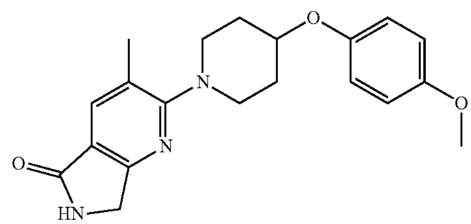 [SMILES: COc1ccc(OC2CCN(c3nc4c(cc3C)C(=O)NC4)CC2)cc1] | 2-(4-(4-methoxyphenoxy)piperidin-1-yl)-3-methyl-6,7-dihydro-5H-pyrrolo[3,4-b]pyridin-5-one | 354 |
| 47A | 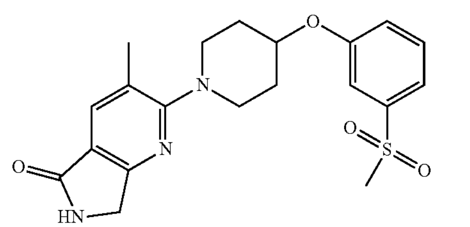 [SMILES: Cc1cc2c(nc1N1CCC(Oc3cccc(S(C)(=O)=O)c3)CC1)CNC2=O] | 3-methyl-2-(4-(3-(methylsulfonyl)phenoxy)piperidin-1-yl)-6,7-dihydro-5H-pyrrolo[3,4-b]pyridin-5-one | 402 |
| 48 | 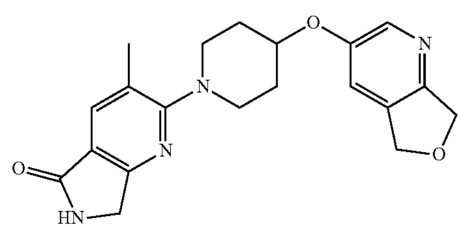 [SMILES: Cc1cc2c(nc1N1CCC(Oc3cnc4c(c3)COC4)CC1)CNC2=O] | 2-(4-((5,7-dihydrofuro[3,4-b]pyridin-3-yl)oxy)piperidin-1-yl)-3-methyl-6,7-dihydro-5H-pyrrolo[3,4-b]pyridin-5-one | 367 |
| 48A | 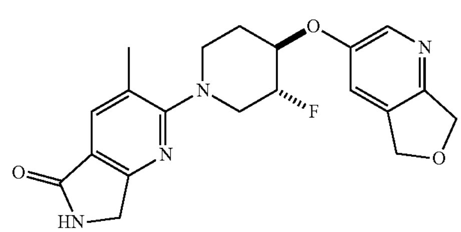 [SMILES: Cc1cc2c(nc1N1CC[C@@H](Oc3cnc4c(c3)COC4)[C@H](F)C1)CNC2=O] | 2-((3R,4R)-4-((5,7-dihydrofuro[3,4-b]pyridin-3-yl)oxy)-3-fluoropiperidin-1-yl)-3-methyl-6,7-dihydro-5H-pyrrolo[3,4-b]pyridin-5-one | 385 |
| 49 | 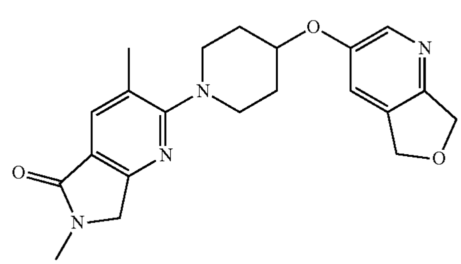 [SMILES: Cc1cc2c(nc1N1CCC(Oc3cnc4c(c3)COC4)CC1)CN(C)C2=O] | 2-(4-((5,7-dihydrofuro[3,4-b]pyridin-3-yl)oxy)piperidin-1-yl)-3,6-dimethyl-6,7-dihydro-5H-pyrrolo[3,4-b]pyridin-5-one | 381 |

TABLE 1-continued

| Example | Structure | Name | MS (M + 1) |
|---|---|---|---|
| 50 | 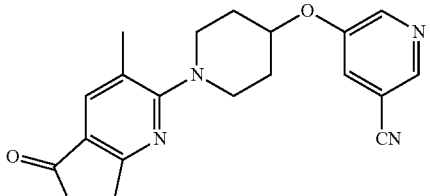 | 5-((1-(3-methyl-5-oxo-6,7-dihydro-5H-pyrrolo[3,4-b]pyridin-2-yl)piperidin-4-yl)oxy)nicotinonitrile | 350 |
| 51 | 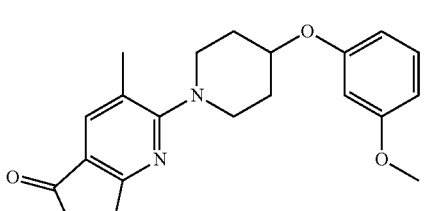 | 2-(4-(3-methoxyphenoxy)piperidin-1-yl)-3-methyl-6,7-dihydro-5H-pyrrolo[3,4-b]pyridin-5-one | 354 |
| 52 | 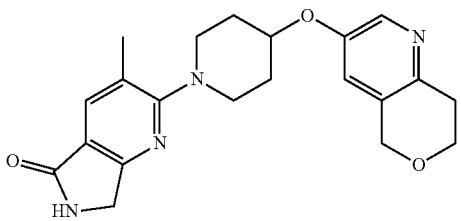 [SMILES: Cc1cc2c(nc1N1CCC(Oc3cnc4c(c3)COCC4)CC1)CNC2=O] | 2-(4-((7,8-dihydro-5H-pyrano[4,3-b]pyridin-3-yl)oxy)piperidin-1-yl)-3-methyl-6,7-dihydro-5H-pyrrolo[3,4-b]pyridin-5-one | 381 |
| 53 | 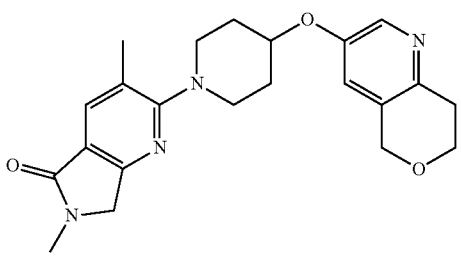 [SMILES: Cc1cc2c(nc1N1CCC(Oc3cnc4c(c3)COCC4)CC1)CN(C)C2=O] | 2-(4-((7,8-dihydro-5H-pyrano[4,3-b]pyridin-3-yl)oxy)piperidin-1-yl)-3,6-dimethyl-6,7-dihydro-5H-pyrrolo[3,4-b]pyridin-5-one | 395 |
| 54 | 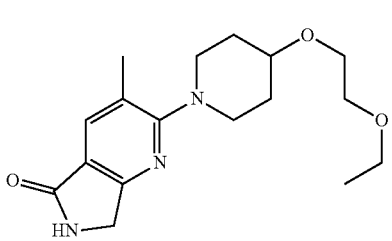 [SMILES: CCOCCOC1CCN(c2nc3c(cc2C)C(=O)NC3)CC1] | 2-(4-(2-ethoxyethoxy)piperidin-1-yl)-3-methyl-6,7-dihydro-5H-pyrrolo[3,4-b]pyridin-5-one | 320 |
| 55 | 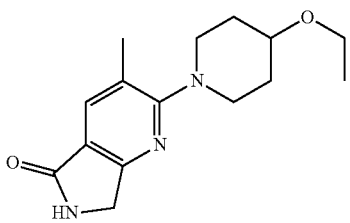 [SMILES: CCOC1CCN(c2nc3c(cc2C)C(=O)NC3)CC1] | 2-(4-ethoxypiperidin-1-yl)-3-methyl-6,7-dihydro-5H-pyrrolo[3,4-b]pyridin-5-one | 276 |

TABLE 1-continued

| Example | Structure | Name | MS (M + 1) |
|---|---|---|---|
| 56 | 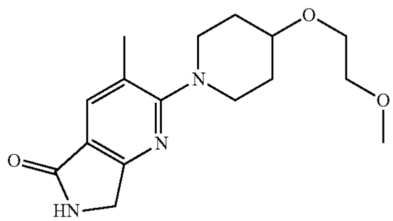 [SMILES: COCCOC1CCN(c2nc3c(cc2C)C(=O)NC3)CC1] | 2-(4-(2-methoxyethoxy)piperidin-1-yl)-3-methyl-6,7-dihydro-5H-pyrrolo[3,4-b]pyridin-5-one | 306 |
| 57 | 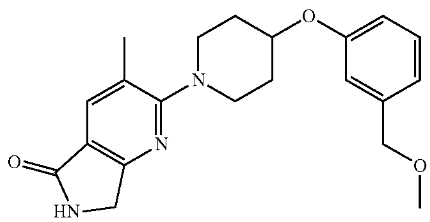 [SMILES: COCc1cccc(OC2CCN(c3nc4c(cc3C)C(=O)NC4)CC2)c1] | 2-(4-(3-(methoxymethyl)phenoxy)piperidin-1-yl)-3-methyl-6,7-dihydro-5H-pyrrolo[3,4-b]pyridin-5-one | 368 |
| 58 | 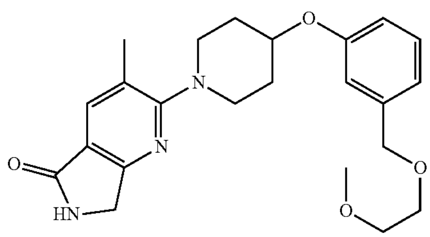 [SMILES: COCCOCc1cccc(OC2CCN(c3nc4c(cc3C)C(=O)NC4)CC2)c1] | 2-(4-(3-((2-methoxyethoxy)methyl)phenoxy)piperidin-1-yl)-3-methyl-6,7-dihydro-5H-pyrrolo[3,4-b]pyridin-5-one | 412 |
| 59 | 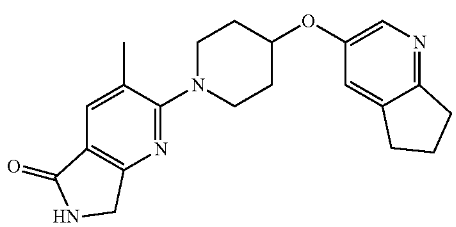 [SMILES: Cc1cc2c(nc1N1CCC(Oc3cnc4c(c3)CCC4)CC1)CNC2=O] | 2-(4-((6,7-dihydro-5H-cyclopenta[b]pyridin-3-yl)oxy)piperidin-1-yl)-3-methyl-6,7-dihydro-5H-pyrrolo[3,4-b]pyridin-5-one | 365 |
| 60 | 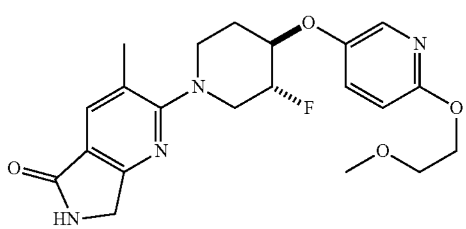 [SMILES: COCCOc1ccc(O[C@@H]2CCN(c3nc4c(cc3C)C(=O)NC4)C[C@H]2F)cn1] | 2-((3R,4R)-3-fluoro-4-((6-(2-methoxyethoxy)pyridin-3-yl)oxy)piperidin-1-yl)-3-methyl-6,7-dihydro-5H-pyrrolo[3,4-b]pyridin-5-one | 417 |
| 61 | 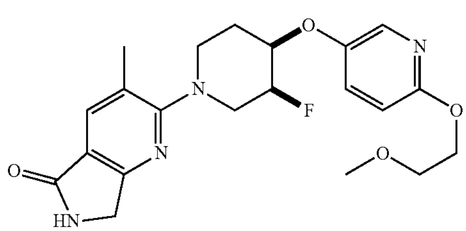 [SMILES: COCCOc1ccc(O[C@@H]2CCN(c3nc4c(cc3C)C(=O)NC4)C[C@@H]2F)cn1] | 2-((3R,4S)-3-fluoro-4-((6-(2-methoxyethoxy)pyridin-3-yl)oxy)piperidin-1-yl)-3-methyl-6,7-dihydro-5H-pyrrolo[3,4-b]pyridin-5-one | 417 |
| 62 | 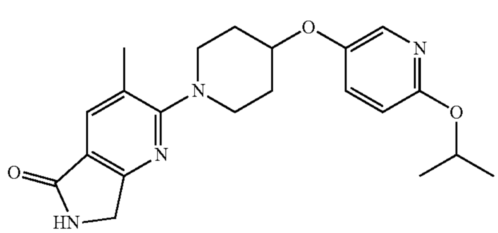 [SMILES: Cc1cc2c(nc1N1CCC(Oc3ccc(OC(C)C)nc3)CC1)CNC2=O] | 2-(4-((6-isopropoxypyridin-3-yl)oxy)piperidin-1-yl)-3-methyl-6,7-dihydro-5H-pyrrolo[3,4-b]pyridin-5-one | 383 |

TABLE 1-continued

| Example | Structure | Name | MS (M + 1) |
|---|---|---|---|
| 63 | 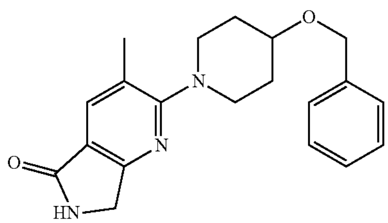 [SMILES: Cc1cc2c(nc1N1CCC(OCc3ccccc3)CC1)CNC2=O] | 2-(4-(benzyloxy)piperidin-1-yl)-3-methyl-6,7-dihydro-5H-pyrrolo[3,4-b]pyridin-5-one | 338 |
| 64 | 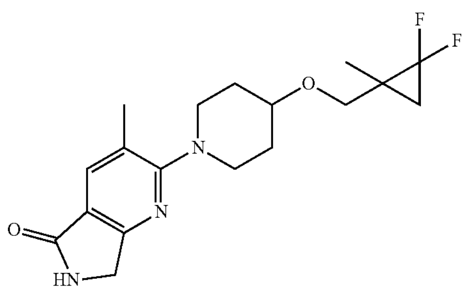 [SMILES: Cc1cc2c(nc1N1CCC(OCC3(C)CC3(F)F)CC1)CNC2=O] | 2-(4-((2,2-difluoro-1-methylcyclopropyl)methoxy)piperidin-1-yl)-3-methyl-6,7-dihydro-5H-pyrrolo[3,4-b]pyridin-5-one | 352 |
| 64A | 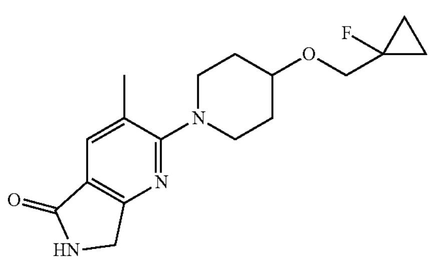 [SMILES: Cc1cc2c(nc1N1CCC(OCC3(F)CC3)CC1)CNC2=O] | 2-(4-((1-fluorocyclopropyl)methoxy)piperidin-1-yl)-3-methyl-6,7-dihydro-5H-pyrrolo[3,4-b]pyridin-5-one | 320 |
| 65 | 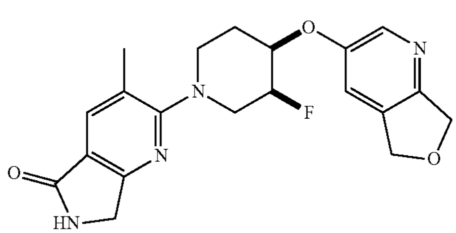 [SMILES: Cc1cc2c(nc1N1CC[C@@H](Oc3cnc4c(c3)COC4)[C@@H](F)C1)CNC2=O] | 2-((3S,4R)-4-((5,7-dihydrofuro[3,4-b]pyridin-3-yl)oxy)-3-fluoropiperidin-1-yl)-3-methyl-6,7-dihydro-5H-pyrrolo[3,4-b]pyridin-5-one | 385 |
| 65A | 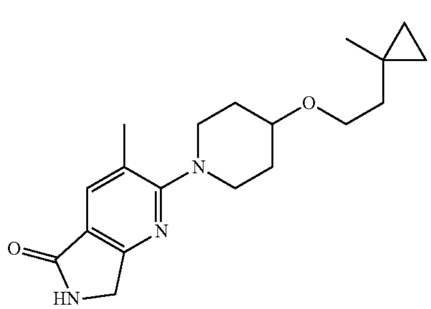 [SMILES: Cc1cc2c(nc1N1CCC(OCCC3(C)CC3)CC1)CNC2=O] | 3-methyl-2-(4-(2-(1-methylcyclopropyl)ethoxy)piperidin-1-yl)-6,7-dihydro-5H-pyrrolo[3,4-b]pyridin-5-one | 330 |

Example 66

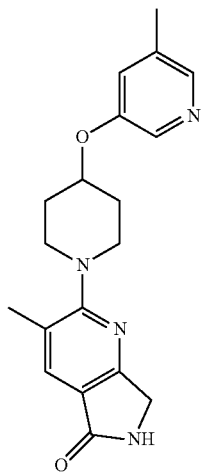 [SMILES: Cc1cncc(OC2CCN(c3nc4c(cc3C)C(=O)NC4)CC2)c1]

3-Methyl-2-(4-((5-methylpyridin-3-yl)oxy)piperidin-1-yl)-6,7-dihydro-5H-pyrrolo[3,4-b]pyridin-5-one (Scheme 2)

To a solution of 2-(4-hydroxypiperidin-1-yl)-3-methyl-6,7-dihydro-5H-pyrrolo[3,4-b]pyridin-5-one (30 mg, 0.121 mmol, intermediate H1), 5-methylpyridin-3-ol (13.24 mg, 0.121 mmol) and triphenylphosphine (47.7 mg, 0.182 mmol) in toluene (1 mL) was added (E)-di-tert-butyl diazene-1,2-dicarboxylate (41.9 mg, 0.182 mmol). The reaction mixture was stirred at 100° C. for 16 h. The solvent was evaporated under reduced pressure and was directly purified by reverse phase HPLC (ACN/water with 0.1% TFA modifier) to yield the title compound. MS: 339 (M+1). $^1$H NMR (400 MHz, methanol-$d_4$): δ 8.49 (1H, s), 8.32 (1H, s), 8.17 (1H, s), 7.82 (1H, s), 4.91-4.92 (1H, m), 4.34 (2H, s), 3.59-3.63 (2H, m), 3.25-3.29 (2H, m), 2.56 (3H, s), 2.40 (3H, s), 2.22-2.26 (2H, m), 1.97-2.06 (2H, m).

The following examples in table 2 were prepared according to scheme 2 using the procedure outlined in the synthesis of Example 66 using a known or prepared phenol. Alternative conditions includes the use of THF as solvent and reaction temperatures that range from 50-100° C. as dictated by each substrate.

TABLE 2

| Example | Structure | Name | MS (M + 1) |
|---|---|---|---|
| 67 | 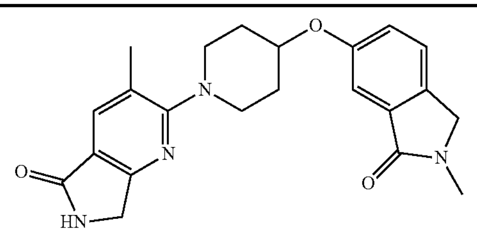 | 3-methyl-2-(4-((2-methyl-3-oxoisoindolin-5-yl)oxy)piperidin-1-yl)-6,7-dihydro-5H-pyrrolo[3,4-b]pyridin-5-one | 393 |
| 68 | 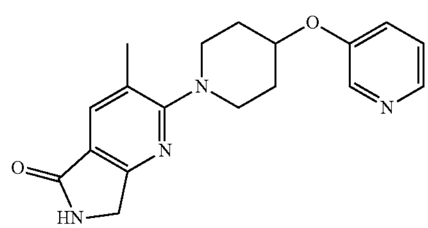 [SMILES: Cc1cc2c(nc1N1CCC(Oc3cccnc3)CC1)CNC2=O] | 3-methyl-2-(4-(pyridin-3-yloxy)piperidin-1-yl)-6,7-dihydro-5H-pyrrolo[3,4-b]pyridin-5-one | 325 |
| 69 | 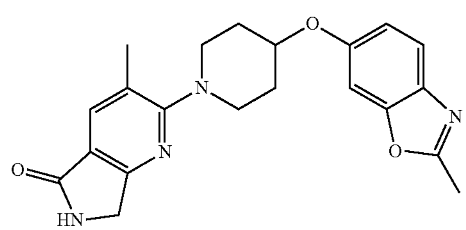 | 3-methyl-2-(4-((2-methylbenzo[d]oxazol-6-yl)oxy)piperidin-1-yl)-6,7-dihydro-5H-pyrrolo[3,4-b]pyridin-5-one | 170 |
| 70 | 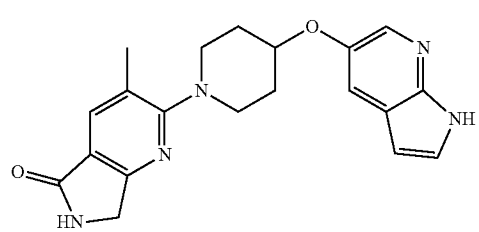 [SMILES: Cc1cc2c(nc1N1CCC(Oc3cnc4[nH]ccc4c3)CC1)CNC2=O] | 2-(4-((1H-pyrrolo[2,3-b]pyridin-5-yl)oxy)piperidin-1-yl)-3-methyl-6,7-dihydro-5H-pyrrolo[3,4-b]pyridin-5-one | 364 |

TABLE 2-continued

| Example | Structure | Name | MS (M + 1) |
|---|---|---|---|
| 71 | 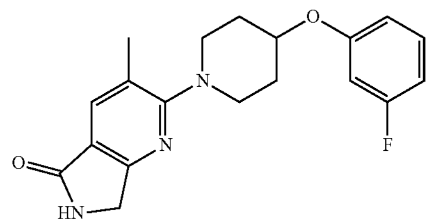 [SMILES: Cc1cc2c(nc1N1CCC(Oc3cccc(F)c3)CC1)CNC2=O] | 2-(4-(3-fluorophenoxy)piperidin-1-yl)-3-methyl-6,7-dihydro-5H-pyrrolo[3,4-b]pyridin-5-one | 342 |
| 72 | 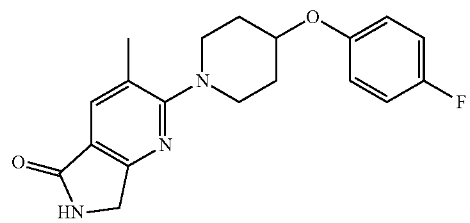 [SMILES: Cc1cc2c(nc1N1CCC(Oc3ccc(F)cc3)CC1)CNC2=O] | 2-(4-(4-fluorophenoxy)piperidin-1-yl)-3-methyl-6,7-dihydro-5H-pyrrolo[3,4-b]pyridin-5-one | 342 |
| 73 | 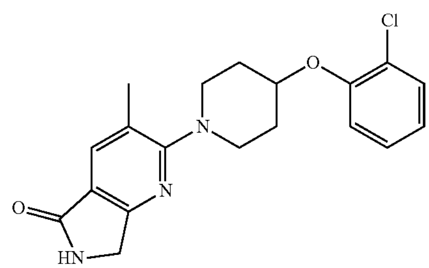 [SMILES: Cc1cc2c(nc1N1CCC(Oc3ccccc3Cl)CC1)CNC2=O] | 2-(4-(2-chlorophenoxy)piperidin-1-yl)-3-methyl-6,7-dihydro-5H-pyrrolo[3,4-b]pyridin-5-one | 358 |
| 74 | 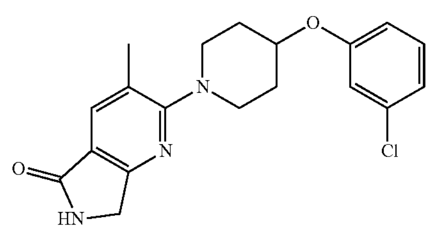 | 2-(4-(3-chlorophenoxy)piperidin-1-yl)-3-methyl-6,7-dihydro-5H-pyrrolo[3,4-b]pyridin-5-one | 358 |
| 75 | 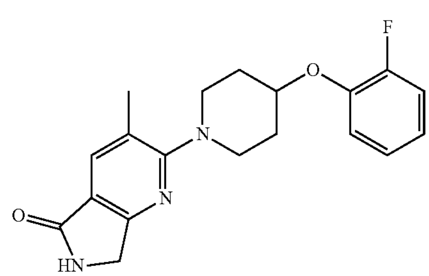 [SMILES: Cc1cc2c(nc1N1CCC(Oc3ccccc3F)CC1)CNC2=O] | 2-(4-(2-fluorophenoxy)piperidin-1-yl)-3-methyl-6,7-dihydro-5H-pyrrolo[3,4-b]pyridin-5-one | 342 |
| 76 | 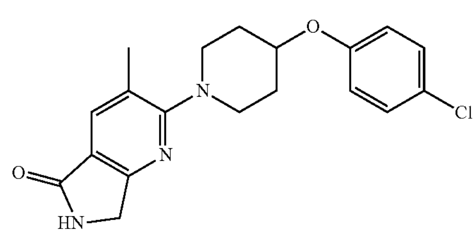 [SMILES: Cc1cc2c(nc1N1CCC(Oc3ccc(Cl)cc3)CC1)CNC2=O] | 2-(4-(4-chlorophenoxy)piperidin-1-yl)-3-methyl-6,7-dihydro-5H-pyrrolo[3,4-b]pyridin-5-one | 358 |

TABLE 2-continued

| Example | Structure | Name | MS (M + 1) |
|---|---|---|---|
| 77 | 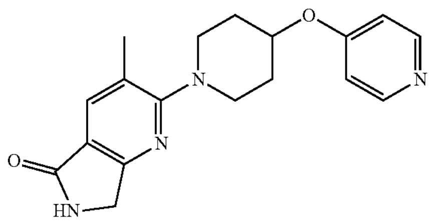 [SMILES: Cc1cc2c(nc1N1CCC(Oc3ccncc3)CC1)CNC2=O] | 3-methyl-2-(4-(pyridin-4-yloxy)piperidin-1-yl)-6,7-dihydro-5H-pyrrolo[3,4-b]pyridin-5-one | 325 |
| 78 | 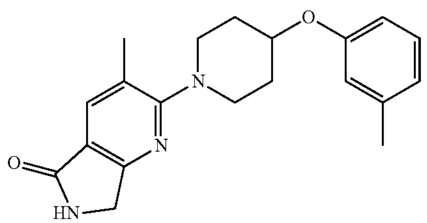 | 3-methyl-2-(4-(m-tolyloxy)piperidin-1-yl)-6,7-dihydro-5H-pyrrolo[3,4-b]pyridin-5-one | 338 |
| 79 | 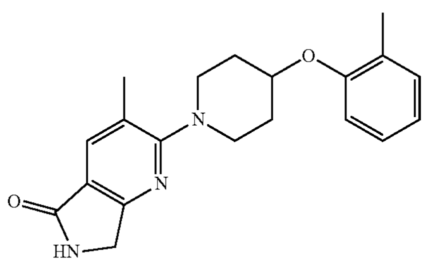 [SMILES: Cc1ccccc1OC1CCN(c2nc3c(cc2C)C(=O)NC3)CC1] | 3-methyl-2-(4-(o-tolyloxy)piperidin-1-yl)-6,7-dihydro-5H-pyrrolo[3,4-b]pyridin-5-one | 338 |
| 80 | 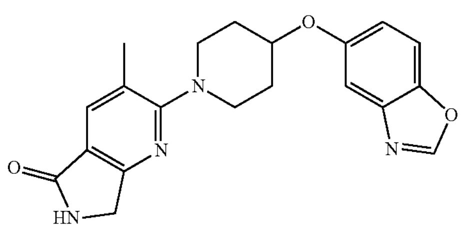 [SMILES: Cc1cc2c(nc1N1CCC(Oc3ccc4ocnc4c3)CC1)CNC2=O] | 2-(4-(benzo[d]oxazol-5-yloxy)piperidin-1-yl)-3-methyl-6,7-dihydro-5H-pyrrolo[3,4-b]pyridin-5-one | 365 |
| 81 | 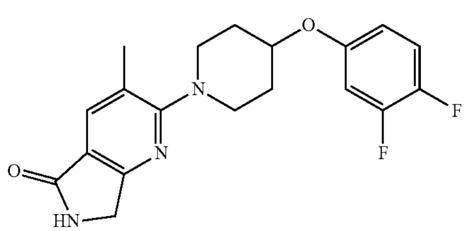 [SMILES: Cc1cc2c(nc1N1CCC(Oc3ccc(F)c(F)c3)CC1)CNC2=O] | 2-(4-(3,4-difluorophenoxy)piperidin-1-yl)-3-methyl-6,7-dihydro-5H-pyrrolo[3,4-b]pyridin-5-one | 360 |
| 82 | 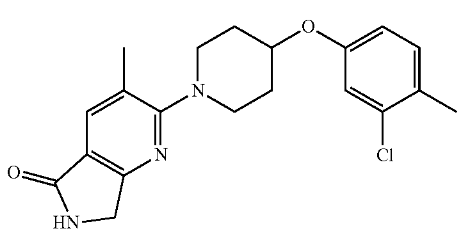 [SMILES: Cc1ccc(OC2CCN(c3nc4c(cc3C)C(=O)NC4)CC2)cc1Cl] | 2-(4-(3-chloro-4-methylphenoxy)piperidin-1-yl)-3-methyl-6,7-dihydro-5H-pyrrolo[3,4-b]pyridin-5-one | 372 |

TABLE 2-continued

| Example | Structure | Name | MS (M + 1) |
|---|---|---|---|
| 83 | 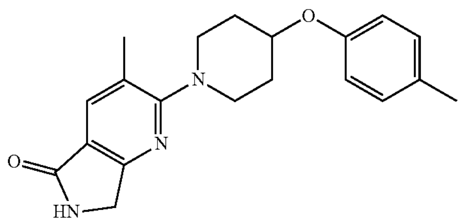 [SMILES: Cc1ccc(OC2CCN(c3nc4c(cc3C)C(=O)NC4)CC2)cc1] | 3-methyl-2-(4-(p-tolyloxy)piperidin-1-yl)-6,7-dihydro-5H-pyrrolo[3,4-b]pyridin-5-one | 338 |
| 84 | 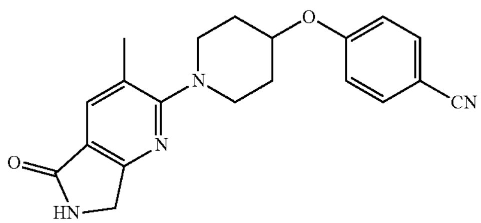 [SMILES: Cc1cc2c(nc1N1CCC(Oc3ccc(C#N)cc3)CC1)CNC2=O] | 4-((1-(3-methyl-5-oxo-6,7-dihydro-5H-pyrrolo[3,4-b]pyridin-2-yl)piperidin-4-yl)oxy)benzonitrile | 349 |
| 85 | 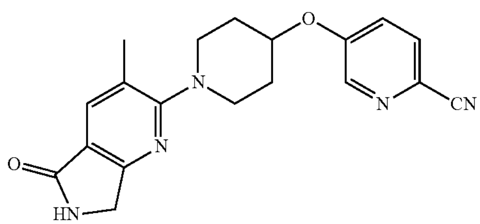 [SMILES: Cc1cc2c(nc1N1CCC(Oc3ccc(C#N)nc3)CC1)CNC2=O] | 5-((1-(3-methyl-5-oxo-6,7-dihydro-5H-pyrrolo[3,4-b]pyridin-2-yl)piperidin-4-yl)oxy)picolinonitrile | 350 |
| 86 | 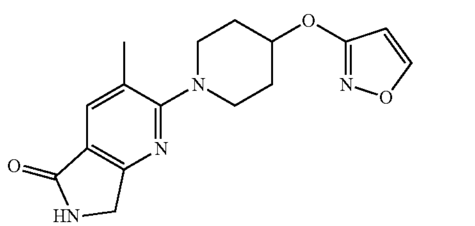 [SMILES: Cc1cc2c(nc1N1CCC(Oc3ccon3)CC1)CNC2=O] | 2-(4-(isoxazol-3-yloxy)piperidin-1-yl)-3-methyl-6,7-dihydro-5H-pyrrolo[3,4-b]pyridin-5-one | 315 |
| 87 | 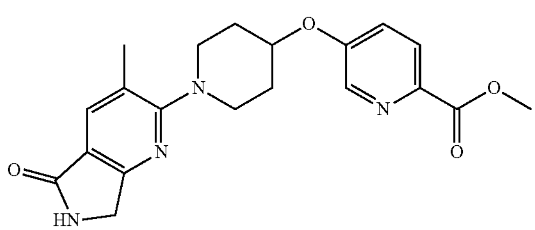 [SMILES: COC(=O)c1ccc(OC2CCN(c3nc4c(cc3C)C(=O)NC4)CC2)cn1] | methyl 5-((1-(3-methyl-5-oxo-6,7-dihydro-5H-pyrrolo[3,4-b]pyridin-2-yl)piperidin-4-yl)oxy)picolinate | 383 |
| 88 | 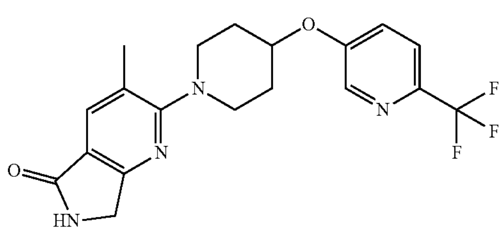 [SMILES: Cc1cc2c(nc1N1CCC(Oc3ccc(C(F)(F)F)nc3)CC1)CNC2=O] | 3-methyl-2-(4-((6-(trifluoromethyl)pyridin-3-yl)oxy)piperidin-1-yl)-6,7-dihydro-5H-pyrrolo[3,4-b]pyridin-5-one | 393 |
| 89 | 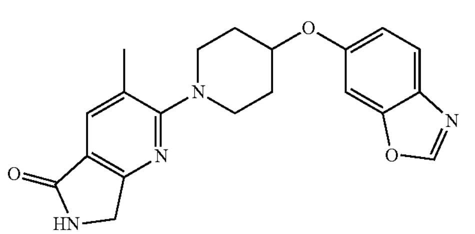 [SMILES: Cc1cc2c(nc1N1CCC(Oc3ccc4ncoc4c3)CC1)CNC2=O] | 2-(4-(benzo[d]oxazol-6-yloxy)piperidin-1-yl)-3-methyl-6,7-dihydro-5H-pyrrolo[3,4-b]pyridin-5-one | 365 |

TABLE 2-continued

| Example | Structure | Name | MS (M + 1) |
|---|---|---|---|
| 90 | 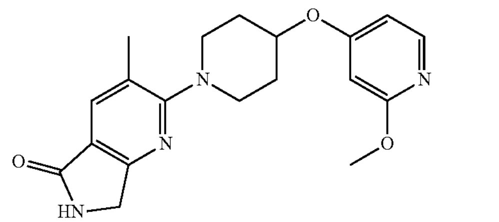 [SMILES: COc1cc(OC2CCN(c3nc4c(cc3C)C(=O)NC4)CC2)ccn1] | 2-(4-((2-methoxypyridin-4-yl)oxy)piperidin-1-yl)-3-methyl-6,7-dihydro-5H-pyrrolo[3,4-b]pyridin-5-one | 355 |
| 91 | 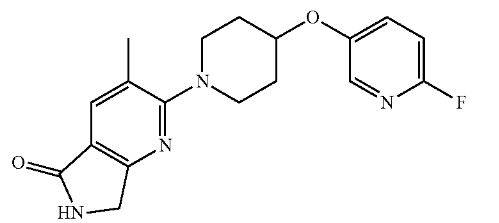 [SMILES: Cc1cc2c(nc1N1CCC(Oc3ccc(F)nc3)CC1)CNC2=O] | 2-(4-((6-fluoropyridin-3-yl)oxy)piperidin-1-yl)-3-methyl-6,7-dihydro-5H-pyrrolo[3,4-b]pyridin-5-one | 343 |
| 92 | 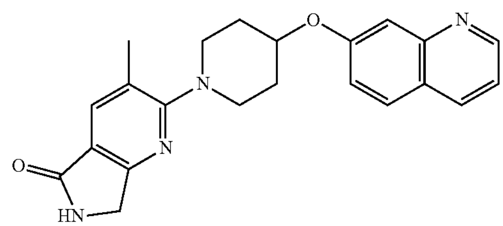 [SMILES: Cc1cc2c(nc1N1CCC(Oc3ccc4cccnc4c3)CC1)CNC2=O] | 3-methyl-2-(4-(quinolin-7-yloxy)piperidin-1-yl)-6,7-dihydro-5H-pyrrolo[3,4-b]pyridin-5-one | 375 |
| 93 | 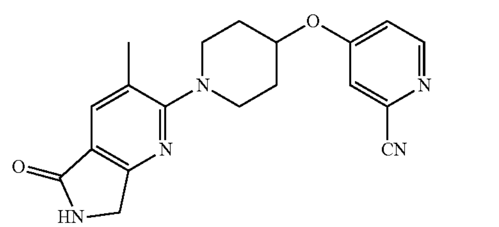 [SMILES: Cc1cc2c(nc1N1CCC(Oc3ccnc(C#N)c3)CC1)CNC2=O] | 4-((1-(3-methyl-5-oxo-6,7-dihydro-5H-pyrrolo[3,4-b]pyridin-2-yl)piperidin-4-yl)oxy)picolinonitrile | 350 |
| 93A | 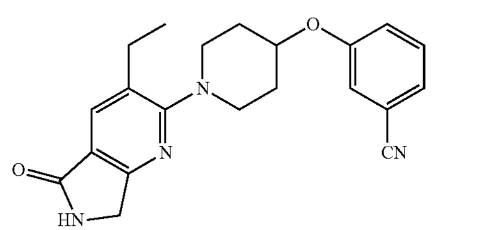 [SMILES: CCc1cc2c(nc1N1CCC(Oc3cccc(C#N)c3)CC1)CNC2=O] | 3-((1-(3-ethyl-5-oxo-6,7-dihydro-5H-pyrrolo[3,4-b]pyridin-2-yl)piperidin-4-yl)oxy)benzonitrile | 363 |
| 94 | 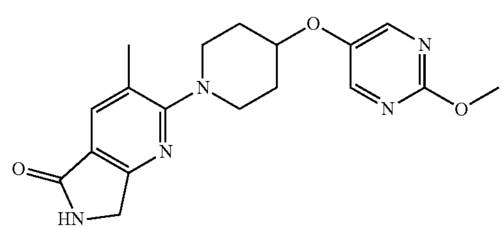 [SMILES: COc1ncc(OC2CCN(c3nc4c(cc3C)C(=O)NC4)CC2)cn1] | 2-(4-((2-methoxypyrimidin-5-yl)oxy)piperidin-1-yl)-3-methyl-6,7-dihydro-5H-pyrrolo[3,4-b]pyridin-5-one | 356 |
| 94A | 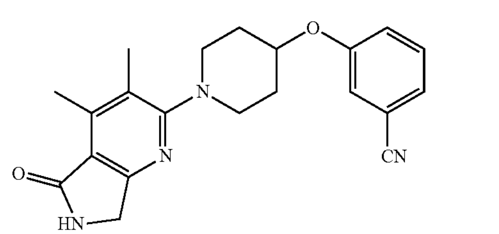 [SMILES: Cc1c(N2CCC(Oc3cccc(C#N)c3)CC2)nc2c(c1C)C(=O)NC2] | 3-((1-(3,4-dimethyl-5-oxo-6,7-dihydro-5H-pyrrolo[3,4-b]pyridin-2-yl)piperidin-4-yl)oxy)benzonitrile | 363 |

TABLE 2-continued

| Example | Structure | Name | MS (M + 1) |
|---|---|---|---|
| 95 | 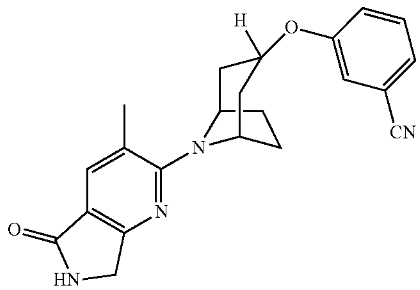 [SMILES: Cc1cc2c(nc1N1C3CCC1CC(Oc1cccc(C#N)c1)C3)CNC2=O] | 3-((endo-8-(3-methyl-5-oxo-6,7-dihydro-5H-pyrrolo[3,4-b]pyridin-2-yl)-8-azabicyclo[3.2.1]octan-3-yl)oxy)benzonitrile | 375 |
| 96 | 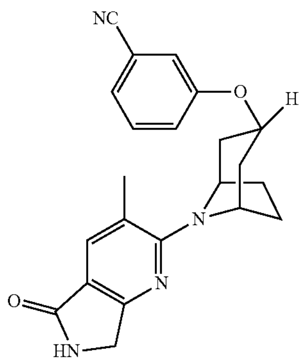 [SMILES: Cc1cc2c(nc1N1C3CCC1CC(Oc1cccc(C#N)c1)C3)CNC2=O] | 3-((exo-8-(3-methyl-5-oxo-6,7-dihydro-5H-pyrrolo[3,4-b]pyridin-2-yl)-8-azabicyclo[3.2.1]octan-3-yl)oxy)benzonitrile | 375 |
| 97 | 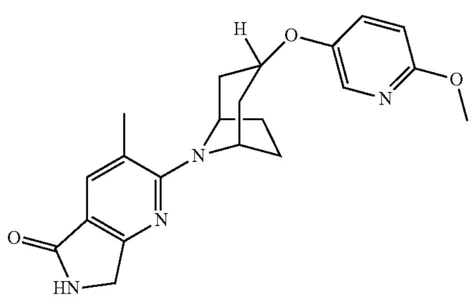 [SMILES: COc1ccc(OC2CC3CCC(C2)N3c2nc3c(cc2C)C(=O)NC3)cn1] | 2-(endo-3-((6-methoxypyridin-3-yl)oxy)-8-azabicyclo[3.2.1]octan-8-yl)-3-methyl-6,7-dihydro-5H-pyrrolo[3,4-b]pyridin-5-one | 381 |
| 98 | 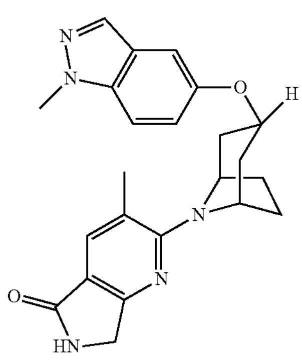 [SMILES: Cc1cc2c(nc1N1C3CCC1CC(Oc1ccc4c(cnn4C)c1)C3)CNC2=O] | 3-methyl-2-(exo-3-((1-methyl-1H-indazol-5-yl)oxy)-8-azabicyclo[3.2.1]octan-8-yl)-6,7-dihydro-5H-pyrrolo[3,4-b]pyridin-5-one | 404 |

TABLE 2-continued

| Example | Structure | Name | MS (M + 1) |
|---|---|---|---|
| 99 | 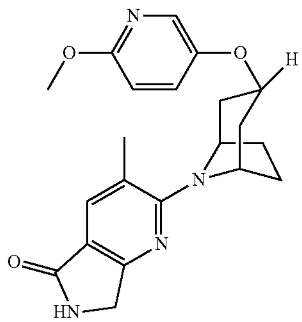 [SMILES: COc1ccc(OC2CC3CCC(C2)N3c2nc3c(cc2C)C(=O)NC3)cn1] | 2-(exo-3-((6-methoxypyridin-3-yl)oxy)-8-azabicyclo[3.2.1]octan-8-yl)-3-methyl-6,7-dihydro-5H-pyrrolo[3,4-b]pyridin-5-one | 381 |
| 100 | 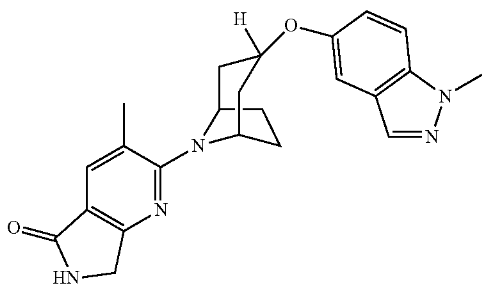 [SMILES: Cc1cc2c(nc1N1C3CCC1CC(Oc1ccc4c(cnn4C)c1)C3)CNC2=O] | 3-methyl-2-(endo-3-((1-methyl-1H-indazol-5-yl)oxy)-8-azabicyclo[3.2.1]octan-8-yl)-6,7-dihydro-5H-pyrrolo[3,4-b]pyridin-5-one | 404 |
| 101 | 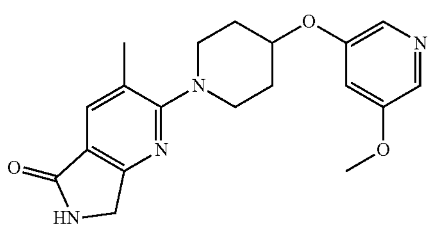 [SMILES: COc1cncc(OC2CCN(c3nc4c(cc3C)C(=O)NC4)CC2)c1] | 2-(4-((5-methoxypyridin-3-yl)oxy)piperidin-1-yl)-3-methyl-6,7-dihydro-5H-pyrrolo[3,4-b]pyridin-5-one | 355 |
| 102 | 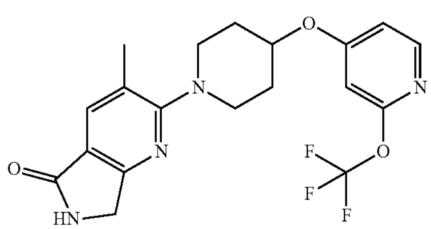 [SMILES: Cc1cc2c(nc1N1CCC(Oc3ccnc(OC(F)(F)F)c3)CC1)CNC2=O] | 3-methyl-2-(4-((2-(trifluoromethoxy)pyridin-4-yl)oxy)piperidin-1-yl)-6,7-dihydro-5H-pyrrolo[3,4-b]pyridin-5-one | 409 |
| 103 | 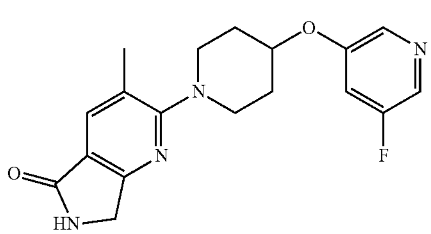 [SMILES: Cc1cc2c(nc1N1CCC(Oc3cncc(F)c3)CC1)CNC2=O] | 2-(4-((5-fluoropyridin-3-yl)oxy)piperidin-1-yl)-3-methyl-6,7-dihydro-5H-pyrrolo[3,4-b]pyridin-5-one | 343 |
| 104 | 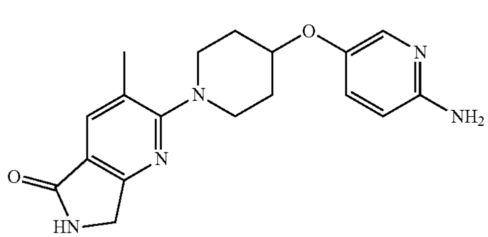 [SMILES: Cc1cc2c(nc1N1CCC(Oc3ccc(N)nc3)CC1)CNC2=O] | 2-(4-((6-aminopyridin-3-yl)oxy)piperidin-1-yl)-3-methyl-6,7-dihydro-5H-pyrrolo[3,4-b]pyridin-5-one | 340 |

TABLE 2-continued

| Example | Structure | Name | MS (M + 1) |
|---|---|---|---|
| 105 | 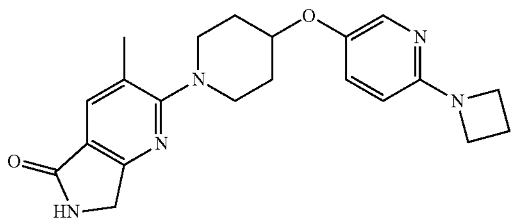 [SMILES: Cc1cc2c(nc1N1CCC(Oc3ccc(N4CCC4)nc3)CC1)CNC2=O] | 2-(4-((6-(azetidin-1-yl)pyridin-3-yl)oxy)piperidin-1-yl)-3-methyl-6,7-dihydro-5H-pyrrolo[3,4-b]pyridin-5-one | 380 |
| 106[1] | 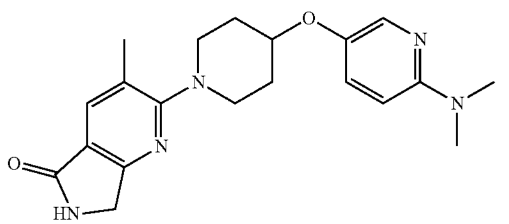 [SMILES: Cc1cc2c(nc1N1CCC(Oc3ccc(N(C)C)nc3)CC1)CNC2=O] | 2-(4-((6-(dimethylamino)pyridin-3-yl)oxy)piperidin-1-yl)-3-methyl-6,7-dihydro-5H-pyrrolo[3,4-b]pyridin-5-one | 368 |
| 107 | 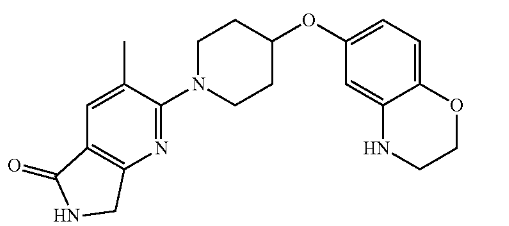 [SMILES: Cc1cc2c(nc1N1CCC(Oc3ccc4c(c3)NCCO4)CC1)CNC2=O] | 2-(4-((3,4-dihydro-2H-benzo[b][1,4]oxazin-6-yl)oxy)piperidin-1-yl)-3-methyl-6,7-dihydro-5H-pyrrolo[3,4-b]pyridin-5-one | 381 |
| 108 | 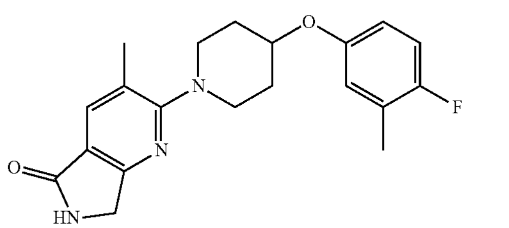 [SMILES: Cc1cc(OC2CCN(c3nc4c(cc3C)C(=O)NC4)CC2)ccc1F] | 2-(4-(4-fluoro-3-methylphenoxy)piperidin-1-yl)-3-methyl-6,7-dihydro-5H-pyrrolo[3,4-b]pyridin-5-one | 356 |
| 109 | 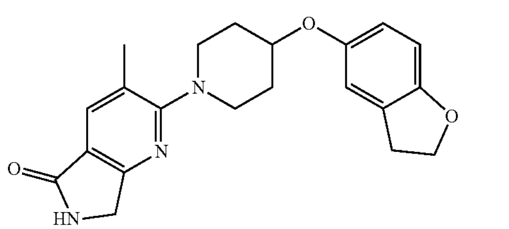 [SMILES: Cc1cc2c(nc1N1CCC(Oc3ccc4c(c3)CCO4)CC1)CNC2=O] | 2-(4-((2,3-dihydrobenzofuran-5-yl)oxy)piperidin-1-yl)-3-methyl-6,7-dihydro-5H-pyrrolo[3,4-b]pyridin-5-one | 366 |
| 110[2] | 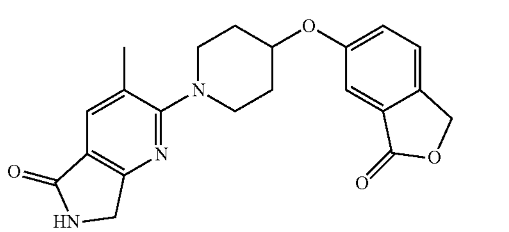 [SMILES: Cc1cc2c(nc1N1CCC(Oc3ccc4c(c3)C(=O)OC4)CC1)CNC2=O] | 3-methyl-2-(4-((3-oxo-1,3-dihydro-2-benzofuran-5-yl)oxy)piperidin-1-yl)-6,7-dihydro-5H-pyrrolo[3,4-b]pyridin-5-one | 380 |
| 111 | 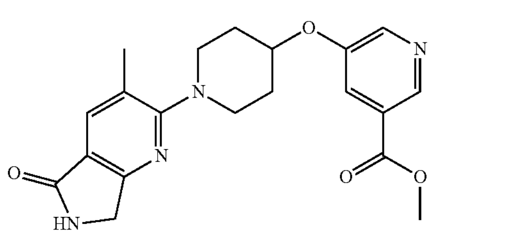 [SMILES: COC(=O)c1cncc(OC2CCN(c3nc4c(cc3C)C(=O)NC4)CC2)c1] | methyl 5-((1-(3-methyl-5-oxo-6,7-dihydro-5H-pyrrolo[3,4-b]pyridin-2-yl)piperidin-4-yl)oxy)nicotinate | 383 |

TABLE 2-continued

| Example | Structure | Name | MS (M + 1) |
|---|---|---|---|
| 112 | 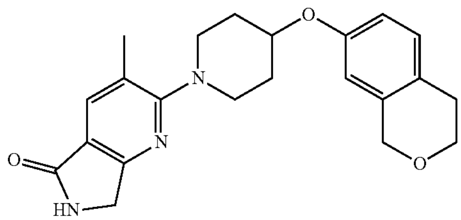 [SMILES: Cc1cc2c(nc1N1CCC(Oc3ccc4c(c3)COCC4)CC1)CNC2=O] | 2-(4-(isochroman-7-yloxy)piperidin-1-yl)-3-methyl-6,7-dihydro-5H-pyrrolo[3,4-b]pyridin-5-one | 380 |
| 113[3] | 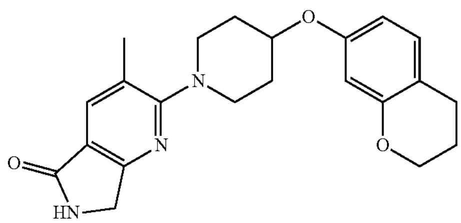 [SMILES: Cc1cc2c(nc1N1CCC(Oc3ccc4c(c3)OCCC4)CC1)CNC2=O] | 2-(4-(chroman-7-yloxy)piperidin-1-yl)-3-methyl-6,7-dihydro-5H-pyrrolo[3,4-b]pyridin-5-one | 380 |
| 114 | 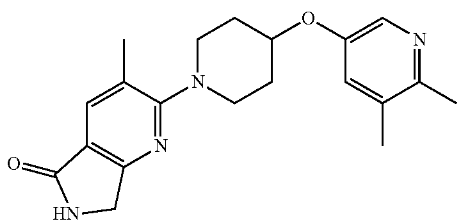 [SMILES: Cc1cc(OC2CCN(c3nc4c(cc3C)C(=O)NC4)CC2)cnc1C] | 2-(4-((5,6-dimethylpyridin-3-yl)oxy)piperidin-1-yl)-3-methyl-6,7-dihydro-5H-pyrrolo[3,4-b]pyridin-5-one | 353 |
| 115 | 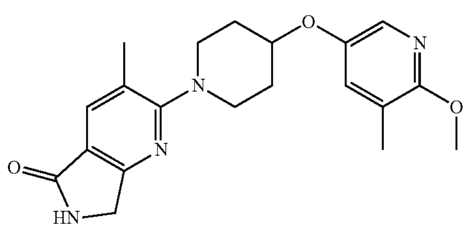 [SMILES: COc1ncc(OC2CCN(c3nc4c(cc3C)C(=O)NC4)CC2)cc1C] | 2-(4-((6-methoxy-5-methylpyridin-3-yl)oxy)piperidin-1-yl)-3-methyl-6,7-dihydro-5H-pyrrolo[3,4-b]pyridin-5-one | 369 |
| 116 | 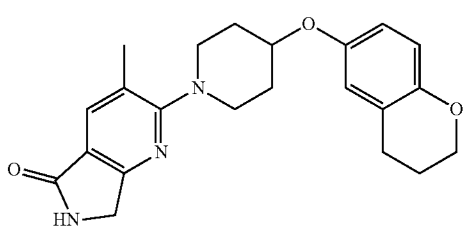 [SMILES: Cc1cc2c(nc1N1CCC(Oc3ccc4c(c3)CCCO4)CC1)CNC2=O] | 2-(4-(chroman-6-yloxy)piperidin-1-yl)-3-methyl-6,7-dihydro-5H-pyrrolo[3,4-b]pyridin-5-one | 380 |
| 117 | 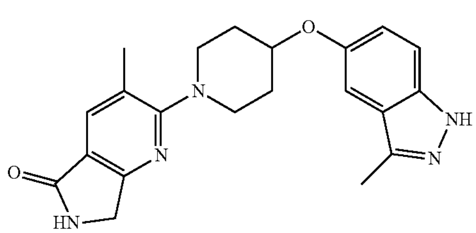 [SMILES: Cc1cc2c(nc1N1CCC(Oc3ccc4[nH]nc(C)c4c3)CC1)CNC2=O] | 3-methyl-2-(4-((3-methyl-1H-indazol-5-yl)oxy)piperidin-1-yl)-6,7-dihydro-5H-pyrrolo[3,4-b]pyridin-5-one | 378 |
| 118 | 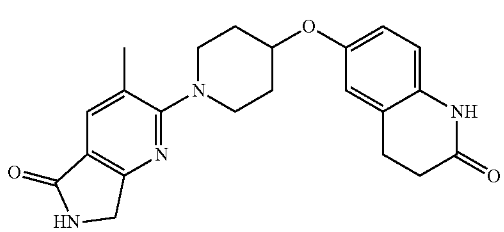 [SMILES: Cc1cc2c(nc1N1CCC(Oc3ccc4c(c3)CCC(=O)N4)CC1)CNC2=O] | 6-((1-(3-methyl-5-oxo-6,7-dihydro-5H-pyrrolo[3,4-b]pyridin-2-yl)piperidin-4-yl)oxy)-3,4-dihydroquinolin-2(1H)-one | 393 |

TABLE 2-continued

| Example | Structure | Name | MS (M + 1) |
|---|---|---|---|
| 119 | 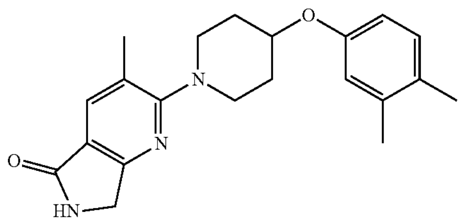 [SMILES: Cc1ccc(OC2CCN(c3nc4c(cc3C)C(=O)NC4)CC2)cc1C] | 2-(4-(3,4-dimethylphenoxy)piperidin-1-yl)-3-methyl-6,7-dihydro-5H-pyrrolo[3,4-b]pyridin-5-one | 352 |
| 120 | 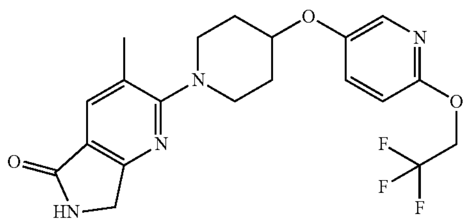 [SMILES: Cc1cc2c(nc1N1CCC(Oc3ccc(OCC(F)(F)F)nc3)CC1)CNC2=O] | 3-methyl-2-(4-((6-(2,2,2-trifluoroethoxy)pyridin-3-yl)oxy)piperidin-1-yl)-6,7-dihydro-5H-pyrrolo[3,4-b]pyridin-5-one | 423 |
| 121[4] | 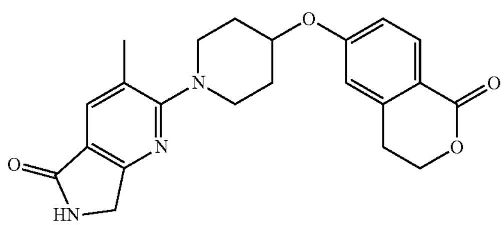 [SMILES: Cc1cc2c(nc1N1CCC(Oc3ccc4c(c3)CCOC4=O)CC1)CNC2=O] | 3-methyl-2-(4-((1-oxoisochroman-6-yl)oxy)piperidin-1-yl)-6,7-dihydro-5H-pyrrolo[3,4-b]pyridin-5-one | 394 |
| 122 | 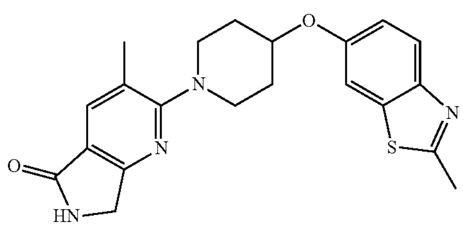 | 3-methyl-2-(4-((2-methylbenzo[d]thiazol-6-yl)oxy)piperidin-1-yl)-6,7-dihydro-5H-pyrrolo[3,4-b]pyridin-5-one | 395 |
| 123 | 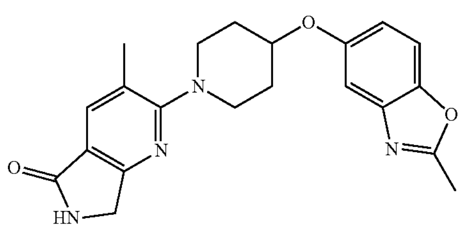 [SMILES: Cc1nc2cc(OC3CCN(c4nc5c(cc4C)C(=O)NC5)CC3)ccc2o1] | 3-methyl-2-(4-((2-methylbenzo[d]oxazol-5-yl)oxy)piperidin-1-yl)-6,7-dihydro-5H-pyrrolo[3,4-b]pyridin-5-one | 379 |
| 124 | 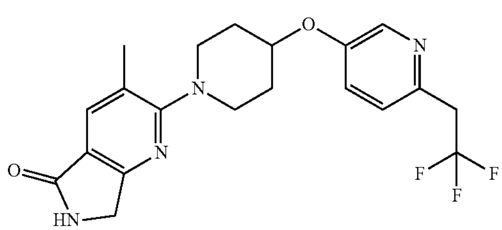 [SMILES: Cc1cc2c(nc1N1CCC(Oc3ccc(CC(F)(F)F)nc3)CC1)CNC2=O] | 3-methyl-2-(4-((6-(trifluoromethoxy)pyridin-3-yl)oxy)piperidin-1-yl)-6,7-dihydro-5H-pyrrolo[3,4-b]pyridin-5-one | 409 |
| 125 | 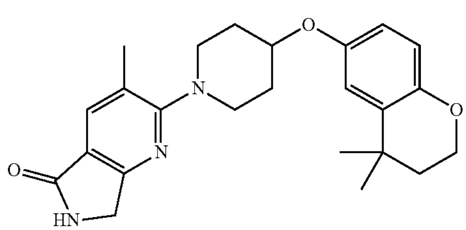 [SMILES: Cc1cc2c(nc1N1CCC(Oc3ccc4c(c3)C(C)(C)CCO4)CC1)CNC2=O] | 2-(4-((4,4-dimethylchroman-6-yl)oxy)piperidin-1-yl)-3-methyl-6,7-dihydro-5H-pyrrolo[3,4-b]pyridin-5-one | 408 |

TABLE 2-continued

| Example | Structure | Name | MS (M + 1) |
|---|---|---|---|
| 126[5] | 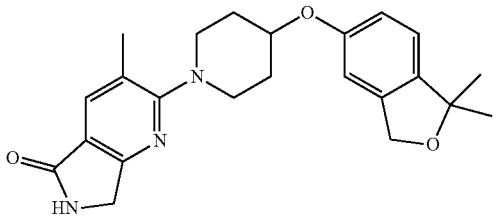 [SMILES: Cc1cc2c(nc1N1CCC(Oc3ccc4c(c3)COC4(C)C)CC1)CNC2=O] | 2-(4-((1,1-dimethyl-1,3-dihydro-2-benzofuran-5-yl)oxy)piperidin-1-yl)-3-methyl-6,7-dihydro-5H-pyrrolo[3,4-b]pyridin-5-one | 394 |
| 127[6] | 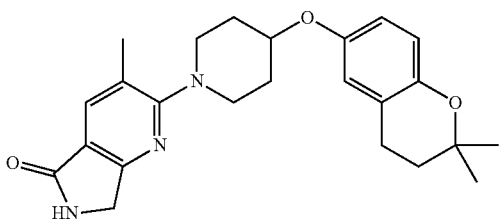 [SMILES: Cc1cc2c(nc1N1CCC(Oc3ccc4c(c3)CCC(C)(C)O4)CC1)CNC2=O] | 2-(4-((2,2-dimethylchroman-6-yl)oxy)piperidin-1-yl)-3-methyl-6,7-dihydro-5H-pyrrolo[3,4-b]pyridin-5-one | 408 |
| 128 | 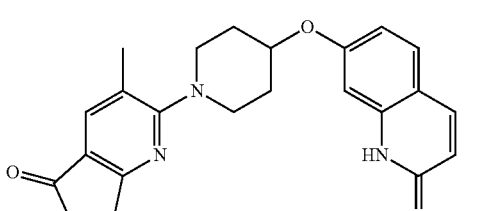 | 7-((1-(3-methyl-5-oxo-6,7-dihydro-5H-pyrrolo[3,4-b]pyridin-2-yl)piperidin-4-yl)oxy)quinolin-2(1H)-one | 391 |
| 129 | 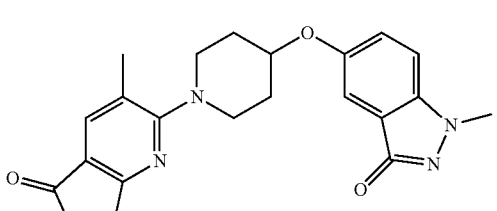 | 2-(4-((1,3-dimethyl-1H-indazol-5-yl)oxy)piperidin-1-yl)-3-methyl-6,7-dihydro-5H-pyrrolo[3,4-b]pyridin-5-one | 392 |
| 130[7] | 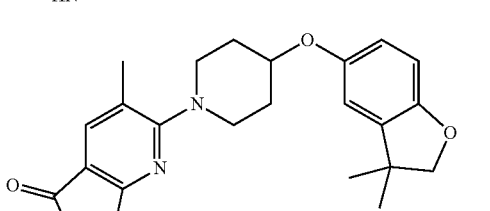 | 2-(4-((3,3-dimethyl-2,3-dihydrobenzofuran-5-yl)oxy)piperidin-1-yl)-3-methyl-6,7-dihydro-5H-pyrrolo[3,4-b]pyridin-5-one | 394 |
| 131 | 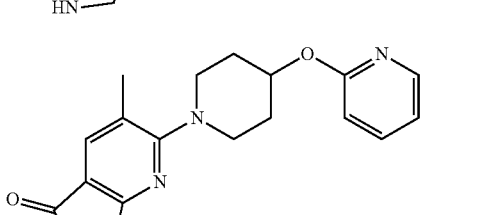 | 3-methyl-2-(4-(pyridin-2-yloxy)piperidin-1-yl)-6,7-dihydro-5H-pyrrolo[3,4-b]pyridin-5-one | 325 |
| 132 | 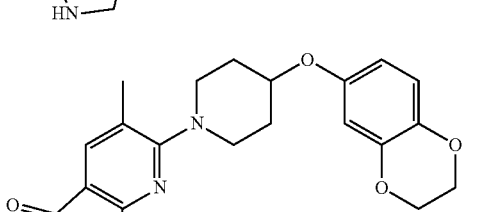 | 2-(4-((2,3-dihydrobenzo[b][1,4]dioxin-6-yl)oxy)piperidin-1-yl)-3-methyl-6,7-dihydro-5H-pyrrolo[3,4-b]pyridin-5-one | 382 |

TABLE 2-continued

| Example | Structure | Name | MS (M + 1) |
|---|---|---|---|
| 133 | 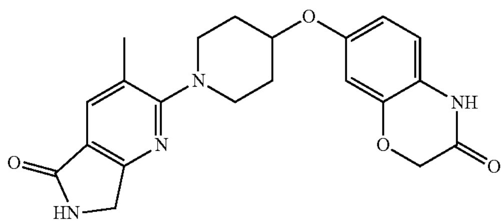 | 7-((1-(3-methyl-5-oxo-6,7-dihydro-5H-pyrrolo[3,4-b]pyridin-2-yl)piperidin-4-yl)oxy)-2H-benzo[b][1,4]oxazin-3(4H)-one | 395 |
| 134 | 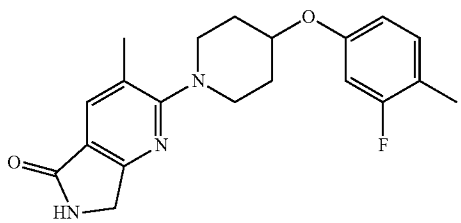 | 2-(4-(3-fluoro-4-methylphenoxy)piperidin-1-yl)-3-methyl-6,7-dihydro-5H-pyrrolo[3,4-b]pyridin-5-one | 356 |
| 135 | 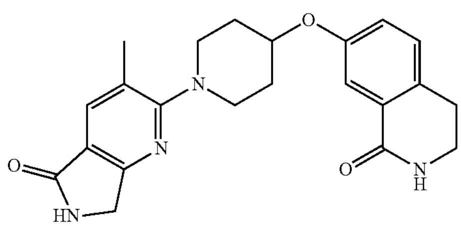 [SMILES: Cc1cc2c(nc1N1CCC(Oc3ccc4c(c3)C(=O)NCC4)CC1)CNC2=O] | 7-((1-(3-methyl-5-oxo-6,7-dihydro-5H-pyrrolo[3,4-b]pyridin-2-yl)piperidin-4-yl)oxy)-3,4-dihydroisoquinolin-1(2H)-one | 393 |
| 136 | 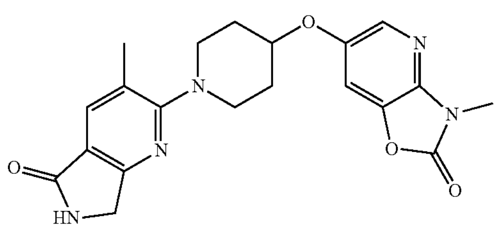 [SMILES: Cc1cc2c(nc1N1CCC(Oc3cnc4c(c3)oc(=O)n4C)CC1)CNC2=O] | 3-methyl-6-((1-(3-methyl-5-oxo-6,7-dihydro-5H-pyrrolo[3,4-b]pyridin-2-yl)piperidin-4-yl)oxy)oxazolo[4,5-b]pyridin-2(3H)-one | 396 |
| 137 | 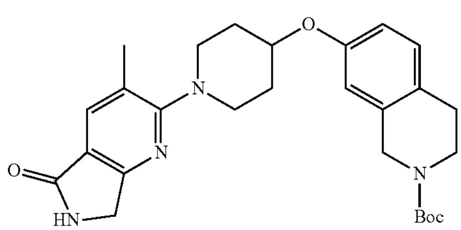 [SMILES: Cc1cc2c(nc1N1CCC(Oc3ccc4c(c3)CN(C(=O)OC(C)(C)C)CC4)CC1)CNC2=O] | tert-butyl 7-((1-(3-methyl-5-oxo-6,7-dihydro-5H-pyrrolo[3,4-b]pyridin-2-yl)piperidin-4-yl)oxy)-3,4-dihydroisoquinoline-2(1H)-carboxylate | 479 |
| 138[8] | 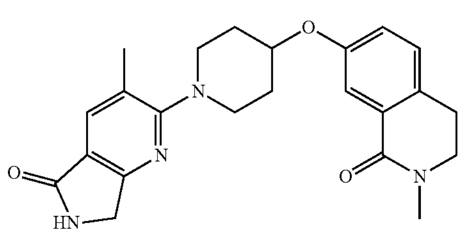 [SMILES: Cc1cc2c(nc1N1CCC(Oc3ccc4c(c3)C(=O)N(C)CC4)CC1)CNC2=O] | 2-methyl-7-((1-(3-methyl-5-oxo-6,7-dihydro-5H-pyrrolo[3,4-b]pyridin-2-yl)piperidin-4-yl)oxy)-3,4-dihydroisoquinolin-1(2H)-one | 480 |

TABLE 2-continued

| Example | Structure | Name | MS (M + 1) |
|---|---|---|---|
| 139 | 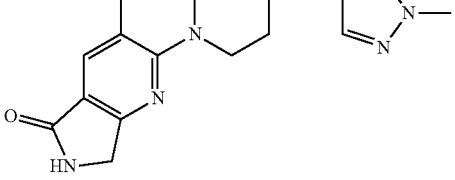 | 3-methyl-2-(4-((1-methyl-1H-pyrazol-4-yl)oxy)piperidin-1-yl)-6,7-dihydro-5H-pyrrolo[3,4-b]pyridin-5-one | 328 |
| 139A[9] | 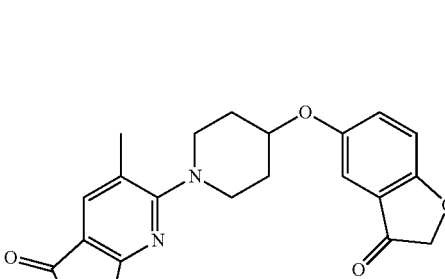 | 3-methyl-2-(4-((3-oxo-2,3-dihydrobenzofuran-5-yl)oxy)piperidin-1-yl)-6,7-dihydro-5H-pyrrolo[3,4-b]pyridin-5-one | 380 |
| 140 | 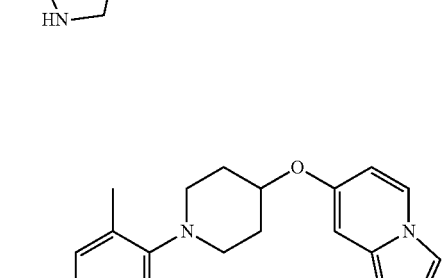 | 2-(4-(imidazo[1,2-a]pyridin-7-yloxy)piperidin-1-yl)-3-methyl-6,7-dihydro-5H-pyrrolo[3,4-b]pyridin-5-one | 314 |

[1]Phenol may be prepared according to literature procedures, see e.g.: Chekler, E. L.; et al. *J. Med. Chem.* 2014, 57, 2462-2471.
[2]Phenol may be prepared according to literature procedures, see e.g.: Teixeira; et al. *J. Mol. Struct.* 2014, 1061, 61-68.
[3]Phenol may be prepared according to literature procedures, see e.g.: Cube, R. V.; et al. *Bioorg. Med. Chem. Letters* 2005, 9, 2389-2393.
[4]Phenol may be prepared according to literature procedures, see e.g.: Schwink, L., et al., PCT Patent Publ'n WO2009/021740.
[5]Phenol may be prepared according to literature procedures, see e.g.: Wu, et al., *J. Org. Chem.* 1998, 63, 5064-5070.
[6]Phenol may be prepared according to literature procedures, see e.g.: Naik, et al., *Tetrahedron* 2014, 34, 5221-5233.
[7]Phenol may be prepared according to literature procedures, see e.g.: Alvaro, G., et al., PCT Patent Publ'n WO2012/168710.
[8]Phenol may be prepared according to literature procedures, see e.g.: Yamashita, H., et al. PCT Patent Publ'n WO2006/112464.
[9]Phenol may be prepared according to literature procedures, see e.g.: Haudecoeur, R., et. al. *J. Med. Chem.* 2011, 54, 5395-5402.

Example 141A and 141B

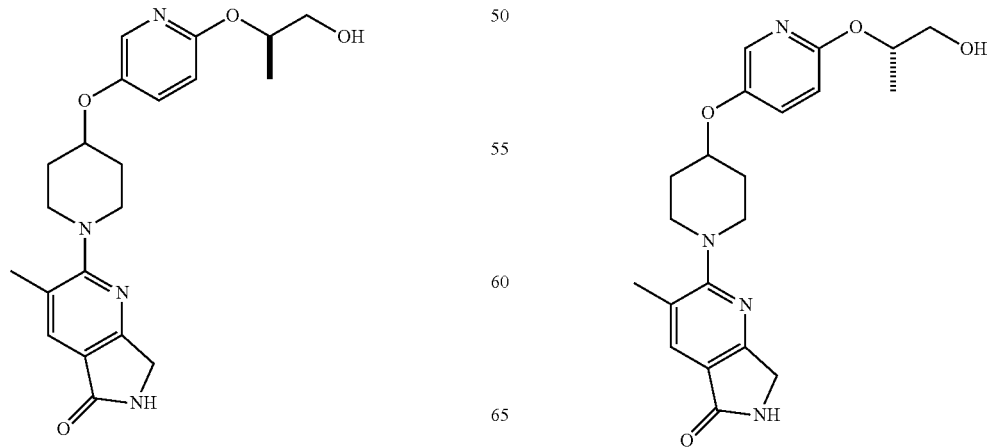

-continued (R)-2-(4-((6-((1-Hydroxypropan-2-yl)oxy)pyridin-3-yl)oxy)piperidin-1-yl)-3-methyl-6,7-dihydro-5H-pyrrolo[3,4-b]pyridin-5-one and (S)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one (Scheme 3)

Step 1: 2-(4-((6-(2-((tert-Butyldiphenylsilyl)oxy)propoxy)pyridin-3-yl)oxy)piperidin-1-yl)-3-methyl-6,7-dihydro-5H-pyrrolo[3,4-b]pyridin-5-one To a solution of 2-(4-hydroxypiperidin-1-yl)-3-methyl-6,7-dihydro-5H-pyrrolo[3,4-b]pyridin-5-one (170 mg, 0.687 mmol, intermediate H1) in toluene (10 mL) was added 6-(2-((tert-butyldiphenylsilyl)oxy)propoxy)pyridin-3-ol (280 mg, 0.343 mmol), triphenylphosphine (270 mg, 1.03 mmol) and (E)-di-tert-butyl diazene-1,2-dicarboxylate (237 mg, 1.03 mmol). This mixture was stirred at 70° C. under a nitrogen atmosphere for 40 h. Volatiles were removed under reduced pressure and the reaction was concentrated. The residue was purified by silica gel chromatography (0-75% EtOAc/petroleum ether) to yield the title compound. MS: 637 (M+1).

Step 2: 2-(4-((6-((1-Hydroxypropan-2-yl)oxy)pyridin-3-yl)oxy)piperidin-1-yl)-3-methyl-6,7-dihydro-5H-pyrrolo[3,4-b]pyridin-5-one To a solution of 2-(4-((6-(2-((tert-butyldiphenylsilyl)oxy)propoxy)pyridin-3-yl)oxy)piperidin-1-yl)-3-methyl-6,7-dihydro-5H-pyrrolo[3,4-b]pyridin-5-one (220 mg, 0.130 mmol) in THF (5 mL) was added TBAF (0.259 mL, 0.259 mmol). The mixture was stirred at 60° C. under a nitrogen atmosphere for 15 h. The reaction was cooled and treated with water (5 mL) and extracted with EtOAc (15 mL×3). The combined organic layers were dried over anhydrous $Na_2SO_4$, filtered and concentrated. The residue was purified by reverse phase HPLC (ACN/water with 0.1% $NH_3OH$ modifier) to afford the title compound. The mixture of the two stereoisomers was purified by chiral SFC (AD column, 40% ethanol with 0.05% DEA modifier/$CO_2$) to afford isomer 141A (faster eluting): MS: 399 (M+1). $^1$H NMR (400 MHz, $CDCl_3$): 7.79 (2H, s), 7.24-7.28 (1H, overlapped), 6.72 (1H, d, J=9.2 Hz), 5.99 (1H, s), 5.02-5.04 (1H, m), 4.33-4.38 (3H, m), 3.98-4.00 (1H, m), 3.72-3.76 (2H, m), 3.52-3.56 (2H, m), 3.10-3.15 (2H, m), 2.34 (3H, s), 2.07-2.09 (2H, m), 1.91-1.95 (2H, m), 1.31 (3H, d, J=6.8 Hz). Isomer 141B (slower eluting): MS: 399 (M+1). $^1$H NMR (500 MHz, $CDCl_3$): δ 7.79 (2H, s), 7.24-7.28 (1H, overlapped), 6.72 (1H, d, J=9.2 Hz), 6.07 (1H, s), 5.02-5.04 (1H, m), 4.33-4.38 (3H, m), 3.98-4.00 (1H, m), 3.72-3.76 (2H, m), 3.52-3.56 (2H, m), 3.10-3.15 (2H, m), 2.34 (3H, s), 2.07-2.09 (2H, m), 1.91-1.95 (2H, m), 1.31 (3H, d, J=6.8 Hz).

The following examples in table 3A were prepared according to scheme 3 using the procedure outlined in the synthesis of Example 141A and 141B using known or prepared intermediates and phenols containing silicon-based protecting groups such as TMS, SEM, TES, etc. Alternative conditions for step 2 include temperature variation from RT-60° C. as dependent on the substrate.

TABLE 3A

| Example | Structure | Name | MS (M + 1) |
|---|---|---|---|
| 142* | 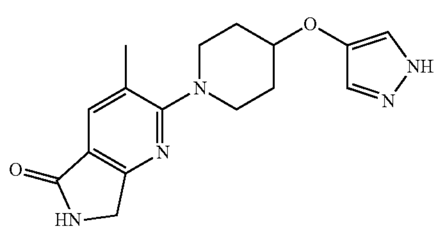 [SMILES: Cc1cc2c(nc1N1CCC(Oc3cn[nH]c3)CC1)CNC2=O] | 2-(4-((1H-pyrazol-4-yl)oxy)piperidin-1-yl)-3-methyl-6,7-dihydro-5H-pyrrolo[3,4-b]pyridin-5-one | 314 |
| 143A 143B | | (S)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one and (R)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one | 399 399 |

*Phenol may be prepared according to literature procedures, see e.g.: Oslob, et al., PCT Patent Publ'n WO2014/008197.

Example 144

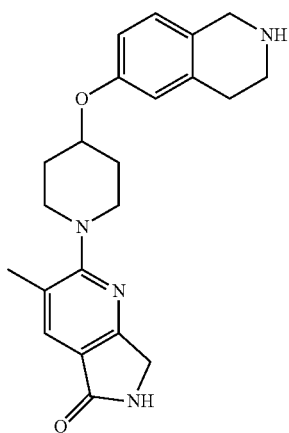 [SMILES: Cc1cc2c(nc1N1CCC(Oc3ccc4c(c3)CCNC4)CC1)CNC2=O]

3-Methyl-2-(4-((1,2,3,4-tetrahydroisoquinolin-6-yl)oxy)piperidin-1-yl)-6,7-dihydro-5H-pyrrolo[3,4-b]pyridin-5-one (Scheme 3)

Step 1: tert-Butyl 6-((1-(3-methyl-5-oxo-6,7-dihydro-5H-pyrrolo[3,4-b]pyridin-2-yl) piperidin-4-yl)oxy)-3,4-dihydroisoquinoline-2(1H)-carboxylate To a solution of tert-butyl 6-hydroxy-3,4-dihydroisoquinoline-2(1H)-carboxylate (200 mg, 0.802 mmol) in toluene (15 mL) was added 2-(4-hydroxypiperidin-1-yl)-3-methyl-6,7-dihydro-5H-pyrrolo[3,4-b]pyridin-5-one (218 mg, 0.882 mmol, intermediate H1), triphenylphosphine (379 mg, 1.444 mmol) and (E)-tert-butyl 2-pivaloyldiazenecarboxylate (309 mg, 1.444 mmol), the resulting mixture was stirred at 80° C. under a nitrogen atmosphere for 15 h. The mixture was filtered and the filtrate was concentrated in vacuo. The residue was purified by silica gel chromatography (10/1 petroleum ether/EtOAc) to afford the title compound. MS: 479 (M+1).

Step 2: 3-Methyl-2-(4-((1,2,3,4-tetrahydroisoquinolin-6-yl)oxy)piperidin-1-yl)-6,7-dihydro-5H-pyrrolo[3,4-b]pyridin-5-one To a solution of tert-butyl 6-((1-(3-methyl-5-oxo-6,7-dihydro-5H-pyrrolo[3,4-b]pyridin-2-yl)piperidin-4-yl)oxy)-3,4-dihydroisoquinoline-2(1H)-carboxylate (170 mg, 0.355 mmol) in MeOH (2 mL) was added HCl (1.0 mL, 12.18 mmol, 4 M in dioxane). The mixture was stirred at RT for 3 h under a nitrogen atmosphere. The mixture was concentrated and diluted with EtOAc (30 mL) and water (10 mL). The organic layer was washed with water (10 mL×2), brine (10 mL), dried over anhydrous sodium sulfate, filtered and concentrated in vacuo. The residue was purified by reverse phase HPLC (ACN/water with 0.1% $NH_3OH$ modifier) to afford the title compound. MS: 379 (M+1). $^1$H NMR (400 MHz, $CDCl_3$): δ 7.82 (1H, s), 6.96 (1H, d, J=8.0 Hz), 6.77 (1H, dd, J=8.0, 2.8 Hz), 6.71 (1H, s), 5.95 (1H, s), 4.50-4.53 (1H, m), 4.37 (2H, s), 3.99 (2H, s), 3.56-3.58 (2H, m), 3.13-3.22 (4H, m), 2.78-2.81 (2H, m), 2.37 (3H, s), 2.12-2.14 (2H, m), 1.96-1.99 (2H, m).

The following examples in table 3B were prepared according to scheme 3 using the procedure outlined in the synthesis of Example 144 using known or prepared intermediates and phenols containing a protecting group susceptible to acid-mediated cleavage using HCl or TFA.

TABLE 3B

| Example | Structure | Name | MS (M + 1) |
|---|---|---|---|
| 145 | 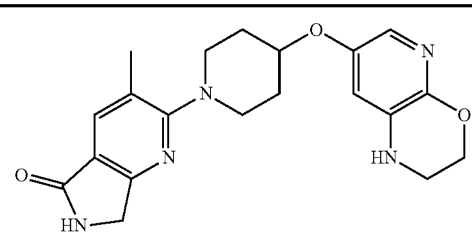 | 2-(4-((2,3-dihydro-1H-pyrido[2,3-b][1,4]oxazin-7-yl)oxy)piperidin-1-yl)-3-methyl-6,7-dihydro-5H-pyrrolo[3,4-b]pyridin-5-one | 382 |
| 146 | 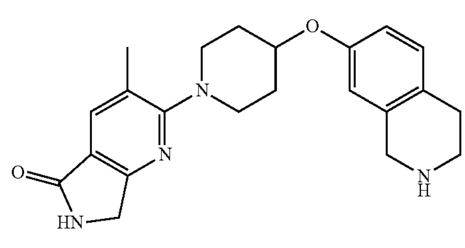 [SMILES: Cc1cc2c(nc1N1CCC(Oc3ccc4c(c3)CNCC4)CC1)CNC2=O] | 3-methyl-2-(4-((1,2,3,4-tetrahydroisoquinolin-7-yl)oxy)piperidin-1-yl)-6,7-dihydro-5H-pyrrolo[3,4-b]pyridin-5-one | 379 |
| 147 | 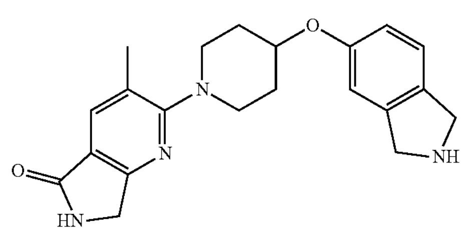 [SMILES: Cc1cc2c(nc1N1CCC(Oc3ccc4c(c3)CNC4)CC1)CNC2=O] | 2-(4-(isoindolin-5-yloxy)piperidin-1-yl)-3-methyl-6,7-dihydro-5H-pyrrolo[3,4-b]pyridin-5-one | 365 |

TABLE 3B-continued

| Example | Structure | Name | MS (M + 1) |
|---|---|---|---|
| 148* | 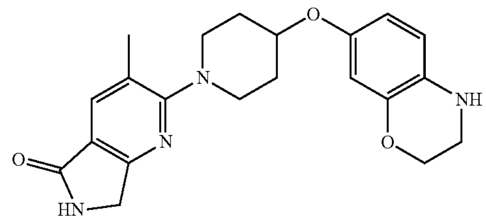 [SMILES: Cc1cc2c(nc1N1CCC(Oc3ccc4c(c3)OCCN4)CC1)CNC2=O] | 2-(4-((3,4-dihydro-2H-benzo[b][1,4]oxazin-7-yl)oxy)piperidin-1-yl)-3-methyl-6,7-dihydro-5H-pyrrolo[3,4-b]pyridin-5-one | 381 |
| 149 | 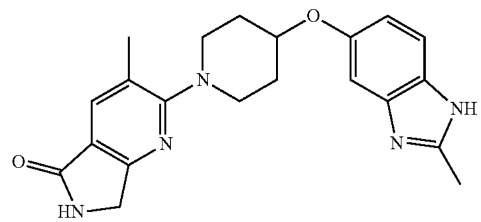 [SMILES: Cc1nc2cc(OC3CCN(c4nc5c(cc4C)C(=O)NC5)CC3)ccc2[nH]1] | 3-methyl-2-(4-((2-methyl-1H-benzo[d]imidazol-5-yl)oxy)piperidin-1-yl)-6,7-dihydro-5H-pyrrolo[3,4-b]pyridin-5-one | 378 |

*Phenol may be prepared according to literature procedures, see e.g.: Yoshino, T. et al., Japan Patent Publication JP 2009/114140.

Example 150A and 150B

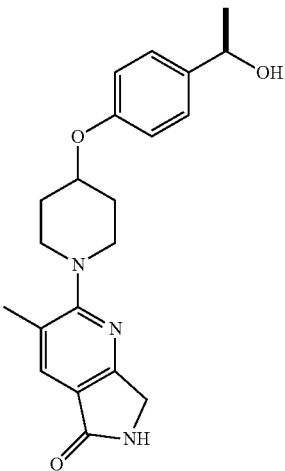

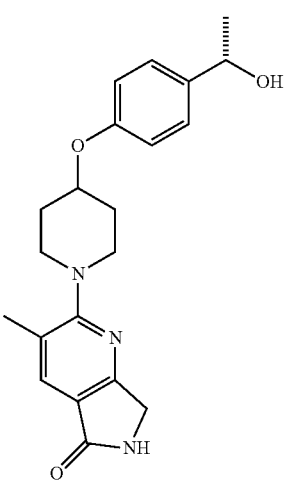

(R)-2-(4-(4-(1-Hydroxyethyl)phenoxy)piperidin-1-yl)-3-methyl-6,7-dihydro-5H-pyrrolo[3,4-b]pyridin-5-one and (S)-2-(4-(4-(1-hydroxyethyl)phenoxy)piperidin-1-yl)-3-methyl-6,7-dihydro-5H-pyrrolo[3,4-b]pyridin-5-one (Scheme 4)

Step 1: 2-(4-(4-Acetylphenoxy)piperidin-1-yl)-3-methyl-6,7-dihydro-5H-pyrrolo[3,4-b]pyridin-5-one A solution of 1-(4-hydroxyphenyl)ethanone (91 mg, 0.667 mmol), 2-(4-hydroxypiperidin-1-yl)-3-methyl-6,7-dihydro-5H-pyrrolo[3,4-b]pyridin-5-one (150 mg, 0.607 mmol, intermediate H1), Ph$_3$P (239 mg, 0.910 mmol), DBAD (210 mg, 0.910 mmol) in toluene (4 mL) was stirred at 80° C. for 16 h under nitrogen. The reaction was concentrated to give a residue which was purified by prep-TLC (100% EtOAc) to give title compound. MS: 366 (M+1).

Step 2: 2-(4-(4-(1-Hydroxyethyl)phenoxy)piperidin-1-yl)-3-methyl-6,7-dihydro-5H-pyrrolo[3,4-b]pyridin-5-one A solution of 2-(4-(4-acetylphenoxy)piperidin-1-yl)-3-methyl-6,7-dihydro-5H-pyrrolo[3,4-b]pyridin-5-one (130 mg, 0.356 mmol) in THF (2 mL) was added LiBH$_4$ (15.50 mg, 0.711 mmol) and was stirred at 20° C. for 16 h. The reaction mixture was concentrated to give a residue which was used purified by silica gel chromatography (20/1 DCM/MeOH) to afford the title compound. The mixture of the two stereoisomers was purified by chiral SFC (OJ column, 5-40% MeOH with 0.05% DEA modifier/CO$_2$) to afford isomer 150A (faster eluting): MS: 368 (M+1). $^1$H NMR (400 MHz, methanol-d$_4$): δ 7.78 (1H, s), 7.27 (2H, J=8.80 Hz, d), 6.93 (2H, J=8.80 Hz, d), 4.72-4.77 (1H, m), 4.54-4.62 (1H, m), 4.32 (2H, s), 3.49-3.60 (2H, m), 3.13-3.25 (2H, m), 2.37 (3H, s), 2.07-2.20 (2H, m), 1.82-1.95 (2H, m), 1.40 (3H, J=6.80 Hz, d). Isomer 150B (slower eluting): MS: 368 (M+1). $^1$H NMR (400 MHz, methanol-d$_4$): δ 7.78 (1H, s), 7.27 (2H, J=8.80 Hz, d), 6.93 (2H, J=8.80 Hz, d), 4.71-4.79 (1H, m), 4.53-4.62 (1H, m), 4.31 (2H, s), 3.49-3.61 (2H, m), 3.13-3.25 (2H, m), 2.36 (3H, s), 2.05-2.18 (2H, m), 1.82-1.96 (2H, m), 1.40 (3H, J=6.40 Hz, d).

The following examples in table 4 were prepared according to scheme 4 using the procedure outlined in the synthesis of Examples 150A and 150B where step 1 includes phenols with ketone or ester substituents. Alternative reaction conditions for step 2 may utilize sodium borohydride as the reagent as appropriate for the substrate.

TABLE 4

| Example | Structure | Name | MS (M + 1) |
|---|---|---|---|
| 151 | 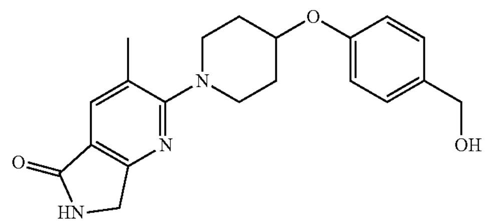 [SMILES: Cc1cc2c(nc1N1CCC(Oc3ccc(CO)cc3)CC1)CNC2=O] | 2-(4-(4-(hydroxymethyl)phenoxy)piperidin-1-yl)-3-methyl-6,7-dihydro-5H-pyrrolo[3,4-b]pyridin-5-one | 354 |
| 152 | 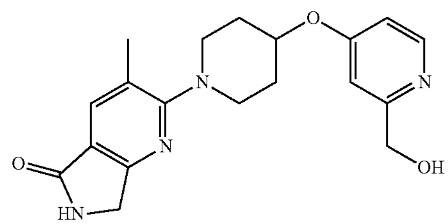 [SMILES: Cc1cc2c(nc1N1CCC(Oc3ccnc(CO)c3)CC1)CNC2=O] | 2-(4-((2-(hydroxymethyl)pyridin-4-yl)oxy)piperidin-1-yl)-3-methyl-6,7-dihydro-5H-pyrrolo[3,4-b]pyridin-5-one | 355 |
| 153 | 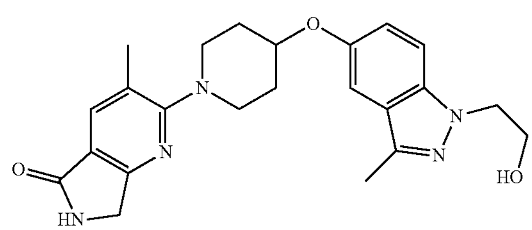 [SMILES: Cc1cc2c(nc1N1CCC(Oc3ccc4c(c3)c(C)nn4CCO)CC1)CNC2=O] | 2-(4-((1-(2-hydroxyethyl)-3-methyl-1H-indazol-5-yl)oxy)piperidin-1-yl)-3-methyl-6,7-dihydro-5H-pyrrolo[3,4-b]pyridin-5-one | 422 |
| 154 | 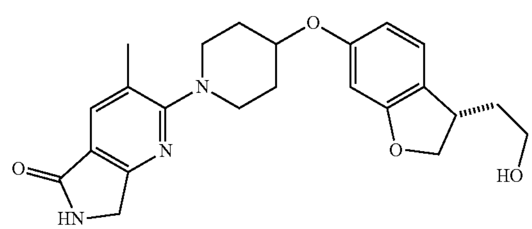 [SMILES: Cc1cc2c(nc1N1CCC(Oc3ccc4c(c3)OC[C@H]4CCO)CC1)CNC2=O] | (S)-2-(4-((3-(2-hydroxyethyl)-2,3-dihydrobenzofuran-6-yl)oxy)piperidin-1-yl)-3-methyl-6,7-dihydro-5H-pyrrolo[3,4-b]pyridin-5-one | 410 |
| 155 | 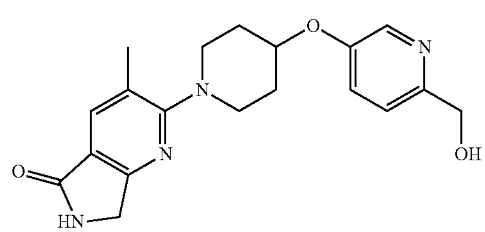 [SMILES: Cc1cc2c(nc1N1CCC(Oc3ccc(CO)nc3)CC1)CNC2=O] | 2-(4-((6-(hydroxymethyl)pyridin-3-yl)oxy)piperidin-1-yl)-3-methyl-6,7-dihydro-5H-pyrrolo[3,4-b]pyridin-5-one | 355 |
| 156 | 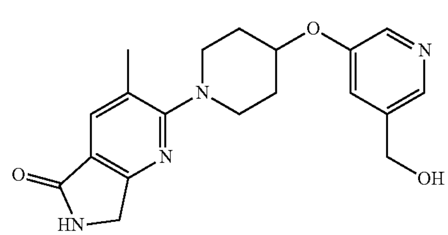 [SMILES: Cc1cc2c(nc1N1CCC(Oc3cncc(CO)c3)CC1)CNC2=O] | 2-(4-((5-(hydroxymethyl)pyridin-3-yl)oxy)piperidin-1-yl)-3-methyl-6,7-dihydro-5H-pyrrolo[3,4-b]pyridin-5-one | 355 |

TABLE 4-continued

| Example | Structure | Name | MS (M + 1) |
|---|---|---|---|
| 157A* 157B* | | (R)-2-(4-((1-(2-hydroxyethyl)-2,3-dihydro-1H-inden-5-yl)oxy)piperidin-1-yl)-3-methyl-6,7-dihydro-5H-pyrrolo[3,4-b]pyridin-5-one and (S)-2-(4-((1-(2-hydroxyethyl)-2,3-dihydro-1H-inden-5-yl)oxy)piperidin-1-yl)-3-methyl-6,7-dihydro-5H-pyrrolo[3,4-b]pyridin-5-one | 408 408 |

*Phenol may be prepared according to literature procedures, see e.g.: Colandrea, et al. PCT Patent Publication WO2005/058848.

Examples 158A and 158B

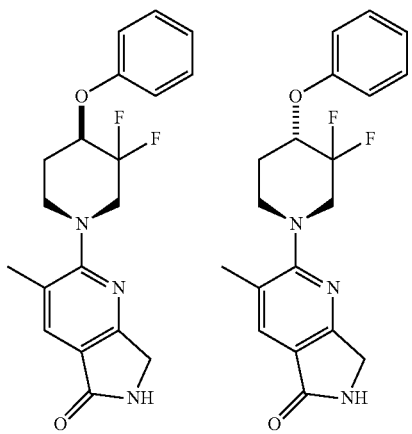

cis-2-(3,3-Difluoro-4-phenoxypiperidin-1-yl)-3-methyl-6,7-dihydro-5H-pyrrolo[3,4-b]pyridin-5-one and trans-2-(3,3-Difluoro-4-phenoxypiperidin-1-yl)-3-methyl-6,7-dihydro-5H-pyrrolo[3,4-b]pyridin-5-one (Scheme 5)

Step 1: Methyl 2-cyano-6-(3,3-difluoro-4-phenoxypiperidin-1-yl)-5-methylnicotinate To a solution of methyl 6-chloro-2-cyano-5-methylnicotinate (230 mg, 1.09 mmol) in NMP (5 mL) was added 3,3-difluoro-4-phenoxypiperidine (233 mg, 1.09 mmol) and triethylamine (0.304 mL, 2.18 mmol). The mixture was stirred at 120° C. for 16 h under a nitrogen atmosphere (balloon). The reaction was concentrated in vacuo and the resultant residue was purified by silica gel chromatography (10:1-1:4 petroleum ether:EtOAc) to give the title compound. MS: 388 (M+1).

Step 2: 2-(3,3-Difluoro-4-phenoxypiperidin-1-yl)-3-methyl-6,7-dihydro-5H-pyrrolo[3,4-b]pyridin-5-one To a solution of methyl 2-cyano-6-(3,3-difluoro-4-phenoxypiperidin-1-yl)-5-methylnicotinate (240 mg, 0.62 mmol) in MeOH (2 mL) and ammonium hydroxide (0.5 mL, 0.622 mmol) was added nickel (72.7 mg, 1.24 mmol). The system was placed under hydrogen (50 psi) and was heated to 30° C. for 3 h. After filtration, washing with methanol, the filtrate was concentrated under reduced pressure. The residue was purified by reverse phase HPLC (ACN/water with 0.1% $NH_3OH$ modifier) to afford the title compound. The mixture of the two stereoisomers was purified by chiral SFC (OD column, 30% isopropanol with 0.05% DEA modifier/ $CO_2$) to afford isomer 158A (faster eluting): MS: 360 (M+1). $^1H$ NMR (400 MHz, $CDCl_3$) δ: 7.77 (1H, s), 7.24 (2H, t, J=8.0 Hz), 7.07 (1H, br s), 6.93-6.97 (3H, m), 4.54-4.55 (1H, m), 4.31 (2H, s), 3.76-3.86 (1H, m), 3.66-3.68 (1H, m), 3.29-3.34 (2H, m), 2.32 (3H, s), 2.12-2.22 (2H, m). Isomer 158B (slower eluting): MS: 360 (M+1). $^1H$ NMR (400 MHz, $CDCl_3$): δ 7.78 (1H, s), 7.25 (2H, t, J=8.0 Hz), 6.94-6.98 (3H, m), 6.61 (1H, br s), 4.55-4.56 (1H, m), 4.31 (2H, s), 3.66-3.72 (1H, m), 3.55-3.58 (1H, m), 3.29-3.34 (2H, m), 2.32 (3H, s), 2.14-2.22 (2H, m).

Example 159

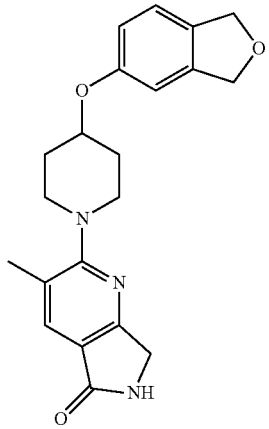 [SMILES: Cc1cc2c(nc1N1CCC(Oc3ccc4c(c3)COC4)CC1)CNC2=O]

2-[4-(1,3-Dihydro-2-benzofuran-5-yloxy)piperidin-1-yl]-3-methyl-6,7-dihydro-5H-pyrrolo[3,4-b]pyridin-5-one (Scheme 5)

Step 1: Methyl 2-cyano-6-(4-((1,3-dihydro-2-benzofuran-5-yl)oxy)piperidin-1-yl)-5-methylnicotinate To a solution of 4-((1,3-dihydro-2-benzofuran-5-yl)oxy)piperidine (4.19 g, 18.4 mmol) and methyl 6-chloro-2- cyano-5-methylnicotinate (3.86 g, 18.4 mmol) in NMP (42 mL) was added N,N-diisopropylethylamine (9.8 mL, 55 mmol) under an atmosphere of nitrogen. The resulting mixture was heated to 60° C. with stirring for 15 h. After cooling to RT, methanol (42 mL) and water (42 mL) were added to the reaction mixture. The solids were isolated by filtration to yield the title compound. MS: 394 (M+1).

Step 2: 2-[4-(1,3-Dihydro-2-benzofuran-5-yloxy)piperidin-1-yl]-3-methyl-6,7-dihydro-H-pyrrolo[3,4-b]pyridin-5-one To a solution of methyl 2-cyano-6-(4-((1,3-dihydro-2-benzofuran-5-yl)oxy)piperidin-1-yl)-5-methylnicotinate (14.6 g, 14.8 mmol) in 2,2,2-trifluoroethanol (175 mL) was added sponge Ni/Mo catalyst (2.92 g) under a nitrogen atmosphere. The system was placed under hydrogen (50 psi) and was heated to 30° C. for 24 h. After filtration, washing with 2,2,2-trifluoroethanol (40 mL×4), the volatiles were removed under reduced pressure. The residue was diluted with THF (60 mL) and was heated to 60° C. The solution was evaporated to approximately half the original volume before IPAc (60 mL) was added at 50° C. The mixture further evaporated and cooled to RT before the title compound was isolated by filtration. MS: 366 (M+1). $^1$H NMR (DMSO-d$_6$): δ 8.33 (1H, s), 7.72 (1H, s), 7.20 (1H, d, J=8.23 Hz), 6.96 (1H, s), 6.90 (1H, d, J=8.33 Hz), 4.94 (4H, d, J=13.22 Hz), 4.56-4.59 (1H, m), 4.24 (2H, s), 3.48 (2H, d, J=12.74 Hz), 3.10 (2H, t, J=10.78 Hz), 2.31 (3H, s), 2.07 (2H, br s), 1.74-1.80 (2H, m).

Example 160

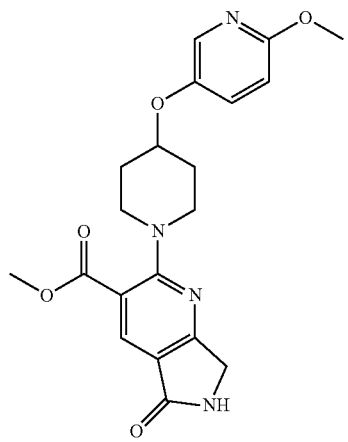

Methyl 2-(4-((6-methoxypyridin-3-yl)oxy)piperidin-1-yl)-5-oxo-6,7-dihydro-5H-pyrrolo[3,4-b]pyridine-3-carboxylate (Scheme 5)

Step 1: Dimethyl 2-cyano-6-(4-((6-methoxypyridin-3-yl)oxy)piperidin-1-yl)pyridine-3,5-dicarboxylate N,N-Diisopropylethylamine (0.634 mL, 3.63 mmol) was added to a stirred mixture of 2-methoxy-5-(piperidin-4-yloxy)pyridine dihydrochloride (409 mg, 1.45 mmol, intermediate F1) and dimethyl 2-chloro-6-cyanopyridine-3,5-dicarboxylate (185 mg, 0.727 mmol, intermediate A4) in dioxane (10 mL). The reaction was stirred at 100° C. for 1 h and was then concentrated. The residue was purified by column chromatography on silica gel (1/3 EtOAc/hexane) to give the title compound. MS: 427 (M+1).

Step 2: 2-(4-((1,3-Dihydro-2-benzofuran-5-yl)oxy)piperidin-1-yl)-3-methyl-6,7-dihydro-5H-pyrrolo[3,4-b]pyridin-5-one Platinum(IV) oxide (1.12 mg, 4.92 μmol) was added to a stirred, room temperature mixture of dimethyl 2-cyano-6-(4-(((6-methoxypyridin-3-yl)oxy)piperidin-1-yl)pyridine-3,5-dicarboxylate (21 mg, 0.049 mmol) in MeOH (10.0 mL). The reaction was stirred at RT under an atmosphere of hydrogen for 3 h. After filtration and removal of solvent, the crude residue was transferred to a microwave vial with dioxane (10 mL), to which triethylamine (68 μL, 0.49 mmol) was added. The resulting mixture was stirred at 100° C. under microwave irradiation. After concentrating the reaction, the residue was purified by mass triggered reverse phase HPLC (ACN/water with 0.1% NH$_3$OH modifier) to afford the title compound. MS: 399 (M+1). $^1$H NMR (500 MHz, CDCl$_3$): δ 8.39 (1H, s), 7.88 (1H, d, J=3.0 Hz), 7.29 (1H, dd, J=8.9, 3.0), 7.02 (1H, s), 6.72 (1H, d, J=8.9 Hz), 4.47 (1H, t, J=5.8 Hz), 4.38 (2H, s), 3.92 (6H, s), 3.79-3.83 (2H, m), 3.46-3.51 (2H, m), 2.06-2.10 (2H, m), 1.90-1.93 (2H, m).

Example 160A and 160B

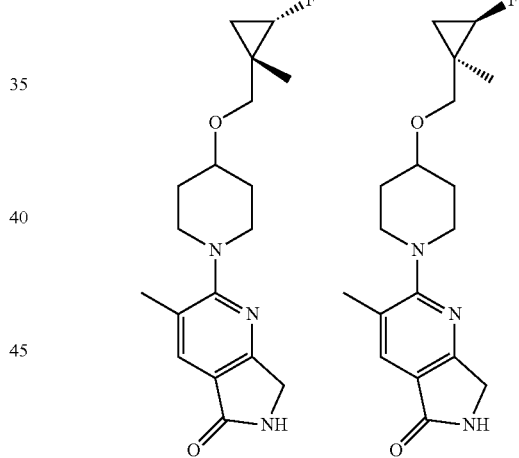

2-(4-(((1S,2S)-2-Fluoro-1-methylcyclopropyl)methoxy)piperidin-1-yl)-3-methyl-6,7-dihydro-5H-pyrrolo[3,4-b]pyridin-5-one and 2-(4-(((1R,2R)-2-fluoro-1-methylcyclopropyl)methoxy)piperidin-1-yl)-3-methyl-6,7-dihydro-5H-pyrrolo[3,4-b]pyridin-5-one (Scheme 5)

Step 1: Methyl 2-cyano-6-(4-(((trans)-2-fluoro-1-methylcyclopropyl)methoxy)piperidin-1-yl)-5-methylnicotinate and methyl 2-cyano-6-(4-(((cis)-2-fluoro-1-methylcyclopropyl)methoxy)piperidin-1-yl)-5-methylnicotinate A solution of 4-((2-fluoro-1-methylcyclopropyl)methoxy)piperidine (intermediate KK, 200 mg) in DMF (5 mL) was added methyl 6-chloro-2-cyano-5-methylnicotinate (intermediate A1, 225 mg, 1.068 mmol) and DIPEA (414 mg, 3.20 mmol) was stirred at 80° C. for 15 h. The mixture was directly purified by reverse phase HPLC (ACN/water with 0.1% TFA modifier) to afford the title compounds, the trans-isomer eluted first and the cis-isomer eluted second. MS: 362 (M+1).

Step 2: 2-(4-(((1S,2S)-2-Fluoro-1-methylcyclopropyl)methoxy)piperidin-1-yl)-3-methyl-6,7-dihydro-5H-pyrrolo[3,4-b]pyridin-5-one and 2-(4-(((1R,2R)-2-fluoro-1-methylcyclopropyl)methoxy)piperidin-1-yl)-3-methyl-6,7-dihydro-5H-pyrrolo[3,4-b]pyridin-5-one A solution of methyl 2-cyano-6-(4-(((trans)-2-fluoro-1-methylcyclopropyl)methoxy)piperidin-1-yl)-5-methylnicotinate in MeOH (5 mL) was added nickel (30 mg, 0.511 mmol) and 2 drops of concentrated ammonia was stirred at RT for 3 h under a hydrogen atmosphere (50 psi). The mixture was filtered and concentrated before the two stereoisomers were purified by chiral SFC (OJ column, 15% ethanol/CO$_2$) to afford isomer 160A (faster eluting isomer): MS: 334 (M+1). $^1$H NMR (400 MHz, CDCl$_3$) δ 7.77 (1H, s), 6.03 (1H, s), 4.32-4.50 (3H, m), 3.67 (1H, dd, J=10.0 Hz, 2.4 Hz), 3.48-3.57 (4H, m), 2.99-3.05 (2H, m), 2.33 (3H, s), 2.01-2.05 (2H, m), 1.73-1.78 (2H, m), 1.09 (3H, d, J=3.2 Hz), 0.81-0.86 (1H, m), 0.62-0.66 (1H, m). Isomer 160B (slower eluting isomer): MS: 334 (M+1). $^1$H NMR (400 MHz, CDCl$_3$) δ 7.77 (1H, s), 6.03 (1H, s), 4.32-4.50 (3H, m), 3.67 (1H, dd, J=10.0 Hz, 2.4 Hz), 3.48-3.57 (4H, m), 2.99-3.05 (2H, m), 2.33 (3H, s), 2.01-2.05 (2H, m), 1.73-1.78 (2H, m), 1.09 (3H, d, J=3.2 Hz), 0.81-0.86 (1H, m), 0.62-0.66 (1H, m).

Example 160C and 160D

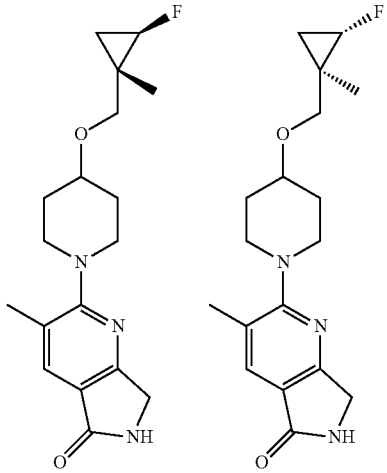 [SMILES: Cc1cc2c(nc1N1CCC(OC[C@]3(C)C[C@H]3F)CC1)CNC2=O ; Cc1cc2c(nc1N1CCC(OC[C@@]3(C)C[C@@H]3F)CC1)CNC2=O]

2-(4-(((1S,2R)-2-Fluoro-1-methylcyclopropyl)methoxy)piperidin-1-yl)-3-methyl-6,7-dihydro-5H-pyrrolo[3,4-b]pyridin-5-one and 2-(4-(((1R,2S)-2-fluoro-1-methylcyclopropyl)methoxy)piperidin-1-yl)-3-methyl-6,7-dihydro-5H-pyrrolo[3,4-b]pyridin-5-one (Scheme 5)

Methyl 2-cyano-6-(4-(((cis)-2-fluoro-1-methylcyclopropyl)methoxy)piperidin-1-yl)-5-methylnicotinate from step 1 in procedure for Example 160A and 160B (vide supra) (100 mg, 0.277 mmol) was dissolved in MeOH (5 mL). Nickel (30 mg, 0.511 mmol) and 2 drops of concentrated ammonia was added to the solution and the reaction was stirred at RT for 3 h under an atmosphere of hydrogen (50 psi). The mixture was filtered and concentrated before resolution by chiral SFC (OJ column, 15% EtOH with 0.1% ammonium hydroxide/CO$_2$) to afford isomer 160C (faster eluting isomer): MS: 334 (M+1). $^1$H NMR (400 MHz, CDCl$_3$): δ 7.77 (1H, s), 6.10 (1H, s), 4.38-4.57 (1H, m), 4.34 (2H, s), 3.47-3.52 (3H, m), 3.33 (1H, dd, J=9.2 Hz, 2.8 Hz), 3.23 (1H, d, J=9.2 Hz), 2.99-3.06 (2H, m), 2.32 (3H, s), 1.95-1.99 (2H, m), 1.57-1.73 (2H, m), 1.09 (3H, d, J=1.6 Hz), 0.73-0.80 (1H, m), 0.63-0.70 (1H, m). Isomer 160D (slower eluting isomer): MS: 334 (M+1). $^1$H NMR (400 MHz, CDCl$_3$): δ 7.77 (1H, s), 6.10 (1H, s), 4.38-4.57 (1H, m), 4.34 (2H, s), 3.47-3.52 (3H, m), 3.33 (1H, dd, J=9.2 Hz, 2.8 Hz), 3.23 (1H, d, J=9.2 Hz), 2.99-3.06 (2H, m), 2.32 (3H, s), 1.95-1.99 (2H, m), 1.57-1.73 (2H, m), 1.09 (3H, d, J=1.6 Hz), 0.73-0.80 (1H, m), 0.63-0.70 (1H, m).

Example 161

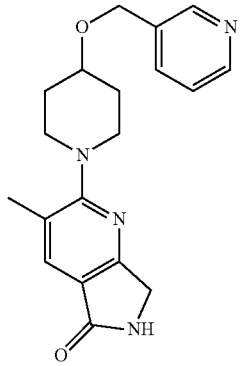 [SMILES: Cc1cc2c(nc1N1CCC(OCc3cccnc3)CC1)CNC2=O]

3-Methyl-2-(4-(pyridin-3-ylmethoxy)piperidin-1-yl)-6,7-dihydro-5H-pyrrolo[3,4-b]pyridin-5-one Step 1: Methyl 2-cyano-5-methyl-6-(4-(pyridin-3-ylmethoxy)piperidin-1-yl)nicotinate To a solution of 3-((piperidin-4-yloxy)methyl)pyridine hydrochloride (80 mg, 0.350 mmol) in DMF (5 mL) was added TEA (0.69 mL, 4.94 mmol). The mixture was stirred 16 h at 80° C. The mixture was cooled to RT, diluted with brine (10 mL) and extracted with EtOAc (20 mL×4). The combined organic layers were washed with brine (5 mL), dried over anhydrous sodium sulfate, filtered and concentrated. The residue was purified by silica gel chromatography (30-80% EtOAc in petroleum ether) to give the title compound. MS: 367 (M+1).

Step 2: 3-Methyl-2-(4-(pyridin-3-ylmethoxy)piperidin-1-yl)-6,7-dihydro-5H-pyrrolo[3,4-b]pyridin-5-one To a solution of methyl 2-cyano-5-methyl-6-(4-(pyridin-3-ylmethoxy)piperidin-1-yl)nicotinate (60 mg, 0.164 mmol) in MeOH (10 mL) was added cobalt(II) chloride (63.8 mg, 0.491 mmol). The mixture was stirred 5 min at RT and NaBH$_4$ (18.59 mg, 0.491 mmol) was added portionwise. The reaction mixture was stirred 1 h at 15° C. before the volatiles were removed under reduced pressure. The residue was diluted with EtOH (20 mL) and DIEA (0.405 mL, 2.32 mmol) and was stirred 2 h at 50° C. The mixture was filtered through a pad of silica gel and the filtrate was concentrated. Purification by reverse phase HPLC (ACN/water with ammonium hydroxide modifier) afforded the title compound. MS: 339 (M+1). $^1$H NMR (400 MHz, CDCl$_3$): δ 8.61 (1H, s), 8.53 (1H, d, J=4.4 Hz), 7.78 (1H, s), 7.72 (1H, d, J=7.6 Hz), 7.25-7.32 (1H, m), 6.04 (1H, s), 4.62 (2H, s), 4.34 (2H, s), 3.58 (1H, br s), 3.54-3.55 (2H, m), 3.04 (2H, t, J=6.0 Hz), 2.34 (3H, s), 2.07 (2H, m), 1.80-1.86 (2H, m).

Example 161A

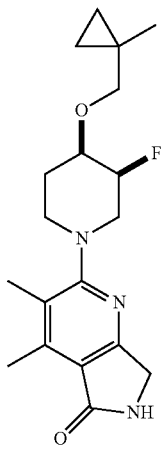

2-((3S,4R)-3-Fluoro-4-((1-methylcyclopropyl)methoxy)piperidin-1-yl)-3,4-dimethyl-6,7-dihydro-5H-pyrrolo[3,4-b]pyridin-5-one Step 1: Methyl 2-cyano-6-((3S,4R)-3-fluoro-4-((1-methylcyclopropyl)methoxy)piperidin-1-yl)-4,5-dimethylnicotinate (3S,4R)-3-fluoro-4-((1-methylcyclopropyl)methoxy)piperidine (intermediate L1A, 492 mg, 2.63 mmol) and methyl 6-chloro-2-cyano-4,5-dimethylnicotinate (intermediate AB, 393 mg, 1.75 mmol) were dissolved in NMP (7.5 mL) and DIPEA (0.611 mL, 3.50 mmol). The reaction was heated to 65° C. for 39 h and was cooled to RT. The mixture was partitioned between aqueous NH$_4$Cl and EtOAc. The organic layer was washed with water, then brine, dried over anhydrous sodium sulfate, filtered and concentrated. The residue was purified by silica gel chromatography (60% DCM/hexanes) to give the title compound. MS: 376 (M+1).

Step 2: 2-((3S,4R)-3-Fluoro-4-((1-methylcyclopropyl)methoxy)piperidin-1-yl)-3,4-dimethyl-6,7-dihydro-5H-pyrrolo[3,4-b]pyridin-5-one Methyl 2-cyano-6-((3S,4R)-3-fluoro-4-((1-methylcyclopropyl)methoxy)piperidin-1-yl)-4,5-dimethylnicotinate (0.395 g, 1.05 mmol) was dissolved in EtOH (7.5 mL) and AcOH (0.30 mL, 5.26 mmol). Palladium on carbon (10 wt %, 0.112 g, 0.105 mmol) was added and the system was placed under a hydrogen atmosphere and stirred for 5 h before the mixture was filtered (EtOH wash). The filtrate was concentrated (azeotrope with toluene) and was dissolved in methanol (6 mL) and triethylamine (1.0 mL, 7.89 mmol) and stirred for 90 min at RT. The volatiles were removed under reduced pressure and the resultant residue was purified by silica gel chromatography (0-50% 3:1 EtOAc:EtOH in DCM) to afford the title compound. MS: 348 (M+1). $^1$H NMR (500 MHz, CDCl$_3$): δ 6.03 (s, 1H), 4.93 (m, 0.5H), 4.83 (m, 0.5H), 4.28 (s, 2H), 3.68 (m, 2H), 3.40 (m, 3H), 3.25 (m, 1H), 2.97 (m, 1H), 2.63 (s, 3H), 2.25 (s, 3H), 2.14 (m, 1H), 1.88 (m, 1H), 1.17 (s, 3H), 0.44 (m, 2H), 0.35 (m, 2H).

The following examples in table 5 were prepared according to scheme 5 using the procedure and conditions outlined in the synthesis of Examples 158A, 158B, 159, 160, 160A, 160B, 160C, 160D, 161 and 161A.

TABLE 5

| Example | Structure | Name | MS (M + 1) |
|---|---|---|---|
| 162 | 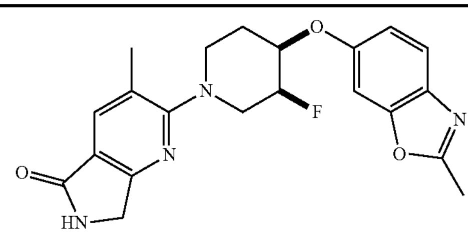 | 2-((3S,4R)-3-fluoro-4-((2-methylbenzo[d]oxazol-6-yl)oxy)piperidin-1-yl)-3-methyl-6,7-dihydro-5H-pyrrolo[3,4-b]pyridin-5-one | 397 |
| 162A<br>162B | | (R)-2-(4-((2-methoxy-2,3-dihydro-1H-inden-5-yl)oxy)piperidin-1-yl)-3-methyl-6,7-dihydro-5H-pyrrolo[3,4-b]pyridin-5-one and<br>(S)-2-(4-((2-methoxy-2,3-dihydro-1H-inden-5-yl)oxy)piperidin-1-yl)-3-methyl-6,7-dihydro-5H-pyrrolo[3,4-b]pyridin-5-one | 394<br>394 |

| Example | Structure | Name | MS (M + 1) |
|---|---|---|---|
| 163 | 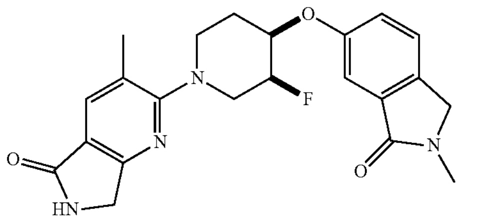 [SMILES: Cc1cc2c(nc1N1CC[C@@H](Oc3ccc4c(c3)C(=O)N(C)C4)[C@@H](F)C1)CNC2=O] | 2-((3S,4R)-3-fluoro-4-((2-methyl-3-oxoisoindolin-5-yl)oxy)piperidin-1-yl)-3-methyl-6,7-dihydro-5H-pyrrolo[3,4-b]pyridin-5-one | 411 |
| 163A | 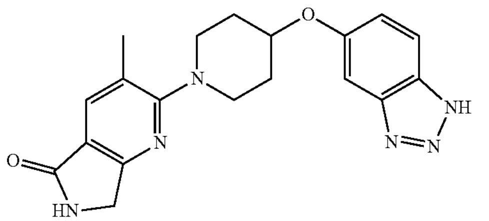 [SMILES: Cc1cc2c(nc1N1CCC(Oc3ccc4[nH]nnc4c3)CC1)CNC2=O] | 2-(4-((1H-benzo[d][1,2,3]triazol-5-yl)oxy)piperidin-1-yl)-3-methyl-6,7-dihydro-5H-pyrrolo[3,4-b]pyridin-5-one | 365 |
| 164 | 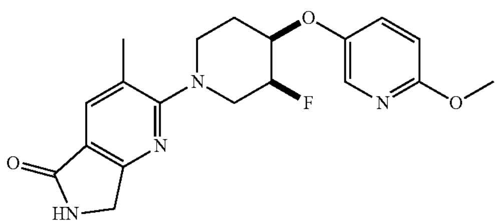 [SMILES: COc1ccc(O[C@@H]2CCN(c3nc4c(cc3C)C(=O)NC4)C[C@@H]2F)cn1] | 2-((3S,4R)-3-fluoro-4-((6-methoxypyridin-3-yl)oxy)piperidin-1-yl)-3-methyl-6,7-dihydro-5H-pyrrolo[3,4-b]pyridin-5-one | 373 |
| 164A | 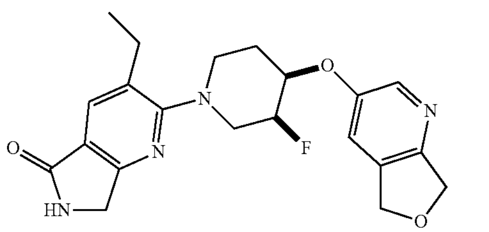 | 2-((3S,4R)-4-((5,7-dihydrofuro[3,4-b]pyridin-3-yl)oxy)-3-fluoropiperidin-1-yl)-3-ethyl-6,7-dihydro-5H-pyrrolo[3,4-b]pyridin-5-one | 399 |
| 165 | 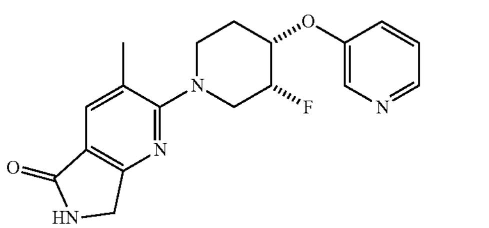 [SMILES: Cc1cc2c(nc1N1CC[C@H](Oc3cccnc3)[C@H](F)C1)CNC2=O] | 2-((3R,4S) or (3S,4R)-3-fluoro-4-(pyridin-3-yloxy)piperidin-1-yl)-3-methyl-6,7-dihydro-5H-pyrrolo[3,4-b]pyridin-5-one | 343 |
| 165A | 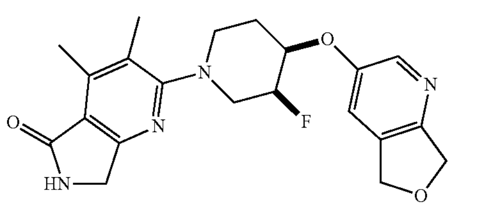 | 2-((3S,4R)-4-((5,7-dihydrofuro[3,4-b]pyridin-3-yl)oxy)-3-fluoropiperidin-1-yl)-3,4-dimethyl-6,7-dihydro-5H-pyrrolo[3,4-b]pyridin-5-one | 399 |
| 166 | 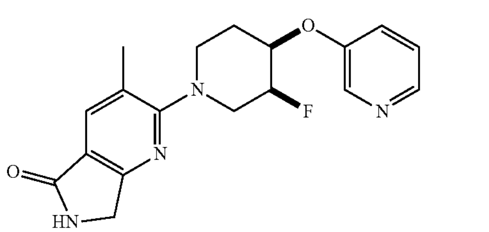 [SMILES: Cc1cc2c(nc1N1CC[C@@H](Oc3cccnc3)[C@@H](F)C1)CNC2=O] | 2-((3S,4R) or (3R,4S)-3-fluoro-4-(pyridin-3-yloxy)piperidin-1-yl)-3-methyl-6,7-dihydro-5H-pyrrolo[3,4-b]pyridin-5-one | 343 |

TABLE 5-continued

| Example | Structure | Name | MS (M + 1) |
|---|---|---|---|
| 166A 166B | | (R)-3-ethyl-2-(4-((2-hydroxy-2,3-dihydro-1H-inden-5-yl)oxy)piperidin-1-yl)-6,7-dihydro-5H-pyrrolo[3,4-b]pyridin-5-one and (S)-3-ethyl-2-(4-((2-hydroxy-2,3-dihydro-1H-inden-5-yl)oxy)piperidin-1-yl)-6,7-dihydro-5H-pyrrolo[3,4-b]pyridin-5-one | 394 394 |
| 167 | 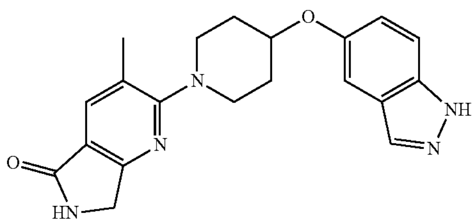 [SMILES: Cc1cc2c(nc1N1CCC(Oc3ccc4[nH]ncc4c3)CC1)CNC2=O] | 2-(4-((1H-indazol-5-yl)oxy)piperidin-1-yl)-3-methyl-6,7-dihydro-5H-pyrrolo[3,4-b]pyridin-5-one | 364 |
| 167A | 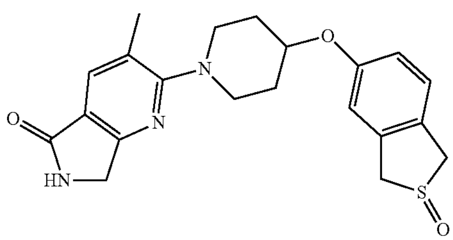 [SMILES: Cc1cc2c(nc1N1CCC(Oc3ccc4c(c3)CS(=O)C4)CC1)CNC2=O] | 3-methyl-2-(4-((2-oxido-1,3-dihydrobenzo[c]thiophen-5-yl)oxy)piperidin-1-yl)-6,7-dihydro-5H-pyrrolo[3,4-b]pyridin-5-one | 398 |
| 168 | 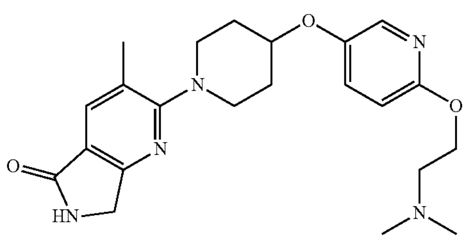 [SMILES: Cc1cc2c(nc1N1CCC(Oc3ccc(OCCN(C)C)nc3)CC1)CNC2=O] | 2-(4-((6-(2-(dimethylamino)ethoxy)pyridin-3-yl)oxy)piperidin-1-yl)-3-methyl-6,7-dihydro-5H-pyrrolo[3,4-b]pyridin-5-one | 412 |
| 168A 168B | | (R)-3-methyl-2-(4-((2-oxido-1,3-dihydrobenzo[c]thiophen-5-yl)oxy)piperidin-1-yl)-6,7-dihydro-5H-pyrrolo[3,4-b]pyridin-5-one and (S)-3-methyl-2-(4-((2-oxido-1,3-dihydrobenzo[c]thiophen-5-yl)oxy)piperidin-1-yl)-6,7-dihydro-5H-pyrrolo[3,4-b]pyridin-5-one | 398 398 |

TABLE 5-continued

| Example | Name | MS (M + 1) |
|---|---|---|
| 169 | 2-(4-((6-(2-amino-2-methylpropoxy)pyridin-3-yl)oxy)piperidin-1-yl)-3-methyl-6,7-dihydro-5H-pyrrolo[3,4-b]pyridin-5-one | 412 |
| 169A | 2-(4-((1-ethyl-1H-pyrazol-4-yl)oxy)piperidin-1-yl)-3-methyl-6,7-dihydro-5H-pyrrolo[3,4-b]pyridin-5-one | 342 |
| 170 | 2-(4-((6-(2-hydroxyethoxy)pyridin-3-yl)oxy)piperidin-1-yl)-3-methyl-6,7-dihydro-5H-pyrrolo[3,4-b]pyridin-5-one | 385 |
| 170A | 3-methyl-2-(4-((1-phenyl-1H-pyrazol-4-yl)oxy)piperidin-1-yl)-6,7-dihydro-5H-pyrrolo[3,4-b]pyridin-5-one | 390 |
| 171 | 2-(4-((6-(2-methoxyethoxy)pyridin-3-yl)oxy)piperidin-1-yl)-3-methyl-6,7-dihydro-5H-pyrrolo[3,4-b]pyridin-5-one | 399 |
| 171A 171B | (R)-2-(3,3-difluoro-4-((1-methylcyclopropyl)methoxy)piperidin-1-yl)-3-methyl-6,7-dihydro-5H-pyrrolo[3,4-b]pyridin-5-one and (S)-2-(3,3-difluoro-4-((1-methylcyclopropyl)methoxy)piperidin-1-yl)-3-methyl-6,7-dihydro-5H-pyrrolo[3,4-b]pyridin-5-one | 352 352 |

TABLE 5-continued

| Example | Name | MS (M + 1) |
|---|---|---|
| 172 | 2-(4-(cyclobutylmethoxy)piperidin-1-yl)-3-methyl-6,7-dihydro-5H-pyrrolo[3,4-b]pyridin-5-one | 316 |
| 172A | 3-methyl-2-(4-(2,2,2-trifluoroethoxy)piperidin-1-yl)-6,7-dihydro-5H-pyrrolo[3,4-b]pyridin-5-one | 330 |
| 173 | 2-(4-((6-(2-(azetidin-1-yl)ethoxy)pyridin-3-yl)oxy)piperidin-1-yl)-3-methyl-6,7-dihydro-5H-pyrrolo[3,4-b]pyridin-5-one | 424 |
| 173A | 3-ethyl-2-(4-((5-methylpyridin-3-yl)oxy)piperidin-1-yl)-6,7-dihydro-5H-pyrrolo[3,4-b]pyridin-5-one | 353 |
| 174 | N-(2-((5-((1-(3-methyl-5-oxo-6,7-dihydro-5H-pyrrolo[3,4-b]pyridin-2-yl)piperidin-4-yl)oxy)pyridin-2-yl)oxy)ethyl)acetamide | 426 |
| 174A | 2-((3R,4R)-3-fluoro-4-((1-methylcyclopropyl)methoxy)piperidin-1-yl)-3,4-dimethyl-6,7-dihydro-5H-pyrrolo[3,4-b]pyridin-5-one | 348 |

TABLE 5-continued

| Example | Structure | Name | MS (M + 1) |
|---|---|---|---|
| 175 | 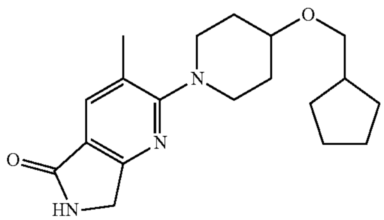 [SMILES: Cc1cc2c(nc1N1CCC(OCC3CCCC3)CC1)CNC2=O] | 2-(4-(cyclopentylmethoxy)piperidin-1-yl)-3-methyl-6,7-dihydro-5H-pyrrolo[3,4-b]pyridin-5-one | 330 |
| 175A | 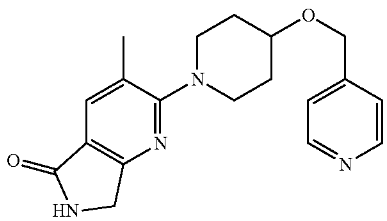 [SMILES: Cc1cc2c(nc1N1CCC(OCc3ccncc3)CC1)CNC2=O] | 3-methyl-2-(4-(pyridin-4-ylmethoxy)piperidin-1-yl)-6,7-dihydro-5H-pyrrolo[3,4-b]pyridin-5-one | 339 |
| 176 | 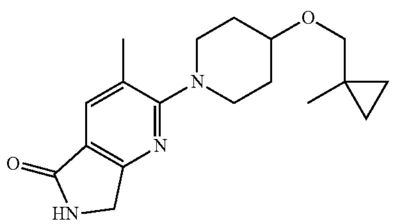 [SMILES: Cc1cc2c(nc1N1CCC(OCC3(C)CC3)CC1)CNC2=O] | 3-methyl-2-(4-((1-methylcyclopropyl)methoxy)piperidin-1-yl)-6,7-dihydro-5H-pyrrolo[3,4-b]pyridin-5-one | 316 |
| 176A | 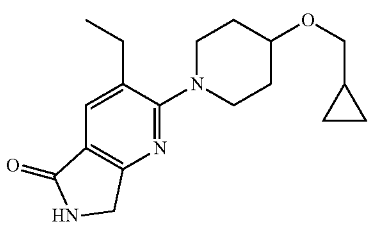 [SMILES: CCc1cc2c(nc1N1CCC(OCC3CC3)CC1)CNC2=O] | 2-(4-(cyclopropylmethoxy)piperidin-1-yl)-3-ethyl-6,7-dihydro-5H-pyrrolo[3,4-b]pyridin-5-one | 316 |
| 177 | 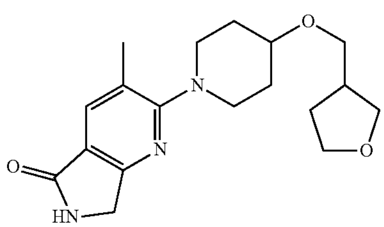 [SMILES: Cc1cc2c(nc1N1CCC(OCC3CCOC3)CC1)CNC2=O] | 3-methyl-2-(4-((tetrahydrofuran-3-yl)methoxy)piperidin-1-yl)-6,7-dihydro-5H-pyrrolo[3,4-b]pyridin-5-one | 332 |
| 178 | 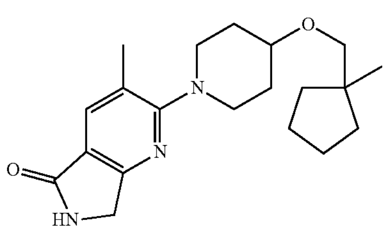 [SMILES: Cc1cc2c(nc1N1CCC(OCC3(C)CCCC3)CC1)CNC2=O] | 3-methyl-2-(4-((1-methylcyclopentyl)methoxy)piperidin-1-yl)-6,7-dihydro-5H-pyrrolo[3,4-b]pyridin-5-one | 344 |
| 178A | 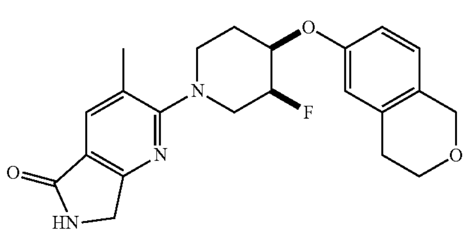 [SMILES: Cc1cc2c(nc1N1CC[C@@H](Oc3ccc4c(c3)CCOC4)[C@@H](F)C1)CNC2=O] | 2-((3S,4R)-3-fluoro-4-(isochroman-6-yloxy)piperidin-1-yl)-3-methyl-6,7-dihydro-5H-pyrrolo[3,4-b]pyridin-5-one | 398 |

TABLE 5-continued

| Example | Name | MS (M + 1) |
|---|---|---|
| 178B | 2-((3S,4R)-3-fluoro-4-(isochroman-7-yloxy)piperidin-1-yl)-3-methyl-6,7-dihydro-5H-pyrrolo[3,4-b]pyridin-5-one | 398 |
| 179 | 3-methyl-2-(4-(3,3,3-trifluoro-2-hydroxypropoxy)piperidin-1-yl)-6,7-dihydro-5H-pyrrolo[3,4-b]pyridin-5-one | 453 |
| 180 | 2-(4-((1-fluorocyclopentyl)methoxy)piperidin-1-yl)-3-methyl-6,7-dihydro-5H-pyrrolo[3,4-b]pyridin-5-one | 348 |
| 181A 181B | (R)-3-methyl-2-(4-(3,3,3-trifluoro-2-hydroxypropoxy)piperidin-1-yl)-6,7-dihydro-5H-pyrrolo[3,4-b]pyridin-5-one and (S)-3-methyl-2-(4-(3,3,3-trifluoro-2-hydroxypropoxy)piperidin-1-yl)-6,7-dihydro-5H-pyrrolo[3,4-b]pyridin-5-one | 453 453 |
| 182 | 3-methyl-2-(4-(neopentyloxy)piperidin-1-yl)-6,7-dihydro-5H-pyrrolo[3,4-b]pyridin-5-one | 318 |
| 182A | 2-(4-(imidazo[1,2-a]pyridin-6-yloxy)piperidin-1-yl)-3-methyl-6,7-dihydro-5H-pyrrolo[3,4-b]pyridin-5-one | 364 |

TABLE 5-continued

| Example | Name | MS (M + 1) |
|---|---|---|
| 183 | 3-methyl-2-(4-(oxazol-2-ylmethoxy)piperidin-1-yl)-6,7-dihydro-5H-pyrrolo[3,4-b]pyridin-5-one | 329 |
| 184 | 3-methyl-2-(4-((1-methylcyclobutyl)methoxy)piperidin-1-yl)-6,7-dihydro-5H-pyrrolo[3,4-b]pyridin-5-one | 330 |
| 185A 185B | 2-((1R,5S)-6-((6-methoxypyridin-3-yl)oxy)-3-azabicyclo[3.1.1]heptan-3-yl)-3-methyl-6,7-dihydro-5H-pyrrolo[3,4-b]pyridin-5-one and 2-((1R,5S)-6-((6-methoxypyridin-3-yl)oxy)-3-azabicyclo[3.1.1]heptan-3-yl)-3-methyl-6,7-dihydro-5H-pyrrolo[3,4-b]pyridin-5-one | 367 367 |
| 186 | 2-(4-((1-ethylcyclopropyl)methoxy)piperidin-1-yl)-3-methyl-6,7-dihydro-5H-pyrrolo[3,4-b]pyridin-5-one | 330 |
| 187 | 2-(4-(bicyclo[1.1.1]pentan-1-ylmethoxy)piperidin-1-yl)-3-methyl-6,7-dihydro-5H-pyrrolo[3,4-b]pyridin-5-one | 328 |
| 187A | 2-(4-((2,2-difluoro-1-methylcyclopropyl)methoxy)piperidin-1-yl)-3-ethyl-6,7-dihydro-5H-pyrrolo[3,4-b]pyridin-5-one | 366 |

TABLE 5-continued

| Example | Structure | Name | MS (M + 1) |
|---|---|---|---|
| 188 | 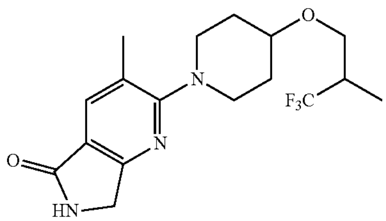 [SMILES: Cc1cc2c(nc1N1CCC(OCC(C)C(F)(F)F)CC1)CNC2=O] | 3-methyl-2-(4-(3,3,3-trifluoro-2-methylpropoxy)piperidin-1-yl)-6,7-dihydro-5H-pyrrolo[3,4-b]pyridin-5-one | 358 |
| 189 | 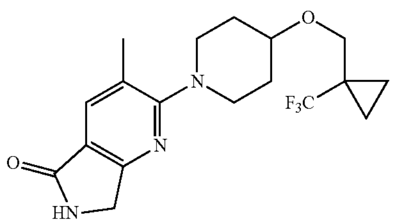 [SMILES: Cc1cc2c(nc1N1CCC(OCC3(C(F)(F)F)CC3)CC1)CNC2=O] | 3-methyl-2-(4-((1-(trifluoromethyl)cyclopropyl)methoxy)piperidin-1-yl)-6,7-dihydro-5H-pyrrolo[3,4-b]pyridin-5-one | 370 |
| 190 | 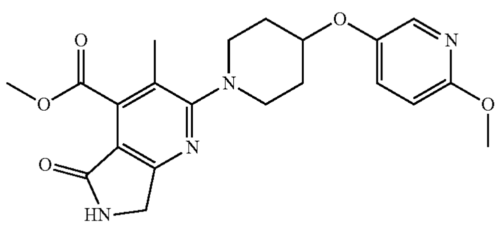 | methyl 2-(4-((6-methoxypyridin-3-yl)oxy)piperidin-1-yl)-3-methyl-5-oxo-6,7-dihydro-5H-pyrrolo[3,4-b]pyridine-4-carboxylate | 413 |
| 190A | 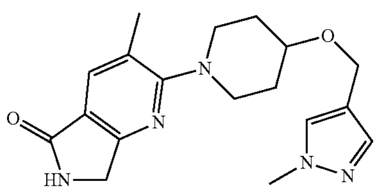 [SMILES: Cc1cc2c(nc1N1CCC(OCc3cnn(C)c3)CC1)CNC2=O] | 3-methyl-2-(4-((1-methyl-1H-pyrazol-4-yl)methoxy)piperidin-1-yl)-6,7-dihydro-5H-pyrrolo[3,4-b]pyridin-5-one | 342 |
| 191 | 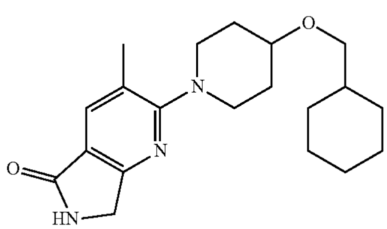 [SMILES: Cc1cc2c(nc1N1CCC(OCC3CCCCC3)CC1)CNC2=O] | 2-(4-(cyclohexylmethoxy)piperidin-1-yl)-3-methyl-6,7-dihydro-5H-pyrrolo[3,4-b]pyridin-5-one | 344 |
| 191A 191B | | (1S,2R)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile and (1R,2S)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile | 341 341 |

TABLE 5-continued

| Example | Structure | Name | MS (M + 1) |
|---|---|---|---|
| 192 | 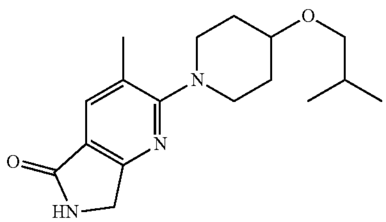 [SMILES: Cc1cc2c(nc1N1CCC(OCC(C)C)CC1)CNC2=O] | 2-(4-isobutoxypiperidin-1-yl)-3-methyl-6,7-dihydro-5H-pyrrolo[3,4-b]pyridin-5-one | 304 |
| 193 | 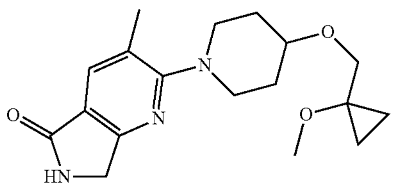 [SMILES: COC1(COC2CCN(c3nc4c(cc3C)C(=O)NC4)CC2)CC1] | 2-(4-((1-methoxycyclopropyl)methoxy)piperidin-1-yl)-3-methyl-6,7-dihydro-5H-pyrrolo[3,4-b]pyridin-5-one | 332 |
| 193A<br>193B | 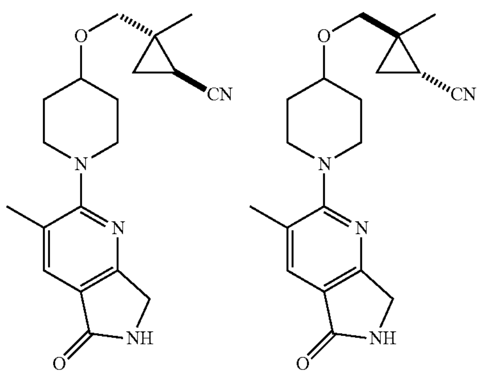 | (1R,2R)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile and (1S,2S)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile | 341<br>341 |
| 194 | 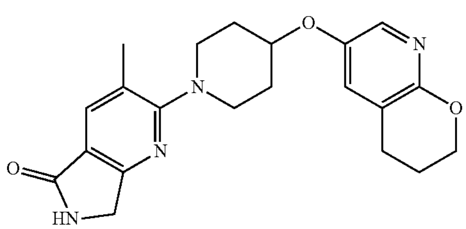 [SMILES: Cc1cc2c(nc1N1CCC(Oc3cnc4c(c3)CCCO4)CC1)CNC2=O] | 2-(4-((3,4-dihydro-2H-pyrano[2,3-b]pyridin-6-yl)oxy)piperidin-1-yl)-3-methyl-6,7-dihydro-5H-pyrrolo[3,4-b]pyridin-5-one | 381 |
| 194A | 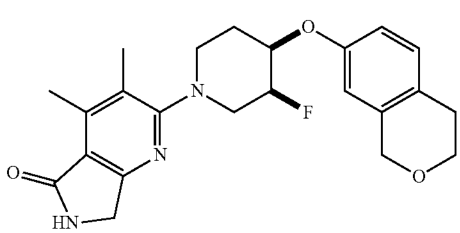 [SMILES: Cc1c(N2CC[C@@H](Oc3ccc4c(c3)COCC4)[C@@H](F)C2)nc2c(c1C)C(=O)NC2] | 2-((3S,4R)-3-fluoro-4-(isochroman-7-yloxy)piperidin-1-yl)-3,4-dimethyl-6,7-dihydro-5H-pyrrolo[3,4-b]pyridin-5-one | 412 |
| 195 | 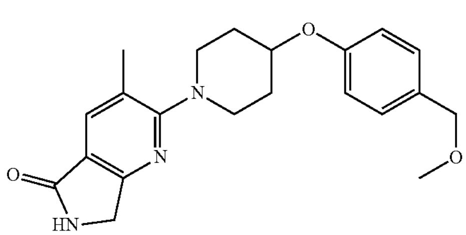 [SMILES: COCc1ccc(OC2CCN(c3nc4c(cc3C)C(=O)NC4)CC2)cc1] | 2-(4-(4-(methoxymethyl)phenoxy)piperidin-1-yl)-3-methyl-6,7-dihydro-5H-pyrrolo[3,4-b]pyridin-5-one | 368 |

TABLE 5-continued

| Example | Structure | Name | MS (M + 1) |
|---|---|---|---|
| 196 | 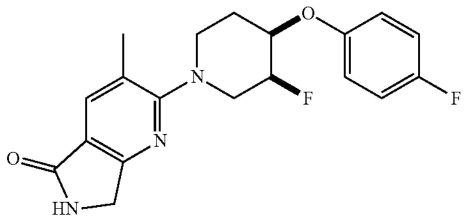 [SMILES: Cc1cc2c(nc1N1CC[C@@H](Oc3ccc(F)cc3)[C@@H](F)C1)CNC2=O] | 2-((3S,4R)-3-fluoro-4-(4-fluorophenoxy)piperidin-1-yl)-3-methyl-6,7-dihydro-5H-pyrrolo[3,4-b]pyridin-5-one | 360 |
| 197 | 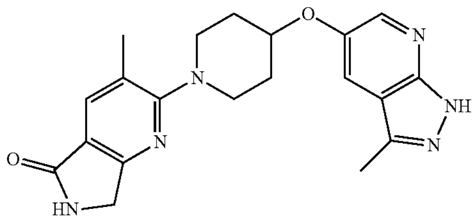 [SMILES: Cc1cc2c(nc1N1CCC(Oc3cnc4[nH]nc(C)c4c3)CC1)CNC2=O] | 3-methyl-2-(4-((3-methyl-1H-pyrazolo[3,4-b]pyridin-5-yl)oxy)piperidin-1-yl)-6,7-dihydro-5H-pyrrolo[3,4-b]pyridin-5-one | 379 |
| 197A | 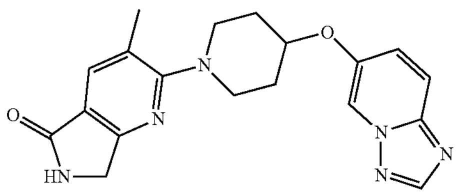 [SMILES: Cc1cc2c(nc1N1CCC(Oc3ccc4ncnn4c3)CC1)CNC2=O] | 2-(4-([1,2,4]triazolo[1,5-a]pyridin-6-yloxy)piperidin-1-yl)-3-methyl-6,7-dihydro-5H-pyrrolo[3,4-b]pyridin-5-one | 365 |
| 198 | 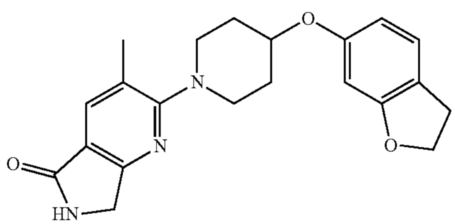 [SMILES: Cc1cc2c(nc1N1CCC(Oc3ccc4c(c3)OCC4)CC1)CNC2=O] | 2-(4-((2,3-dihydrobenzofuran-6-yl)oxy)piperidin-1-yl)-3-methyl-6,7-dihydro-5H-pyrrolo[3,4-b]pyridin-5-one | 366 |
| 198A | 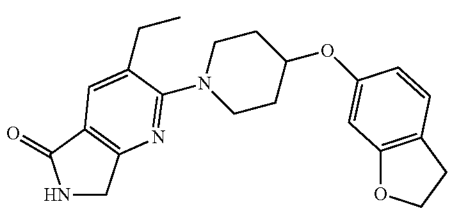 [SMILES: CCc1cc2c(nc1N1CCC(Oc3ccc4c(c3)OCC4)CC1)CNC2=O] | 2-(4-((2,3-dihydrobenzofuran-6-yl)oxy)piperidin-1-yl)-3-ethyl-6,7-dihydro-5H-pyrrolo[3,4-b]pyridin-5-one | 380 |
| 199A<br>199B | | (R)-3-methyl-2-(4-((1-methyl-1,3-dihydro-2-benzofuran-5-yl)oxy)piperidin-1-yl)-6,7-dihydro-5H-pyrrolo[3,4-b]pyridin-5-one and (S)-3-methyl-2-(4-((1-methyl-1,3-dihydro-2-benzofuran-5-yl)oxy)piperidin-1-yl)-6,7-dihydro-5H-pyrrolo[3,4-b]pyridin-5-one | 380<br>380 |

| Example | Structure | Name | MS (M + 1) |
|---|---|---|---|
| 200 | 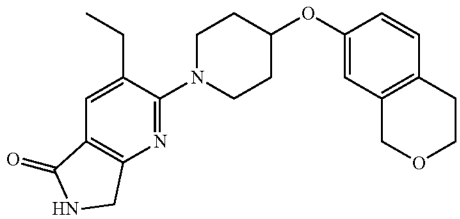 [SMILES: CCc1cc2c(nc1N1CCC(Oc3ccc4c(c3)COCC4)CC1)CNC2=O] | 3-ethyl-2-(4-(isochroman-7-yloxy)piperidin-1-yl)-6,7-dihydro-5H-pyrrolo[3,4-b]pyridin-5-one | 394 |
| 200A | 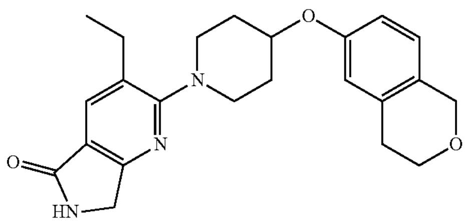 [SMILES: CCc1cc2c(nc1N1CCC(Oc3ccc4c(c3)CCOC4)CC1)CNC2=O] | 3-ethyl-2-(4-(isochroman-6-yloxy)piperidin-1-yl)-6,7-dihydro-5H-pyrrolo[3,4-b]pyridin-5-one | 394 |
| 201 | 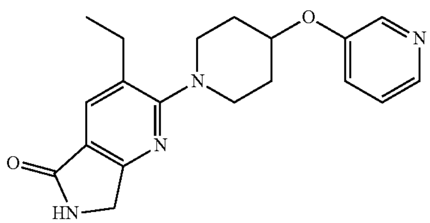 [SMILES: CCc1cc2c(nc1N1CCC(Oc3cccnc3)CC1)CNC2=O] | 3-ethyl-2-(4-(pyridin-3-yloxy)piperidin-1-yl)-6,7-dihydro-5H-pyrrolo[3,4-b]pyridin-5-one | 339 |
| 201A | 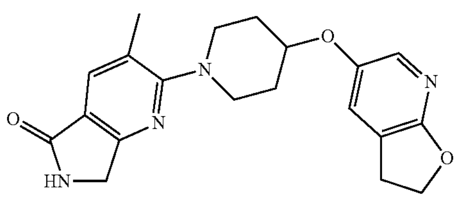 [SMILES: Cc1cc2c(nc1N1CCC(Oc3cnc4c(c3)CCO4)CC1)CNC2=O] | 2-(4-((2,3-dihydrofuro[2,3-b]pyridin-5-yl)oxy)piperidin-1-yl)-3-methyl-6,7-dihydro-5H-pyrrolo[3,4-b]pyridin-5-one | 367 |
| 202 | 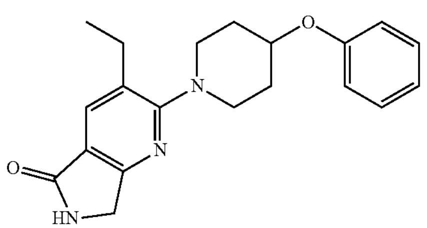 [SMILES: CCc1cc2c(nc1N1CCC(Oc3ccccc3)CC1)CNC2=O] | 3-ethyl-2-(4-phenoxypiperidin-1-yl)-6,7-dihydro-5H-pyrrolo[3,4-b]pyridin-5-one | 338 |
| 202A | 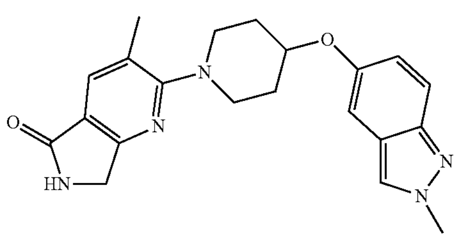 [SMILES: Cc1cc2c(nc1N1CCC(Oc3ccc4nn(C)cc4c3)CC1)CNC2=O] | 3-methyl-2-(4-((2-methyl-2H-indazol-5-yl)oxy)piperidin-1-yl)-6,7-dihydro-5H-pyrrolo[3,4-b]pyridin-5-one | 378 |
| 203 | 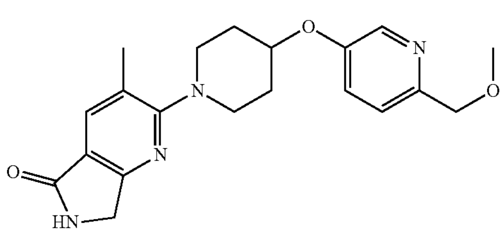 [SMILES: COCc1ccc(OC2CCN(c3nc4c(cc3C)C(=O)NC4)CC2)cn1] | 2-(4-((6-(methoxymethyl)pyridin-3-yl)oxy)piperidin-1-yl)-3-methyl-6,7-dihydro-5H-pyrrolo[3,4-b]pyridin-5-one | 369 |

TABLE 5-continued

| Example | Structure | Name | MS (M + 1) |
|---|---|---|---|
| 204 | 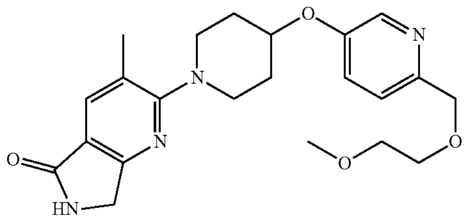 [SMILES: COCCOCc1ccc(OC2CCN(c3nc4c(cc3C)C(=O)NC4)CC2)cn1] | 2-(4-((6-((2-methoxyethoxy)methyl)pyridin-3-yl)oxy)piperidin-1-yl)-3-methyl-6,7-dihydro-5H-pyrrolo[3,4-b]pyridin-5-one | 413 |
| 205 | 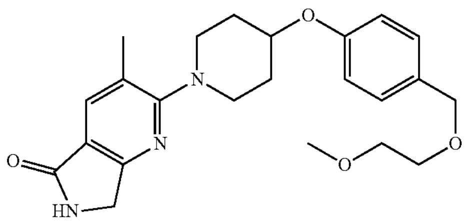 [SMILES: COCCOCc1ccc(OC2CCN(c3nc4c(cc3C)C(=O)NC4)CC2)cc1] | 2-(4-(4-((2-methoxyethoxy)methyl)phenoxy)piperidin-1-yl)-3-methyl-6,7-dihydro-5H-pyrrolo[3,4-b]pyridin-5-one | 412 |
| 205A | 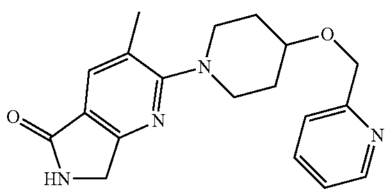 [SMILES: Cc1cc2c(nc1N1CCC(OCc3ccccn3)CC1)CNC2=O] | 3-methyl-2-(4-(pyridin-2-ylmethoxy)piperidin-1-yl)-6,7-dihydro-5H-pyrrolo[3,4-b]pyridin-5-one | 339 |
| 206 | 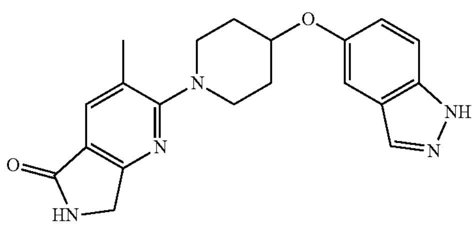 [SMILES: Cc1cc2c(nc1N1CCC(Oc3ccc4[nH]ncc4c3)CC1)CNC2=O] | 2-(4-((1H-pyrazolo[3,4-b]pyridin-5-yl)oxy)piperidin-1-pyrazolo[3,4-b]yl)-3-methyl-6,7-dihydro-5H-pyrrolo[3,4-b]pyridin-5-one | 365 |
| 206A | 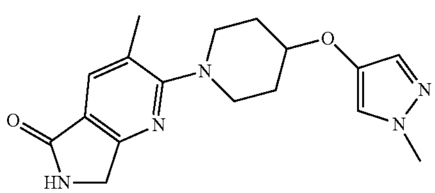 [SMILES: Cc1cc2c(nc1N1CCC(Oc3cnn(C)c3)CC1)CNC2=O] | 3-methyl-2-(4-((1-methyl-1H-pyrazol-4-yl)oxy)piperidin-1-yl)-6,7-dihydro-5H-pyrrolo[3,4-b]pyridin-5-one | 342 |
| 207 | 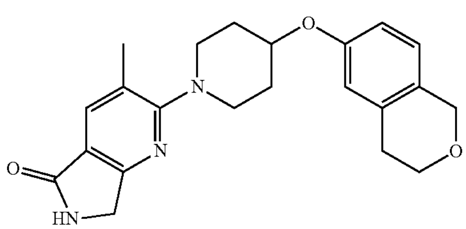 [SMILES: Cc1cc2c(nc1N1CCC(Oc3ccc4c(c3)CCOC4)CC1)CNC2=O] | 2-(4-(isochroman-6-yloxy)piperidin-1-yl)-3-methyl-6,7-dihydro-5H-pyrrolo[3,4-b]pyridin-5-one | 380 |
| 208 | 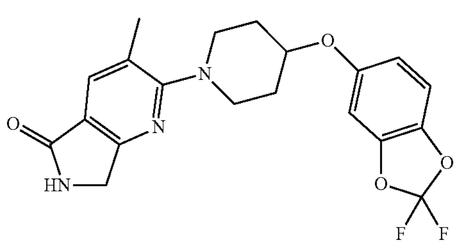 [SMILES: Cc1cc2c(nc1N1CCC(Oc3ccc4c(c3)OC(F)(F)O4)CC1)CNC2=O] | 2-(4-((2,2-difluorobenzo[d][1,3]dioxol-5-yl)oxy)piperidin-1-yl)-3-methyl-6,7-dihydro-5H-pyrrolo[3,4-b]pyridin-5-one | 404 |

TABLE 5-continued

| Example | Structure | Name | MS (M + 1) |
|---|---|---|---|
| 208A | 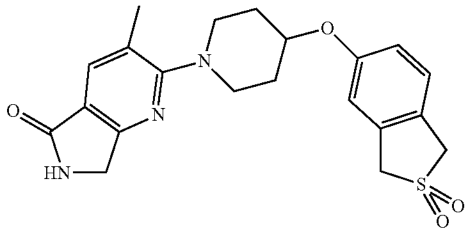 [SMILES: Cc1cc2c(nc1N1CCC(Oc3ccc4c(c3)CS(=O)(=O)C4)CC1)CNC2=O] | 2-(4-((2,2-dioxido-1,3-dihydrobenzo[c]thiophen-5-yl)oxy)piperidin-1-yl)-3-methyl-6,7-dihydro-5H-pyrrolo[3,4-b]pyridin-5-one | 414 |
| 209 | 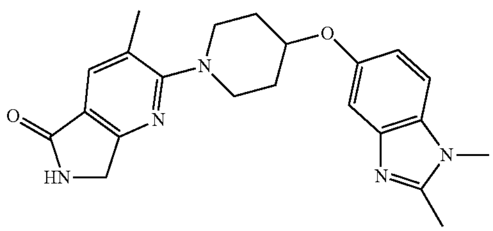 [SMILES: Cc1cc2c(nc1N1CCC(Oc3ccc4c(c3)nc(C)n4C)CC1)CNC2=O] | 2-(4-((1,2-dimethyl-1H-benzo[d]imidazol-5-yl)oxy)piperidin-1-yl)-3-methyl-6,7-dihydro-5H-pyrrolo[3,4-b]pyridin-5-one | 392 |
| 210 | 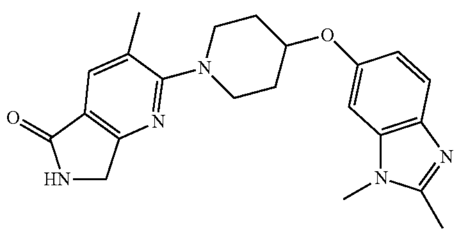 [SMILES: Cc1cc2c(nc1N1CCC(Oc3ccc4nc(C)n(C)c4c3)CC1)CNC2=O] | 2-(4-((1,2-dimethyl-1H-benzo[d]imidazol-6-yl)oxy)piperidin-1-yl)-3-methyl-6,7-dihydro-5H-pyrrolo[3,4-b]pyridin-5-one | 392 |
| 211 | 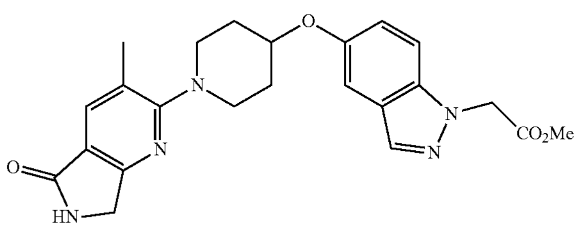 [SMILES: COC(=O)Cn1ncc2cc(OC3CCN(c4nc5c(cc4C)C(=O)NC5)CC3)ccc21] | methyl 2-(5-((1-(3-methyl-5-oxo-6,7-dihydro-5H-pyrrolo[3,4-b]pyridin-2-yl)piperidin-4-yl)oxy)-1H-indazol-1-yl)acetate | 436 |
| 212 | 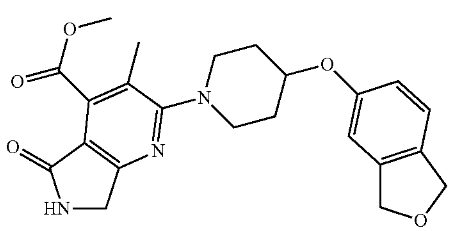 [SMILES: COC(=O)c1c(C)c(N2CCC(Oc3ccc4c(c3)COC4)CC2)nc2c1C(=O)NC2] | methyl 2-(4-((1,3-dihydro-2-benzofuran-5-yl)oxy)piperidin-1-yl)-3-methyl-5-oxo-6,7-dihydro-5H-pyrrolo[3,4-b]pyridine-4-carboxylate | 424 |
| 212A | 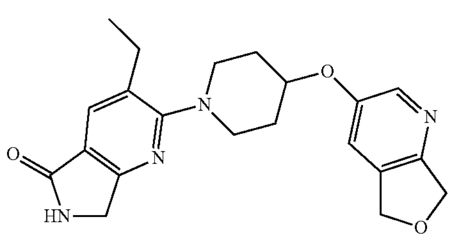 [SMILES: CCc1cc2c(nc1N1CCC(Oc3cnc4c(c3)COC4)CC1)CNC2=O] | 2-(4-((5,7-dihydrofuro[3,4-b]pyridin-3-yl)oxy)piperidin-1-yl)-3-ethyl-6,7-dihydro-5H-pyrrolo[3,4-b]pyridin-5-one | 381 |

TABLE 5-continued

| Example | Name | MS (M + 1) |
|---|---|---|
| 213 | 2-(4-((1,3-dihydro-2-benzofuran-5-yl)oxy)piperidin-1-yl)-3-ethyl-6,7-dihydro-5H-pyrrolo[3,4-b]pyridin-5-one | 380 |
| 213A | 2-((3R,4R)-4-((5,7-dihydrofuro[3,4-b]pyridin-3-yl)oxy)-3-fluoropiperidin-1-yl)-3-ethyl-6,7-dihydro-5H-pyrrolo[3,4-b]pyridin-5-one | 399 |
| 214 | 2-((3S,4R)-4-((1,3-dihydro-2-benzofuran-5-yl)oxy)-3-fluoropiperidin-1-yl)-3-ethyl-6,7-dihydro-5H-pyrrolo[3,4-b]pyridin-5-one | 398 |
| 215 | 3-ethyl-2-((3S,4R)-or (3R,4S)-3-fluoro-4-(pyridin-3-yloxy)piperidin-1-yl)-6,7-dihydro-5H-pyrrolo[3,4-b]pyridin-5-one | 357 |
| 216 | 3-ethyl-2-((3R,4S)- or (3S,4R)-3-fluoro-4-(pyridin-3-yloxy)piperidin-1-yl)-6,7-dihydro-5H-pyrrolo[3,4-b]pyridin-5-one | 357 |
| 216A | 2-(4-((2,3-dihydrofuro[3,2-b]pyridin-6-yl)oxy)piperidin-1-yl)-3-methyl-6,7-dihydro-5H-pyrrolo[3,4-b]pyridin-5-one | 367 |
| 217 | 2-((3R,4R)-4-((1,3-dihydro-2-benzofuran-5-yl)oxy)-3-fluoropiperidin-1-yl)-3-ethyl-6,7-dihydro-5H-pyrrolo[3,4-b]pyridin-5-one | 398 |

Example 218

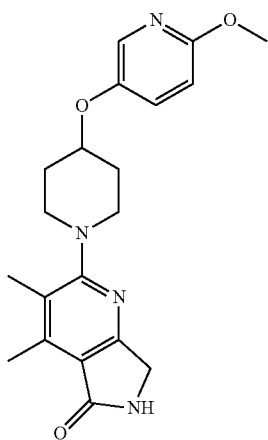

2-(4-((6-Methoxypyridin-3-yl)oxy)piperidin-1-yl)-3,4-dimethyl-6,7-dihydro-5H-pyrrolo[3,4-b]pyridin-5-one (Scheme 6)

Step 1: Methyl 2-cyano-6-(4-((6-methoxypyridin-3-yl)oxy)piperidin-1-yl)-4-methylnicotinate To a solution of methyl 6-chloro-2-cyano-4-methylnicotinate (210 mg, 0.997 mmol, intermediate I1) and DIPEA (0.52 mL, 2.99 mmol) in DMF (4 mL) was added 2-methoxy-5-(piperidin-4-yloxy)pyridine (270 mg, 1.296 mmol, intermediate F1). The reaction was stirred at 80° C. for 14 h. The mixture was diluted with water (10 mL) and extracted by EtOAc (10 mL×3). The combined organic phases were washed with water (15 mL×3), dried over anhydrous $Na_2SO_4$, filtered and concentrated to dryness. The residue was purified by flash silica gel chromatography (0-25% EtOAc/petroleum ether) to afford the title compound. MS: 383 (M+1).

Step 2: 2-(4-((6-Methoxypyridin-3-yl)oxy)piperidin-1-yl)-4-methyl-6,7-dihydro-5H-pyrrolo[3,4-b]pyridin-5-one To a solution of methyl 2-cyano-6-(4-((6-methoxypyridin-3-yl)oxy)piperidin-1-yl)-4-methylnicotinate (295 mg, 0.771 mmol) in EtOH (10 mL) was added molybdenum-promoted nickel (skeletal, 200 mg, 1.293 mmol). The mixture was degassed and placed under hydrogen (50 psi) at 40° C. for 4 h. The reaction was filtered and the filtrate was concentrated under reduced pressure. The residue was purified by reverse phase HPLC (ACN/water with 0.1% TFA modifier) to yield the title compound. MS: 355 (M+1)

Step 3: 3-Bromo-2-(4-((6-methoxypyridin-3-yl)oxy)piperidin-1-yl)-4-methyl-6,7-dihydro-5H-pyrrolo[3,4-b]pyridin-5-one To a solution of 2-(4-((6-methoxypyridin-3-yl)oxy)piperidin-1-yl)-4-methyl-6,7-dihydro-5H-pyrrolo[3,4-b]pyridin-5-one (140 mg, 0.395 mmol) in $CHCl_3$ (3 mL) was added NBS (77 mg, 0.435 mmol). The reaction was stirred at 80° C. for 14 h and was then concentrated to form a residue. The crude material was purified by reverse phase HPLC (ACN/water with 0.1% TFA modifier) to yield the title compound. MS: 433, 435 (M+1)

Step 4: 2-(4-((6-Methoxypyridin-3-yl)oxy)piperidin-1-yl)-3,4-dimethyl-6,7-dihydro-5H-pyrrolo[3,4-b]pyridin-5-one To a solution of 3-bromo-2-(4-((6-methoxypyridin-3-yl)oxy)piperidin-1-yl)-4-methyl-6,7-dihydro-5H-pyrrolo[3,4-b]pyridin-5-one (40 mg, 0.092 mmol), trimethylboroxine (23.18 mg, 0.185 mmol) and tribasic potassium phosphate (39.2 mg, 0.185 mmol) was added [1,1'-bis(di-tert-butylphosphino)ferrocene]dichloropalladium(II) (6.02 mg, 9.23 µmol). The mixture was degassed and backfilled with $N_2(g)$ (3×) and stirred at 70° C. for 14 h. The solvent was removed in vacuo and the crude residue was purified by reverse phase HPLC (ACN/water with 0.1% TFA modifier) to give the title compound. MS: 369 (M+1). $^1$H NMR (400 MHz, methanol-$d_4$) δ 7.88 (1H, d, J=2.4 Hz), 7.55 (1H, dd, J=3.2 Hz, 9.2 Hz), 6.88 (1H, d, J=9.2 Hz), 4.53-4.54 (1H, m), 4.29 (2H, s), 3.90 (3H, s), 3.50-3.52 (2H, m), 3.15-3.20 (2H, m), 2.64 (3H, s), 2.29 (3H, s), 2.12-2.16 (2H, m), 1.93-1.96 (2H, m).

The following examples in table 6 were prepared according to scheme 6 using the procedure and conditions outlined in the synthesis of Example 218 using prepared or known reactants in step 1 and appropriate boronic esters/acids or alkylzinc reagents in step 4. In some cases, the final step may be omitted.

TABLE 6

| Example | Structure | Name | MS (M + 1) |
|---|---|---|---|
| 219 | 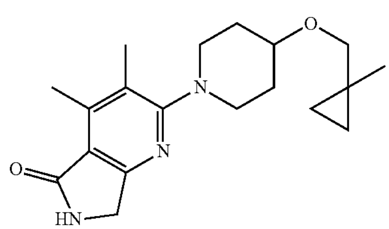 [SMILES: Cc1c(N2CCC(OCC3(C)CC3)CC2)nc2c(c1C)C(=O)NC2] | 3,4-dimethyl-2-(4-((1-methylcyclopropyl)methoxy)piperidin-1-yl)-6,7-dihydro-5H-pyrrolo[3,4-b]pyridin-5-one | 330 |
| 219A | 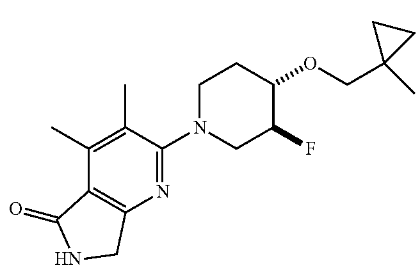 [SMILES: Cc1c(N2CC[C@H](OCC3(C)CC3)[C@@H](F)C2)nc2c(c1C)C(=O)NC2] | 2-((3S,4S)-3-fluoro-4-((1-methylcyclopropyl)methoxy)piperidin-1-yl)-3,4-dimethyl-6,7-dihydro-5H-pyrrolo[3,4-b]pyridin-5-one | 438 |

TABLE 6-continued

| Example | Name | MS (M + 1) |
|---|---|---|
| 220 | 2-(4-((6-(2-methoxyethoxy)pyridin-3-yl)oxy)piperidin-1-yl)-3,4-dimethyl-6,7-dihydro-5H-pyrrolo[3,4-b]pyridin-5-one | 413 |
| 220A | 3,4-dimethyl-2-(4-((5-methylpyridin-3-yl)oxy)piperidin-1-yl)-6,7-dihydro-5H-pyrrolo[3,4-b]pyridin-5-one | 353 |
| 221 | 3-cyclopropyl-2-(4-((6-methoxypyridin-3-yl)oxy)piperidin-1-yl)-6,7-dihydro-5H-pyrrolo[3,4-b]pyridin-5-one | 381 |
| 222 | 2-(4-((6-methoxypyridin-3-yl)oxy)piperidin-1-yl)-3-vinyl-6,7-dihydro-5H-pyrrolo[3,4-b]pyridin-5-one | 341 |
| 223 | 2-(4-((6-methoxypyridin-3-yl)oxy)piperidin-1-yl)-5-oxo-6,7-dihydro-5H-pyrrolo[3,4-b]pyridine-3-carbonitrile | 366 |
| 224 | 4-methyl-2-(4-((1-methylcyclopropyl)methoxy)piperidin-1-yl)-6,7-dihydro-5H-pyrrolo[3,4-b]pyridin-5-one | 316 |
| 225 | 2-((3S,4R)-4-((1,3-dihydro-2-benzofuran-5-yl)oxy)-3-fluoropiperidin-1-yl)-3,4-dimethyl-6,7-dihydro-5H-pyrrolo[3,4-b]pyridin-5-one | 398 |

TABLE 6-continued

| Example | Structure | Name | MS (M + 1) |
|---|---|---|---|
| 226 | 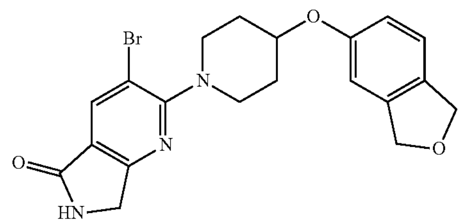 [SMILES: O=C1NCc2nc(N3CCC(Oc4ccc5c(c4)COC5)CC3)c(Br)cc21] | 3-bromo-2-(4-((1,3-dihydro-2-benzofuran-5-yl)oxy)piperidin-1-yl)-6,7-dihydro-5H-pyrrolo[3,4-b]pyridin-5-one | 430, 432 |
| 227 | 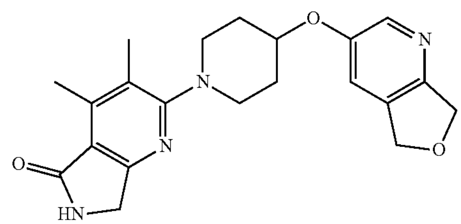 [SMILES: Cc1c(N2CCC(Oc3cnc4c(c3)COC4)CC2)nc2c(c1C)C(=O)NC2] | 2-(4-((5,7-dihydrofuro[3,4-b]pyridin-3-yl)oxy)piperidin-1-yl)-3,4-dimethyl-6,7-dihydro-5H-pyrrolo[3,4-b]pyridin-5-one | 381 |

Example 228

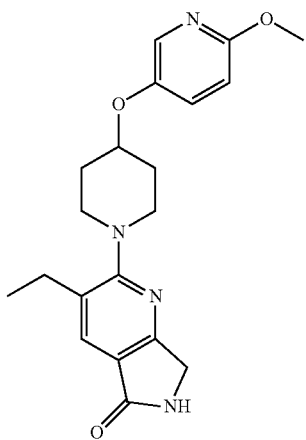 [SMILES: CCc1cc2c(nc1N1CCC(Oc3ccc(OC)nc3)CC1)CNC2=O]

3-Ethyl-2-(4-((6-methoxypyridin-3-yl)oxy)piperidin-1-yl)-6,7-dihydro-5H-pyrrolo[3,4-b]pyridin-5-one (Scheme 7)

To a solution of 2-(4-((6-methoxypyridin-3-yl)oxy)piperidin-1-yl)-3-vinyl-6,7-dihydro-5H-pyrrolo[3,4-b]pyridin-5-one (53 mg, 0.145 mmol, Example 222 in MeOH (10 mL) was added Pd/C (10%, 154 mg, 0.145 mmol). The reaction was stirred under an atmosphere of hydrogen (15 psi) at 15° C. for 1 h. The mixture was filtered and the filtrate was concentrated in vacuo. The residue was purified by reverse phase HPLC (ACN/water with 0.1% TFA modifier) to give the title compound. MS: 369 (M+1). $^1$H NMR (400 MHz, methanol-$d_4$): δ 7.19 (1H, s), 7.86 (1H, d, J=2.4 Hz), 7.52 (1H, dd, J=2.8 Hz, 9.2 Hz), 6.85 (1H, d, J=8.8 Hz), 4.52-4.53 (1H, m), 4.35 (2H, s), 3.89 (3H, s), 3.51-3.55 (2H, m), 3.15-3.19 (2H, m), 2.76 (2H, q, J=7.2 Hz), 2.13-2.16 (2H, m), 1.91-1.95 (2H, m), 1.31 (3H, t, J=7.2 Hz).

The following example in table 7 were prepared according to scheme 7 using the procedure and conditions outlined in the synthesis of Example 228.

TABLE 7

| Example | Structure | Name | MS (M + 1) |
|---|---|---|---|
| 229 | 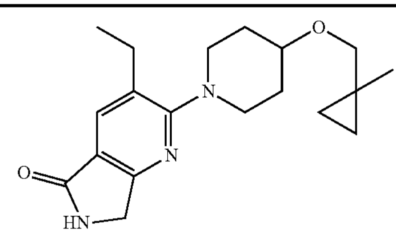 | 3-ethyl-2-(4-((1-methylcyclopropyl)methoxy)piperidin-1-yl)-6,7-dihydro-5H-pyrrolo[3,4-b]pyridin-5-one | 330 |
| 229A | 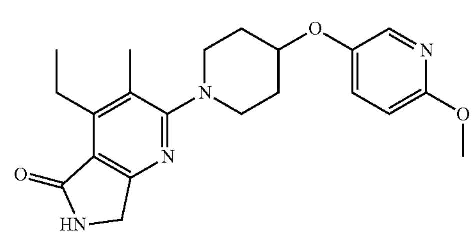 [SMILES: CCc1c(C)c(N2CCC(Oc3ccc(OC)nc3)CC2)nc2c1C(=O)NC2] | 4-ethyl-2-(4-((6-methoxypyridin-3-yl)oxy)piperidin-1-yl)-3-methyl-6,7-dihydro-5H-pyrrolo[3,4-b]pyridin-5-one | 383 |

Example 230

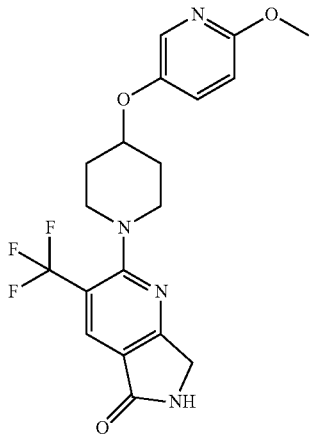 [SMILES: COc1ccc(OC2CCN(c3nc4c(cc3C(F)(F)F)C(=O)NC4)CC2)cn1]

2-(4-((6-Methoxypyridin-3-yl)oxy)piperidin-1-yl)-3-(trifluoromethyl)-6,7-dihydro-5H-pyrrolo[3,4-b]pyridin-5-one (Scheme 8)

To a solution of 3-bromo-2-(4-((6-methoxypyridin-3-yl)oxy)piperidin-1-yl)-6,7-dihydro-5H-pyrrolo[3,4-b]pyridin-5-one (20 mg, 0.048 mmol) in DMF (1 mL) was added methyl 2,2-difluoro-2-(fluorosulfonyl)acetate (12.83 mg, 0.067 mmol) and copper(I) iodide (4.54 mg, 0.024 mmol) at 15° C. The resulting mixture was stirred at 90° C. under microwave irradiation for 30 min. After filtration and concentration, the residue was purified by reverse phase HPLC (ACN/water with 0.1% TFA modifier) to afford the title compound. MS: 409 (M+1). $^1$H NMR (400 MHz, methanol-$d_4$): δ 8.26 (1H, s), 7.86 (1H, d, J=2.8 Hz), 7.49 (1H, dd, J=9.2, 2.8 Hz), 6.82 (1H, d, J=9.2 Hz), 4.53-4.55 (1H, m), 4.42 (2H, s), 3.88 (3H, s), 3.75-3.80 (2H, m), 3.40-3.45 (2H, m), 2.08-2.14 (2H, m), 1.86-1.90 (2H, m).

Example 231

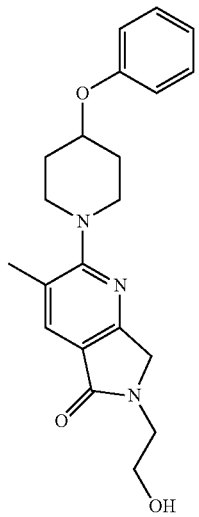 [SMILES: Cc1cc2c(nc1N1CCC(Oc3ccccc3)CC1)CN(CCO)C2=O]

6-(2-Hydroxyethyl)-3-methyl-2-(4-phenoxypiperidin-1-yl)-6,7-dihydro-5H-pyrrolo[3,4-b]pyridin-5-one (Scheme 9)

Step 1: 6-(2-((tert-Butyldimethylsilyl)oxy)ethyl)-3-methyl-2-(4-phenoxypiperidin-1-yl)-6,7-dihydro-5H-pyrrolo[3,4-b]pyridin-5-one To a solution of 2-(4-((6-methoxypyridin-3-yl)oxy)piperidin-1-yl)-3-methyl-6,7-dihydro-5H-pyrrolo[3,4-b]pyridin-5-one (120 mg, 0.339 mmol, Example 5) in DMSO (5 mL) was added lithium bis(trimethylsilyl)amide (0.339 mL, 0.339 mmol) at RT. The reaction was stirred for 20 min before (2-bromoethoxy)(tert-butyl)dimethylsilane (81 mg, 0.339 mmol) was added. The reaction was stirred for 4 h and the mixture was directly purified by reverse phase HPLC (ACN/water with 0.1% TFA modifier) to yield the title compound. MS: 482 (M+1).

Step 2: 6-(2-Hydroxyethyl)-3-methyl-2-(4-phenoxypiperidin-1-yl)-6,7-dihydro-5H-pyrrolo[3,4-b]pyridin-5-one A solution of 6-(2-((tert-butyldimethylsilyl)oxy)ethyl)-3-methyl-2-(4-phenoxypiperidin-1-yl)-6,7-dihydro-5H-pyrrolo[3,4-b]pyridin-5-one (141 mg, 0.293 mmol) in THF (8 mL) was treated with TBAF (221 mg, 0.846 mmol) at RT for 8 h. The volatiles were removed under reduced pressure and the residue was purified by silica gel column chromatography (15% MeOH in DCM) to yield the title compound. MS: 368 (M+1). $^1$H NMR (500 MHz, CDCl$_3$): δ 7.75 (s, 1H), 7.30 (t, J=9.0 Hz, 2H), 6.96-6.94 (m, 3H), 4.54 (m, 1H), 4.41 (s, 2H), 3.91 (q, J=5.0 Hz, 2H), 3.76 (t, J=5.0 Hz, 2H), 3.55 (m, 2H), 3.17 (m, 2H), 2.35 (s, 3H), 2.12 (m, 2H), 1.97 (m, 2H).

Example 232

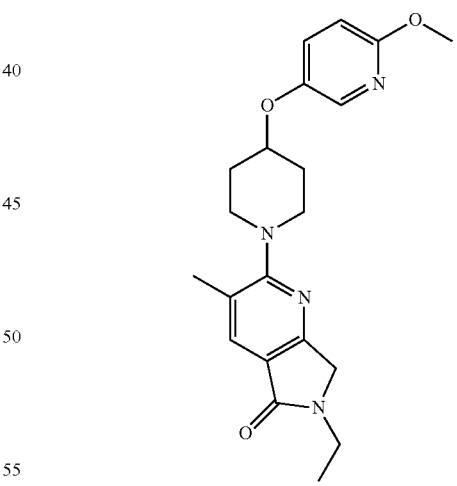

6-Ethyl-2-(4-((6-methoxypyridin-3-yl)oxy)piperidin-1-yl)-3-methyl-6,7-dihydro-5H-pyrrolo[3,4-b]pyridin-5-one (Scheme 9)

To a solution of 2-(4-((6-methoxypyridin-3-yl)oxy)piperidin-1-yl)-3-methyl-6,7-dihydro-5H-pyrrolo[3,4-b]pyridin-5-one (100 mg, 0.282 mmol, Example 1) in DMSO (5 mL) was added lithium bis(trimethylsilyl)amide (0.423 mL, 0.423 mmol, 1 M in THF). The reaction was stirred at RT for 20 min and iodoethane (0.068 mL, 0.846 mmol) was added. The mixture was diluted with water (30 mL), extracted with EtOAc (50 mL×3), and the combined organic layers were washed with water (30 mL) and brine (30 mL), dried over anhydrous sodium sulfate, filtered and concentrated. The resultant residue was purified by reverse phase HPLC (ACN/water with 0.1% TFA modifier) to provide the title compound. MS: 383 (M+1). $^1$H NMR (400 MHz, methanol-$d_4$): δ 7.81 (1H, d, J=2.8 Hz), 7.74 (1H, s), 7.42 (1H, dd, J=8.8, 3.2 Hz), 6.74 (1H, d, J=8.8 Hz), 4.47-4.52 (1H, m), 4.37 (s, 2H), 3.83 (s, 3H), 3.50-3.65 (4H, m), 3.10-3.20 (2H, m), 2.36 (3H, s), 2.09-2.15 (2H, m), 1.80-1.91 (2H, m), 1.24 (3H, t, J=7.2 Hz).

Example 233

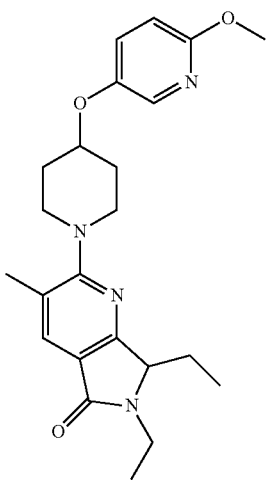

6,7-Diethyl-2-(4-((6-methoxypyridin-3-yl)oxy)piperidin-1-yl)-3-methyl-6,7-dihydro-5H-pyrrolo[3,4-b]pyridin-5-one (Scheme 9)

From the same reaction as described in the procedure for Example 232 (vide supra) was obtained the title compound. MS: 411 (M+1). $^1$H NMR (400 MHz, methanol-$d_4$): δ 7.81 (1H, d, J=2.4 Hz), 7.74 (1H, s), 7.41 (1H, dd, J=8.8, 2.8 Hz), 6.74 (1H, d, J=9.2 Hz), 4.40-4.55 (2H, m), 3.83-3.89 (1H, m), 3.57 (s, 3H), 3.45-3.55 (2H, m), 3.10-3.23 (3H, m), 2.13 (3H, s), 2.10-2.42 (3H, m), 1.78-1.99 (3H, m) 1.22 (3H, t, J=6.8 Hz), 0.55 (3H, t, J=6.4 Hz).

Examples 234A and 234B

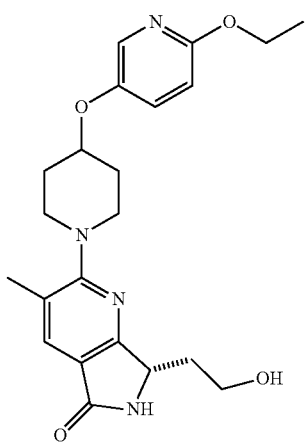

(S)-2-(4-((6-Ethoxypyridin-3-yl)ox)piperidin-1-yl)-7-(2-hydroxyethyl)-3-methyl-6,7-dihydro-5H-pyrrolo[3,4-b]pyridin-5-one and (R)-2-(4-((6-ethoxypyridin-3-yl)oxy)piperidin-1-yl)-7-(2-hydroxyethyl)-3-methyl-6,7-dihydro-5H-pyrrolo[3,4-b]pyridin-5-one (Scheme 9)

Step 1: 7-(2-((tert-Butyldimethylsilyl)oxy)ethyl)-2-(4-((6-ethoxypyridin-3-yl)oxy)piperidin-1-yl)-3-methyl-6,7-dihydro-5H-pyrrolo[3,4-b]pyridin-5-one 2-(4-((6-Ethoxypyridin-3-yl)oxy)piperidin-1-yl)-3-methyl-6,7-dihydro-5H-pyrrolo[3,4-b]pyridin-5-one (0.87 g, 2.361 mmol) was dissolved in degassed DMSO (15.7 mL). LHMDS (1.5 M in THF, 2.36 mL, 3.54 mmol) was added dropwise to the solution at 0° C. under a nitrogen atmosphere. The reaction was allowed to warm to RT and was sonicated before the addition of (2-bromoethoxy)(tert-butyl)dimethylsilane (0.760 mL, 3.54 mmol). After stirring for 90 min, the reaction was quenched with saturated, aqueous ammonium chloride and was diluted with dichloromethane. The organic was separated, dried over anhydrous sodium sulfate, filtered, and concentrated under reduced pressure. The residue was purified by column chromatography on silica gel (15-20% 3:1 EtOAc:EtOH in hexanes) to afford the title compound. MS: 527 (M+1).

Step 2: 2-(4-((6-Ethoxypyridin-3-yl)oxy)piperidin-1-yl)-7-(2-hydroxyethyl)-3-methyl-6,7-dihydro-5H-pyrrolo[3,4-b]pyridin-5-one To a solution of 7-(2-((tert-butyldimethylsilyl)oxy)ethyl)-2-(4-((6-ethoxypyridin-3-yl)oxy)piperidin-1-yl)-3-methyl-6,7-dihydro-5H-pyrrolo[3,4-b]pyridin-5-one (358 mg, 0.680 mmol) in THF (1 mL) was added TBAF (1.36 mL, 1.36 mmol). The reaction was stirred at RT for 15 h and was then concentrated to dryness. The residue was purified by silica gel column chromatography (10-60% 3:1 EtOAc:EtOH in hexanes) to afford the title compound. The mixture of the two stereoisomers was purified by chiral SFC (OJ-H column, 30% methanol/$CO_2$) to afford isomer 234A (faster eluting): MS: 413 (M+1). $^1$H NMR (500 MHz, $CDCl_3$) δ 7.84 (1H, d, J=15.31 Hz), 7.27 (1H, s), 6.71 (1H, d, J=8.67 Hz), 6.19 (1H, s), 4.56 (1H, s), 4.39 (1H, s), 4.33 (2H, d, J=7.78 Hz), 4.00 (2H, d, J=38.9 Hz), 3.56 (2H, br s), 3.17 (2H, d, J=11.5 Hz), 2.37 (3H, s), 1.95-2.12 (6H, m), 1.40 (3H, t, J=7.11 Hz). Isomer 234B (slower eluting): MS: 413 (M+1). $^1$H NMR (500 MHz, $CDCl_3$): δ 7.82-7.86 (1H, m), 7.24-7.26 (1H, m), 6.97 (1H, br s), 6.69 (1H, d, J=8.92 Hz), 4.56 (1H, t, J=6.86 Hz), 4.37-4.39 (1H, m), 4.30 (2H, q, J=7.07 Hz), 4.00-4.05 (2H, m), 3.92-3.96 (2H, m), 3.52-3.55 (2H, br m), 3.12-3.18 (2H, m), 2.36 (3H, s), 2.12 (2H, br s), 2.05 (2H, d, J=6.13 Hz), 1.95 (2H, br s), 1.39 (3H, t, J=7.05 Hz).

The following examples in table 9 were prepared according to scheme 9 using the procedure and conditions outlined in the synthesis of Examples 231, 232, 233, 234A and 234B. Commerically available alkyl halides are used in step 1. The final step is omitted in cases where there is no silyl protecting group present in the compound.

TABLE 9

| Example | Structure | Name | MS (M + 1) |
|---|---|---|---|
| 235 | 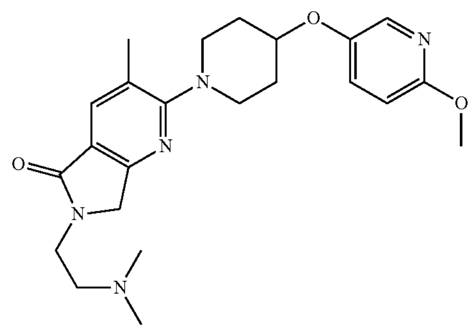 [SMILES: COc1ccc(OC2CCN(c3nc4c(cc3C)C(=O)N(CCN(C)C)C4)CC2)cn1] | 6-(2-(dimethylamino)ethyl)-2-(4-((6-methoxypyridin-3-yl)oxy)piperidin-1-yl)-3-methyl-6,7-dihydro-5H-pyrrolo[3,4-b]pyridin-5-one | 426 |
| 236 | 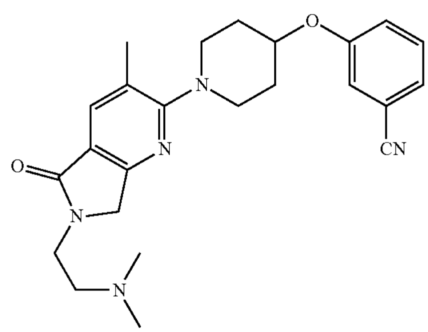 [SMILES: Cc1cc2c(nc1N1CCC(Oc3cccc(C#N)c3)CC1)CN(CCN(C)C)C2=O] | 3-((1-(6-(2-(dimethylamino)ethyl)-3-methyl-5-oxo-6,7-dihydro-5H-pyrrolo[3,4-b]pyridin-2-yl)piperidin-4-yl)oxy)benzonitrile | 420 |
| 236A | 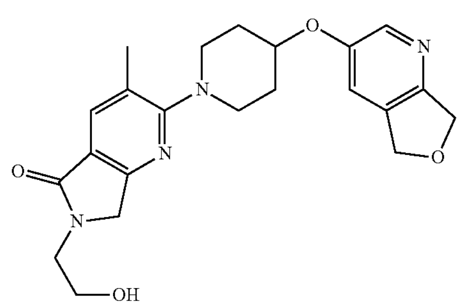 [SMILES: Cc1cc2c(nc1N1CCC(Oc3cnc4c(c3)COC4)CC1)CN(CCO)C2=O] | 2-(4-((5,7-dihydrofuro[3,4-b]pyridin-3-yl)oxy)piperidin-1-yl)-6-(2-hydroxyethyl)-3-methyl-6,7-dihydro-5H-pyrrolo[3,4-b]pyridin-5-one | 411 |
| 237 | 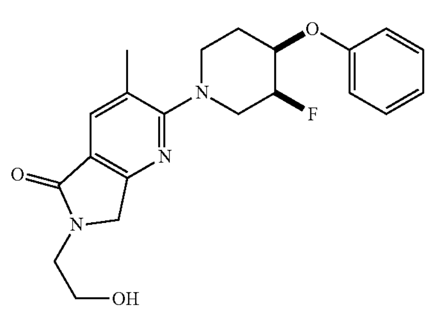 | 2-((3S,4R)-3-fluoro-4-phenoxypiperidin-1-yl)-6-(2-hydroxyethyl)-3-methyl-6,7-dihydro-5H-pyrrolo[3,4-b]pyridin-5-one | 386 |

TABLE 9-continued

| Example | Name | MS (M + 1) |
|---|---|---|
| 238 | 6-(2-hydroxyethyl)-2-(4-((6-methoxypyridin-3-yl)oxy)piperidin-1-yl)-3-methyl-6,7-dihydro-5H-pyrrolo[3,4-b]pyridin-5-one | 399 |
| 238A[1] | (R) or (S)-2-(4-((1,3-dihydro-2-benzofuran-5-yl)oxy)piperidin-1-yl)-6-(2-hydroxypropyl)-3-methyl-6,7-dihydro-5H-pyrrolo[3,4-b]pyridin-5-one | 413 |
| 239 | 3-((1-(6-(2-hydroxyethyl)-3-methyl-5-oxo-6,7-dihydro-5H-pyrrolo[3,4-b]pyridin-2-yl)piperidin-4-yl)oxy)benzonitrile | 393 |
| 239A | 6-(2-hydroxyethyl)-3-methyl-2-(4-((1-methyl-1H-indazol-5-yl)oxy)piperidin-1-yl)-6,7-dihydro-5H-pyrrolo[3,4-b]pyridin-5-one | 422 |
| 240 | 3,6-dimethyl-2-(4-phenoxypiperidin-1-yl)-6,7-dihydro-5H-pyrrolo[3,4-b]pyridin-5-one | 338 |

TABLE 9-continued

| Example | Structure | Name | MS (M + 1) |
|---|---|---|---|
| 240A | 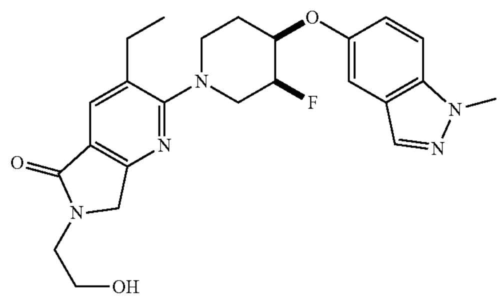 | 3-ethyl-2-((3S,4R)-3-fluoro-4-((1-methyl-1H-indazol-5-yl)oxy)piperidin-1-yl)-6-(2-hydroxyethyl)-6,7-dihydro-5H-pyrrolo[3,4-b]pyridin-5-one | 454 |
| 241 | 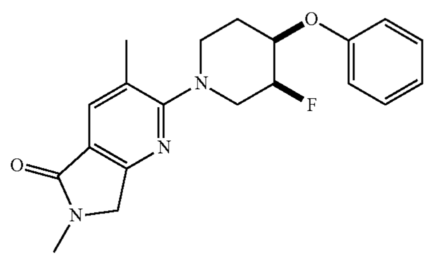 | 2-((3S,4R)-3-fluoro-4-phenoxypiperidin-1-yl)-3,6-dimethyl-6,7-dihydro-5H-pyrrolo[3,4-b]pyridin-5-one | 356 |
| 241A | 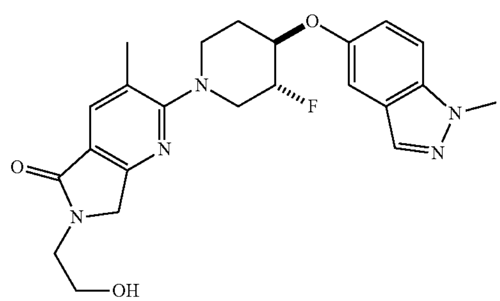 | 2-((3R,4R)-3-fluoro-4-((1-methyl-1H-indazol-5-yl)oxy)piperidin-1-yl)-6-(2-hydroxyethyl)-3-methyl-6,7-dihydro-5H-pyrrolo[3,4-b]pyridin-5-one | 440 |
| 242 | 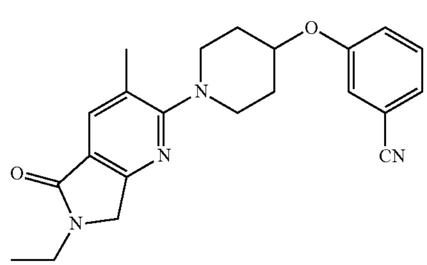 [SMILES: CCN1Cc2nc(N3CCC(Oc4cccc(C#N)c4)CC3)c(C)cc2C1=O] | 3-((1-(6-ethyl-3-methyl-5-oxo-6,7-dihydro-5H-pyrrolo[3,4-b]pyridin-2-yl)piperidin-4-yl)oxy)benzonitrile | 377 |
| 243 | 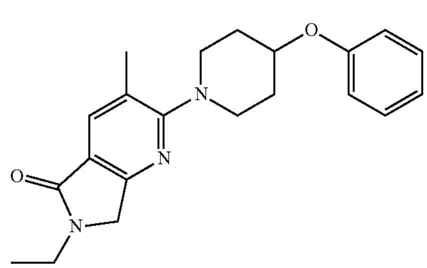 [SMILES: CCN1Cc2nc(N3CCC(Oc4ccccc4)CC3)c(C)cc2C1=O] | 6-ethyl-3-methyl-2-(4-phenoxypiperidin-1-yl)-6,7-dihydro-5H-pyrrolo[3,4-b]pyridin-5-one | 352 |

TABLE 9-continued

| Example | Structure | Name | MS (M + 1) |
|---|---|---|---|
| 244 | 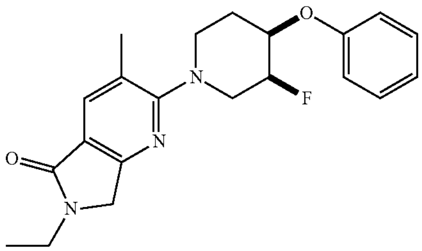 | 6-ethyl-2-((3S,4R)-3-fluoro-4-phenoxypiperidin-1-yl)-3-methyl-6,7-dihydro-5H-pyrrolo[3,4-b]pyridin-5-one | 370 |
| 244A | 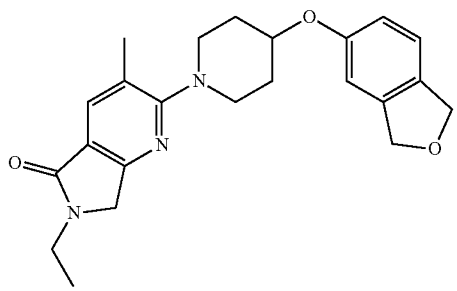 [SMILES: CCN1Cc2nc(N3CCC(Oc4ccc5c(c4)COC5)CC3)c(C)cc2C1=O] | 2-(4-((1,3-dihydro-2-benzofuran-5-yl)oxy)piperidin-1-yl)-6-ethyl-3-methyl-6,7-dihydro-5H-pyrrolo[3,4-b]pyridin-5-one | 394 |
| 245 | 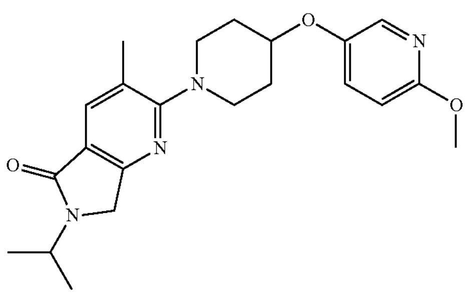 [SMILES: COc1ccc(OC2CCN(c3nc4c(cc3C)C(=O)N(C(C)C)C4)CC2)cn1] | 6-isopropyl-2-(4-((6-methoxypyridin-3-yl)oxy)piperidin-1-yl)-3-methyl-6,7-dihydro-5H-pyrrolo[3,4-b]pyridin-5-one | 397 |
| 246 | 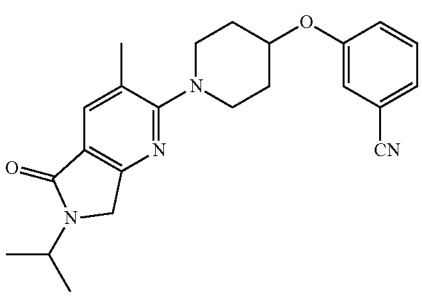 [SMILES: Cc1cc2c(nc1N1CCC(Oc3cccc(C#N)c3)CC1)CN(C(C)C)C2=O] | 3-((1-(6-isopropyl-3-methyl-5-oxo-6,7-dihydro-5H-pyrrolo[3,4-b]pyridin-2-yl)piperidin-4-yl)oxy)benzonitrile | 391 |
| 247 | 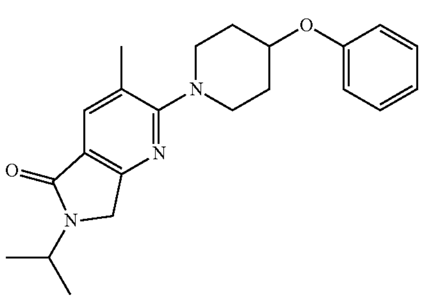 [SMILES: Cc1cc2c(nc1N1CCC(Oc3ccccc3)CC1)CN(C(C)C)C2=O] | 6-isopropyl-3-methyl-2-(4-phenoxypiperidin-1-yl)-6,7-dihydro-5H-pyrrolo[3,4-b]pyridin-5-one | 366 |

TABLE 9-continued

| Example | Structure | Name | MS (M + 1) |
|---|---|---|---|
| 248 | 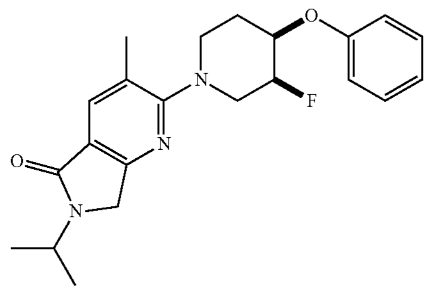 | 2-((3S,4R)-3-fluoro-4-phenoxypiperidin-1-yl)-6-isopropyl-3-methyl-6,7-dihydro-5H-pyrrolo[3,4-b]pyridin-5-one | 384 |
| 249 | 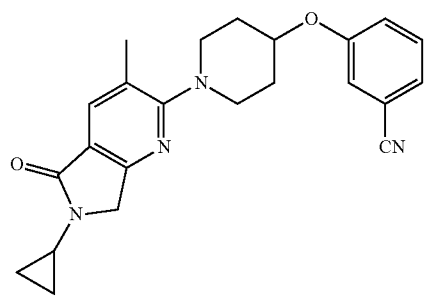 [SMILES: Cc1cc2c(nc1N1CCC(Oc3cccc(C#N)c3)CC1)CN(C1CC1)C2=O] | 3-((1-(6-cyclopropyl-3-methyl-5-oxo-6,7-dihydro-5H-pyrrolo[3,4-b]pyridin-2-yl)piperidin-4-yl)oxy)benzonitrile | 389 |
| 250 | 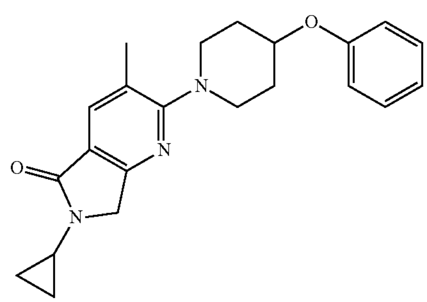 [SMILES: Cc1cc2c(nc1N1CCC(Oc3ccccc3)CC1)CN(C1CC1)C2=O] | 6-cyclopropyl-3-methyl-2-(4-phenoxypiperidin-1-yl)-6,7-dihydro-5H-pyrrolo[3,4-b]pyridin-5-one | 364 |
| 250A | 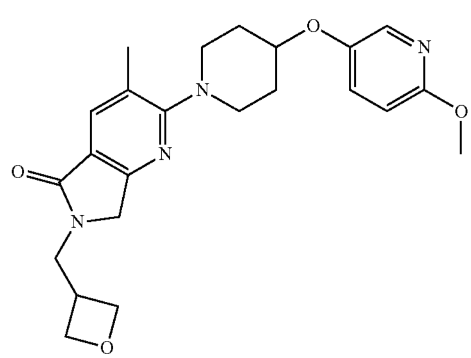 [SMILES: COc1ccc(OC2CCN(c3nc4c(cc3C)C(=O)N(CC3COC3)C4)CC2)cn1] | 2-(4-((6-methoxypyridin-3-yl)oxy)piperidin-1-yl)-3-methyl-6-(oxetan-3-ylmethyl)-6,7-dihydro-5H-pyrrolo[3,4-b]pyridin-5-one | 425 |
| 251 | 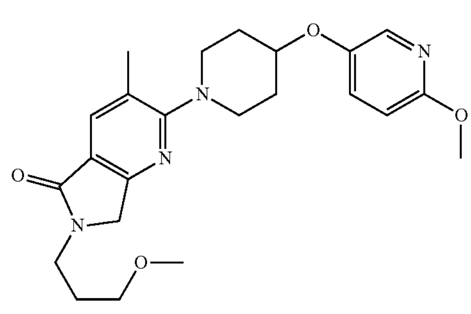 [SMILES: COCCCN1Cc2nc(N3CCC(Oc4ccc(OC)nc4)CC3)c(C)cc2C1=O] | 6-(3-methoxypropyl)-2-(4-((6-methoxypyridin-3-yl)oxy)piperidin-1-yl)-3-methyl-6,7-dihydro-5H-pyrrolo[3,4-b]pyridin-5-one | 427 |

TABLE 9-continued

| Example | Structure | Name | MS (M + 1) |
|---|---|---|---|
| 252 | 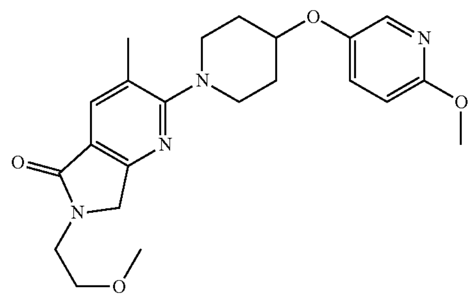 [SMILES: COCCN1Cc2nc(N3CCC(Oc4ccc(OC)nc4)CC3)c(C)cc2C1=O] | 6-(2-methoxyethyl)-2-(4-((6-methoxypyridin-3-yl)oxy)piperidin-1-yl)-3-methyl-6,7-dihydro-5H-pyrrolo[3,4-b]pyridin-5-one | 382 |
| 253 | 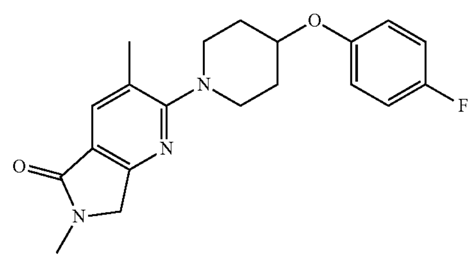 [SMILES: Cc1cc2c(nc1N1CCC(Oc3ccc(F)cc3)CC1)CN(C)C2=O] | 2-(4-(4-fluorophenoxy)piperidin-1-yl)-3,6-dimethyl-6,7-dihydro-5H-pyrrolo[3,4-b]pyridin-5-one | 356 |
| 254 | 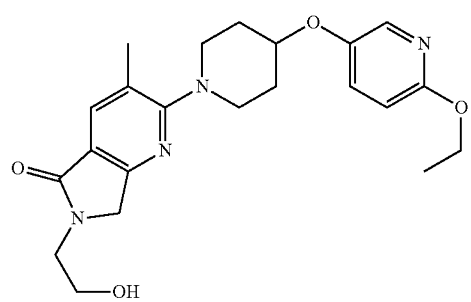 [SMILES: CCOc1ccc(OC2CCN(c3nc4c(cc3C)C(=O)N(CCO)C4)CC2)cn1] | 2-(4-((6-ethoxy-pyridin-3-yl)oxy)piperidin-1-yl)-6-(2-hydroxyethyl)-3-methyl-6,7-dihydro-5H-pyrrolo[3,4-b]pyridin-5-one | 413 |
| 255 | 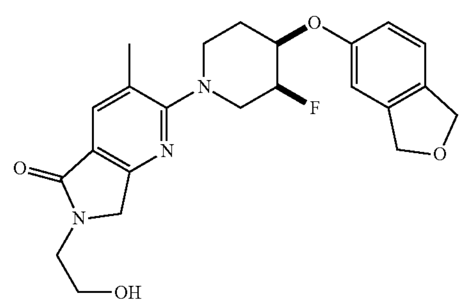 | 2-((3S,4R)-4-((1,3-dihydro-2-benzofuran-5-yl)oxy)-3-fluoropiperidin-1-yl)-6-(2-hydroxyethyl)-3-methyl-6,7-dihydro-5H-pyrrolo[3,4-b]pyridin-5-one | 428 |
| 255A | 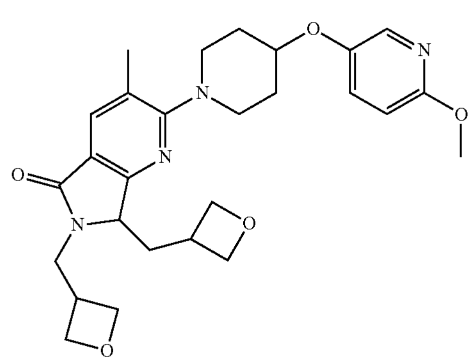 [SMILES: COc1ccc(OC2CCN(c3nc4c(cc3C)C(=O)N(CC3COC3)C4CC3COC3)CC2)cn1] | 2-(4-((6-methoxypyridin-3-yl)oxy)piperidin-1-yl)-3-methyl-6,7-bis(oxetan-3-yl-methyl)-6,7-dihydro-5H-pyrrolo[3,4-b]pyridin-5-one | 495 |

TABLE 9-continued

| Example | Structure | Name | MS (M + 1) |
|---|---|---|---|
| 256 | 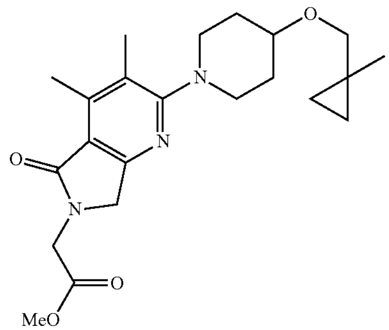 [SMILES: COC(=O)CN1Cc2nc(N3CCC(OCC4(C)CC4)CC3)c(C)c(C)c2C1=O] | methyl 2-(3,4-dimethyl-2-(4-((1-methylcyclopropyl)methoxy)piperidin-1-yl)-5-oxo-5,7-dihydro-6H-pyrrolo[3,4-b]pyridin-6-yl)acetate | 402 |
| 257 | 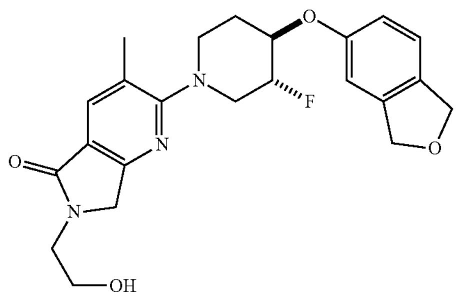 | 2-((3R,4R)-4-((1,3-dihydro-2-benzofuran-5-yl)oxy)-3-fluoropiperidin-1-yl)-6-(2-hydroxyethyl)-3-methyl-6,7-dihydro-5H-pyrrolo[3,4-b]pyridin-5-one | 428 |
| 258 | 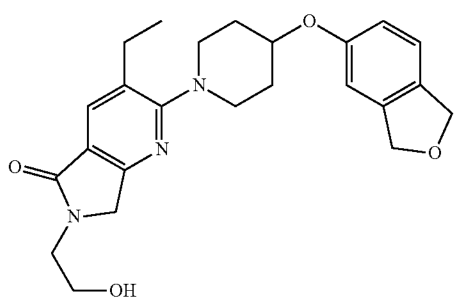 [SMILES: CCc1cc2c(nc1N1CCC(Oc3ccc4c(c3)COC4)CC1)CN(CCO)C2=O] | 2-(4-((1,3-dihydro-2-benzofuran-5-yl)oxy)piperidin-1-yl)-3-ethyl-6-(2-hydroxyethyl)-6,7-dihydro-5H-pyrrolo[3,4-b]pyridin-5-one | 424 |
| 259 | 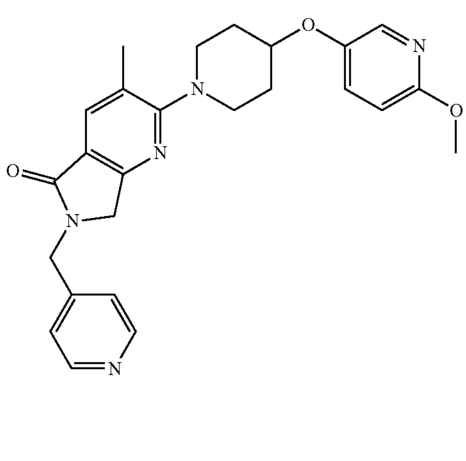 [SMILES: COc1ccc(OC2CCN(c3nc4c(cc3C)C(=O)N(Cc3ccncc3)C4)CC2)cn1] | 2-(4-((6-methoxypyridin-3-yl)oxy)piperidin-1-yl)-3-methyl-6-(pyridin-4-ylmethyl)-6,7-dihydro-5H-pyrrolo[3,4-b]pyridin-5-one | 446 |

TABLE 9-continued

| Example | Structure | Name | MS (M + 1) |
|---|---|---|---|
| 259A | 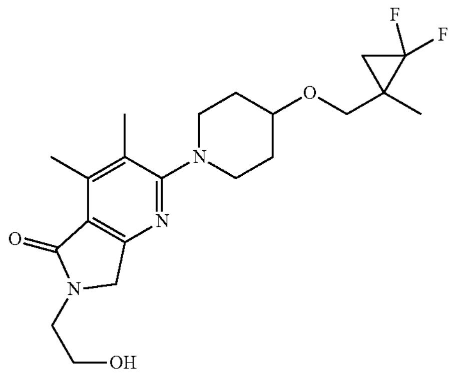 [SMILES: Cc1c(N2CCC(OCC3(C)CC3(F)F)CC2)nc2c(c1C)C(=O)N(CCO)C2] | 2-(4-((2,2-difluoro-1-methylcyclopropyl)methoxy)piperidin-1-yl)-6-(2-hydroxyethyl)-3,4-dimethyl-6,7-dihydro-5H-pyrrolo[3,4-b]pyridin-5-one | 410 |
| 260 | 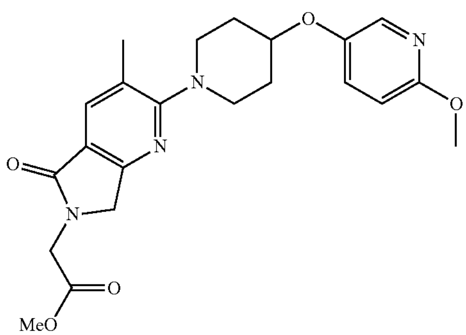 [SMILES: COC(=O)CN1Cc2nc(N3CCC(Oc4ccc(OC)nc4)CC3)c(C)cc2C1=O] | methyl 2-(2-(4-((6-methoxypyridin-3-yl)oxy)piperidin-1-yl)-3-methyl-5-oxo-5,7-dihydro-6H-pyrrolo[3,4-b]pyridin-6-yl)acetate | 427 |
| 260A | 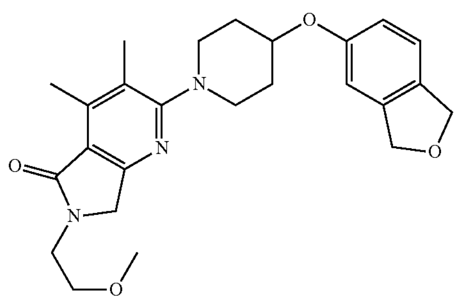 [SMILES: COCCN1Cc2nc(N3CCC(Oc4ccc5c(c4)COC5)CC3)c(C)c(C)c2C1=O] | 2-(4-((1,3-dihydro-2-benzofuran-5-yl)oxy)piperidin-1-yl)-6-(2-methoxyethyl)-3,4-dimethyl-6,7-dihydro-5H-pyrrolo[3,4-b]pyridin-5-one | 438 |
| 261 | 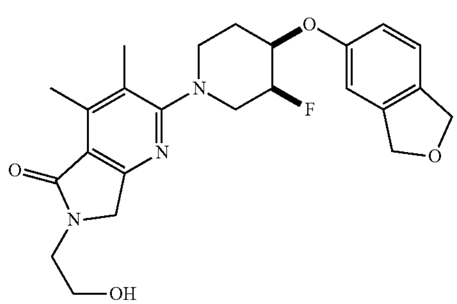 | 2-((3S,4R)-4-((1,3-dihydro-2-benzofuran-5-yl)oxy)-3-fluoropiperidin-1-yl)-6-(2-hydroxyethyl)-3,4-dimethyl-6,7-dihydro-5H-pyrrolo[3,4-b]pyridin-5-one | 442 |
| 262 | 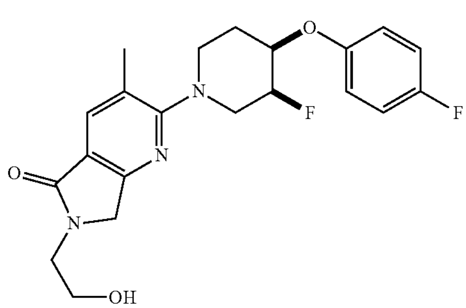 | 2-((3S,4R)-3-fluoro-4-(4-fluorophenoxy)piperidin-1-yl)-6-(2-hydroxyethyl)-3-methyl-6,7-dihydro-5H-pyrrolo[3,4-b]pyridin-5-one | 404 |

TABLE 9-continued

| Example | Structure | Name | MS (M + 1) |
| --- | --- | --- | --- |
| 263 | 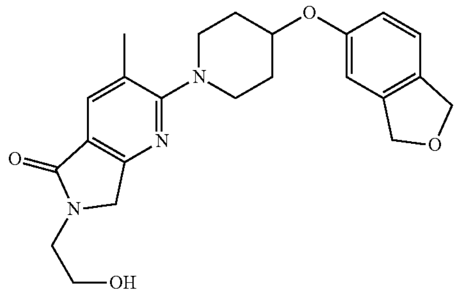 [SMILES: Cc1cc2c(nc1N1CCC(Oc3ccc4c(c3)COC4)CC1)CN(CCO)C2=O] | 2-(4-((1,3-dihydro-2-benzofuran-5-yl)oxy)piperidin-1-yl)-6-(2-hydroxyethyl)-3-methyl-6,7-dihydro-5H-pyrrolo[3,4-b]pyridin-5-one | 410 |
| 263A | 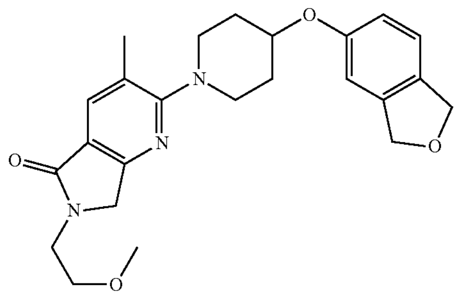 [SMILES: COCCN1Cc2nc(N3CCC(Oc4ccc5c(c4)COC5)CC3)c(C)cc2C1=O] | 2-(4-((1,3-dihydro-2-benzofuran-5-yl)oxy)piperidin-1-yl)-6-(2-methoxyethyl)-3-methyl-6,7-dihydro-5H-pyrrolo[3,4-b]pyridin-5-one | 424 |

[1]Protected bromide electrophile may be prepared according to literature procedure, see e.g.: Duffield, J. J.; Pettit, G. R. *J. Nat. Prod.* 2001, 10, 472-479.

Example 264

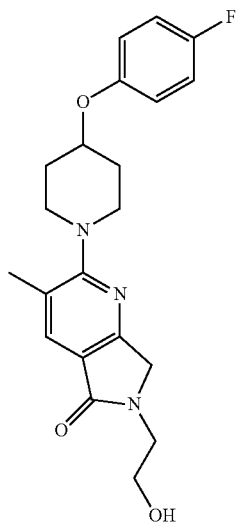 [SMILES: Cc1cc2c(nc1N1CCC(Oc3ccc(F)cc3)CC1)CN(CCO)C2=O]

2-(4-(4-Fluorophenoxy)piperidin-1-yl)-6-(2-hydroxyethyl)-3-methyl-6,7-dihydro-5H-pyrrolo[3,4-b]pyridin-5-one (Scheme 10)

Step 1: 2-(2-(4-(4-Fluorophenoxy)piperidin-1-yl)-3-methyl-5-oxo-5H-pyrrolo[3,4-b]pyridin-6(7H)-yl) acetic acid To a solution of 2-(4-(4-fluorophenoxy)piperidin-1-yl)-3-methyl-6,7-dihydro-5H-pyrrolo[3,4-b]pyridin-5-one (120 mg, 0.352 mmol, Example 72) and methyl 2-bromoacetate (215 mg, 1.406 mmol) in THF (5 mL) was added NaH (42.2 mg, 1.055 mmol). The reaction was stirred at 20° C. for 15 h after which time an aqueous solution of NaOH (20%, 1.45 g, 7.26 mmol) was added. After stirring the reaction for an additional 2 h at RT, aqueous 2N HCl was added to pH-4 and the mixture was extracted with DCM (10 mL×3). The combined organic layers were washed with water (20 mL×3), dried with anhydrous Na$_2$SO$_4$, filtered and the filtrate was evaporated under reduced pressure to yield the title compound. MS: 400 (M+1).

Step 2: 2-(4-(4-Fluorophenoxy)piperidin-1-yl)-6-(2-hydroxyethyl)-3-methyl-6,7-dihydro-5H-pyrrolo[3,4-b]pyridin-5-one To a solution of 2-(2-(4-(4-fluorophenoxy)piperidin-1-yl)-3-methyl-5-oxo-5H-pyrrolo[3,4-b]pyridin-6(7H)-yl) acetic acid (150 mg, 0.376 mmol) in THF (5 mL) was added BH$_3$.DMS (2 M in THF, 0.357 mL, 3.76 mmol). The reaction was stirred at 15° C. for 15 h before quenching with MeOH (5 mL) and then concentrating the mixture to dryness. The residue was The residue was purified by reverse phase HPLC (ACN/water with 0.1% NH$_3$OH modifier) to give the title compound. MS: 386 (M+1). $^1$H NMR (400 MHz, CDCl$_3$): δ 7.77 (1H, s), 6.95-7.07 (2H, m), 6.84-6.95 (2H, m), 4.45 (1H, d, J=3.91 Hz), 4.42 (s, 2H), 3.90-3.92 (2H, m), 3.73-3.81 (2H, m), 3.48-3.60 (2H, m), 3.11-3.21 (2H, m), 3.03 (1H, br s), 2.35 (3H, s), 2.07-2.17 (2H, m), 1.90-1.99 (2H, m).

Example 264A

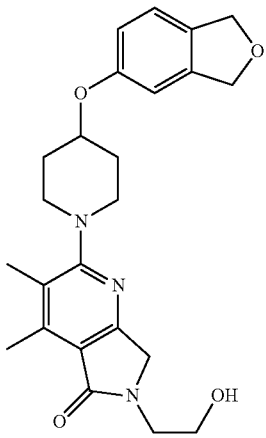 [SMILES: Cc1c(N2CCC(Oc3ccc4c(c3)COC4)CC2)nc2c(c1C)C(=O)N(CCO)C2]

2-(4-((1,3-Dihydro-2-benzofuran-5-yl)oxy)piperidin-1-yl)-6-(2-hydroxyethyl)-3,4-dimethyl-6,7-dihydro-5H-pyrrolo[3,4-b]pyridin-5-one (Scheme 10)

Step 1: Methyl 2-(2-(4-((1,3-dihydro-2-benzofuran-5-yl)oxy)piperidin-1-yl)-3,4-dimethyl-5-oxo-5H-pyrrolo[3,4-b]pyridin-6(7H)-yl)acetate To a solution of 2-(4-((1,3-dihydro-2-benzofuran-5-yl)oxy)piperidin-1-yl)-3,4-dimethyl-6,7-dihydro-5H-pyrrolo[3,4-b]pyridin-5-one (1.68 g, 4.43 mmol) in degassed DMSO (29.5 mL) was added LHMDS (1.5 M in THF, 3.54 mL, 5.31 mmol) at RT. After aging the solution for 15 min, methyl bromoacetate (0.813 g, 5.31 mmol) was added dropwise as a solution in THF (2 mL) under an atmosphere of nitrogen. After stirring for 15 min, the reaction mixture was quenched with water (50 mL) and extracted with DCM (3×100 mL). The combined organic layers were dried over anhydrous sodium sulfate, filtered and the filtrate was concentrated in vacuo. The residue was purified by column chromatography on silica gel (10-30% 3:1 EtOAc:EtOH in hexanes) to yield the title compound. MS: 452 (M+1).

Step 2: 2-(4-((1,3-Dihydro-2-benzofuran-5-yl)oxy)piperidin-1-yl)-6-(2-hydroxyethyl)-3,4-dimethyl-6,7-dihydro-5H-pyrrolo[3,4-b]pyridin-5-one To an ice cold solution of methyl 2-(2-(4-((1,3-dihydro-2-benzofuran-5-yl)oxy)piperidin-1-yl)-3,4-dimethyl-5-oxo-5H-pyrrolo[3,4-b]pyridin-6(7H)-yl)acetate (273 mg, 0.605 mmol) in THF (3.0 mL) was added lithium borohydride (39.5 mg, 1.814 mmol). The reaction was stirred at 0° C. for 10 min and was stirred at 15° C. for 1 h. The reaction was slowly quenched with water and was then diluted with EtOAc and aqueous saturated solution of Rochelle's salt. The organic layer was separated, dried over anhydrous sodium sulfate, filtered and then concentrated to dryness. The material was purified by SFC (OJ-H column, 30% MeOH/CO$_2$) to afford the title compound. MS: 424 (M+1). $^1$H NMR (500 MHz, CDCl$_3$): δ 7.14 (d, J=8.2 Hz, 1H), 6.86 (d, 1H), 6.82 (s, 1H), 5.07 (d, 4H), 4.53-4.44 (m, 1H), 4.35 (s, 2H), 3.89 (s, 2H), 3.75 (t, J=5.0 Hz, 2H), 3.51-3.42 (m, 2H), 3.13-3.04 (m, 3H), 2.62 (s, 3H), 2.23 (s, 3H), 2.13 (s, 2H), 2.01-1.91 (m, 2H).

Examples 264B and 264C

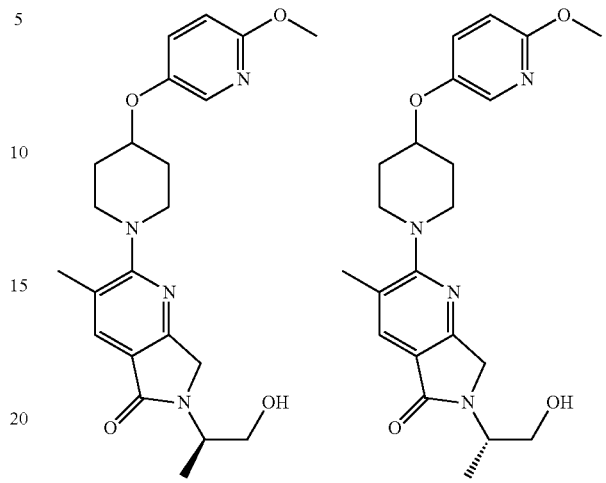

(R)-6-(1-Hydroxypropan-2-yl)-2-(4-((6-methoxypyridin-3-yl)oxy)piperidin-1-yl)-3-methyl-6,7-dihydro-5H-pyrrolo[3,4-b]pyridin-5-one and (S)-6-(1-hydroxypropan-2-yl)-2-(4-((6-methoxypyridin-3-yl)oxy)piperidin-1-yl)-3-methyl-6,7-dihydro-5H-pyrrolo[3,4-b]pyridin-5-one (Scheme 10)

Step 1: Methyl 2-(2-(4-((6-methoxypyridin-3-yl)oxy)piperidin-1-yl)-3-methyl-5-oxo-5H-pyrrolo[3,4-b]pyridin-6(7H)-yl)propanoate To a solution of 2-(4-((6-methoxypyridin-3-yl)oxy)piperidin-1-yl)-3-methyl-6,7-dihydro-5H-pyrrolo[3,4-b]pyridin-5-one (153 mg, 0.432 mmol) in degassed DMSO (2 mL) was added LHMDS (1.5 M in THF, 0.35 mL, 0.525 mmol) at 0° C. The mixture was allowed to warm to RT and was stirred for 15 min before the addition of methyl 2-bromopropionate (0.072 mL, 0.648 mmol). The reaction was stirred for 2 h at RT and was then cooled in an ice bath before quenching with saturated aqueous ammonium chloride. EtOAc was used to extract the material and the organic was washed with water, then brine, dried over anhydrous sodium sulfate, filtered and concentrated. The resultant residue was purified by silica gel chromatography (15-60% EtOAc in hexanes) to furnish the title compound. MS: 441 (M+1).

Step 2: (R)-6-(1-Hydroxypropan-2-yl)-2-(4-((6-methoxypyridin-3-yl)oxy)piperidin-1-yl)-3-methyl-6,7-dihydro-5H-pyrrolo[3,4-b]pyridin-5-one and (S)-6-(1-hydroxypropan-2-yl)-2-(4-((6-methoxypyridin-3-yl)oxy)piperidin-1-yl)-3-methyl-6,7-dihydro-5H-pyrrolo[3,4-b]pyridin-5-one Methyl 2-(2-(4-((6-methoxypyridin-3-yl)oxy)piperidin-1-yl)-3-methyl-5-oxo-5H-pyrrolo[3,4-b]pyridin-6(7H)-yl)propanoate (103 mg, 0.234 mmol) was dissolved in THF (2 mL) under a nitrogen atmosphere. After cooling the system to 0° C., LiBH$_4$ (20.4 mg, 0.935 mmol) was added and the reaction was allowed to warm gradually to RT. The reaction was quenched with saturated aqueous ammonium chloride at 0° C. and partitioned with EtOAc. The organic layer was washed with brine, dried over anhydrous sodium sulfate, filtered and concentrated. The resultant residue was purified by silica gel chromatography (10-40% 3:1 EtOAc:EtOH in hexanes). The racemate was resolved by chiral SFC (AD column, 30% EtOH/CO$_2$) to afford isomer 264B (faster eluting): MS: 413 (M+1). $^1$H NMR (500 MHz, CDCl$_3$): δ 7.87 (s, 1H), 7.73 (s, 1H), 7.26 (s, 1H), 6.70 (d, 1H), 4.35 (m, 4H), 3.90 (s, 3H), 3.85 (m, 1H), 3.72 (m, 1H), 3.52 (br s, 2H), 3.10 (br s, 2H), 2.32 (s, 3H), 2.09 (br s, 2H), 1.92 (br s, 2H), 1.31 (d, 3H). Isomer 264C (slower eluting): MS: 413 (M+1). $^1$H NMR (500 MHz, CDCl$_3$): δ 7.87 (s, 1H), 7.73 (s, 1H), 7.26 (s, 1H), 6.70 (d, 1H), 4.35 (m, 4H), 3.90 (s, 3H), 3.85 (m, 1H), 3.72 (m, 1H), 3.52 (br s, 2H), 3.10 (br s, 2H), 2.32 (s, 3H), 2.09 (br s, 2H), 1.92 (br s, 2H), 1.31 (d, 3H).

The following examples in table 10 were prepared according to scheme 10 using the procedure and conditions outlined in the synthesis of Examples 264, 264A, 264B, and 264C In cases where the ester is saponified, the reduction step may be omitted.

TABLE 10

| Example | Structure | Name | MS (M + 1) |
| --- | --- | --- | --- |
| 264D 264E | | (R)-2-(4-((2-hydroxy-2,3-dihydro-1H-inden-5-yl)oxy)piperidin-1-yl)-6-(2-hydroxyethyl)-3,4-dimethyl-6,7-dihydro-5H-pyrrolo[3,4-b]pyridin-5-one and (S)-2-(4-((2-hydroxy-2,3-dihydro-1H-inden-5-yl)oxy)piperidin-1-yl)-6-(2-hydroxyethyl)-3,4-dimethyl-6,7-dihydro-5H-pyrrolo[3,4-b]pyridin-5-one | 438 438 |
| 265 | 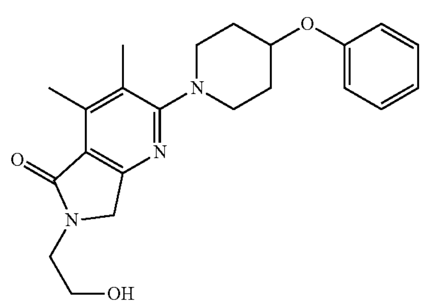 [SMILES: Cc1c(N2CCC(Oc3ccccc3)CC2)nc2c(c1C)C(=O)N(CCO)C2] | 6-(2-hydroxyethyl)-3,4-dimethyl-2-(4-phenoxypiperidin-1-yl)-6,7-dihydro-5H-pyrrolo[3,4-b]pyridin-5-one | 382 |
| 265A | 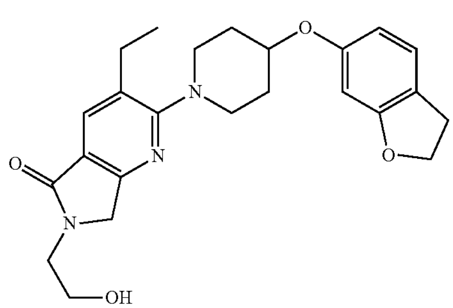 [SMILES: CCc1cc2c(nc1N1CCC(Oc3ccc4c(c3)OCC4)CC1)CN(CCO)C2=O] | 2-(4-((2,3-dihydrobenzofuran-6-yl)oxy)piperidin-1-yl)-3-ethyl-6-(2-hydroxyethyl)-6,7-dihydro-5H-pyrrolo[3,4-b]pyridin-5-one | 424 |

TABLE 10-continued

| Example | Name | MS (M + 1) |
|---|---|---|
| 265B 265C | (R)-2-(4-((2,2-difluoro-1-methylcyclopropyl)methoxy)piperidin-1-yl)-6-(2-hydroxyethyl)-3,4-dimethyl-6,7-dihydro-5H-pyrrolo[3,4-b]pyridin-5-one and (S)-2-(4-((2,2-difluoro-1-methylcyclopropyl)methoxy)piperidin-1-yl)-6-(2-hydroxyethyl)-3,4-dimethyl-6,7-dihydro-5H-pyrrolo[3,4-b]pyridin-5-one | 410 410 |
| 265D | 6-(2-hydroxyethyl)-3,4-dimethyl-2-(4-((1-methyl-1H-indazol-5-yl)oxy)piperidin-1-yl)-6,7-dihydro-5H-pyrrolo[3,4-b]pyridin-5-one | 436 |
| 265E | 6-(2-hydroxyethyl)-2-(4-(isochroman-7-yloxy)piperidin-1-yl)-3-methyl-6,7-dihydro-5H-pyrrolo[3,4-b]pyridin-5-one | 424 |
| 265F | 6-(2-hydroxyethyl)-2-(4-(isochroman-6-yloxy)piperidin-1-yl)-3,4-dimethyl-6,7-dihydro-5H-pyrrolo[3,4-b]pyridin-5-one | 438 |

TABLE 10-continued

| Example | Structure | Name | MS (M + 1) |
|---|---|---|---|
| 266 | 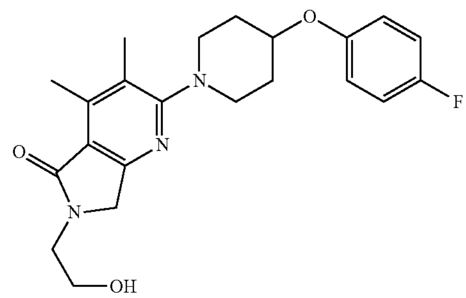 [SMILES: Cc1c(N2CCC(Oc3ccc(F)cc3)CC2)nc2c(c1C)C(=O)N(CCO)C2] | 2-(4-(4-fluorophenoxy)piperidin-1-yl)-6-(2-hydroxyethyl)-3,4-dimethyl-6,7-dihydro-5H-pyrrolo[3,4-b]pyridin-5-one | 400 |
| 266A | 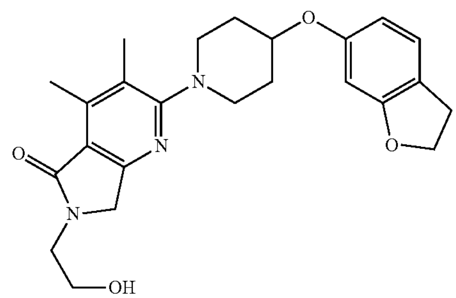 [SMILES: Cc1c(N2CCC(Oc3ccc4c(c3)OCC4)CC2)nc2c(c1C)C(=O)N(CCO)C2] | 2-(4-((2,3-dihydrobenzofuran-6-yl)oxy)piperidin-1-yl)-6-(2-hydroxyethyl)-3,4-dimethyl-6,7-dihydro-5H-pyrrolo[3,4-b]pyridin-5-one | 424 |
| 266B | 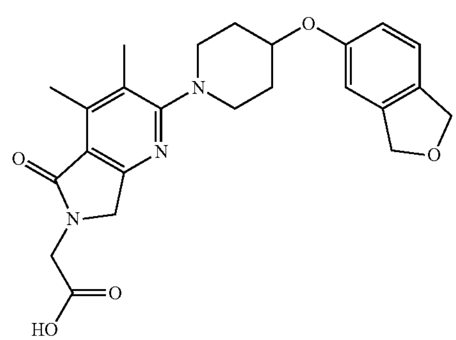 [SMILES: Cc1c(N2CCC(Oc3ccc4c(c3)COC4)CC2)nc2c(c1C)C(=O)N(CC(=O)O)C2] | 2-(2-(4-((1,3-dihydro-2-benzofuran-5-yl)oxy)piperidin-1-yl)-3,4-dimethyl-5-oxo-5,7-dihydro-6H-pyrrolo[3,4-b]pyridin-6-yl)acetic acid | 438 |
| 266C<br>266D | | (R)-2-(4-((1,3-dihydro-2-benzofuran-5-yl)oxy)piperidin-1-yl)-6-(1-hydroxypropan-2-yl)-3,4-dimethyl-6,7-dihydro-5H-pyrrolo[3,4-b]pyridin-5-one and (S)-2-(4-((1,3-dihydro-2-benzofuran-5-yl)oxy)piperidin-1-yl)-6-(1-hydroxypropan-2-yl)-3,4-dimethyl-6,7-dihydro-5H-pyrrolo[3,4-b]pyridin-5-one | 438<br>438 |

TABLE 10-continued

| Example | Structure | Name | MS (M + 1) |
|---|---|---|---|
| 266E | 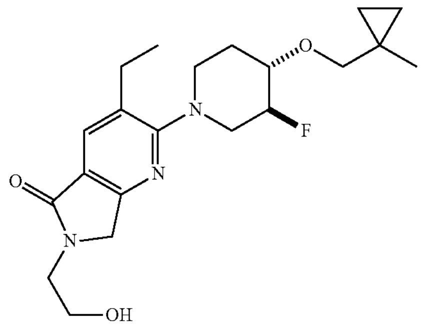 [SMILES: CCc1cc2c(nc1N1CC[C@H](OCC3(C)CC3)[C@@H](F)C1)CN(CCO)C2=O] | 3-ethyl-2-((3S,4S)-3-fluoro-4-((1-methylcyclopropyl)methoxy)piperidin-1-yl)-6-(2-hydroxyethyl)-6,7-dihydro-5H-pyrrolo[3,4-b]pyridin-5-one | 392 |
| 266F | 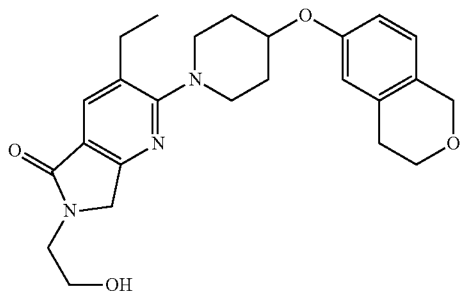 [SMILES: CCc1cc2c(nc1N1CCC(Oc3ccc4c(c3)CCOC4)CC1)CN(CCO)C2=O] | 3-ethyl-6-(2-hydroxyethyl)-2-(4-(isochroman-6-yloxy)piperidin-1-yl)-6,7-dihydro-5H-pyrrolo[3,4-b]pyridin-5-one | 438 |
| 266G | 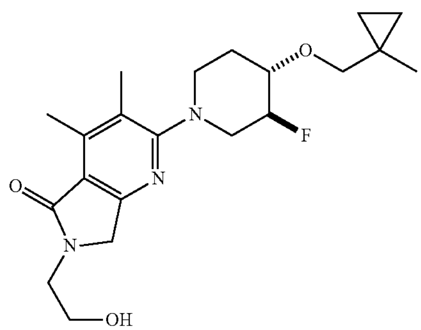 [SMILES: Cc1c(N2CC[C@H](OCC3(C)CC3)[C@@H](F)C2)nc2c(c1C)C(=O)N(CCO)C2] | 2-((3S,4S)-3-fluoro-4-((1-methylcyclopropyl)methoxy)piperidin-1-yl)-6-(2-hydroxyethyl)-3,4-dimethyl-6,7-dihydro-5H-pyrrolo[3,4-b]pyridin-5-one | 392 |
| 267 | 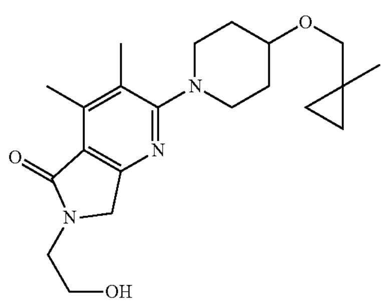 [SMILES: Cc1c(N2CCC(OCC3(C)CC3)CC2)nc2c(c1C)C(=O)N(CCO)C2] | 6-(2-hydroxyethyl)-3,4-dimethyl-2-(4-((1-methylcyclopropyl)methoxy)piperidin-1-yl)-6,7-dihydro-5H-pyrrolo[3,4-b]pyridin-5-one | 374 |
| 267A | 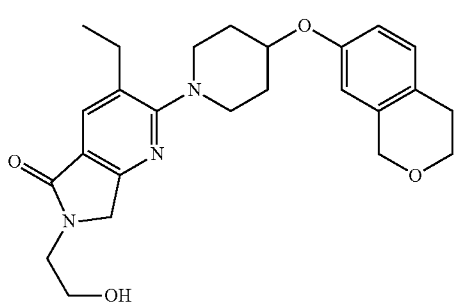 [SMILES: CCc1cc2c(nc1N1CCC(Oc3ccc4c(c3)COCC4)CC1)CN(CCO)C2=O] | 3-ethyl-6-(2-hydroxyethyl)-2-(4-(isochroman-7-yloxy)piperidin-1-yl)-6,7-dihydro-5H-pyrrolo[3,4-b]pyridin-5-one | 438 |

TABLE 10-continued

| Example | Structure | Name | MS (M + 1) |
|---|---|---|---|
| 267B | 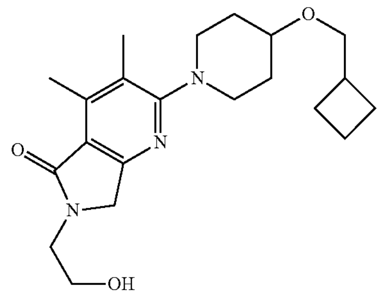 [SMILES: Cc1c(N2CCC(OCC3CCC3)CC2)nc2c(c1C)C(=O)N(CCO)C2] | 2-(4-(cyclobutylmethoxy)piperidin-1-yl)-6-(2-hydroxyethyl)-3,4-dimethyl-6,7-dihydro-5H-pyrrolo[3,4-b]pyridin-5-one | 374 |
| 267C 267D | | (R)-6-(2-hydroxyethyl)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one and (S)-6-(2-hydroxyethyl)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one | 452 452 |
| 267E | 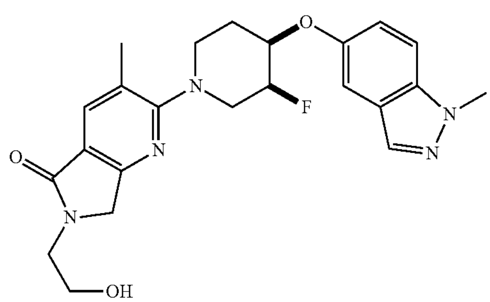 [SMILES: Cc1cc2c(nc1N1CC[C@@H](Oc3ccc4c(cnn4C)c3)[C@@H](F)C1)CN(CCO)C2=O] | 2-((3S,4R)-3-fluoro-4-((1-methyl-1H-indazol-5-yl)oxy)piperidin-1-yl)-6-(2-hydroxyethyl)-3-methyl-6,7-dihydro-5H-pyrrolo[3,4-b]pyridin-5-one | 440 |
| 267F | 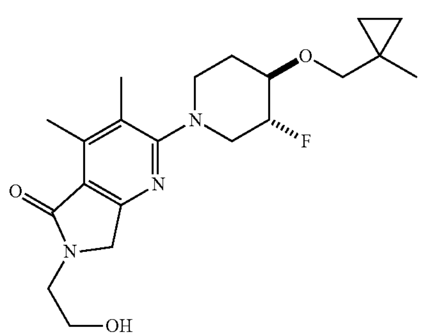 [SMILES: Cc1c(N2CC[C@@H](OCC3(C)CC3)[C@H](F)C2)nc2c(c1C)C(=O)N(CCO)C2] | 2-((3R,4R)-3-fluoro-4-((1-methylcyclopropyl)methoxy)piperidin-1-yl)-6-(2-hydroxyethyl)-3,4-dimethyl-6,7-dihydro-5H-pyrrolo[3,4-b]pyridin-5-one | 392 |

| Example | Structure | Name | MS (M + 1) |
|---|---|---|---|
| 268 | 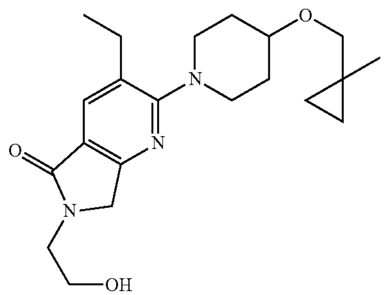 [SMILES: CCc1cc2c(nc1N1CCC(OCC3(C)CC3)CC1)CN(CCO)C2=O] | 3-ethyl-6-(2-hydroxyethyl)-2-(4-((1-methylcyclopropyl)methoxy)piperidin-1-yl)-6,7-dihydro-5H-pyrrolo[3,4-b]pyridin-5-one | 374 |
| 268A | 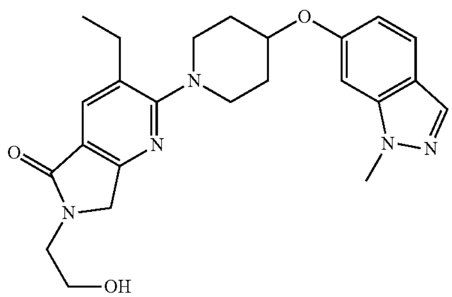 [SMILES: CCc1cc2c(nc1N1CCC(Oc3ccc4cnn(C)c4c3)CC1)CN(CCO)C2=O] | 3-ethyl-6-(2-hydroxyethyl)-2-(4-((1-methyl-1H-indazol-6-yl)oxy)piperidin-1-yl)-6,7-dihydro-5H-pyrrolo[3,4-b]pyridin-5-one | 436 |
| 268B | 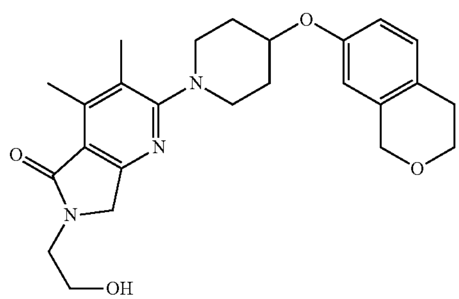 [SMILES: Cc1c(N2CCC(Oc3ccc4c(c3)COCC4)CC2)nc2c(c1C)C(=O)N(CCO)C2] | 6-(2-hydroxyethyl)-2-(4-(isochroman-7-yloxy)piperidin-1-yl)-3,4-dimethyl-6,7-dihydro-5H-pyrrolo[3,4-b]pyridin-5-one | 438 |
| 268C 268D | | (R)-2-(4-((1,3-dihydro-2-benzofuran-5-yl)oxy)piperidin-1-yl)-6-(1-hydroxypropan-2-yl)-3-methyl-6,7-dihydro-5H-pyrrolo[3,4-b]pyridin-5-one and (S)-2-(4-((1,3-dihydro-2-benzofuran-5-yl)oxy)piperidin-1-yl)-6-(1-hydroxypropan-2-yl)-3-methyl-6,7-dihydro-5H-pyrrolo[3,4-b]pyridin-5-one | 424 424 |

TABLE 10-continued

| Example | Structure | Name | MS (M + 1) |
|---|---|---|---|
| 268E | 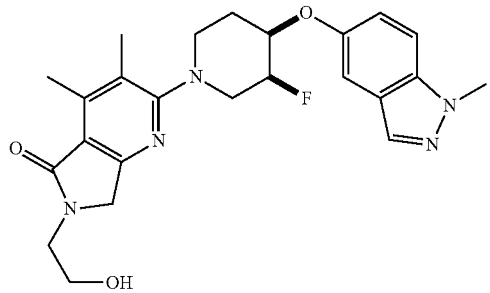 [SMILES: Cc1c(N2CC[C@@H](Oc3ccc4c(cnn4C)c3)[C@@H](F)C2)nc2c(c1C)C(=O)N(CCO)C2] | 2-((3S,4R)-3-fluoro-4-((1-methyl-1H-indazol-5-yl)oxy)piperidin-1-yl)-6-(2-hydroxyethyl)-3,4-dimethyl-6,7-dihydro-5H-pyrrolo[3,4-b]pyridin-5-one | 454 |
| 268F | 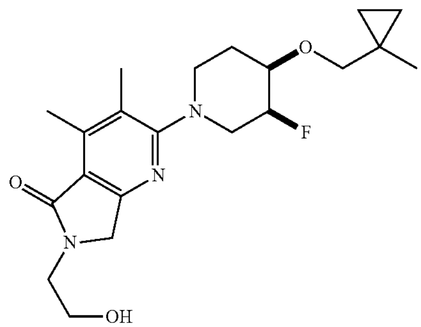 [SMILES: Cc1c(N2CC[C@@H](OCC3(C)CC3)[C@@H](F)C2)nc2c(c1C)C(=O)N(CCO)C2] | 2-((3S,4R)-3-fluoro-4-((1-methylcyclopropyl)methoxy)piperidin-1-yl)-6-(2-hydroxyethyl)-3,4-dimethyl-6,7-dihydro-5H-pyrrolo[3,4-b]pyridin-5-one | 392 |

Example 269

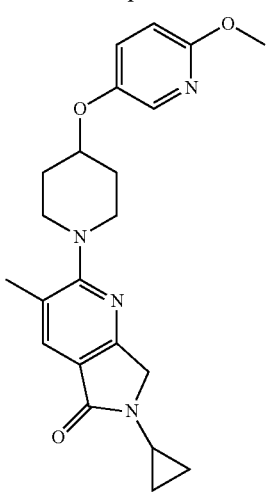

6-Cyclopropyl-2-(4-((6-methoxypyridin-3-yl)oxy)piperidin-1-yl)-3-methyl-6,7-dihydro-5H-pyrrolo[3,4-b]pyridin-5-one (Scheme 11)

The mixture of acetoxy copper (18.16 mg, 0.148 mmol), 2-(4-((6-methoxypyridin-3-yl)oxy)piperidin-1-yl)-3-methyl-6,7-dihydro-5H-pyrrolo[3,4-b]pyridin-5-one (50 mg, 0.141 mmol, Example 1), cyclopropylboronic acid (36.4 mg, 0.423 mmol), DMAP (51.7 mg, 0.423 mmol) in toluene (5 mL) was added NaHMDS (0.141 mL, 0.141 mmol). The reaction was stirred at 80° C. under an $O_2$ atmosphere for 6 h. The mixture was diluted with EtOAc (20 mL), quenched with water (10 mL) and acidified with aqueous 1 M HCl (10 mL). The aqueous phase was extracted with EtOAc (10 mL×3). The combined organic layers were washed with aqueous 1 M HCl and brine (10 mL) and dried over anhydrous sodium sulfate. The solvent was evaporated in vacuo and the residue was purified by reverse phase HPLC (ACN/water with 0.1% TFA modifier) to give the title compound. MS: 395 (M+1). $^1$H NMR (400 MHz, methanol-$d_4$): δ 7.89 (s, 1H), 7.74 (s, 1H), 7.58 (dd, J=9.20, 2.80 Hz, 1H), 6.91 (d, J=9.20 Hz, 1H), 4.52-4.55 (m, 1H), 4.31 (s, 2H), 3.91 (s, 3H), 3.50-3.64 (m, 2H), 3.11-3.25 (m, 2H), 2.82-2.98 (m, 1H), 2.38 (s, 3H), 2.04-2.21 (m, 2H), 1.82-1.97 (m, 2H), 0.80-0.97 (m, 4H).

Example 270

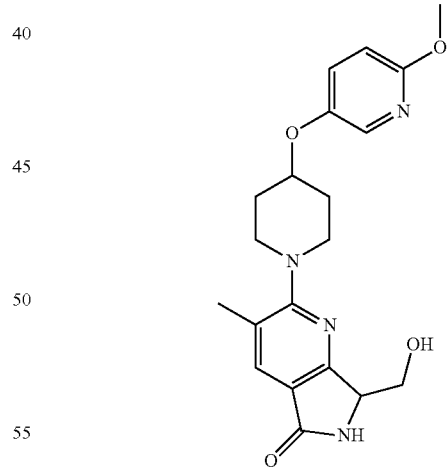

7-(Hydroxymethyl)-2-(4-((6-methoxypyridin-3-yl)oxy)piperidin-1-yl)-3-methyl-6,7-dihydro-5H-pyrrolo[3,4-b]pyridin-5-one (Scheme 12)

Step 1: 2-(4-((6-Methoxypyridin-3-yl)oxy)piperidin-1-yl)-3-methyl-6-((2-(trimethylsilyl)ethoxy)methyl)-6,7-dihydro-5H-pyrrolo[3,4-b]pyridin-5-one To 2-(4-((6-methoxypyridin-3-yl)oxy)piperidin-1-yl)-3-methyl-6,7-dihydro-5H-pyrrolo[3,4-b]pyridin-5-one (1 g, 2.82 mmol, Example 1) in THF (18.8 mL) at 0° C. was added SEM-Cl (1.0 mL, 5.64 mmol). The system was evacuated and placed under an atmosphere of nitrogen and NaH (60%, 0.226 g, 5.64 mmol) was added. After the addition, the reaction was allowed to warm up to RT. The mixture was quenched with aqueous sodium carbonate and was diluted with dichloromethane. The organic was separated, dried over anhydrous sodium sulfate, filtered, and concentrated under reduced pressure. The residue was purified by silica gel chromatography (EtOAc/hexanes) to yield the title compound. MS: 485 (M+1).

Step 2: 7-(Hydroxymethyl)-2-(4-((6-methoxypyridin-3-yl)oxy)piperidin-1-yl)-3-methyl-6-((2-(trimethylsilyl)ethoxy)methyl)-6,7-dihydro-5H-pyrrolo[3,4-b]pyridin-5-one A solution of 2-(4-((6-methoxypyridin-3-yl)oxy)piperidin-1-yl)-3-methyl-6-((2-(trimethylsilyl)ethoxy)methyl)-6,7-dihydro-5H-pyrrolo[3,4-b]pyridin-5-one (472.6 mg, 0.975 mmol) in THF (5 mL) at −78° C. was degassed and placed under an atmosphere of nitrogen. LDA (2 M in THF, 1.46 mL, 2.93 mmol) was added dropwise and the reaction was aged 15 min. (1H-Benzo[d][1,2,3]triazol-1-yl)methanol (291 mg, 1.950 mmol) was added as slurry in THF (1.5 mL) to the reaction at −78° C. and the reaction was aged for 2 h. The reaction was quenched with water and was partitioned with DCM (50 mL). The organic layer was washed with aqueous 1 M NaOH and brine, dried over anhydrous sodium sulfate, filtered, and concentrated in vacuo. The residue was purified by column chromatography on silica gel (10-80% EtOAc in hexanes) to provide the title compound. MS: 515 (M+1).

Step 3: 7-(Hydroxymethyl)-2-(4-((6-methoxypyridin-3-yl)oxy)piperidin-1-yl)-3-methyl-6,7-dihydro-5H-pyrrolo[3,4-b]pyridin-5-one To 7-(hydroxymethyl)-2-(4-((6-methoxypyridin-3-yl)oxy)piperidin-1-yl)-3-methyl-6-((2-(trimethylsilyl)ethoxy)methyl)-6,7-dihydro-5H-pyrrolo[3,4-b]pyridin-5-one (178 mg, 0.346 mmol) in DCM (2.3 mL) was added TFA (1.15 mL). The reaction was stirred for 1 h at RT. Concentrate solution and neutralize with saturated aqueous sodium bicarbonate and dilute with DCM. The organic was separated, dried over anhydrous sodium sulfate, filtered, and concentrated under reduced pressure. The residue was diluted with MeOH (2 mL) and Hunig's base (144 µL, 0.824 mmol) and the reaction was heated to 100° C. for 1 h. The mixture was diluted with water and dichloromethane. The organic was separated, dried over anhydrous sodium sulfate, filtered, and concentrated under reduced pressure. The residue was purified by column chromatography on silica gel (10-90% 3:1 EtOAc:EtOH in hexanes) to provide the title compound. MS: 385 (M+1). ¹H NMR (500 MHz, CDCl₃): δ 7.90 (1H, d, J=3.00 Hz), 7.77 (1H, s), 7.36 (1H, br s), 7.28-7.30 (1H, m), 6.73 (1H, d, J=8.90 Hz), 4.62 (1H, s), 4.39-4.42 (1H, m), 4.04 (1H, br s), 3.93 (3H, s), 3.87 (1H, br s), 3.60 (2H, d, J=11.31 Hz), 3.18-3.22 (2H, m), 2.35 (3H, s), 2.13 (2H, br s), 1.96 (2H, br s).

Examples 271A and 271B

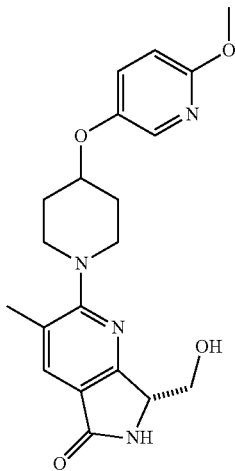

271A

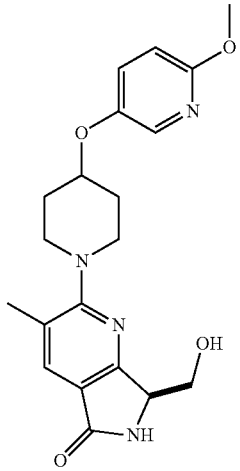

271B (R)-7-(Hydroxymethyl)-2-(4-((6-methoxypyridin-3-yl)oxy)piperidin-1-yl)-3-methyl-6,7-dihydro-5H-pyrrolo[3,4-b]pyridin-5-one (271A) and (S)-7-(hydroxymethyl)-2-(4-((6-methoxypyridin-3-yl)oxy)piperidin-1-yl)-3-methyl-6,7-dihydro-5H-pyrrolo[3,4-b]pyridin-5-one (271B) (Scheme 12)

7-(Hydroxymethyl)-2-(4-((6-methoxypyridin-3-yl)oxy)piperidin-1-yl)-3-methyl-6,7-dihydro-5H-pyrrolo[3,4-b]pyridin-5-one (Example 270) from the procedure for Example 270 (vide supra) was resolved by chiral SFC (AS-H column, 30% MeOH with 0.1% DEA/CO₂) to afford isomer 271A (faster eluting, R-isomer): MS: 385 (M+1). ¹H NMR (500 MHz, CDCl₃): δ 7.90 (1H, d, J=2.94 Hz), 7.78 (1H, s), 7.28-7.30 (1H, m), 7.14 (1H, s), 6.73 (1H, d, J=8.91 Hz), 4.62 (1H, s), 4.39-4.42 (1H, m), 4.01 (1H, dd, J=10.85, 5.58 Hz), 3.93 (3H, s), 3.88 (1H, t, J=8.38 Hz), 3.59-3.61 (2H, m), 3.17-3.23 (2H, m), 2.36 (3H, s), 2.14 (2H, br s), 1.96 (2H, dt, J=12.40, 6.48 Hz). Isomer 271B (slower eluting, S-isomer): MS: 385 (M+1). ¹H NMR (500 MHz, CDCl₃): δ 7.90 (1H, d, J=3.00 Hz), 7.77 (1H, s), 7.36 (1H, br s), 7.28-7.30 (1H, m), 6.73 (1H, d, J=8.90 Hz), 4.62 (1H, s), 4.39-4.42 (1H, m), 4.04 (1H, br s), 3.93 (3H, s), 3.87 (1H, br s), 3.60 (2H, d, J=11.31 Hz), 3.18-3.22 (2H, m), 2.35 (3H, s), 2.13 (2H, br s), 1.96 (2H, br s).

Example 272

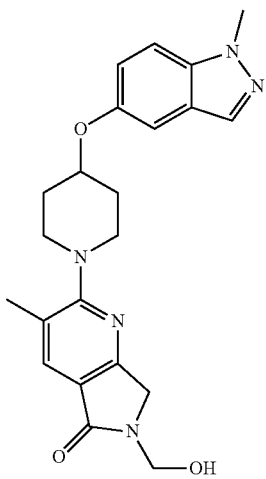 [SMILES: Cc1cc2c(nc1N1CCC(Oc3ccc4c(cnn4C)c3)CC1)CN(CO)C2=O]

6-(Hydroxymethyl)-3-methyl-2-(4-((1-methyl-1H-indazol-5-yl)oxy)piperidin-1-yl)-6,7-dihydro-5H-pyrrolo[3,4-b]pyridin-5-one (Scheme 12)

Step 1: 3-Methyl-2-(4-((1-methyl-1H-indazol-5-yl)oxy)piperidin-1-yl)-6-((2-(trimethylsilyl)ethoxy)methyl)-6,7-dihydro-5H-pyrrolo[3,4-b]pyridin-5-one SEM-Cl (0.141 mL, 0.795 mmol) was added to a stirred mixture of 3-methyl-2-(4-((1-methyl-1H-indazol-5-yl)oxy)piperidin-1-yl)-6,7-dihydro-5H-pyrrolo[3,4-b]pyridin-5-one (200 mg, 0.530 mmol) in DMF (8 mL) at 0° C. NaH (42.4 mg, 1.06 mmol) was added and the the reaction was stirred at 0° C. for 1 h. The reaction was warmed to RT and was partioned with saturated NH$_4$Cl(aq) and EtOAc (10 mL×3). The combined organic layers were dried over anhydrous sodium sulfate, filtered and concentrated in vacuo. The residue was purified by silica gel chromatography (1/1 EtOAc/petroleum ether) to afford the title compound. MS: 508 (M+1).

Step 2: 6-(Hydroxymethyl)-3-methyl-2-(4-((1-methyl-1H-indazol-5-yl)oxy)piperidin-1-yl)-6,7-dihydro-5H-pyrrolo[3,4-b]pyridin-5-one To a solution of 3-methyl-2-(4-((1-methyl-1H-indazol-5-yl)oxy)piperidin-1-yl)-6-((2-(trimethylsilyl)ethoxy)methyl)-6,7-dihydro-5H-pyrrolo[3,4-b]pyridin-5-one (20 mg, 0.039 mmol) in THF (2 mL) was added LDA (1 M in THF, 0.039 mL, 0.079 mmol) at −65° C. under a nitrogen atmosphere. After stirring for 1 h at −65° C., (1H-benzo[d][1,2,3]triazol-1-yl)methanol (5.88 mg, 0.039 mmol) was added to the mixture. After an additional 1 h at this temperature, the reaction was warmed to RT and was directly purified by reverse phase HPLC (ACN/water with 0.1% TFA modifier) to give the title compound. MS: 408 (M+1). $^1$H NMR (400 MHz, methanol-d$_4$): δ 7.86 (1H, s), 7.78 (1H, s), 7.45 (1H, d, J=9.2 Hz), 7.15 (1H, s), 7.13 (1H, dd, J=9.2, 2.4 Hz), 4.96 (2H, s), 4.59-4.61 (1H, m), 4.43 (2H, s), 4.01 (3H, s), 3.59-3.62 (2H, m), 3.212-3.25 (2H, m), 2.37 (3H, s), 2.14-2.17 (2H, m), 1.92-1.95 (2H, m).

Examples 273A and 273B

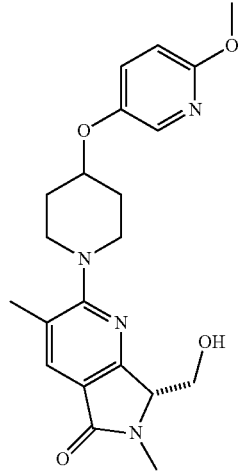

273A

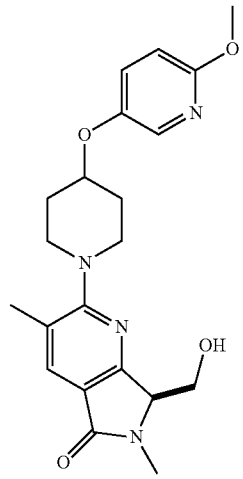

273B (R)-7-(Hydroxymethyl)-2-(4-((6-methoxypyridin-3-yl)oxy)piperidin-1-yl)-3,6-dimethyl-6,7-dihydro-5H-pyrrolo[3,4-b]pyridin-5-one (273A) and (S)-7-(hydroxymethyl)-2-(4-((6-methoxypyridin-3-yl)oxy)piperidin-1-yl)-3,6-dimethyl-6,7-dihydro-5H-pyrrolo[3,4-b]pyridin-5-one (273B) (Scheme 13)

A solution of 2-(4-((6-methoxypyridin-3-yl)oxy)piperidin-1-yl)-3,6-dimethyl-6,7-dihydro-5H-pyrrolo[3,4-b]pyridin-5-one (96 mg, 0.261 mmol, Example 18) in THF (1.3 mL) at −78° C. was degassed and placed under an atmosphere of nitrogen. LDA (2 M in THF, 391 μL, 0.782 mmol) was added dropwise at −78° C. and the reaction was aged 15 min. 1H-Benzo[d][1,2,3]triazol-1-yl)methanol (78 mg, 0.521 mmol) was added as a slurry in THF (0.4 mL) to the reaction at −78° C. and the reaction was aged for 1 h at this temperature. The reaction was quenched with water and was extracted with chloroform. The organic layer was dried over anhydrous sodium sulfate, filtered, and concentrated in vacuo. The residue was purified by column chromatography on silica gel (15-40% 3:1 EtOAc:EtOH in hexanes) to yield the racemate. The title compounds were resolved by chiral SFC (AS-H column, 40% MeOH with 0.1% DEA/CO$_2$) to afford isomer 273A (faster eluting, R-isomer): MS: 399 (M+1). $^1$H NMR (500 MHz, CDCl$_3$): δ 7.86 (1H, s), 7.70 (1H, s), 6.70 (1H, d, J=8.99 Hz), 4.38 (1H, s), 4.31 (1H, s), 4.19 (2H, s), 3.90 (3H, d, J=2.34 Hz), 3.81 (1H, t, J=8.83 Hz), 3.54 (4H, br s), 3.13-3.15 (4H, m), 2.31 (3H, s), 2.11 (2H, br s), 1.93 (2H, br s). Isomer 273B (slower eluting, S-isomer): MS: 399 (M+1). ¹H NMR (500 MHz, CDCl₃): δ 7.86 (1H, s), 7.71 (1H, s), 6.71 (1H, d, J=9.02 Hz), 4.38 (1H, s), 4.32 (1H, s), 4.19 (2H, br s), 3.90 (3H, d, J=2.29 Hz), 3.80 (1H, t, J=9.41 Hz), 3.53 (4H, br s), 3.14 (4H, br s), 2.31 (3H, s), 2.11 (2H, br s), 1.94 (2H, br s).

Example 274

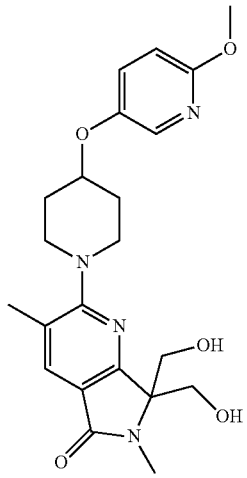

7,7-Bis(hydroxymethyl)-2-(4-((6-methoxypyridin-3-yl)oxy)piperidin-1-yl)-3,6-dimethyl-6,7-dihydro-5H-pyrrolo[3,4-b]pyridin-5-one (Scheme 13)

From the same reaction as described in the procedure for Examples 273A and 273B (vide supra) was obtained the title compound. MS: 429 (M+1). ¹H NMR (400 MHz, methanol-d₄): δ 7.83 (1H, d, J=3.00 Hz), 7.70 (1H, s), 7.42 (1H, dd, J=8.98, 3.04 Hz), 6.76 (1H, d, J=8.96 Hz), 4.47-4.51 (1H, m), 3.94 (4H, s), 3.85 (3H, s), 3.60-3.63 (3H, m), 3.22 (3H, br s), 3.11 (3H, s), 2.35 (3H, s), 2.11-2.15 (3H, m), 1.86-1.93 (3H, m).

The following examples in table 13 were prepared according to scheme 13 using the procedure and conditions outlined in the synthesis of Example 273A, 273B and 274.

TABLE 13

| Example | Structure | Name | MS (M + 1) |
|---|---|---|---|
| 275 | 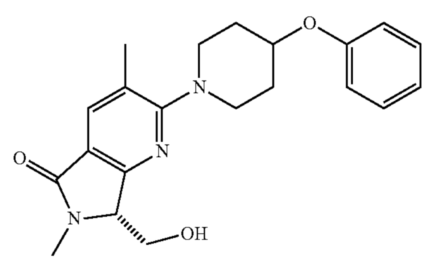 [SMILES: Cc1cc2c(nc1N1CCC(Oc3ccccc3)CC1)[C@H](CO)N(C)C2=O] | (R)-7-(hydroxymethyl)-3,6-dimethyl-2-(4-phenoxypiperidin-1-yl)-6,7-dihydro-5H-pyrrolo[3,4-b]pyridin-5-one | 368 |
| 276 | 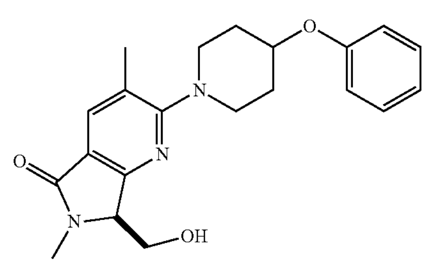 [SMILES: Cc1cc2c(nc1N1CCC(Oc3ccccc3)CC1)[C@@H](CO)N(C)C2=O] | (S)-7-(hydroxymethyl)-3,6-dimethyl-2-(4-phenoxypiperidin-1-yl)-6,7-dihydro-5H-pyrrolo[3,4-b]pyridin-5-one | 368 |
| 277 | 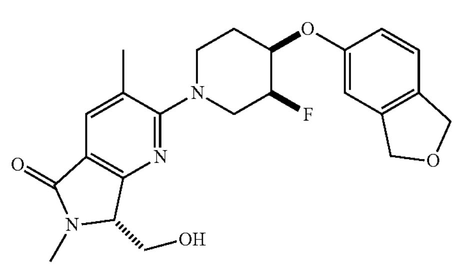 [SMILES: Cc1cc2c(nc1N1CC[C@@H](Oc3ccc4c(c3)COC4)[C@@H](F)C1)[C@H](CO)N(C)C2=O] | (R)-2-((3S,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one | 428 |

TABLE 13-continued

| Example | Structure | Name | MS (M + 1) |
|---|---|---|---|
| 277A | 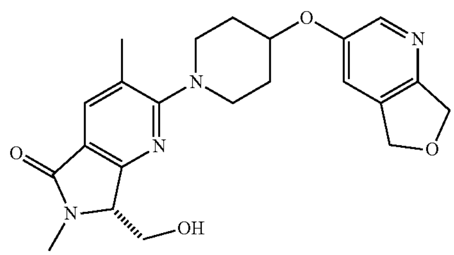 [SMILES: Cc1cc2c(nc1N1CCC(Oc3cnc4c(c3)COC4)CC1)[C@H](CO)N(C)C2=O] | (R)-2-(4-((5,7-dihydrofuro[3,4-b]pyridin-3-yl)oxy)piperidin-1-yl)-7-(hydroxymethyl)-3,6-dimethyl-6,7-dihydro-5H-pyrrolo[3,4-b]pyridin-5-one | 411 |
| 278 | 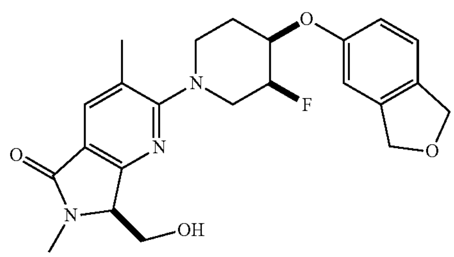 [SMILES: Cc1cc2c(nc1N1CC[C@@H](Oc3ccc4c(c3)COC4)[C@@H](F)C1)[C@@H](CO)N(C)C2=O] | (S)-2-((3S,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one | 428 |
| 278A | 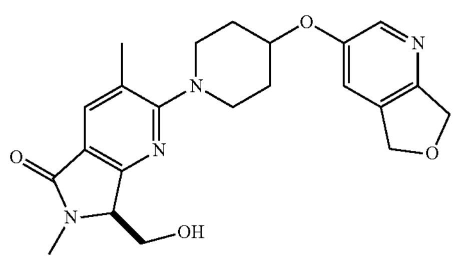 [SMILES: Cc1cc2c(nc1N1CCC(Oc3cnc4c(c3)COC4)CC1)[C@@H](CO)N(C)C2=O] | (S)-2-(4-((5,7-dihydrofuro[3,4-b]pyridin-3-yl)oxy)piperidin-1-yl)-7-(hydroxymethyl)-3,6-dimethyl-6,7-dihydro-5H-pyrrolo[3,4-b]pyridin-5-one | 411 |
| 279 | 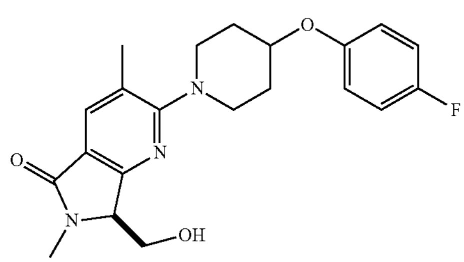 [SMILES: Cc1cc2c(nc1N1CCC(Oc3ccc(F)cc3)CC1)[C@@H](CO)N(C)C2=O] | (S)-2-(4-(4-fluorophenoxy)piperidin-1-yl)-7-(hydroxymethyl)-3,6-dimethyl-6,7-dihydro-5H-pyrrolo[3,4-b]pyridin-5-one | 386 |
| 279A | 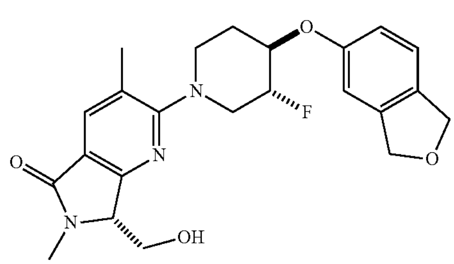 [SMILES: Cc1cc2c(nc1N1CC[C@@H](Oc3ccc4c(c3)COC4)[C@H](F)C1)[C@H](CO)N(C)C2=O] | (R)-2-((3R,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one | 428 |
| 280 | 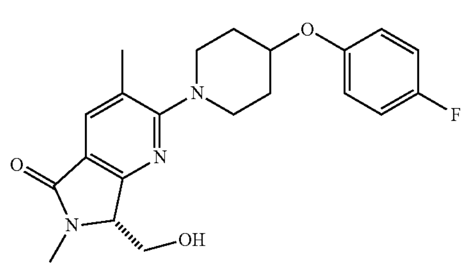 [SMILES: Cc1cc2c(nc1N1CCC(Oc3ccc(F)cc3)CC1)[C@H](CO)N(C)C2=O] | (R)-2-(4-(4-fluorophenoxy)piperidin-1-yl)-7-(hydroxymethyl)-3,6-dimethyl-6,7-dihydro-5H-pyrrolo[3,4-b]pyridin-5-one | 386 |

TABLE 13-continued

| Example | Structure | Name | MS (M + 1) |
|---|---|---|---|
| 280A | 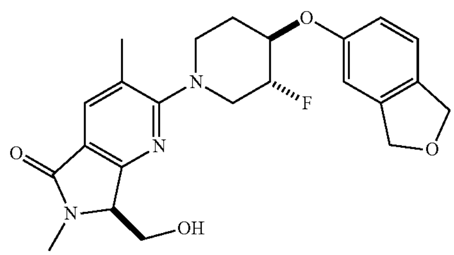 [SMILES: Cc1cc2c(nc1N1CC[C@@H](Oc3ccc4c(c3)COC4)[C@H](F)C1)[C@@H](CO)N(C)C2=O] | (S)-2-((3R,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one | 428 |
| 281 | 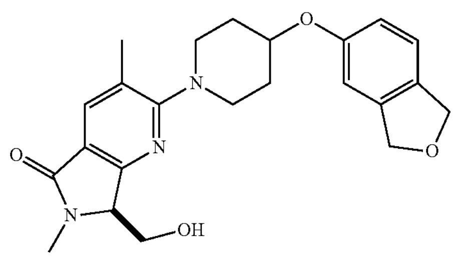 [SMILES: Cc1cc2c(nc1N1CCC(Oc3ccc4c(c3)COC4)CC1)[C@@H](CO)N(C)C2=O] | (S)-2-(4-((1,3-dihydro-2-benzofuran-5-yl)oxy)piperidin-1-yl)-7-(hydroxymethyl)-3,6-dimethyl-6,7-dihydro-5H-pyrrolo[3,4-b]pyridin-5-one | 410 |
| 281A | 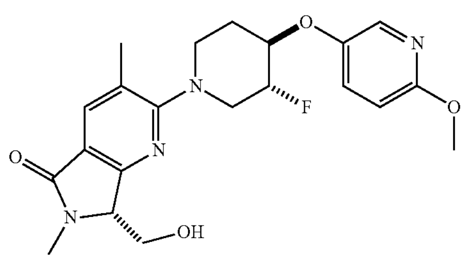 [SMILES: COc1ccc(O[C@@H]2CCN(c3nc4c(cc3C)C(=O)N(C)[C@H]4CO)C[C@H]2F)cn1] | (R)-2-((3R,4R)-3-fluoro-4-((6-methoxypyridin-3-yl)oxy)piperidin-1-yl)-7-(hydroxymethyl)-3,6-dimethyl-6,7-dihydro-5H-pyrrolo[3,4-b]pyridin-5-one | 417 |
| 282 | 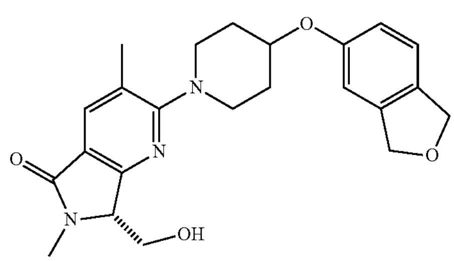 [SMILES: Cc1cc2c(nc1N1CCC(Oc3ccc4c(c3)COC4)CC1)[C@H](CO)N(C)C2=O] | (R)-2-(4-((1,3-dihydro-2-benzofuran-5-yl)oxy)piperidin-1-yl)-7-(hydroxymethyl)-3,6-dimethyl-6,7-dihydro-5H-pyrrolo[3,4-b]pyridin-5-one | 410 |
| 282A | 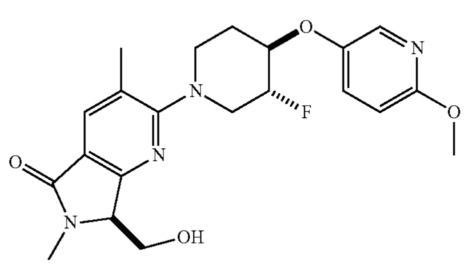 [SMILES: COc1ccc(O[C@@H]2CCN(c3nc4c(cc3C)C(=O)N(C)[C@@H]4CO)C[C@H]2F)cn1] | (S)-2-((3R,4R)-3-fluoro-4-((6-methoxypyridin-3-yl)oxy)piperidin-1-yl)-7-(hydroxymethyl)-3,6-dimethyl-6,7-dihydro-5H-pyrrolo[3,4-b]pyridin-5-one | 417 |
| 283 | 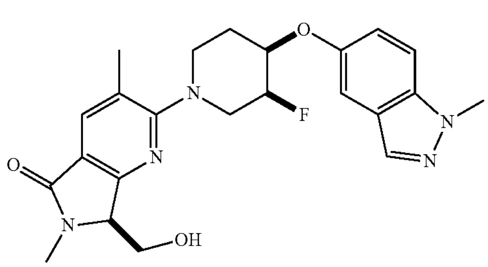 [SMILES: Cc1cc2c(nc1N1CC[C@@H](Oc3ccc4c(cnn4C)c3)[C@@H](F)C1)[C@@H](CO)N(C)C2=O] | (S)-2-((3S,4R)-3-fluoro-4-((1-methyl-1H-indazol-5-yl)oxy)piperidin-1-yl)-7-(hydroxymethyl)-3,6-dimethyl-6,7-dihydro-5H-pyrrolo[3,4-b]pyridin-5-one | 440 |

TABLE 13-continued
| Example | Structure | Name | MS (M + 1) |
|---|---|---|---|
| 284 | 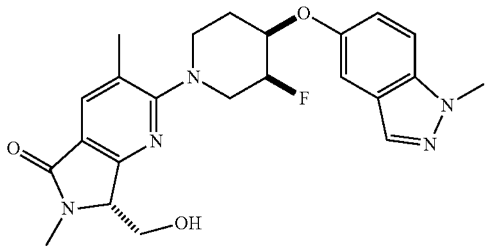 [SMILES: Cc1cc2c(nc1N1CC[C@@H](Oc3ccc4c(cnn4C)c3)[C@@H](F)C1)[C@H](CO)N(C)C2=O] | (R)-2-((3S,4R)-3-fluoro-4-((1-methyl-1H-indazol-5-yl)oxy)piperidin-1-yl)-7-(hydroxymethyl)-3,6-dimethyl-6,7-dihydro-5H-pyrrolo[3,4-b]pyridin-5-one | 440 |
| 285 | 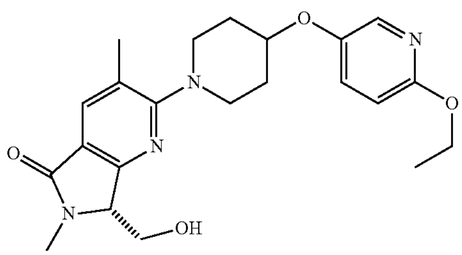 [SMILES: CCOc1ccc(OC2CCN(c3nc4c(cc3C)C(=O)N(C)[C@H]4CO)CC2)cn1] | (R)-2-(4-((6-ethoxypyridin-3-yl)oxy)piperidin-1-yl)-7-(hydroxymethyl)-3,6-dimethyl-6,7-dihydro-5H-pyrrolo[3,4-b]pyridin-5-one | 413 |
| 286 | 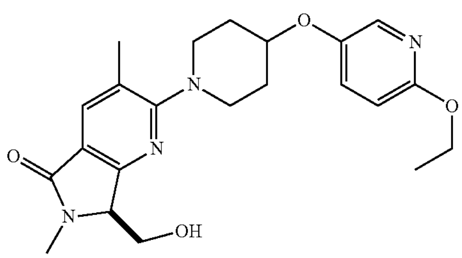 [SMILES: CCOc1ccc(OC2CCN(c3nc4c(cc3C)C(=O)N(C)[C@@H]4CO)CC2)cn1] | (S)-2-(4-((6-ethoxypyridin-3-yl)oxy)piperidin-1-yl)-7-(hydroxymethyl)-3,6-dimethyl-6,7-dihydro-5H-pyrrolo[3,4-b]pyridin-5-one | 413 |
Examples 287A and 287B
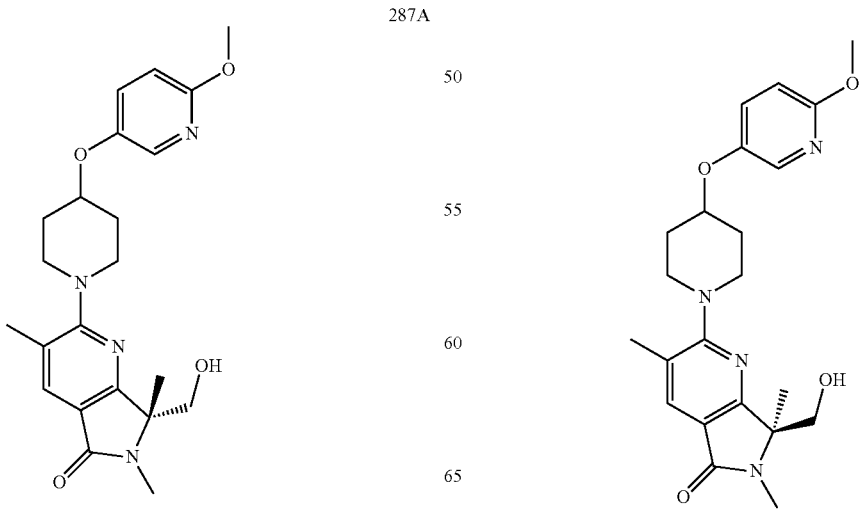

(R)-7-(hydroxymethyl)-2-(4-((6-methoxypyridin-3-yl)oxy)piperidin-1-yl)-3,6,7-trimethyl-6,7-dihydro-5H-pyrrolo[3,4-b]pyridin-5-one (287A) and (S)-7-(hydroxymethyl)-2-(4-((6-methoxypyridin-3-yl)oxy)piperidin-1-yl)-3,6,7-trimethyl-6,7-dihydro-5H-pyrrolo[3,4-b]pyridin-5-one (287B) (Scheme 14)

A solution of 7-(hydroxymethyl)-2-(4-((6-methoxypyridin-3-yl)oxy)piperidin-1-yl)-3,6-dimethyl-6,7-dihydro-5H-pyrrolo[3,4-b]pyridin-5-one (410 mg, 1.029 mmol) in THF (5 mL) at −78° C. was degassed and placed under an atmosphere of nitrogen. LDA (2 M in THF, 2.06 mL, 4.12 mmol) was added at −78° C. the reaction was aged 15 min. MeI (0.257 mL, 4.12 mmol) was added dropwise to the reaction at −78° C. and the reaction was aged for 1 h at this temperature. The reaction was quenched with water and was extracted with chloroform. The organic layer was dried over anhydrous sodium sulfate, filtered, and concentrated in vacuo. The residue was purified by column chromatography on silica gel (10-60% 3:1 EtOAc:EtOH in hexanes) to yield the racemate. The mixture of the two stereoisomers was purified by chiral SFC (AD-H column, 30% MeOH/CO$_2$) to afford isomer 287A (faster eluting, R-isomer): MS: 413 (M+1). $^1$H NMR (500 MHz, acetone-d$_6$): δ 7.96 (1H, s), 7.66 (1H, s), 7.49 (1H, d, J=8.87 Hz), 6.78 (1H, d, J=8.93 Hz), 4.59 (1H, s), 4.16 (1H, s), 3.97-3.93 (2H, m), 3.89 (3H, s), 3.64 (3H, br s), 3.23 (2H, q, J=11.14 Hz), 3.03 (4H, s), 2.39 (2H, s), 2.20 (2H, br s), 1.94 (2H, br s), 1.43 (2H, s). Isomer 287B (slower eluting, S-isomer): MS: 413 (M+1). $^1$H NMR (500 MHz, acetone-d$_6$): δ 7.94 (1H, d, J=2.90 Hz), 7.63 (1H, s), 7.46 (1H, dd, J=8.92, 2.92 Hz), 6.76 (1H, d, J=8.92 Hz), 4.55-4.58 (1H, m), 4.15 (1H, s), 3.88-3.97 (2H, m), 3.87 (3H, s), 3.62 (3H, br s), 3.21 (2H, q, J=11.23 Hz), 3.01 (4H, s), 2.36 (2H, s), 2.18 (2H, br s), 1.90-1.94 (2H, m), 1.41 (2H, s).

Example 288

2-(4-((6-Methoxypyridin-3-yl)ox)piperidin-1-yl)-3,7,7-trimethyl-6,7-dihydro-5H-pyrrolo[3,4-b]pyridin-5-one (Scheme 15)

Step 1: 2-(4-((6-Methoxypyridin-3-yl)oxy)piperidin-1-yl)-3,7,7-trimethyl-6-((2-(trimethylsilyl)ethoxy)methyl)-6,7-dihydro-5H-pyrrolo[3,4-b]pyridin-5-one To a solution of 2-(4-((6-methoxypyridin-3-yl)oxy)piperidin-1-yl)-3-methyl-6-((2-(trimethylsilyl)methoxy)methyl)-6,7-dihydro-5H-pyrrolo[3,4-b]pyridin-5-one (140 mg, 0.289 mmol) in THF (5 mL) was added iodomethane (123 mg, 0.867 mmol) in a schlenk flask at 0° C. under an atmosphere of nitrogen. LiHMDS (2 M in THF, 0.433 mL, 0.867 mmol) was added dropwise to the reaction and the mixture was stirred at 0° C. for 30 min. Saturated, aqueous NH$_4$Cl (1 mL) and water (10 mL) were added and the solution was extracted with EtOAc (10 mL×3). The organic layers were combined and concentrated to provide the title compound, which was used without further purification. MS: 395 (M+1).

Step 2: 2-(4-((6-Methoxypyridin-3-yl)oxy)piperidin-1-yl)-3,7,7-trimethyl-6,7-dihydro-5H-pyrrolo[3,4-b]pyridin-5-one To a solution of 2-(4-((6-methoxypyridin-3-yl)oxy)piperidin-1-yl)-3,7,7-trimethyl-6-((2-(trimethylsilyl)ethoxy)methyl)-6,7-dihydro-5H-pyrrolo[3,4-b]pyridin-5-one (50 mg, 0.098 mmol) in THF (3 mL) was added TBAF (1 M, 1.95 mL, 1.95 mmol). The reaction was stirred at 70° C. for 48 h. Water (20 mL) and EtOAc (20 mL) were added and the organic was separated, washed with water (10 mL×4), and concentrated under reduced pressure. The residue was purified by reverse phase HPLC (ACN/water with 0.1% TFA modifier) to give the title compound. MS: 383 (M+1). $^1$H NMR (400 MHz, methanol-d$_4$): δ 7.86 (1H, s), 7.68 (1H, s), 7.53 (1H, d, J=2.8 Hz), 6.87 (1H, d, J=9.2 Hz), 4.47-4.53 (1H, m), 3.88 (3H, s), 3.50-3.60 (2H, m), 3.15-3.22 (2H, m), 2.33 (3H, s), 2.03-2.12 (2H, m), 1.84-1.89 (2H, m), 1.44 (6H, s).

Example 289

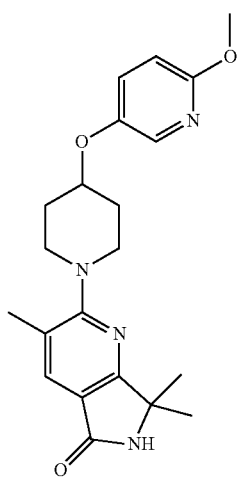

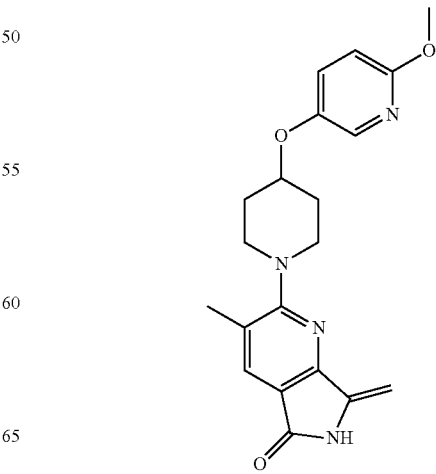

2-(4-((6-Methoxypyridin-3-yl)oxy)piperidin-1-yl)-3-methyl-7-methylene-6,7-dihydro-5H-pyrrolo[3,4-b]pyridin-5-one (Scheme 16)

Step 1: 2-(4-((6-Methoxypyridin-3-yl)oxy)piperidin-1-yl)-3-methyl-7-methylene-6-((2-(trimethylsilyl)ethoxy)methyl)-6,7-dihydro-5H-pyrrolo[3,4-b]pyridin-5-one To a solution of 7-(hydroxymethyl)-2-(4-((6-methoxypyridin-3-yl)oxy)piperidin-1-yl)-3-methyl-6-((2-(trimethylsilyl)ethoxy)methyl)-6,7-dihydro-5H-pyrrolo[3,4-b]pyridin-5-one (153 mg, 0.297 mmol) in THF (991 μL) was added DBU (67.2 μL, 0.446 mmol). The reaction was refluxed for 5 h and the reaction was concentrated to dryness to provide the title compound, which was used without further purification. MS: 497 (M+1).

Step 2: 2-(4-((6-Methoxypyridin-3-yl)oxy)piperidin-1-yl)-3-methyl-7-methylene-6,7-dihydro-5H-pyrrolo[3,4-b]pyridin-5-one 2-(4-((6-Methoxypyridin-3-yl)oxy)piperidin-1-yl)-3-methyl-7-methylene-6-((2-(trimethylsilyl)ethoxy)methyl)-6,7-dihydro-5H-pyrrolo[3,4-b]pyridin-5-one (148 mg, 0.297 mmol) was dissolved in 1/1 TFA/DCM (2 mL) and was stirred at RT for 2 h. The reaction was slowly quenched With aq. Saturated sodium bicarbonate and aqueous 1 M NaOH. Partition and extract the mixture with chloroform and dry the organic over anhydrous sodium sulfate before concentration. Dilute residue with MeOH (1 mL) and Hunig's base (400 uL) and heat for 1 h at 70° C. Remove solvent under reduced pressure and purify crude material by mass triggered reverse phase HPLC (ACN/water with 0.1% NH₃OH modifier) to afford the title compound. MS: 367 (M+1). $^1$H NMR (500 MHz, CDCl₃): δ 7.84-7.90 (1H, m), 7.74-7.78 (1H, m), 7.30 (1H, s), 6.69-6.75 (1H, m), 5.48-5.52 (1H, m), 4.86-4.91 (1H, m), 4.36-4.44 (1H, m), 3.87-3.93 (3H, m), 3.56-3.65 (2H, m), 3.16-3.25 (2H, m), 2.33-2.39 (3H, m), 2.06-2.17 (2H, m), 1.86-2.02 (2H, m).

Example 290

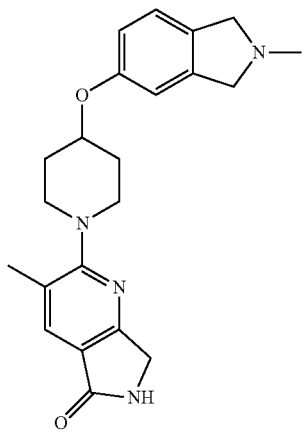

3-Methyl-2-(4-((2-methylisoindolin-5-yl)oxy)piperidin-1-yl)-6,7-dihydro-5H-pyrrolo[3,4-b]pyridin-5-one (Scheme 17)

To a solution of 2-(4-(isoindolin-5-yloxy)piperidin-1-yl)-3-methyl-6,7-dihydro-5H-pyrrolo[3,4-b]pyridin-5-one (50 mg, 0.105 mmol, Example 147) in THF (1 mL) was added paraformaldehyde (40 mg, 0.105 mmol). The reaction was stirred at 40° C. for 0.5 h before sodium triacetoxyborohydride (44.3 mg, 0.209 mmol) was added. The mixture was stirred at 20° C. for 2 h and was then concentrated to dryness. The residue was purified by reverse phase HPLC (ACN/water with 0.1% TFA modifier) to afford the title compound. MS: 379 (M+1). $^1$H NMR (400 MHz, methanol-d₄): δ 7.78 (1H, s), 7.22 (1H, d, J=8.4 Hz), 7.01-7.04 (2H, m), 4.87-4.89 (2H, m), 4.62-4.64 (1H, m), 4.30-4.57 (4H, m), 2.64-2.56 (2H, m), 3.18-3.22 (2H, m), 3.10 (3H, s), 3.37 (3H, s), 2.12-2.15 (2H, m), 1.87-1.91 (2H, m).

The following examples in table 17 were prepared according to scheme 17 using the procedure and conditions outlined in the synthesis of Example 290.

TABLE 17

| Example | Structure | Name | MS (M + 1) |
|---|---|---|---|
| 291 | 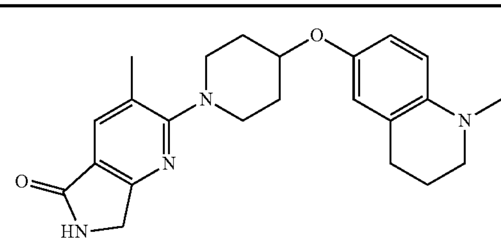 | 3-methyl-2-(4-((1-methyl-1,2,3,4-tetrahydroquinolin-6-yl)oxy)piperidin-1-yl)-6,7-dihydro-5H-pyrrolo[3,4-b]pyridin-5-one | 393 |
| 292 | 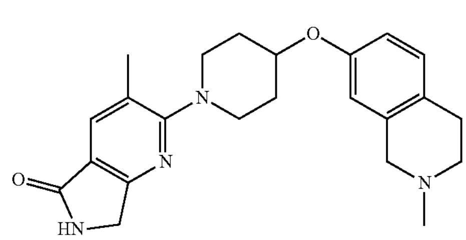 [SMILES: Cc1cc2c(nc1N1CCC(Oc3ccc4c(c3)CN(C)CC4)CC1)CNC2=O] | 3-methyl-2-(4-((2-methyl-1,2,3,4-tetrahydroisoquinolin-7-yl)oxy)piperidin-1-yl)-6,7-dihydro-5H-pyrrolo[3,4-b]pyridin-5-one | 393 |

TABLE 17-continued

| Example | Structure | Name | MS (M + 1) |
|---|---|---|---|
| 293 | 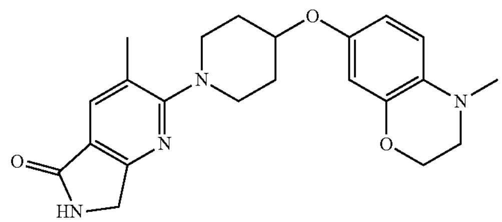 [SMILES: Cc1cc2c(nc1N1CCC(Oc3ccc4c(c3)OCCN4C)CC1)CNC2=O] | 3-methyl-2-(4-((4-methyl-3,4-dihydro-2H-benzo[b][1,4]oxazin-7-yl)oxy)piperidin-1-yl)-6,7-dihydro-5H-pyrrolo[3,4-b]pyridin-5-one | 395 |

Example 294

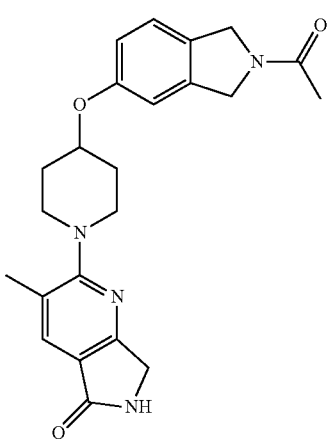 [SMILES: CC(=O)N1Cc2ccc(OC3CCN(c4nc5c(cc4C)C(=O)NC5)CC3)cc2C1]

2-(4-((2-Acetylisoindolin-5-yl)oxy)piperidin-1-yl)-3-methyl-6,7-dihydro-5H-pyrrolo[3,4-b]pyridin-5-one (Scheme 18)

To a solution of 2-(4-(isoindolin-5-yloxy)piperidin-1-yl)-3-methyl-6,7-dihydro-5H-pyrrolo[3,4-b]pyridin-5-one (20 mg, 0.042 mmol) and Et$_3$N (0.017 mL, 0.125 mmol) in DCM (2 mL) was added acetyl chloride (3.61 mg, 0.046 mmol) at 0° C. The reaction was allowed to warm to RT and was stirred for an additional 1 h. The reaction was concentrated to dryness and the residue was purified by reverse phase HPLC (ACN/water with 0.1% TFA modifier) to afford the title compound. MS: 407 (M+1). $^1$H NMR (400 MHz, methanol-d$_4$): δ 7.80 (1H, s), 7.22 (1H, d, J=8.4 Hz), 6.96-6.98 (2H, m), 4.61-4.70 (5H, m), 4.33 (2H, s), 3.56-3.59 (2H, m), 3.20-3.23 (2H, m), 2.39 (3H, s), 2.15-2.17 (5H, m), 1.91-1.93 (2H, m).

The following examples in table 18 were prepared according to scheme 18 using the procedure and conditions outlined in the synthesis of Example 294.

TABLE 18

| Example | Structure | Name | MS (M + 1) |
|---|---|---|---|
| 295 | 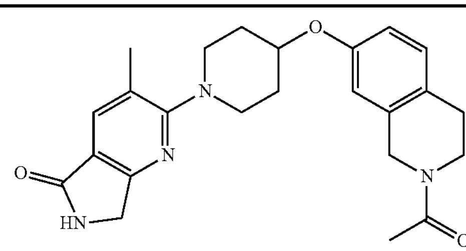 | 2-(4-((2-acetyl-1,2,3,4-tetrahydro-isoquinolin-7-yl)oxy)piperidin-1-yl)-3-methyl-6,7-dihydro-5H-pyrrolo[3,4-b]pyridin-5-one | 421 |

Example 296

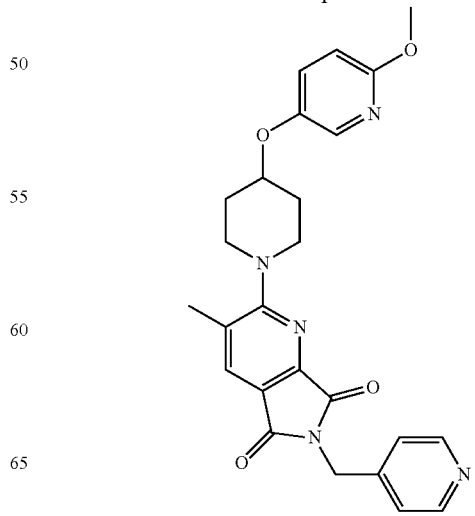

2-(4-((6-Methoxypyridin-3-yl)oxy)piperidin-1-yl)-3-methyl-6-(pyridin-4-ylmethyl)-5H-pyrrolo[3,4-b]pyridine-5,7(6H)-dione (Scheme 19)

Step 1: 2-Cyano-6-(4-((6-methoxypyridin-3-yl)oxy)piperidin-1-yl)-5-methylnicotinic acid To methyl 2-cyano-6-(4-((6-methoxypyridin-3-yl)oxy)piperidin-1-yl)-5-methylnicotinate (485 mg, 1.268 mmol) in tetrahydrofuran (3.81 mL) and MeOH (1.27 mL) was added a solution of LiOH (60.7 mg, 2.54 mmol) in water (1.27 mL) at RT. The reaction was sonicated and stirred at RT and upon completion the solution was neutralized to pH-5 with aqueous 1 M HCl and was diluted with additional water and 2/1/1 DCM/THF/MeOH. The organic layer was separated, dried over anhydrous sodium sulfate and filtered before concentrating to dryness. The title compound was used without further purification. MS: 367 (M+1).

Step 2: 2-(4-((6-Methoxypyridin-3-yl)oxy)piperidin-1-yl)-3-methyl-6-(pyridin-4-ylmethyl)-5H-pyrrolo[3,4-b]pyridine-5,7(6H)-dione To a solution of 2-cyano-6-(4-((6-methoxypyridin-3-yl)oxy)piperidin-1-yl)-5-methylnicotinic acid (150 mg, 0.407 mmol) in DMA (1.36 mL) was added HATU (232 mg, 0.611 mmol) and DIPEA (213 µL, 1.22 mmol). The mixture was sonicated and then pyridin-4-ylmethanamine (52.8 mg, 0.489 mmol) was added to the solution and the reaction was stirred at RT. Upon completion, the mixture was quenched with water and was diluted with dichloromethane. The organic was separated, dried over anhydrous sodium sulfate, filtered, and concentrated under reduced pressure. The residue was purified by column chromatography on silica gel (20-70% 3:1 EtOAc:EtOH in hexanes) to give the title compound as a minor product. MS: 369 (M+1). $^1$H NMR (500 MHz, methanol-$d_4$): δ 8.49 (2H, d, J=5.31 Hz), 7.88 (1H, s), 7.85 (1H, d, J=3.07 Hz), 7.43 (1H, dd, J=8.95, 3.05 Hz), 7.40 (2H, d, J=5.12 Hz), 6.76 (1H, d, J=8.94 Hz), 4.88 (2H, s), 4.53 (1H, tt, J=7.58, 3.73 Hz), 3.86 (3H, s), 3.68-3.73 (2H, m), 3.32-3.35 (2H, m), 2.44 (3H, s), 2.12-2.16 (2H, m), 1.86-1.93 (2H, m).

Example 297

2-(4-((6-Methoxypyridin-3-yl)oxy)piperidin-1-yl)-3-methyl-5H-pyrrolo[3,4-b]pyridine-5,7(6H)-dione (Scheme 19)

Step 1: 2-Cyano-6-(4-((6-methoxypyridin-3-yl)oxy)piperidin-1-yl)-5-methyl-N-(pyridin-4-ylmethyl)nicotinamide From the same reaction as described in step 2 of the procedure in the synthesis of Example 296 (vide supra) was obtained the title compound as the major product. MS: 459 (M+1).

Step 2: 6-(4-((6-Methoxypyridin-3-yl)oxy)piperidin-1-yl)-5-methyl-3-((pyridin-4-ylmethyl)carbamoyl)picolinic acid To 2-cyano-6-(4-((6-methoxypyridin-3-yl)oxy)piperidin-1-yl)-5-methyl-N-(pyridin-4-ylmethyl)nicotinamide (179 mg, 0.390 mmol) in dioxane (781 µL) was added aqueous NaOH (1 M, 781 µL, 0.781 mmol). The reaction was heated to 60° C. Upon completion, the reaction was cooled and neutralized to pH-4 and diluted with DCM. The organic separated and was dried over anhydrous sodium sulfate, filtered and concentrated to dryness. The title compound was used without further purification. MS: 478 (M+1).

Step 3: 2-(4-((6-Methoxypyridin-3-yl)oxy)piperidin-1-yl)-3-methyl-5H-pyrrolo[3,4-b]pyridine-5,7(6H)-dione To a mixture of 6-(4-((6-methoxypyridin-3-yl)oxy)piperidin-1-yl)-5-methyl-3-((pyridin-4-ylmethyl)carbamoyl)picolinic acid (148.7 mg, 0.311 mmol) in DCM (1.56 mL) was added DMF (2.41 µL, 0.031 mmol). The addition of oxalyl chloride (82 µL, 0.934 mmol) produced an exothermic reaction and the solution was stirred for 5 min. NaBH$_4$ (35.3 mg, 0.934 mmol) and MeOH (1 mL) were added to the mixture and the reaction was stirred for 10 min before quenching with aqueous, saturated Rochelle's salt. The mixture was partitioned with DCM and the organic was separated, dried over anhydrous sodium sulfate, filtered and concentrated. The residue was purified by mass triggered reverse phase HPLC (ACN/water with 0.1% TFA modifier) to afford the title compound. MS: 483 (M+1). $^1$H NMR (500 MHz, methanol-$d_4$): δ 7.84-7.85 (2H, m), 7.44 (1H, dd, J=8.95, 3.06 Hz), 6.76-6.78 (1H, m), 4.51-4.54 (1H, m), 3.87 (3H, s), 3.66-3.71 (2H, m), 3.38-3.24 (2H, m), 2.44 (3H, s), 2.11-2.16 (2H, m), 1.86-1.94 (2H, m).

Example 298

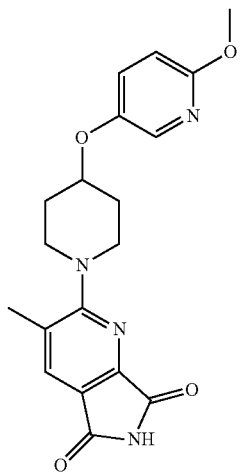

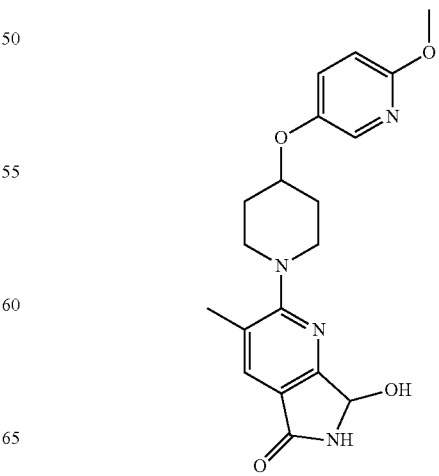

313

7-Hydroxy-2-(4-((6-methoxypyridin-3-yl)oxy)piperidin-1-yl)-3-methyl-6,7-dihydro-5H-pyrrolo[3,4-b]pyridin-5-one (Scheme 19)

From the same reaction as described in the procedure of Example 297 (vide supra) was obtained the title compound. MS: 485 (M+1). $^1$H NMR (500 MHz, methanol-$d_4$): δ 8.03 (1H, d, J=3.05 Hz), 7.92 (1H, dd, J=9.32, 3.31 Hz), 7.78 (1H, s), 7.24 (1H, d, J=9.33 Hz), 5.78 (1H, s), 4.63-4.66 (1H, m), 4.06 (3H, s), 3.63 (2H, br s), 3.25-3.32 (2H, m), 2.39 (3H, s), 2.18 (2H, br s), 1.95 (2H, br s).

Example 299

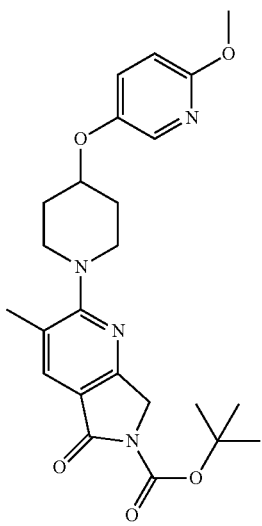 [SMILES: COc1ccc(OC2CCN(c3nc4c(cc3C)C(=O)N(C(=O)OC(C)(C)C)C4)CC2)cn1]

tert-Butyl 2-(4-((6-methoxypyridin-3-yl)oxy)piperidin-1-yl)-3-methyl-5-oxo-5,7-dihydro-6H-pyrrolo[3,4-b]pyridine-6-carboxylate (Scheme 20)

To 2-(4-((6-methoxypyridin-3-yl)oxy)piperidin-1-yl)-3-methyl-6,7-dihydro-5H-pyrrolo[3,4-b]pyridin-5-one (120 mg, 0.339 mmol, Example 1) in DCM (1.69 mL) was added DMAP (4.14 mg, 0.034 mmol) and triethylamine (142 L, 1.016 mmol). At 0° C. was added BOC-anhydride (118 μL, 0.508 mmol), and the reaction was allowed to warm to RT with stirring. After 24 h at RT, the mixture was diluted with water and chloroform. The organic was separated, dried over anhydrous sodium sulfate, filtered, and concentrated under reduced pressure. The residue was purified by column chromatography on silica gel (10-20% 3:1 EtOAc:EtOH in hexanes) to obtain the title compound. MS: 456 (M+1). $^1$H NMR (500 MHz, CDCl$_3$): δ 7.90 (1H, d, J=3.00 Hz), 7.81 (1H, s), 7.27-7.28 (1H, m), 6.74 (1H, d, J=8.89 Hz), 4.66 (2H, s), 4.41-4.44 (1H, m), 3.93 (2H, s), 3.63-3.67 (3H, m), 3.21-3.26 (2H, m), 2.37 (3H, s), 2.12-2.16 (2H, m), 1.93-1.99 (2H, m), 1.62 (9H, s).

314

Example 300

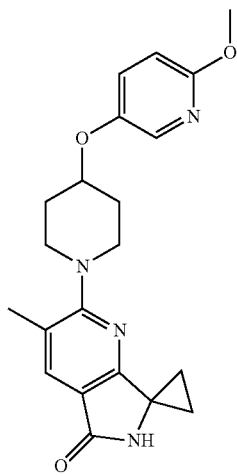

2-(4-((6-Methoxypyridin-3-yl)oxy)piperidin-1-yl)-3-methylspiro[cyclopropane-1,7-pyrrolo[3,4-b]pyridine-5-(6H)-one (Scheme 21)

In a 30 mL schlenk tube, a mixture of methyl 2-cyano-6-(4-((6-methoxypyridin-3-yl)oxy)piperidin-1-yl)-5-methylnicotinate (100 mg, 0.261 mmol), titanium(IV) isopropoxide (149 mg, 0.523 mmol) in THF (3 mL) was prepared. Ethylmagnesium bromide (3 M, 0.18 mL, 0.523 mmol) was added at 0° C. and the reaction was stirred at RT for 6 h. The mixture was diluted with water (10 mL) and extracted with EtOAc (10 mL×3). The combined organic layers were dried over anhydrous magnesium sulfate, filtered, and concentrated in vacuo. The residue was purified by reverse phase HPLC (ACN/water with 0.1% TFA modifier) to afford the title compound. MS: 381 (M+1). $^1$H NMR (400 MHz, methanol-$d_4$): δ 7.87 (1H, d, J=2.8 Hz), 7.75 (1H, s), 7.55 (1H, dd, J=9.2, 2.8 Hz), 6.88 (1H, d, J=9.2 Hz), 4.50-4.52 (1H, m), 3.90 (3H, s), 3.56-3.58 (2H, m), 3.15-3.20 (2H, m), 2.35 (3H, s), 2.10-2.12 (2H, m), 1.86-1.88 (2H, m), 1.53-1.56 (2H, m), 1.46-1.47 (2H, m).

Example 301

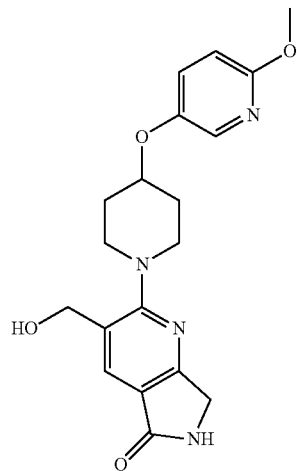 [SMILES: COc1ccc(OC2CCN(c3nc4c(cc3CO)C(=O)NC4)CC2)cn1]

3-(Hydroxymethyl)-2-(4-((6-methoxypyridin-3-yl)oxy)piperidin-1-yl)-6,7-dihydro-5H-pyrrolo[3,4-b]pyridin-5-one (Scheme 22)

DIBAL-H (1 M in DCM, 4.52 mL, 4.52 mmol) was added to a stirred mixture of methyl 2-(4-((6-methoxypyridin-3-yl)oxy)piperidin-1-yl)-5-oxo-6,7-dihydro-5H-pyrrolo[3,4-b]pyridine-3-carboxylate (180 mg, 0.452 mmol, Example 160) in THF (10 mL) at 0° C. After the addition the reaction was allowed to warm to RT and was stirred for 1 h. The volatiles were removed under reduced pressure and the crude residue was purified by column chromatography on silica gel (20/1 DCM/MeOH) to give the title compound. MS: 371 (M+1). $^1$H NMR (500 MHz, methanol-$d_4$): δ 8.16 (1H, s), 7.84 (1H, d, J=3.0 Hz), 7.43 (1H, dd, J=9.0, 3.1 Hz), 6.76 (1H, d, J=8.9 Hz), 4.65 (2H, s), 4.49-4.52 (1H, m), 4.36 (2H, s), 3.86 (3H, s), 3.59-3.63 (2H, m), 3.21-3.26 (2H, m), 2.11-2.15 (2H, m), 1.86-1.93 (2H, m).

The following examples in table 22A were prepared according to scheme 22 using the procedure and conditions outlined in the synthesis of Example 301.

TABLE 22A

| Example | Structure | Name | MS (M + 1) |
| --- | --- | --- | --- |
| 302 | 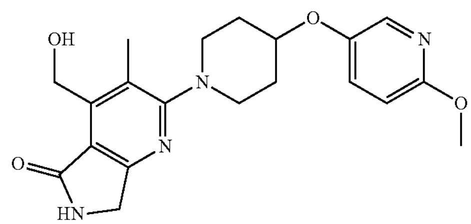 [SMILES: COc1ccc(OC2CCN(c3nc4c(c(CO)c3C)C(=O)NC4)CC2)cn1] | 4-(hydroxymethyl)-2-(4-((6-methoxy-pyridin-3-yl)oxy)piperidin-1-yl)-3-methyl-6,7-dihydro-5H-pyrrolo[3,4-b]pyridin-5-one | 385 |
| 303 | 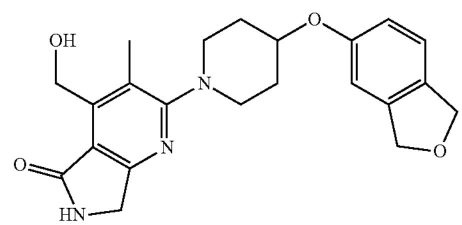 [SMILES: Cc1c(N2CCC(Oc3ccc4c(c3)COC4)CC2)nc2c(c1CO)C(=O)NC2] | 2-(4-((1,3-dihydro-2-benzofuran-5-yl)oxy)piperidin-1-yl)-4-(hydroxymethyl)-3-methyl-6,7-dihydro-5H-pyrrolo[3,4-b]pyridin-5-one | 396 |

Example 304

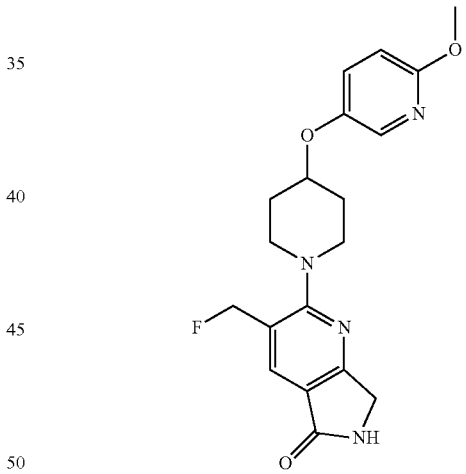

3-(Fluoromethyl)-2-(4-((6-methoxypyridin-3-yl)oxy)piperidin-1-yl)-6,7-dihydro-5H-pyrrolo[3,4-b]pyridin-5-one (Scheme 22)

DAST (0.018 mL, 0.135 mmol) was added to a stirred mixture of 3-(hydroxymethyl)-2-(4-((6-methoxypyridin-3-yl)oxy)piperidin-1-yl)-6,7-dihydro-5H-pyrrolo[3,4-b]pyridin-5-one (10 mg, 0.027 mmol, Example 301) in 1/1 DCM/CHCl$_3$ (6 mL) at −78° C. The reaction was stirred at −78° C. for 1 h and was warmed to RT. The reaction was directly purified by column chromatography on silica gel (20/1 DCM/MeOH) to give the title compound. MS: 373 (M+1). 1H NMR (500 MHz, CDCl$_3$): δ 8.14 (1H, s), 7.90 (1H, d, J=3.0 Hz), 6.73 (1H, d, J=8.9 Hz), 6.28 (1H, s), 5.42 (2H, d, J=48.5 Hz), 4.40-4.42 (3H, m), 3.93 (3H, s), 3.66 (2H, t, J=9.3 Hz), 3.25-3.30 (2H, m), 2.12-2.15 (2H, m), 1.98 (2H, m).

The following examples in table 22B were prepared according to scheme 22 using the procedure and conditions outlined in the synthesis of Example 304.

TABLE 22B

| Example | Structure | Name | MS (M + 1) |
|---------|-----------|------|------------|
| 305 | 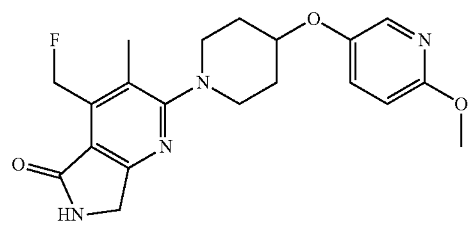 [SMILES: COc1ccc(OC2CCN(c3nc4c(c(CF)c3C)C(=O)NC4)CC2)cn1] | 4-(fluoromethyl)-2-(4-((6-methoxypyridin-3-yl)oxy)piperidin-1-yl)-3-methyl-6,7-dihydro-5H-pyrrolo[3,4-b]pyridin-5-one | 387 |

Example 306

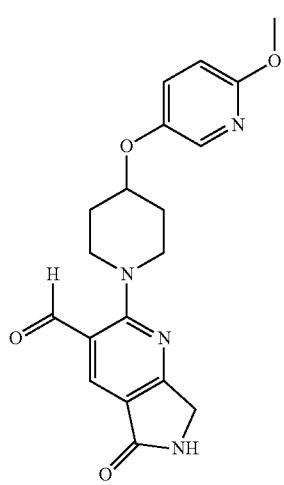 [SMILES: COc1ccc(OC2CCN(c3nc4c(cc3C=O)C(=O)NC4)CC2)cn1]

2-(4-((6-Methoxypyridin-3-yl)oxy)piperidin-1-yl)-5-oxo-6,7-dihydro-5H-pyrrolo[3,4-b]pyridine-3-carbaldehyde (Scheme 23)

DMP (34.4 mg, 0.081 mmol) was added to a stirred mixture of 3-(hydroxymethyl)-2-(4-((6-methoxypyridin-3-yl)oxy)piperidin-1-yl)-6,7-dihydro-5H-pyrrolo[3,4-b]pyridin-5-one (25 mg, 0.067 mmol, Example 301) in CHCl$_3$ (3 mL) at 0° C. The reaction was stirred for 1 hr at 0° C. The mixture was directly purified by column chromatography on silica gel (20/1 DCM/MeOH) to give the title compound. MS: 369 (M+1). $^1$H NMR (500 MHz, CDCl$_3$): δ 9.96 (1H, s), 8.40 (1H, s), 7.89 (1H, d, J=3.0 Hz), 6.74 (1H, d, J=8.9 Hz), 6.54 (1H, s), 4.49-4.52 (1H, m), 4.43 (2H, s), 3.86-3.92 (5H, m), 3.58-3.63 (2H, m), 2.13-2.17 (2H, m), 1.97-2.03 (2H, m).

Example 307

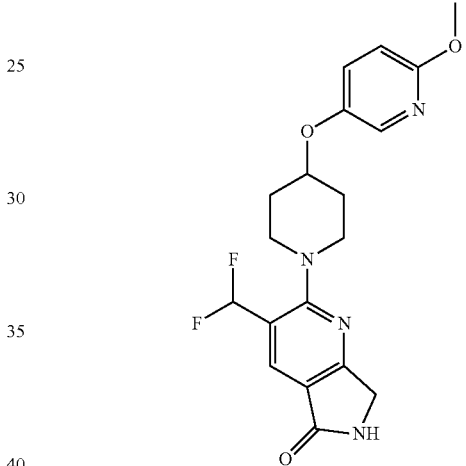

3-(Difluoromethyl)-2-(4-((6-methoxypyridin-3-yl)oxy)piperidin-1-yl)-6,7-dihydro-5H-pyrrolo[3,4-b]pyridin-5-one (Scheme 23)

DAST (0.065 mL, 0.489 mmol) was added to a stirred mixture of 2-(4-((6-methoxypyridin-3-yl)oxy)piperidin-1-yl)-5-oxo-6,7-dihydro-5H-pyrrolo[3,4-b]pyridine-3-carbaldehyde (18 mg, 0.049 mmol, Example 306) in 1/1 DCM/CHCl$_3$ (6 mL) at −78° C. The reaction was stirred at −78° C. for 1 h and was further aged for 2 h at RT. The reaction was quenched with MeOH and concentrated to be purified on silica gel by column chromatography to (10/1 DCM/MeOH) to give the title compound. MS: 391 (M+1). $^1$H NMR (500 MHz, CDCl$_3$): δ 8.32 (1H, s), 7.87 (1H, m), 6.78 (1H, t, J=60 Hz), 6.71 (1H, d, J=8.9 Hz), 6.53 (1H, s), 4.44 (3H, m), 3.90 (3H, s), 3.30 (2H, m), 3.15 (2H, d, J=7.7 Hz), 2.11 (2H, m), 1.99 (2H, m).

The following example in table 23 were prepared according to scheme 23 using the procedure and conditions outlined in the synthesis of Examples 306 and 307.

TABLE 23

| Example | Structure | Name | MS (M + 1) |
|---|---|---|---|
| 307A | 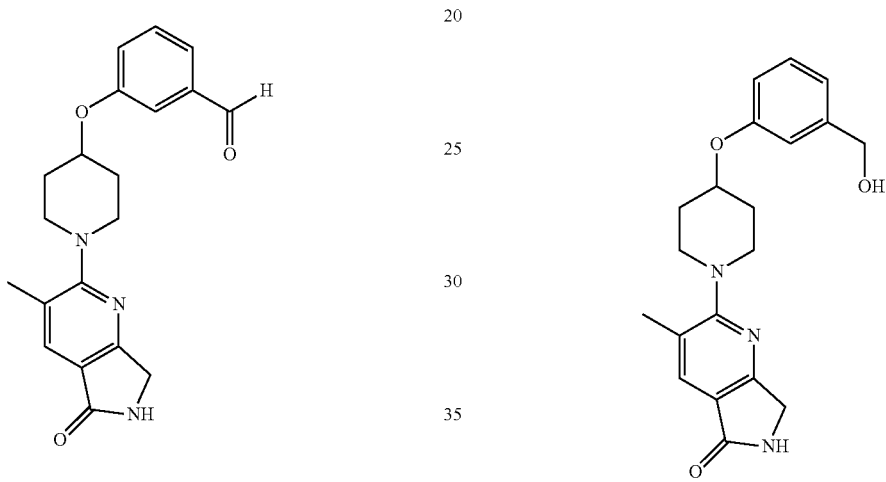 | 4-(difluoromethyl)-2-(4-((6-methoxypyridin-3-yl)oxy)piperidin-1-yl)-3-methyl-6,7-dihydro-5H-pyrrolo[3,4-b]pyridin-5-one | 405 |

Example 308

3-((1-(3-Methyl-5-oxo-6,7-dihydro-5H-pyrrolo[3,4-b]pyridin-2-yl)piperidin-4-yl)oxy)benzaldehyde (Scheme 24)

DIBAL-H (1 M in DCM, 5.63 mL, 5.63 mmol) was added to a stirred mixture of 3-((1-(3-methyl-5-oxo-6,7-dihydro-5H-pyrrolo[3,4-b]pyridin-2-yl)piperidin-4-yl)oxy)benzonitrile (490 mg, 1.406 mmol, Example 3) in DCM (10 mL) at −78° C. The reaction was aged for 1 h and was allowed to warm to RT. Saturated, aqueous NH$_4$Cl and DCM were added to the reaction and the organic was separated, dried over anhydrous sodium sulfate and concentrated. The residue was purified by column chromatography on silica gel (20/1 DCM/MeOH) to provide the title compound. MS: 352 (M+1). $^1$H NMR (500 MHz, CDCl$_3$): δ 9.99 (1H, s), 7.81 (1H, s), 7.47 (1H, d, J=4.8 Hz), 7.45 (1H, br s), 7.23 (1H, m), 6.43 (1H, br s), 4.63-4.66 (1H, m), 4.38 (2H, s), 3.57 (2H, t, J=9.4 Hz), 3.20-3.24 (2H, m), 2.37 (3H, s), 2.15-2.19 (2H, m), 1.96-2.02 (2H, m).

Example 309

2-(4-(3-(Hydroxymethyl)phenoxy)piperidin-1-yl)-3-methyl-6,7-dihydro-5H-pyrrolo[3,4-b]pyridin-5-one (Scheme 24)

NaBH$_4$ (33.6 mg, 0.888 mmol) was added to a stirred mixture of 3-((1-(3-methyl-5-oxo-6,7-dihydro-5H-pyrrolo[3,4-b]pyridin-2-yl)piperidin-4-yl)oxy)benzaldehyde (156 mg, 0.444 mmol, Example 308) in 1/1 MeOH/THF (6 mL) at 0° C. The reaction was stirred for 15 min and was concentrated to dryness. The residue was purified by column chromatography on silica gel (20/1 DCM/MeOH) to provide the title compound. MS: 354 (M+1). $^1$H NMR (500 MHz, CDCl$_3$): δ 7.81 (1H, s), 6.94-6.99 (2H, m), 6.88 (1H, d, J=8.3 Hz), 6.24 (1H, s), 4.69 (2H, s), 4.57 (1H, m), 4.37 (2H, s), 3.58 (2H, s), 3.20 (2H, m), 2.37 (3H, s), 2.14 (2H, m), 1.98 (2H, m).

Example 310

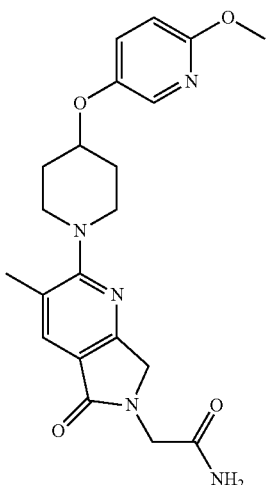

2-(2-(4-((6-methoxypyridin-3-yl)oxy)piperidin-1-yl)-3-methyl-5-oxo-5,7-dihydro-6H-pyrrolo[3,4-b]pyridin-6-yl)acetamide (Scheme 25)

To a solution of methyl 2-(2-(4-((6-methoxypyridin-3-yl)oxy)piperidin-1-yl)-3-methyl-5-oxo-5H-pyrrolo[3,4-b]pyridin-6(7H)-yl)acetate (20 mg, 0.047 mmol, Example 260) in MeOH (2 mL) was added ammonium hydroxide (4.93 mg, 0.141 mmol) at 0° C. over 20 min. The mixture was heated to 20° C. and stirred for 2 h. The mixture was concentrated under reduce pressure. The residue was purified by reverse phase HPLC (ACN/water with 0.1% NH$_3$OH modifier) to give the title compound. MS: 412 (M+1). $^1$H NMR (400 MHz, methanol-d$_4$): δ 7.82 (1H, d, J=3.2 Hz), 7.77 (1H, s), 7.41 (1H, dd, J=8.8, 2.8 Hz), 6.74 (1H, d, J=8.8 Hz), 4.46-4.52 (1H, m), 4.41 (2H, s), 4.25 (2H, s), 3.84 (3H, s), 3.52-3.63 (2H, m), 3.14-3.24 (2H, m), 2.37 (3H, s), 2.08-2.16 (2H, m), 1.83-1.94 (2H, m).

The following example in table 25 were prepared according to scheme 25 using the procedure and conditions outlined in the synthesis of Example 310.

Example 311

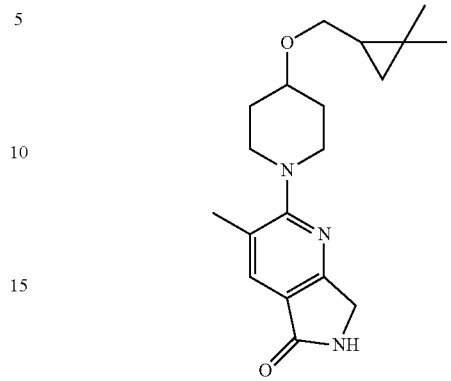

2-(4-((2,2-Dimethylcyclopropyl)methoxy)piperidin-1-yl)-3-methyl-6,7-dihydro-5H-pyrrolo[3,4-b]pyridin-5-one (Scheme 26)

Step 1:
4-((2,2-Dimethylcyclopropyl)methoxy)piperidine tert-Butyl 4-((2,2-dimethylcyclopropyl)methoxy)piperidine-1-carboxylate (25 mg, 0.059 mmol, intermediate L2) in HCl (2 M in EtOAc, 0.5 mL) was stirred at 20° C. for 1 h. The reaction was concentrated to dryness to provide the title compound, which was used without further purification.

Step 2: Methyl 2-cyano-6-(4-((2,2-dimethylcyclopropyl)methoxy)piperidin-1-yl)-5-methylnicotinate To a solution of methyl 6-chloro-2-cyano-5-methylnicotinate (11.50 mg, 0.055 mmol, intermediate A1) in DMF (1 mL) was added 4-((2,2-dimethylcyclopropyl)methoxy)piperidine (20 mg, 0.055 mmol) and DIPEA (0.038 mL, 0.218 mmol). The reaction was stirred at 80° C. for 15 h. After cooling the reaction to RT, it was poured into water (10 mL) and extracted with EtOAc (20 mL×3). The combined organic layers were dried over anhydrous Na$_2$SO$_4$, filtered and concentrated to provide the title compound, which was used without further purification. MS: 358 (M+1).

TABLE 25

| Example | Structure | Name | MS (M + 1) |
| --- | --- | --- | --- |
| 310A | 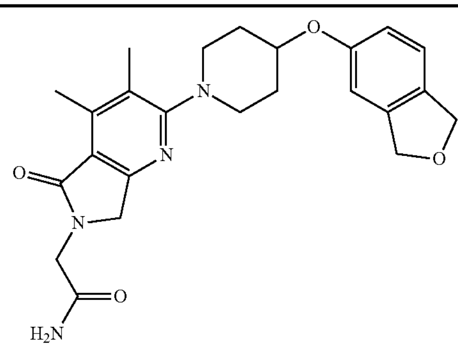 | 2-(2-(4-((1,3-dihydro-2-benzofuran-5-yl)oxy)piperidin-1-yl)-3,4-dimethyl-5-oxo-5,7-dihydro-6H-pyrrolo[3,4-b]pyridin-6-yl)acetamide | 437 |

Step 3: 2-(4-((2,2-Dimethylcyclopropyl)methoxy) piperidin-1-yl)-3-methyl-6,7-dihydro-5H-pyrrolo[3,4-b]pyridin-5-one To a solution of methyl 2-cyano-6-(4-((2,2-dimethylcyclopropyl)methoxy)piperidin-1-yl)-5-methylnicotinate (25 mg, 0.035 mmol) in MeOH (5 mL) was added ammonium hydroxide (0.024 mL, 0.175 mmol) and Raney® nickel (25 mg, 0.426 mmol). The suspension was degassed and purged with hydrogen several times. The mixture was stirred at 20° C. for 3 h under a hydrogen atmosphere (50 psi). The suspension was filtered and the filtrate was concentrated. The residue was purified by reverse phase HPLC (ACN/water with 0.1% TFA modifier) to give the title compound. MS: 330 (M+1). $^1$H NMR (400 MHz, CDCl$_3$): δ 7.78 (1H, s), 6.26 (1H, s), 4.35 (2H, s), 3.50-3.61 (4H, m), 3.41-3.43 (1H, m), 2.90-3.03 (2H, m), 2.34 (3H, s), 1.95-2.05 (2H, m), 1.70-1.75 (2H, m), 1.11 (3H, s), 1.09 (3H, s), 0.80-0.91 (1H, m), 0.48-0.53 (1H, m), 0.11-0.13 (1H, m).

The following examples in table 26 were prepared according to scheme 26 using the procedure and conditions outlined in the synthesis of Example 311. Alternative reaction conditions for step 1 includes the use of TFA as the reagent and DCM as the solvent or else exposure to Pd/C catalyst under a hydrogen atmosphere.

Example 313

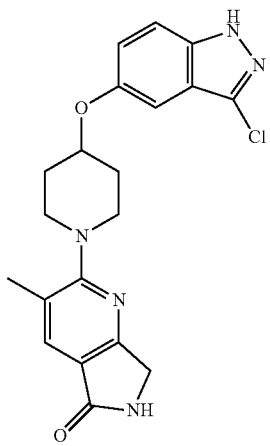

2-(4-((3-Chloro-1H-indazol-5-yl)ox)piperidin-1-yl)-3-methyl-6,7-dihydro-5H-pyrrolo[3,4-b]pyridin-5-one (Scheme 27)

NCS (36.7 mg, 0.275 mmol) was added to a stirred mixture of 2-(4-((1H-indazol-5-yl)oxy)piperidin-1-yl)-3-

TABLE 26

| Example | Structure | Name | MS (M + 1) |
|---|---|---|---|
| 311A | 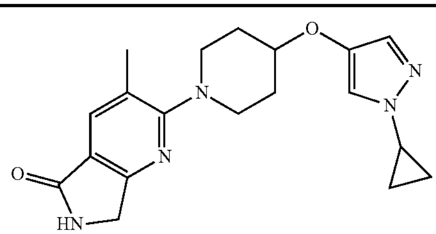 | 2-(4-((1-cyclopropyl-1H-pyrazol-4-yl)oxy)piperidin-1-yl)-3-methyl-6,7-dihydro-5H-pyrrolo[3,4-b]pyridin-5-one | 354 |
| 312 | 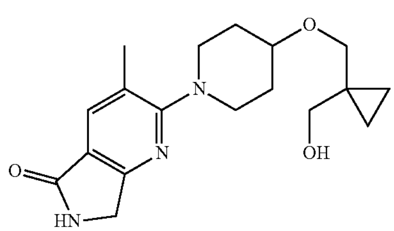 [SMILES: Cc1cc2c(nc1N1CCC(OCC3(CO)CC3)CC1)CNC2=O] | 2-(4-((1-(hydroxymethyl)cyclopropyl)methoxy)piperidin-1-yl)-3-methyl-6,7-dihydro-5H-pyrrolo[3,4-b]pyridin-5-one | 332 |
| 312A | 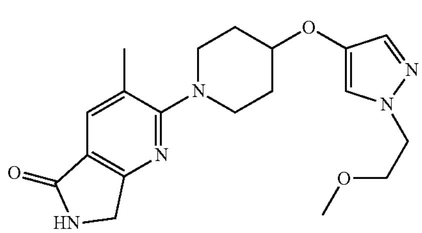 [SMILES: COCCn1cc(OC2CCN(c3nc4c(cc3C)C(=O)NC4)CC2)cn1] | 2-(4-((1-(2-methoxyethyl)-1H-pyrazol-4-yl)oxy)piperidin-1-yl)-3-methyl-6,7-dihydro-5H-pyrrolo[3,4-b]pyridin-5-one | 372 |
| 312B | | 2-(4-((1-hydroxycyclopropyl)methoxy)piperidin-1-yl)-3-methyl-6,7-dihydro-5H-pyrrolo[3,4-b]pyridin-5-one | 318 | methyl-6,7-dihydro-5H-pyrrolo[3,4-b]pyridin-5-one (100 mg, 0.275 mmol, Example 167) in DMF (5 mL) at 0° C. The reaction was stirred at RT for 15 h and then at 100° C. for 2 h. The volatiles removed in vacuo and the residue was purified by column chromatography on silica gel (20/1 DCM/MeOH) to afford the title compound as the major product. MS: 398 (M+1). $^1$H NMR (500 MHz, methanol-d$_4$): δ 7.78 (1H, s), 7.43 (1H, d, J=9.0 Hz), 7.17 (1H, d, J=9.2 Hz), 7.11 (1H, s), 4.66 (1H, s), 4.33 (2H, s), 3.59 (2H, t, J=9.3 Hz), 3.24 (2H, t, J=10.3 Hz), 2.38 (3H, s), 2.18 (2H, m), 1.97 (2H, t, J=10.4 Hz).

Example 314

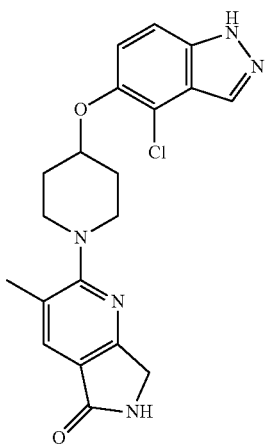 [SMILES: Cc1cc2c(nc1N1CCC(Oc3ccc4[nH]ncc4c3Cl)CC1)CNC2=O]

2-(4-((4-Chloro-1H-indazol-5-yl)oxy)piperidin-1-yl)-3-methyl-6,7-dihydro-5H-pyrrolo[3,4-b]pyridin-5-one (Scheme 27)

From the same reaction as described in the procedure for Example 313 (vide supra) was obtained the title compound. MS: 398 (M+1). $^1$H NMR (500 MHz, methanol-d$_4$): δ 8.03 (1H, s), 7.81 (1H, s), 7.48 (1H, d, J=8.9 Hz), 7.36 (1H, d, J=9.0 Hz), 4.63 (1H, m), 4.35 (2H, s), 3.67 (2H, m), 3.23 (2H, m), 2.40 (3H, s), 2.14 (2H, m), 2.01 (2H, m).

The following example in table 27 were prepared according to scheme 27 using the procedure and conditions outlined in the synthesis of Example 314.

Example 316

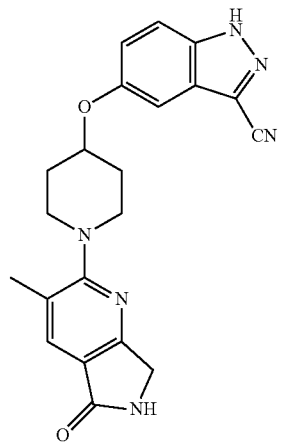 [SMILES: Cc1cc2c(nc1N1CCC(Oc3ccc4[nH]nc(C#N)c4c3)CC1)CNC2=O]

5-((1-(3-Methyl-5-oxo-6,7-dihydro-5H-pyrrolo[3,4-b]pyridin-2-yl)piperidin-4-yl)oxy)-1H-indazole-3-carbonitrile (Scheme 28)

Chloro(2-dicyclohexylphosphino-2',4',6'-triisopropyl-1,1'-biphenyl)[2-(2'-amino-1,1'-biphenyl)]palladium(II) (4.27 mg, 5.43 μmol) was added to a stirred mixture of 2-(4-((3-bromo-1H-indazol-5-yl)oxy)piperidin-1-yl)-3-methyl-6,7-dihydro-5H-pyrrolo[3,4-b]pyridin-5-one (24 mg, 0.054 mmol, Example 315) and dicyanozinc (12.74 mg, 0.109 mmol) in DMF (4 mL). The reaction was stirred at 200° C. for 30 min under microwave irradiation. The crude mixture was purified by reverse phase HPLC (ACN/water with 0.1% TFA modifier) to provide the title compound. MS: 389 (M+1). $^1$H NMR (500 MHz, CDCl$_3$): δ 7.83 (1H, s), 7.61 (1H, d, J=9.1 Hz), 7.28 (1H, s), 7.24 (1H, d, J=9.2 Hz), 4.7 (1H, m), 4.36 (2H, s), 3.62 (2H, m), 3.31 (2H, m) 2.41 (3H, s), 2.22 (2H, m), 1.99 (2H, m).

TABLE 27

| Example | Structure | Name | MS (M + 1) |
|---|---|---|---|
| 315 | 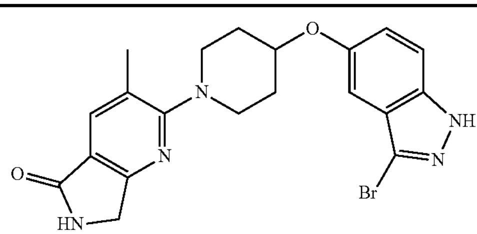 | 2-(4-((3-bromo-1H-indazol-5-yl)oxy)piperidin-1-yl)-3-methyl-6,7-dihydro-5H-pyrrolo[3,4-b]pyridin-5-one | 442, 444 |

Example 317

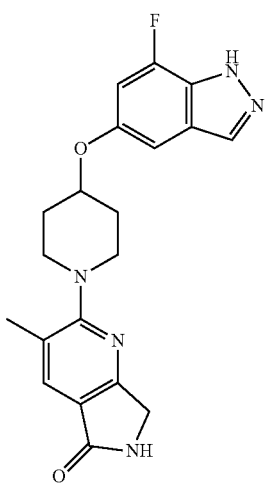 [SMILES: Cc1cc2c(nc1N1CCC(Oc3cc(F)c4[nH]ncc4c3)CC1)CNC2=O]

2-(4-((7-Fluoro-1H-indazol-5-yl)ox)piperidin-1-yl)-3-methyl-6,7-dihydro-5H-pyrrolo[3,4-b]pyridin-5-one (Scheme 29)

Selectfluor® (39.0 mg, 0.110 mmol) was added to a stirred mixture of 2-(4-((1H-indazol-5-yl)oxy)piperidin-1-yl)-3-methyl-6,7-dihydro-5H-pyrrolo[3,4-b]pyridin-5-one (40 mg, 0.110 mmol, Example 167) in 1/1 DMF/MeCN (10 mL) at 0° C. The reaction was then stirred at 100° C. under microwave irradiation for 1 h. The mixture was concentrated and was residue was purified by reverse phase HPLC (ACN/water with 0.1% TFA modifier) to provide the title compound. MS: 382 (M+1). $^1$H NMR (500 MHz, methanol-$d_4$): δ 8.07 (1H, s), 7.83 (1H, s), 7.30-7.33 (2H, m), 4.48 (1H, m), 4.36 (2H, s), 3.65 (2H, br s), 3.22 (3H, t, J=10.1 Hz), 2.40 (3H, s), 2.12 (2H, m), 1.98 (2H, m).

Example 318

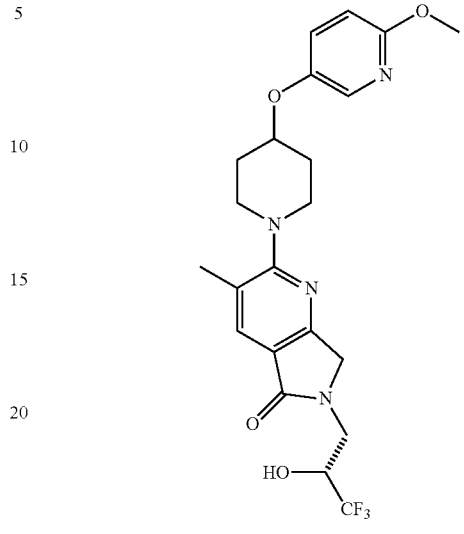

(R)-2-(4-((6-Methoxypyridin-3-yl)oxy)piperidin-1-yl)-3-methyl-6-(3,3,3-trifluoro-2-hydroxypropyl)-6,7-dihydro-5H-pyrrolo[3,4-b]pyridin-5-one (Scheme 30)

To a solution of 2-(4-((6-methoxypyridin-3-yl)oxy)piperidin-1-yl)-3-methyl-6,7-dihydro-5H-pyrrolo[3,4-b]pyridin-5-one (100 mg, 0.282 mmol, Example 1) in DMSO (5 mL) was added LHMDS (1 M, 0.282 mL, 0.282 mmol). The reaction was stirred at RT b®re (R)-2-(trifluoromethyl)oxirane (31.6 mg, 0.282 mmol) was added. After stirring for 4 h, the crude mixture was directly purified by reverse phase HPLC (ACN/water with 0.1% NH$_3$OH modifier) to yield the title compound. MS: 467 (M+1). $^1$H NMR (500 MHz, CDCl$_3$): δ 7.87 (d, J=3.0 Hz, 1H), 7.76 (s, 1H), 7.27 (m, 1H), 6.71 (d, J=9.0 Hz, 1H), 5.22 (s, 1H), 4.46 (d, J=17 Hz, 1H), 4.39-4.37 (m, 1H), 4.27 (m, 1H), 4.00 (d, J=13.5 Hz, 1H), 3.90 (s, 3H), 3.85 (m, 1H), 3.57 (m, 2H), 3.16 (m, 2H), 2.35 (s, 3H), 2.10 (m, 2H), 1.94 (m, 2H).

The following examples in table 30 were prepared according to scheme 30 using the procedure and conditions outlined in the synthesis of Example 318.

TABLE 30

| Example | Structure | Name | MS (M + 1) |
|---|---|---|---|
| 319 | ![structure] | (S)-2-(4-((6-methoxypyridin-3-yl)oxy)piperidin-1-yl)-3-methyl-6-(3,3,3-trifluoro-2-hydroxypropyl)-6,7-dihydro-5H-pyrrolo[3,4-b]pyridin-5-one | 467 |

Example 320

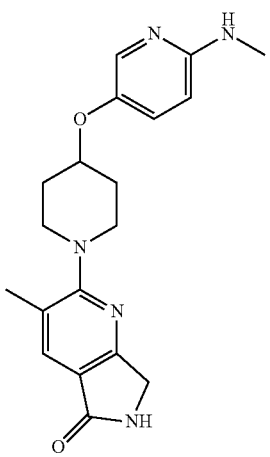

3-Methyl-2-(4-((6-(methylamino)pyridin-3-yl)oxy)piperidin-1-yl)-6,7-dihydro-5H-pyrrolo[3,4-b]pyridin-5-one (Scheme 31)

Step 1: 6-(Methylamino)pyridin-3-ol

To a solution of 5-(benzyloxy)-N-methylpyridin-2-amine (60 mg, 0.280 mmol, intermediate V) in MeOH (10 mL) was added Pd/C (10%, 29.8 mg, 0.028 mmol). The reaction mixture was stirred at 10° C. for 1.5 h under a hydrogen atmosphere. The mixture was filtered, washing with MeOH (20 mL) and the filtrate was evaporated under reduced pressure. The residue was purified by prep-TLC (1/1 petroleum ether/EtOAc) to yield the title compound.

Step 2: 3-Methyl-2-(4-((6-(methylamino)pyridin-3-yl)oxy)piperidin-1-yl)-6,7-dihydro-5H-pyrrolo[3,4-b]pyridin-5-one To a solution of 6-(methylamino)pyridin-3-ol (20 mg, 0.161 mmol), 2-(4-hydroxypiperidin-1-yl)-3-methyl-6,7-dihydro-5H-pyrrolo[3,4-b]pyridin-5-one (30 mg, 0.121 mmol, intermediate H1) and (E)-di-tert-butyl diazene-1,2-dicarboxylate (41.9 mg, 0.182 mmol) in toluene (2 mL) was added triphenylphosphine (47.7 mg, 0.182 mmol). The reaction mixture was stirred at 80° C. for 15 h. The crude mixture was directly purified by reverse phase HPLC (ACN/water with 0.1% TFA modifier) to yield the title compound. MS: 354 (M+1). $^1$H NMR (400 MHz, methanol-$d_4$): δ 7.79 (1H, s), 7.71 (1H, d, J=2.8 Hz), 7.30 (1H, dd, J=9.2, 2.8 Hz), 6.53 (1H, d, J=8.8 Hz), 4.35-4.38 (1H, m), 4.33 (2H, s), 3.56-3.60 (2H, m), 3.17-3.20 (2H, m), 2.84 (3H, s), 2.38 (3H, s), 2.08-2.10 (2H, m), 1.87-1.90 (2H, m).

Example 321

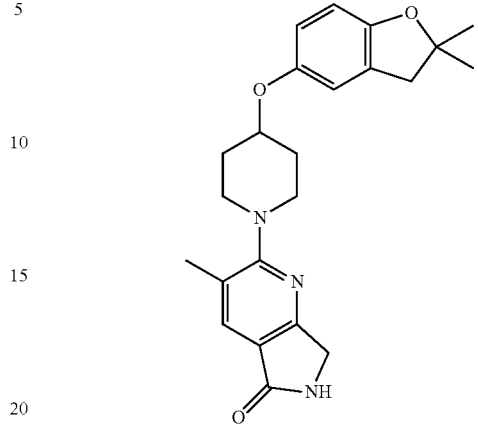

2-(4-((2,2-Dimethyl-2,3-dihydrobenzofuran-5-yl)oxy)piperidin-1-yl)-3-methyl-6,7-dihydro-5H-pyrrolo[3,4-b]pyridin-5-one (Scheme 31)

Step 1: 2,2-Dimethyl-2,3-dihydrobenzofuran-5-ol

To a solution of (2,2-dimethyl-2,3-dihydrobenzofuran-5-yl)-4,4,5,5-tetramethyl-1,3,2-dioxaborolane (60 mg, 0.219 mmol) in anhydrous MeOH (2 mL) was added $H_2O_2$ (35%, 0.192 mL, 2.188 mmol) dropwise. The reaction was stirred at 30° C. for 16 h and was quenched with $Na_2SO_3$ and water (10 mL). The mixture was extracted with EtOAc (3×10 mL) and the combined organic layers were washed with brine, dried over anhydrous $Na_2SO_4$ and concentrated. The residue was purified by prep-TLC (3/1 petroleum ether/EtOAc) to give the title compound.

Step 2: 2-(4-((2,2-Dimethyl-2,3-dihydrobenzofuran-5-yl)oxy)piperidin-1-yl)-3-methyl-6,7-dihydro-5H-pyrrolo[3,4-b]pyridin-5-one A solution of 2-(4-hydroxypiperidin-1-yl)-3-methyl-6,7-dihydro-5H-pyrrolo[3,4-b]pyridin-5-one (30 mg, 0.121 mmol, intermediate H1) in toluene (3 mL) was added 2,2-dimethyl-2,3-dihydrobenzofuran-5-ol (29.9 mg, 0.182 mmol), triphenylphosphine (47.7 mg, 0.182 m®) and (E)-di-tert-butyl diazene-1,2-dicarboxylate (41.9 mg, 0.182 mmol). The mixture was stirred at 70° C. for 15 h under a nitrogen atmosphere. Then mixture was concentrated and was directly purified by reverse phase HPLC (ACN/water with 0.1% $NH_3OH$ modifier) to yield the title compound. MS: 394 (M+1). $^1$H NMR (400 MHz, $CDCl_3$): δ 7.80 (1H, s), 6.80 (1H, s), 6.74 (1H, d, J=8.8 Hz), 6.65 (1H, d, J=8.8 Hz), 5.98 (1H, s), 4.32-4.36 (3H, m), 3.50-3.56 (2H, m), 3.12-3.17 (2H, m), 2.99 (2H, s), 2.36 (3H, s), 2.05-2.15 (2H, m), 1.82-1.90 (2H, m), 1.48 (6H, s).

The following examples in table 31 were prepared according to scheme 31 using the procedure and conditions outlined in the synthesis of Example 320 or 321 from prepared or commercially available starting materials.

TABLE 31

| Example | Structure | Name | MS (M + 1) |
| --- | --- | --- | --- |
| 321A | 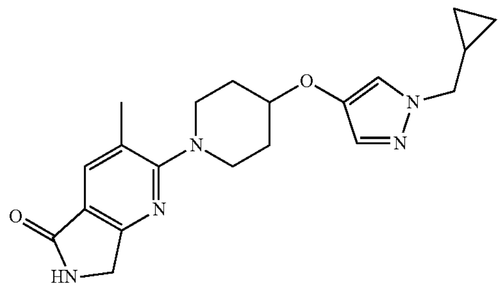 [SMILES: Cc1cc2c(nc1N1CCC(Oc3cnn(CC4CC4)c3)CC1)CNC2=O] | 2-(4-((1-(cyclopropylmethyl)-1H-pyrazol-4-yl)oxy)piperidin-1-yl)-3-methyl-6,7-dihydro-5H-pyrrolo[3,4-b]pyridin-5-one | 368 |
| 321B | 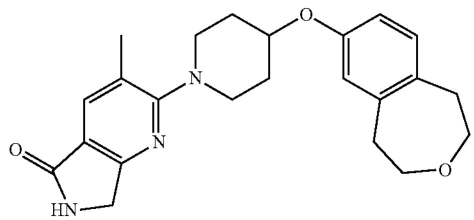 [SMILES: Cc1cc2c(nc1N1CCC(Oc3ccc4c(c3)CCOCC4)CC1)CNC2=O] | 3-methyl-2-(4-((1,2,4,5-tetrahydrobenzo[d]oxepin-7-yl)oxy)piperidin-1-yl)-6,7-dihydro-5H-pyrrolo[3,4-b]pyridin-5-one | 394 |

Example 322

Examples 323A and 323B

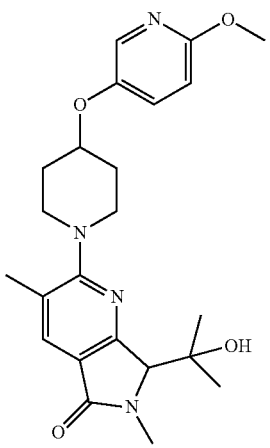

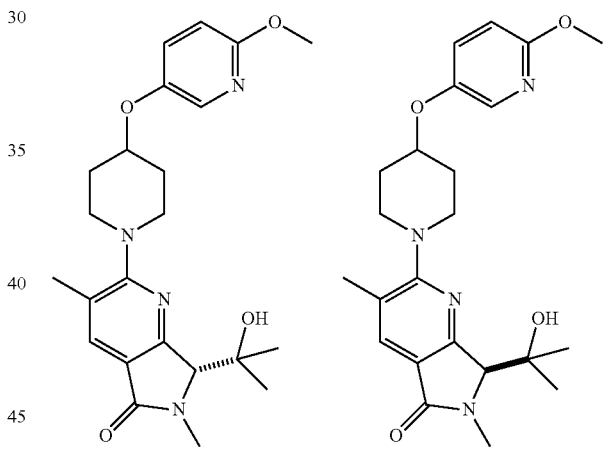

7-(2-Hydroxypropan-2-yl)-2-(4-((6-methoxypyridin-3-yl)oxy)piperidin-1-yl)-3,6-dimethyl-6,7-dihydro-5H-pyrrolo[3,4-b]pyridin-5-one (Scheme 32)

To a solution of 2-(4-((6-methoxypyridin-3-yl)oxy)piperidin-1-yl)-3,6-dimethyl-6,7-dihydro-5H-pyrrolo[3,4-b]pyridin-5-one (30 mg, 0.081 mmol, Example 18) in THF (5 mL) was added LDA (2 M, 0.081 mL, 0.163 mmol) at −78° C. under an atmosphere of nitrogen. After 5 min, propan-2-one (5.20 mg, 0.090 mmol) was added to the reaction and the mixture was allowed to warm to RT and was aged for 1 h. The mixture was concentrated and purified by reverse phase HPLC (ACN/water with 0.05% $NH_3OH$ modifier) to yield the title compound. MS: 427 (M+1). $^1H$ NMR (400 MHz, $CDCl_3$): δ 7.84 (1H, d, J=2.8 Hz), 7.77 (1H, s), 7.24 (1H, dd, J=8.4, 2.4 Hz), 6.68 (1H, d, J=8.4 Hz), 5.32 (1H, s), 4.30-4.40 (1H, m), 4.15 (1H, s), 3.88 (3H, s), 3.42-3.60 (2H, m), 3.19 (3H, s), 3.06-3.18 (2H, m), 2.33 (3H, s), 2.05-2.15 (2H, m), 1.86-2.02 (2H, m), 1.44 (3H, s), 0.83 (3H, s).

(R)-7-(2-Hydroxypropan-2-yl)-2-(4-((6-methoxpyridin-3-yl)oxy)piperidin-1-yl)-3,6-dimethyl-6,7-dihydro-5H-pyrrolo[3,4-b]pyridin-5-one and (S)-7-(2-hydroxypropan-2-yl)-2-(4-((6-methoxypyridin-3-yl)oxy)piperidin-1-yl)-3,6-dimethyl-6,7-dihydro-5H-pyrrolo[3,4-b]pyridin-5-one (Scheme 32)

7-(Hydroxymethyl)-2-(4-((6-methoxypyridin-3-yl)oxy)piperidin-1-yl)-3-methyl-6,7-dihydro-5H-pyrrolo[3,4-b]pyridin-5-one (Example 322) from the procedure for Example 322 (vide supra) was resolved by chiral SFC (AD column, 30% $EtOH/CO_2$) to afford isomer 323A (faster eluting): MS: 379 (M+1). $^1H$ NMR (500 MHz, methanol-$d_4$): δ 7.83 (1H, d, J=3.2 Hz), 7.73 (1H, s), 7.42 (1H, dd, J=8.8, 3.2 Hz), 6.75 (1H, d, J=8.8 Hz), 4.45-4.55 (1H, m), 4.29 (1H, s), 3.85 (3H, s), 3.48-3.63 (2H, m), 3.07-3.33 (5H, m), 2.36 (3H, s), 2.07-2.17 (2H, m), 1.77-1.97 (2H, m), 1.59 (3H, s), 0.81 (3H, s). Isomer 323B (slower eluting): MS: 379

(M+1). ¹H NMR (500 MHz, methanol-d₄): δ 7.83 (1H, d, J=2.8 Hz), 7.73 (1H, s), 7.42 (1H, dd, J=8.8, 2.8 Hz), 6.75 (1H, d, J=8.8 Hz), 4.45-4.55 (1H, m), 4.29 (1H, s), 3.85 (3H, s), 3.48-3.63 (2H, m), 3.07-3.33 (5H, m), 2.36 (3H, s), 2.07-2.17 (2H, m), 1.77-1.97 (2H, m), 1.59 (3H, s), 0.81 (3H, s).

Example 324

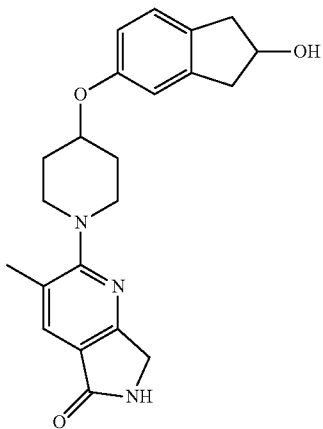 [SMILES: Cc1cc2c(nc1N1CCC(Oc3ccc4c(c3)CC(O)C4)CC1)CNC2=O]

2-(4-((2-Hydroxy-2,3-dihydro-1H-inden-5-yl)oxy) piperidin-1-yl)-3-methyl-6,7-dihydro-5H-pyrrolo[3,4-b]pyridin-5-one (Scheme 33)

Step 1: Methyl 6-(4-((2-(benzyloxy)-2,3-dihydro-1H-inden-5-yl)oxy)piperidin-1-yl)-2-cyano-5-methylnicotinate To a solution of methyl 6-chloro-2-cyano-5-methylnicotinate (20.51 mg, 0.097 mmol, intermediate A1) in N-methyl-2-pyrrolidinone (0.5 mL) was added 4-((2-(benzyloxy)-2,3-dihydro-1H-inden-5-yl)oxy)piperidine (21 mg, 0.065 mmol) and DIPEA (0.034 mL, 0.195 mmol). The reaction was heated at 80° C. for 15 h. The mixture was cooled to RT and partitioned with water and EtOAc. The organic layer was dried over anhydrous sodium sulfate, filtered, and concentrated to yield the title compound, which was used directly without further purification. MS: 498 (M+1).

Step 2: 2-(4-((2-(Benzyloxy)-2,3-dihydro-1H-inden-5-yl)oxy)piperidin-1-yl)-3-methyl-6,7-dihydro-5H-pyrrolo[3,4-b]pyridin-5-one A mixture of methyl 6-(4-((2-(benzyloxy)-2,3-dihydro-1H-inden-5-yl)oxy)piperidin-1-yl)-2-cyano-5-methylnicotinate (32 mg, 0.064 mmol) and Raney® nickel (5.51 mg, 0.064 mmol) in methanol (1 mL) was degassed and placed under a hydrogen atmosphere (45 psi). The mixture was stirred at 25° C. for 2 h. The mixture was filtered through a celite pad and the filtrate was concentrated to yield the title compound, which was used directly without further purification. MS: 470 (M+1).

Step 3: 2-(4-((2-Hydroxy-2,3-dihydro-1H-inden-5-yl)oxy)piperidin-1-yl)-3-methyl-6,7-dihydro-5H-pyrrolo[3,4-b]pyridin-5-one A mixture of 2-(4-((2-(benzyloxy)-2,3-dihydro-1H-inden-5-yl)oxy)piperidin-1-yl)-3-methyl-6,7-dihydro-5H-pyrrolo[3,4-b]pyridin-5-one (25 mg, 0.053 mmol) and Pd/C (10%, 56.7 mg, 0.053 mmol) in methanol (10 mL) was degassed and placed under a hydrogen atmosphere (45 psi). The mixture was stirred at 45° C. for 3 h. The mixture was cooled to RT, filtered and concentrated to dryness. The residue was purified by reverse phase HPLC (ACN/water with 0.1% NH₃OH modifier) to afford the title compound. MS: 380 (M+1). ¹H NMR (400 MHz, CDCl₃): δ 7.80 (1H, s), 7.15 (1H, d, J=7.6 Hz), 6.86 (1H, s), 6.79 (1H, d, J=8.0 Hz), 6.28 (1H, br s), 4.70-4.75 (1H, m), 4.46-4.50 (1H, m), 4.36 (2H, s), 3.52-3.62 (2H, m), 3.14-3.25 (4H, m), 2.88 (2H, td, J=10.8, 4.8 Hz), 2.36 (3H, s), 2.10-2.25 (2H, m), 1.89-2.02 (2H, m).

Examples 324A and 324B

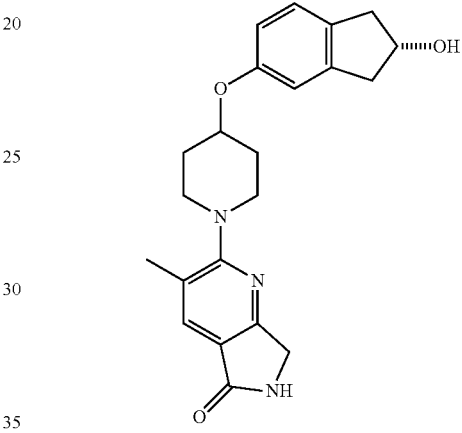

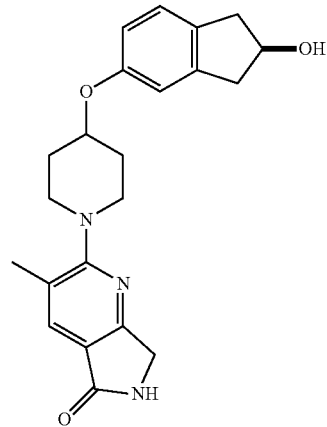

(S)-2-(4-((2-Hydroxy-2,3-dihydro-1H-inden-5-yl)oxy)piperidin-1-yl)-3-methyl-6,7-dihydro-5H-pyrrolo[3,4-b]pyridin-5-one and (R)-2-(4-((2-hydroxy-2,3-dihydro-1H-inden-5-yl)oxy)piperidin-1-yl)-3-methyl-6,7-dihydro-5H-pyrrolo[3,4-b]pyridin-5-one (Scheme 33)

2-(4-((2-Hydroxy-2,3-dihydro-1H-inden-5-yl)oxy)piperidin-1-yl)-3-methyl-6,7-dihydro-5H-pyrrolo[3,4-b]pyridin-5-one was resolved by chiral SFC (OJ column, 40% EtOH with 0.1% NH₃ modifier/CO₂) to afford isomer 324A (faster eluting, S-isomer): MS: 380 (M+1). ¹H NMR (400 MHz, CDCl₃): δ 7.80 (1H, s), 7.14 (1H, d, J=8.0 Hz), 6.86 (1H, s), 6.79 (1H, d, J=8.0 Hz), 6.26 (1H, br s), 4.72 (1H, br s), 4.43-4.53 (1H, m), 4.36 (2H, s), 3.55-3.58 (2H, m), 3.12-3.22 (4H, m), 2.81-2.94 (2H, m), 2.36 (3H, s), 2.07-2.18 (2H, m), 1.90-2.01 (2H, m). Isomer 324B (slower eluting, R-isomer): MS: 380 (M+1). ¹H NMR (400 MHz, CDCl₃): δ 7.80 (1H, s), 7.15 (1H, d, J=8.0 Hz), 6.86 (1H, s), 6.79 (1H, d, J=8.0 Hz), 4.72 (1H, br s), 4.49 (1H, br s), 4.36 (2H, s), 3.51-3.63 (2H, m), 3.13-3.25 (4H, m), 2.81-2.94 (2H, m), 2.36 (3H, s), 2.12 (2H, s), 1.90-2.01 (2H, m).

Examples 324C and 324D

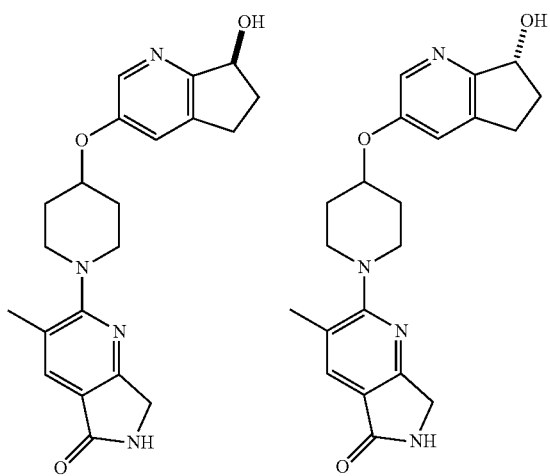 [SMILES: Cc1cc2c(nc1N1CCC(Oc3cnc4c(c3)CC[C@@H]4O)CC1)CNC2=O ; Cc1cc2c(nc1N1CCC(Oc3cnc4c(c3)CC[C@H]4O)CC1)CNC2=O]

(S)-2-(4-((7-Hydroxy-6,7-dihydro-5H-cyclopenta[b]pyridin-3-yl)oxy)piperidin-1-yl)-3-methyl-6,7-dihydro-5H-pyrrolo[3,4-b]pyridin-5-one and (R)-2-(4-((7-hydroxy-6,7-dihydro-5H-cyclopenta[b]pyridin-3-yl)oxy)piperidin-1-yl)-3-methyl-6,7-dihydro-5H-pyrrolo[3,4-b]pyridin-5-one (Scheme 33)

Step 1: Methyl 6-(4-((7-((tert-butyldimethylsilyl)oxy)-6,7-dihydro-5H-cyclopenta[b]pyridin-3-yl)oxy)piperidin-1-yl)-2-cyano-5-methylnicotinate To a solution of methyl 6-chloro-2-cyano-5-methylnicotinate (34.8 mg, 0.165 mmol) in DMF (5 mL) was added 7-((tert-butyldimethylsilyl)oxy)-3-(piperidin-4-yloxy)-6,7-dihydro-5H-cyclopenta[b]pyridine (60 mg, 0.138 mmol) and TEA (0.058 mL, 0.413 mmol) at RT. The reaction was then heated 80° C. for 2 h before cooling to RT and quenching with water (50 mL). The mixture was extracted with EtOAc (3×30 mL) and the combined organic layer were dried over anhydrous sodium sulfate, filtered and concentrated in vacuo. The residue was purified by silica gel chromatography (1:3 petroleum ether:THF) to give the title compound.

Step 2: 2-(4-((7-((tert-Butyldimethylsilyl)oxy)-6,7-dihydro-5H-cyclopenta[b]pyridin-3-yl)oxy)piperidin-1-yl)-3-methyl-6,7-dihydro-5H-pyrrolo[3,4-b]pyridin-5-one To a solution of methyl 6-(4-((7-((tert-butyldimethylsilyl)oxy)-6,7-dihydro-5H-cyclopenta[b]pyridin-3-yl)oxy)piperidin-1-yl)-2-cyano-5-methylnicotinate (40 mg, 0.077 mmol) in MeOH (10 mL) was added nickel (4.49 mg, 0.077 mmol) and ammonium hydroxide (0.5 mL). The system was stirred under 50 psi under an hydrogen atmosphere at 25° C. for 3 h. The mixture was filtered and the filtrate was concentrated in vacuo to provide the title compound.

Step 3: (S)-2-(4-((7-Hydroxy-6,7-dihydro-5H-cyclopenta[b]pyridin-3-yl)oxy)piperidin-1-yl)-3-methyl-6,7-dihydro-5H-pyrrolo[3,4-b]pyridin-5-one and (R)-2-(4-((7-hydroxy-6,7-dihydro-5H-cyclopenta[b]pyridin-3-yl)oxy)piperidin-1-yl)-3-methyl-6,7-dihydro-5H-pyrrolo[3,4-b]pyridin-5-one In a solution of 2-(4-((7-((tert-butyldimethylsilyl)oxy)-6,7-dihydro-5H-cyclopenta[b]pyridin-3-yl)oxy)piperidin-1-yl)-3-methyl-6,7-dihydro-5H-pyrrolo[3,4-b]pyridin-5-one (25 mg, 0.051 mmol) in THF (3 mL) was added TBAF (1 mL, 1.0 mmol) and stirred at RT for 1 h. The mixture was diluted with water (30 mL) and extracted with EtOAc (3×30 mL) and the combined organic layers were washed with brine (30 mL), dried over sodium sulfate, filtered, and concentrated in vacuo. The residue was purified by prep-TLC (10% MeOH in DCM) to give racemic product which was resolved by chiral SFC (AD column, 50% EtOH/CO₂) to afford isomer 324C (faster eluting): MS: 381 (M+1). ¹H NMR (400 MHz, CDCl₃): δ 8.10 (s, 1H), 7.74 (s, 1H), 7.08 (s, 1H), 5.90 (s, 1H), 5.05-5.19 (m, 1H), 4.46-4.48 (m, 1H), 4.29 (s, 2H), 3.45-3.55 (m, 2H), 3.10-3.20 (m, 2H), 2.92-3.03 (m, 2H), 2.45-2.55 (m, 2H), 2.29 (s, 3H), 2.14-1.85 (m, 4H). Isomer 324D (slower eluting): MS: 381 (M+1). ¹H NMR (400 MHz, CDCl₃): δ 8.09 (s, 1H), 7.74 (s, 1H), 7.08 (s, 1H), 6.01 (s, 1H), 5.05-5.19 (m, 1H), 5.43-5.53 (m, 1H), 4.29 (s, 2H), 3.45-3.55 (m, 2H), 3.10-3.20 (m, 2H), 2.92-3.03 (m, 2H), 2.45-2.55 (m, 2H), 2.29 (s, 3H), 2.14-1.85 (m, 4H).

Example 324E

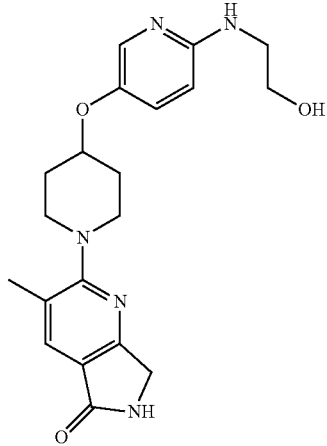 [SMILES: Cc1cc2c(nc1N1CCC(Oc3ccc(NCCO)nc3)CC1)CNC2=O]

2-(4-((6-((2-Hydroxyethyl)amino)pyridin-3-yl)oxy)piperidin-1-yl)-3-methyl-6,7-dihydro-5H-pyrrolo[3,4-b]pyridin-5-one (Scheme 33)

Step 1: Methyl 6-(4-((6-((2-(benzyloxy)ethyl)amino)pyridin-3-yl)oxy)piperidin-1-yl)-2-cyano-5-methylnicotinate To a solution of methyl 6-chloro-2-cyano-5-methylnicotinate (77 mg, 0.367 mmol, intermediate A1) and N-(2-(benzyloxy)ethyl)-5-(piperidin-4-yloxy)pyridin-2-amine (80 mg, 0.244 mmol, intermediate O) in DMF (5 mL) was added DIPEA (0.21 mL, 1.22 mmol). The reaction mixture was stirred at 80° C. for 15 h. The solvent was evaporated under reduced pressure and purified by silica gel chromatography (0-50% EtOAc/petroleum ether) to give the title compound. MS: 502 (M+1).

Step 2: 2-(4-((6-((2-(Benzyloxy)ethyl)amino)pyridin-3-yl)oxy)piperidin-1-yl)-3-methyl-6,7-dihydro-5H-pyrrolo[3,4-b]pyridin-5-one To a solution of methyl 6-(4-((6-((2-(benzyloxy)ethyl)amino)pyridin-3-yl)oxy)piperidin-1-yl)-2-cyano-5-methylnicotinate (100 mg, 0.199 mmol) in MeOH (15 mL) was added nickel (5.85 mg, 0.10 mmol). The reaction was stirred at 15° C. for 3 h under an atmosphere of hydrogen (50 psi). The mixture was filtered and solvent was evaporated under reduced pressure to give the title compound, which was used to next step without further purification. MS: 474 (M+1).

Step 3: 2-(4-((6-((2-Hydroxyethyl)amino)pyridin-3-yl)oxy)piperidin-1-yl)-3-methyl-6,7-dihydro-5H-pyrrolo[3,4-b]pyridin-5-one To a solution of 2-(4-((6-((2-(benzyloxy)ethyl)amino)pyridin-3-yl)oxy)piperidin-1-yl)-3-methyl-6,7-dihydro-5H-pyrrolo[3,4-b]pyridin-5-one (90 mg, 0.190 mmol) in MeOH (15 mL) was added Pd/C (20.2 mg, 0.019 mmol, 10%). The reaction was stirred at 15° C. for 15 h under an atmosphere of hydrogen (30 psi). The mixture wacaniltered and concentrated before being purified by reverse phase HPLC (ACN/water with 0.1% TFA modifier) to yield the title compound. MS: 384 (M+1). $^1$H NMR (400 MHz, methanol-$d_4$): δ 7.74-7.83 (2H, m), 7.56 (1H, s), 7.10 (1H, d, J=9.78 Hz), 4.47-4.59 (1H, m), 4.33 (s, 2H), 3.80 (2H, t, J=4.89 Hz), 3.52-3.62 (2H, m), 3.49 (2H, t, J=4.89 Hz), 3.19-3.23 (2H, m), 2.38 (3H, s), 2.10-2.22 (2H, m), 1.85-1.99 (2H, m).

Example 325

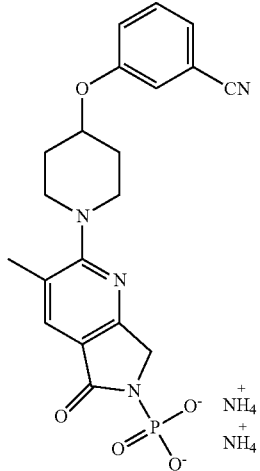

Ammonium (2-(4-(3-cyanophenoxy)piperidin-1-yl)-3-methyl-5-oxo-5,7-dihydro-6H-pyrrolo[3,4-b]pyridin-6-yl)phosphonate (Scheme 34)

Step 1: Diethyl (2-(4-(3-cyanophenoxy)piperidin-1-yl)-3-methyl-5-oxo-5,7-dihydro-6H-pyrrolo[3,4-b]pyridin-6-yl)phosphonate To a solution of 3-((1-(3-methyl-5-oxo-6,7-dihydro-5H-pyrrolo[3,4-b]pyridin-2-yl)piperidin-4-yl)oxy)benzonitrile (0.348 g, 4.02 mmol, Example 3) and diethyl phosphorochloridate (173 mg, 4.82 mmol) in THF (10 mL) was added NaH (60%, 24 mg, 4.82 mmol) at RT. The reaction was stirred at RT under an atmosphere of nitrogen for 15 h before quenching with saturated, aqueous ammonium chloride (10 mL) and partitioning with EtOAc (50 mL×3). The combined organic layers were dried over anhydrous sodium sulfate, filtered and concentrated. The residue was purified by silica gel chromatography (10:1 to 2:3 petroleum ether:EtOAc) to yield the title compound. MS: 485 (M+1).

Step 2: Ammonium (2-(4-(3-cyanophenoxy)piperidin-1-yl)-3-methyl-5-oxo-5,7-dihydro-6H-pyrrolo[3,4-b]pyridin-6-yl)phosphonate To a solution of diethyl (2-(4-(3-cyanophenoxy)piperidin-1-yl)-3-methyl-5-oxo-5H-pyrrolo[3,4-b]pyridin-6(7H)-yl)phosphonate (300 mg, 0.619 mmol) in dry MeCN (5 mL) was added TMS-Br (0.402 mL, 3.10 mmol). The reaction was stirred at 60° C. for 2 h under a nitrogen atmosphere. The volatiles were removed in vacuo and the residue was treated with MeCN (5 mL) and Et$_3$N (0.25 mL) and then concentrated again. The residue was purified by reverse phase HPLC (ACN/water with 0.05% NH$_3$OH modifier) to afford the title compound. MS: 429 (M+1). $^1$H NMR (400 MHz, CDCl$_3$): δ 7.77 (1H, s), 7.46 (1H, t, J=8.0), 7.35 (1H, s), 7.27-7.32 (2H, m), 4.69-4.75 (1H, m), 4.57 (2H, s), 3.56-3.65 (2H, m), 3.22-3.27 (2H, m), 2.37 (3H, s), 2.10-2.19 (2H, m), 1.85-1.95 (2H, m).

Example 326

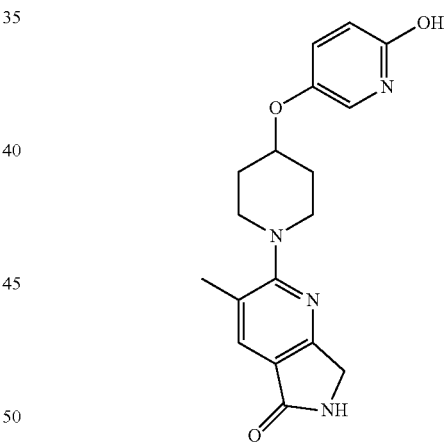

2-(4-((6-Hydroxypyridin-3-yl)ox)piperidin-1-yl)-3-methyl-6,7-dihydro-5H-pyrrolo[3,4-b]pyridin-5-one (Scheme 35)

To 2-(4-((6-methoxypyridin-3-yl)oxy)piperidin-1-yl)-3-methyl-6,7-dihydro-5H-pyrrolo[3,4-b]pyridin-5-one (50 mg, 0.141 mmol, Example 1) in chloroform (564 µL) was added iodotrimethylsilane (60.2 µL, 0.423 mmol) dropwise at RT. The reaction was heated to 70° C. for 3 h and was then cooled to RT before the volatiles were removed under reduced pressure. The residue was purified by mass-directed reverse phase HPLC (ACN/water with 0.1% NH$_3$OH modifier) to afford the title compound. MS: 341 (M+1). $^1$H NMR (500 MHz, DMSO-$d_6$): δ 8.33 (1H, s), 7.72 (1H, s), 7.47

(1H, d, J=9.64 Hz), 7.34 (1H, s), 6.47 (1H, d, J=9.59 Hz), 4.32 (1H, m), 4.24 (2H, s), 3.47 (2H, br s), 3.05 (2H, t, J=10.86 Hz), 2.30 (3H, s), 2.02 (2H, br s), 1.73 (2H, d, J=11.08 Hz).

Example 327

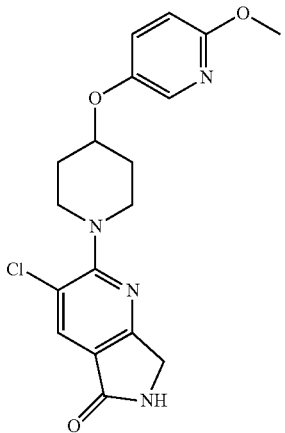 [SMILES: COc1ccc(OC2CCN(c3nc4c(cc3Cl)C(=O)NC4)CC2)cn1]

3-Chloro-2-(4-((6-methoxypyridin-3-yl)ox)piperidin-1-yl)-6,7-dihydro-5H-pyrrolo[3,4-b]pyridin-5-one (Scheme 36)

Step 1: Methyl 2-fluoro-6-(4-((6-methoxypyridin-3-yl)oxy)piperidin-1-yl)nicotinate To a solution of 2-methoxy-5-(piperidin-4-yloxy)pyridine hydrochloride (1.55 g, 6.35 mmol, intermediate F1) in DMF (8 mL) was added methyl 2,6-difluoronicotinate (1.0 g, 5.78 mmol) at RT. The mixture was cooled to 0° C., before N-ethyl-N-isopropylpropan-2-amine (2.24 g, 17.3 mmol) was added. The reaction mixture was allowed to warm to RT and was stirred 18 h before diluting with EtOAc (30 mL) and water (30 mL). The aqueous layer was extracted with EtOAc (30 mL×3) and the combined the organic layers were washed with brine (30 mL×4), dried over anhydrous sodium sulfate and filtered. The filtrate was concentrated and purified by silica gel column chromatography (2/1 petroleum ether/EtOAc) to yield the title compound. MS: 362 (M+1).

Step 2: Methyl 5-chloro-2-fluoro-6-(4-((6-methoxypyridin-3-yl)oxy)piperidin-1-yl)nicotinate In a 20 mL schlenk tube was prepared a stirred solution of methyl 2-fluoro-6-(4-((6-methoxypyridin-3-yl)oxy)piperidin-1-yl)nicotinate (200 mg, 0.553 mmol) in CHCl₃ (4 mL). 1-Chloropyrrolidine-2,5-dione (81 mg, 0.609 mmol) was added and the reaction mixture was stirred for 4 h at 80° C. The reaction was cooled and concentrated in vacuo and residue was purified by silica gel column chromatography (3/1 petroleum ether/EtOAc) to give the title compound. MS: 396 (M+1).

Step 3: 5-Chloro-2-cyano-6-(4-((6-methoxypyridin-3-yl)oxy)piperidin-1-yl)nicotinic acid To a solution of methyl 5-chloro-2-fluoro-6-(4-((6-methoxypyridin-3-yl)oxy)piperidin-1-yl)nicotinate (240 mg, 0.606 mmol) in DMSO (5 mL) was added sodium cyanide (44.6 mg, 0.910 mmol). The mixture was stirred at 80° C. for 16 h. After cooling to RT, the mixture was diluted with EtOAc (30 mL) and water (30 mL). The aqueous layer was extracted with EtOAc (30 mL×3) and the combined the organic layers were washed with brine (30 mL×4), dried over anhydrous sodium sulfate and filtered. The filtrate was concentrated and was used to the next step without further purification. MS: 389 (M+1).

Step 4: Methyl 5-chloro-2-cyano-6-(4-((6-methoxypyridin-3-yl)oxy)piperidin-1-yl)nicotinate To a solution of 5-chloro-2-cyano-6-(4-((6-methoxypyridin-3-yl)oxy)piperidin-1-yl)nicotinic acid (100 mg, 0.257 mmol) in DMF (5 mL) was added potassium carbonate (71.1 mg, 0.514 mmol) and iodomethane (43.8 mg, 0.309 mmol). The mixture was stirred for 3H at Rt. Before diluting with EtOAc (30 mL) and water (30 mL). The aqueous layer was extracted with EtOAc (30 mL×3) and the combined the organic layers were washed with brine (30 mL×4), dried over anhydrous magnesium sulfate and filtered. The filtrate concentrated was used without further purification. MS: 403 (M+1).

Step 5: 3-Chloro-2-(4-((6-methoxypyridin-3-yl)oxy)piperidin-1-yl)-6,7-dihydro-5H-pyrrolo[3,4-b]pyridin-5-one To a solution of methyl 5-chloro-2-cyano-6-(4-((6-methoxypyridin-3-yl)oxy)piperidin-1-yl)nicotinate (50 mg, 0.099 mmol) in MeOH (20 mL) was added molybdenum promoted nickel (skeletal) (15.36 mg, 0.099 mmol). The suspension was degassed and purged with hydrogen several times. The mixture was stirred at 20° C. for 3 h under an atmosphere of hydrogen (50 psi). After placing the system under an atmosphere of nitrogen, the suspension was filtered and the filtrate was concentrated, the residue was purified HPLC (ACN/water with 0.1% NH₃OH modifier) to provide the title compound. MS: 375 (M+1). ¹H NMR (400 MHz, methanol-d₄): δ 7.95 (1H, s), 7.82 (1H, d, J=2.8 Hz), 7.42 (1H, dd, J=8.8, 2.8 Hz), 6.74 (1H, d, J=9.2 Hz), 4.49-4.53 (1H, m), 4.34 (2H, s), 3.84 (3H, s), 3.75-3.82 (2H, m), 3.34-3.42 (2H, m), 2.02-2.15 (2H, m), 1.78-1.94 (2H, m).

Example 328

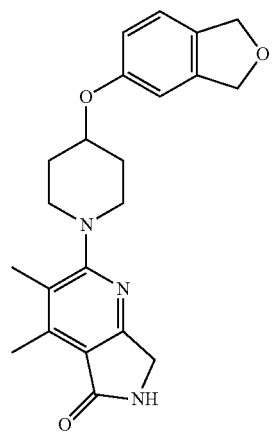 [SMILES: Cc1c(N2CCC(Oc3ccc4c(c3)COC4)CC2)nc2c(c1C)C(=O)NC2]

2-(4-((1,3-Dihydro-2-benzofuran-5-yl)oxy)piperidin-1-yl)-3,4-dimethyl-6,7-dihydro-5H-pyrrolo[3,4-b]pyridin-5-one (Scheme 37)

Step 1: Dimethyl 2-cyano-6-(4-((1,3-dihydro-2-benzofuran-5-yl)oxy)piperidin-1-yl)-5-methylpyridine-3,4-dicarboxylate To a solution of dimethyl 6-chloro-2-cyano-5-methylpyridine-3,4-dicarboxylate (2.8 g, 10.4 mmol) in DMF (20 mL) was added 4-((1,3-dihydro-2-benzofuran-5-yl)oxy)piperidine hydrochloride (4.0 g, 15.6 mmol) and triethylamine (3.16 g, 31.3 mmol) under an atmosphere of nitrogen. The reaction was heated to 80° C. with stirring for 2 h before the mixture was cooled to RT and quenched with water (50 mL). After extracting with EtOAc (30 mL×3), the combined organic layers were dried over anhydrous sodium sulfate, filtered and the filtrate was concentrated in vacuo. The residue was purified by silica gel chromatography (3:1 petroleum ether:EtOAc) to provide the title compound. MS: 452 (M+1).

Step 2: Methyl 2-(4-((1,3-dihydro-2-benzofuran-5-yl)oxy)piperidin-1-yl)-3-methyl-5-oxo-6,7-dihydro-5H-pyrrolo[3,4-b]pyridine-4-carboxylate To a solution of dimethyl 2-cyano-6-(4-((1,3-dihydro-2-benzofuran-5-yl)oxy)piperidin-1-yl)-5-methylpyridine-3,4-dicarboxylate (4.4 g, 8.77 mmol) in MeOH (100 mL) and THF (5 mL) was added Raney® nickel (0.515 g, 8.77 mmol) and ammonium hydroxide (5 mL). The reaction was stirred at 30° C. for 3 h under 50 psi of hydrogen. The mixture was filtered and the filtrate was concentrated in vacuo to afford the title compound. MS: 424 (M+1).

Step 3. 2-(4-((1,3-Dihydro-2-benzofuran-5-yl)oxy)piperidin-1-yl)-4-(hydroxymethyl)-3-methyl-6,7-dihydro-5H-pyrrolo[3,4-b]pyridin-5-one To a solution of methyl 2-(4-((1,3-dihydro-2-benzofuran-5-yl)oxy)piperidin-1-yl)-3-methyl-5-oxo-6,7-dihydro-5H-pyrrolo[3,4-b]pyridine-4-carboxylate (4.0 g, 9.45 mmol) in THF (50 mL) was added LiBH$_4$ (0.617 g, 28.3 mmol) at 30° C. for 16 h. The reaction mixture was quenched with water (100 mL) and extracted with EtOAc (100 mL×3), the organic layers were dried over anhydrous sodium sulfate, filtered and the filtrate was concentrated in vacuo to give the title compound. MS: 396 (M+1).

Step 4: 2-(4-((1,3-Dihydro-2-benzofuran-5-yl)oxy)piperidin-1-yl)-3,4-dimethyl-6,7-dihydro-5H-pyrrolo[3,4-b]pyridin-5-one To a solution of 2-(4-((1,3-dihydro-2-benzofuran-5-yl)oxy)piperidin-1-yl)-4-(hydroxymethyl)-3-methyl-6,7-dihydro-5H-pyrrolo[3,4-b]pyridin-5-one (4.0 g, 10.12 mmol) in AcOH (70 mL) was added zinc (1.98 g, 30.3 mmol) at 100° C. for 16 h. The reaction mixture was filtered and the filtrate was concentrated in vacuo. The material was dissolved in 10% MeOH in DCM to load onto a column for purification by silica gel chromatography (5-35% 3:1 EtOAc:EtOH in hexanes with 1% NH$_4$OH modifier) to afford the title compound. MS: 380 (M+1). $^1$H NMR (300 MHz, DMSO-d$_6$): δ 8.29 (1H, s), 6.17-6.19 (1H, m), 6.87-6.94 (2H, m), 4.91-4.93 (4H, m), 4.54 (1H, s), 4.15 (2H, s), 3.30-3.38 (2H, m), 2.98-3.04 (2H, m), 2.47-2.49 (3H, m), 2.16 (3H, s), 2.03-2.07 (2H, m), 1.72-1.78 (2H, m),

Examples 329A and 329B

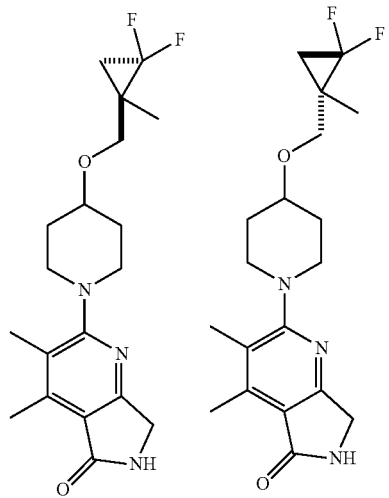

(R)-2-(4-((2,2-Difluoro-1-methylcyclopropyl)methoxy)piperidin-1-yl)-3,4-dimethyl-6,7-dihydro-5H-pyrrolo[3,4-b]pyridin-5-one and (S)-2-(4-((2,2-difluoro-1-methylcyclopropyl)methoxy)piperidin-1-yl)-3,4-dimethyl-6,7-dihydro-5H-pyrrolo[3,4-b]pyridin-5-one (Scheme 37)

Step 1: Methyl 2-cyano-6-(4-((2,2-difluoro-1-methylcyclopropyl)methoxy)piperidin-1-yl)-4-methylnicotinate 4-((2,2-Difluoro-1-methylcyclopropyl)methoxy)piperidine (205 mg, 1.0 mmol) and methyl 6-chloro-2-cyano-4-methylnicotinate (211 mg, 1.0 mmol) were added to a flask and was dissolved in NMP (3 mL). DIPEA (0.524 mL, 3.0 mmol) was then added and the system was sealed and heated to 80° C. for 2 h. After cooling to RT, the reaction was partitioned between water and ethyl acetate. The organic layer was washed twice more with water and then with brine, dried over anhydrous sodium sulfate, filtered and concentrated. The residue was purified on a silica gel column eluting with 10-50% EtOAc in hexanes to afford the title product. MS: 380 (M+1).

Step 2: 2-(4-((2,2-Difluoro-1-methylcyclopropyl)methoxy)piperidin-1-yl)-4-methyl-6,7-dihydro-5H-pyrrolo[3,4-b]pyridin-5-one Methyl 2-cyano-6-(4-((2,2-difluoro-1-methylcyclopropyl)methoxy)piperidin-1-yl)-4-methylnicotinate (303 mg, 0.80 mmol) was dissolved in 2,2,2-trifluoroethanol (4 mL) and AcOH (0.14 mL, 2.4 mmol). The system was evacuated and charged with nitrogen before 10% Pd/C (85 mg, 0.08 mmol) was added. The system was evacuated and charged with hydrogen and was stirred for 3 h. The reaction was placed under nitrogen and then filtered (celite) and the filtrate was concentrated. Toluene was used to azeotrope remaining AcOH before the residue was dissolved in MeOH (4 mL) and TEA (0.83 mL, 6.0 mmol). After stirring the mixture at RT for 15 h, the reaction was concentrated and the residue was purified by silica gel chromatography (0-30% 3:1 EtOAc:EtOH in DCM) to provide the title compound. MS: 352 (M+1).

Step 3: 3-Bromo-2-(4-((2,2-difluoro-1-methylcyclopropyl)methoxy)piperidin-1-yl)-4-methyl-6,7-dihydro-5H-pyrrolo[3,4-b]pyridin-5-one 2-(4-((2,2-Difluoro-1-methylcyclopropyl)methoxy)piperidin-1-yl)-4-methyl-6,7-dihydro-5H-pyrrolo[3,4-b]pyridin-5-one (269 mg, 0.766 mmol) was suspended in 5 mL DCE. NBS (150 mg, 0.842 mmol) was added and the reaction was stirred for 15 h at RT. The material was directly purified by silica gel chromatography (10-50% 3:1 EtOAc: EtOH in hexanes) to give the title compound. M®430, 432 (M+1).

Step 4: (R)-2-(4-((2,2-Difluoro-1-methylcyclopropyl)methoxy)piperidin-1-yl)-3,4-dimethyl-6,7-dihydro-5H-pyrrolo[3,4-b]pyridin-5-one and (S)-2-(4-((2,2-difluoro-1-methylcyclopropyl)methoxy)piperidin-1-yl)-3,4-dimethyl-6,7-dihydro-5H-pyrrolo[3,4-b]pyridin-5-one 3-Bromo-2-(4-((2,2-difluoro-1-methylcyclopropyl)methoxy)piperidin-1-yl)-4-methyl-6,7-dihydro-5H-pyrrolo[3,4-b]pyridin-5-one (100 mg, 0.232 mmol) was suspended in 1,4-dioxane (2 mL). The addition of methylzinc chloride (2 M in THF, 0.58 mL, 1.16 mmol) was followed by Pd(Ph$_3$P)$_4$ (13.4 mg, 0.012 mmol). The system was sealed and then heated to 80° C. with stirring for 3 h. The reaction was then cooled in an ice bath and quenched by the dropwise addition of MeOH (1 mL). The volatiles were removed and the residue was directly purified by silica gel chromatography (20% 3:1 EtOAc:EtOH in hexanes) to afford the racemate. Resolution was carried out by chiral SFC (Lux-Amylose-1 AD-H, 15% MeOH/CO$_2$) to afford isomer 329A (faster eluting): MS: 366 (M+1). $^1$H NMR (500 MHz, CDCl$_3$): δ 5.91 (br s, 1H), 4.34 (br s, 2H), 3.50 (m, 5H), 3.02 (br s, 2H), 2.64 (s, 3H), 2.23 (s, 3H), 2.03 (br s, 2H), 1.77 (br s, 2H), 1.26 (s, 3H), 1.18 (m, 1H), 1.08 (m, 1H). Isomer 324D (slower eluting): MS: 366 (M+1). $^1$H NMR (500 MHz, CDCl$_3$): δ 5.91 (br s, 1H), 4.34 (br s, 2H), 3.50 (m, 5H), 3.02 (br s, 2H), 2.64 (s, 3H), 2.23 (s, 3H), 2.03 (br s, 2H), 1.77 (br s, 2H), 1.26 (s, 3H), 1.18 (m, 1H), 1.08 (m, 1H).

The following examples in table 37 were prepared according to scheme 37 using the procedure and conditions outlined in the synthesis of Examples 328, 329A and 329B, from prepared or known starting materials.

TABLE 37

| Example | Structure | Name | MS (M + 1) |
|---|---|---|---|
| 330 | 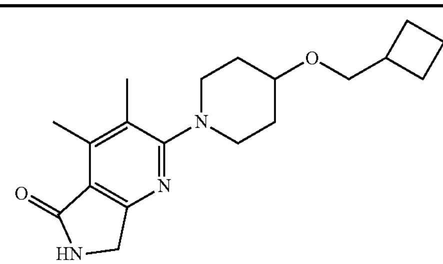 | 2-(4-(cyclobutylmethoxy)piperidin-1-yl)-3,4-dimethyl-6,7-dihydro-5H-pyrrolo[3,4-b]pyridin-5-one | 330 |
| 331 | 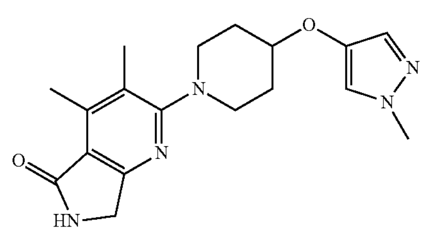 [SMILES: Cc1c(N2CCC(Oc3cnn(C)c3)CC2)nc2c(c1C)C(=O)NC2] | 3,4-dimethyl-2-(4-((1-methyl-1H-pyrazol-4-yl)oxy)piperidin-1-yl)-6,7-dihydro-5H-pyrrolo[3,4-b]pyridin-5-one | 342 |
| 332 | 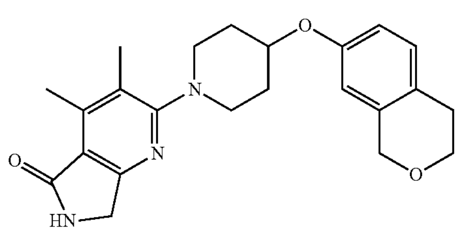 [SMILES: Cc1c(N2CCC(Oc3ccc4c(c3)COCC4)CC2)nc2c(c1C)C(=O)NC2] | 2-(4-(isochroman-7-yloxy)piperidin-1-yl)-3,4-dimethyl-6,7-dihydro-5H-pyrrolo[3,4-b]pyridin-5-one | 394 |
| 333 | 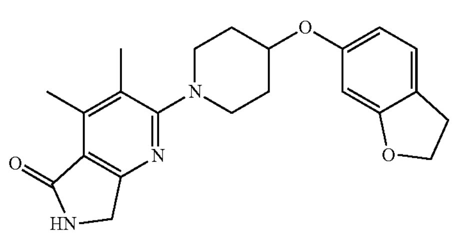 [SMILES: Cc1c(N2CCC(Oc3ccc4c(c3)OCC4)CC2)nc2c(c1C)C(=O)NC2] | 2-(4-((2,3-dihydrobenzofuran-6-yl)oxy)piperidin-1-yl)-3,4-dimethyl-6,7-dihydro-5H-pyrrolo[3,4-b]pyridin-5-one | 380 |

TABLE 37-continued

| Example | Structure | Name | MS (M + 1) |
|---|---|---|---|
| 334A 334B | | (R)-2-(4-((2-hydroxy-2,3-dihydro-1H-inden-5-yl)oxy)piperidin-1-yl)-3,4-dimethyl-6,7-dihydro-5H-pyrrolo[3,4-b]pyridin-5-one and (S)-2-(4-((2-hydroxy-2,3-dihydro-1H-inden-5-yl)oxy)piperidin-1-yl)-3,4-dimethyl-6,7-dihydro-5H-pyrrolo[3,4-b]pyridin-5-one | 394 394 |
| 335A 335B | | (R)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one and (S)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one | 408 408 |
| 336 | 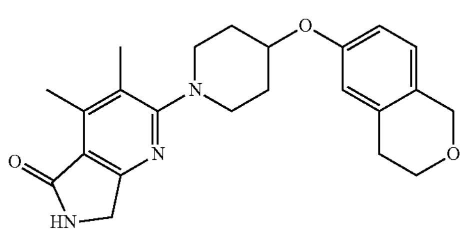 [SMILES: Cc1c(N2CCC(Oc3ccc4c(c3)CCOC4)CC2)nc2c(c1C)C(=O)NC2] | 2-(4-(isochroman-6-yloxy)piperidin-1-yl)-3,4-dimethyl-6,7-dihydro-5H-pyrrolo[3,4-b]pyridin-5-one | 394 |
| 226A | 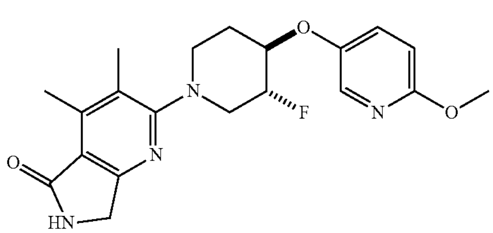 [SMILES: COc1ccc(O[C@@H]2CCN(c3nc4c(c(C)c3C)C(=O)NC4)C[C@H]2F)cn1] | 2-((3R,4R)-3-fluoro-4-((6-methoxypyridin-3-yl)oxy)piperidin-1-yl)-3,4-dimethyl-6,7-dihydro-5H-pyrrolo[3,4-b]pyridin-5-one | 387 |

TABLE 37-continued

| Example | Structure | Name | MS (M + 1) |
|---|---|---|---|
| 336B 336C | | (R)-2-(3,3-difluoro-4-((1-methyl-1H-pyrazol-4-yl)oxy)piperidin-1-yl)-3,4-dimethyl-6,7-dihydro-5H-pyrrolo[3,4-b]pyridin-5-one and (S)-2-(3,3-difluoro-4-((l-methyl-1H-pyrazol-4-yl)oxy)piperidin-1-yl)-3,4-dimethyl-6,7-dihydro-5H-pyrrolo[3,4-b]pyridin-5-one | 378 378 |

Examples 337A and 337B

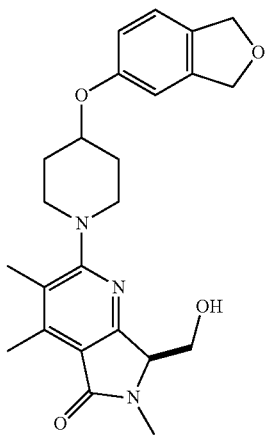
337A

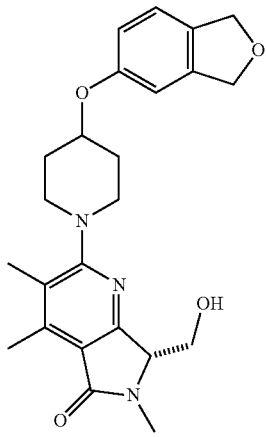
337B (S)-2-(4-((1,3-dihydro-2-benzofuran-5-yl)oxy)piperidin-1-yl)-7-(hydroxymethyl)-3,4,6-trimethyl-6,7-dihydro-5H-pyrrolo[3,4-b]pyridin-5-one (337A) and (R)-2-(4-((1,3-dihydro-2-benzofuran-5-yl)oxy)piperidin-1-yl)-7-(hydroxymethyl)-3,4,6-trimethyl-6,7-dihydro-5H-pyrrolo[3,4-b]pyridin-5-one (337B) (Scheme 38)

Step 1: 2-(4-((1,3-Dihydro-2-benzofuran-5-yl)oxy)piperidin-1-yl)-3,4,6-trimethyl-6,7-dihydro-5H-pyrrolo[3,4-b]pyridin-5-one 2-(4-((1,3-Dihydro-2-benzofuran-5-yl)oxy)piperidin-1-yl)-3,4-dimethyl-6,7-dihydro-5H-pyrrolo[3,4-b]pyridin-5-one (208 mg, 0.548 mmol) in degassed DMSO (3.0 mL) was cooled in ice bath under an atmosphere of nitrogen. LHMDS (1.5 M in THF, 400 µL, 0.60 mmol) was added dropwise and the reaction was allowed to warm to ambient temperature followed by methyl iodide (39 µl, 0.62 mmol). After 2 h at RT, the reaction was quenched with saturated aqueous ammonium chloride and partitioned with EtOAc. The organic layer was washed with water, brine, dried (anhydrous sodium sulfate) and concentrated. The material was purified by silica gel chromatography (5-30% 3:1 EtOAc:EtOH with 1% NH$_4$OH modifier in hexanes) to yield the title compound. MS: 394 (M+1).

Step 2: (S)-2-(4-((1,3-Dihydro-2-benzofuran-5-yl)oxy)piperidin-1-yl)-7-(hydroxymethyl)-3,4,6-trimethyl-6,7-dihydro-5H-pyrrolo[3,4-b]pyridin-5-one and (R)-2-(4-((1,3-dihydro-2-benzofuran-5-yl)oxy)piperidin-1-yl)-7-(hydroxymethyl)-3,4,6-trimethyl-6,7-dihydro-5H-pyrrolo[3,4-b]pyridin-5-one To a solution of 2-(4-((1,3-dihydro-2-benzofuran-5-yl)oxy)piperidin-1-yl)-3,4,6-trimethyl-6,7-dihydro-5H-pyrrolo[3,4-b]pyridin-5-one (122 mg, 0.31 mmol) in THF (3 mL) was added LDA (2 M in THF, 0.47 mL, 0.93 mmol) at −78° C. under an atmosphere of nitrogen. After 15 min, a slurry of 1H-benzo[d][1,2,3]triazol-1-yl)methanol (92 mg, 0.62 mmol) in THF (0.5 mL) was added to the reaction at −78° C. and the reaction was aged for 1 h at this temperature. The reaction was quenched with saturated aqueous ammonium chloride and extracted with EtOAc (2×). The combined organic extracts were washed with water (2×), brine, dried (anhydrous sodium sulfate), filtered, and concentrated. The material was purified by silica gel chromatography (10-40% 3:1 EtOAc:EtOH with 1% NH$_4$OH modifier in hexanes) to yield the racemate. The title compounds were resolved by chiral SFC (AD-H column, 40% isopropanol/CO$_2$) to afford isomer 337A (faster eluting, S-isomer): MS: 424 (M+1). $^1$H NMR (400 MHz, CDCl$_3$): δ 7.15 (1H, d, J=8.0 Hz), 6.82-6.89 (2H, m), 5.06-5.09 (4H, m), 4.20-4.27 (2H, m), 3.62-3.65 (2H, m), 3.48 (2H, br s), 3.11 (5H, br s), 2.64 (3H, s), 2.23 (3H, s), 2.14 (2H, m), 1.99 (2H, m). Isomer 337B (slower eluting, R-isomer): MS: 424 (M+1). ¹H NMR (400 MHz, CDCl₃): δ 7.86 (1H, s), 7.71 (1H, s), 6.71 (1H, d, J=9.02 Hz), 4.38 (1H, s), 4.32 (1H, s), 4.19 (2H, br s), 3.90 (3H, d, J=2.29 Hz), 3.80 (1H, t, J=9.41 Hz), 3.53 (4H, br s), 3.14 (4H, br s), 2.31 (3H, s), 2.11 (2H, br s), 1.94 (2H, br s).

Examples 337C and 337D

337C

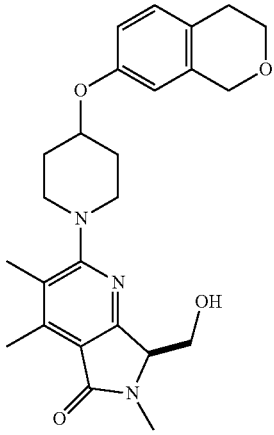

337D

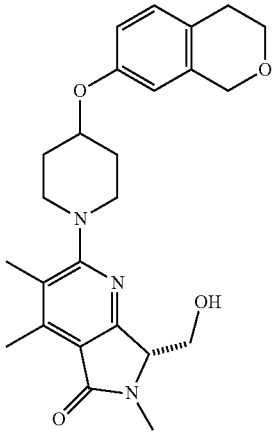

(S)-7-(hydroxymethyl)-2-(4-(isochroman-7-yloxy) piperidin-1-yl)-3,4,6-trimethyl-6,7-dihydro-5H-pyr-rolo[3,4-b]pyridin-5-one (337C) and (R)-7-(hy-droxymethyl)-2-(4-(isochroman-7-yloxy)piperidin-1-yl)-3,4,6-trimethyl-6,7-dihydro-5H-pyrrolo[3,4-b] pyridin-5-one (337D) (Scheme 38)

Step 1

Step 2: (S)-7-(hydroxymethyl)-2-(4-(isochroman-7-yloxy)piperidin-1-yl)-3,4,6-trimethyl-6,7-dihydro-5H-pyrrolo[3,4-b]pyridin-5-one and (R)-7-(hy-droxymethyl)-2-(4-(isochroman-7-yloxy)piperidin-1-yl)-3,4,6-trimethyl-6,7-dihydro-5H-pyrrolo[3,4-b] pyridin-5-one To a solution of 2-(4-(isochroman-7-yloxy)piperidin-1-yl)-3,4,6-trimethyl-6,7-dihydro-5H-pyrrolo[3,4-b]pyridin-5-one (1.12 g, 2.75 mmol) in THF (20 mL) was added lithium bis(trimethylsilyl)amide (1 M, 8.25 mL, 8.25 mmol) dropwise at −70° C. under an inert nitrogen atmosphere. After aging for 30 min, a slurry of (1H-benzo[d][1,2,3] triazol-1-yl)methanol (0.574 g, 3.85 mmol) in THF (5 mL) was added dropwise and the reaction mixture was stirred at −70° C. for 30 min. The reaction was quenched by the addition of aqueous NH₄Cl (saturated, 15 mL) and was subsequently treated with water (25 mL) and extracted with EtOAc (25 mL×3). The combined organic layers were dried over anhydrous sodium sulfate, filtered and concentrated. The material was purified by silica gel chromatography (1:1 THF:petroleum ether) to yield the racemate. The title compounds were resolved by chiral SFC (AD column, 40% EtOH with 0.05% diethylamine modifier/CO₂) to afford isomer 337C (faster eluting, S-isomer): MS: 438 (M+1). ¹H NMR (400 MHz, MeOD): δ 7.03 (1H, d, J=8.4 Hz), 6.79 (1H, dd, J=8.4, 2.4 Hz), 6.64 (1H, d, J=2.4 Hz), 4.70 (2H, s), 4.50-4.52 (1H, m), 4.25-4.27 (1H, m), 4.08-4.18 (2H, m), 3.93 (2H, t, J=5.6 Hz), 3.49-3.52 (2H, m), 3.05-3.17 (5H, m), 2.76 (2H, t, J=5.6 Hz), 2.59 (3H, s), 2.25 (3H, s), 2.05-2.14 (2H, m), 1.78-1.95 (2H, m). Isomer 337D (slower eluting, R-isomer): MS: 438 (M+1). ¹H NMR (400 MHz, MeOD): δ 7.01 (1H, d, J=8.8 Hz), 6.76 (1H, d, J=8.4, 2.4 Hz), 6.61 (1H, d, J=2.4 Hz), 4.68 (2H, s), 4.49-4.52 (1H, m), 4.24-4.27 (1H, m), 4.06-4.16 (2H, m), 3.91 (2H, t, J=5.6 Hz), 3.41-3.50 (2H, m), 3.05-3.15 (5H, m), 2.74 (2H, t, J=5.6 Hz), 2.56 (3H, s), 2.23 (3H, s), 2.04-2.12 (2H, m), 1.76-1.92 (2H, m). The following examples in table 38 were prepared according to scheme 38 using the procedure and conditions outlined in the synthesis of Examples 337A, 337B, 337C and 337D from prepared or commercially available starting materials.

TABLE 38

| Example | Structure | Name | MS (M + 1) |
|---|---|---|---|
| 338 | 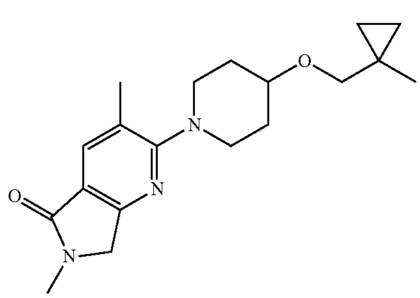 [SMILES: Cc1cc2c(nc1N1CCC(OCC3(C)CC3)CC1)CN(C)C2=O] | 3,6-dimethyl-2-(4-((1-methylcyclopropyl)methoxy)piperidin-1-yl)-6,7-dihydro-5H-pyrrolo[3,4-b]pyridin-5-one | 330 |

TABLE 38-continued

| Example | Structure | Name | MS (M + 1) |
|---|---|---|---|
| 339 | 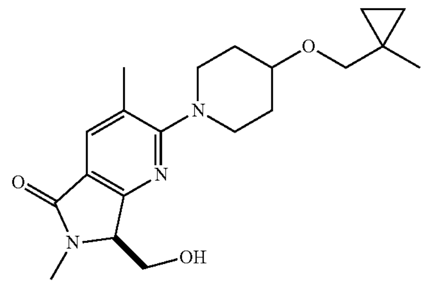 [SMILES: Cc1cc2c(nc1N1CCC(OCC3(C)CC3)CC1)[C@@H](CO)N(C)C2=O] | (S)-7-(hydroxymethyl)-3,6-dimethyl-2-(4-((1-methylcyclopropyl)methoxy)piperidin-1-yl)-6,7-dihydro-5H-pyrrolo[3,4-b]pyridin-5-one | 360 |
| 340 | 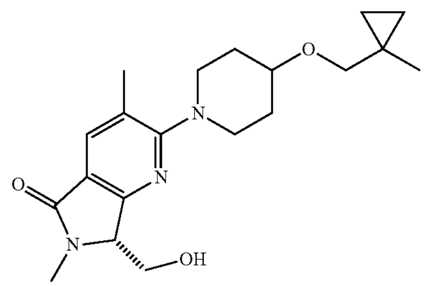 [SMILES: Cc1cc2c(nc1N1CCC(OCC3(C)CC3)CC1)[C@H](CO)N(C)C2=O] | (R)-7-(hydroxymethyl)-3,6-dimethyl-2-(4-((1-methylcyclopropyl)methoxy)piperidin-1-yl)-6,7-dihydro-5H-pyrrolo[3,4-b]pyridin-5-one | 360 |
| 341 | 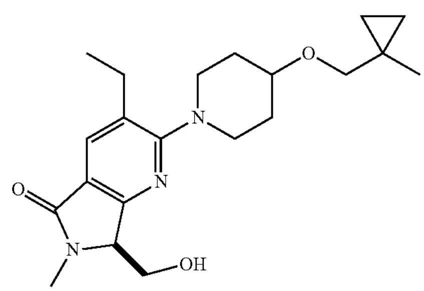 [SMILES: CCc1cc2c(nc1N1CCC(OCC3(C)CC3)CC1)[C@@H](CO)N(C)C2=O] | (S)-3-ethyl-7-(hydroxymethyl)-6-methyl-2-(4-((1-methylcyclopropyl)methoxy)piperidin-1-yl)-6,7-dihydro-5H-pyrrolo[3,4-b]pyridin-5-one | 374 |
| 341A | 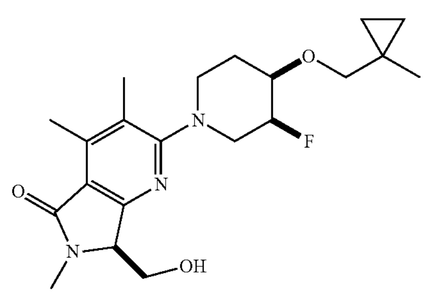 [SMILES: Cc1c(N2CC[C@@H](OCC3(C)CC3)[C@@H](F)C2)nc2c(c1C)C(=O)N(C)[C@@H]2CO] | (S)-2-((3S,4R)-3-fluoro-4-((1-methylcyclopropyl)methoxy)piperidin-1-yl)-7-(hydroxymethyl)-3,4,6-trimethyl-6,7-dihydro-5H-pyrrolo[3,4-b]pyridin-5-one | 392 |
| 342 | 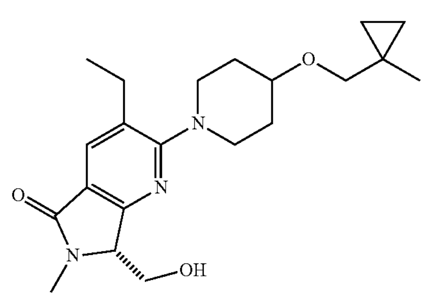 [SMILES: CCc1cc2c(nc1N1CCC(OCC3(C)CC3)CC1)[C@H](CO)N(C)C2=O] | (R)-3-ethyl-7-(hydroxymethyl)-6-methyl-2-(4-((1-methylcyclopropyl)methoxy)piperidin-1-yl)-6,7-dihydro-5H-pyrrolo[3,4-b]pyridin-5-one | 374 |

TABLE 38-continued

| Example | Structure | Name | MS (M + 1) |
|---|---|---|---|
| 342A | 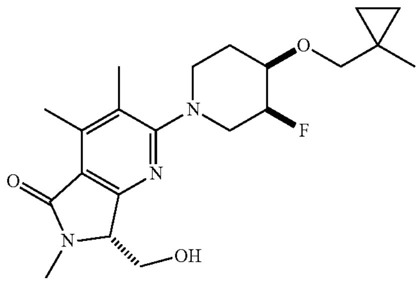 [SMILES: Cc1c(N2CC[C@@H](OCC3(C)CC3)[C@@H](F)C2)nc2c(c1C)C(=O)N(C)[C@H]2CO] | (R)-2-((3S,4R)-3-fluoro-4-((1-methylcyclopropyl)methoxy)piperidin-1-yl)-7-(hydroxymethyl)-3,4,6-trimethyl-6,7-dihydro-5H-pyrrolo[3,4-b]pyridin-5-one | 392 |
| 343 | 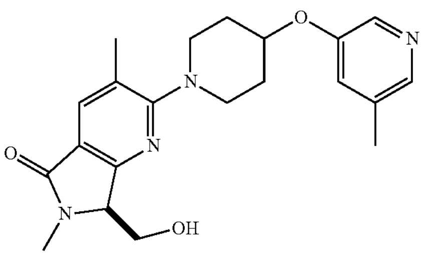 [SMILES: Cc1cncc(OC2CCN(c3nc4c(cc3C)C(=O)N(C)[C@@H]4CO)CC2)c1] | (S)-7-(hydroxymethyl)-3,6-dimethyl-2-(4-((5-methylpyridin-3-yl)oxy)piperidin-1-yl)-6,7-dihydro-5H-pyrrolo[3,4-b]pyridin-5-one | 383 |
| 343A | 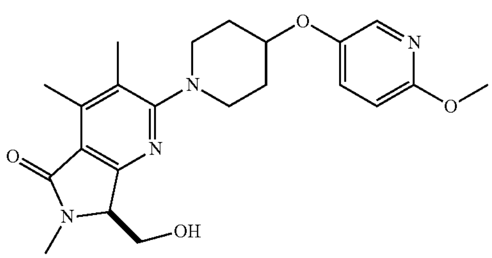 [SMILES: COc1ccc(OC2CCN(c3nc4c(c(C)c3C)C(=O)N(C)[C@@H]4CO)CC2)cn1] | (S)-7-(hydroxymethyl)-2-(4-((6-methoxypyridin-3-yl)oxy)piperidin-1-yl)-3,4,6-trimethyl-6,7-dihydro-5H-pyrrolo[3,4-b]pyridin-5-one | 413 |
| 344 | 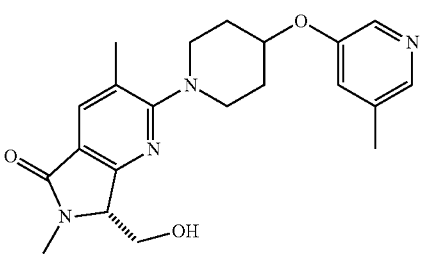 [SMILES: Cc1cncc(OC2CCN(c3nc4c(cc3C)C(=O)N(C)[C@H]4CO)CC2)c1] | (R)-7-(hydroxymethyl)-3,6-dimethyl-2-(4-((5-methylpyridin-3-yl)oxy)piperidin-1-yl)-6,7-dihydro-5H-pyrrolo[3,4-b]pyridin-5-one | 383 |
| 344A | 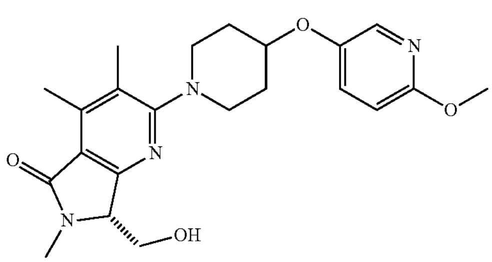 [SMILES: COc1ccc(OC2CCN(c3nc4c(c(C)c3C)C(=O)N(C)[C@H]4CO)CC2)cn1] | (R)-7-(hydroxymethyl)-2-(4-((6-methoxypyridin-3-yl)oxy)piperidin-1-yl)-3,4,6-trimethyl-6,7-dihydro-5H-pyrrolo[3,4-b]pyridin-5-one | 413 |
| 345 | 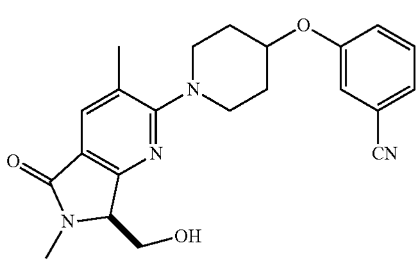 [SMILES: Cc1cc2c(nc1N1CCC(Oc3cccc(C#N)c3)CC1)[C@@H](CO)N(C)C2=O] | (S)-3-((1-(7-(hydroxymethyl)-3,6-dimethyl-5-oxo-6,7-dihydro-5H-pyrrolo[3,4-b]pyridin-2-yl)piperidin-4-yl)oxy)benzonitrile | 393 |

TABLE 38-continued

| Example | Structure | Name | MS (M + 1) |
|---|---|---|---|
| 346 | 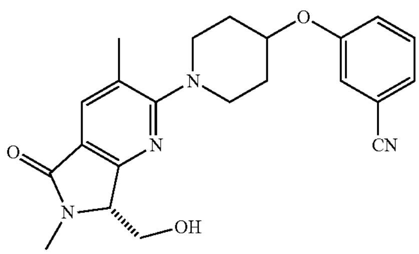 [SMILES: Cc1cc2c(nc1N1CCC(Oc3cccc(C#N)c3)CC1)[C@H](CO)N(C)C2=O] | (R)-3-((1-(7-(hydroxymethyl)-3,6-dimethyl-5-oxo-6,7-dihydro-5H-pyrrolo[3,4-b]pyridin-2-yl)piperidin-4-yl)oxy)benzonitrile | 393 |
| 347 | 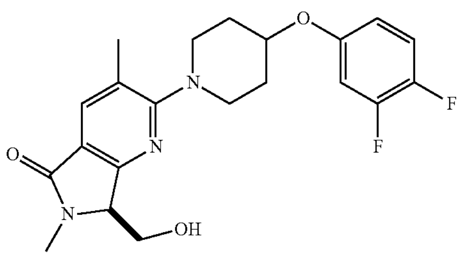 [SMILES: Cc1cc2c(nc1N1CCC(Oc3ccc(F)c(F)c3)CC1)[C@@H](CO)N(C)C2=O] | (S)-2-(4-(3,4-difluorophenoxy)piperidin-1-yl)-7-(hydroxymethyl)-3,6-dimethyl-6,7-dihydro-5H-pyrrolo[3,4-b]pyridin-5-one | 404 |
| 348 | 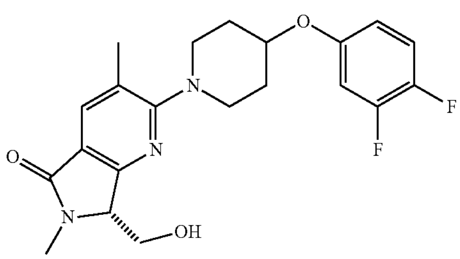 [SMILES: Cc1cc2c(nc1N1CCC(Oc3ccc(F)c(F)c3)CC1)[C@H](CO)N(C)C2=O] | (R)-2-(4-(3,4-difluorophenoxy)piperidin-1-yl)-7-(hydroxymethyl)-3,6-dimethyl-6,7-dihydro-5H-pyrrolo[3,4-b]pyridin-5-one | 404 |
| 349 | 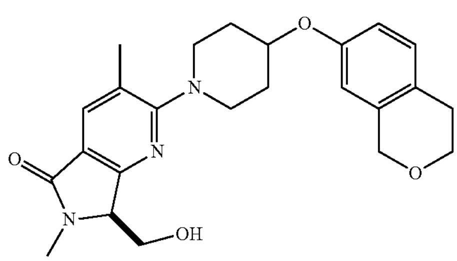 [SMILES: Cc1cc2c(nc1N1CCC(Oc3ccc4c(c3)COCC4)CC1)[C@@H](CO)N(C)C2=O] | (S)-7-(hydroxymethyl)-2-(4-(isochroman-7-yloxy)piperidin-1-yl)-3,6-dimethyl-6,7-dihydro-5H-pyrrolo[3,4-b]pyridin-5-one | 424 |
| 349A | 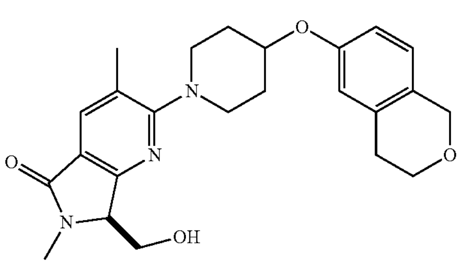 [SMILES: Cc1cc2c(nc1N1CCC(Oc3ccc4c(c3)CCOC4)CC1)[C@@H](CO)N(C)C2=O] | (S)-7-(hydroxymethyl)-2-(4-(isochroman-6-yloxy)piperidin-1-yl)-3,6-dimethyl-6,7-dihydro-5H-pyrrolo[3,4-b]pyridin-5-one | 424 |
| 350 | 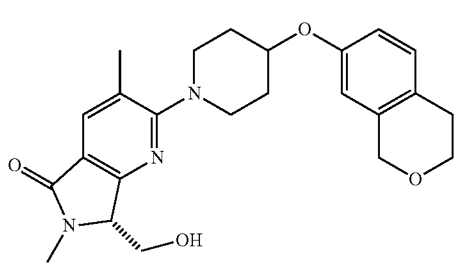 [SMILES: Cc1cc2c(nc1N1CCC(Oc3ccc4c(c3)COCC4)CC1)[C@H](CO)N(C)C2=O] | (R)-7-(hydroxymethyl)-2-(4-(isochroman-7-yloxy)piperidin-1-yl)-3,6-dimethyl-6,7-dihydro-5H-pyrrolo[3,4-b]pyridin-5-one | 424 |

TABLE 38-continued

| Example | Structure | Name | MS (M + 1) |
|---|---|---|---|
| 350A | 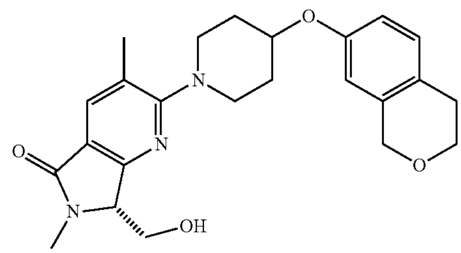 [SMILES: Cc1cc2c(nc1N1CCC(Oc3ccc4c(c3)COCC4)CC1)[C@H](CO)N(C)C2=O] | (R)-7-(hydroxymethyl)-2-(4-(isochroman-6-yloxy)piperidin-1-yl)-3,6-dimethyl-6,7-dihydro-5H-pyrrolo[3,4-b]pyridin-5-one | 424 |
| 351 | 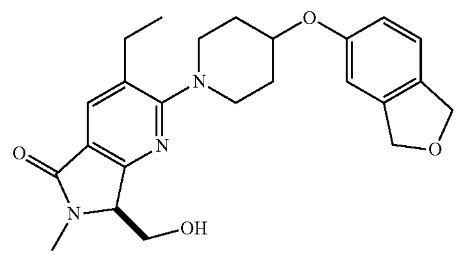 [SMILES: CCc1cc2c(nc1N1CCC(Oc3ccc4c(c3)COC4)CC1)[C@@H](CO)N(C)C2=O] | (S)-2-(4-((1,3-dihydro-2-benzofuran-5-yl)oxy)piperidin-1-yl)-3-ethyl-7-(hydroxymethyl)-6-methyl-6,7-dihydro-5H-pyrrolo[3,4-b]pyridin-5-one | 424 |
| 351A | 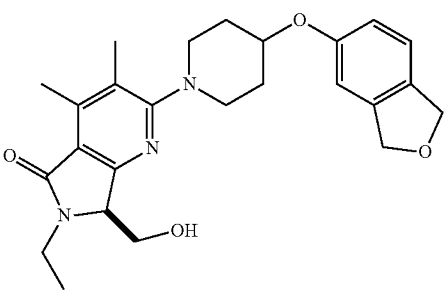 [SMILES: CCN1C(=O)c2c(nc(N3CCC(Oc4ccc5c(c4)COC5)CC3)c(C)c2C)[C@H]1CO] | (S)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one | 438 |
| 352 | 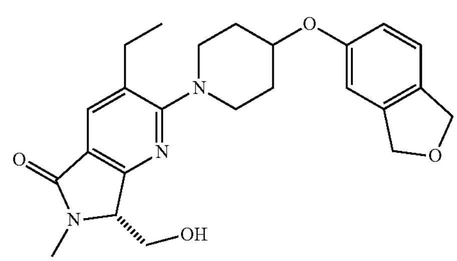 [SMILES: CCc1cc2c(nc1N1CCC(Oc3ccc4c(c3)COC4)CC1)[C@H](CO)N(C)C2=O] | can-2-(4-((1,3-dihydro-2-benzofuran-5-yl)oxy)piperidin-1-yl)-3-ethyl-7-(hydroxymethyl)-6-methyl-6,7-dihydro-5H-pyrrolo[3,4-b]pyridin-5-one | 424 |
| 352A | 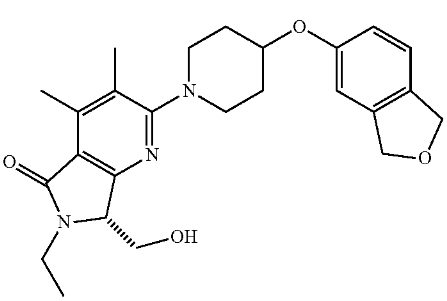 [SMILES: CCN1C(=O)c2c(nc(N3CCC(Oc4ccc5c(c4)COC5)CC3)c(C)c2C)[C@@H]1CO] | (R)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one | 438 |

TABLE 38-continued

| Example | Structure | Name | MS (M + 1) |
|---|---|---|---|
| 353 | 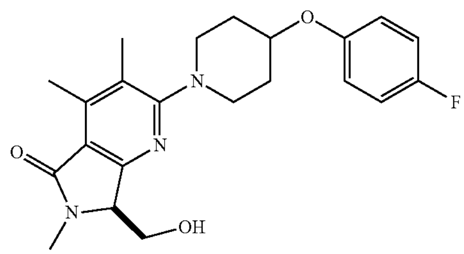 [SMILES: Cc1c(N2CCC(Oc3ccc(F)cc3)CC2)nc2c(c1C)C(=O)N(C)[C@@H]2CO] | (S)-2-(4-(4-fluorophenoxy)piperidin-1-yl)-7-(hydroxymethyl)-3,4,6-trimethyl-6,7-dihydro-5H-pyrrolo[3,4-b]pyridin-5-one | 400 |
| 354 | 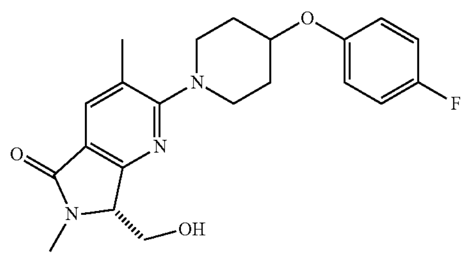 [SMILES: Cc1cc2c(nc1N1CCC(Oc3ccc(F)cc3)CC1)[C@H](CO)N(C)C2=O] | (R)-2-(4-(4-fluorophenoxy)piperidin-1-yl)-7-(hydroxymethyl)-3,4,6-trimethyl-6,7-dihydro-5H-pyrrolo[3,4-b]pyridin-5-one | 400 |
| 355 | 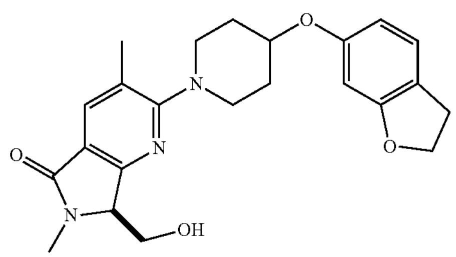 [SMILES: Cc1cc2c(nc1N1CCC(Oc3ccc4c(c3)OCC4)CC1)[C@@H](CO)N(C)C2=O] | (S)-2-(4-((2,3-dihydrobenzofuran-6-yl)oxy)piperidin-1-yl)-7-(hydroxymethyl)-3,6-dimethyl-6,7-dihydro-5H-pyrrolo[3,4-b]pyridin-5-one | 410 |
| 356 | 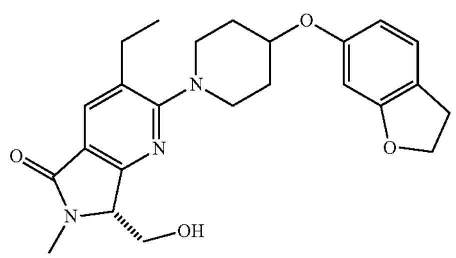 [SMILES: CCc1cc2c(nc1N1CCC(Oc3ccc4c(c3)OCC4)CC1)[C@H](CO)N(C)C2=O] | (R)-2-(4-((2,3-dihydrobenzofuran-6-yl)oxy)piperidin-1-yl)-7-(hydroxymethyl)-3,6-dimethyl-6,7-dihydro-5H-pyrrolo[3,4-b]pyridin-5-one | 410 |
| 357 | 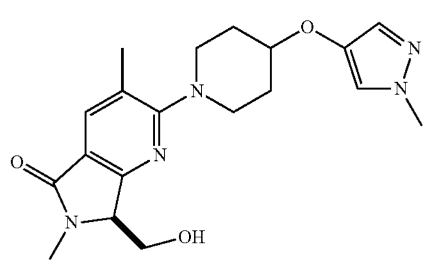 [SMILES: Cc1cc2c(nc1N1CCC(Oc3cnn(C)c3)CC1)[C@@H](CO)N(C)C2=O] | (S)-7-(hydroxymethyl)-3,6-dimethyl-2-(4-((1-methyl-1H-pyrazol-4-yl)oxy)piperidin-1-yl)-6,7-dihydro-5H-pyrrolo[3,4-b]pyridin-5-one | 372 |
| 358 | 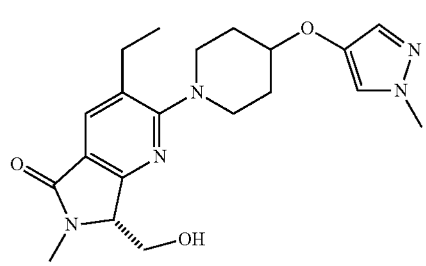 [SMILES: CCc1cc2c(nc1N1CCC(Oc3cnn(C)c3)CC1)[C@H](CO)N(C)C2=O] | (R)-7-(hydroxymethyl)-3,6-dimethyl-2-(4-((1-methyl-1H-pyrazol-4-yl)oxy)piperidin-1-yl)-6,7-dihydro-5H-pyrrolo[3,4-b]pyridin-5-one | 372 |

TABLE 38-continued

| Example | Structure | Name | MS (M + 1) |
|---|---|---|---|
| 359 | 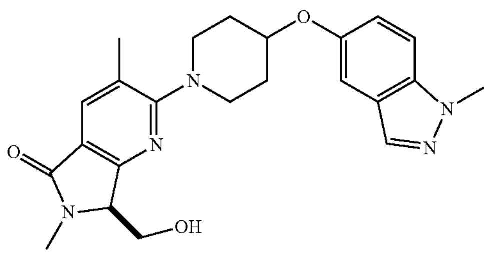 [SMILES: Cc1cc2c(nc1N1CCC(Oc3ccc4c(cnn4C)c3)CC1)[C@@H](CO)N(C)C2=O] | (S)-7-(hydroxymethyl)-3,6-dimethyl-2-(4-((1-methyl-1H-indazol-5-yl)oxy)piperidin-1-yl)-6,7-dihydro-5H-pyrrolo[3,4-b]pyridin-5-one | 422 |
| 360 | 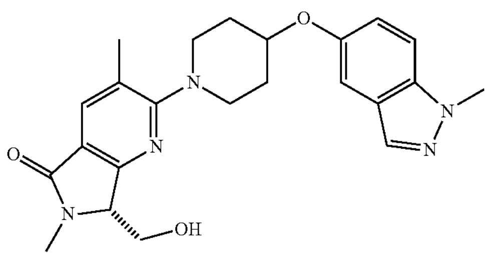 [SMILES: Cc1cc2c(nc1N1CCC(Oc3ccc4c(cnn4C)c3)CC1)[C@H](CO)N(C)C2=O] | (R)-7-(hydroxymethyl)-3,6-dimethyl-2-(4-((1-methyl-1H-indazol-5-yl)oxy)piperidin-1-yl)-6,7-dihydro-5H-pyrrolo[3,4-b]pyridin-5-one | 422 |
| 361 | 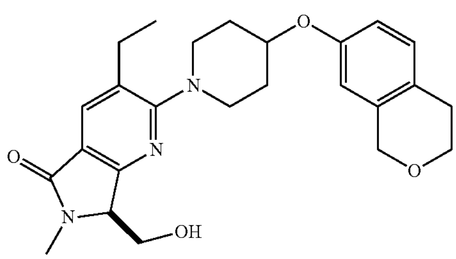 [SMILES: CCc1cc2c(nc1N1CCC(Oc3ccc4c(c3)COCC4)CC1)[C@@H](CO)N(C)C2=O] | (S)-3-ethyl-7-(hydroxymethyl)-2-(4-(isochroman-7-yloxy)piperidin-1-yl)-6-methyl-6,7-dihydro-5H-pyrrolo[3,4-b]pyridin-5-one | 438 |
| 362 | 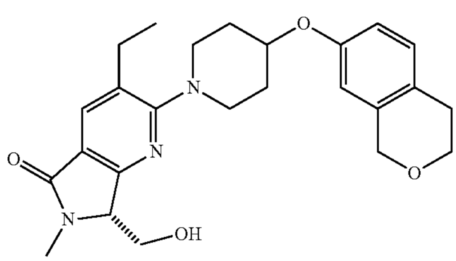 [SMILES: CCc1cc2c(nc1N1CCC(Oc3ccc4c(c3)COCC4)CC1)[C@H](CO)N(C)C2=O] | (R)-3-ethyl-7-(hydroxymethyl)-2-(4-(isochroman-7-yloxy)piperidin-1-yl)-6-methyl-6,7-dihydro-5H-pyrrolo[3,4-b]pyridin-5-one | 438 |
| 363 | 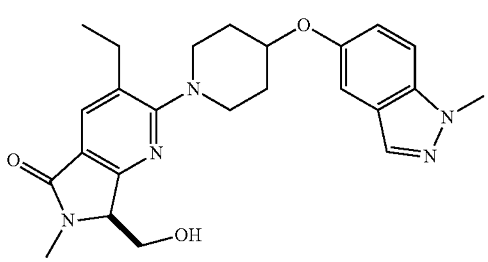 [SMILES: CCc1cc2c(nc1N1CCC(Oc3ccc4c(cnn4C)c3)CC1)[C@@H](CO)N(C)C2=O] | (S)-3-ethyl-7-(hydroxymethyl)-6-methyl-2-(4-((1-methyl-1H-indazol-5-yl)oxy)piperidin-1-yl)-6,7-dihydro-5H-pyrrolo[3,4-b]pyridin-5-one | 436 |
| 364 | 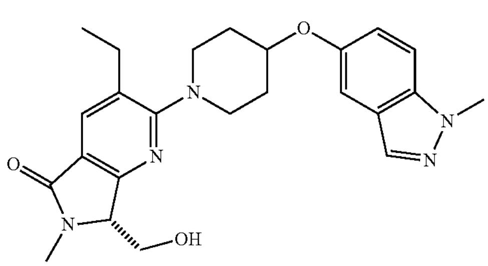 [SMILES: CCc1cc2c(nc1N1CCC(Oc3ccc4c(cnn4C)c3)CC1)[C@H](CO)N(C)C2=O] | (R)-3-ethyl-7-(hydroxymethyl)-6-methyl-2-(4-((1-methyl-1H-indazol-5-yl)oxy)piperidin-1-yl)-6,7-dihydro-5H-pyrrolo[3,4-b]pyridin-5-one | 424 |

TABLE 38-continued

| Example | Structure | Name | MS (M + 1) |
| --- | --- | --- | --- |
| 365 | 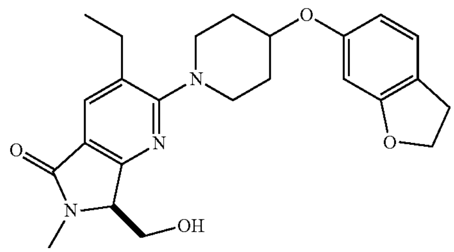 [SMILES: CCc1cc2c(nc1N1CCC(Oc3ccc4c(c3)OCC4)CC1)[C@@H](CO)N(C)C2=O] | (S)-2-(4-((2,3-dihydrobenzofuran-6-yl)oxy)piperidin-1-yl)-3-ethyl-7-(hydroxymethyl)-6-methyl-6,7-dihydro-5H-pyrrolo[3,4-b]pyridin-5-one | 424 |
| 366 | 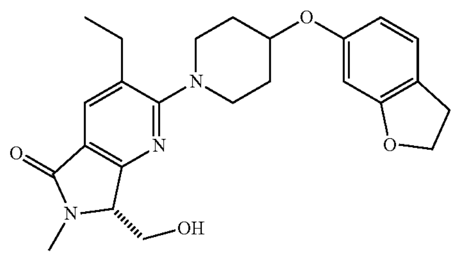 [SMILES: CCc1cc2c(nc1N1CCC(Oc3ccc4c(c3)OCC4)CC1)[C@H](CO)N(C)C2=O] | (R)-2-(4-((2,3-dihydrobenzofuran-6-yl)oxy)piperidin-1-yl)-3-ethyl-7-(hydroxymethyl)-6-methyl-6,7-dihydro-5H-pyrrolo[3,4-b]pyridin-5-one | 436 |
| 367 | 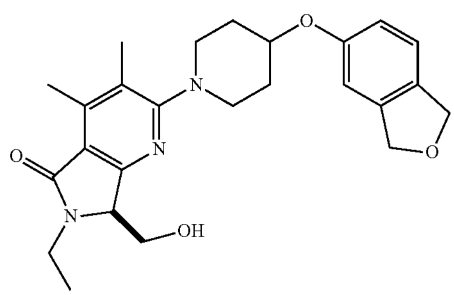 [SMILES: CCN1C(=O)c2c(nc(N3CCC(Oc4ccc5c(c4)COC5)CC3)c(C)c2C)[C@H]1CO] | (S)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one | 438 |
| 368 | 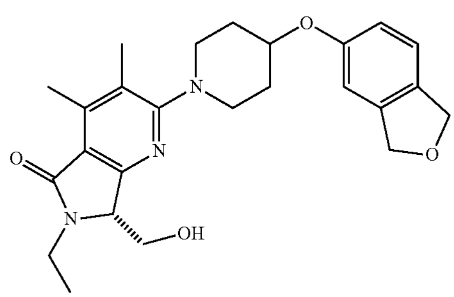 [SMILES: CCN1C(=O)c2c(nc(N3CCC(Oc4ccc5c(c4)COC5)CC3)c(C)c2C)[C@@H]1CO] | (R)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one | 438 |
| 369 | 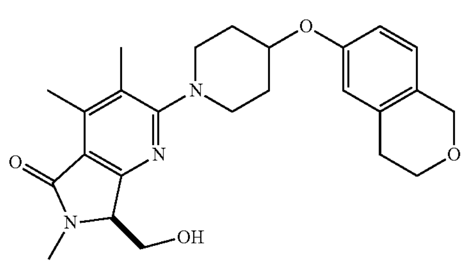 [SMILES: Cc1c(N2CCC(Oc3ccc4c(c3)CCOC4)CC2)nc2c(c1C)C(=O)N(C)[C@@H]2CO] | (S)-7-(hydroxymethyl)-2-(4-(isochroman-6-yloxy)piperidin-1-yl)-3,4,6-trimethyl-6,7-dihydro-5H-pyrrolo[3,4-b]pyridin-5-one | 438 |

TABLE 38-continued

| Example | Structure | Name | MS (M + 1) |
|---|---|---|---|
| 370 | 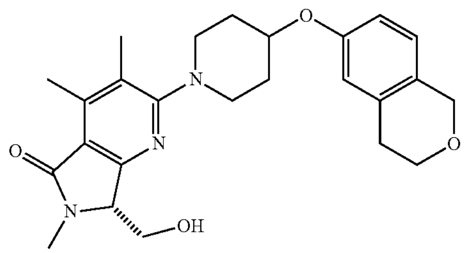 [SMILES: Cc1c(N2CCC(Oc3ccc4c(c3)CCOC4)CC2)nc2c(c1C)C(=O)N(C)[C@H]2CO] | (R)-7-(hydroxymethyl)-2-(4-(isochroman-6-yloxy)piperidin-1-yl)-3,4,6-trimethyl-6,7-dihydro-5H-pyrrolo[3,4-b]pyridin-5-one | 438 |

Example 371

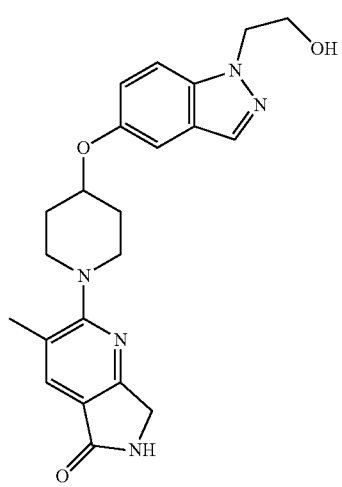 [SMILES: Cc1cc2c(nc1N1CCC(Oc3ccc4c(cnn4CCO)c3)CC1)CNC2=O]

2-(4-((1-(2-Hydroxyethyl)-1H-indazol-5-yl)oxy)piperidin-1-yl)-3-methyl-6,7-dihydro-5H-pyrrolo[3,4-b]pyridin-5-one (Scheme 39)

To a solution of methyl 2-(5-(((1-(3-methyl-5-oxo-6,7-dihydro-5H-pyrrolo[3,4-b]pyridin-2-yl)piperidin-4-yl)oxy)-1H-indazol-1-yl)acetate (100 mg, 0.230 mmol) in THF (10 mL) was added LiBH₄ (10.0 mg, 0.459 mmol). The reaction mixture was stirred 16 h at 25° C. before being quenched with MeOH (5 mL). After stirring for 30 min at RT the volatiles were removed under reduced pressure and the residue was partitioned with saturated aqueous NaHCO₃ (10 mL) and extracted with DCM (20 mL×3). The combined organic layers were washed with brine (10 mL), dried over anhydrcan sodium sulfate, filtered and concentrated. The residue was purified by HPLC (CAN/water with 0.1% TFA modifier) to provide the title compound. MS: 408 (M+1). ¹H NMR (400 MHz, MeOD): δ 7.90 (1H, s), 7.78 (1H, s), 7.51 (1H, d, J=8.8 Hz), 7.25 (1H, s), 7.10-7.14 (1H, m), 4.28-4.54 (1H, m) 4.44 (d, 2H, J=5.2 Hz), 4.32 (2H, s), 3.93 (2H, br s), 3.55-3.61 (2H, m), 3.18-3.23 (2H, m), 2.37 (3H, s), 2.14-2.15 (2H, m), 1.91-1.96 (2H, m).

Example 372

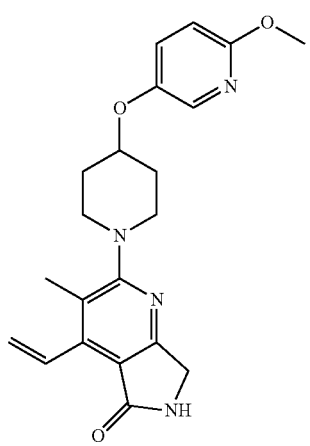 [SMILES: C=Cc1c(C)c(N2CCC(Oc3ccc(OC)nc3)CC2)nc2c1C(=O)NC2]

2-(4-((6-Methoxypyridin-3-yl)oxy)piperidin-1-yl)-3-methyl-4-vinyl-6,7-dihydro-5H-pyrrolo[3,4-b]pyridin-5-one (Scheme 40)

Step 1: 2-(4-((6-Methoxypyridin-3-yl)oxy)piperidin-1-yl)-3-methyl-5-oxo-6,7-dihydro-5H-pyrrolo[3,4-b]pyridine-4-carbaldehyde To a solution of 4-(hydroxymethyl)-2-(4-((6-methoxypyridin-3-yl)oxy)piperidin-1-yl)-3-methyl-6,7-dihydro-5H-pyrrolo[3,4-b]pyridin-5-one (80 mg, 0.208 mmol) in DCM (3 mL) was added DMP (177 mg, 0.416 mmol) under an atmosphere of nitrogen. The reaction mixture was stirred at 0° C. for 2 h. The reaction mixture was diluted with water (50 mL) and extracted with EtOAc (30 mL×3). The combined organic layers were washed with brine (10 mL), dried over anhydrous sodium sulfate, filtered and concentrated in vacuo to yield the title compound. MS: 383 (M+1).

Step 2: 2-(4-((6-Methoxypyridin-3-yl)oxy)piperidin-1-yl)-3-methyl-4-vinyl-6,7-dihydro-5H-pyrrolo[3,4-b]pyridin-5-one To a solution of methyltriphenylphosphonium bromide (42.0 mg, 0.118 mmol) in THF (2 mL) was added LiHMDS (1 M in THF, 0.157 mL, 0.157 mmol) dropwise at −60° C. the reaction mixture was stirred at this temperature for 30 min and then 2-(4-((6-methoxypyridin-3-yl)oxy)piperidin-1-yl)-3-methyl-5-oxo-6,7-dihydro-5H-pyrrolo[3,4-b]pyridine-4-carbaldehyde (30 mg, 0.078 mmol) in THF (1 mL) was added dropwise at −60° C. The reaction mixture was cooled to RT and was stirred for 12 h before diluting with water (50 mL) and extracting with EtOAc (30 mL×3). The combined organic layers were washed with brine (10 mL), dried over anhydrous sodiucanulfate, filtered and concentrated in vacuo. The residue was purified by HPLC (CAN/water with 0.1% TFA modifier) to afford the title compound. MS: 381 (M+1). $^1$H NMR (400 MHz, CDCl$_3$): δ 7.87 (1H, d, J=3.2 Hz), 7.25-7.28 (1H, m), 6.68-6.72 (2H, m), 5.82 (1H, d, J=11.6 Hz), 5.71 (d, 1H, J=18.0 Hz), 4.35-4.37 (1H, m), 4.32 (2H, s), 3.88 (3H, s), 3.50-3.60 (2H, m), 3.10-3.20 (2H, m), 2.35 (3H, s), 2.09-2.11 (2H, m), 1.90-1.95 (2H, m).

Example 373

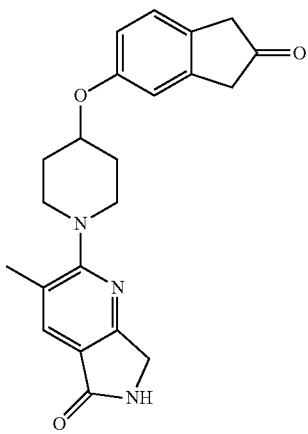 [SMILES: Cc1cc2c(nc1N1CCC(Oc3ccc4c(c3)CC(=O)C4)CC1)CNC2=O]

3-Methyl-2-(4-((2-oxo-2,3-dihydro-1H-inden-5-yl)oxy)piperidin-1-yl)-6,7-dihydro-5H-pyrrolo[3,4-b]pyridin-5-one (Scheme 41)

To a solution of 2-(4-((2-hydroxy-2,3-dihydro-1H-inden-5-yl)oxy)piperidin-1-yl)-3-methyl-6,7-dihydro-5H-pyrrolo[3,4-b]pyridin-5-one (15 mg, 0.040 mmol) in DCM (1 mL) was added DMP (25.1 mg, 0.059 mmol). The mixture was stirred at 15° C. for 10 h and was then cantered and concentrated to give a residue. The material was purified by HPLC (MeCN/water with 0.1% TFA modifier) to afford the title compound. MS: 378 (M+1). $^1$H NMR (400 MHz, CDCl$_3$): δ 7.80 (1H, s), 7.22 (1H, d, J=7.6 Hz), 6.70-6.92 (2H, m), 6.77 (1H, br s), 4.53 (1H, br s), 4.38 (2H, s), 3.50-3.57 (6H, m), 3.17-3.25 (2H, m), 2.36 (3H, s), 2.14 (2H, br s), 1.99 (2H, br s).

Example 374A and 374B

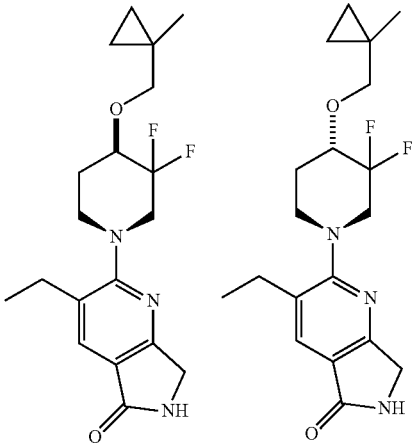

(R)-2-(3,3-Difluoro-4-((1-methylcyclopropyl)methoxy)piperidin-1-yl)-3-ethyl-6,7-dihydro-5H-pyrrolo[3,4-b]pyridin-5-one and (S)-2-(3,3-Difluoro-4-((1-methylcyclopropyl)methoxy)piperidin-1-yl)-3-ethyl-6,7-dihydro-5H-pyrrolo[3,4-b]pyridin-5-one (Scheme 42)

Step 1: Methyl 2-cyano-6-(3,3-difluoro-4-((2-methylallyl)oxy)piperidin-1-yl)-5-ethylnicotinate To a solution of methyl 2-cyano-6-(3,3-difluoro-4-hydroxypiperidin-1-yl)-5-ethylnicotinate (250 mg, 0.768 mmol) in dry DMF (5 mL) was added NaH (36.9 mg, 0.922 mmol) at 0° C. After 30 min, a solution of 3-bromo-2-methylprop-1-ene (124 mg, 0.922 mmol) in DMF (1 mL) was added dropwise to the reaction the system was allowed to warm to RT. After stirring for 6 h, the reaction was treated with saturated aqueous ammonium chloride (1 mL) and water (20 mL). The mixture was extracted with EtOAc (20 mL×3) and the combined organic layers were dried over anhydrous sodium sulfate, filtered and concentrated. The residue dissolved in a solution of MeOH (5 mL) and TMSCHN$_2$ (1 M in diethyl ether, 1 mL). After 30 min, the reaction was quenched with AcOH and the volatiles were removed under reduced pressure. Purification by silica gel chromatography (0-30% EtOAc/petroleum ether) provided the title compound. MS: 380 (M+1).

Step 2: Methyl 2-cyano-6-(3,3-difluoro-4-((1-methylcyclopropyl)methoxy)piperidin-1-yl)-5-ethylnicotinate To a solution of diiodomethane (1.06 g, 3.95 mmol) in DCM (5 mL) was added diethylzinc (1.1 M, 2.40 mL, 2.64 mmol) dropwise at 0° C. under and inert atmosphere. After 30 min, a solution of methyl 2-cyano-6-(3,3-difluoro-4-((2-methylallyl)oxy)piperidin-1-yl)-5-ethylnicotinate (250 mg, 0.659 mmol) in dry DCM (1 mL) was added dropwise and the reaction was allowed to warm to 15° C. After 42 h, the reaction was treated with saturated aqueous ammonium chloride (1 mL) and water (10 mL). The mixture was extracted with DCM (20 mL×3) and the combined organic layers were dried over anhydrous sodium sulfate, filtered and concentrated. Purification by silica gel chromatography (0-30% EtOAc/petroleum ether) afforded the title compound. MS: 394 (M+1).

Step 3: (R)-2-(3,3-Difluoro-4-((1-methylcyclopropyl)methoxy)piperidin-1-yl)-3-ethyl-6,7-dihydro-5H-pyrrolo[3,4-b]pyridin-5-one and (S)-2-(3,3-Difluoro-4-((1-methylcyclopropyl)methoxy)piperidin-1-yl)-3-ethyl-6,7-dihydro-5H-pyrrolo[3,4-b]pyridin-5-one To a solution of methyl 2-cyano-6-(3,3-difluoro-4-((1-methylcyclopropyl)methoxy)piperidin-1-yl)-5-ethylnicotinate (160 mg, 0.407 mmol) in MeOH (2 mL) was added nickel (23.9 mg, 0.407 mmol) and 2 drops of concentrated $NH_3$. The mixture was stirred at 20° C. for 3 h under a hydrogen atmosphere (50 psi). The mixture was filtered and the filtrate was concentrated to give the racemate. The title compounds were resolved by chiral SFC (AD-H column, 25% MeOH with 0.1% $NH_4OH$ modifier/$CO_2$) to afford isomer 374A (faster eluting isomer): MS: 366 (M+1). $^1H$ NMR (400 MHz, $CDCl_3$): δ 7.94 (1H, s), 6.07 (1H, br s), 4.38 (2H, s), 3.59-3.71 (2H, m), 3.54 (1H, d, J=9.6 Hz), 3.25-3.40 (3H, m), 3.17-3.20 (1H, m), 2.71 (2H, q, J=7.2 Hz), 2.12-2.14 (1H, m), 2.02-2.04 (1H, m), 1.30 (3H, t, J=7.6 Hz), 1.16 (3H, s), 0.43-0.45 (2H, m), 0.32-0.35 (2H, m). Isomer 374B (slower eluting isomer): MS: 366 (M+1). $^1H$ NMR (400 MHz, $CDCl_3$): δ 7.94 (1H, s), 6.14 (1H, brs), 4.38 (2H, s), 3.59-3.71 (2H, m), 3.54 (1H, d, J=9.6 Hz), 3.25-3.40 (3H, m), 3.17-3.20 (1H, m), 2.71 (2H, q, J=7.2 Hz), 2.12-2.14 (1H, m), 2.02-2.04 (1H, m), 1.30 (3H, t, J=7.6 Hz), 1.16 (3H, s), 0.43-0.45 (2H, m), 0.32-0.35 (2H, m).

Example 375

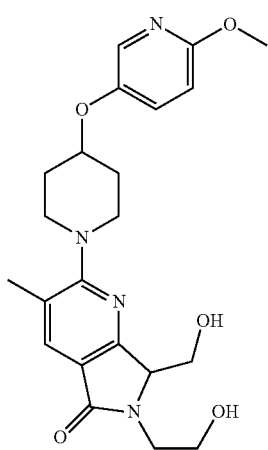

6-(2-Hydroxyethyl)-7-(hydroxymethyl)-2-(4-((6-methoxypyridin-3-yl)oxy)piperidin-1-yl)-3-methyl-6,7-dihydro-5H-pyrrolo[3,4-b]pyridin-5-one
(Scheme 43)

Step 1: Methyl 2-(7-(hydroxymethyl)-2-(4-((6-methoxypyridin-3-yl)oxy)piperidin-1-yl)-3-methyl-5-oxo-5H-pyrrolo[3,4-b]pyridin-6(7H)-yl)acetate To a solution of methyl 2-(2-(4-((6-methoxypyridin-3-yl)oxy)piperidin-1-yl)-3-methyl-5-oxo-5H-pyrrolo[3,4-b]pyridin-6(7H)-yl)acetate (40 mg, 0.094 mmol) in THF (2 mL) was added lithium bis(trimethylsilyl)amide (47.1 mg, 0.281 mmol) dropwise at −70° C. After stirring for 15 min, a solution of (1H-benzo[d][1,2,3]triazol-1-yl)methanol (21.0 mg, 0.141 mmol) in THF (0.5 mL) was added dropwise and then stirred for 30 min at −70° C. The reaction was quenched with saturated aqueous $NH_4Cl$ (0.5 mL), treated with water (10 mL) and the mixture was extracted with EtOAc (20 mL×3). The combined organic layers were dried over anhydrous sodium sulfate, filtered and concentrated. The residue was purified by prep-TLC (100% EtOAc) to give the title compound. MS: 457 (M+1).

Step 2: 6-(2-Hydroxyethyl)-7-(hydroxymethyl)-2-(4-((6-methoxypyridin-3-yl)oxy)piperidin-1-yl)-3-methyl-6,7-dihydro-5H-pyrrolo[3,4-b]pyridin-5-one To a solution of methyl 2-(7-(hydroxymethyl)-2-(4-((6-methoxypyridin-3-yl)oxy)piperidin-1-yl)-3-methyl-5-oxo-5H-pyrrolo[3,4-b]pyridin-6(7H)-yl)acetate (20.0 mg, 0.04 mmol) in THF (1 mL) was added $LiBH_4$ (2.39 mg, 0.11 mmol) at 15° C. The reaction was stirred for 15 h before quenching with saturated aqueous $NH_4Cl$ (0.5 mL), treating with water (10 mL) and extracting the mixture with EtOAc (20 mL×3). The combined organic layers were dried over anhydrous sodium sulfate, filtered and concentrated. The residue was purified by HPLC (ACN/water with 0.1% TFA modifier) to afford the title compound. MS: 429 (M+1). 1H NMR (400 MHz, methanol-$d_4$): δ 7.87 (1H, d, J=2.8 Hz), 7.74 (1H, s), 7.50 (1H, dd, J=8.8, 2.8 Hz), 6.84 (1H, d, J=8.8 Hz), 4.50-4.58 (2H, m), 4.19 (1H, dd, J=7.2, 2.8 Hz), 4.06 (1H, dd, J=7.2, 2.8 Hz), 3.75-3.95 (6H, m), 3.53-3.61 (3H, m), 3.15-3.21 (2H, m), 2.37 (3H, s), 2.12-2.16 (2H, m), 1.88-1.94 (2H, m).

Assay Protocol

The utility of the compounds as M4 muscarinic receptor allosteric modulators may be demonstrated by methodology known in the art, including by the assay described herein.

CHO-K1 cells stably transfected with human M4 receptor and chimeric G-protein Gαqi5 are thawed from liquid $N_2$ storage, resuspended in growth medium, plated in black, clear bottom 384 well plates, and incubated 16-20 hours at 37° C., 5% $CO_2$.

On the day of assay, growth medium is removed, the cells are washed 2 times with wash buffer, and cells are incubated in dye loading buffer at 37° C., 5% $CO_2$ for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 44

| Example | M4 PAM IP (nM) |
|---|---|
| 1 | 27 |
| 2A | 86 |
| 2B | 734 |
| 3 | 25 |
| 3A | 637 |
| 4 | 49 |
| 4A | 2770 |
| 5 | 21 |
| 5A | 121 |
| 6 | 17 |
| 6A | 150 |
| 7 | 30 |
| 8 | 14 |
| 8A | 87 |
| 8B | 501 |
| 9 | 83 |
| 10 | 179 |
| 11 | 38 |
| 12 | 16 |
| 13 | 174 |
| 14 | 52 |
| 15 | 1990 |
| 16 | 81 |
| 17 | 1166 |
| 18 | 36 |
| 19 | 57 |
| 20 | 83 |
| 21 | 50 |
| 22 | 32 |
| 23 | 70 |
| 24 | 167 |
| 25 | 75 |
| 26 | 28 |
| 27 | 43 |
| 28A | 84 |
| 28B | 1976 |
| 29A | 63 |
| 29B | 30000 |
| 30 | 25 |
| 31 | 42 |
| 32 | 37 |
| 33 | 22 |
| 34 | 26 |
| 35 | 24 |
| 36 | 302 |
| 37 | 172 |
| 38 | 30 |
| 39 | 1597 |
| 40 | 17 |
| 41 | 11340 |
| 42 | 1732 |
| 43A | 155 |
| 43B | 367 |
| 44 | 130 |
| 45 | 53 |
| 46 | 32 |
| 47 | 41 |
| 47A | 287 |
| 48 | 61 |
| 48A | 67 |
| 49 | 94 |
| 50 | 657 |
| 51 | 51 |
| 52 | 238 |
| 53 | 449 |
| 54 | 8762 |
| 55 | 1121 |
| 56 | 11180 |
| 57 | 61 |
| 58 | 192 |
| 59 | 123 |
| 60 | 207 |
| 61 | 135 |
| 62 | 55 |
| 63 | 145 |

TABLE 44-continued

| Example | M4 PAM IP (nM) |
|---|---|
| 64 | 206 |
| 64A | 192 |
| 65 | 75 |
| 65A | 164 |
| 66 | 84 |
| 67 | 136 |
| 68 | 79 |
| 69 | 88 |
| 70 | 79 |
| 71 | 42 |
| 72 | 30 |
| 73 | 2247 |
| 74 | 46 |
| 75 | 236 |
| 76 | 80 |
| 77 | 214 |
| 78 | 33 |
| 79 | 2277 |
| 80 | 69 |
| 81 | 37 |
| 82 | 121 |
| 83 | 48 |
| 84 | 229 |
| 85 | 2617 |
| 86 | 5690 |
| 87 | 1001 |
| 88 | 381 |
| 89 | 83 |
| 90 | 94 |
| 91 | 60 |
| 92 | 461 |
| 93 | 944 |
| 93A | 148 |
| 94 | 1734 |
| 94A | 193 |
| 95 | 616 |
| 96 | 1426 |
| 97 | 800 |
| 98 | 522 |
| 99 | 735 |
| 100 | 1027 |
| 101 | 869 |
| 102 | 690 |
| 103 | 138 |
| 104 | 60 |
| 105 | 104 |
| 106 | 298 |
| 107 | 87 |
| 108 | 59 |
| 109 | 20 |
| 110 | 39 |
| 111 | 4356 |
| 112 | 20 |
| 113 | 50 |
| 114 | 88 |
| 115 | 119 |
| 116 | 45 |
| 117 | 17 |
| 118 | 141 |
| 119 | 149 |
| 120 | 256 |
| 121 | 1919 |
| 122 | 2106 |
| 123 | 144 |
| 124 | 362 |
| 125 | 612 |
| 126 | 216 |
| 127 | 480 |
| 128 | 2374 |
| 129 | 1094 |
| 130 | 105 |
| 131 | 1520 |
| 132 | 30 |
| 133 | 611 |
| 134 | 167 |

TABLE 44-continued

| Example | M4 PAM IP (nM) |
|---|---|
| 135 | 217 |
| 136 | 3471 |
| 137 | 515 |
| 138 | 390 |
| 139 | 106 |
| 139A | 628 |
| 140 | 4710 |
| 141A | 82 |
| 141B | 55 |
| 142 | 270 |
| 143A | 101 |
| 143B | 117 |
| 144 | 316 |
| 145 | 2163 |
| 146 | 286 |
| 147 | 313 |
| 148 | 31 |
| 149 | 1000 |
| 150A | 124 |
| 150B | 197 |
| 151 | 32 |
| 152 | 1150 |
| 153 | 528 |
| 154 | 128 |
| 155 | 117 |
| 156 | 1222 |
| 157A | 93 |
| 157B | 144 |
| 158A | 452 |
| 158B | 17 |
| 159 | 28 |
| 160 | 231 |
| 160A | 627 |
| 160B | 96 |
| 160C | 58 |
| 160D | 37 |
| 161 | 1519 |
| 161A | 21 |
| 162 | 51 |
| 162A | 59 |
| 162B | 47 |
| 163 | 277 |
| 163A | 1135 |
| 164 | 82 |
| 164A | 202 |
| 165 | 467 |
| 165A | 83 |
| 166 | 90 |
| 166A | 61 |
| 166B | 57 |
| 167 | 14 |
| 167A | 188 |
| 168 | 119 |
| 168A | 209 |
| 168B | 166 |
| 169 | 183 |
| 169A | 180 |
| 170 | 40 |
| 170A | 129 |
| 171 | 79 |
| 171A | 491 |
| 171B | 14 |
| 172 | 125 |
| 172A | 905 |
| 173 | 313 |
| 173A | 207 |
| 174 | 45 |
| 174A | 22 |
| 175 | 139 |
| 175A | 3099 |
| 176 | 39 |
| 176A | 264 |
| 177 | 1813 |
| 178 | 2479 |
| 178A | 18 |
| 178B | 18 |
| 179 | 168 |
| 180 | 1653 |
| 181A | 55 |
| 181B | 183 |
| 182 | 3787 |
| 182A | 473 |
| 183 | 4778 |
| 184 | 246 |
| 185A | 8632 |
| 185B | 2529 |
| 186 | 77 |
| 187 | 223 |
| 187A | 295 |
| 188 | 1218 |
| 189 | 265 |
| 190 | 5610 |
| 190A | 820 |
| 191 | 492 |
| 191A | 1475 |
| 191B | 30000 |
| 192 | 310 |
| 193 | 1218 |
| 193A | 312 |
| 193B | 875 |
| 194 | 532 |
| 194A | 20 |
| 195 | 68 |
| 196 | 22 |
| 197 | 6065 |
| 197A | 285 |
| 198 | 18 |
| 198A | 110 |
| 199A | 60 |
| 199B | 72 |
| 200 | 96 |
| 200A | 58 |
| 201 | 230 |
| 201A | 68 |
| 202 | 148 |
| 202A | 96 |
| 203 | 531 |
| 204 | 1112 |
| 205 | 238 |
| 205A | 5632 |
| 206 | 589 |
| 206A | 259 |
| 207 | 30 |
| 208 | 329 |
| 208A | 123 |
| 209 | 2655 |
| 210 | 2583 |
| 211 | 216 |
| 212 | 1832 |
| 212A | 116 |
| 213 | 61 |
| 213A | 126 |
| 214 | 93 |
| 215 | 304 |
| 216 | 888 |
| 216A | 288 |
| 217 | 42 |
| 218 | 38 |
| 219 | 25 |
| 219A | 46 |
| 220 | 109 |
| 220A | 83 |
| 221 | 1078 |
| 222 | 50 |
| 223 | 344 |
| 224 | 3523 |
| 225 | 19 |
| 226 | 136 |
| 227 | 435 |
| 228 | 86 |
| 229 | 36 |
| 229A | 600 |
| 230 | 2117 |
| 231 | 51 |

TABLE 44-continued

| Example | M4 PAM IP (nM) |
|---|---|
| 232 | 81 |
| 233 | 394 |
| 234A | 382 |
| 234B | 78 |
| 235 | 324 |
| 236 | 317 |
| 236A | 146 |
| 237 | 68 |
| 238 | 49 |
| 238A | 87 |
| 239 | 36 |
| 239A | 86 |
| 240 | 40 |
| 240A | 127 |
| 241 | 22 |
| 241A | 93 |
| 242 | 74 |
| 243 | 73 |
| 244 | 32 |
| 244A | 28 |
| 245 | 75 |
| 246 | 125 |
| 247 | 137 |
| 248 | 88 |
| 249 | 32 |
| 250 | 149 |
| 250A | 70 |
| 251 | 198 |
| 252 | 94 |
| 253 | 49 |
| 254 | 69 |
| 255 | 29 |
| 255A | 803 |
| 256 | 85 |
| 257 | 84 |
| 258 | 126 |
| 259 | 87 |
| 259A | 117 |
| 260 | 141 |
| 260A | 43 |
| 261 | 39 |
| 262 | 43 |
| 263 | 57 |
| 263A | 40 |
| 264 | 36 |
| 264A | 38 |
| 264B | 108 |
| 264C | 40 |
| 264D | 79 |
| 264E | 125 |
| 265 | 46 |
| 265A | 100 |
| 265B | 123 |
| 265C | 41 |
| 265D | 65 |
| 256E | 34 |
| 265F | 46 |
| 266 | 105 |
| 266A | 44 |
| 266B | 53 |
| 266C | 64 |
| 266D | 43 |
| 266E | 159 |
| 266F | 57 |
| 266G | 69 |
| 267 | 34 |
| 267A | 102 |
| 267B | 80 |
| 267C | 109 |
| 267D | 87 |
| 267E | 69 |
| 267F | 17 |
| 268 | 87 |
| 268A | 169 |
| 268B | 63 |
| 268C | 53 |
| 268D | 28 |
| 268E | 68 |
| 268F | 39 |
| 269 | 65 |
| 270 | 48 |
| 271A | 941 |
| 271B | 38 |
| 272 | 395 |
| 273A | 4500 |
| 273B | 23 |
| 274 | 1163 |
| 275 | 3966 |
| 276 | 145 |
| 277 | 3403 |
| 277A | 30000 |
| 278 | 19 |
| 278A | 76 |
| 279 | 30 |
| 279A | 909 |
| 280 | 438 |
| 280A | 14 |
| 281 | 23 |
| 281A | 8063 |
| 282 | 623 |
| 282A | 38 |
| 283 | 44 |
| 284 | 4327 |
| 285 | 8623 |
| 286 | 38 |
| 287A | 3868 |
| 287B | 214 |
| 288 | 1793 |
| 289 | 156 |
| 290 | 353 |
| 291 | 204 |
| 292 | 174 |
| 293 | 104 |
| 294 | 202 |
| 295 | 137 |
| 296 | 83 |
| 297 | 22 |
| 298 | 24 |
| 299 | 265 |
| 300 | 286 |
| 301 | 1145 |
| 302 | 819 |
| 303 | 302 |
| 304 | 1116 |
| 305 | 241 |
| 306 | 320 |
| 307 | 1312 |
| 307A | 279 |
| 308 | 176 |
| 309 | 47 |
| 310 | 101 |
| 310A | 35 |
| 311 | 686 |
| 311A | 108 |
| 312 | 651 |
| 312A | 2512 |
| 312B | 1122 |
| 313 | 30 |
| 314 | 676 |
| 315 | 80 |
| 316 | 198 |
| 317 | 125 |
| 318 | 155 |
| 319 | 96 |
| 320 | 150 |
| 321 | 193 |
| 321A | 434 |
| 321B | 91 |
| 322 | 499 |
| 323A | 261 |
| 323B | 30000 |
| 324 | 17 |
| 324A | 22 |
| 324B | 28 |
| 324C | 1143 |
| 324D | 682 |

TABLE 44-continued

| Example | M4 PAM IP (nM) |
| --- | --- |
| 324E | 420 |
| 325 | 204 |
| 326 | 1655 |
| 327 | 205 |
| 328 | 61 |
| 329A | 47 |
| 329B | 241 |
| 330 | 51 |
| 331 | 33 |
| 332 | 368 |
| 333 | 37 |
| 334A | 67 |
| 334B | 38 |
| 335A | 245 |
| 335B | 259 |
| 336 | 182 |
| 336A | 19 |
| 336B | 650 |
| 336C | 33 |
| 337A | 20 |
| 337B | 867 |
| 337C | 42 |
| 337D | 613 |
| 338 | 40 |
| 339 | 13 |
| 340 | 2977 |
| 341 | 23 |
| 341A | 9 |
| 342 | 3440 |
| 342A | 884 |
| 343 | 55 |
| 343A | 27 |
| 344 | 1218 |
| 344A | 760 |
| 345 | 23 |
| 346 | 3076 |
| 347 | 28 |
| 348 | 8173 |
| 349 | 22 |
| 349A | 22 |
| 350 | 980 |
| 350A | 601 |
| 351 | 40 |
| 351A | 19 |
| 352 | 2103 |
| 352A | 239 |
| 353 | 30 |
| 354 | 1465 |
| 355 | 16 |
| 356 | 788 |
| 357 | 87 |
| 358 | 8072 |
| 359 | 37 |
| 360 | 1684 |
| 361 | 85 |
| 362 | 1292 |
| 363 | 100 |
| 364 | 3770 |
| 365 | 26 |
| 366 | 1237 |
| 367 | 19 |
| 368 | 239613 |
| 369 | 57 |
| 370 | 1189 |
| 371 | 100 |
| 372 | 634 |
| 373 | 69 |
| 374A | 416 |
| 374B | 45 |
| 375 | 69 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

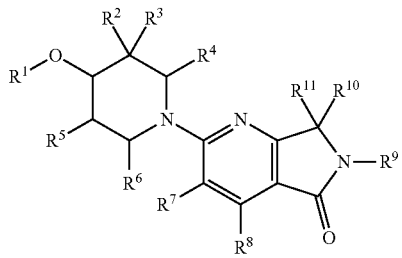

wherein:

$R^1$ is selected from the group consisting of:

(1) hydrogen;

(2) —$C_{1-6}$alkyl, which is unsubstituted or substituted with substituents selected from the group consisting of: hydroxy, fluoro, —CN, —O—$C_{1-6}$alkyl, $C_{3-6}$cycloalkyl, bicycle[1.1.1]pentane, tetrahydrofuranyl, phenyl, pyridyl, oxazolyl, —$NH_2$, —NH(—$C_{1-6}$ alkyl), —N(—$C_{1-6}$alkyl)$_2$, and —N(C=O)—$C_{1-6}$ alkyl, wherein the $C_{1-6}$alkyl or $C_{3-6}$cycloalkyl is unsubstituted or substituted with substituents selected from the group consisting of: fluoro, cyano, $CF_3$, $C_{1-6}$alkyl or —O—$C_{1-6}$alkyl;

(3) a phenyl, heteroaryl or heterocyclyl ring, wherein the phenyl, heteroaryl or heterocyclyl ring is substituted with one or more $R^{1a}$, $R^{1b}$ and $R^{1c}$, wherein $R^{1a}$, $R^{1b}$ and $R^{1c}$ are independently selected from the group consisting of:

(a) hydrogen, (b) hydroxy, (c) halogen, (d) $C_{1-6}$alkyl, which is unsubstituted or substituted with substituents selected from the group consisting of: hydroxy, cyclopropyl, cyclobutyl, cyclopentyl, azetidinyl, fluoro, —$OCH_3$, —$OCH_2CH_2OCH_3$, —(C=O)—$C_{1-6}$alkyl, —$NH_2$, —NH($C_{1-6}$alkyl), and —N($C_{1-6}$alkyl)$_2$, (e) —O—$C_{1-6}$alkyl, which is unsubstituted or substituted with substituents selected from the group consisting of: hydroxy, cyclopropyl, cyclobutyl, cyclopentyl, azetidinyl, fluoro, —$OCH_3$, —$NH_2$, —NH($C_{1-6}$alkyl), —N($C_{1-6}$alkyl)$_2$, and —NH(C=O)($C_{1-6}$alkyl), (f) $C_{3-6}$cycloalkyl, which is unsubstituted or substituted with substituents selected from the group consisting of: $C_{1-6}$alkyl, hydroxy, cyclopropyl, cyclobutyl, cyclopentyl, azetidinyl, fluoro, —$OCH_3$, —$NH_2$, —NH($C_{1-6}$alkyl), and —N($C_{1-6}$ alkyl)$_2$, (g) —$NH_2$, (h) —NH($C_{1-6}$alkyl), (i) —NH($C_{2-6}$alkyl)-OH, (j) —N($C_{1-6}$alkyl)$_2$, (k) —$SO_2$—$C_{1-6}$alkyl, (l) —(C=O)H, (m) —(C=O)—$C_{1-6}$alkyl, (n) —(C=O)O—$C_{1-6}$alkyl, and (o) —CN;

$R^2$ and $R^3$ are independently selected from the group consisting of:
(1) hydrogen,
(2) fluoro,
(3) hydroxy, and
(4) —$CH_3$;

$R^4$ is hydrogen or methyl, and $R^6$ is hydrogen or methyl, or $R^4$ and $R^6$ are joined together with a —$(CH_2)_2$— to form a bridged ring with the piperidine ring to which they are attached;

$R^5$ is hydrogen, or where $R^2$ is hydrogen, $R^3$ and $R^5$ may be joined together with a —$(CH_2)$— to form a bridged ring with the piperidine ring to which they are attached;

$R^7$ and $R^8$ are independently selected from the group consisting of:
(1) hydrogen,
(2) $C_{1-6}$alkyl, which is unsubstituted or substituted with substituents selected from the group consisting of: hydroxy, fluoro, and —$OCH_3$,
(3) —CH=$CH_2$,
(4) cyclopropyl,
(5) -fluoro,
(6) -chloro,
(7) -bromo,
(8) —CN,
(9) —(C=O)H, and
(10) —(C=O)O—$C_{1-6}$alkyl;

$R^9$ is selected from the group consisting of:
(1) hydrogen,
(2) —$C_{1-6}$alkyl, which is unsubstituted or substituted with substituents selected from the group consisting of: hydroxy, methoxy, fluoro, —C(C=O)O—$C_{1-6}$alkyl, —$NH_2$, —$NH(C_{1-6}alkyl)$, —$N(C_{1-6}alkyl)_2$, —C(C=O)$NH_2$, —C(C=O)OH, oxetanyl, or pyridyl;
(3) —$C_{3-6}$cycloalkyl,
(4) —C(C=O)O—$C_{1-6}$alkyl, and
(5) —P(O)(OH)$_2$;

each of $R^{10}$ and $R^{11}$ is independently selected from the group consisting of:
(1) hydrogen,
(2) —OH,
(3) —$CH_3$,
(4) —$CH_2$OH,
(5) —$CH_2CH_2$OH, and
(6) —C($CH_3$)$_2$OH,
or $R^{10}$ and $R^{11}$ taken together form a cyclopropyl group, a =$CH_2$ group or a keto group;

or a pharmaceutically acceptable salt thereof; with the proviso that the compound is other than:
2-(4-((6-methoxypyridin-3-yl)oxy)piperidin-1-yl)-3-methyl-6,7-dihydro,5H-pyrrolo[3,4-b]pyridin-5-one;
3-((1-(3-methyl-5-oxo-6,7-dihydro-5H-pyrrolo[3,4-b]pyridin-2-yl)piperidin-4-yl)oxy)benzonitrile;
3-methyl-2-(4-4((1-methyl-1H-indazol-5-yl)oxy)piperidin-1-yl)-6,7-dihydro-5H-pyrrolo[3,4-b]pyridin-5-one;
3-methyl-2-(4-phenoxypiperidin-1-yl)-6,7-dihydro-5H-pyrrolo[3,4-b]pyridin-5-one;
3-methyl-2-(4-((5-methylpyridin-3-yl)oxy)piperidin-1-yl)-6,7-dihydro-5H-pyrrolo[3,4-b]pyridin-5-one;
2-(4-(isochroman-7-yloxy)piperidin-1-yl)-3-methyl-6,7-dihydro-5H-pyrrolo[3,4-b]pyridin-5-one;
3-methyl-2-(4-((1-methyl-1H-pyrazol-4-yl)oxy)piperidin-1-yl)-6,7-dihydro-5H-pyrrolo[3,4-b]poyridin-5-one;
2-[4-(1,3-dihydro-2-benzofuran-5-yloxy)piperidin-1-yl]-3-methyl-6,7-dihydro-5H-pyrrolo[3,4-b]pyridin-5-one;
3-methyl-2-(4-((1-methylcyclopropyl)methoxy)piperidin-1-yl)-6,7-dihydro-5H-pyrrolo[3,4-b]pyridin-5-one;
2-(4-((2,3-dihydrobenzofuran-6-yl)oxy)piperidin-1-yl)-3-methyl-6,7-dihydro-5H-pyrrolo[3,4-b]pyridin-5-one;
2-(4-(isochroman-6-yloxy)piperidin-1-yl)-3-methyl-6,7-dihydro-5H-pyrrolo[3,4-b]pyridin-5-one;
2-(4-((6-methoxypyridin-3-yl)oxy)piperidin-1-yl)-3,4-dimethyl-6,7-dihydro-5H-pyrrolo[3,4-b]pyridin-5-one;
3,4-dimethyl-2-(4-((1-methylcyclopropyl)methoxy)piperidin-1-yl)-6,7-dihydro-5H-pyrrolo[3,4-b]pyridin-5-one;
6-(2-hydroxyethyl)-3,4-dimethyl-2-(4-phenoxylpiperidin-1-yl)-6,7-dihydro-5H-pyrrolo[3,4-b]pyridin-5-one;
6-(2-hydroxyethyl)-3,4-dimethyl-2-(4-((1-methycyclopropyl)methoxy)piperidin-1-yl)-6,7-dihydro-5H-pyrrolo[3,4-b]pyridin-5-one; or
2-(4-((1,3-dihydro-2-benzofuran-5-yl)oxy)piperidin-1-yl)-3,4-dimethyl-6,7-dihydro-5H-pyrrolo[3,4-b]pyridin-5-one.

2. The compound of claim 1, or a pharmaceutically acceptable salt thereof, wherein $R^1$ is selected from the group consisting of: benzodioxolyl, benzoimidazolyl, benzoxazolyl, benzoxazinone, benzoxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more $R^{1a}$, $R^{1b}$ and $R^{1c}$.

3. The compound of claim 1, or a pharmaceutically acceptable salt thereof, wherein $R^1$ is phenyl or pyridyl, which is substituted with one or more $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-6}$alkyl, which is unsubstituted or substituted with substituents selected from the group consisting of: hydroxy, fluoro, and —$OCH_3$,
(e) —O—$C_{1-6}$alkyl, which is unsubstituted or substituted with substituents selected from the group consisting of: hydroxy, fluoro, and —$OCH_3$,
(g) —CN.

4. The compound of claim 1, or a pharmaceutically acceptable salt thereof, wherein $R^1$ is phenyl, which is unsubstituted or substituted with —CN.

5. The compound of claim 1, or a pharmaceutically acceptable salt thereof, wherein $R^1$ is pyridyl, which is unsubstituted or substituted with —$OCH_3$.

6. The compound of claim 1, or a pharmaceutically acceptable salt thereof, wherein $R^2$, $R^3$, $R^4$, $R^5$ and $R^6$ are each hydrogen.

7. The compound of claim 1, or a pharmaceutically acceptable salt thereof, wherein $R^7$ is selected from the group consisting of:
(1) hydrogen,
(2) methyl,
(3) ethyl,
(4) —$CH_2$OH,
(5) —$CH_2$F, (6) —CHF$_2$,
(7) —CF$_3$,
(8) —CH=CH$_2$,
(9) cyclopropyl,
(10) -fluoro,
(11) -chloro,
(12) -bromo,
(13) —CN,
(14) —(C=O)H, and
(15) —(C=O)O—C$_{1-6}$alkyl.

8. The compound of claim 1, or a pharmaceutically acceptable salt thereof, wherein R$^8$ is selected from the group consisting of:
   (1) hydrogen,
   (2) methyl,
   (3) ethyl,
   (4) —CH$_2$OH,
   (5) —CH$_2$F,
   (6) —CHF$_2$,
   (7) —CF$_3$, and
   (8) —(C=O)O—C$_{1-6}$alkyl.

9. The compound of claim 1, or a pharmaceutically acceptable salt thereof, wherein R$^9$ is selected from the group consisting of:
   (1) hydrogen, and
   (2) —C$_{1-6}$alkyl, which is unsubstituted or substituted with hydroxy, methoxy, 1-3 fluoro.

10. A compound which is selected from the group consisting of:
   2-((3R,4R)-4-((6-methoxypyridin-3-yl)oxy)-3-methylpiperidin-1-yl)-3-methyl-6,7-dihydro-5H-pyrrolo[3,4-b]pyridin-5-one;
   2-((3S,4S)-4-((6-methoxypyridin-3-yl)oxy)-3-methylpiperidin-1-yl)-3-methyl-6,7-dihydro-5H-pyrrolo[3,4-b]pyridin-5-one;
   3-methyl-2-(4-(((trans-2-(trifluoromethyl)cyclopropyl)methoxy)piperidin-1-yl)-6,7-dihydro-5H-pyrrolo[3,4-b]pyridin-5-one;
   2-(4-(difluoromethoxy)piperidin-1-yl)-3-methyl-6,7-dihydro-5H-pyrrolo[3,4-b]pyridin-5-one;
   3-ethyl-2-((3S,4R)-3-fluoro-4-((1-methyl-1H-indazol-5-yl)oxy)piperidin-1-yl)-6,7-dihydro-5H-pyrrolo[3,4-b]pyridin-5-one;
   2-((3S,4R)-3-fluoro-4-((1-methyl-1H-indazol-5-yl)oxy)piperidin-1-yl)-3-methyl-6,7-dihydro-5H-pyrrolo[3,4-b]pyridin-5-one;
   3-ethyl-2-((3S,4S)-3-fluoro-4-(((1-methyl cyclopropyl)methoxy)piperidin-1-yl)-6,7-dihydro-5H-pyrrolo[3,4-b]pyridin-5-one;
   3-((cis-3-fluoro-1-(3-methyl-5-oxo-6,7-dihydro-5H-pyrrolo[3,4-b]pyridin-2-yl)piperidin-4-yl)oxy)benzonitrile;
   2-((3S,4R)-4-((1H-indazol-5-yl)oxy)-3-fluoropiperidin-1-yl)-3-methyl-6,7-dihydro-5H-pyrrolo[3,4-b]pyridin-5-one;
   (R)-2-(4-((2,2-difluoro-1-methylcyclopropyl)methoxy)piperidin-1-yl)-3-methyl-6,7-dihydro-5H-pyrrolo[3,4-b]pyridin-5-one;
   (S)-2-(4-((2,2-difluoro-1-methylcyclopropyl)methoxy)piperidin-1-yl)-3-methyl-6,7-dihydro-5H-pyrrolo[3,4-b]pyridin-5-one;
   2-(4-(cyclopropylmethoxy)piperidin-1-yl)-3-methyl-6,7-dihydro-5H-pyrrolo[3,4-b]pyridin-5-one;
   2-(4-((2-cyclopropyl-3-oxoisoindolin-5-yl)oxy)piperidin-1-yl)-3-methyl-6,7-dihydro-5H-pyrrolo[3,4-b]pyridin-5-one;
   3-((1-(3,6-dimethyl-5-oxo-6,7-dihydro-5H-pyrrolo[3,4-b]pyridin-2-yl)piperidin-4-yl)oxy)benzonitrile;
   2-(4-((1H-indazol-5-yl)oxy)piperidin-1-yl)-3,6-dimethyl-6,7-dihydro-5H-pyrrolo[3,4-b]pyridin-5-one;
   3-((1-(3,6,7-trimethyl-5-oxo-6,7-dihydro-5H-pyrrolo[3,4-b]pyridin-2-yl)piperidin-4-yl)oxy)benzonitrile;
   2-(4-((1H-indazol-5-yl)oxy)piperidin-1-yl)-3,6,7-trimethyl-6,7-dihydro-5H-pyrrolo[3,4-b]pyridin-5-one;
   3-((1-(3,6,7,7-tetramethyl-5-oxo-6,7-dihydro-5H-pyrrolo[3,4-b]pyridin-2-yl)piperidin-4-yl)oxy)benzonitrile;
   2-(4-((6-methoxypyridin-3-yl)oxy)piperidin-1-yl)-3,6,7-trimethyl-6,7-dihydro-5H-pyrrolo[3,4-b]pyridin-5-one;
   2-(4-((6-methoxypyridin-3-yl)oxy)piperidin-1-yl)-3,6,7,7-tetramethyl-6,7-dihydro-5H-pyrrolo[3,4-b]pyridin-5-one;
   2-(4-((6-methoxypyridin-3-yl)oxy)piperidin-1-yl)-3,6-dimethyl-6,7-dihydro-5H-pyrrolo[3,4-b]pyridin-5-one;
   3-(((3R,4S)-3-fluoro-1-(3-methyl-5-oxo-6,7-dihydro-5H-pyrrolo[3,4-b]pyridin-2-yl)piperidin-4-yl)oxy)benzonitrile;
   3-(((3S,4S)-3-fluoro-1-(3-methyl-5-oxo-6,7-dihydro-5H-pyrrolo[3,4-b]pyridin-2-yl)piperidin-4-yl)oxy)benzonitrile;
   3-(((3R,4R)-3-fluoro-1-(3-methyl-5-oxo-6,7-dihydro-5H-pyrrolo[3,4-b]pyridin-2-yl)piperidin-4-yl)oxy)benzonitrile;
   3-methyl-2-(4-(((1,2,3,4-tetrahydroquinolin-6-yl)oxy)piperidin-1-yl)-6,7-dihydro-5H-pyrrolo[3,4-b]pyridin-5-one;
   2-((3R,4S)-3-fluoro-4-((1-methyl-1H-indazol-5-yl)oxy)piperidin-1-yl)-3-methyl-6,7-dihydro-5H-pyrrolo[3,4-b]pyridin-5-one;
   2-((3S,4S)-3-fluoro-4-((1-methyl-1H-indazol-5-yl)oxy)piperidin-1-yl)-3-methyl-6,7-dihydro-5H-pyrrolo[3,4-b]pyridin-5-one;
   2-((3R,4R)-3-fluoro-4-((1-methyl-1H-indazol-5-yl)oxy)piperidin-1-yl)-3-methyl-6,7-dihydro-5H-pyrrolo[3,4-b]pyridin-5-one;
   2-(4-((1H-indol-5-yl)oxy)piperidin-1-yl)-3-methyl-6,7-dihydro-5H-pyrrolo[3,4-b]pyridin-5-one;
   3-methyl-2-(4-((1-methyl-1H-indol-5-yl)oxy)piperidin-1-yl)-6,7-dihydro-5H-pyrrolo[3,4-b]pyridin-5-one;
   (R)-3-((1-(3,6,7-trimethyl-5-oxo-6,7-dihydro-5H-pyrrolo[3,4-b]pyridin-2-yl)piperidin-4-yl)oxy)benzonitrile;
   (S)-3-((1-(3,6,7-trimethyl-5-oxo-6,7-dihydro-5H-pyrrolo[3,4-b]pyridin-2-yl)piperidin-4-yl)oxy)benzonitrile;
   2-((3S,4R)-4-((6-methoxypyridin-3-yl)oxy)-3-methylpiperidin-1-yl)-3-methyl-6,7-dihydro-5H-pyrrolo[3,4-b]pyridin-5-one;
   2-((3R,4S)-4-((6-methoxypyridin-3-yl)oxy)-3-methylpiperidin-1-yl)-3-methyl-6,7-dihydro-5H-pyrrolo[3,4-b]pyridin-5-one;
   2-((3R,4R)-3-fluoro-4-((6-methoxypyridin-3-yl)oxy)piperidin-1-yl)-3-methyl-6,7-dihydro-5H-pyrrolo[3,4-b]pyridin-5-one;
   2-((3S,4R)-3-fluoro-4-((1-methyl-1H-indazol-5-yl)oxy)piperidin-1-yl)-3,6-dimethyl-6,7-dihydro-5H-pyrrolo[3,4-b]pyridin-5-one;
   3,6-dimethyl-2-(4-((1-methyl-1H-indazol-5-yl)oxy)piperidin-1-yl)-6,7-dihydro-5H-pyrrolo[3,4-b]pyridin-5-one;
   2-((3S,4R)-3-fluoro-4-((6-methoxypyridin-3-yl)oxy)piperidin-1-yl)-3,6-dimethyl-6,7-dihydro-5H-pyrrolo[3,4-b]pyridin-5-one;
   2-(4-((6-ethoxypyridin-3-yl)oxy)piperidin-1-yl)-3-methyl-6,7-dihydro-5H-pyrrolo[3,4-b]pyridin-5-one;

2-((3S,4R)-3-fluoro-4-phenoxypiperidin-1-yl)-3-methyl-6,7-dihydro-5H-pyrrolo[3,4-b]pyridin-5-one;
1-(((1-(3-methyl-5-oxo-6,7-dihydro-5H-pyrrolo[3,4-b]pyridin-2-yl)piperidin-4-yl)oxy)methyl)cyclopropane-1-carbonitrile;
2-(4-((6-cyclobutoxypyridin-3-yl)oxy)piperidin-1-yl)-3-methyl-6,7-dihydro-5H-pyrrolo[3,4-b]pyridin-5-one;
2-(4-((1,3-dihydro-2-benzofuran-5-yl)oxy)piperidin-1-yl)-3,6-dimethyl-6,7-dihydro-5H-pyrrolo[3,4-b]pyridin-5-one;
2-((3S,4R)-4-((1,3-dihydro-2-benzofuran-4-yl)oxy)-3-fluoropiperidin-1-yl)-3-methyl-6,7-dihydro-5H-pyrrolo[3,4-b]pyridin-5-one;
2-((3S,4R)-4-((1,3-dihydro-2-benzofuran-5-yl)oxy)-3-fluoropiperidin-1-yl)-3-methyl-6,7-dihydro-5H-pyrrolo[3,4-b]pyridin-5-one;
3-methyl-2-(4-((tetrahydrofuran-3-yl)oxy)piperidin-1-yl)-6,7-dihydro-5H-pyrrolo[3,4-b]pyridin-5-one;
3-methyl-2-(4-((tetrahydro-2H-pyran-4-yl)oxy)piperidin-1-yl)-6,7-dihydro-5H-pyrrolo[3,4-b]pyridin-5-one;
3-(((3R,4R)-3-hydroxy-1-(3-methyl-5-oxo-6,7-dihydro-5H-pyrrolo[3,4-b]pyridin-2-yl)piperidin-4-yl)oxy)benzonitrile;
3-(((3S,4S)-3-hydroxy-1-(3-methyl-5-oxo-6,7-dihydro-5H-pyrrolo[3,4-b]pyridin-2-yl)piperidin-4-yl)oxy)benzonitrile;
2-(4-((2,3-dihydro-1H-inden-5-yl)oxy)piperidin-1-yl)-3-methyl-6,7-dihydro-5H-pyrrolo[3,4-b]pyridin-5-one;
3-(((3S,4R)-1-(3,6-dimethyl-5-oxo-6,7-dihydro-5H-pyrrolo[3,4-b]pyridin-2-yl)-3-fluoropiperidin-4-yl)oxy)benzonitrile;
2-((3S,4R)-4-((1,3-dihydro-2-benzofuran-5-yl)oxy)-3-fluoropiperidin-1-yl)-3,6-dimethyl-6,7-dihydro-5H-pyrrolo[3,4-b]pyridin-5-one;
2-(4-(4-methoxyphenoxy)piperidin-1-yl)-3-methyl-6,7-dihydro-5H-pyrrolo[3,4-b]pyridin-5-one;
3-methyl-2-(4-(3-(methylsulfonyl)phenoxy)piperidin-1-yl)-6,7-dihydro-5H-pyrrolo[3,4-b]pyridin-5-one;
2-(4-((5,7-dihydrofuro[3,4-b]pyridin-3-yl)oxy)piperidin-1-yl)-3-methyl-6,7-dihydro-5H-pyrrolo[3,4-b]pyridin-5-one;
2-((3R,4R)-4-((5,7-dihydrofuro[3,4-b]pyridin-3-yl)oxy)-3-fluoropiperidin-1-yl)-3-methyl-6,7-dihydro-5H-pyrrolo[3,4-b]pyridin-5-one;
2-(4-((5,7-dihydrofuro[3,4-b]pyridin-3-yl)oxy)piperidin-1-yl)-3,6-dimethyl-6,7-dihydro-5H-pyrrolo[3,4-b]pyridin-5-one;
5-((1-(3-methyl-5-oxo-6,7-dihydro-5H-pyrrolo[3,4-b]pyridin-2-yl)piperidin-4-yl)oxy)nicotinonitrile;
2-(4-(3-methoxyphenoxy)piperidin-1-yl)-3-methyl-6,7-dihydro-5H-pyrrolo[3,4-b]pyridin-5-one;
2-(4-((7,8-dihydro-5H-pyrano[4,3-b]pyridin-3-yl)oxy)piperidin-1-yl)-3-methyl-6,7-dihydro-5H-pyrrolo[3,4-b]pyridin-5-one;
2-(4-((7,8-dihydro-5H-pyrano[4,3-b]pyridin-3-yl)oxy)piperidin-1-yl)-3,6-dimethyl-6,7-dihydro-5H-pyrrolo[3,4-b]pyridin-5-one;
2-(4-(2-ethoxyethoxy)piperidin-1-yl)-3-methyl-6,7-dihydro-5H-pyrrolo[3,4-b]pyridin-5-one;
2-(4-ethoxypiperidin-1-yl)-3-methyl-6,7-dihydro-5H-pyrrolo[3,4-b]pyridin-5-one;
2-(4-(2-methoxyethoxy)piperidin-1-yl)-3-methyl-6,7-dihydro-5H-pyrrolo[3,4-b]pyridin-5-one;
2-(4-(3-(methoxymethyl)phenoxy)piperidin-1-yl)-3-methyl-6,7-dihydro-5H-pyrrolo[3,4-b]pyridin-5-one;
2-(4-(3-((2-methoxyethoxy)methyl)phenoxy)piperidin-1-yl)-3-methyl-6,7-dihydro-5H-pyrrolo[3,4-b]pyridin-5-one;
2-(4-((6,7-dihydro-5H-cyclopenta[b]pyridin-3-yl)oxy)piperidin-1-yl)-3-methyl-6,7-dihydro-5H-pyrrolo[3,4-b]pyridin-5-one;
2-((3R,4R)-3-fluoro-4-((6-(2-methoxyethoxy)pyridin-3-yl)oxy)piperidin-1-yl)-3-methyl-6,7-dihydro-5H-pyrrolo[3,4-b]pyridin-5-one;
2-((3R,4S)-3-fluoro-4-((6-(2-methoxyethoxy)pyridin-3-yl)oxy)piperidin-1-yl)-3-methyl-6,7-dihydro-5H-pyrrolo[3,4-b]pyridin-5-one;
2-(4-((6-isopropoxypyridin-3-yl)oxy)piperidin-1-yl)-3-methyl-6,7-dihydro-5H-pyrrolo[3,4-b]pyridin-5-one;
2-(4-(benzyloxy)piperidin-1-yl)-3-methyl-6,7-dihydro-5H-pyrrolo[3,4-b]pyridin-5-one;
2-(4-((2,2-difluoro-1-methylcyclopropyl)methoxy)piperidin-1-yl)-3-methyl-6,7-dihydro-5H-pyrrolo[3,4-b]pyridin-5-one;
2-(4-((1-fluorocyclopropyl)methoxy)piperidin-1-yl)-3-methyl-6,7-dihydro-5H-pyrrolo[3,4-b]pyridin-5-one;
2-((3S,4R)-4-((5,7-dihydrofuro[3,4-b]pyridin-3-yl)oxy)-3-fluoropiperidin-1-yl)-3-methyl-6,7-dihydro-5H-pyrrolo[3,4-b]pyridin-5-one;
3-methyl-2-(4-(2-(1-methylcyclopropyl)ethoxy)piperidin-1-yl)-6,7-dihydro-5H-pyrrolo[3,4-b]pyridin-5-one;
3-methyl-2-(4-((2-methyl-3-oxoisoindolin-5-yl)oxy)piperidin-1-yl)-6,7-dihydro-5H-pyrrolo[3,4-b]pyridin-5-one;
3-methyl-2-(4-(pyridin-3-yloxy)piperidin-1-yl)-6,7-dihydro-5H-pyrrolo[3,4-b]pyridin-5-one;
3-methyl-2-(4-((2-methylbenzo[d]oxazol-6-yl)oxy)piperidin-1-yl)-6,7-dihydro-5H-pyrrolo[3,4-b]pyridin-5-one;
2-(4-((1H-pyrrolo[2,3-b]pyridin-5-yl)oxy)piperidin-1-yl)-3-methyl-6,7-dihydro-5H-pyrrolo[3,4-b]pyridin-5-one;
2-(4-(3-fluorophenoxy)piperidin-1-yl)-3-methyl-6,7-dihydro-5H-pyrrolo[3,4-b]pyridin-5-one;
2-(4-(4-fluorophenoxy)piperidin-1-yl)-3-methyl-6,7-dihydro-5H-pyrrolo[3,4-b]pyridin-5-one;
2-(4-(2-chlorophenoxy)piperidin-1-yl)-3-methyl-6,7-dihydro-5H-pyrrolo[3,4-b]pyridin-5-one;
2-(4-(3-chlorophenoxy)piperidin-1-yl)-3-methyl-6,7-dihydro-5H-pyrrolo[3,4-b]pyridin-5-one;
2-(4-(2-fluorophenoxy)piperidin-1-yl)-3-methyl-6,7-dihydro-5H-pyrrolo[3,4-b]pyridin-5-one;
2-(4-(4-chlorophenoxy)piperidin-1-yl)-3-methyl-6,7-dihydro-5H-pyrrolo[3,4-b]pyridin-5-one;
3-methyl-2-(4-(pyridin-4-yloxy)piperidin-1-yl)-6,7-dihydro-5H-pyrrolo[3,4-b]pyridin-5-one;
3-methyl-2-(4-(m-tolyloxy)piperidin-1-yl)-6,7-dihydro-5H-pyrrolo[3,4-b]pyridin-5-one;
3-methyl-2-(4-(o-tolyloxy)piperidin-1-yl)-6,7-dihydro-5H-pyrrolo[3,4-b]pyridin-5-one;
2-(4-(benzo[d]oxazol-5-yloxy)piperidin-1-yl)-3-methyl-6,7-dihydro-5H-pyrrolo[3,4-b]pyridin-5-one;
2-(4-(3,4-difluorophenoxy)piperidin-1-yl)-3-methyl-6,7-dihydro-5H-pyrrolo[3,4-b]pyridin-5-one;
2-(4-(3-chloro-4-methylphenoxy)piperidin-1-yl)-3-methyl-6,7-dihydro-5H-pyrrolo[3,4-b]pyridin-5-one;
3-methyl-2-(4-(p-tolyloxy)piperidin-1-yl)-6,7-dihydro-5H-pyrrolo[3,4-b]pyridin-5-one;
4-((1-(3-methyl-5-oxo-6,7-dihydro-5H-pyrrolo[3,4-b]pyridin-2-yl)piperidin-4-yl)oxy)benzonitrile;
5-((1-(3-methyl-5-oxo-6,7-dihydro-5H-pyrrolo[3,4-b]pyridin-2-yl)piperidin-4-yl)oxy)picolinonitrile;

2-(4-(isoxazol-3-yloxy)piperidin-1-yl)-3-methyl-6,7-dihydro-5H-pyrrolo[3,4-b]pyridin-5-one;
methyl-5-((1-(3-methyl-5-oxo-6,7-dihydro-5H-pyrrolo[3,4-b]pyridin-2-yl)piperidin-4-yl)oxy)picolinate
3-methyl-2-(4-(((6-(trifluoromethyl)pyridin-3-yl)oxy)piperidin-1-yl)-6,7-dihydro-5H-pyrrolo[3,4-b]pyridin-5-one;
2-(4-(benzo[d]oxazol-6-yloxy)piperidin-1-yl)-3-methyl-6,7-dihydro-5H-pyrrolo[3,4-b]pyridin-5-one;
2-(4-((2-methoxypyridin-4-yl)oxy)piperidin-1-yl)-3-methyl-6,7-dihydro-5H-pyrrolo[3,4-b]pyridin-5-one;
2-(4-((6-fluoropyridin-3-yl)oxy)piperidin-1-yl)-3-methyl-6,7-dihydro-5H-pyrrolo[3,4-b]pyridin-5-one;
3-methyl-2-(4-(quinolin-7-yloxy)piperidin-1-yl)-6,7-dihydro-5H-pyrrolo[3,4-b]pyridin-5-one;
4-((1-(3-methyl-5-oxo-6,7-dihydro-5H-pyrrolo[3,4-b]pyridin-2-yl)piperidin-4-yl)oxy)picolinonitrile;
3-((1-(3-ethyl-5-oxo-6,7-dihydro-5H-pyrrolo[3,4-b]pyridin-2-yl)piperidin-4-yl)oxy)benzonitrile;
2-(4-((2-methoxypyrimidin-5-yl)oxy)piperidin-1-yl)-3-methyl-6,7-dihydro-5H-pyrrolo[3,4-b]pyridin-5-one;
3-((1-(3,4-dimethyl-5-oxo-6,7-dihydro-5H-pyrrolo[3,4-b]pyridin-2-yl)piperidin-4-yl)oxy)benzonitrile;
3-((endo-8-(3-methyl-5-oxo-6,7-dihydro-5H-pyrrolo[3,4-b]pyridin-2-yl)-8-azabicyclo[3.2.1]octan-3-yl)oxy)benzonitrile;
3-((exo-8-(3-methyl-5-oxo-6,7-dihydro-5H-pyrrolo[3,4-b]pyridin-2-yl)-8-azabicyclo[3.2.1]octan-3-yl)oxy)benzonitrile;
2-(endo-3-((6-methoxypyridin-3-yl)oxy)-8-azabicyclo[3.2.1]octan-8-yl)-3-methyl-6,7-dihydro-5H-pyrrolo[3,4-b]pyridin-5-one;
3-methyl-2-(exo-3-((1-methyl-1H-indazol-5-yl)oxy)-8-azabicyclo[3.2.1]octan-8-yl)-6,7-dihydro-5H-pyrrolo[3,4-b]pyridin-5-one;
2-(exo-3-((6-methoxypyridin-3-yl)oxy)-8-azabicyclo[3.2.1]octan-8-yl)-3-methyl-6,7-dihydro-5H-pyrrolo[3,4-b]pyridin-5-one;
3-methyl-2-(endo-3-((1-methyl-1H-indazol-5-yl)oxy)-8-azabicyclo[3.2.1]octan-8-yl)-6,7-dihydro-5H-pyrrolo[3,4-b]pyridin-5-one;
2-(4-((5-methoxypyridin-3-yl)oxy)piperidin-1-yl)-3-methyl-6,7-dihydro-5H-pyrrolo[3,4-b]pyridin-5-one;
3-methyl-2-(4-((2-(trifluoromethoxy)pyridin-4-yl)oxy)piperidin-1-yl)-6,7-dihydro-5H-pyrrolo[3,4-b]pyridin-5-one;
2-(4-((5-fluoropyridin-3-yl)oxy)piperidin-1-yl)-3-methyl-6,7-dihydro-5H-pyrrolo[3,4-b]pyridin-5-one;
2-(4-((6-aminopyridin-3-yl)oxy)piperidin-1-yl)-3-methyl-6,7-dihydro-5H-pyrrolo[3,4-b]pyridin-5-one;
2-(4-((6-(azetidin-1-yl)pyridin-3-yl)oxy)piperidin-1-yl)-3-methyl-6,7-dihydro-5H-pyrrolo[3,4-b]pyridin-5-one;
2-(4-((6-(dimethylamino)pyridin-3-yl)oxy)piperidin-1-yl)-3-methyl-6,7-dihydro-5H-pyrrolo[3,4-b]pyridin-5-one;
2-(4-((3,4-dihydro-2H-benzo[b][1,4]oxazin-6-yl)oxy)piperidin-1-yl)-3-methyl-6,7-dihydro-5H-pyrrolo[3,4-b]pyridin-5-one;
2-(4-(4-fluoro-3-methylphenoxy)piperidin-1-yl)-3-methyl-6,7-dihydro-5H-pyrrolo[3,4-b]pyridin-5-one;
2-(4-((2,3-dihydrobenzofuran-5-yl)oxy)piperidin-1-yl)-3-methyl-6,7-dihydro-5H-pyrrolo[3,4-b]pyridin-5-one;
3-methyl-2-(4-((3-oxo-1,3-dihydro-2-benzofuran-5-yl)oxy)piperidin-1-yl)-6,7-dihydro-5H-pyrrolo[3,4-b]pyridin-5-one;
methyl-5-((1-(3-methyl-5-oxo-6,7-dihydro-5H-pyrrolo[3,4-b]pyridin-2-yl)piperidin-4-yl)oxy)nicotinate;
2-(4-(chroman-7-yloxy)piperidin-1-yl)-3-methyl-6,7-dihydro-5H-pyrrolo[3,4-b]pyridin-5-one;
2-(4-((5,6-dimethylpyridin-3-yl)oxy)piperidin-1-yl)-3-methyl-6,7-dihydro-5H-pyrrolo[3,4-b]pyridin-5-one;
2-(4-((6-methoxy-5-methylpyridin-3-yl)oxy)piperidin-1-yl)-3-methyl-6,7-dihydro-5H-pyrrolo[3,4-b]pyridin-5-one;
2-(4-(chroman-6-yloxy)piperidin-1-yl)-3-methyl-6,7-dihydro-5H-pyrrolo[3,4-b]pyridin-5-one;
3-methyl-2-(4-((3-methyl-1H-indazol-5-yl)oxy)piperidin-1-yl)-6,7-dihydro-5H-pyrrolo[3,4-b]pyridin-5-one;
6-((1-(3-methyl-5-oxo-6,7-dihydro-5H-pyrrolo[3,4-b]pyridin-2-yl)piperidin-4-yl)oxy)-3,4-dihydroquinolin-2(1H)-one;
2-(4-(3,4-dimethylphenoxy)piperidin-1-yl)-3-methyl-6,7-dihydro-5H-pyrrolo[3,4-b]pyridin-5-one;
3-methyl-2-(4-((6-(2,2,2-trifluoroethoxy)pyridin-3-yl)oxy)piperidin-1-yl)-6,7-dihydro-5H-pyrrolo[3,4-b]pyridin-5-one;
3-methyl-2-(4-((1-oxoisochroman-6-yl)oxy)piperidin-1-yl)-6,7-dihydro-5H-pyrrolo[3,4-b]pyridin-5-one;
3-methyl-2-(4-((2-methylbenzo[d]thiazol-6-yl)oxy)piperidin-1-yl)-6,7-dihydro-5H-pyrrolo[3,4-b]pyridin-5-one;
3-methyl-2-(4-((2-methylbenzo[d]oxazol-5-yl)oxy)piperidin-1-yl)-6,7-dihydro-5H-pyrrolo[3,4-b]pyridin-5-one;
3-methyl-2-(4-((6-(trifluoromethoxy)pyridin-3-yl)oxy)piperidin-1-yl)-6,7-dihydro-5H-pyrrolo[3,4-b]pyridin-5-one;
2-(4-((4,4-dimethylchroman-6-yl)oxy)piperidin-1-yl)-3-methyl-6,7-dihydro-5H-pyrrolo[3,4-b]pyridin-5-one;
2-(4-((1,1-dimethyl-1,3-dihydro-2-benzofuran-5-yl)oxy)piperidin-1-yl)-3-methyl-6,7-dihydro-5H-pyrrolo[3,4-b]pyridin-5-one;
2-(4-((2,2-dimethylchroman-6-yl)oxy)piperidin-1-yl)-3-methyl-6,7-dihydro-5H-pyrrolo[3,4-b]pyridin-5-one;
7-((1-(3-methyl-5-oxo-6,7-dihydro-5H-pyrrolo[3,4-b]pyridin-2-yl)piperidin-4-yl)oxy)quinolin-2(1H)-one;
2-(4-((1,3-dimethyl-1H-indazol-5-yl)oxy)piperidin-1-yl)-3-methyl-6,7-dihydro-5H-pyrrolo[3,4-b]pyridin-5-one;
2-(4-((3,3-dimethyl-2,3-dihydrobenzofuran-5-yl)oxy)piperidin-1-yl)-3-methyl-6,7-dihydro-5H-pyrrolo[3,4-b]pyridin-5-one;
3-methyl-2-(4-(pyridin-2-yloxy)piperidin-1-yl)-6,7-dihydro-5H-pyrrolo[3,4-b]pyridin-5-one;
2-(4-((2,3-dihydrobenzo[b][1,4]dioxin-6-yl)oxy)piperidin-1-yl)-3-methyl-6,7-dihydro-5H-pyrrolo[3,4-b]pyridin-5-one;
7-((1-(3-methyl-5-oxo-6,7-dihydro-5H-pyrrolo[3,4-b]pyridin-2-yl)piperidin-4-yl)oxy)-2H-benzo[b][1,4]oxazin-3(4H)-one;
2-(4-(3-fluoro-4-methylphenoxy)piperidin-1-yl)-3-methyl-6,7-dihydro-5H-pyrrolo[3,4-b]pyridin-5-one;
7-((1-(3-methyl-5-oxo-6,7-dihydro-5H-pyrrolo[3,4-b]pyridin-2-yl)piperidin-4-yl)oxy)-3,4-dihydroisoquinolin-1-(2H)-one;
3-methyl-6-((1-(3-methyl-5-oxo-6,7-dihydro-5H-pyrrolo[3,4-b]pyridin-2-yl)piperidin-4-yl)oxy)oxazolo[4,5-b]pyridin-2(3H)-one;
tert-butyl-7-((1-(3-methyl-5-oxo-6,7-dihydro-5H-pyrrolo[3,4-b]pyridin-2-yl)piperidin-4-yl)oxy)-3,4-dihydroisoquinoline-2(1H)-carboxylate;
2-methyl-7-((1-(3-methyl-5-oxo-6,7-dihydro-5H-pyrrolo[3,4-b]pyridin-2-yl)piperidin-4-yl)oxy)-3,4-dihydroisoquinolin-1(2H)-one;

3-methyl-2-(4-((3-oxo-2,3-dihydrobenzofuran-5-yl)oxy)piperidin-1-yl)-6,7-dihydro-5H-pyrrolo[3,4-b]pyridin-5-one;
2-(4-(imidazo[1,2-a]pyridin-7-yloxy)piperidin-1-yl)-3-methyl-6,7-dihydro-5H-pyrrolo[3,4-b]pyridin-5-one;
(R)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one;
(S)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one;
2-(4-((1H-pyrazol-4-yl)oxy)piperidin-1-yl)-3-methyl-6,7-dihydro-5H-pyrrolo[3,4-b]pyridin-5-one;
(S)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one;
(R)-2-(4-((6-((1-hydroxypropan-2-yl)oxy)pyridin-3-yl)oxy)piperidin-1-yl)-3-methyl-6,7-dihydro-5H-pyrrolo[3,4-b]pyridin-5-one;
3-methyl-2-(4-((1,2,3,4-tetrahydroisoquinolin-6-yl)oxy)piperidin-1-yl)-6,7-dihydro-5H-pyrrolo[3,4-b]pyridin-5-one;
2-(4-((2,3-dihydro-1H-pyrido[2,3-b][1,4]oxazin-7-yl)oxy)piperidin-1-yl)-3-methyl-6,7-dihydro-5H-pyrrolo[3,4-b]pyridin-5-one;
3-methyl-2-(4-((1,2,3,4-tetrahydroisoquinolin-7-yl)oxy)piperidin-1-yl)-6,7-dihydro-5H-pyrrolo[3,4-b]pyridin-5-one;
2-(4-(isoindolin-5-yloxy)piperidin-1-yl)-3-methyl-6,7-dihydro-5H-pyrrolo[3,4-b]pyridin-5-one;
2-(4-((3,4-dihydro-2H-benzo[b][1,4]oxazin-7-yl)oxy)piperidin-1-yl)-3-methyl-6,7-dihydro-5H-pyrrolo[3,4-b]pyridin-5-one;
3-methyl-2-(4-((2-methyl-1H-benzo[d]imidazol-5-yl)oxy)piperidin-1-yl)-6,7-dihydro-5H-pyrrolo[3,4-b]pyridin-5-one;
(R)-2-(4-(4-(1-hydroxyethyl)phenoxy)piperidin-1-yl)-3-methyl-6,7-dihydro-5H-pyrrolo[3,4-b]pyridin-5-one;
(S)-2-(4-(4-(1-hydroxyethyl)phenoxy)piperidin-1-yl)-3-methyl-6,7-dihydro-5H-pyrrolo[3,4-b]pyridin-5-one;
2-(4-(4-(hydroxymethyl)phenoxy)piperidin-1-yl)-3-methyl-6,7-dihydro-5H-pyrrolo[3,4-b]pyridin-5-one;
2-(4-((2-(hydroxymethyl)pyridin-4-yl)oxy)piperidin-1-yl)-3-methyl-6,7-dihydro-5H-pyrrolo[3,4-b]pyridin-5-one;
2-(4-((1-(2-hydroxyethyl)-3-methyl-1H-indazol-5-yl)oxy)piperidin-1-yl)-3-methyl-6,7-dihydro-5H-pyrrolo[3,4-b]pyridin-5-one;
(S)-2-(4-((3-(2-hydroxyethyl)-2,3-dihydrobenzofuran-6-yl)oxy)piperidin-1-yl)-3-methyl-6,7-dihydro-5H-pyrrolo[3,4-b]pyridin-5-one;
2-(4-((6-(hydroxymethyl)pyridin-3-yl)oxy)piperidin-1-yl)-3-methyl-6,7-dihydro-5H-pyrrolo[3,4-b]pyridin-5-one;
2-(4-((5-(hydroxymethyl)pyridin-3-yl)oxy)piperidin-1-yl)-3-methyl-6,7-dihydro-5H-pyrrolo[3,4-b]pyridin-5-one;
(R)-2-(4-((1-(2-hydroxyethyl)-2,3-dihydro-1H-inden-5-yl)oxy)piperidin-1-yl)-3-methyl-6,7-dihydro-5H-pyrrolo[3,4-b]pyridin-5-one;
(S)-2-(4-((1-(2-hydroxyethyl)-2,3-dihydro-1H-inden-5-yl)oxy)piperidin-1-yl)-3-methyl-6,7-dihydro-5H-pyrrolo[3,4-b]pyridin-5-one;
cis-2-(3,3-difluoro-4-phenoxypiperidin-1-yl)-3-methyl-6,7-dihydro-5H-pyrrolo[3,4-b]pyridin-5-one;
trans-2-(3,3-difluoro-4-phenoxypiperidin-1-yl)-3-methyl-6,7-dihydro-5H-pyrrolo[3,4-b]pyridin-5-one;
methyl-2-(4-((6-methoxypyridin-3-yl)oxy)piperidin-1-yl)-5-oxo-6,7-dihydro-5H-pyrrolo[3,4-b]pyridine-3-carboxylate;
2-(4-(((1S,2S)-2-fluoro-1-methylcyclopropyl)methoxy)piperidin-1-yl)-3-methyl-6,7-dihydro-5H-pyrrolo[3,4-b]pyridin-5-one;
2-(4-(((1R,2R)-2-fluoro-1-methylcyclopropyl)methoxy)piperidin-1-yl)-3-methyl-6,7-dihydro-5H-pyrrolo[3,4-b]pyridin-5-one;
2-(4-(((1S,2R)-2-fluoro-1-methylcyclopropyl)methoxy)piperidin-1-yl)-3-methyl-6,7-dihydro-5H-pyrrolo[3,4-b]pyridin-5-one;
2-(4-(((1R,2S)-2-fluoro-1-methylcyclopropyl)methoxy)piperidin-1-yl)-3-methyl-6,7-dihydro-5H-pyrrolo[3,4-b]pyridin-5-one;
3-methyl-2-(4-(pyridin-3-ylmethoxy)piperidin-1-yl)-6,7-dihydro-5H-pyrrolo[3,4-b]pyridin-5-one;
2-((3S,4R)-3-fluoro-4-((1-methylcyclopropyl)methoxy)piperidin-1-yl)-3,4-dimethyl-6,7-dihydro-5H-pyrrolo[3,4-b]pyridin-5-one;
2-((3S,4R)-3-fluoro-4-((2-methylbenzo[d]oxazol-6-yl)oxy)piperidin-1-yl)-3-methyl-6,7-dihydro-5H-pyrrolo[3,4-b]pyridin-5-one;
(R)-2-(4-((2-methoxy-2,3-dihydro-1H-inden-5-yl)oxy)piperidin-1-yl)-3-methyl-6,7-dihydro-5H-pyrrolo[3,4-b]pyridin-5-one;
(S)-2-(4-((2-methoxy-2,3-dihydro-1H-inden-5-yl)oxy)piperidin-1-yl)-3-methyl-6,7-dihydro-5H-pyrrolo[3,4-b]pyridin-5-one;
2-((3S,4R)-3-fluoro-4-((2-methyl-3-oxoisoindolin-5-yl)oxy)piperidin-1-yl)-3-methyl-6,7-dihydro-5H-pyrrolo[3,4-b]pyridin-5-one;
2-(4-((1H-benzo[d][1,2,3]triazol-5-yl)oxy)piperidin-1-yl)-3-methyl-6,7-dihydro-5H-pyrrolo[3,4-b]pyridin-5-one;
2-((3S,4R)-3-fluoro-4-((6-methoxypyridin-3-yl)oxy)piperidin-1-yl)-3-methyl-6,7-dihydro-5H-pyrrolo[3,4-b]pyridin-5-one;
2-((3S,4R)-4-((5,7-dihydrofuro[3,4-b]pyridin-3-yl)oxy)-3-fluoropiperidin-1-yl)-3-ethyl-6,7-dihydro-5H-pyrrolo[3,4-b]pyridin-5-one;
2-((3R,4S)-3-fluoro-4-(pyridin-3-yloxy)piperidin-1-yl)-3-methyl-6,7-dihydro-5H-pyrrolo[3,4-b]pyridin-5-one;
2-(3S,4R)-3-fluoro-4-(pyridin-3-yloxy)piperidin-1-yl)-3-methyl-6,7-dihydro-5H-pyrrolo[3,4-b]pyridin-5-one;
(3S,4R)-3-fluoro-4-(pyridin-3-yloxy)piperidin-1-yl)-3-methyl-6,7-dihydro-5H-pyrrolo[3,4-b]pyridin-5-one;
2-((3S,4R)-4-((5,7-dihydrofuro[3,4-b]pyridin-3-yl)oxy)-3-fluoropiperidin-1-yl)-3,4-dimethyl-6,7-dihydro-5H-pyrrolo[3,4-b]pyridin-5-one;
2-((3S,4R)-3-fluoro-4-(pyridin-3-yloxy)piperidin-1-yl)-3-methyl-6,7-dihydro-5H-pyrrolo[3,4-b]pyridin-5-one;
2-(3R,4S)-3-fluoro-4-(pyridin-3-yloxy)piperidin-1-yl)-3-methyl-6,7-dihydro-5H-pyrrolo[3,4-b]pyridin-5-one;
(R)-3-ethyl-2-(4-((2-hydroxy-2,3-dihydro-1H-inden-5-yl)oxy)piperidin-1-yl)-6,7-dihydro-5H-pyrrolo[3,4-b]pyridin-5-one;
(S)-3-ethyl-2-(4-((2-hydroxy-2,3-dihydro-1H-inden-5-yl)oxy)piperidin-1-yl)-6,7-dihydro-5H-pyrrolo[3,4-b]pyridin-5-one;
2-(4-((1H-indazol-5-yl)oxy)piperidin-1-yl)-3-methyl-6,7-dihydro-5H-pyrrolo[3,4-b]pyridin-5-one;
3-methyl-2-(4-((2-oxido-1,3-dihydrobenzo[c]thiophen-5-yl)oxy)piperidin-1-yl)-6,7-dihydro-5H-pyrrolo[3,4-b]pyridin-5-one;

2-(4-((6-(2-(dimethylamino)ethoxy)pyridin-3-yl)oxy)piperidin-1-yl)-3-methyl-6,7-dihydro-5H-pyrrolo[3,4-b]pyridin-5-one;
(R)-3-methyl-2-(4-((2-oxido-1,3-dihydrobenzo[c]thiophen-5-yl)oxy)piperidin-1-yl)-6,7-dihydro-5H-pyrrolo[3,4-b]pyridin-5-one;
(S)-3-methyl-2-(4-((2-oxido-1,3-dihydrobenzo[c]thiophen-5-yl)oxy)piperidin-1-yl)-6,7-dihydro-5H-pyrrolo[3,4-b]pyridin-5-one;
2-(4-((6-(2-amino-2-methylpropoxy)pyridin-3-yl)oxy)piperidin-1-yl)-3-methyl-6,7-dihydro-5H-pyrrolo[3,4-b]pyridin-5-one;
2-(4-((1-ethyl-1H-pyrazol-4-yl)oxy)piperidin-1-yl)-3-methyl-6,7-dihydro-5H-pyrrolo[3,4-b]pyridin-5-one;
2-(4-((6-(2-hydroxyethoxy)pyridin-3-yl)oxy)piperidin-1-yl)-3-methyl-6,7-dihydro-5H-pyrrolo[3,4-b]pyridin-5-one;
3-methyl-2-(4-((1-phenyl-1H-pyrazol-4-yl)oxy)piperidin-1-yl)-6,7-dihydro-5H-pyrrolo[3,4-b]pyridin-5-one;
2-(4-((6-(2-methoxyethoxy)pyridin-3-yl)oxy)piperidin-1-yl)-3-methyl-6,7-dihydro-5H-pyrrolo[3,4-b]pyridin-5-one;
(R)-2-(3,3-difluoro-4-((1-methylcyclopropyl)methoxy)piperidin-1-yl)-3-methyl-6,7-dihydro-5H-pyrrolo[3,4-b]pyridin-5-one;
(S)-2-(3,3-difluoro-4-((1-methylcyclopropyl)methoxy)piperidin-1-yl)-3-methyl-6,7-dihydro-5H-pyrrolo[3,4-b]pyridin-5-one;
2-(4-(cyclobutylmethoxy)piperidin-1-yl)-3-methyl-6,7-dihydro-5H-pyrrolo[3,4-b]pyridin-5-one;
3-methyl-2-(4-(2,2,2-trifluoroethoxy)piperidin-1-yl)-6,7-dihydro-5H-pyrrolo[3,4-b]pyridin-5-one;
2-(4-((6-(2-(azetidin-1-yl)ethoxy)pyridin-3-yl)oxy)piperidin-1-yl)-3-methyl-6,7-dihydro-5H-pyrrolo[3,4-b]pyridin-5-one;
3-ethyl-2-(4-((5-methylpyridin-3-yl)oxy)piperidin-1-yl)-6,7-dihydro-5H-pyrrolo[3,4-b]pyridin-5-one;
N-(2-((5-((1-(3-methyl-5-oxo-6,7-dihydro-5H-pyrrolo[3,4-b]pyridin-2-yl)piperidin-4-yl)oxy)pyridin-2-yl)oxy)ethyl)acetamide
2-((3R,4R)-3-fluoro-4-((1-methylcyclopropyl)methoxy)piperidin-1-yl)-3,4-dimethyl-6,7-dihydro-5H-pyrrolo[3,4-b]pyridin-5-one;
2-(4-(cyclopentylmethoxy)piperidin-1-yl)-3-methyl-6,7-dihydro-5H-pyrrolo[3,4-b]pyridin-5-one;
3-methyl-2-(4-(pyridin-4-ylmethoxy)piperidin-1-yl)-6,7-dihydro-5H-pyrrolo[3,4-b]pyridin-5-one;
2-(4-(cyclopropylmethoxy)piperidin-1-yl)-3-ethyl-6,7-dihydro-5H-pyrrolo[3,4-b]pyridin-5-one;
3-methyl-2-(4-((tetrahydrofuran-3-yl)methoxy)piperidin-1-yl)-6,7-dihydro-5H-pyrrolo[3,4-b]pyridin-5-one;
3-methyl-2-(4-((1-methylcyclopentyl)methoxy)piperidin-1-yl)-6,7-dihydro-5H-pyrrolo[3,4-b]pyridin-5-one;
2-((3S,4R)-3-fluoro-4-(isochroman-6-yloxy)piperidin-1-yl)-3-methyl-6,7-dihydro-5H-pyrrolo[3,4-b]pyridin-5-one;
2-((3S,4R)-3-fluoro-4-(isochroman-7-yloxy)piperidin-1-yl)-3-methyl-6,7-dihydro-5H-pyrrolo[3,4-b]pyridin-5-one;
3-methyl-2-(4-(3,3,3-trifluoro-2-hydroxypropoxy)piperidin-1-yl)-6,7-dihydro-5H-pyrrolo[3,4-b]pyridin-5-one;
2-(4-((1-fluorocyclopentyl)methoxy)piperidin-1-yl)-3-methyl-6,7-dihydro-5H-pyrrolo[3,4-b]pyridin-5-one;
(R)-3-methyl-2-(4-(3,3,3-trifluoro-2-hydroxypropoxy)piperidin-1-yl)-6,7-dihydro-5H-pyrrolo[3,4-b]pyridin-5-one;
(S)-3-methyl-2-(4-(3,3,3-trifluoro-2-hydroxypropoxy)piperidin-1-yl)-6,7-dihydro-5H-pyrrolo[3,4-b]pyridin-5-one;
3-methyl-2-(4-(neopentyloxy)piperidin-1-yl)-6,7-dihydro-5H-pyrrolo[3,4-b]pyridin-5-one;
2-(4-(imidazo[1,2-a]pyridin-6-yloxy)piperidin-1-yl)-3-methyl-6,7-dihydro-5H-pyrrolo[3,4-b]pyridin-5-one;
3-methyl-2-(4-(oxazol-2-ylmethoxy)piperidin-1-yl)-6,7-dihydro-5H-pyrrolo[3,4-b]pyridin-5-one;
3-methyl-2-(4-((1-methylcyclobutyl)methoxy)piperidin-1-yl)-6,7-dihydro-5H-pyrrolo[3,4-b]pyridin-5-one;
2-((1R,5S)-6-((6-methoxypyridin-3-yl)oxy)-3-azabicyclo[3.1.1]heptan-3-yl)-3-methyl-6,7-dihydro-5H-pyrrolo[3,4-b]pyridin-5-one;
2-((1R,5S)-6-((6-methoxypyridin-3-yl)oxy)-3-azabicyclo[3.1.1]heptan-3-yl)-3-methyl-6,7-dihydro-5H-pyrrolo[3,4-b]pyridin-5-one;
2-(4-((1-ethylcyclopropyl)methoxy)piperidin-1-yl)-3-methyl-6,7-dihydro-5H-pyrrolo[3,4-b]pyridin-5-one;
2-(4-(bicyclo[1.1.1]pentan-1-ylmethoxy)piperidin-1-yl)-3-methyl-6,7-dihydro-5H-pyrrolo[3,4-b]pyridin-5-one;
2-(4-((2,2-difluoro-1-methylcyclopropyl)methoxy)piperidin-1-yl)-3-ethyl-6,7-dihydro-5H-pyrrolo[3,4-b]pyridin-5-one;
3-methyl-2-(4-(3,3,3-trifluoro-2-methylpropoxy)piperidin-1-yl)-6,7-dihydro-5H-pyrrolo[3,4-b]pyridin-5-one;
3-methyl-2-(4-((1-(trifluoromethyl)cyclopropyl)methoxy)piperidin-1-yl)-6,7-dihydro-5H-pyrrolo[3,4-b]pyridin-5-one;
methyl 2-(4-((6-methoxypyridin-3-yl)oxy)piperidin-1-yl)-3-methyl-5-oxo-6,7-dihydro-5H-pyrrolo[3,4-b]pyridine-4-carboxylate;
3-methyl-2-(4-((1-methyl-1H-pyrazol-4-yl)methoxy)piperidin-1-yl)-6,7-dihydro-5H-pyrrolo[3,4-b]pyridin-5-one;
2-(4-(cyclohexylmethoxy)piperidin-1-yl)-3-methyl-6,7-dihydro-5H-pyrrolo[3,4-b]pyridin-5-one;
(1S,2R)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile;
(1R,2S)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile;
2-(4-isobutoxypiperidin-1-yl)-3-methyl-6,7-dihydro-5H-pyrrolo[3,4-b]pyridin-5-one;
2-(4-((1-methoxycyclopropyl)methoxy)piperidin-1-yl)-3-methyl-6,7-dihydro-5H-pyrrolo[3,4-b]pyridin-5-one;
(1R,2R)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile;
(1S,2S)-2-methyl-2-(((1-(3-methyl-5-oxo-6,7-dihydro-5H-pyrrolo[3,4-b]pyridin-2-yl)piperidin-4-yl)oxy)methyl)cyclopropane-1-carbonitrile;
2-(4-((3,4-dihydro-2H-pyrano[2,3-b]pyridin-6-yl)oxy)piperidin-1-yl)-3-methyl-6,7-dihydro-5H-pyrrolo[3,4-b]pyridin-5-one;
2-((3S,4R)-3-fluoro-4-(isochroman-7-yloxy)piperidin-1-yl)-3,4-dimethyl-6,7-dihydro-5H-pyrrolo[3,4-b]pyridin-5-one;
2-(4-(4-(methoxymethyl)phenoxy)piperidin-1-yl)-3-methyl-6,7-dihydro-5H-pyrrolo[3,4-b]pyridin-5-one;
2-((3S,4R)-3-fluoro-4-(4-fluorophenoxy)piperidin-1-yl)-3-methyl-6,7-dihydro-5H-pyrrolo[3,4-b]pyridin-5-one;
3-methyl-2-(4-((3-methyl-1H-pyrazolo[3,4-b]pyridin-5-yl)oxy)piperidin-1-yl)-6,7-dihydro-5H-pyrrolo[3,4-b]pyridin-5-one;

2-(4-([1,2,4]triazolo[1,5-a]pyridin-6-yloxy)piperidin-1-yl)-3-methyl-6,7-dihydro-5H-pyrrolo[3,4-b]pyridin-5-one;
2-(4-((2,3-dihydrobenzofuran-6-yl)oxy)piperidin-1-yl)-3-ethyl-6,7-dihydro-5H-pyrrolo[3,4-b]pyridin-5-one;
(R)-3-methyl-2-(4-((1-methyl-1,3-dihydro-2-benzofuran-5-yl)oxy)piperidin-1-yl)-6,7-dihydro-5H-pyrrolo[3,4-b]pyridin-5-one;
(S)-3-methyl-2-(4-((1-methyl-1,3-dihydro-2-benzofuran-5-yl)oxy)piperidin-1-yl)-6,7-dihydro-5H-pyrrolo[3,4-b]pyridin-5-one;
3-ethyl-2-(4-(isochroman-7-yloxy)piperidin-1-yl)-6,7-dihydro-5H-pyrrolo[3,4-b]pyridin-5-one;
3-ethyl-2-(4-(isochroman-6-yloxy)piperidin-1-yl)-6,7-dihydro-5H-pyrrolo[3,4-b]pyridin-5-one;
3-ethyl-2-(4-(pyridin-3-yloxy)piperidin-1-yl)-6,7-dihydro-5H-pyrrolo[3,4-b]pyridin-5-one;
2-(4-((2,3-dihydrofuro[2,3-b]pyridin-5-yl)oxy)piperidin-1-yl)-3-methyl-6,7-dihydro-5H-pyrrolo[3,4-b]pyridin-5-one;
3-ethyl-2-(4-phenoxypiperidin-1-yl)-6,7-dihydro-5H-pyrrolo[3,4-b]pyridin-5-one;
3-methyl-2-(4-((2-methyl-2H-indazol-5-yl)oxy)piperidin-1-yl)-6,7-dihydro-5H-pyrrolo[3,4-b]pyridin-5-one;
2-(4-((6-(methoxymethyl)pyridin-3-yl)oxy)piperidin-1-yl)-3-methyl-6,7-dihydro-5H-pyrrolo[3,4-b]pyridin-5-one;
2-(4-((6-((2-methoxyethoxy)methyl)pyridin-3-yl)oxy)piperidin-1-yl)-3-methyl-6,7-dihydro-5H-pyrrolo[3,4-b]pyridin-5-one;
2-(4-(4-((2-methoxyethoxy)methyl)phenoxy)piperidin-1-yl)-3-methyl-6,7-dihydro-5H-pyrrolo[3,4-b]pyridin-5-one;
3-methyl-2-(4-(pyridin-2-ylmethoxy)piperidin-1-yl)-6,7-dihydro-5H-pyrrolo[3,4-b]pyridin-5-one;
2-(4-((1H-pyrazolo[3,4-b]pyridin-5-yl)oxy)piperidin-1-yl)-3-methyl-6,7-dihydro-5H-pyrrolo[3,4-b]pyridin-5-one;
2-(4-((2,2-difluorobenzo[d][1,3]dioxol-5-yl)oxy)piperidin-1-yl)-3-methyl-6,7-dihydro-5H-pyrrolo[3,4-b]pyridin-5-one;
2-(4-((2,2-dioxido-1,3-dihydrobenzo[c]thiophen-5-yl)oxy)piperidin-1-yl)-3-methyl-6,7-dihydro-5H-pyrrolo[3,4-b]pyridin-5-one;
2-(4-((1,2-dimethyl-1H-benzo[d]imidazol-5-yl)oxy)piperidin-1-yl)-3-methyl-6,7-dihydro-5H-pyrrolo[3,4-b]pyridin-5-one;
2-(4-((1,2-dimethyl-1H-benzo[d]imidazol-6-yl)oxy)piperidin-1-yl)-3-methyl-6,7-dihydro-5H-pyrrolo[3,4-b]pyridin-5-one;
methyl 2-(5-((1-(3-methyl-5-oxo-6,7-dihydro-5H-pyrrolo[3,4-b]pyridin-2-yl)piperidin-4-yl)oxy)-1H-indazol-1-yl)acetate;
methyl 2-(4-((1,3-dihydro-2-benzofuran-5-yl)oxy)piperidin-1-yl)-3-methyl-5-oxo-6,7-dihydro-5H-pyrrolo[3,4-b]pyridine-4-carboxylate;
2-(4-((5,7-dihydrofuro[3,4-b]pyridin-3-yl)oxy)piperidin-1-yl)-3-ethyl-6,7-dihydro-5H-pyrrolo[3,4-b]pyridin-5-one;
2-(4-((1,3-dihydro-2-benzofuran-5-yl)oxy)piperidin-1-yl)-3-ethyl-6,7-dihydro-5H-pyrrolo[3,4-b]pyridin-5-one;
2-((3R,4R)-4-((5,7-dihydrofuro[3,4-b]pyridin-3-yl)oxy)-3-fluoropiperidin-1-yl)-3-ethyl-6,7-dihydro-5H-pyrrolo[3,4-b]pyridin-5-one;
2-((3S,4R)-4-((1,3-dihydro-2-benzofuran-5-yl)oxy)-3-fluoropiperidin-1-yl)-3-ethyl-6,7-dihydro-5H-pyrrolo[3,4-b]pyridin-5-one;
3-ethyl-2-((3S,4R)-3-fluoro-4-(pyridin-3-yloxy)piperidin-1-yl)-6,7-dihydro-5H-pyrrolo[3,4-b]pyridin-5-one;
3-ethyl-2-((3R,4S)-3-fluoro-4-(pyridin-3-yloxy)piperidin-1-yl)-6,7-dihydro-5H-pyrrolo[3,4-b]pyridin-5-one;
3-ethyl-2-((3R,4S)-3-fluoro-4-(pyridin-3-yloxy)piperidin-1-yl)-6,7-dihydro-5H-pyrrolo[3,4-b]pyridin-5-one;
3-ethyl-2-((3S,4R)-3-fluoro-4-(pyridin-3-yloxy)piperidin-1-yl)-6,7-dihydro-5H-pyrrolo[3,4-b]pyridin-5-one;
2-(4-((2,3-dihydrofuro[3,2-b]pyridin-6-yl)oxy)piperidin-1-yl)-3-methyl-6,7-dihydro-5H-pyrrolo[3,4-b]pyridin-5-one;
2-((3R,4R)-4-((1,3-dihydro-2-benzofuran-5-yl)oxy)-3-fluoropiperidin-1-yl)-3-ethyl-6,7-dihydro-5H-pyrrolo[3,4-b]pyridin-5-one;
2-((3S,4S)-3-fluoro-4-((1-methylcyclopropyl)methoxy)piperidin-1-yl)-3,4-dimethyl-6,7-dihydro-5H-pyrrolo[3,4-b]pyridin-5-one;
2-(4-((6-(2-methoxyethoxy)pyridin-3-yl)oxy)piperidin-1-yl)-3,4-dimethyl-6,7-dihydro-5H-pyrrolo[3,4-b]pyridin-5-one;
3,4-dimethyl-2-(4-((5-methylpyridin-3-yl)oxy)piperidin-1-yl)-6,7-dihydro-5H-pyrrolo[3,4-b]pyridin-5-one;
3-cyclopropyl-2-(4-((6-methoxypyridin-3-yl)oxy)piperidin-1-yl)-6,7-dihydro-5H-pyrrolo[3,4-b]pyridin-5-one;
2-(4-((6-methoxypyridin-3-yl)oxy)piperidin-1-yl)-3-vinyl-6,7-dihydro-5H-pyrrolo[3,4-b]pyridin-5-one;
2-(4-((6-methoxypyridin-3-yl)oxy)piperidin-1-yl)-5-oxo-6,7-dihydro-5H-pyrrolo[3,4-b]pyridine-3-carbonitrile;
4-methyl-2-(4-((1-methylcyclopropyl)methoxy)piperidin-1-yl)-6,7-dihydro-5H-pyrrolo[3,4-b]pyridin-5-one;
2-((3S,4R)-4-((1,3-dihydro-2-benzofuran-5-yl)oxy)-3-fluoropiperidin-1-yl)-3,4-dimethyl-6,7-dihydro-5H-pyrrolo[3,4-b]pyridin-5-one;
3-bromo-2-(4-((1,3-dihydro-2-benzofuran-5-yl)oxy)piperidin-1-yl)-6,7-dihydro-5H-pyrrolo[3,4-b]pyridin-5-one;
2-(4-((5,7-dihydrofuro[3,4-b]pyridin-3-yl)oxy)piperidin-1-yl)-3,4-dimethyl-6,7-dihydro-5H-pyrrolo[3,4-b]pyridin-5-one;
3-Ethyl-2-(4-((6-methoxypyridin-3-yl)oxy)piperidin-1-yl)-6,7-dihydro-5H-pyrrolo[3,4-b]pyridin-5-one;
3-ethyl-2-(4-((1-methylcyclopropyl)methoxy)piperidin-1-yl)-6,7-dihydro-5H-pyrrolo[3,4-b]pyridin-5-one;
4-ethyl-2-(4-((6-methoxypyridin-3-yl)oxy)piperidin-1-yl)-3-methyl-6,7-dihydro-5H-pyrrolo[3,4-b]pyridin-5-one;
2-(4-((6-methoxypyridin-3-yl)oxy)piperidin-1-yl)-3-(trifluoromethyl)-6,7-dihydro-5H-pyrrolo[3,4-b]pyridin-5-one;
6-(2-hydroxyethyl)-3-methyl-2-(4-phenoxypiperidin-1-yl)-6,7-dihydro-5H-pyrrolo[3,4-b]pyridin-5-one;
6-Ethyl-2-(4-((6-methoxypyridin-3-yl)oxy)piperidin-1-yl)-3-methyl-6,7-dihydro-5H-pyrrolo[3,4-b]pyridin-5-one;
6,7-diethyl-2-(4-((6-methoxypyridin-3-yl)oxy)piperidin-1-yl)-3-methyl-6,7-dihydro-5H-pyrrolo[3,4-b]pyridin-5-one;
(S)-2-(4-((6-ethoxypyridin-3-yl)oxy)piperidin-1-yl)-7-(2-hydroxyethyl)-3-methyl-6,7-dihydro-5H-pyrrolo[3,4-b]pyridin-5-one;
(R)-2-(4-((6-ethoxypyridin-3-yl)oxy)piperidin-1-yl)-7-(2-hydroxyethyl)-3-methyl-6,7-dihydro-5H-pyrrolo[3,4-b]pyridin-5-one;

6-(2-(dimethylamino)ethyl)-2-(4-((6-methoxypyridin-3-yl)oxy)piperidin-1-yl)-3-methyl-6,7-dihydro-5H-pyrrolo[3,4-b]pyridin-5-one;
3-((1-(6-(2-(dimethylamino)ethyl)-3-methyl-5-oxo-6,7-dihydro-5H-pyrrolo[3,4-b]pyridin-2-yl)piperidin-4-yl)oxy)benzonitrile;
2-(4-((5,7-dihydrofuro[3,4-b]pyridin-3-yl)oxy)piperidin-1-yl)-6-(2-hydroxyethyl)-3-methyl-6,7-dihydro-5H-pyrrolo[3,4-b]pyridin-5-one;
2-((3S,4R)-3-fluoro-4-phenoxypiperidin-1-yl)-6-(2-hydroxyethyl)-3-methyl-6,7-dihydro-5H-pyrrolo[3,4-b]pyridin-5-one;
6-(2-hydroxyethyl)-2-(4-((6-methoxypyridin-3-yl)oxy)piperidin-1-yl)-3-methyl-6,7-dihydro-5H-pyrrolo[3,4-b]pyridin-5-one;
(R)-2-(4-((1,3-dihydro-2-benzofuran-5-yl)oxy)piperidin-1-yl)-6-(2-hydroxypropyl)-3-methyl-6,7-dihydro-5H-pyrrolo[3,4-b]pyridin-5-one;
(S)-2-(4-((1,3-dihydro-2-benzofuran-5-yl)oxy)piperidin-1-yl)-6-(2-hydroxypropyl)-3-methyl-6,7-dihydro-5H-pyrrolo[3,4-b]pyridin-5-one;
3-((1-(6-(2-hydroxyethyl)-3-methyl-5-oxo-6,7-dihydro-5H-pyrrolo[3,4-b]pyridin-2-yl)piperidin-4-yl)oxy)benzonitrile;
6-(2-hydroxyethyl)-3-methyl-2-(4-((1-methyl-1H-indazol-5-yl)oxy)piperidin-1-yl)-6,7-dihydro-5H-pyrrolo[3,4-b]pyridin-5-one;
3,6-dimethyl-2-(4-phenoxypiperidin-1-yl)-6,7-dihydro-5H-pyrrolo[3,4-b]pyridin-5-one;
3-ethyl-2-((3S,4R)-3-fluoro-4-((1-methyl-1H-indazol-5-yl)oxy)piperidin-1-yl)-6-(2-hydroxyethyl)-6,7-dihydro-5H-pyrrolo[3,4-b]pyridin-5-one;
2-((3S,4R)-3-fluoro-4-phenoxypiperidin-1-yl)-3,6-dimethyl-6,7-dihydro-5H-pyrrolo[3,4-b]pyridin-5-one;
2-((3R,4R)-3-fluoro-4-((1-methyl-1H-indazol-5-yl)oxy)piperidin-1-yl)-6-(2-hydroxyethyl)-3-methyl-6,7-dihydro-5H-pyrrolo[3,4-b]pyridin-5-one;
3-((1-(6-ethyl-3-methyl-5-oxo-6,7-dihydro-5H-pyrrolo[3,4-b]pyridin-2-yl)piperidin-4-yl)oxy)benzonitrile;
6-ethyl-3-methyl-2-(4-phenoxypiperidin-1-yl)-6,7-dihydro-5H-pyrrolo[3,4-b]pyridin-5-one;
6-ethyl-2-((3S,4R)-3-fluoro-4-phenoxypiperidin-1-yl)-3-methyl-6,7-dihydro-5H-pyrrolo[3,4-b]pyridin-5-one;
2-(4-((1,3-dihydro-2-benzofuran-5-yl)oxy)piperidin-1-yl)-6-ethyl-3-methyl-6,7-dihydro-5H-pyrrolo[3,4-b]pyridin-5-one;
6-isopropyl-2-(4-((6-methoxypyridin-3-yl)oxy)piperidin-1-yl)-3-methyl-6,7-dihydro-5H-pyrrolo[3,4-b]pyridin-5-one;
3-((1-(6-isopropyl-3-methyl-5-oxo-6,7-dihydro-5H-pyrrolo[3,4-b]pyridin-2-yl)piperidin-4-yl)oxy)benzonitrile;
6-isopropyl-3-methyl-2-(4-phenoxypiperidin-1-yl)-6,7-dihydro-5H-pyrrolo[3,4-b]pyridin-5-one;
2-((3S,4R)-3-fluoro-4-phenoxypiperidin-1-yl)-6-isopropyl-3-methyl-6,7-dihydro-5H-pyrrolo[3,4-b]pyridin-5-one;
3-((1-(6-cyclopropyl-3-methyl-5-oxo-6,7-dihydro-5H-pyrrolo[3,4-b]pyridin-2-yl)piperidin-4-yl)oxy)benzonitrile;
6-cyclopropyl-3-methyl-2-(4-phenoxypiperidin-1-yl)-6,7-dihydro-5H-pyrrolo[3,4-b]pyridin-5-one;
2-(4-((6-methoxypyridin-3-yl)oxy)piperidin-1-yl)-3-methyl-6-(oxetan-3-ylmethyl)-6,7-dihydro-5H-pyrrolo[3,4-b]pyridin-5-one;
6-(3-methoxypropyl)-2-(4-((6-methoxypyridin-3-yl)oxy)piperidin-1-yl)-3-methyl-6,7-dihydro-5H-pyrrolo[3,4-b]pyridin-5-one;
6-(2-methoxyethyl)-2-(4-((6-methoxypyridin-3-yl)oxy)piperidin-1-yl)-3-methyl-6,7-dihydro-5H-pyrrolo[3,4-b]pyridin-5-one;
2-(4-(4-fluorophenoxy)piperidin-1-yl)-3,6-dimethyl-6,7-dihydro-5H-pyrrolo[3,4-b]pyridin-5-one;
2-(4-((6-ethoxypyridin-3-yl)oxy)piperidin-1-yl)-6-(2-hydroxyethyl)-3-methyl-6,7-dihydro-5H-pyrrolo[3,4-b]pyridin-5-one;
2-((3S,4R)-4-((1,3-dihydro-2-benzofuran-5-yl)oxy)-3-fluoropiperidin-1-yl)-6-(2-hydroxyethyl)-3-methyl-6,7-dihydro-5H-pyrrolo[3,4-b]pyridin-5-one;
2-(4-((6-methoxypyridin-3-yl)oxy)piperidin-1-yl)-3-methyl-6,7-bis(oxetan-3-ylmethyl)-6,7-dihydro-5H-pyrrolo[3,4-b]pyridin-5-one;
methyl 2-(3,4-dimethyl-2-(4-((1-methylcyclopropyl)methoxy)piperidin-1-yl)-5-oxo-5,7-dihydro-6H-pyrrolo[3,4-b]pyridin-6-yl)acetate;
2-((3R,4R)-4-((1,3-dihydro-2-benzofuran-5-yl)oxy)-3-fluoropiperidin-1-yl)-6-(2-hydroxyethyl)-3-methyl-6,7-dihydro-5H-pyrrolo[3,4-b]pyridin-5-one;
2-(4-((1,3-dihydro-2-benzofuran-5-yl)oxy)piperidin-1-yl)-3-ethyl-6-(2-hydroxyethyl)-6,7-dihydro-5H-pyrrolo[3,4-b]pyridin-5-one;
2-(4-((6-methoxypyridin-3-yl)oxy)piperidin-1-yl)-3-methyl-6-(pyridin-4-ylmethyl)-6,7-dihydro-5H-pyrrolo[3,4-b]pyridin-5-one;
2-(4-((2,2-difluoro-1-methylcyclopropyl)methoxy)piperidin-1-yl)-6-(2-hydroxyethyl)-3,4-dimethyl-6,7-dihydro-5H-pyrrolo[3,4-b]pyridin-5-one;
methyl 2-(2-(4-((6-methoxypyridin-3-yl)oxy)piperidin-1-yl)-3-methyl-5-oxo-5,7-dihydro-6H-pyrrolo[3,4-b]pyridin-6-yl)acetate;
2-(4-((1,3-dihydro-2-benzofuran-5-yl)oxy)piperidin-1-yl)-6-(2-methoxyethyl)-3,4-dimethyl-6,7-dihydro-5H-pyrrolo[3,4-b]pyridin-5-one;
2-((3S,4R)-4-((1,3-dihydro-2-benzofuran-5-yl)oxy)-3-fluoropiperidin-1-yl)-6-(2-hydroxyethyl)-3,4-dimethyl-6,7-dihydro-5H-pyrrolo[3,4-b]pyridin-5-one;
2-((3S,4R)-3-fluoro-4-(4-fluorophenoxy)piperidin-1-yl)-6-(2-hydroxyethyl)-3-methyl-6,7-dihydro-5H-pyrrolo[3,4-b]pyridin-5-one;
2-(4-((1,3-dihydro-2-benzofuran-5-yl)oxy)piperidin-1-yl)-6-(2-hydroxyethyl)-3-methyl-6,7-dihydro-5H-pyrrolo[3,4-b]pyridin-5-one;
2-(4-((1,3-dihydro-2-benzofuran-5-yl)oxy)piperidin-1-yl)-6-(2-methoxyethyl)-3-methyl-6,7-dihydro-5H-pyrrolo[3,4-b]pyridin-5-one;
2-(4-(4-fluorophenoxy)piperidin-1-yl)-6-(2-hydroxyethyl)-3-methyl-6,7-dihydro-5H-pyrrolo[3,4-b]pyridin-5-one;
2-(4-((1,3-dihydro-2-benzofuran-5-yl)oxy)piperidin-1-yl)-6-(2-hydroxyethyl)-3,4-dimethyl-6,7-dihydro-5H-pyrrolo[3,4-b]pyridin-5-one;
(R)-6-(1-hydroxypropan-2-yl)-2-(4-((6-methoxypyridin-3-yl)oxy)piperidin-1-yl)-3-methyl-6,7-dihydro-5H-pyrrolo[3,4-b]pyridin-5-one;
(S)-6-(1-hydroxypropan-2-yl)-2-(4-((6-methoxypyridin-3-yl)oxy)piperidin-1-yl)-3-methyl-6,7-dihydro-5H-pyrrolo[3,4-b]pyridin-5-one;
(R)-2-(4-((2-hydroxy-2,3-dihydro-1H-inden-5-yl)oxy)piperidin-1-yl)-6-(2-hydroxyethyl)-3,4-dimethyl-6,7-dihydro-5H-pyrrolo[3,4-b]pyridin-5-one;

(S)-2-(4-((2-hydroxy-2,3-dihydro-1H-inden-5-yl)oxy)piperidin-1-yl)-6-(2-hydroxyethyl)-3,4-dimethyl-6,7-dihydro-5H-pyrrolo[3,4-b]pyridin-5-one;
2-(4-((2,3-dihydrobenzofuran-6-yl)oxy)piperidin-1-yl)-3-ethyl-6-(2-hydroxyethyl)-6,7-dihydro-5H-pyrrolo[3,4-b]pyridin-5-one;
(R)-2-(4-((2,2-difluoro-1-methylcyclopropyl)methoxy)piperidin-1-yl)-6-(2-hydroxyethyl)-3,4-dimethyl-6,7-dihydro-5H-pyrrolo[3,4-b]pyridin-5-one;
(S)-2-(4-((2,2-difluoro-1-methylcyclopropyl)methoxy)piperidin-1-yl)-6-(2-hydroxyethyl)-3,4-dimethyl-6,7-dihydro-5H-pyrrolo[3,4-b]pyridin-5-one;
6-(2-hydroxyethyl)-3,4-dimethyl-2-(4-((1-methyl-1H-indazol-5-yl)oxy)piperidin-1-yl)-6,7-dihydro-5H-pyrrolo[3,4-b]pyridin-5-one;
6-(2-hydroxyethyl)-2-(4-(isochroman-7-yloxy)piperidin-1-yl)-3-methyl-6,7-dihydro-5H-pyrrolo[3,4-b]pyridin-5-one;
6-(2-hydroxyethyl)-2-(4-(isochroman-6-yloxy)piperidin-1-yl)-3,4-dimethyl-6,7-dihydro-5H-pyrrolo[3,4-b]pyridin-5-one;
2-(4-(4-fluorophenoxy)piperidin-1-yl)-6-(2-hydroxyethyl)-3,4-dimethyl-6,7-dihydro-5H-pyrrolo[3,4-b]pyridin-5-one;
2-(4-((2,3-dihydrobenzofuran-6-yl)oxy)piperidin-1-yl)-6-(2-hydroxyethyl)-3,4-dimethyl-6,7-dihydro-5H-pyrrolo[3,4-b]pyridin-5-one;
2-(2-(4-((1,3-dihydro-2-benzofuran-5-yl)oxy)piperidin-1-yl)-3,4-dimethyl-5-oxo-5,7-dihydro-6H-pyrrolo[3,4-b]pyridin-6-yl)acetic acid
(R)-2-(4-((1,3-dihydro-2-benzofuran-5-yl)oxy)piperidin-1-yl)-6-(1-hydroxypropan-2-yl)-3,4-dimethyl-6,7-dihydro-5H-pyrrolo[3,4-b]pyridin-5-one;
(S)-2-(4-((1,3-dihydro-2-benzofuran-5-yl)oxy)piperidin-1-yl)-6-(1-hydroxypropan-2-yl)-3,4-dimethyl-6,7-dihydro-5H-pyrrolo[3,4-b]pyridin-5-one;
3-ethyl-2-((3S,4S)-3-fluoro-4-((1-methylcyclopropyl)methoxy)piperidin-1-yl)-6-(2-hydroxyethyl)-6,7-dihydro-5H-pyrrolo[3,4-b]pyridin-5-one;
3-ethyl-6-(2-hydroxyethyl)-2-(4-(isochroman-6-yloxy)piperidin-1-yl)-6,7-dihydro-5H-pyrrolo[3,4-b]pyridin-5-one;
2-((3S,4S)-3-fluoro-4-((1-methylcyclopropyl)methoxy)piperidin-1-yl)-6-(2-hydroxyethyl)-3,4-dimethyl-6,7-dihydro-5H-pyrrolo[3,4-b]pyridin-5-one;
3-ethyl-6-(2-hydroxyethyl)-2-(4-(isochroman-7-yloxy)piperidin-1-yl)-6,7-dihydro-5H-pyrrolo[3,4-b]pyridin-5-one;
2-(4-(cyclobutylmethoxy)piperidin-1-yl)-6-(2-hydroxyethyl)-3,4-dimethyl-6,7-dihydro-5H-pyrrolo[3,4-b]pyridin-5-one;
(R)-6-(2-hydroxyethyl)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one;
(S)-6-(2-hydroxyethyl)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one;
2-((3S,4R)-3-fluoro-4-((1-methyl-1H-indazol-5-yl)oxy)piperidin-1-yl)-6-(2-hydroxyethyl)-3-methyl-6,7-dihydro-5H-pyrrolo[3,4-b]pyridin-5-one;
2-((3R,4R)-3-fluoro-4-((1-methylcyclopropyl)methoxy)piperidin-1-yl)-6-(2-hydroxyethyl)-3,4-dimethyl-6,7-dihydro-5H-pyrrolo[3,4-b]pyridin-5-one;
3-ethyl-6-(2-hydroxyethyl)-2-(4-(((1-methyl cyclopropyl)methoxy)piperidin-1-yl)-6,7-dihydro-5H-pyrrolo[3,4-b]pyridin-5-one;
3-ethyl-6-(2-hydroxyethyl)-2-(4-((1-methyl-1H-indazol-6-yl)oxy)piperidin-1-yl)-6,7-dihydro-5H-pyrrolo[3,4-b]pyridin-5-one;
6-(2-hydroxyethyl)-2-(4-(isochroman-7-yloxy)piperidin-1-yl)-3,4-dimethyl-6,7-dihydro-5H-pyrrolo[3,4-b]pyridin-5-one;
(R)-2-(4-((1,3-dihydro-2-benzofuran-5-yl)oxy)piperidin-1-yl)-6-(1-hydroxypropan-2-yl)-3-methyl-6,7-dihydro-5H-pyrrolo[3,4-b]pyridin-5-one;
(S)-2-(4-((1,3-dihydro-2-benzofuran-5-yl)oxy)piperidin-1-yl)-6-(1-hydroxypropan-2-yl)-3-methyl-6,7-dihydro-5H-pyrrolo[3,4-b]pyridin-5-one;
2-((3S,4R)-3-fluoro-4-((1-methyl-1H-indazol-5-yl)oxy)piperidin-1-yl)-6-(2-hydroxyethyl)-3,4-dimethyl-6,7-dihydro-5H-pyrrolo[3,4-b]pyridin-5-one;
2-((3S,4R)-3-fluoro-4-((1-methylcyclopropyl)methoxy)piperidin-1-yl)-6-(2-hydroxyethyl)-3,4-dimethyl-6,7-dihydro-5H-pyrrolo[3,4-b]pyridin-5-one;
6-Cyclopropyl-2-(4-((6-methoxypyridin-3-yl)oxy)piperidin-1-yl)-3-methyl-6,7-dihydro-5H-pyrrolo[3,4-b]pyridin-5-one;
7-(hydroxymethyl)-2-(4-((6-methoxypyridin-3-yl)oxy)piperidin-1-yl)-3-methyl-6,7-dihydro-5H-pyrrolo[3,4-b]pyridin-5-one;
(R)-7-(hydroxymethyl)-2-(4-((6-methoxypyridin-3-yl)oxy)piperidin-1-yl)-3-methyl-6,7-dihydro-5H-pyrrolo[3,4-b]pyridin-5-one;
(S)-7-(hydroxymethyl)-2-(4-((6-methoxypyridin-3-yl)oxy)piperidin-1-yl)-3-methyl-6,7-dihydro-5H-pyrrolo[3,4-b]pyridin-5-one;
6-(hydroxymethyl)-3-methyl-2-(4-((1-methyl-1H-indazol-5-yl)oxy)piperidin-1-yl)-6,7-dihydro-5H-pyrrolo[3,4-b]pyridin-5-one;
(R)-7-(hydroxymethyl)-2-(4-((6-methoxypyridin-3-yl)oxy)piperidin-1-yl)-3,6-dimethyl-6,7-dihydro-5H-pyrrolo[3,4-b]pyridin-5-one;
(S)-7-(hydroxymethyl)-2-(4-((6-methoxypyridin-3-yl)oxy)piperidin-1-yl)-3,6-dimethyl-6,7-dihydro-5H-pyrrolo[3,4-b]pyridin-5-one;
7,7-bis(hydroxymethyl)-2-(4-((6-methoxypyridin-3-yl)oxy)piperidin-1-yl)-3,6-dimethyl-6,7-dihydro-5H-pyrrolo[3,4-b]pyridin-5-one;
(R)-7-(hydroxymethyl)-3,6-dimethyl-2-(4-phenoxypiperidin-1-yl)-6,7-dihydro-5H-pyrrolo[3,4-b]pyridin-5-one;
(S)-7-(hydroxymethyl)-3,6-dimethyl-2-(4-phenoxypiperidin-1-yl)-6,7-dihydro-5H-pyrrolo[3,4-b]pyridin-5-one;
(R)-2-((3S,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one;
(R)-2-(4-((5,7-dihydrofuro[3,4-b]pyridin-3-yl)oxy)piperidin-1-yl)-7-(hydroxymethyl)-3,6-dimethyl-6,7-dihydro-5H-pyrrolo[3,4-b]pyridin-5-one;
(S)-2-((3S,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one;
(S)-2-(4-((5,7-dihydrofuro[3,4-b]pyridin-3-yl)oxy)piperidin-1-yl)-7-(hydroxymethyl)-3,6-dimethyl-6,7-dihydro-5H-pyrrolo[3,4-b]pyridin-5-one;
(S)-2-(4-(4-fluorophenoxy)piperidin-1-yl)-7-(hydroxymethyl)-3,6-dimethyl-6,7-dihydro-5H-pyrrolo[3,4-b]pyridin-5-one;
(R)-2-((3R,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one;

(R)-2-(4-(4-fluorophenoxy)piperidin-1-yl)-7-(hydroxymethyl)-3,6-dimethyl-6,7-dihydro-5H-pyrrolo[3,4-b]pyridin-5-one;
(S)-2-((3R,4R)-4-((1,3-dihydro-2-benzofuran-5-yl)oxy)-3-fluoropiperidin-1-yl)-7-(hydroxymethyl)-3,6-dimethyl-6,7-dihydro-5H-pyrrolo[3,4-b]pyridin-5-one;
(S)-2-(4-((1,3-dihydro-2-benzofuran-5-yl)oxy)piperidin-1-yl)-7-(hydroxymethyl)-3,6-dimethyl-6,7-dihydro-5H-pyrrolo[3,4-b]pyridin-5-one;
(R)-2-((3R,4R)-3-fluoro-4-((6-methoxypyridin-3-yl)oxy)piperidin-1-yl)-7-(hydroxymethyl)-3,6-dimethyl-6,7-dihydro-5H-pyrrolo[3,4-b]pyridin-5-one;
(R)-2-(4-((1,3-dihydro-2-benzofuran-5-yl)oxy)piperidin-1-yl)-7-(hydroxymethyl)-3,6-dimethyl-6,7-dihydro-5H-pyrrolo[3,4-b]pyridin-5-one;
(S)-2-((3R,4R)-3-fluoro-4-((6-methoxypyridin-3-yl)oxy)piperidin-1-yl)-7-(hydroxymethyl)-3,6-dimethyl-6,7-dihydro-5H-pyrrolo[3,4-b]pyridin-5-one;
(S)-2-((3S,4R)-3-fluoro-4-((1-methyl-1H-indazol-5-yl)oxy)piperidin-1-yl)-7-(hydroxymethyl)-3,6-dimethyl-6,7-dihydro-5H-pyrrolo[3,4-b]pyridin-5-one;
(R)-2-((3S,4R)-3-fluoro-4-((1-methyl-1H-indazol-5-yl)oxy)piperidin-1-yl)-7-(hydroxymethyl)-3,6-dimethyl-6,7-dihydro-5H-pyrrolo[3,4-b]pyridin-5-one;
(R)-2-(4-((6-ethoxypyridin-3-yl)oxy)piperidin-1-yl)-7-(hydroxymethyl)-3,6-dimethyl-6,7-dihydro-5H-pyrrolo[3,4-b]pyridin-5-one;
(S)-2-(4-((6-ethoxypyridin-3-yl)oxy)piperidin-1-yl)-7-(hydroxymethyl)-3,6-dimethyl-6,7-dihydro-5H-pyrrolo[3,4-b]pyridin-5-one;
(R)-7-(hydroxymethyl)-2-(4-((6-methoxypyridin-3-yl)oxy)piperidin-1-yl)-3,6,7-trimethyl-6,7-dihydro-5H-pyrrolo[3,4-b]pyridin-5-one;
(S)-7-(hydroxymethyl)-2-(4-((6-methoxypyridin-3-yl)oxy)piperidin-1-yl)-3,6,7-trimethyl-6,7-dihydro-5H-pyrrolo[3,4-b]pyridin-5-one;
2-(4-((6-methoxypyridin-3-yl)oxy)piperidin-1-yl)-3,7,7-trimethyl-6,7-dihydro-5H-pyrrolo[3,4-b]pyridin-5-one;
2-(4-((6-methoxypyridin-3-yl)oxy)piperidin-1-yl)-3-methyl-7-methylene-6,7-dihydro-5H-pyrrolo[3,4-b]pyridin-5-one;
3-methyl-2-(4-((2-methylisoindolin-5-yl)oxy)piperidin-1-yl)-6,7-dihydro-5H-pyrrolo[3,4-b]pyridin-5-one;
3-methyl-2-(4-((1-methyl-1,2,3,4-tetrahydroquinolin-6-yl)oxy)piperidin-1-yl)-6,7-dihydro-5H-pyrrolo[3,4-b]pyridin-5-one;
3-methyl-2-(4-((2-methyl-1,2,3,4-tetrahydroisoquinolin-7-yl)oxy)piperidin-1-yl)-6,7-dihydro-5H-pyrrolo[3,4-b]pyridin-5-one;
3-methyl-2-(4-((4-methyl-3,4-dihydro-2H-benzo[1,4]oxazin-7-yl)oxy)piperidin-1-yl)-6,7-dihydro-5H-pyrrolo[3,4-b]pyridin-5-one;
2-(4-((2-acetylisoindolin-5-yl)oxy)piperidin-1-yl)-3-methyl-6,7-dihydro-5H-pyrrolo[3,4-b]pyridin-5-one;
2-(4-((2-acetyl-1,2,3,4-tetrahydroisoquinolin-7-yl)oxy)piperidin-1-yl)-3-methyl-6,7-dihydro-5H-pyrrolo[3,4-b]pyridin-5-one;
2-(4-((6-methoxypyridin-3-yl)oxy)piperidin-1-yl)-3-methyl-6-(pyridin-4-ylmethyl)-5H-pyrrolo[3,4-b]pyridine-5,7(6H)-dione;
2-(4-((6-methoxypyridin-3-yl)oxy)piperidin-1-yl)-3-methyl-5H-pyrrolo[3,4-b]pyridine-5,7(6H)-dione;
7-hydroxy-2-(4-((6-methoxypyridin-3-yl)oxy)piperidin-1-yl)-3-methyl-6,7-dihydro-5H-pyrrolo[3,4-b]pyridin-5-one;
tert-butyl-2-(4-((6-methoxypyridin-3-yl)oxy)piperidin-1-yl)-3-methyl-5-oxo-5,7-dihydro-6H-pyrrolo[3,4-b]pyridine-6-carboxylate;
2-(4-((6-methoxypyridin-3-yl)oxy)piperidin-1-yl)-3-methylspiro[cyclopropane-1,7-pyrrolo[3,4-b]pyridine-5-(6H)-one;
3-(hydroxymethyl)-2-(4-((6-methoxypyridin-3-yl)oxy)piperidin-1-yl)-6,7-dihydro-5H-pyrrolo[3,4-b]pyridin-5-one;
4-(hydroxymethyl)-2-(4-((6-methoxypyridin-3-yl)oxy)piperidin-1-yl)-3-methyl-6,7-dihydro-5H-pyrrolo[3,4-b]pyridin-5-one;
2-(4-((1,3-dihydro-2-benzofuran-5-yl)oxy)piperidin-1-yl)-4-(hydroxymethyl)-3-methyl-6,7-dihydro-5H-pyrrolo[3,4-b]pyridin-5-one;
3-(fluoromethyl)-2-(4-((6-methoxypyridin-3-yl)oxy)piperidin-1-yl)-6,7-dihydro-5H-pyrrolo[3,4-b]pyridin-5-one;
4-(fluoromethyl)-2-(4-((6-methoxypyridin-3-yl)oxy)piperidin-1-yl)-3-methyl-6,7-dihydro-5H-pyrrolo[3,4-b]pyridin-5-one;
2-(4-((6-methoxypyridin-3-yl)oxy)piperidin-1-yl)-5-oxo-6,7-dihydro-5H-pyrrolo[3,4-b]pyridine-3-carbaldehyde;
3-(difluoromethyl)-2-(4-((6-methoxypyridin-3-yl)oxy)piperidin-1-yl)-6,7-dihydro-5H-pyrrolo[3,4-b]pyridin-5-one;
4-(difluoromethyl)-2-(4-((6-methoxypyridin-3-yl)oxy)piperidin-1-yl)-3-methyl-6,7-dihydro-5H-pyrrolo[3,4-b]pyridin-5-one;
3-((1-(3-methyl-5-oxo-6,7-dihydro-5H-pyrrolo[3,4-b]pyridin-2-yl)piperidin-4-yl)oxy)benzaldehyde;
2-(4-(3-(hydroxymethyl)phenoxy)piperidin-1-yl)-3-methyl-6,7-dihydro-5H-pyrrolo[3,4-b]pyridin-5-one;
2-(2-(4-((6-methoxypyridin-3-yl)oxy)piperidin-1-yl)-3-methyl-5-oxo-5,7-dihydro-6H-pyrrolo[3,4-b]pyridin-6-yl)acetamide
2-(2-(4-((1,3-dihydro-2-benzofuran-5-yl)oxy)piperidin-1-yl)-3,4-dimethyl-5-oxo-5,7-dihydro-6H-pyrrolo[3,4-b]pyridin-6-yl)acetamide
2-(4-((2,2-dimethylcyclopropyl)methoxy)piperidin-1-yl)-3-methyl-6,7-dihydro-5H-pyrrolo[3,4-b]pyridin-5-one;
2-(4-((1-cyclopropyl-1H-pyrazol-4-yl)oxy)piperidin-1-yl)-3-methyl-6,7-dihydro-5H-pyrrolo[3,4-b]pyridin-5-one;
2-(4-((1-(hydroxymethyl)cyclopropyl)methoxy)piperidin-1-yl)-3-methyl-6,7-dihydro-5H-pyrrolo[3,4-b]pyridin-5-one;
2-(4-((1-(2-methoxyethyl)-1H-pyrazol-4-yl)oxy)piperidin-1-yl)-3-methyl-6,7-dihydro-5H-pyrrolo[3,4-b]pyridin-5-one;
2-(4-((1-hydroxycyclopropyl)methoxy)piperidin-1-yl)-3-methyl-6,7-dihydro-5H-pyrrolo[3,4-b]pyridin-5-one;
2-(4-((3-chloro-1H-indazol-5-yl)oxy)piperidin-1-yl)-3-methyl-6,7-dihydro-5H-pyrrolo[3,4-b]pyridin-5-one;
2-(4-((4-chloro-1H-indazol-5-yl)oxy)piperidin-1-yl)-3-methyl-6,7-dihydro-5H-pyrrolo[3,4-b]pyridin-5-one;
2-(4-((3-bromo-1H-indazol-5-yl)oxy)piperidin-1-yl)-3-methyl-6,7-dihydro-5H-pyrrolo[3,4-b]pyridin-5-one;
5-((1-(3-methyl-5-oxo-6,7-dihydro-5H-pyrrolo[3,4-b]pyridin-2-yl)piperidin-4-yl)oxy)-1H-indazole-3-carbonitrile;
2-(4-((7-fluoro-1H-indazol-5-yl)oxy)piperidin-1-yl)-3-methyl-6,7-dihydro-5H-pyrrolo[3,4-b]pyridin-5-one;
(R)-2-(4-((6-methoxypyridin-3-yl)oxy)piperidin-1-yl)-3-methyl-6-(3,3,3-trifluoro-2-hydroxypropyl)-6,7-dihydro-5H-pyrrolo[3,4-b]pyridin-5-one;

(S)-2-(4-((6-methoxypyridin-3-yl)oxy)piperidin-1-yl)-3-methyl-6-(3,3,3-trifluoro-2-hydroxypropyl)-6,7-dihydro-5H-pyrrolo[3,4-b]pyridin-5-one;

3-methyl-2-(4-((6-(methylamino)pyridin-3-yl)oxy)piperidin-1-yl)-6,7-dihydro-5H-pyrrolo[3,4-b]pyridin-5-one;

2-(4-((2,2-Dimethyl-2,3-dihydrobenzofuran-5-yl)oxy)piperidin-1-yl)-3-methyl-6,7-dihydro-5H-pyrrolo[3,4-b]pyridin-5-one;

2-(4-((1-(cyclopropylmethyl)-1H-pyrazol-4-yl)oxy)piperidin-1-yl)-3-methyl-6,7-dihydro-5H-pyrrolo[3,4-b]pyridin-5-one;

3-methyl-2-(4-((1,2,4,5-tetrahydrobenzo[d]oxepin-7-yl)oxy)piperidin-1-yl)-6,7-dihydro-5H-pyrrolo[3,4-b]pyridin-5-one;

7-(2-hydroxypropan-2-yl)-2-(4-((6-methoxypyridin-3-yl)oxy)piperidin-1-yl)-3,6-dimethyl-6,7-dihydro-5H-pyrrolo[3,4-b]pyridin-5-one;

(R)-7-(2-hydroxypropan-2-yl)-2-(4-((6-methoxypyridin-3-yl)oxy)piperidin-1-yl)-3,6-dimethyl-6,7-dihydro-5H-pyrrolo[3,4-b]pyridin-5-one;

(S)-7-(2-hydroxypropan-2-yl)-2-(4-((6-methoxypyridin-3-yl)oxy)piperidin-1-yl)-3,6-dimethyl-6,7-dihydro-5H-pyrrolo[3,4-b]pyridin-5-one;

2-(4-((2-hydroxy-2,3-dihydro-1H-inden-5-yl)oxy)piperidin-1-yl)-3-methyl-6,7-dihydro-5H-pyrrolo[3,4-b]pyridin-5-one;

(S)-2-(4-((2-hydroxy-2,3-dihydro-1H-inden-5-yl)oxy)piperidin-1-yl)-3-methyl-6,7-dihydro-5H-pyrrolo[3,4-b]pyridin-5-one;

(R)-2-(4-((2-hydroxy-2,3-dihydro-1H-inden-5-yl)oxy)piperidin-1-yl)-3-methyl-6,7-dihydro-5H-pyrrolo[3,4-b]pyridin-5-one;

(S)-2-(4-((7-hydroxy-6,7-dihydro-5H-cyclopenta[b]pyridin-3-yl)oxy)piperidin-1-yl)-3-methyl-6,7-dihydro-5H-pyrrolo[3,4-b]pyridin-5-one;

(R)-2-(4-((7-hydroxy-6,7-dihydro-5H-cyclopenta[b]pyridin-3-yl)oxy)piperidin-1-yl)-3-methyl-6,7-dihydro-5H-pyrrolo[3,4-b]pyridin-5-one;

2-(4-((6-((2-hydroxyethyl)amino)pyridin-3-yl)oxy)piperidin-1-yl)-3-methyl-6,7-dihydro-5H-pyrrolo[3,4-b]pyridin-5-one;

(2-(4-(3-cyanophenoxy)piperidin-1-yl)-3-methyl-5-oxo-5,7-dihydro-6H-pyrrolo[3,4-b]pyridin-6-yl)phosphoric acid;

2-(4-((6-hydroxypyridin-3-yl)oxy)piperidin-1-yl)-3-methyl-6,7-dihydro-5H-pyrrolo[3,4-b]pyridin-5-one;

3-chloro-2-(4-((6-methoxypyridin-3-yl)oxy)piperidin-1-yl)-6,7-dihydro-5H-pyrrolo[3,4-b]pyridin-5-one;

(R)-2-(4-((2,2-difluoro-1-methylcyclopropyl)methoxy)piperidin-1-yl)-3,4-dimethyl-6,7-dihydro-5H-pyrrolo[3,4-b]pyridin-5-one;

(S)-2-(4-((2,2-difluoro-1-methylcyclopropyl)methoxy)piperidin-1-yl)-3,4-dimethyl-6,7-dihydro-5H-pyrrolo[3,4-b]pyridin-5-one;

2-(4-(cyclobutylmethoxy)piperidin-1-yl)-3,4-dimethyl-6,7-dihydro-5H-pyrrolo[3,4-b]pyridin-5-one;

3,4-dimethyl-2-(4-((1-methyl-1H-pyrazol-4-yl)oxy)piperidin-1-yl)-6,7-dihydro-5H-pyrrolo[3,4-b]pyridin-5-one;

2-(4-(isochroman-7-yloxy)piperidin-1-yl)-3,4-dimethyl-6,7-dihydro-5H-pyrrolo[3,4-b]pyridin-5-one;

2-(4-((2,3-dihydrobenzofuran-6-yl)oxy)piperidin-1-yl)-3,4-dimethyl-6,7-dihydro-5H-pyrrolo[3,4-b]pyridin-5-one;

(R)-2-(4-((2-hydroxy-2,3-dihydro-1H-inden-5-yl)oxy)piperidin-1-yl)-3,4-dimethyl-6,7-dihydro-5H-pyrrolo[3,4-b]pyridin-5-one;

(S)-2-(4-((2-hydroxy-2,3-dihydro-1H-inden-5-yl)oxy)piperidin-1-yl)-3,4-dimethyl-6,7-dihydro-5H-pyrrolo[3,4-b]pyridin-5-one;

(R)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one;

(S)-2-(4-((2-methoxy-2,3-dihydro-1H-inden-5-yl)oxy)piperidin-1-yl)-3,4-dimethyl-6,7-dihydro-5H-pyrrolo[3,4-b]pyridin-5-one;

2-(4-(isochroman-6-yloxy)piperidin-1-yl)-3,4-dimethyl-6,7-dihydro-5H-pyrrolo[3,4-b]pyridin-5-one;

2-((3R,4R)-3-fluoro-4-((6-methoxypyridin-3-yl)oxy)piperidin-1-yl)-3,4-dimethyl-6,7-dihydro-5H-pyrrolo[3,4-b]pyridin-5-one;

(R)-2-(3,3-difluoro-4-((1-methyl-1H-pyrazol-4-yl)oxy)piperidin-1-yl)-3,4-dimethyl-6,7-dihydro-5H-pyrrolo[3,4-b]pyridin-5-one;

(S)-2-(3,3-difluoro-4-((1-methyl-1H-pyrazol-4-yl)oxy)piperidin-1-yl)-3,4-dimethyl-6,7-dihydro-5H-pyrrolo[3,4-b]pyridin-5-one;

(S)-2-(4-((1,3-dihydro-2-benzofuran-5-yl)oxy)piperidin-1-yl)-7-(hydroxymethyl)-3,4,6-trimethyl-6,7-dihydro-5H-pyrrolo[3,4-b]pyridin-5-one;

(R)-2-(4-((1,3-dihydro-2-benzofuran-5-yl)oxy)piperidin-1-yl)-7-(hydroxymethyl)-3,4,6-trimethyl-6,7-dihydro-5H-pyrrolo[3,4-b]pyridin-5-one;

(S)-7-(hydroxymethyl)-2-(4-(isochroman-7-yloxy)piperidin-1-yl)-3,4,6-trimethyl-6,7-dihydro-5H-pyrrolo[3,4-b]pyridin-5-one;

(R)-7-(hydroxymethyl)-2-(4-(isochroman-7-yloxy)piperidin-1-yl)-3,4,6-trimethyl-6,7-dihydro-5H-pyrrolo[3,4-b]pyridin-5-one;

3,6-dimethyl-2-(4-((1-methylcyclopropyl)methoxy)piperidin-1-yl)-6,7-dihydro-5H-pyrrolo[3,4-b]pyridin-5-one;

(S)-7-(hydroxymethyl)-3,6-dimethyl-2-(4-((1-methylcyclopropyl)methoxy)piperidin-1-yl)-6,7-dihydro-5H-pyrrolo[3,4-b]pyridin-5-one;

(R)-7-(hydroxymethyl)-3,6-dimethyl-2-(4-((1-methylcyclopropyl)methoxy)piperidin-1-yl)-6,7-dihydro-5H-pyrrolo[3,4-b]pyridin-5-one;

(S)-3-ethyl-7-(hydroxymethyl)-6-methyl-2-(4-((1-methylcyclopropyl)methoxy)piperidin-1-yl)-6,7-dihydro-5H-pyrrolo[3,4-b]pyridin-5-one;

(S)-2-((3S,4R)-3-fluoro-4-((1-methylcyclopropyl)methoxy)piperidin-1-yl)-7-(hydroxymethyl)-3,4,6-trimethyl-6,7-dihydro-5H-pyrrolo[3,4-b]pyridin-5-one;

(R)-3-ethyl-7-(hydroxymethyl)-6-methyl-2-(4-((1-methylcyclopropyl)methoxy)piperidin-1-yl)-6,7-dihydro-5H-pyrrolo[3,4-b]pyridin-5-one;

(R)-2-((3S,4R)-3-fluoro-4-((1-methylcyclopropyl)methoxy)piperidin-1-yl)-7-(hydroxymethyl)-3,4,6-trimethyl-6,7-dihydro-5H-pyrrolo[3,4-b]pyridin-5-one;

(S)-7-(hydroxymethyl)-3,6-dimethyl-2-(4-((5-methylpyridin-3-yl)oxy)piperidin-1-yl)-6,7-dihydro-5H-pyrrolo[3,4-b]pyridin-5-one;

(S)-7-(hydroxymethyl)-2-(4-((6-methoxypyridin-3-yl)oxy)piperidin-1-yl)-3,4,6-trimethyl-6,7-dihydro-5H-pyrrolo[3,4-b]pyridin-5-one;

(R)-7-(hydroxymethyl)-3,6-dimethyl-2-(4-((5-methylpyridin-3-yl)oxy)piperidin-1l-yl)-6,7-dihydro-5H-pyrrolo[3,4-b]pyridin-5-one;

(R)-7-(hydroxymethyl)-2-(4-((6-methoxypyridin-3-yl)oxy)piperidin-1-yl)-3,4,6-trimethyl-6,7-dihydro-5H-pyrrolo[3,4-b]pyridin-5-one;

(S)-3-((1-(7-(hydroxymethyl)-3,6-dimethyl-5-oxo-6,7-dihydro-5H-pyrrolo[3,4-b]pyridin-2-yl)piperidin-4-yl)oxy)benzonitrile;

(R)-3-((1-(7-(hydroxymethyl)-3,6-dimethyl-5-oxo-6,7-dihydro-5H-pyrrolo[3,4-b]pyridin-2-yl)piperidin-4-yl)oxy)benzonitrile;

(S)-2-(4-(3,4-difluorophenoxy)piperidin-1-yl)-7-(hydroxymethyl)-3,6-dimethyl-6,7-dihydro-5H-pyrrolo[3,4-b]pyridin-5-one;

(R)-2-(4-(3,4-difluorophenoxy)piperidin-1-yl)-7-(hydroxymethyl)-3,6-dimethyl-6,7-dihydro-5H-pyrrolo[3,4-b]pyridin-5-one;

(S)-7-(hydroxymethyl)-2-(4-(isochroman-7-yloxy)piperidin-1-yl)-3,6-dimethyl-6,7-dihydro-5H-pyrrolo[3,4-b]pyridin-5-one;

(S)-7-(hydroxymethyl)-2-(4-(isochroman-6-yloxy)piperidin-1-yl)-3,6-dimethyl-6,7-dihydro-5H-pyrrolo[3,4-b]pyridin-5-one;

(R)-7-(hydroxymethyl)-2-(4-(isochroman-7-yloxy)piperidin-1-yl)-3,6-dimethyl-6,7-dihydro-5H-pyrrolo[3,4-b]pyridin-5-one;

(R)-7-(hydroxymethyl)-2-(4-(isochroman-6-yloxy)piperidin-1-yl)-3,6-dimethyl-6,7-dihydro-5H-pyrrolo[3,4-b]pyridin-5-one;

(S)-2-(4-((1,3-dihydro-2-benzofuran-5-yl)oxy)piperidin-1-yl)-3-ethyl-7-(hydroxymethyl)-6-methyl-6,7-dihydro-5H-pyrrolo[3,4-b]pyridin-5-one;

(S)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one;

can-2-(4-((1,3-dihydro-2-benzofuran-5-yl)oxy)piperidin-1-yl)-3-ethyl-7-(hydroxymethyl)-6-methyl-6,7-dihydro-5H-pyrrolo[3,4-b]pyridin-5-one;

(R)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one;

(S)-2-(4-(4-fluorophenoxy)piperidin-1-yl)-7-(hydroxymethyl)-3,4,6-trimethyl-6,7-dihydro-5H-pyrrolo[3,4-b]pyridin-5-one;

(R)-2-(4-(4-fluorophenoxy)piperidin-1-yl)-7-(hydroxymethyl)-3,4,6-trimethyl-6,7-dihydro-5H-pyrrolo[3,4-b]pyridin-5-one;

(S)-2-(4-((2,3-dihydrobenzofuran-6-yl)oxy)piperidin-1-yl)-7-(hydroxymethyl)-3,6-dimethyl-6,7-dihydro-5H-pyrrolo[3,4-b]pyridin-5-one;

(R)-2-(4-((2,3-dihydrobenzofuran-6-yl)oxy)piperidin-1-yl)-7-(hydroxymethyl)-3,6-dimethyl-6,7-dihydro-5H-pyrrolo[3,4-b]pyridin-5-one;

(S)-7-(hydroxymethyl)-3,6-dimethyl-2-(4-((1-methyl-1H-pyrazol-4-yl)oxy)piperidin-1-yl)-6,7-dihydro-5H-pyrrolo[3,4-b]pyridin-5-one;

(R)-7-(hydroxymethyl)-3,6-dimethyl-2-(4-((1-methyl-1H-pyrazol-4-yl)oxy)piperidin-1-yl)-6,7-dihydro-5H-pyrrolo[3,4-b]pyridin-5-one;

(S)-7-(hydroxymethyl)-3,6-dimethyl-2-(4-((1-methyl-1H-indazol-5-yl)oxy)piperidin-1-yl)-6,7-dihydro-5H-pyrrolo[3,4-b]pyridin-5-one;

(R)-7-(hydroxymethyl)-3,6-dimethyl-2-(4-((1-methyl-1H-indazol-5-yl)oxy)piperidin-1-yl)-6,7-dihydro-5H-pyrrolo[3,4-b]pyridin-5-one;

(S)-3-ethyl-7-(hydroxymethyl)-2-(4-(isochroman-7-yloxy)piperidin-1-yl)-6-methyl-6,7-dihydro-5H-pyrrolo[3,4-b]pyridin-5-one;

(R)-3-ethyl-7-(hydroxymethyl)-2-(4-(isochroman-7-yloxy)piperidin-1-yl)-6-methyl-6,7-dihydro-5H-pyrrolo[3,4-b]pyridin-5-one;

(S)-3-ethyl-7-(hydroxymethyl)-6-methyl-2-(4-((1-methyl-1H-indazol-5-yl)oxy)piperidin-1-yl)-6,7-dihydro-5H-pyrrolo[3,4-b]pyridin-5-one;

(R)-3-ethyl-7-(hydroxymethyl)-6-methyl-2-(4-((1-methyl-1H-indazol-5-yl)oxy)piperidin-1-yl)-6,7-dihydro-5H-pyrrolo[3,4-b]pyridin-5-one;

(S)-2-(4-((2,3-dihydrobenzofuran-6-yl)oxy)piperidin-1-yl)-3-ethyl-7-(hydroxymethyl)-6-methyl-6,7-dihydro-5H-pyrrolo[3,4-b]pyridin-5-one;

(R)-2-(4-((2,3-dihydrobenzofuran-6-yl)oxy)piperidin-1-yl)-3-ethyl-7-(hydroxymethyl)-6-methyl-6,7-dihydro-5H-pyrrolo[3,4-b]pyridin-5-one;

(S)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one;

(R)-2-(4-((1,3-dihydroisobenzofuran-5-yl)oxy)piperidin-1-yl)-6-ethyl-7-(hydroxymethyl)-3,4-dimethyl-6,7-dihydro-5H-pyrrolo[3,4-b]pyridin-5-one;

(S)-7-(hydroxymethyl)-2-(4-(isochroman-6-yloxy)piperidin-1-yl)-3,4,6-trimethyl-6,7-dihydro-5H-pyrrolo[3,4-b]pyridin-5-one;

(R)-7-(hydroxymethyl)-2-(4-(isochroman-6-yloxy)piperidin-1-yl)-3,4,6-trimethyl-6,7-dihydro-5H-pyrrolo[3,4-b]pyridin-5-one;

2-(4-((1-(2-hydroxyethyl)-1H-indazol-5-yl)oxy)piperidin-1-yl)-3-methyl-6,7-dihydro-5H-pyrrolo[3,4-b]pyridin-5-one;

2-(4-((6-methoxypyridin-3-yl)oxy)piperidin-1-yl)-3-methyl-4-vinyl-6,7-dihydro-5H-pyrrolo[3,4-b]pyridin-5-one;

3-methyl-2-(4-((2-oxo-2,3-dihydro-1H-inden-5-yl)oxy)piperidin-1-yl)-6,7-dihydro-5H-pyrrolo[3,4-b]pyridin-5-one;

(R)-2-(3,3-difluoro-4-((1-methylcyclopropyl)methoxy)piperidin-1-yl)-3-ethyl-6,7-dihydro-5H-pyrrolo[3,4-b]pyridin-5-one;

(S)-2-(3,3-difluoro-4-((1-methylcyclopropyl)methoxy)piperidin-1-yl)-3-ethyl-6,7-dihydro-5H-pyrrolo[3,4-b]pyridin-5-one; and 6-(2-hydroxyethyl)-7-(hydroxymethyl)-2-(4-((6-methoxypyridin-3-yl)oxy)piperidin-1-yl)-3-methyl-6,7-dihydro-5H-pyrrolo[3,4-b]pyridin-5-one;

or a pharmaceutically acceptable salt thereof.

11. A pharmaceutical composition which comprises an inert carrier and a compound of claim 1 or a pharmaceutically acceptable salt thereof.

12. A method for the treatment of a neurological and/or psychiatric disorder characterized by muscarinic acetylcholine receptor dysfunction comprising the step of administering at least one compound of claim 1, or a pharmaceutically acceptable salt of said compound, to a mammalian patient in need thereof in an amount effective for the treatment of said disorder.

13. The method of claim 12, wherein the patient has been diagnosed with a need for treatment of the disorder prior to the administering step.

14. The method of claim 12, wherein the disorder is a neurological and/or psychiatric disorder characterized by mAChR M4 dysfunction.

15. The method of claim 12, wherein the disorder is a psychotic disorder.

16. The method of claim 15, wherein the psychotic disorder is selected from schizophrenia, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder.

17. The method of claim 12, wherein the disorder is a cognitive disorder.

18. The method of claim 17, wherein the cognitive disorder is selected from amnesia, dementia, delirium, amnestic disorder, substance-induced persisting delirium, dementia due to HIV disease, dementia due to Huntington's disease, dementia due to Parkinson's disease, Parkinsonian-ALS dementail complex, dementia of the Alzheimer's type, age-related cognitive decline, and mild cognitive impairment.

19. A method for the treatment of a disorder selected from schizophrenia, brief psychotic disorder, schizophreniform disorder, schizoaffective disorder, delusional disorder, shared psychotic disorder, catastrophic schizophrenia, positive and negative symptoms of schizophrenia, secondary psychotic disorder, bipolar I disorder with psychotic features, and substance-induced psychotic disorder, in a human patient comprising administering a compound of claim 1, or a pharmaceutically acceptable salt of said compound, to the patient in need thereof in an amount effective for the treatment of said disorder.

20. A method for the treatment of a disorder selected from amnesia, dementia, delirium, amnestic disorder, dementia of the Alzheimer's type, dementia associated with Alzheimer's disease, age-related cognitive decline, and mild cognitive impairment, in a human patient comprising administering a compound of claim 1, or a pharmaceutically acceptable salt of said compound, to the patient in need thereof in an amount effective for the treatment of said disorder.

\* \* \* \* \*